(12) United States Patent
Zhang et al.

(10) Patent No.: US 10,399,944 B2
(45) Date of Patent: Sep. 3, 2019

(54) PYRIDIN-2-ONE DERIVATIVES OF FORMULA (III) USEFUL AS EP3 RECEPTOR ANTAGONISTS

(71) Applicant: Janssen Pharmaceutica NV, Beerse (BE)

(72) Inventors: Xuqing Zhang, Audubon, PA (US); Mark J. Macielag, Gwynedd Valley, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/059,075

(22) Filed: Aug. 9, 2018

(65) Prior Publication Data

US 2019/0047961 A1    Feb. 14, 2019

Related U.S. Application Data

(60) Provisional application No. 62/543,458, filed on Aug. 10, 2017.

(51) Int. Cl.
| | | |
|---|---|---|
| *A61P 3/10* | (2006.01) | |
| *C07D 213/64* | (2006.01) | |
| *C07D 413/04* | (2006.01) | |
| *C07D 417/04* | (2006.01) | |

(52) U.S. Cl.
CPC .............. *C07D 213/64* (2013.01); *A61P 3/10* (2018.01); *C07D 413/04* (2013.01); *C07D 417/04* (2013.01)

(58) Field of Classification Search
CPC .. C07D 213/64; C07D 413/04; C07D 417/00; A61P 3/10
USPC ........................................................ 514/345
See application file for complete search history.

(56) References Cited

U.S. PATENT DOCUMENTS

| | | |
|---|---|---|
| 2003/0152520 A1 | 8/2003 | Ge et al. |
| 2005/0014767 A1 | 1/2005 | Pfahl et al. |
| 2009/0170887 A1 | 7/2009 | Hagihara et al. |
| 2013/0244932 A1 | 9/2013 | Keller et al. |
| 2015/0099782 A1 | 4/2015 | Bahnck et al. |
| 2016/0176851 A1 | 6/2016 | Bahnck et al. |
| 2019/0047959 A1* | 2/2019 | Zhang ................ C07D 213/64 |
| 2019/0047960 A1* | 2/2019 | Zhang ................ C07D 213/64 |

FOREIGN PATENT DOCUMENTS

| | | |
|---|---|---|
| WO | WO 1995/06636 A1 | 3/1995 |
| WO | WO 2012/061012 A2 | 5/2012 |

OTHER PUBLICATIONS

Yee; Bioorganic and Medicinal Chemistry Letters 26 (2016) 2670-2675. (Year: 2016).*
Li; Bioorganic and Medicinal Chemistry Letters 20 (2010) 6744-6747. (Year: 2010).*
Asada; Bioorganic and Medicinal Chemistry Letters 20 (2010) 2639-2643. (Year: 2010).*
Zeller; Tetrahedron Letters 51 (2010) 1380-1382. (Year: 2010).*
Hategan; Bioorganic and Medicinal Chemistry Letters 19 (2009) 6797-6800. (Year: 2009).*
Tilly; Cardiovascular Research (2014) 101, 482-491. (Year: 2014).*
Jin et al., "Novel 3-Oxazolidinedione-6-aryl-pyridinones as Potent, Selective, and Orally Active EP3 Receptor Antagonists.", *ACS Med. Chem. Lett.*, 2010, pp316-320, vol. 1.
Morales-Ramos et al., "Structure—activity relationship studies of novel 3-oxazolidinedione-6-naphthyl-2-pyridinones as potent and orally bioavailable EP3 receptor antagonists.", *Biororg & Med Chem Lett.*, 2011, pp. 2806-2811, vol. 21.

* cited by examiner

*Primary Examiner* — Daniel R Carcanague

(57) ABSTRACT

The present invention is directed to pyridin-2-one derivatives, pharmaceutical compositions containing them and their use as antagonists of the EP3 receptor, for the treatment of for example, impaired oral glucose tolerance, elevated fasting glucose, Type II Diabetes Mellitus, Syndrome X (also known as Metabolic Syndrome) and related disorders and complications thereof.

16 Claims, No Drawings

PYRIDIN-2-ONE DERIVATIVES OF FORMULA (III) USEFUL AS EP3 RECEPTOR ANTAGONISTS

CROSS-REFERENCE TO RELATED APPLICATIONS

This Application claims priority to U.S. Provisional Patent Application No. 62/543,458, filed Aug. 10, 2017, the disclosure of which is hereby incorporated by reference in its entirety.

FIELD OF THE INVENTION

The present invention is directed to pyridin-2-one derivatives, pharmaceutical compositions containing them and their use as antagonists of the EP3 receptor, for the treatment of for example, impaired oral glucose tolerance, elevated fasting glucose, Type II Diabetes Mellitus, Syndrome X (also known as Metabolic Syndrome) and related disorders and complications thereof.

BACKGROUND OF THE INVENTION

Type I diabetes represents about 5-10% of all diabetes cases and occurs as a result of destruction of the pancreatic beta cells, which produce the hormone insulin, by the body's own immune system. The patients are completely dependent on insulin treatment for survival. Type II diabetes is more common (90-95% of all cases). It starts as insulin resistance particularly in the cells of liver, muscle, and adipose tissue that become resistant to the effects of insulin in stimulating glucose and lipid metabolism. As the disease progresses the pancreas gradually loses its ability to produce insulin and if not properly controlled with medication it may lead to pancreatic β-cell failure requiring complete dependence on insulin. While there are five different categories of Type II diabetes medications, they may be ineffective and/or cause undesirable adverse effects such as hypoglycemia, gastrointestinal disturbances, lactic acidosis, weight gain, edema, and anemia.

There continues to be a need to introduce new effective treatments that may be used less frequently, preferably causing fewer side effects and can act either by increasing the endogenous insulin secretion or independently from the actions of insulin.

Prostanoid receptors consist of EP, FP, IP, TP and DP receptors. The EP receptor family is divided into four distinct subtypes EP1, EP2, EP3 and EP4. The EP3 receptor is a 7-transmembrane G-protein coupled receptor found in various human tissues including the kidney, uterus, bladder, stomach and brain. Prostaglandin E2 (PGE2), a primary product of arachidonic acid metabolism by the cyclooxygenase pathway, is the natural ligand of EP3 as well as other EP receptor subtypes. Clinical studies have provided strong evidence of the role of increased levels of PGE2 as a contributor to defective insulin secretion in diabetic patients. Recently, the functional link between PGE2 suppression of glucose-stimulated insulin secretion (GSIS) and the EP3 receptor was confirmed using β-cell lines and isolated islets. It is hypothesized that increased PGE2 signaling through the EP3 receptor might be coincident with the development of diabetes and contribute to β-cell dysfunction. Therefore, EP3 receptor antagonists, may be an effective treatment for Type I and Type II Diabetes Mellitus, by relieving the inhibitory action of PGE2 to partially restore defective GSIS in diabetic patients. EP3 receptor antagonists may also be useful for the treatment of bladder over-activity, cerebrovascular disease, coronary artery disease, hypertension, neurodegenerative disorders, pain, premature labor, restenosis, thrombosis and colon cancer (KAWAMORI, T., et al., "Prostanoid receptors and colon carcinogenesis", Carcinogenesis and Modification of Carcinogenesis (2005), pp 243-251.).

JIN, J., et al., in *ACS Med. Chem. Lett.*, 2010, pp 316-320, Vol. 1 describe novel 3-oxazolidinedione-6-aryl pyridinones as potent, selective and orally active EP3 receptor antagonists. MORALES-RAMOS, A. I., et al., in *Biororg & Med Chem Lett.*, 2011, pp 2806-2811, Vol. 21 describe structure-activity relationship studies of novel 3-oxazolidinedione-6-naphthyl-2-pyridinones as potent and orally available EP3 receptor antagonists.

BAHNCK, K., et al., in US Patent Publication 2016/0176851 A1 (Published Jun. 23, 2016) and BAHNCK, K., et al., in US Patent Publication 2015/0099782 A1 (Published Apr. 9, 2015) describe antagonists of prostaglandin EP3 receptor.

SUMMARY OF THE INVENTION

The present invention is directed to compounds of formula (I)

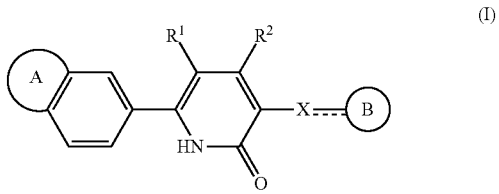

wherein

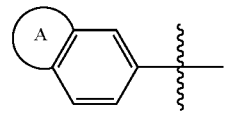

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl;

wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is optionally substituted on the phenyl portion of the

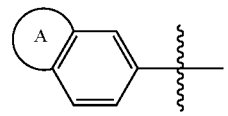

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is further optionally substituted on the

portion of the

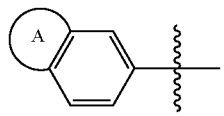

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

$R^1$ is selected from the group consisting of hydrogen, halogen and $C_{1-4}$alkyl;

$R^2$ is selected from the group consisting of hydrogen, halogen and $C_{1-4}$alkyl;

—X⇌ is selected from the group consisting of —$CR^AR^B$—, —$CR^AR^B$—$CH_2$—, $CH_2$—$CHR^C$—, —$CR^AR^B$—$CR^C$=, —$C(R^A)$=, —$CR^AR^B$—$N(R^D)$—, —$CR^AR^B$—$CH_2$—$N(R^D)$—, —$CR^AR^B$—$C(O)$—$N(R^D)$—, —$CR^AR^B$—$CH_2$—$C(O)$—$N(R^D)$—, —$CR^AR^B$—$C(O)$—$N(R^D)$—$SO_2$—, —$CR^AR^B$—$CH_2$—$C(O)$—$N(R^D)$—$SO_2$—, —$CR^AR^B$—$N(R^D)$—$SO_2$—, —$CR^AR^B$—$CH_2$—$N(R^D)$—$SO_2$, and —$CR^AR^B$—$CH_2$—$SO_2$—; wherein the X group is incorporated in the orientation as listed;

wherein $R^A$ and $R^B$ are each independently selected from the group consisting of hydrogen, fluoro, $C_{1-6}$alkyl, fluorinated $C_{1-2}$alkyl, $C_{3-6}$cycloalkyl, phenyl, benzyl, phenylethyl- and —$C(O)$—$OC_{1-2}$alkyl; provided that when one of $R^A$ or $R^B$ is $C_{3-6}$cycloalkyl, phenyl, benzyl, phenyl-ethyl- or —$C(O)O$—$C_{1-2}$alkyl, then the other of $R^A$ or $R^B$ is hydrogen;

alternatively, when X is selected from the group consisting of —$CR^AR^B$—, —$CR^AR^B$—$CH_2$— and —$CR^AR^B$—$CR^C$=, $R^A$ and $R^B$ may be taken together with the carbon atom to which they are bound to form $C_{3-6}$cycloalkyl;

$R^C$ is selected from the group consisting of hydrogen and $C_{1-3}$alkyl;

$R^D$ is selected from the group consisting of hydrogen and $C_{1-3}$alkyl;

is selected from the group consisting of $C_{5-6}$cycloalkyl, $C_{5-6}$cycloalkenyl, phenyl, four to six membered monocyclic heterocyclyl and nine to ten membered bicyclic heterocyclyl;

wherein the phenyl, four to six membered monocyclic heterocyclyl or nine to ten membered bicyclic heterocyclyl is optionally substituted with one or more substituents independently selected from the group consisting of halogen, oxo, $C_{1-4}$alkyl, fluorinated $C_{1-2}$alkyl, —$NR^DR^E$, cyano, imino, cyanoimino, —S—($C_{1-4}$alkyl), —SO—($C_{1-4}$alkyl), —$SO_2$—($C_{1-4}$alkyl), —$C(O)OH$, —$C(O)O$—($C_{1-3}$alkyl) and —$C(O)$—$NR^DR^E$;

wherein $R^D$ and $R^E$ are each independently selected from the group consisting of hydrogen and $C_{1-4}$alkyl;

and tautomers and pharmaceutically acceptable salts thereof.

The present invention is further directed to compounds of formula (II)

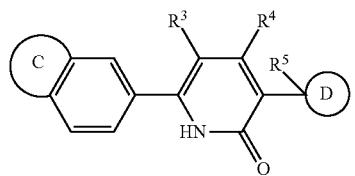

(II)

wherein

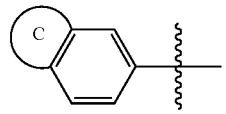

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl;

wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is optionally substituted on the phenyl portion of the

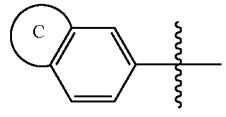

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is further optionally substituted on the

portion of the

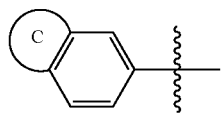

bicycle with one to two substituents independently selected from the group consisting of halogen, oxo, cyano, $C_{1-2}$alkyl, fluorinated $C_{1-2}$alkyl, $C_{1-3}$alkoxy, fluorinated $C_{1-2}$alkoxy and $C_{3-6}$cycloalkyl;

$R^3$ is selected from the group consisting of hydrogen, halogen and $C_{1-4}$alkyl;

$R^4$ is selected from the group consisting of hydrogen, halogen and $C_{1-4}$alkyl;

$R^5$ is selected from the group consisting of hydrogen, fluoro, hydroxy, $C_{1-4}$alkyl, $C_{3-6}$cycloalkyl and —C(O)NR$^U$R$^V$; wherein R$^U$ and R$^V$ are each independently selected from the group consisting of hydrogen and $C_{1-2}$alkyl;

is a ring structure selected from the group consisting of cyclopentyl, cyclohexyl, azetidin-3-yl, pyrrolidin-3-yl, piperidin-3-yl, piperidin-4-yl, morpholin-2-yl, thiomorpholin-4-yl, tetrahydropyran-4-yl, 4,5,6,7-tetrahydro-2H-indazol-5-yl, 1,5-dihydro-imidazol-5-yl, 3,5-dihydro-imidazol-5-yl, 4,5-dihydro-imidazol-4-yl, 4,5-dihydro-imidazol-5-yl, imidazolidin-4-yl, imidazolidin-5-yl, 4,5-dihydro-pyrrol-3-yl, 4,5-dihydro-pyrazol-5-yl, 1,2,5-thiadiazolidin-3-yl, 4,5,6,7-tetrahydro-benzo[d]isoxazol-5-yl, imidazo[1,2-a]imdazol-3-yl, imidazo[2,1-c][1,2,4]triazol-5-yl, 6,7-dihydro-5H-imidazo[2,1-c][1,2,4]triazol-6-yl, tetrahydro-1H,3H-pyrrolo[1,2-c]oxazol-6-yl, 6-oxabicyclo[3.2.1]octan-5-yl, 8-azabicyclo[3.2.1]octan-3-yl, 6-azabicyclo[3.2.1]octan-4-yl, 1-oxa-3-azaspiro[4.5]decan-7-yl, 2-azaspiro[4.5]decan-8-yl, 1λ²,3-diazaspiro[4.5]decan-7-yl, 2-azaspiro[5.5]undecan-9-yl, 3-azaspiro[5.5]undecan-9-yl, 1,3-diazaspiro[4.5]decan-8-yl and octahydro-cyclopenta[c]pyrrol-5-yl;

wherein the

ring structure is optionally substituted with one or more substituents independently selected from the group consisting of $C_{1-4}$alkyl, hydroxy, oxo, thioxo, cyano, —NR$^F$R$^G$, —NH(CN), =NH, =N(CN), =N(OH), =N(O—$C_{1-2}$alkyl), —CH$_2$—NR$^F$R$^G$—C(O)—NR$^F$R$^G$, —OC(O)—NR$^F$R$^G$, —C(O)—CH$_2$OH, —SO$_2$—($C_{1-4}$alkyl), —NR$^F$—SO$_2$—($C_{1-4}$alkyl) and —C(NR$^F$R$^G$)(=N—CN);

wherein R$^F$ and R$^G$ are each independently selected from the group consisting of hydrogen and $C_{1-4}$alkyl;

provided that when $R^3$ is hydrogen, $R^4$ is hydrogen, $R^5$ is selected from the group consisting of hydrogen, $C_{1-4}$alkyl and $C_{3-6}$cycloalkyl, and

is selected from the group consisting of pyrrolidin-3-yl-2-one and piperidin-3-yl-2-one, then

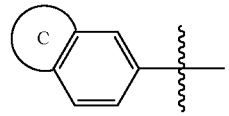

is other than indol-5-yl, indazol-5-yl, indazol-6-yl, benzimidazol-5-yl or benzimidazol-6-yl; wherein the indol-5-yl, indazol-5-yl, indazol-6-yl, benzimidazol-5-yl or benzimidazol-6-yl is optionally substituted with one or more substituents independently selected from the group consisting of halogen, $C_{1-3}$alkyl and $C_{3-6}$cycloalkyl;

provided further that when

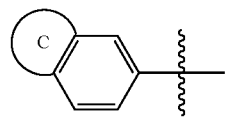

is selected from the group consisting of indol-5-yl, indazol-6-yl and benzimidazol-6-yl; wherein the indol-5-yl, indazol-6-yl or benzimidazol-6-yl is optionally substituted with one to two substituents independently selected from the group consisting of halogen and $C_{1-3}$alkyl, $R^3$ is hydrogen, $R^4$ is hydrogen and $R^5$ is methyl, then

is other than pyrrolidin-3-yl-2-one or piperidin-3-yl-2-one;

provided further than when

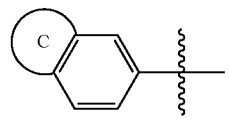

is selected from the group consisting of naphth-2-yl and 8-fluoro-naphth-2-yl, $R^3$ is selected from the group consisting of hydrogen, halogen and $C_{1-3}$alkyl, $R^4$ is hydrogen and $R^5$ is selected from the group consisting of hydrogen, $C_{1-4}$alkyl and $C_{3-6}$cycloalkyl, then

is other than imidazolidin-4-yl-2-one;

and tautomers and pharmaceutically acceptable salts thereof.

The present invention is directed to compounds of formula (III)

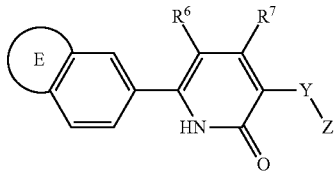

wherein

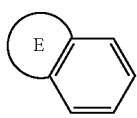

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl;

wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is optionally substituted on the phenyl portion of the

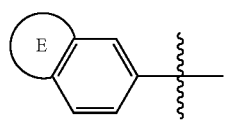

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is further optionally substituted on the

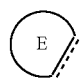

portion of the

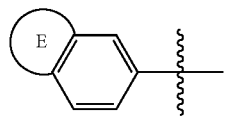

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

$R^6$ is selected from the group consisting of hydrogen, halogen and $C_{1-4}$alkyl;

$R^7$ is selected from the group consisting of hydrogen, halogen and $C_{1-4}$alkyl;

Y is selected from the group consisting of —$CR^H R^J$— and —$CR^H R^J$—$CHR^K$—;

wherein $R^H$ and $R^J$ are each independently selected from the group consisting of hydrogen, halogen, hydroxy, $C_{1-4}$alkyl, fluorinated $C_{1-2}$alkyl, $C_{3-6}$cycloalkyl, $C_{5-6}$cycloalkenyl, phenyl, benzyl and phenyl-ethyl-; provided that when one of $R^H$ or $R^J$ is $C_{3-6}$cycloalkyl, $C_{5-6}$cycloalkenyl, phenyl, benzyl or phenylethyl-, then the other of $R^H$ or $R^J$ is hydrogen; and wherein $R^K$ is selected from the group consisting of hydrogen and $C_{1-4}$alkyl;

alternatively, when Y is —$CR^H R^J$—, then $R^H$ and $R^J$ may be taken together with the carbon atom to which they are bound to form $C_{3-6}$cycloalkyl;

Z is selected from the group consisting of —C(O)—$NR^L R^M$, —C(O)—NH—$OR^N$, —C(O)—NH—$SO_2$—$R^N$; —C(O)—NH(CH($CH_2$OH)$_2$), —C(O)—NH(C($CH_2$OH)$_3$), —C(O)—NH—($CH_2CH_2$O)$_a$—$R^N$, —C(O)—NH—CH($CH_2$O—($CH_2CH_2$O)$_b$—$R^N$)$_2$, —C(O)—NH—C($CH_2$O—($CH_2CH_2$O)$_b$—$R^N$)$_3$), —C(O)—NH—$CH_2CH_2$—$NR^P R^Q$, —C(O)—NH—($CH_2CH_2$O)$_a$—$CH_2CH_2$—$NR^P R^Q$, —$NR^S$—C(O)—$NR^P R^Q$, —$NR^S$—C(O)—NH—$CH_2CH_2$—$NR^P R^Q$ and —$NR^S$—C($NH_2$)=N—CN;

wherein a is an integer from 1 to 6;

wherein b is an integer from 0 to 3;

wherein $R^L$ and $R^M$ are each independently selected from the group consisting of hydrogen and $C_{1-4}$alkyl;

wherein $R^N$ is selected from the group consisting of hydrogen and $C_{1-2}$alkyl;

wherein $R^P$ and $R^Q$ are each independently selected from the group consisting of hydrogen and $C_{1-2}$alkyl;

and wherein $R^S$ is selected from the group consisting of hydrogen and $C_{1-2}$alkyl;

and tautomers and pharmaceutically acceptable salts thereof.

The present invention is further directed to processes for the preparation of the compounds of formula (I), compounds of formula (II) and compounds of formula (III). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the EP3 receptor (selected from the group consisting Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders (such as Alzheimer's disease, intracerebral hemorrhage, and the like), non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain (for example, arthritic pain, neuropathic pain, and the like) and cancer (for example, prostate cancer, pancreatic cancer, colon cancer, liver cancer, thyroid cancer, breast cancer, and the like)) comprising administering to a subject in need thereof a therapeutically effective amount of any of the compounds or pharmaceutical compositions described above.

In an embodiment, the present invention is directed to a compound of formula (I) or compound of formula (II) or compound of formula (III) for use as a medicament. In another embodiment, the present invention is directed to a compound of formula (I) or compound of formula (II) or compound of formula (III) for use in the treatment of a disorder mediated by the EP3 receptor (selected from the group consisting of Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders (such as Alzheimer's disease, intracerebral hemorrhage, and the like), non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain (for example, arthritic pain, neuropathic pain, and the like) and cancer (for example, prostate cancer, pancreatic cancer, colon cancer, liver cancer, thyroid cancer, breast cancer, and the like)).

In another embodiment, the present invention is directed to a composition comprising a compound of formula (I) or compound of formula (II) or compound of formula (III) for the treatment of a disorder mediated by the EP3 receptor (selected from the group consisting of Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders (such as Alzheimer's disease, intracerebral hemorrhage, and the like), non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain (for example, arthritic pain, neuropathic pain, and the like) and cancer (for example, prostate cancer, pancreatic cancer, colon cancer, liver cancer, thyroid cancer, breast cancer, and the like)).

Another example of the invention is the use of any of the compounds described herein in the preparation of a medicament for treating: (a) Type I diabetes mellitus, (b) impaired glucose tolerance (IGT), (c) impaired fasting glucose (IFG), (d) gestational diabetes, (e) Type II diabetes mellitus, (f) Syndrome X (also known as Metabolic Syndrome), (g) obesity, (h) nephropathy, (i) neuropathy, (j) retinopathy, (k) restenosis, (l) thrombosis, (m) coronary artery disease, (n) hypertension, (o) angina, (p) atherosclerosis, (q) heart disease, (r) heart attack, (s) ischemia, (t) stroke, (u) nerve damage or poor blood flow in the feet, (v) neurodegenerative disorders (such as Alzheimer's disease, intracerebral hemorrhage, and the like), (w) non-alcoholic steatohepatitis (NASH), (x) non-alcoholic fatty liver disease (NAFLD), (y) liver fibrosis, (z) cataracts, (aa) polycystic ovarian syndrome, (ab) premature labor, (ac) irritable bowel syndrome, (ad) bladder over-activity, (ae) inflammation, (af) pain (for example, arthritic pain, neuropathic pain, and the like) and (ag) cancer (for example, prostate cancer, pancreatic cancer, colon cancer, liver cancer, thyroid cancer, breast cancer, and the like), in a subject in need thereof.

In another example, the present invention is directed to a compound as described herein for use in a methods for treating a disorder selected from the group consisting of Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders (such as Alzheimer's disease, intracerebral hemorrhage, and the like), non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain (for example, arthritic pain, neuropathic pain, and the like) and cancer (for example, prostate cancer, pancreatic cancer, colon cancer, liver cancer, thyroid cancer, breast cancer, and the like), in a subject in need thereof.

DETAILED DESCRIPTION OF THE INVENTION

The present invention is directed to compounds of formula (I)

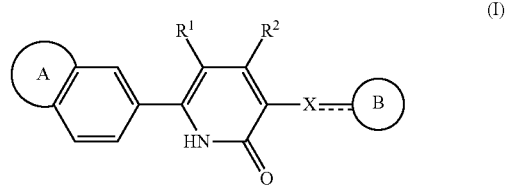

wherein

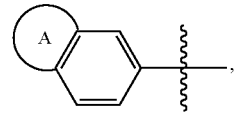

$R^1$, $R^2$, X and

are as herein defined.

The present invention is further directed to compounds of formula (II)

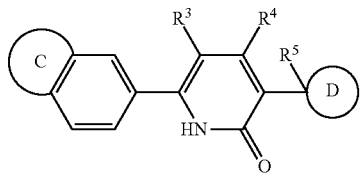

wherein

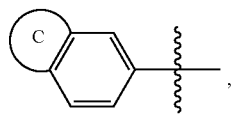

$R^3$, $R^4$, $R^5$ and

are as herein defined.

The present invention is further directed to compounds of formula (III)

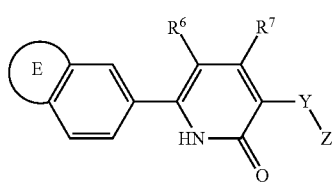

wherein

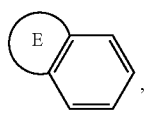

$R^6$, $R^7$, Y and Z are as herein defined.

The compounds of formula (I), compounds of formula (II) and compounds of formula (III) of the present invention are antagonists of the EP3 receptor, useful in the treatment of disorders and conditions that respond to antagonism of the EP3 receptor, including, but not limited to: Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders (such as Alzheimer's disease, intracerebral hemorrhage, and the like), non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain (for example, arthritic pain, neuropathic pain, and the like) and cancer (for example, prostate cancer, pancreatic cancer, colon cancer, liver cancer, thyroid cancer, breast cancer, and the like).

In an embodiment, the present invention is directed to compounds of formula (I) wherein

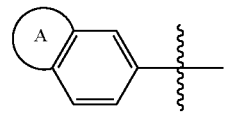

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl, and 2,3-dihydro-benzo[b][1,4]dioxin-6-yl; wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is optionally substituted on the phenyl portion of the

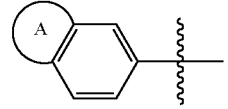

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl; and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is further optionally substituted on the

portion of the

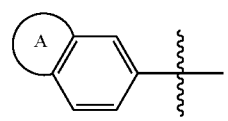

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl.

In another embodiment, the present invention is directed to compounds of formula (I) wherein

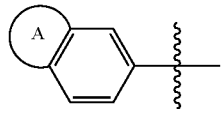

is selected from the group consisting of naphth-2-yl, indol-5-yl, indazol-5-yl, indazol-6-yl, benzimidazol-5-yl, benzimidazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl and 2,3-dihydro-benzo[b][1,4]dioxin-6-yl; wherein the naphth-2-yl, indol-5-yl, indazol-5-yl, indazol-6-yl, benzimidazol-5-yl, benzimidazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl or 2,3-dihydro-benzo[b][1,4]dioxin-6-yl; is optionally substituted on the phenyl portion of the

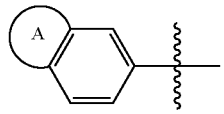

bicycle with one to two substituents independently selected from the group consisting of halogen, oxo, cyano, $C_{1-3}$alkyl, fluorinated $C_{1-2}$alkyl and $C_{3-6}$cycloalkyl; and wherein the naphth-2-yl, indol-5-yl, indazol-5-yl, indazol-6-yl, benzimidazol-5-yl, benzimidazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, or 2,3-dihydro-benzo[b][1,4]dioxin-6-yl is further optionally substituted on the

portion of the

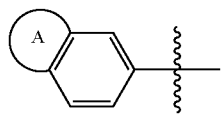

bicycle with one to two substituents independently selected from the group consisting of halogen, oxo, cyano, $C_{1-3}$alkyl, fluorinated $C_{1-2}$alkyl and $C_{3-6}$cycloalkyl.

In another embodiment, the present invention is directed to compounds of formula (I) wherein

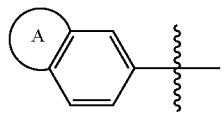

is selected from the group consisting of naphth-2-yl, 8-fluoro-naphth-2-yl, 5,7-difluoro-naphth-2-yl, 6,8-difluoro-naphth-2-yl, 8-ethyl-naphth-2-yl, 8-isopropyl-naphth-2-yl, 8-trifluoromethyl-naphth-2-yl, 8-cyano-naphth-2-yl, 2,2-dimethyl-chroman-7-yl, 2,2-dimethyl-chromen-7-yl, 1-methyl-indol-5-yl, 2-ethyl-indazol-6-yl, 1-ethyl-4-chloro-indazol-6-yl, 1-ethyl-4-fluoro-indazol-6-yl, 2-ethyl-4-fluoro-indazol-5-yl, 2-ethyl-4-methyl-indazol-6-yl, 1-ethyl-3-methyl-indazol-6-yl, 1-ethyl-4-methyl-indazol-6-yl, 1-ethyl-5-methyl-indazol-6-yl, 1-ethyl-5-fluoro-indazol-6-yl, 2-ethyl-4-methyl-indazol-6-yl, 1-isopropyl-4-fluoro-indazol-6-yl, 1-cyclopentyl-4-fluoro-indazol-6-yl, 1-methyl-7-chloro-benzimidazol-5-yl, 1-ethyl-7-fluoro-benzimidazol-6-yl, benzoisothiazol-6-yl, 4-methyl-3,4-dihydro-benzo[b][1,4]oxazin-6-yl, 4-ethyl-3,4-dihydro-benzo[b][1,4]oxazin-6-yl, 4-ethyl-8-fluoro-3,4-dihydro-benzo[b][1,4]oxazin-6-yl, 4-ethyl-3,4-dihydro-benzo[b][1,4]oxazin-6-yl-3-one, 2,3-dihydro-benzo[b][1,4]dioxin-6-yl and 2,2-difluoro-benzo[d][1,3]dioxol-5-yl.

In another embodiment, the present invention is directed to compounds of formula (I) wherein

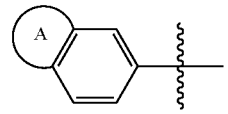

is selected from the group consisting of naphth-2-yl, 8-fluoro-naphth-2-yl, 5,7-difluoro-naphth-2-yl, 6,8-difluoro-naphth-2-yl, 8-ethyl-naphth-2-yl, 8-isopropyl-naphth-2-yl, 8-trifluoromethyl-naphth-2-yl, 8-cyano-naphth-2-yl, 1-methyl-indol-5-yl, 1-ethyl-4-chloro-indazol-6-yl, 1-ethyl-4-fluoro-indazol-6-yl, 1-ethyl-5-fluoro-indazol-6-yl, 1-ethyl-4-methyl-indazol-6-yl, 2-ethyl-4-methyl-indazol-6-yl, 1-isopropyl-4-fluoro-indazol-6-yl, 1-cyclopentyl-4-fluoro-indazol-6-yl, 1-methyl-7-chloro-benzimidazol-5-yl, 4-methyl-3,4-dihydro-benzo[b][1,4]oxazin-6-yl, 4-ethyl-3,4-dihydro-benzo[b][1,4]oxazin-6-yl, 4-ethyl-8-fluoro-3,4-dihydro-benzo[b][1,4]oxazin-6-yl, 4-ethyl-3,4-dihydro-benzo[b][1,4]oxazin-6-yl-3-one and 2,3-dihydro-benzo[b][1,4]dioxin-6-yl.

In another embodiment, the present invention is directed to compounds of formula (III) wherein

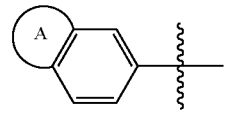

is selected from the group consisting of naphth-2-yl, 8-fluoro-naphth-2-yl, 5,7-difluoro-naphth-2-yl, 8-ethyl-naphth-2-yl, 1-methyl-indol-5-yl, 1-ethyl-4-chloro-indazol-6-yl, 1-ethyl-4-fluoro-indazol-6-yl, 1-isopropyl-4-fluoro-indazol-6-yl, 4-ethyl-8-fluoro-3,4-dihydro-benzo[b][1,4]oxazin-6-yl and 2,3-dihydro-benzo[b][1,4]dioxin-6-yl.

In another embodiment, the present invention is directed to compounds of formula (I) wherein

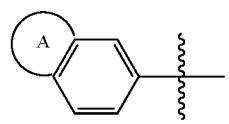

is selected from the group consisting of 8-fluoro-naphth-2-yl, 8-ethyl-naphth-2-yl, 1-ethyl-4-chloro-indazol-6-yl, 1-ethyl-4-fluoro-indazol-6-yl and 4-ethyl-8-fluoro-3,4-dihydro-benzo[b][1,4]oxazin-6-yl.

In another embodiment, the present invention is directed to compounds of formula (I) wherein

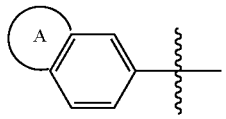

is selected from the group consisting of 8-fluoro-naphth-2-yl, 1-ethyl-4-chloro-indazol-6-yl, 1-ethyl-4-fluoro-indazol-6-yl and 4-ethyl-8-fluoro-3,4-dihydro-benzo[b][1,4]oxazin-6-yl.

In another embodiment, the present invention is directed to compounds of formula (I) wherein

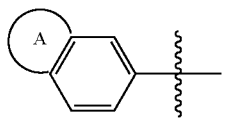

is selected from the group consisting of 8-fluoro-naphth-2-yl and 1-ethyl-4-fluoro-indazol-6-yl.

In an embodiment, the present invention is directed to compounds of formula (I) wherein $R^1$ is selected from the group consisting of hydrogen, halogen and $C_{1-2}$alkyl. In another embodiment, the present invention is directed to compounds of formula (I) wherein $R^1$ is selected from the group consisting of hydrogen, fluoro, chloro, bromo and methyl. In another embodiment, the present invention is directed to compounds of formula (I) wherein $R^1$ is selected from the group consisting of hydrogen, fluoro and methyl. In another embodiment, the present invention is directed to compounds of formula (I) wherein $R^1$ is hydrogen.

In an embodiment, the present invention is directed to compounds of formula (I) wherein $R^2$ is selected from the group consisting of hydrogen, halogen and $C_{1-2}$alkyl. In another embodiment, the present invention is directed to compounds of formula (I) wherein $R^2$ is selected from the group consisting of hydrogen, chloro, bromo and methyl. In another embodiment, the present invention is directed to compounds of formula (I) wherein $R^2$ is selected from the group consisting of hydrogen, fluoro and methyl. In another embodiment, the present invention is directed to compounds of formula (I) wherein $R^2$ is hydrogen.

In an embodiment, the present invention is directed to compounds of formula (I) wherein —X═ is selected from the group consisting of —$CR^AR^B$—, —$CR^AR^B$—$CH_2$—, —$CH_2$—$CHR^C$—, —$CR^AR^B$—$CR^C$═, —$C(R^A)$═, —$CR^AR^B$—$N(R^D)$—, —$CR^AR^B$—$CH_2$—$N(R^D)$—, —$CR^AR^B$—$C(O)$—$N(R^D)$—, —$CR^AR^B$—$CH_2$—$C(O)$—$N(R^D)$—, —$CR^AR^B$—$C(O)$—$N(R^D)$—$SO_2$—, —$CR^AR^B$—$CH_2$—$C(O)$—$N(R^D)$—$SO_2$—, —$CR^AR^B$—$N(R^D)$—$SO_2$—, —$CR^AR^B$—$CH_2$—$N(R^D)$—$SO_2$; and —$CR^AR^B$—$CH_2$—$SO_2$—; wherein the X group is incorporated in the orientation as listed; wherein $R^A$ and $R^B$ are each independently selected from the group consisting of hydrogen, fluoro, $C_{1-6}$alkyl, $C_{3-6}$cycloalkyl, phenyl, benzyl and —C(O)—$OC_{1-2}$alkyl; provided that when one of $R^A$ or $R^B$ is $C_{3-6}$cycloalkyl, phenyl, benzyl, or —C(O)O—$C_{1-2}$alkyl, then the other of $R^A$ or $R^B$ is hydrogen; alternatively, when X is selected from the group consisting of —$CR^AR^B$—

$CH_2$— and —$CR^AR^B$—$CR^C$═, $R^A$ and $R^B$ may be taken together with the carbon atom to which they are bound to form $C_{3-6}$cycloalkyl; wherein $R^C$ is selected from the group consisting of hydrogen and $C_{1-3}$alkyl; and wherein $R^D$ is selected from the group consisting of hydrogen and $C_{1-3}$alkyl.

In another embodiment, the present invention is directed to compounds of formula (I) wherein —X═ is selected from the group consisting of —$CR^AR^B$—, —$CR^AR^B$—$CH_2$—, —$CH_2$—$CHR^C$—, —$CR^AR^B$—$CR^C$═, —$C(R^A)$═, —$CR^AR^B$—$N(R^D)$—, —$CR^AR^B$—$C(O)$—$N(R^D)$—, —$CR^AR^B$—$CH_2$—$C(O)$—$N(R^D)$—, —$CR^AR^B$—$C(O)$—$N(R^D)$—$SO_2$—, —$CR^AR^B$—$CH_2$—$C(O)$—$N(R^D)$—$SO_2$—, —$CR^AR^B$—$N(R^D)$—$SO_2$— and —$CR^AR^B$—$CH_2$—$SO_2$—; wherein the X group is incorporated in the orientation as listed; wherein $R^A$ and $R^B$ are each independently selected from the group consisting of hydrogen, fluoro, $C_{1-6}$alkyl, $C_{3-6}$cycloalkyl, phenyl, benzyl and —C(O)O—($C_{1-2}$alkyl); provided that when one of $R^A$ or $R^B$ is $C_{3-6}$cycloalkyl, phenyl, benzyl or —C(O)O—$C_{1-2}$alkyl, then the other of $R^A$ or $R^B$ is hydrogen; alternatively, when X is selected from the group consisting of —$CR^AR^B$—$CH_2$— and —$CR^AR^B$—$CR^C$═, $R^A$ and $R^B$ may be taken together with the carbon atom to which they are bound to form $C_{3-5}$cycloalkyl; wherein $R^C$ is selected from the group consisting of hydrogen and $C_{1-4}$alkyl; and wherein $R^D$ is hydrogen.

In an embodiment, the present invention is directed to compounds of formula (I) wherein $R^A$ and $R^B$ are each independently selected from the group consisting of hydrogen, fluoro, $C_{1-6}$alkyl, $C_{3-6}$cycloalkyl, phenyl, benzyl and —C(O)—$OC_{1-2}$alkyl; provided that when one of $R^A$ or $R^B$ is $C_{3-6}$cycloalkyl, phenyl, benzyl, or —C(O)O—$C_{1-2}$alkyl, then the other of $R^A$ or $R^B$ is hydrogen.

In another embodiment, the present invention is directed to compounds of formula (I) wherein X is selected from the group consisting of —$CR^AR^B$—$CH_2$— and —$CR^AR^B$—$CR^C$═, and $R^A$ and $R^B$ are taken together with the carbon atom to which they are bound to form $C_{3-6}$cycloalkyl. In another embodiment, the present invention is directed to compounds of formula (I) wherein X is selected from the group consisting of —$CR^AR^B$—$CH_2$— and —$CR^AR^B$—$CR^C$═, and $R^A$ and $R^B$ are taken together with the carbon atom to which they are bound to form $C_{3-5}$cycloalkyl.

In an embodiment, the present invention is directed to compounds of formula (I) wherein X is —$CR^AR^B$, and $R^A$ and $R^B$ are taken together with the carbon atom to which they are bound to form $C_{3-6}$cycloalkyl. In another embodiment, the present invention is directed to compounds of formula (I) wherein X is —$CR^AR^B$—$CH_2$—, and $R^A$ and $R^B$ are taken together with the carbon atom to which they are bound to form $C_{3-6}$cycloalkyl. In another embodiment, the present invention is directed to compounds of formula (I) wherein X is —$CR^AR^B$—$CR^C$═, and $R^A$ and $R^B$ are taken together with the carbon atom to which they are bound to form $C_{3-6}$cycloalkyl.

In another embodiment, the present invention is directed to compounds of formula (I) wherein —X═ is selected from the group consisting of —$CH_2$—, —$C(ethyl)_2$-, —CH(isopropyl)-, -(syn)-CH(isopropyl)-, -(anti)-CH(isopropyl)-, -(syn)-CH(S-isopropyl)-$CH_2$—, -(anti)-CH(S-isopropyl)-$CH_2$—, —CH(C(O)O-ethyl)-, —$C(methyl)_2$-$CH_2$—, —$C(ethyl)_2$-$CH_2$—, —CH(isopropyl)-$CH_2$—, —$CH_2$—CH(isopropyl)-, -(syn)-CH(isopropyl)-$CH_2$—, -(anti)-CH(isopropyl)-$CH_2$—, —$C(methyl)_2$-CH═, —$C(methyl)_2$-(Z)—CH═, —$C(methyl)_2$-(E)-CH═, —$C(ethyl)_2$-CH═, —$C(ethyl)_2$-(E)-CH═, —$C(ethyl)_2$-(Z)—CH═, —CH(isopropyl)-CH═, —CH(isopropyl)-(E)-CH═, —CH(isopropyl)-(Z)—CH=, —CH(R*-isopropyl)-(Z)—CH=, —CH(S*-isopropyl)-(Z)—CH=, —CH(isopropyl)-C(methyl)=, —CH(isopropyl)-(E)-C(methyl)=, —CH(isopropyl)-(Z)—C(methyl)=, —CH(t-butyl)-CH=, —CH(t-butyl)-(E)-CH=, —CH(n-pent-3-yl)-CH=, —CH(n-pent-3-yl)-(Z)—CH=, —CH(n-pent-3-yl)-(E)-CH=, —CH(cyclopropyl)-CH=, —CH(cyclopropyl)-(Z)—CH=, —CH(cyclopropyl)-(E)-CH=, —CH(cyclopentyl)-CH=, —CH(cyclopentyl)-(Z)—CH=, —CH(cyclopentyl)-(E)-CH=, —CH(cyclohexyl)-CH=, —CH(cyclohexyl)-(Z)—CH=, —CH(cyclohexyl)-(E)-CH=, —CH(phenyl)-CH=, —CH(phenyl)-(E)-CH=, —CH(phenyl)-(Z)—CH=, —CH(benzyl)-CH=, —CH(benzyl)-(E)-CH=, —CH(benzyl)-(Z)—CH=, —CH$_2$—C(isopropyl)=, —CH$_2$-(E)-C(isopropyl)=, —CH$_2$—(Z)—C(isopropyl)=, —CH(C(O)O-ethyl)=, —C(isopropyl)=, —(Z)—C(isopropyl)=, -(E)-C(isopropyl)=, -cyclopropyl-1,1-yl-CH=, -cyclopropyl-1,1-yl-(E)-CH=, -cyclopropyl-1,1-yl-(Z)—CH=, -cyclopent-1,1-yl-CH$_2$—, -cyclopent-1,1-yl-CH=, -cyclopent-1,1-yl-(E)-CH=, -cyclopent-1,1-yl-(Z)—CH=, —CH(isopropyl)-CH$_2$—SO$_2$—, —CH(isopropyl)-NH—, —CH(isopropyl)-C(O)—NH—, —CH(isopropyl)-CH$_2$—C(O)—NH—, —CH(isopropyl)-C(O)—NH—SO$_2$—, —CF(isopropyl)-C(O)—NH—SO$_2$—, —CH(isopropyl)-CH$_2$—C(O)—NH—SO$_2$, and —CH(isopropyl)-NH—SO$_2$—; wherein the X group is incorporated in the orientation as listed.

In another embodiment, the present invention is directed to compounds of formula (I) wherein —X= is selected from the group consisting of —CH$_2$—, —C(ethyl)$_2$-, —CH(isopropyl)-, -(syn)-CH(isopropyl)-, -(anti)-CH(isopropyl)-, -(syn)-CH(S-isopropyl)-CH$_2$—, -(anti)-CH(S-isopropyl)-CH$_2$—, —CH(C(O)O-ethyl)-, —C(methyl)$_2$—CH$_2$—, —C(ethyl)$_2$-CH$_2$—, —CH(isopropyl)-CH$_2$—, —CH$_2$—CH(isopropyl)-, -(syn)-CH(isopropyl)-CH$_2$—, -(anti)-CH(isopropyl)-CH$_2$—, —C(methyl)$_2$-CH=, —C(methyl)$_2$-(Z)—CH=, —C(methyl)$_2$-(E)-CH=, —C(ethyl)$_2$-CH=, —C(ethyl)$_2$-(E)-CH=, —C(ethyl)$_2$-(Z)—CH=, —CH(isopropyl)-CH=, —CH(isopropyl)-(E)-CH=, —CH(isopropyl)-(Z)—CH=, —CH(R*-isopropyl)-(Z)—CH=, —CH(S*-isopropyl)-(Z)—CH=, —CH(isopropyl)-(E)-C(methyl)=, —CH(isopropyl)-(Z)—C(methyl)=, —CH(t-butyl)-(E)-CH=, —CH(n-pent-3-yl)-(E)-CH=, —CH(cyclopropyl)-(Z)—CH=, —CH(cyclopentyl)-(Z)—CH=, —CH(cyclopentyl)-(E)-CH=, —CH(cyclohexyl)-(Z)—CH=—CH(cyclohexyl)-(E)-CH=, —CH(phenyl)-(Z)—CH=, —CH(benzyl)-(E)-CH=, —CH$_2$-(E)-C(isopropyl)=, —CH(C(O)O-ethyl)=, —(Z)—C(isopropyl)=, -(E)-C(isopropyl)=, -cyclopropyl-1,1-yl-(E)-CH=, -cyclopent-1,1,-yl-CH$_2$—, -cyclopent-1,1,-yl-(E)-CH=, —CH(isopropyl)-CH$_2$—SO$_2$—, —CH(isopropyl)-NH—, —CH(isopropyl)-C(O)—NH—, —CH(isopropyl)-CH$_2$—C(O)—NH—, —CH(isopropyl)-C(O)—NH—SO$_2$—, —CF(isopropyl)-C(O)—NH—SO$_2$—, —CH(isopropyl)-CH$_2$—C(O)—NH—SO$_2$, and —CH(isopropyl)-NH—SO$_2$—; wherein the X group is incorporated in the orientation as listed.

In another embodiment, the present invention is directed to compounds of formula (I) wherein —X= is selected from the group consisting of —C(ethyl)$_2$-, —CH(isopropyl)-, -(anti)-CH(isopropyl)-, —C(methyl)$_2$—CH$_2$—, —C(ethyl)$_2$-CH$_2$—, —CH(isopropyl)-CH$_2$—, -(syn)-CH(isopropyl)-CH$_2$—, -(anti)-CH(isopropyl)-CH$_2$—, -(syn)-CH(S-isopropyl)-CH$_2$—, -(anti)-CH(S-isopropyl)-CH$_2$—, —CH$_2$—CH(isopropyl)-, —C(methyl)$_2$-(Z)—CH=, —C(ethyl)$_2$-(E)-CH=, —C(ethyl)$_2$-(Z)—CH=, —CH(isopropyl)-(E)-CH=, —CH(isopropyl)-(Z)—CH=, —CH(R*-isopropyl)-(Z)—CH=, —CH(S*-isopropyl)-(Z)—CH=, —CH(isopropyl)-(E)-C(methyl)=, —CH(isopropyl)-(Z)—C(methyl)=, —CH(n-pent-3-yl)-(E)-CH=, —CH(cyclopropyl)-(Z)—CH=, —CH(cyclopentyl)-(E)-CH=, —CH(cyclopentyl)-(Z)—CH=, —CH(cyclohexyl)-(E)-CH=, —CH(cyclohexyl)-(Z)—CH=, —CH(phenyl)-(Z)—CH=, —CH(benzyl)-(E)-CH=, —CH(C(O)O-ethyl)=, —(Z)—C(isopropyl)=, -(E)-C(isopropyl)=, -cyclopropyl-1,1-yl-(E)-CH=, -cyclopent-1,1,-yl-CH$_2$—, -cyclopent-1,1,-yl-(E)-CH=, —CH(isopropyl)-CH$_2$—SO$_2$—, —CH(isopropyl)-NH—, —CH(isopropyl)-C(O)—NH—, —CH(isopropyl)-CH$_2$—C(O)—NH—, and —CH(isopropyl)-NH—SO$_2$—; wherein the X group is incorporated in the orientation as listed.

In another embodiment, the present invention is directed to compounds of formula (I) wherein —X= is selected from the group consisting of —C(ethyl)$_2$-, —CH(isopropyl)-, —C(ethyl)$_2$-CH$_2$—, —CH(isopropyl)-CH$_2$—, -(syn)-CH(isopropyl)-CH$_2$—, -(anti)-CH(isopropyl)-CH$_2$—, -(syn)-CH(S-isopropyl)-CH$_2$—, -(anti)-CH(S-isopropyl)-CH$_2$—, —CH$_2$—CH(isopropyl)-, —C(ethyl)$_2$-(E)-CH=, —C(ethyl)$_2$-(Z)—CH=, —CH(isopropyl)-(E)-CH=, —CH(isopropyl)-(Z)—CH=, —CH(R*-isopropyl)-(Z)—CH=, —CH(S*-isopropyl)-(Z)—CH=, —CH(isopropyl)-(E)-C(methyl)=, —CH(isopropyl)-(Z)—C(methyl)=, —CH(cyclopropyl)-(Z)—CH=, —CH(cyclopentyl)-(E)-CH=, —CH(cyclopentyl)-(Z)—CH=, —CH(cyclohexyl)-(Z)—CH=, —CH(phenyl)-(Z)—CH=, —(Z)—C(isopropyl)=, -(E)-C(isopropyl)=, —CH(isopropyl)-NH— and —CH(isopropyl)-C(O)—NH—; wherein the X group is incorporated in the orientation as listed.

In another embodiment, the present invention is directed to compounds of formula (I) wherein —X= is selected from the group consisting of —C(ethyl)$_2$-, —CH(isopropyl)-, —C(ethyl)$_2$-CH$_2$—, —CH(isopropyl)-CH$_2$—, -(syn)-CH(isopropyl)-CH$_2$—, -(anti)-CH(isopropyl)-CH$_2$—, -(syn)-CH(S-isopropyl)-CH$_2$—, -(anti)-CH(S-isopropyl)-CH$_2$—, —C(ethyl)$_2$-(E)-CH=, —C(ethyl)$_2$-(Z)—CH=, —CH(isopropyl)-(E)-CH=, —CH(isopropyl)-(Z)—CH=, —CH(S*-isopropyl)-(Z)—CH=, —CH(isopropyl)-(E)-C (methyl)=, —CH(cyclopentyl)-(Z)—CH=, —CH(cyclohexyl)-(Z)=CH=, —CH(isopropyl)-NH— and —CH(isopropyl)-C(O)—NH—; wherein the X group is incorporated in the orientation as listed.

In another embodiment, the present invention is directed to compounds of formula (I) wherein —X= is selected from the group consisting of —C(ethyl)$_2$-, —C(ethyl)$_2$-CH$_2$—, —CH(isopropyl)-CH$_2$—, -(anti)-CH(isopropyl)-CH$_2$—, —C(ethyl)$_2$-(E)-CH=, —C(ethyl)$_2$-(Z)—CH=, —CH(isopropyl)-(E)-CH=, —CH(isopropyl)-(Z)—CH=, and —CH(isopropyl)-C(O)—NH—; wherein the X group is incorporated in the orientation as listed.

In an embodiment, the present invention is directed to compounds of formula (I) wherein (B)

is selected from the group consisting of $C_{5-6}$cycloalkyl, $C_{5-6}$cycloalkenyl, phenyl, four to six membered monocyclic heterocyclyl and nine to ten membered bicyclic heterocyclyl; wherein the phenyl, four to six membered monocyclic heterocyclyl or nine to ten membered bicyclic heterocyclyl is optionally substituted with one to three substituents independently selected from the group consisting of halogen, oxo, $C_{1-4}$alkyl, fluorinated $C_{1-2}$alkyl, —NR$^D$R$^E$, cyano, imino, cyanoimino, —SO$_2$—($C_{1-2}$alkyl), —C(O)OH, —C(O)O—($C_{1-3}$alkyl) and —C(O)—NR$^D$R$^E$; wherein R$^D$ and R$^E$ are each independently selected from the group consisting of hydrogen and $C_{1-2}$alkyl.

In another embodiment, the present invention is directed to compounds of formula (I) wherein (B)

is selected from the group consisting of $C_{5-6}$cycloalkyl, $C_{5-6}$cycloalkenyl, phenyl, four to six membered monocyclic heterocyclyl and nine to ten membered bicyclic heterocyclyl; wherein the phenyl, four to six membered monocyclic heterocyclyl or nine to ten membered bicyclic heterocyclyl is optionally substituted with one to three substituents independently selected from the group consisting of halogen, oxo, $C_{1-4}$alkyl, trifluoromethyl, —NR$^D$R$^E$, imino, cyanoimino and —SO$_2$—($C_{1-2}$alkyl); wherein R$^D$ and R$^E$ are each independently selected from the group consisting of hydrogen and $C_{1-2}$alkyl.

In another embodiment, the present invention is directed to compounds of formula (I) wherein (B)

is selected from the group consisting of cyclohexyl, cyclohex-1-en-1-yl, 3,5-difluoro-phenyl, azetidin-3-yl, 1-methyl-azetidin-3-yl, pyrrolidin-3-yl, pyrrolidin-3-yl-2-one, R-pyrrolidin-3-yl-2-one, S-pyrrolidin-3-yl-2-one, 3-methyl-pyrrolidin-3-yl-2-one, piperidin-1-yl-2-one, piperidin-3-yl-2-one, 1-(methylsulfonyl)-piperidin-4-yl, 4-(methylsulfonyl)-piperazin-1-yl, morpholin-4-yl, thiomorpholin-4-yl, thiomorpholin-4-yl-1,1-dioxide, tetrahydropyran-4-yl, tetrahydro-thiopyran-4-yl, tetrahydro-thiopyran-4-yl-1,1-dioxide, 1,2-thiazinan-2-yl-1,1-dioxide, imidazol-2-yl, 5-methyl-imidazol-2-yl, 4,5-dimethyl-imidazol-2-yl, 2-amino-imidazol-1-yl, imidazolidin-1-yl-2-one, imidazolidin-5-yl-2,4-dione, 1-methyl-imidazolidin-5-yl-2,4-dione, 2-(cyanoimino)-imidazolidin-1-yl, 5-isopropyl-imidazolidin-5-yl-2,4-dione, 1-methyl-benzimidazol-5-yl, 1,5-dihydro-pyrrol-3-yl-2-one, 4,5-dichloro-thien-2-yl, pyridin-3-yl, oxazol-2-yl, oxazolidin-5-yl-2,4-dione, 5-isopropyl-oxazolidin-5-yl-2,4-dione, thiazolidin-5-yl-2,4-dione, isoxazol-3-yl, 1,2,4-oxadiazol-3-yl-5-one, 1,3,4-oxadiazol-2-yl, 5-methyl-1,3,4-oxadiazol-2-yl, 5-ethyl-1,3,4-oxadiazol-2-yl, 5-isopropyl-1,3,4-oxadiazol-2-yl, 5-trifluoromethyl-1,3,4-oxadiazol-2-yl, 5-amino-1,3,4-oxadiazol-2-yl, 5-(dimethylamino)-1,3,4-oxadiazol-2-yl, thiazol-2-yl, 2-amino-thiazol-5-yl, 2-imino-thiazol-3-yl, 5-amino-1,3,4-thiadiazol-2-yl, 5-(dimethylamino)-1,3,4-thiadiazol-2-yl, 1,3,4-triazol-2-yl, 1-methyl-1,3,4-triazol-5-yl, 5-methyl-1,3,4-triazol-2-yl, 2-amino-1,3,4-triazol-1-yl, 1-methyl-1,2,4-triazol-3-yl, 1,2,4-triazol-5-yl, 3-amino-1,2,4-triazol-1-yl, 1,2,3,4-tetrazol-1-yl, 1,2,3,4-tetrazol-5-yl and 1,2,3,5-tetrazol-4-yl.

In another embodiment, the present invention is directed to compounds of formula (I) wherein (B)

is selected from the group consisting of cyclohexyl, cyclohex-1-en-1-yl, 3,5-difluoro-phenyl, azetidin-3-yl, 1-methyl-azetidin-3-yl, pyrrolidin-3-yl, pyrrolidin-3-yl-2-one, R-pyrrolidin-3-yl-2-one, S-pyrrolidin-3-yl-2-one, 3-methyl-pyrrolidin-3-yl-2-one, piperidin-1-yl-2-one, piperidin-3-yl-2-one, 1-(methylsulfonyl)-piperidin-4-yl, 4-(methylsulfonyl)-piperazin-1-yl, morpholin-4-yl, thiomorpholin-4-yl, thiomorpholin-4-yl-1,1-dioxide, tetrahydropyran-4-yl, tetrahydro-thiopyran-4-yl, tetrahydro-thiopyran-4-yl-1,1-dioxide, 1,2-thiazinan-2-yl-1,1-dioxide, imidazol-2-yl, 5-methyl-imidazol-2-yl, 4,5-dimethyl-imidazol-2-yl, 2-amino-imidazol-1-yl, imidazolidin-1-yl-2-one, imidazolidin-5-yl-2,4-dione, 1-methyl-imidazolidin-5-yl-2,4-dione, 2-(cyanoimino)-imidazolidin-1-yl, 5-isopropyl-imidazolidin-5-yl-2,4-dione, 1-methyl-benzimidazol-5-yl, 4,5-dichloro-thien-2-yl, pyridin-3-yl, oxazol-2-yl, oxazolidin-5-yl-2,4-dione, 5-isopropyl-oxazolidin-5-yl-2,4-dione, thiazolidin-5-yl-2,4-dione, isoxazol-3-yl, 1,2,4-oxadiazol-3-yl-5-one, 1,3,4-oxadiazol-2-yl, 5-methyl-1,3,4-oxadiazol-2-yl, 5-ethyl-1,3,4-oxadiazol-2-yl, 5-isopropyl-1,3,4-oxadiazol-2-yl, 5-trifluoromethyl-1,3,4-oxadiazol-2-yl, 5-(dimethylamino)-1,3,4-oxadiazol-2-yl, thiazol-2-yl, 2-amino-thiazol-5-yl, 2-imino-thiazol-3-yl, 5-amino-1,3,4-thiadiazol-2-yl, 5-(dimethylamino)-1,3,4-thiadiazol-2-yl, 1,3,4-triazol-2-yl, 1-methyl-1,3,4-triazol-5-yl, 5-methyl-1,3,4-triazol-2-yl, 2-amino-1,3,4-triazol-1-yl, 1-methyl-1,2,4-triazol-3-yl, 1,2,4-triazol-5-yl, 3-amino-1,2,4-triazol-1-yl, 1,2,3,4-tetrazol-1-yl, 1,2,3,4-tetrazol-5-yl and 1,2,3,5-tetrazol-4-yl.

In another embodiment, the present invention is directed to compounds of formula (I) wherein (B)

is selected from the group consisting of cyclohexyl, azetidin-3-yl, 1-methyl-azetidin-3-yl, pyrrolidin-3-yl, pyrrolidin-3-yl-2-one, R-pyrrolidin-3-yl-2-one, S-pyrrolidin-3-yl-2- one, 3-methyl-pyrrolidin-3-yl-2-one, piperidin-1-yl-2-one, piperidin-3-yl-2-one, 1-(methylsulfonyl)-piperidin-4-yl, 4-(methylsulfonyl)-piperazin-1-yl, morpholin-4-yl, thiomorpholin-4-yl, thiomorpholin-4-yl-1,1-dioxide, tetrahydropyran-4-yl, tetrahydro-thiopyran-4-yl, tetrahydro-thiopyran-4-yl-1,1-dioxide, 1,2-thiazinan-2-yl-1,1-dioxide, imidazol-2-yl, 5-methyl-imidazol-2-yl, 4,5-dimethyl-imidazol-2-yl, 2-amino-imidazol-1-yl, imidazolidin-1-yl-2-one, imidazolidin-5-yl-2,4-dione, 1-methyl-imidazolidin-5-yl-2,4-dione, 2-(cyanoimino)-imidazolidin-1-yl, 1-methyl-benzimidazol-5-yl, pyridin-3-yl, oxazol-2-yl, oxazolidin-5-yl-2,4-dione, thiazolidin-5-yl-2,4-dione, isoxazol-3-yl, 1,2,4-oxadiazol-3-yl-5-one, 1,3,4-oxadiazol-2-yl, 5-methyl-1,3,4-oxadiazol-2-yl, 5-ethyl-1,3,4-oxadiazol-2-yl, 5-isopropyl-1,3,4-oxadiazol-2-yl, 5-(dimethylamino)-1,3,4-oxadiazol-2-yl, thiazol-2-yl, 2-amino-thiazol-5-yl, 2-imino-thiazol-3-yl, 5-amino-1,3,4-thiadiazol-2-yl, 5-(dimethylamino)-1,3,4-thiadiazol-2-yl, 1,3,4-triazol-2-yl, 5-methyl-1,3,4-triazol-2-yl, 2-amino-1,3,4-triazol-1-yl, 1-methyl-1,2,4-triazol-3-yl, 1,2,4-triazol-5-yl, 3-amino-1,2,4-triazol-1-yl, 1,2,3,4-tetrazol-1-yl, 1,2,3,4-tetrazol-5-yl and 1,2,3,5-tetrazol-4-yl.

In another embodiment, the present invention is directed to compounds of formula (I) wherein

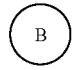

is selected from the group consisting of azetidin-3-yl, pyrrolidin-3-yl, pyrrolidin-3-yl-2-one, R-pyrrolidin-3-yl-2-one, S-pyrrolidin-3-yl-2-one, 3-methyl-pyrrolidin-3-yl-2-one, piperidin-1-yl-2-one, piperidin-3-yl-2-one, 1-(methylsulfonyl)-piperidin-4-yl, 4-(methylsulfonyl)-piperazin-1-yl, morpholin-4-yl, thiomorpholin-4-yl-1,1-dioxide, tetrahydropyran-4-yl, tetrahydro-thiopyran-4-yl, tetrahydro-thiopyran-4-yl-1,1-dioxide, 1,2-thiazinan-2-yl-1,1-dioxide, imidazol-2-yl, 5-methyl-imidazol-2-yl, 4,5-dimethyl-imidazol-2-yl, 2-amino-imidazol-1-yl, imidazolidin-1-yl-2-one, 1-methyl-imidazolidin-5-yl-2,4-dione, 2-(cyanoimino)-imidazolidin-1-yl, 1-methyl-benzimidazol-5-yl, pyridin-3-yl, oxazol-2-yl, oxazolidin-5-yl-2,4-dione, thiazolidin-5-yl-2,4-dione, isoxazol-3-yl, 1,2,4-oxadiazol-3-yl-5-one, 1,3,4-oxadiazol-2-yl, 5-methyl-1,3,4-oxadiazol-2-yl, 5-ethyl-1,3,4-oxadiazol-2-yl, 5-isopropyl-1,3,4-oxadiazol-2-yl, 5-(dimethylamino)-1,3,4-oxadiazol-2-yl, thiazol-2-yl, 2-amino-thiazol-5-yl, 2-imino-thiazol-3-yl, 5-amino-1,3,4-thiadiazol-2-yl, 5-(dimethylamino)-1,3,4-thiadiazol-2-yl, 1,3,4-triazol-2-yl, 2-amino-1,3,4-triazol-1-yl, 1,2,4-triazol-5-yl and 1,2,3,4-tetrazol-5-yl.

In another embodiment, the present invention is directed to compounds of formula (I) wherein

is selected from the group consisting of pyrrolidin-3-yl-2-one, R-pyrrolidin-3-yl-2-one, S-pyrrolidin-3-yl-2-one, 3-methyl-pyrrolidin-3-yl-2-one, piperidin-1-yl-2-one, piperidin-3-yl-2-one, 1-(methylsulfonyl)-piperidin-4-yl, morpholin-4-yl, thiomorpholin-4-yl-1,1-dioxide, tetrahydropyran-4-yl, tetrahydro-thiopyran-4-yl, tetrahydro-thiopyran-4-yl-1,1-dioxide, imidazol-2-yl, 4,5-dimethyl-imidazol-2-yl, imidazolidin-1-yl-2-one, 1-methyl-imidazolidin-5-yl-2,4-dione, 1-methyl-benzimidazol-5-yl, pyridin-3-yl, oxazol-2-yl, oxazolidin-5-yl-2,4-dione, thiazolidin-5-yl-2,4-dione, isoxazol-3-yl, 1,3,4-oxadiazol-2-yl, 5-methyl-1,3,4-oxadiazol-2-yl, 5-ethyl-1,3,4-oxadiazol-2-yl, 5-(dimethylamino)-1,3,4-oxadiazol-2-yl, thiazol-2-yl, 5-(dimethylamino)-1,3,4-thiadiazol-2-yl and 1,3,4-triazol-2-yl.

In another embodiment, the present invention is directed to compounds of formula (I) wherein

is selected from the group consisting of pyrrolidin-3-yl-2-one, S-pyrrolidin-3-yl-2-one, piperidin-1-yl-2-one, 1-(methylsulfonyl)-piperidin-4-yl, morpholin-4-yl, tetrahydropyran-4-yl, tetrahydro-thiopyran-4-yl, tetrahydro-thiopyran-4-yl-1,1-dioxide, 1-methyl-benzimidazol-5-yl, oxazol-2-yl, oxazolidin-5-yl-2,4-dione, isoxazol-3-yl and 5-(dimethylamino)-1,3,4-thiadiazol-2-yl.

In an embodiment, the present invention is directed to compounds of formula (II) wherein

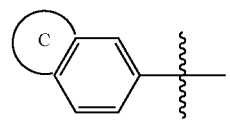

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl; wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is optionally substituted on the phenyl portion of the

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy; and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is further optionally substituted on the portion of the

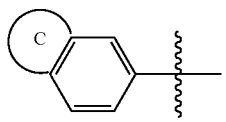

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy.

In another embodiment, the present invention is directed to compounds of formula (II) wherein

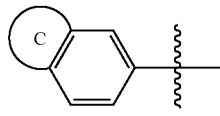

is selected from the group consisting of naphth-2-yl and indazol-6-yl; wherein the naphth-2-yl or indazol-6-yl is optionally substituted on either the phenyl or

portion of the

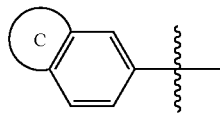

bicycle with one to two substituents independently selected from the group consisting of halogen and $C_{1-3}$alkyl.

In another embodiment, the present invention is directed to compounds of formula (II) wherein

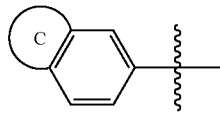

is selected from the group consisting of naphth-2-yl, 6-fluoro-naphth-2-yl, 8-fluoro-naphth-2-yl and 1-ethyl-4-fluoro-indazol-6-yl. In another embodiment, the present invention is directed to compounds of formula (II) wherein

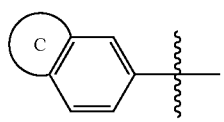

is selected from the group consisting of naphth-2-yl, 8-fluoro-naphth-2-yl and 1-ethyl-4-fluoro-indazol-6-yl.

In an embodiment, the present invention is directed to compounds of formula (II) wherein $R^3$ is selected from the group consisting of hydrogen, fluoro and $C_{1-2}$alkyl. In another embodiment, the present invention is directed to compounds of formula (II) wherein $R^3$ is hydrogen.

In an embodiment, the present invention is directed to compounds of formula (II) wherein $R^4$ is selected from the group consisting of hydrogen, fluoro and $C_{1-2}$alkyl. In another embodiment, the present invention is directed to compounds of formula (II) wherein $R^4$ is hydrogen.

In an embodiment, the present invention is directed to compounds of formula (II) wherein $R^5$ is selected from the group consisting of hydrogen, fluoro, hydroxy, $C_{1-4}$alkyl and —C(O)NR$^U$R$^V$; wherein R$^U$ and R$^V$ are each independently selected from the group consisting of hydrogen and $C_{1-2}$alkyl.

In an embodiment, the present invention is directed to compounds of formula (II) wherein $R^5$ is selected from the group consisting of hydrogen, hydroxy, fluoro, methyl, isopropyl and amino-carbonyl-. In an embodiment, the present invention is directed to compounds of formula (II) wherein $R^5$ is selected from the group consisting of hydrogen, hydroxy, fluoro, methyl and isopropyl. In an embodiment, the present invention is directed to compounds of formula (II) wherein $R^5$ is selected from the group consisting of hydrogen, hydroxy, fluoro, and isopropyl.

In an embodiment, the present invention is directed to compounds of formula (II) wherein

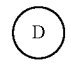

is a ring structure selected from the group consisting of cyclopentyl, cyclohexyl, azetidin-3-yl, pyrrolidin-3-yl, piperidin-3-yl, piperidin-4-yl, morpholin-2-yl, tetrahydropyran-4-yl, 4,5,6,7-tetrahydro-2H-indazol-5-yl, 1,5-dihydro-imidazol-5-yl, 3,5-dihydro-imidazol-5-yl, 4,5-dihydro-imidazol-4-yl, 4,5-dihydro-imidazol-5-yl, imidazolidin-4-yl, imidazolidin-5-yl, 4,5-dihydro-pyrrol-3-yl, 4,5-dihydro-pyrazol-5-yl, 1,2,5-thiadiazolidin-3-yl, 4,5,6,7-tetrahydro-benzo[d]isoxazol-5-yl, imidazo[1,2-a]imidazol-3-yl, imidazo[2,1-c][1,2,4]triazol-5-yl, 6,7-dihydro-5H-imidazo[2,1-c][1,2,4]triazol-6-yl, tetrahydro-1H,3H-pyrrolo[1,2-c]oxazol-6-yl, 6-oxabicyclo[3.2.1]octan-5-yl, 8-azabicyclo[3.2.1]octan-3-yl, 6-azabicyclo[3.2.1]octan-4-yl, 1-oxa-3-azaspiro[4.5]decan-7-yl, 2-azaspiro[4.5]decan-8-yl, $1\lambda^2$,3-diazaspiro[4.5]decan-7-yl, 2-azaspiro[5.5]undecan-9-yl, 3-azaspiro[5.5]undecan-9-yl, 1,3-diazaspiro[4.5]decan-8-yl and octahydro-cyclopenta[c]pyrrol-5-yl; wherein the

ring structure is optionally substituted with one or more substituents independently selected from the group consisting of $C_{1-4}$alkyl, hydroxy, oxo, thioxo, cyano, —NR$^F$R$^G$, —NH(CN), =NH, =N(CN), =N(OH), =N(O—$C_{1-2}$alkyl), —CH$_2$—NR$^F$R$^G$ —C(O)—NR$^F$R$^G$, —OC(O)—NR$^F$R$^G$, —C(O)—CH$_2$OH, —SO$_2$—($C_{1-4}$alkyl), —NR$^F$—SO$_2$—($C_{1-4}$alkyl) and —C(NR$^F$R$^G$)(=N—CN); and wherein R$^F$ and R$^G$ are each independently selected from the group consisting of hydrogen and $C_{1-4}$alkyl.

In another embodiment, the present invention is directed to compounds of formula (II) wherein (D)

is selected from the group consisting of cyclopentyl, 3-cyano-3-(aminocarbonyloxy)-cyclohex-1-yl, 3-(aminocarbonyl)-3-hydroxy-cyclohex-1-yl, 1-(isopropyl-sulfonyl)-azetidin-3-yl, 1-(isopropyl-sulfonyl)-pyrrolidin-3-yl, piperidin-4-yl, 1-(isopropyl-sulfonyl)-piperidin-3-yl, 1-(methyl-sulfonyl)-piperidin-4-yl, 1-(ethyl-sulfonyl)-piperidin-4-yl, 1-(isopropyl-sulfonyl)-piperidin-4-yl, 1-(hydroxy-methyl-carbonyl)-piperidin-4-yl, morpholin-2-yl-3-one, tetrahydro-pyran-4-yl, 1-(isopropyl-sulfonyl)-4,5-dihydro-pyrrol-3-yl, 2-(dimethylamino)-4,5-dihydro-imidazol-4-yl, 1,5-dihydro-2-(cyanoamino)-imidazol-5-yl-4-one, 3,5-dihydro-imidazol-5-yl-4-one, 2-methyl-3,5-dihydro-imidazol-5-yl-4-one, 2-(methylsulfonylamino)-4,5-dihydro-imidazol-5-yl, 2-(cyanoimino)-4,5-dihydro-imidazol-5-yl, imidazolidin-5-yl-2-thione, 2-imino-imidazolidin-4-yl, 2-(hydroxyimino)-imidazolidin-4-yl, 2-(cyanoimino)-imidazolidin-4-yl, 2-(methoxyimino)-imidazolidin-4-yl, (Z)-2-(methoxyimino)-imidazolidin-4-yl, (E)-2-(methoxyimino)-imidazolidin-4-yl, (Z)-2-(methoxyimino)-imidazolidin-5-yl-4-one, 5-oxo-2-thioxo-imidazolidin-4-yl, 4,5-dihydro-pyrazol-5-yl, 4,5,6,7-tetrahydro-2H-indazol-5-yl, 4,5,6,7-tetrahydro-benzo[d]isoxazol-5-yl, 1,2,5-thiadiazolidin-3-yl-1,1-dioxide, imidazo[1,2-a]imdazol-3-yl-2-one, imidazo[2,1-c][1,2,4]triazol-5-yl-6-one, 6,7-dihydro-5H-imidazo[2,1-c][1,2,4]triazol-6-yl, tetrahydro-1H,3H-pyrrolo[1,2-c]oxazol-6-yl-3-one, 1-(isopropyl-amino-carbonyl)-octahydro-cyclopenta[c]pyrrol-5-yl, 1-(1-(cyanoimino)-1-(isopropylamino)methyl)-octahydro-cyclopenta[c]pyrrol-5-yl, 2-(isopropylsulfonyl)-octahydro-cyclopenta[c]pyrrol-5-yl, 7-oxo-6-oxabicyclo[3.2.1]octan-5-yl, 6-azabicyclo[3.2.1]octan-4-yl-7-one, 8-(isopropylaminocarbonyl)-8-azabicyclo[3.2.1]octan-3-yl, 8-(isopropylsulfonyl)-8-azabicyclo[3.2.1]octan-3-yl, (anti)-1-oxa-3-azaspiro[4.5]decan-7-yl-2,4-dione, (syn)-1-oxa-3-azaspiro[4.5]decan-7-yl-2,4-dione, 1,3-diazaspiro[4.5]decan-8-yl-2,4-dione, 1λ²,3-diazaspiro[4.5]decan-7-yl-2,4-dione, 2-azaspiro[4.5]decan-8-yl-1-one, 2-azaspiro[5.5]undecan-9-yl-1-one and 3-(isopropylsulfonyl)-3-azaspiro[5.5]undecan-9-yl.

In another embodiment, the present invention is directed to compounds of formula (II) wherein (D)

is selected from the group consisting of cyclopentyl, 3-cyano-3-(aminocarbonyloxy)-cyclohex-1-yl, 3-(aminocarbonyl)-3-hydroxy-cyclohex-1-yl, 1-(isopropyl-sulfonyl)-pyrrolidin-3-yl, 1-(isopropyl-sulfonyl)-piperidin-3-yl, 1-(methyl-sulfonyl)-piperidin-4-yl, 1-(ethyl-sulfonyl)-piperidin-4-yl, 1-(isopropyl-sulfonyl)-piperidin-4-yl, 1-(hydroxy-methyl-carbonyl)-piperidin-4-yl, morpholin-2-yl-3-one, tetrahydro-pyran-4-yl, 1-(isopropyl-sulfonyl)-4,5-dihydro-pyrrol-3-yl, 1,5-dihydro-2-(cyanoamino)-imidazol-5-yl-4-one, 2-(methylsulfonylamino)-4,5-dihydro-imidazol-5-yl, imidazolidin-5-yl-2-thione, 2-(cyanoimino)-4,5-dihydro-imidazol-5-yl, 2-imino-imidazolidin-4-yl, 2-(hydroxyimino)-imidazolidin-4-yl, 2-(cyanoimino)-imidazolidin-4-yl, 2-(methoxyimino)-imidazolidin-4-yl, (Z)-2-(methoxyimino)-imidazolidin-4-yl, (E)-2-(methoxyimino)-imidazolidin-4-yl, (Z)-2-(methoxyimino)-imidazolidin-5-yl-4-one, 5-oxo-2-thioxo-imidazolidin-4-yl, 4,5,6,7-tetrahydro-2H-indazol-5-yl, imidazo[2,1-a]imdazol-3-yl-2-one, imidazo[2,1-c][1,2,4]triazol-5-yl-6-one, 6,7-dihydro-5H-imidazo[2,1-c][1,2,4]triazol-6-yl, tetrahydro-1H,3H-pyrrolo[1,2-c]oxazol-6-yl-3-one, 1-(isopropyl-amino-carbonyl)-octahydro-cyclopenta[c]pyrrol-5-yl, 1-(1-(cyanoimino)-1-(isopropylamino)methyl)-octahydro-cyclopenta[c]pyrrol-5-yl, 2-(isopropylsulfonyl)-octahydro-cyclopenta[c]pyrrol-5-yl, 7-oxo-6-oxabicyclo[3.2.1]octan-5-yl, 6-azabicyclo[3.2.1]octan-4-yl-7-one, 8-(isopropylaminocarbonyl)-8-azabicyclo[3.2.1]octan-3-yl, 8-(isopropylsulfonyl)-8-azabicyclo[3.2.1]octan-3-yl, (anti)-1-oxa-3-azaspiro[4.5]decan-7-yl-2,4-dione, (syn)-1-oxa-3-azaspiro[4.5]decan-7-yl-2,4-dione, 1,3-diazaspiro[4.5]decan-8-yl-2,4-dione, 1λ²,3-diazaspiro[4.5]decan-7-yl-2,4-dione, 2-azaspiro[4.5]decan-8-yl-1-one, 2-azaspiro[5.5]undecan-9-yl-1-one and 3-(isopropylsulfonyl)-3-azaspiro[5.5]undecan-9-yl.

In another embodiment, the present invention is directed to compounds of formula (II) wherein (D)

is selected from the group consisting of cyclopentyl, 3-cyano-3-(aminocarbonyloxy)-cyclohex-1-yl, 3-(amino-carbonyl)-3-hydroxy-cyclohex-1-yl, 1-(isopropyl-sulfonyl)-pyrrolidin-3-yl, 1-(isopropyl-sulfonyl)-piperidin-3-yl, 1-(methyl-sulfonyl)-piperidin-4-yl, 1-(ethyl-sulfonyl)-piperidin-4-yl, 1-(isopropyl-sulfonyl)-piperidin-4-yl, morpholin-2-yl-3-one, 1-(isopropyl-sulfonyl)-4,5-dihydro-pyrrol-3-yl, 1,5-dihydro-2-(cyanoamino)-imidazol-5-yl-4-one, 2-(cyanoimino)-4,5-dihydro-imidazol-5-yl, 2-(cyanoimino)-imidazolidin-4-yl, 2-(methoxyimino)-imidazolidin-4-yl, (Z)-2-(methoxyimino)-imidazolidin-4-yl, (E)-2-(methoxyimino)-imidazolidin-4-yl, (Z)-2-(methoxyimino)-imidazolidin-5-yl-4-one, 5-oxo-2-thioxo-imidazolidin-4-yl, 4,5,6,7-tetrahydro-2H-indazol-5-yl, imidazo[2,1-a]imdazol-3-yl-2-one, 1-(isopropyl-amino-carbonyl)-octahydro-cyclopenta[c]pyrrol-5-yl, 1-(1-(cyanoimino)-1-(isopropylamino)methyl)-octahydro-cyclopenta[c]pyrrol-5-yl, 7-oxo-6-oxabicyclo[3.2.1]octan-5-yl, 6-azabicyclo[3.2.1]octan-4-yl-7-one, 8-(isopropylsulfonyl)-8-azabicyclo[3.2.1]octan-3-yl, (anti)-1-oxa-3-azaspiro[4.5]decan-7-yl-2,4-dione, (syn)-1-oxa-3-azaspiro[4.5]decan-7-yl-2,4-dione, imidazo[2,1-a]imdazol-3-yl-2-one, 1λ²,3-diazaspiro[4.5]decan-7-yl-2,4-dione, 2-azaspiro[4.5]decan-8-yl-1-one, 2-azaspiro[5.5]undecan-9-yl-1-one and 3-(isopropylsulfonyl)-3-azaspiro[5.5]undecan-9-yl.

In another embodiment, the present invention is directed to compounds of formula (II) wherein (D)

is selected from the group consisting of 3-(amino-carbonyl)-3-hydroxy-cyclohex-1-yl, 1-(isopropyl-sulfonyl)-pyrrolidin-3-yl, 1-(isopropyl-sulfonyl)-piperidin-3-yl, 1-(isopropyl-sulfonyl)-piperidin-4-yl, morpholin-2-yl-3-one, 1-(isopropyl-sulfonyl)-4,5-dihydro-pyrrol-3-yl, 1,5-dihydro-2-(cyanoamino)-imidazol-5-yl-4-one, 2-(cyanoimino)-4,5-dihydro-imidazol-5-yl, (Z)-2-(methoxyimino)-imidazolidin-4-yl, (E)-2-(methoxyimino)-imidazolidin-4-yl, (Z)-2-(methoxyimino)-imidazolidin-5-yl-4-one, 5-oxo-2-thioxo-imidazolidin-4-yl, 6-azabicyclo[3.2.1]octan-4-yl-7-one, 8-(isopropylsulfonyl)-8-azabicyclo[3.2.1]octan-3-yl, (anti)-1-oxa-3-azaspiro[4.5]decan-7-yl-2,4-dione, (syn)-1-oxa-3-azaspiro[4.5]decan-7-yl-2,4-dione, imidazo[2,1-a]imdazol-3-yl-2-one, $1\lambda^2$,3-diazaspiro[4.5]decan-7-yl-2,4-dione, 2-azaspiro[4.5]decan-8-yl-1-one, 2-azaspiro[5.5]undecan-9-yl-1-one and 3-(isopropylsulfonyl)-3-azaspiro[5.5]undecan-9-yl.

In another embodiment, the present invention is directed to compounds of formula (II) wherein

is selected from the group consisting of 3-(amino-carbonyl)-3-hydroxy-cyclohex-1-yl, 1-(isopropyl-sulfonyl)-pyrrolidin-3-yl, 1-(isopropyl-sulfonyl)-piperidin-3-yl, morpholin-2-yl-3-one, 1-(isopropyl-sulfonyl)-4,5-dihydro-pyrrol-3-yl, 1,5-dihydro-2-(cyanoamino)-imidazol-5-yl-4-one, 2-(cyanoimino)-4,5-dihydro-imidazol-5-yl, (Z)-2-(methoxyimino)-imidazolidin-4-yl, (Z)-2-(methoxyimino)-imidazolidin-5-yl-4-one, 5-oxo-2-thioxo-imidazolidin-4-yl, 6-azabicyclo[3.2.1]octan-4-yl-7-one, imidazo[2,1-a]imdazol-3-yl-2-one, $1\lambda^2$,3-diazaspiro[4.5]decan-7-yl-2,4-dione and 2-azaspiro[5.5]undecan-9-yl-1-one.

In another embodiment, the present invention is directed to compounds of formula (II) wherein

is selected from the group consisting of 1-(isopropyl-sulfonyl)-piperidin-3-yl, 1,5-dihydro-2-(cyanoamino)-imidazol-5-yl-4-one, 2-(cyanoimino)-4,5-dihydro-imidazol-5-yl, (Z)-2-(methoxyimino)-imidazolidin-4-yl, (Z)-2-(methoxyimino)-imidazolidin-5-yl-4-one, 6-azabicyclo[3.2.1]octan-4-yl-7-one and imidazo[2,1-a]imdazol-3-yl-2-one, $1\lambda^2$,3-diazaspiro[4.5]decan-7-yl-2,4-dione.

In an embodiment, the present invention is directed to compounds of formula (III) wherein

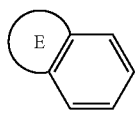

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl; wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is optionally substituted on the phenyl portion of the

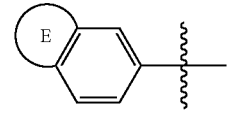

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy; and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is further optionally substituted on the

portion of the

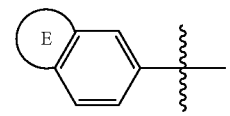

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy.

In another embodiment, the present invention is directed to compounds of formula (III) wherein

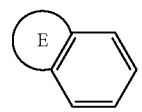

is selected from the group consisting of naphth-2-yl, benzothiazol-5-yl, benzothiazol-6-yl, 3,4-dihydro-benzo[b][1,4]oxazin-6-yl and 3,4-dihydro-benzo[b][1,4]oxazin-7-yl; wherein the naphth-2-yl, benzothiazol-5-yl, benzothiazol-6-yl, 3,4-dihydro-benzo[b][1,4]oxazin-6-yl or 3,4-dihydro-benzo[b][1,4]oxazin-7-yl is optionally substituted on the phenyl or

portion of the

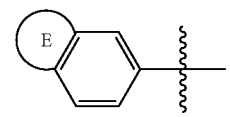

with a substituent selected from the group consisting of halogen, $C_{1-3}$alkyl and $C_{1-2}$alkoxy.

In another embodiment, the present invention is directed to compounds of formula (II) wherein

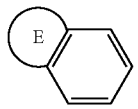

is selected from the group consisting of naphth-2-yl, 6-fluoro-naphth-2-yl, 8-fluoro-naphth-2-yl, 6-methoxy-naphth-2-yl, benzothiazol-5-yl, benzothiazol-6-yl, 4-methyl-3,4-dihydro-benzo[b][1,4]oxazin-6-yl and 4-methyl-3,4-dihydro-benzo[b][1,4]oxazin-7-yl.

In another embodiment, the present invention is directed to compounds of formula (III) wherein

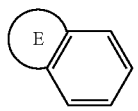

is selected from the group consisting of naphth-2-yl and 8-fluoro-naphth-2-yl.

In an embodiment, the present invention is directed to compounds of formula (III) wherein $R^6$ is selected from the group consisting of hydrogen, fluoro and $C_{1-2}$alkyl. In another embodiment, the present invention is directed to compounds of formula (III) wherein $R^6$ is hydrogen.

In another embodiment, the present invention is directed to compounds of formula (III) wherein $R^7$ is selected from the group consisting of hydrogen, fluoro and $C_{1-2}$alkyl. In another embodiment, the present invention is directed to compounds of formula (III) wherein $R^7$ is hydrogen.

In an embodiment, the present invention is directed to compounds of formula (III) wherein Y is selected from the group consisting of —$CR^H R^J$— and —$CR^H R^J$—$CHR^K$—; wherein $R^H$ and $R^J$ are each independently selected from the group consisting of hydrogen, halogen, hydroxy, $C_{1-4}$alkyl, fluorinated $C_{1-2}$alkyl, $C_{3-6}$cycloalkyl and $C_{5-6}$cycloalkenyl; provided that when one of $R^H$ or $R^J$ is $C_{3-6}$cycloalkyl or $C_{5-6}$cycloalkenyl, then the other of $R^H$ or $R^J$ is hydrogen; and wherein $R^K$ is selected from the group consisting of hydrogen and $C_{1-4}$alkyl; alternatively, when Y is —$CR^H R^J$—, then $R^H$ and $R^J$ may be taken together with the carbon atom to which they are bound to form $C_{5-6}$cycloalkyl.

In another embodiment, the present invention is directed to compounds of formula (III) wherein Y is —$CR^H R^J$—, and $R^H$ and $R^J$ may be taken together with the carbon atom to which they are bound to form $C_{5-6}$cycloalkyl.

In another embodiment, the present invention is directed to compounds of formula (III) wherein Y is selected from the group consisting of —$CR^H R^J$— and —$CR^H R^J$—$CHR^K$—; wherein $R^H$ and $R^J$ are each independently selected from the group consisting of hydrogen, halogen, hydroxy, $C_{1-4}$alkyl and $C_{5-6}$cycloalkenyl; provided that when one of $R^H$ or $R^J$ is $C_{5-6}$cycloalkenyl, then the other of $R^H$ or $R^J$ is hydrogen; and wherein $R^K$ is selected from the group consisting of hydrogen and $C_{1-4}$alkyl.

In another embodiment, the present invention is directed to compounds of formula (III) wherein Y is selected from the group consisting of —CH(isopropyl), —C(OH)(isopropyl)-, —C(F)(isopropyl)-, —C(methyl)(isopropyl)-, —CH(cyclohex-1-en-1-yl), —CH(isopropyl)-$CH_2$— and —$CH_2$—CH(isopropyl)-.

In another embodiment, the present invention is directed to compounds of formula (III) wherein Y is selected from the group consisting of —CH(isopropyl), —C(OH)(isopropyl)-, —C(F)(isopropyl)-, —CH(isopropyl)-$CH_2$— and —$CH_2$—CH(isopropyl)-. In another embodiment, the present invention is directed to compounds of formula (III) wherein Y is selected from the group consisting of —CH(isopropyl), —C(OH)(isopropyl)-, —CH(isopropyl)-$CH_2$— and —$CH_2$—CH(isopropyl)-. In another embodiment, the present invention is directed to compounds of formula (III) wherein Y is selected from the group consisting of —CH(isopropyl), —C(OH)(isopropyl)- and —CH(isopropyl)-$CH_2$—. In another embodiment, the present invention is directed to compounds of formula (III) wherein Y is selected from the group consisting of —CH(isopropyl), and —CH(isopropyl)-$CH_2$—.

In an embodiment, the present invention is directed to compounds of formula (III) wherein Z is selected from the group consisting of —C(O)—$NR^L R^M$, —C(O)—NH—$OR^N$, —C(O)—NH—$SO_2$—$R^N$; —C(O)—NH(CH($CH_2OH$)$_2$), —C(O)—NH(C($CH_2OH$)$_3$), —C(O)—NH—($CH_2CH_2O$)$_a$—$R^N$, —C(O)—NH—CH($CH_2O$—($CH_2CH_2O$)$_b$—$R^N$)$_2$, —C(O)—NH—C($CH_2O$—($CH_2CH_2O$)$_b$—$R^N$)$_3$), —C(O)—NH—$CH_2CH_2$—$NR^P R^Q$, —C(O)—NH—($CH_2CH_2O$)$_a$—$CH_2CH_2$—$NR^P R^Q$, —$NR^S$—C(O)—$NR^P R^Q$, —$NR^S$—C(O)—NH—$CH_2CH_2$—$NR^P R^Q$ and —$NR^S$—C($NH_2$)=N—CN; wherein a is an integer from 1 to 4; wherein b is an integer from 0 to 3; wherein $R^L$ and $R^M$ are each independently selected from the group consisting of hydrogen and $C_{1-4}$alkyl; wherein $R^N$ is selected from the group consisting of hydrogen and $C_{1-2}$alkyl; wherein $R^P$ and $R^Q$ are each independently selected from the group consisting of hydrogen and $C_{1-2}$alkyl; and wherein $R^S$ is selected from the group consisting of hydrogen and $C_{1-2}$alkyl.

In another embodiment, the present invention is directed to compounds of formula (III) wherein Z is selected from the group consisting of —C(O)—$NR^L R^M$, —C(O)—NH—$OR^N$, —C(O)—NH—$SO_2$—$R^N$; —C(O)—NH(CH($CH_2OH$)$_2$), —C(O)—NH(C($CH_2OH$)$_3$), —C(O)—NH—($CH_2CH_2O$)$_a$—$R^N$, —C(O)—NH—$CH_2CH_2$—$NR^P R^Q$, —C(O)—NH—($CH_2CH_2O$)$_a$—$CH_2CH_2$—$NR^P R^Q$, —$NR^S$—C(O)—$NR^P R^Q$, —$NR^S$—C(O)—NH—$CH_2CH_2$—$NR^P R^Q$ and —$NR^S$—C($NH_2$)=N—CN; wherein a is an integer from 1 to 3; wherein $R^L$ and $R^M$ are each independently selected from the group consisting of hydrogen and $C_{1-4}$alkyl; wherein $R^N$ is selected from the group consisting of hydrogen and methyl; wherein $R^P$ and $R^Q$ are each independently selected from the group consisting of hydrogen and methyl; and wherein $R^S$ is selected from the group consisting of hydrogen and methyl.

In another embodiment, the present invention is directed to compounds of formula (III) wherein a is an integer from 1 to 3. In another embodiment, the present invention is directed to compounds of formula (III) wherein a is an integer from 1 to 2.

In another embodiment, the present invention is directed to compounds of formula (III) wherein b is an integer from 0 to 2. In another embodiment, the present invention is directed to compounds of formula (III) wherein b is an integer from 1 to 2.

In another embodiment, the present invention is directed to compounds of formula (III) wherein $R^L$ and $R^M$ are each independently selected from the group consisting of hydrogen and $C_{1-4}$alkyl. In another embodiment, the present invention is directed to compounds of formula (III) wherein $R^L$ and $R^M$ are each independently selected from the group consisting of hydrogen, methyl and ethyl. In another embodiment, the present invention is directed to compounds of formula (III) wherein $R^L$ and $R^M$ are each independently selected from the group consisting of hydrogen and methyl.

In another embodiment, the present invention is directed to compounds of formula (III) wherein $P^N$ is selected from the group consisting of hydrogen and methyl.

In another embodiment, the present invention is directed to compounds of formula (III) wherein $R^P$ and $R^Q$ are each independently selected from the group consisting of hydrogen and methyl.

In another embodiment, the present invention is directed to compounds of formula (III) wherein $R^S$ is selected from the group consisting of hydrogen and methyl.

In another embodiment, the present invention is directed to compounds of formula (III) wherein Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$—N(CH$_3$)$_2$, —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$O—CH$_3$, —C(O)—NH—SO$_2$—CH$_3$, —NH—C(O)—NH$_2$, —N(CH$_3$)—C(O)—NH$_2$, —NH—C(O)—NH—CH$_2$CH$_2$—N(CH$_3$)$_2$ and —NH-(E)-C(NH$_2$)=N—CN;

In another embodiment, the present invention is directed to compounds of formula (III) wherein Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$O—CH$_3$, —NH—C(O)—NH$_2$, and —NH-(E)-C(NH$_2$)=N—CN.

In another embodiment, the present invention is directed to compounds of formula (III) wherein Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH—CH$_2$CH$_2$OH, —C(O)—NH—CH$_2$CH$_2$O—CH$_2$CH$_2$O—CH$_2$CH$_2$O—CH$_3$, —NH—C(O)—NH$_2$, and —NH-(E)-C(NH$_2$)=N—CN.

In another embodiment, the present invention is directed to compounds of formula (III) wherein Z is selected from the group consisting of —C(O)—NH$_2$, —C(O)—NH(isopropyl), —C(O)—NH(OCH$_3$), —C(O)—NH—CH$_2$CH$_2$OH and —C(O)—NH—CH$_2$CH$_2$O—CH$_2$CH$_2$O—CH$_2$CH$_2$O—CH$_3$.

In certain embodiments,

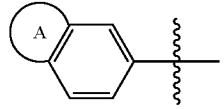

is other than indol-5-yl, indol-6-yl, indazol-5-yl, indazol-6-yl, benzimidazol-5-yl or benzimidazol-5-yl; wherein the indol-5-yl, indol-6-yl, indazol-5-yl, indazol-6-yl, benzimidazol-5-yl or benzimidazol-5-yl is optionally substituted with one or more (for example one to three, one to two or one) substituents independently selected from the group consisting of halogen, $C_{1-3}$alkyl and $C_{3-6}$cycloalkyl.

In certain embodiments,

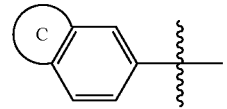

is other than indol-5-yl, indol-6-yl, indazol-5-yl, indazol-6-yl, benzimidazol-5-yl or benzimidazol-5-yl; wherein the indol-5-yl, indol-6-yl, indazol-5-yl, indazol-6-yl, benzimidazol-5-yl or benzimidazol-5-yl is optionally substituted with one or more (for example one to three, one to two or one) substituents independently selected from the group consisting of halogen, $C_{1-3}$alkyl and $C_{3-6}$cycloalkyl.

In certain embodiments,

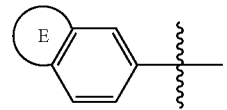

is other than indol-5-yl, indol-6-yl, indazol-5-yl, indazol-6-yl, benzimidazol-5-yl or benzimidazol-5-yl; wherein the indol-5-yl, indol-6-yl, indazol-5-yl, indazol-6-yl, benzimidazol-5-yl or benzimidazol-5-yl is optionally substituted with one or more (for example one to three, one to two or one) substituents independently selected from the group consisting of halogen, $C_{1-3}$alkyl and $C_{3-6}$cycloalkyl.

In certain embodiments of the present invention,

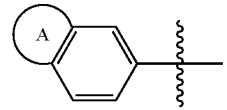

is other than benzimidazol-5-yl. In certain embodiments of the present invention,

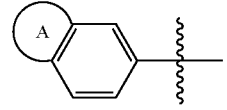

is other than indazol-6-yl.

In certain embodiments of the present invention,

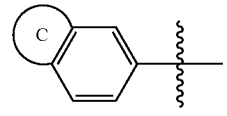

is other than benzimidazol-5-yl. In certain embodiments of the present invention,

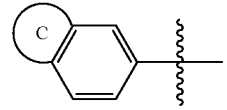

is other than indazol-6-yl.

In certain embodiments of the present invention,

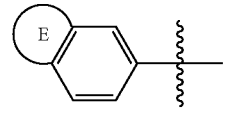

is other than benzimidazol-5-yl. In certain embodiments of the present invention, is other than indazol-6-yl.

In certain embodiments, (D)

is other than azabicyclo[3.2.1]octan-3-yl.

In certain embodiments, (D)

is other than pyrrolidin-3-yl-2-one or piperidin-3-yl-2-one.

Additional embodiments of the present invention, include those wherein the substituents selected for one or more of the variables defined herein (i.e.

(A)

$R^1$, $R^2$, X, (B), (C)

$R^3$, $R^4$, $R^5$, (D), (E)

$R^6$, $R^7$, Y, Z, etc.) are independently selected to be any individual substituent or any subset of substituents independently selected from the complete list as defined herein.

Additional embodiments of the present invention, include those wherein the substituents selected for one or more of the variables defined herein (i.e.

(A)

$R^1$, $R^2$, X, (B), (C)

$R^3$, $R^4$, $R^5$, (D), (E)

$R^6$, $R^7$, Y, Z, etc.) are independently selected to be any individual substituent or any subset of substituents independently selected from the substituents listed in Tables 1-3 below. In certain embodiments, the present invention is directed to any single compound or subset of compounds selected from the representative compounds listed in Tables 1-3 below.

Representative compounds of the present invention are as listed in Table 1 to 3, below. Unless otherwise noted, wherein a double bond is present in the listed compound, the compound was prepared as either E or Z configuration. Where a stereogenic center is present in the listed compound, the compound was prepared as a racemic mixture. Where a stereogenic center is present, and the compound was prepared in an enantiomeric excess of a particular stereo-isomer, the S*- and R* designations are intended to indicate that the exact stereo-configuration of the center has not been determined. Where two stereogenic centers are present, the compound was prepared as a particular diastereomeric isomer, where the syn and anti designations are intended to indicate that relative stereo-configurations of two centers of the racemic mixtures and the exact stereo-configuration of the centers has not been determined.

TABLE 1

Representative Compounds of Formula (I)

| ID No. | (A) | $R^1$ | $R^2$ | —X— | (B) |
|---|---|---|---|---|---|
| 1 | 8-fluoro-naphth-2-yl | H | H | —C(methyl)$_2$—CH$_2$— | oxazolidin-5-yl-2,4-dione |
| 2 | 8-fluoro-naphth-2-yl | H | H | —C(methyl)$_2$-(Z)—CH= | oxazolidin-5-yl-2,4-dione |
| 3 | 1-ethyl-4-fluoro-indazol-6-yl | H | H | —C(ethyl)$_2$- | 1,2,3,4-tetrazol-5-yl |

TABLE 1-continued

Representative Compounds of Formula (I)

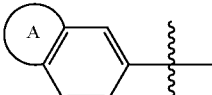

| ID No. | A  | R¹ | R² | 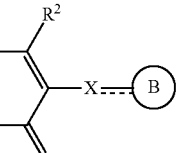 X 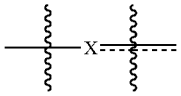 | B  |
|---|---|---|---|---|---|
| 4 | 1-ethyl-4-fluoro-indazol-6-yl | H | H | —C(ethyl)₂- | 1,2,4-oxadiazol-3-yl-5-one |
| 5 | 1-ethyl-4-fluoro-indazol-6-yl | H | H | —C(ethyl)₂- | 1,3,4-triazol-2-yl |
| 6 | 8-fluoro-naphth-2-yl | H | H | —C(ethyl)₂-(E)-CH= | oxazolidin-5-yl-2,4-dione |
| 7 | 8-fluoro-naphth-2-yl | H | H | -cyclopent-1,1-yl-CH₂— | oxazolidin-5-yl-2,4-dione |
| 8 | 8-fluoro-naphth-2-yl | H | H | -cyclopent-1,1-yl-(E)-CH= | oxazolidin-5-yl-2,4-dione |
| 9 | 8-fluoro-naphth-2-yl | H | H | —C(ethyl)₂-CH₂— | oxazolidin-5-yl-2,4-dione |
| 10 | 5,7-difluoro-naphth-2-yl | H | H | -cyclopent-1,1-yl-(E)-CH= | oxazolidin-5-yl-2,4-dione |
| 11 | 8-fluoro-naphth-2-yl | H | H | -cycloprop-1,1,-yl-(E)-CH= | oxazolidin-5-yl-2,4-dione |
| 12 | 1-ethyl-4-fluoro-indazol-6-yl | H | H | —C(ethyl)₂-(E)-CH= | oxazolidin-5-yl-2,4-dione |
| 13 | 1-ethyl-4-fluoro-indazol-6-yl | H | H | —C(ethyl)₂-(E)-CH= | pyrrolidin-3-yl-2-one |
| 14 | 2-ethyl-4-fluoro-indazol-5-yl | H | H | —C(ethyl)₂-(E)-CH= | oxazolidin-5-yl-2,4-dione |
| 15 | 1-ethyl-4-fluoro-indazol-6-yl | H | H | —C(ethyl)₂-CH₂— | 1,3,4-triazol-2-yl |
| 16 | 1-ethyl-4-fluoro-indazol-6-yl | H | H | —C(ethyl)₂-(E)-CH= | pyrrolidin-3-yl-2-one |
| 17 | 4-ethyl-8-fluoro-3,4-dihydro-2H-benzo[b]1,4]oxazin-6-yl | H | H | —C(ethyl)₂-CH₂— | pyrrolidin-3-yl-2-one |
| 18 | 2,2-dimethyl-chromen-7-yl | H | H | —C(ethyl)₂-(Z)-CH= | oxazolidin-5-yl-2,4-dione |
| 19 | 8-isopropyl-naphth-2-yl | H | H | —C(ethyl)₂-(E)-CH= | oxazolidin-5-yl-2,4-dione |
| 20 | 1-ethyl-4-fluoro-indazol-6-yl | H | H | —C(ethyl)₂-CH₂— | imidazol-2-yl |
| 21 | 1-ethyl-4-fluoro-indazol-6-yl | H | H | —C(ethyl)₂- | 5-methyl-1,3,4-triazol-2-yl |
| 22 | 4-ethyl-8-fluoro-3,4-dihydro-2H-benzo[b][1,4]oxazin-6-yl | H | H | —C(ethyl)₂- | 1,3,4-triazol-2-yl |
| 23 | 8-trifluoromethyl-naphth-2-yl | H | H | —C(ethyl)₂-(Z)-CH= | oxazolidin-5-yl-2,4-dione |
| 24 | 1-ethyl-4-fluoro-indazol-6-yl | H | H | —C(ethyl)₂- | 1-methyl-1,3,4-triazol-5-yl |

TABLE 1-continued

Representative Compounds of Formula (I)

| ID No. | A | R¹ | R² | X | B |
|---|---|---|---|---|---|
| 25 | 4-ethyl-8-fluoro-3,4-dihydro-2H-benzo[b][1,4]oxazin-6-yl | H | H | —C(ethyl)₂-(E)-CH═ | pyrrolidin-3-yl-2-one |
| 26 | 1-ethyl-4-fluoro-indazol-6-yl | H | H | —C(ethyl)₂- | 1-methyl-1,3,4-triazol-5-yl |
| 27 | 1-ethyl-4-fluoro-indazol-6-yl | H | H | —C(ethyl)₂- | 1-methyl-1,2,4-triazol-3-yl |
| 28 | 2,2-dimethyl-2H-chromen-7-yl | H | H | —C(ethyl)₂-(Z)-CH═ | oxazolidin-5-yl-2,4-dione |
| 29 | 1-ethyl-4-fluoro-indazol-6-yl | H | H | —C(ethyl)₂- | isoxazol-3-yl |
| 30 | 1-ethyl-4-fluoro-indazol-6-yl | H | H | —C(ethyl)₂- | oxazol-2-yl |
| 31 | 1-ethyl-4-fluoro-indazol-6-yl | H | H | —C(ethyl)₂- | imidazol-2-yl |
| 32 | 6,8-difluoro-naphth-2-yl | H | H | —C(ethyl)₂-(E)-CH═ | oxazolidin-5-yl-2,4-dione |
| 33 | 6,8-difluoro-naphth-2-yl | H | H | —C(ethyl)₂- | 1,3,4-triazol-2-yl |
| 34 | 1-ethyl-3-methyl-indazol-6-yl | H | H | —C(ethyl)₂-(E)-CH═ | oxazolidin-5-yl-2,4-dione |
| 35 | 4-ethyl-3,4-dihydro-2H-benzo[b][1,4]oxazin-6-yl | H | H | —C(ethyl)₂-(E)-CH═ | oxazolidin-5-yl-2,4-dione |
| 36 | 1-ethyl-4-fluoro-indazol-6-yl | fluoro | H | —C(ethyl)₂- | 1,3,4-triazol-2-yl |
| 37 | 1-ethyl-4-fluoro-indazol-6-yl | fluoro | H | —C(ethyl)₂- | oxazol-2-yl |
| 38 | 1-ethyl-4-fluoro-indazol-6-yl | H | H | —C(ethyl)₂- | 5-isopropyl-1,3,4-oxadiazol-2-yl |
| 39 | 5,7-difluoro-naphth-2-yl | H | H | —C(ethyl)₂- | 1,3,4-triazol-2-yl |
| 40 | 1-ethyl-4-fluoro-indazol-6-yl | H | H | —C(ethyl)₂-CH₂— | pyrrolidin-3-yl-2-one |
| 41 | 1-ethyl-4-fluoro-indazol-6-yl | H | H | —C(ethyl)₂-CH₂— | oxazol-2-yl |
| 42 | 1-ethyl-4-fluoro-indazol-6-yl | H | H | —C(ethyl)₂- | 1,3,4-triazol-2-yl |
| 43 | 1-ethyl-5-methyl-indazol-6-yl | H | H | —C(ethyl)₂-(E)-CH═ | oxazolidin-5-yl-2,4-dione |
| 44 | 4-ethyl-3,4-dihydro-2H-benzo[b][1,4]oxazin-6-yl | H | H | —C(ethyl)₂-CH₂— | oxazolidin-5-yl-2,4-dione |

TABLE 1-continued

Representative Compounds of Formula (I)

| ID No. | A | R¹ | R² | X | B |
|---|---|---|---|---|---|
| 45 | 1-ethyl-4-fluoro-indazol-6-yl | H | H | —C(ethyl)₂— | 5-trifluoromethyl-1,3,4-oxadiazol-2-yl |
| 46 | 1-ethyl-4-fluoro-indazol-6-yl | fluoro | H | —C(ethyl)₂-CH₂— | 1,5-dihydro-2H-pyrrol-3-yl-2-one |
| 47 | 1-ethyl-4-fluoro-indazol-6-yl | fluoro | H | —C(ethyl)₂-(E)-CH= | pyrrolidin-3-yl-2-one |
| 48 | 1-ethyl-4-fluoro-indazol-6-yl | H | H | —C(ethyl)₂— | 5-(dimethylamino)-1,3,4-thiadiazol-2-yl |
| 49 | 8-ethyl-naphth-2-yl | H | H | —C(ethyl)₂-(E)-CH= | oxazolidin-5-yl-2,4-dione |
| 50 | 6,8-difluoro-naphth-2-yl | H | H | —C(ethyl)₂— | imidazol-2-yl |
| 51 | 1-ethyl-4-fluoro-indazol-6-yl | H | H | —C(ethyl)₂— | 5-amino-1,3,4-oxadiazol-2-yl |
| 52 | 1-ethyl-4-fluoro-indazol-6-yl | H | H | —C(ethyl)₂— | 5-amino-1,3,4-thiadiazol-2-yl |
| 53 | 1-ethyl-4-fluoro-indazol-6-yl | H | H | —C(ethyl)₂— | 5-ethyl-1,3,4-oxadiazol-2-yl |
| 54 | 1-ethyl-5-fluoro-indazol-6-yl | H | H | —C(ethyl)₂-(E)-CH= | oxazolidin-5-yl-2,4-dione |
| 55 | 1-ethyl-4-fluoro-indazol-6-yl | H | H | —C(ethyl)₂-(Z)-CH= | oxazolidin-5-yl-2,4-dione |
| 56 | 1-ethyl-4-fluoro-indazol-6-yl | H | H | —C(ethyl)₂-CH₂— | oxazolidin-5-yl-2,4-dione |
| 57 | 1-ethyl-4-fluoro-indazol-6-yl | H | H | —C(ethyl)₂— | 5-(dimethylamino)-1,3,4-oxadiazol-2-yl |
| 58 | 1-ethyl-4-fluoro-indazol-6-yl | H | H | —C(ethyl)₂-CH₂— | piperidin-3-yl-2-one |
| 59 | 8-fluoro-naphth-2-yl | H | H | -(syn)-CH(isopropyl)- | oxazolidin-5-yl-2,4-dione |
| 60 | 8-fluoro-naphth-2-yl | H | H | -(anti)-CH(isopropyl)- | oxazolidin-5-yl-2,4-dione |
| 61 | naphth-2-yl | H | H | —CH(isopropyl)- | 1,2,3,5-tetrazol-4-yl |
| 62 | 8-fluoro-naphth-2-yl | H | H | —CH(isopropyl)-(Z)-CH= | oxazolidin-5-yl-2,4-dione |
| 63 | 8-fluoro-naphth-2-yl | H | H | —CH(isopropyl)-(Z)-CH= | thiazolidin-5-yl-2,4-dione |
| 64 | 8-fluoro-naphth-2-yl | H | H | -(syn)-CH(isopropyl)-CH₂— | thiazolidin-5-yl-2,4-dione |
| 65 | 8-fluoro-naphth-2-yl | H | H | -(anti)-CH(isopropyl)-CH₂— | thiazolidin-5-yl-2,4-dione |
| 66 | 8-fluoro-naphth-2-yl | H | H | —CH(isopropyl)-CH₂— | morpholin-4-yl |
| 67 | 8-fluoro-naphth-2-yl | H | H | —CH(isopropyl)- | 4,5-dimethyl-imidazol-2-yl |
| 68 | 8-fluoro-naphth-2-yl | H | H | —CH(isopropyl)- | 2-amino-thiazol-5-yl |
| 69 | 8-fluoro-naphth-2-yl | H | H | —CH(isopropyl)- | 1-methyl-imidazolidin-5-yl-2,4-dione |

TABLE 1-continued

Representative Compounds of Formula (I)

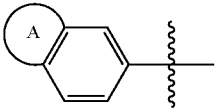

| ID No. | A | R¹ | R² | X | B |
|---|---|---|---|---|---|
| 70 | 8-fluoro-naphth-2-yl | H | H | —CH(isopropyl)-CH₂— | 1,2,3,5-tetrazol-4-yl |
| 71 | 8-fluoro-naphth-2-yl | H | H | —CH(isopropyl)- | thiazolidin-5-yl-2,4-dione |
| 72 | 8-fluoro-naphth-2-yl | H | H | —CH(isopropyl)-CH₂— | 1,2,4-oxadiazol-3-yl-5-one |
| 73 | 8-fluoro-naphth-2-yl | H | H | —CH(isopropyl)-CH₂— | 1-methyl-imidazolidin-5-yl-2,4-dione |
| 74 | 8-fluoro-naphth-2-yl | H | H | -(anti)-CH(isopropyl)-CH₂— | oxazolidin-5-yl-2,4-dione |
| 75 | 8-fluoro-naphth-2-yl | methyl | H | —CH(isopropyl)-(Z)-CH═ | oxazolidin-5-yl-2,4-dione |
| 76 | 8-fluoro-naphth-2-yl | H | H | —CH(isopropyl)- | imidazol-2-yl |
| 77 | 8-fluoro-naphth-2-yl | H | H | —CH(isopropyl)-CH₂— | oxazolidin-5-yl-2,4-dione |
| 78 | 8-fluoro-naphth-2-yl | H | H | —CH(R*-isopropyl)-(Z)-CH═ | oxazolidin-5-yl-2,4-dione |
| 79 | 8-fluoro-naphth-2-yl | H | H | —CH(S*-isopropyl)-(Z)-CH═ | oxazolidin-5-yl-2,4-dione |
| 80 | 8-fluoro-naphth-2-yl | H | H | —CH(isopropyl)-(E)-CH═ | 1-methyl-imidazolidin-5-yl-2,4-dione |
| 81 | 8-fluoro-naphth-2-yl | H | H | -(syn)-CH(isopropyl)-CH₂— | oxazolidin-5-yl-2,4-dione |
| 82 | 8-fluoro-naphth-2-yl | methyl | H | —CH(isopropyl)- | imidazol-2-yl |
| 83 | 8-fluoro-naphth-2-yl | bromo | H | —CH(isopropyl)-(Z)-CH═ | oxazolidin-5-yl-2,4-dione |
| 84 | 8-fluoro-naphth-2-yl | H | H | —CH(isopropyl)-(E)-C(methyl)═ | oxazolidin-5-yl-2,4-dione |
| 85 | 2,3-dihydrobenzo[b][1,4]dioxin-6-yl | H | H | —CH(isopropyl)-(Z)-CH═ | oxazolidin-5-yl-2,4-dione |
| 86 | 2-ethyl-4-methyl-2H-indazol-6-yl | H | H | —CH(isopropyl)-CH₂— | oxazolidin-5-yl-2,4-dione |
| 87 | 1-ethyl-4-fluoro-indazol-6-yl | H | H | —CH(isopropyl)-CH₂— | oxazolidin-5-yl-2,4-dione |
| 88 | 8-fluoro-naphth-2-yl | H | H | —CH(isopropyl)-(E)-CH═ | 1-methyl-imidazolidin-5-yl-2,4-dione |
| 89 | 8-fluoro-naphth-2-yl | H | H | —CH(isopropyl)-CH₂— | oxazolidin-5-yl-2,4-dione |
| 90 | 1-ethyl-4-fluoro-indazol-6-yl | H | H | —CH(isopropyl)-(Z)-CH═ | oxazolidin-5-yl-2,4-dione |
| 91 | 1-ethyl-7-fluoro-benzimidazol-6-yl | H | H | —CH(isopropyl)-(Z)-CH═ | oxazolidin-5-yl-2,4-dione |
| 92 | 8-fluoro-naphth-2-yl | H | H | —CH(cyclopentyl)-(Z)-CH═ | oxazolidin-5-yl-2,4-dione |
| 93 | benzo-isothiazol-6-yl | H | H | —CH(isopropyl)-(Z)-CH═ | oxazolidin-5-yl-2,4-dione |
| 94 | 1-ethyl-4-fluoro-indazol-6-yl | H | H | —CH(isopropyl)-(Z)-CH═ | oxazolidin-5-yl-2,4-dione |
| 95 | 8-fluoro-naphth-2-yl | H | H | —CH(isopropyl)- | 1,2,4-oxadiazol-3-yl-5-one |
| 96 | 8-fluoro-naphth-2-yl | H | H | —CH(isopropyl)-(Z)-C(methyl)═ | oxazolidin-5-yl-2,4-dione |

TABLE 1-continued

Representative Compounds of Formula (I)

| ID No. | A | R¹ | R² | X | B |
|---|---|---|---|---|---|
| 97 | 1-methyl-7-chloro-benzimidazol-5-yl | H | H | —CH(isopropyl)-(Z)-CH= | oxazolidin-5-yl-2,4-dione |
| 98 | 2-ethyl-4-methyl-2H-indazol-6-yl | H | H | —CH(isopropyl)-(Z)-CH= | oxazolidin-5-yl-2,4-dione |
| 99 | 1-ethyl-4-fluoro-indazol-6-yl | H | H | —CH(isopropyl)-CH= | 1,2,4-oxadiazol-3-yl-5-one |
| 100 | 8-fluoro-naphth-2-yl | H | H | —CH(isopropyl)-CH$_2$— | 1,2,4-oxadiazol-3-yl-5-one |
| 101 | 8-fluoro-naphth-2-yl | H | H | —CH(isopropyl)-CH$_2$— | 4-(methyl-sulfonyl)-piperazin-1-yl |
| 102 | 8-fluoro-naphth-2-yl | methyl | H | —CH(isopropyl)-(Z)-CH= | oxazolidin-5-yl-2,4-dione |
| 103 | 8-fluoro-naphth-2-yl | H | H | —CH(cyclopropyl)-(Z)-CH= | oxazolidin-5-yl-2,4-dione |
| 104 | 4-ethyl-3,4-dihydro-2H-benzo[b][1,4]oxazin-6-yl | H | H | —CH(isopropyl)-CH$_2$— | thiomorpholin-4-yl 1,1-dioxide |
| 105 | 8-fluoro-naphth-2-yl | H | H | —CH(n-pent-3-yl)-(E)-CH= | oxazolidin-5-yl-2,4-dione |
| 106 | 1-ethyl-4-fluoro-indazol-6-yl | H | H | —CH(isopropyl)-(Z)-CH= | oxazolidin-5-yl-2,4-dione |
| 107 | 1-methyl-7-chloro-benzimidazol-5-yl | H | H | —CH(isopropyl)-CH$_2$— | oxazolidin-5-yl-2,4-dione |
| 108 | 4-methyl-3,4-dihydro-2H-benzo[b][1,4]oxazin-6-yl | H | H | —CH(isopropyl)-(Z)-CH= | oxazolidin-5-yl-2,4-dione |
| 109 | 1-ethyl-4-fluoro-indazol-6-yl | H | H | —CH(isopropyl)-CH$_2$— | 4-(methyl-sulfonyl)-piperazin-1-yl |
| 110 | 2-ethyl-4-methyl-2H-indazol-6-yl | H | H | —CH(isopropyl)-CH$_2$— | oxazolidin-5-yl-2,4-dione |
| 111 | 1-ethyl-4-fluoro-indazol-6-yl | methyl | H | —CH(isopropyl)-(Z)-CH= | oxazolidin-5-yl-2,4-dione |
| 112 | 8-fluoro-naphth-2-yl | methyl | H | —CH(isopropyl)-(Z)-CH$_2$— | oxazolidin-5-yl-2,4-dione |
| 113 | 8-fluoro-naphth-2-yl | H | H | —CH(isopropyl)-(Z)-C(methyl)= | oxazolidin-5-yl-2,4-dione |
| 114 | 8-fluoro-naphth-2-yl | H | H | —CH(isopropyl)-(E)-C(methyl)= | oxazolidin-5-yl-2,4-dione |
| 115 | 8-fluoro-naphth-2-yl | H | H | —CH(isopropyl)-CH$_2$— | piperidin-1-yl-2-one |
| 116 | 1-ethyl-4-chloro-indazol-6-yl | H | H | —CH(isopropyl)-(Z)-CH= | oxazolidin-5-yl-2,4-dione |
| 117 | 8-fluoro-naphth-2-yl | H | H | —CH(benzyl)-(E)-CH= | oxazolidin-5-yl-2,4-dione |
| 118 | 1-methyl-indol-5-yl | H | H | —CH(isopropyl)-(Z)-CH= | oxazolidin-5-yl-2,4-dione |
| 119 | 8-fluoro-naphth-2-yl | H | H | —CH(isopropyl)-CH$_2$— | thiomorpholin-4-yl 1,1-dioxide |

TABLE 1-continued

Representative Compounds of Formula (I)

| ID No. | A | R¹ | R² | X | B |
|---|---|---|---|---|---|
| 120 | 2-ethyl-indazol-6-yl | H | H | —CH(isopropyl)-CH₂— | oxazolidin-5-yl-2,4-dione |
| 121 | 4-ethyl-3,4-dihydro-2H-benzo[b][1,4]oxazin-6-yl | H | H | —CH(isopropyl)-(Z)-CH= | oxazolidin-5-yl-2,4-dione |
| 122 | 1-isopropyl-4-fluoro-indazol-6-yl | H | H | —CH(isopropyl)-(Z)-CH= | oxazolidin-5-yl-2,4-dione |
| 123 | 8-fluoro-naphth-2-yl | H | H | —CH(phenyl)-(Z)-CH= | oxazolidin-5-yl-2,4-dione |
| 124 | 1-cyclopentyl-4-fluoro-indazol-6-yl | H | H | —CH(isopropyl)-(Z)-CH= | oxazolidin-5-yl-2,4-dione |
| 125 | 1-ethyl-4-fluoro-indazol-6-yl | chloro | H | —CH(isopropyl)-(Z)-CH= | oxazolidin-5-yl-2,4-dione |
| 126 | 1-ethyl-4-methyl-indazol-6-yl | H | H | —CH(isopropyl)-CH₂— | oxazolidin-5-yl-2,4-dione |
| 127 | 1-ethyl-4-fluoro-indazol-6-yl | H | H | —CH(cyclohexyl)-(E)-CH= | oxazolidin-5-yl-2,4-dione |
| 128 | 4-ethyl-3,4-dihydro-2H-benzo[b][1,4]oxazin-6-yl-3-one | H | H | —CH(isopropyl)-CH₂— | thiomorpholin-4-yl 1,1-dioxide |
| 129 | 4-ethyl-3,4-dihydro-2H-benzo[b][1,4]oxazin-6-yl | H | H | —CH(isopropyl)-CH₂— | thiomorpholin-4-yl 1,1-dioxide |
| 130 | 1-ethyl-4-fluoro-indazol-6-yl | H | H | —CH(cyclopentyl)-(E)-CH= | oxazolidin-5-yl-2,4-dione |
| 131 | 8-fluoro-naphth-2-yl | H | H | —CH(isopropyl)- | 5-methyl-imidazol-2-yl |
| 132 | 8-fluoro-naphth-2-yl | H | H | —CH(isopropyl)- | imidazolidin-5-yl-2,4-dione |
| 133 | 1-ethyl-4-fluoro-indazol-6-yl | H | H | —CH(isopropyl)-CH₂— | thiomorpholin-4-yl 1,1-dioxide |
| 134 | 8-fluoro-naphth-2-yl | H | H | —CH(cyclohexyl)-(Z)-CH= | oxazolidin-5-yl-2,4-dione |
| 135 | 8-isopropyl-naphth-2-yl | H | H | —CH(isopropyl)-(Z)-CH= | oxazolidin-5-yl-2,4-dione |
| 136 | 8-fluoro-naphth-2-yl | chloro | H | —CH(isopropyl)-(Z)-CH= | oxazolidin-5-yl-2,4-dione |
| 137 | 4-ethyl-3,4-dihydro-2H-benzo[b][1,4]oxazin-6-yl | H | H | —CH(isopropyl)-CH= | oxazolidin-5-yl-2,4-dione |
| 138 | 8-fluoro-naphth-2-yl | H | H | —CH(isopropyl)- | 1,2,4-triazol-5-yl- |
| 139 | 8-fluoro-naphth-2-yl | H | H | —CH(isopropyl)-CH₂— | 1,2,4-triazol-5-yl- |
| 140 | 8-fluoro-naphth-2-yl | H | H | —CH(isopropyl)-CH₂— | imidazol-2-yl |
| 141 | 8-ethyl-naphth-2-yl | H | H | —CH(isopropyl)-(Z)-CH= | oxazolidin-5-yl-2,4-dione |
| 142 | 8-cyano-naphth-2-yl | H | H | —CH(isopropyl)-(Z)-CH= | oxazolidin-5-yl-2,4-dione |

TABLE 1-continued

Representative Compounds of Formula (I)

| ID No. | A | R¹ | R² | X | B |
|---|---|---|---|---|---|
| 143 | 8-trifluoromethyl-naphth-2-yl | H | H | —CH(isopropyl)-(Z)-CH= | oxazolidin-5-yl-2,4-dione |
| 144 | 8-fluoro-naphth-2-yl | H | H | -(syn)-CH(S-isopropyl)-CH₂— | R-pyrrolidin-3-yl-2-one |
| 145 | 8-fluoro-naphth-2-yl | H | H | -(anti)-CH(S-isopropyl)-CH₂— | S-pyrrolidin-3-yl-2-one |
| 146 | 1-ethyl-4-fluoro-indazol-6-yl | H | H | —CH(isopropyl)-CH₂— | 3-methyl-pyrrolidin-3-yl-2-one |
| 147 | 1-ethyl-4-fluoro-indazol-6-yl | H | H | -(syn)-CH(S-isopropyl)-CH₂— | R-pyrrolidin-3-yl-2-one |
| 148 | 1-ethyl-4-fluoro-indazol-6-yl | H | H | -(anti)-CH(S-isopropyl)-CH₂— | S-pyrrolidin-3-yl-2-one |
| 149 | 8-fluoro-naphth-2-yl | H | H | —CH(isopropyl)-(E)-CH= | pyrrolidin-3-yl-2-one |
| 150 | 8-fluoro-naphth-2-yl | H | H | —CH(isopropyl)-(Z)-CH= | pyrrolidin-3-yl-2-one |
| 151 | 1-ethyl-4-fluoro-indazol-6-yl | H | H | —CH(isopropyl)-CH₂— | pyrrolidin-3-yl-2-one |
| 154 | 8-fluoro-naphth-2-yl | H | H | —CH(isopropyl)- | imidazolidin-1-yl-2-one |
| 157 | 8-fluoro-naphth-2-yl | H | H | —CH(isopropyl)- | 2-(imino)-thiazol-3-yl |
| 158 | 8-fluoro-naphth-2-yl | H | H | —CH(isopropyl)-NH— | thiazol-2-yl |
| 159 | 8-fluoro-naphth-2-yl | H | H | —CH(isopropyl)-NH— | 1,3,4-triazol-2-yl |
| 160 | 8-fluoro-naphth-2-yl | H | H | —CH(isopropyl)- | 2-amino-1,3,4-triazol-1-yl |
| 161 | 8-fluoro-naphth-2-yl | H | H | —CH(isopropyl)- | 3-amino-1,2,4-triazol-1-yl |
| 162 | 8-fluoro-naphth-2-yl | H | H | —CH(isopropyl)- | 2-amino-imidazol-1-yl |
| 163 | 8-fluoro-naphth-2-yl | H | H | —CH(isopropyl)- | 1,2-thiazinan-2-yl-1,1-dioxide |
| 164 | 4-ethyl-3,4-dihydro-2H-benzo[b][1,4]oxazin-6-yl | H | H | —CH(isopropyl)- | thiomorpholin-4-yl |
| 165 | 8-fluoro-naphth-2-yl | H | H | —CH(isopropyl)-NH—SO₂— | cyclohexyl |
| 166 | 8-fluoro-naphth-2-yl | H | H | —CH(isopropyl)- | piperidin-1-yl-2-one |
| 168 | 1-ethyl-4-fluoro-indazol-6-yl | H | H | —CH(isopropyl)- | thiomorpholin-4-yl-1,1-dioxide |
| 169 | 4-ethyl-3,4-dihydro-2H-benzo[b][1,4]oxazin-6-yl | H | H | —CH(isopropyl)- | thiomorpholin-4-yl-1,1-dioxide |
| 170 | 8-fluoro-naphth-2-yl | H | H | —CH(isopropyl)- | 2-(cyanoimino)-imidazolidin-1-yl |
| 171 | 1-ethyl-4-fluoro-indazol-6-yl | H | H | —CH(isopropyl)- | 1,2,3,4-tetrazol-1-yl |
| 172 | 1-ethyl-4-fluoro-indazol-6-yl | H | H | —CH(isopropyl)- | 1,3,4-triazol-1-yl |

TABLE 1-continued

Representative Compounds of Formula (I)

| ID No. | A | R¹ | R² | X | B |
|---|---|---|---|---|---|
| 173 | 8-fluoro-naphth-2-yl | H | H | —CF(isopropyl)-C(O)—NH—SO₂— | 3,5-difluoro-phenyl |
| 174 | 8-fluoro-naphth-2-yl | H | H | —CH(isopropyl)-C(O)—NH— | tetrahydro-pyran-4-yl |
| 175 | 8-fluoro-naphth-2-yl | H | H | —CH(isopropyl)-C(O)—NH—SO₂— | 4,5-dichloro-thien-2-yl |
| 176 | 8-fluoro-naphth-2-yl | H | H | —CH(isopropyl)-C(O)—NH— | thiazol-2-yl |
| 177 | 8-fluoro-naphth-2-yl | H | H | —CH(isopropyl)-C(O)—NH— | azetidin-3-yl |
| 178 | 8-fluoro-naphth-2-yl | H | H | —CH(isopropyl)-C(O)—NH— | pyrrolidin-3-yl |
| 179 | 8-fluoro-naphth-2-yl | H | H | —CH(isopropyl)-C(O)—NH— | tetrahydro-thiopyran-4-yl-1,1-dioxide |
| 180 | 8-fluoro-naphth-2-yl | H | H | —CH(isopropyl)-C(O)—NH— | pyridin-3-yl |
| 181 | 8-fluoro-naphth-2-yl | H | H | —CH(isopropyl)-C(O)—NH— | 1-methyl-benzimidazol-5-yl |
| 182 | 8-fluoro-naphth-2-yl | H | H | —CH(isopropyl)-C(O)—NH— | 1-methyl-azetidin-3-yl |
| 183 | 8-fluoro-naphth-2-yl | H | H | —CH(isopropyl)-C(O)—NH— | tetrahydro-thiopyran-4-yl |
| 184 | 8-fluoro-naphth-2-yl | H | H | —CH(isopropyl)-C(O)—NH— | 1-(methyl-sulfonyl)-piperidin-4-yl |
| 252 | 8-fluoro-naphth-2-yl | H | H | —CH₂— | oxazolidin-5-yl-2,4-dione |
| 254 | 8-fluoro-naphth-2-yl | H | H | —CH(isopropyl)-CH₂—C(O)—NH— | thiazol-2-yl |
| 256 | 8-fluoro-naphth-2-yl | H | H | —CH(isopropyl)-CH₂—C(O)—NH—SO₂— | 4,5-dichloro-thien-2-yl |
| 261 | 8-fluoro-naphth-2-yl | H | H | —CH(isopropyl)-CH₂—C(O)—NH— | imidazol-2-yl |
| 262 | 8-fluoro-naphth-2-yl | H | H | —CH₂— | 5-isopropyl-imidazolidin-5-yl-2,4-dione |
| 263 | 8-fluoro-naphth-2-yl | H | H | —CH₂— | 5-isopropyl-oxazolidin-5-yl-2,4-dione |
| 264 | 8-fluoro-naphth-2-yl | H | H | —CH(isopropyl)- | imidazolidin-5-yl-2,4-dione |
| 270 | 8-fluoro-naphth-2-yl | H | H | —CH₂—CH(isopropyl)- | 1,2,3,4-tetrazol-5-yl |
| 271 | 1-ethyl-4-fluoro-indazol-6-yl | H | H | —C(ethyl)₂- | 5-methyl-1,3,4-oxadiazol-2-yl |
| 272 | 8-fluoro-naphth-2-yl | chloro | H | —CH₂—CH(isopropyl)- | 1,2,4-oxadiazol-3-yl-5-one |
| 273 | 8-fluoro-naphth-2-yl | H | H | —CH(isopropyl)-CH₂—SO₂— | cyclohexyl |
| 274 | 8-fluoro-naphth-2-yl | H | H | —CH(isopropyl)-(Z)-CH= | oxazolidin-5-yl-2,4-dione |
| 275 | 8-fluoro-naphth-2-yl | H | H | —CH(t-butyl)-(E)-CH= | oxazolidin-5-yl-2,4-dione |
| 276 | 2,2-difluoro-benzo[d][1,3]dioxol-5-yl | H | H | —CH(isopropyl)-(Z)-CH= | oxazolidin-5-yl-2,4-dione |
| 277 | 1-ethyl-4-fluoro-1H-indazol-6-yl | H | H | —CH(isopropyl)- | 1,2,4-oxadiazol-3-yl-5-one |

TABLE 1-continued

Representative Compounds of Formula (I)

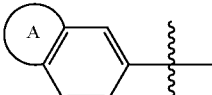

| ID No. | A | R¹ | R² | —X⋯ | B |
|---|---|---|---|---|---|
| 278 | 4-ethyl-3,4-dihydro-2H-benzo[b][1,4]oxazin-6-yl | H | H | —CH(isopropyl)- | 1,2,4-oxadiazol-3-yl-5-one |
| 279 | 6,8-difluoro-naphth-2-yl | H | H | —C(ethyl)₂- | 1,3,4-triazol-2-yl- |
| 280 | naphth-2-yl | H | H | —CH(-carbonyl-oxy-ethyl)- | cyclohex-1-en-1-yl |
| 281 | naphth-2-yl | H | H | —C(-carbonyl-oxy-ethyl)= | cyclohexyl |
| 303 | 8-fluoro-naphth-2-yl | H | H | -(Z)-C(isopropyl)= | oxazolidin-5-yl-2,4-dione |
| 304 | 8-fluoro-naphth-2-yl | H | H | -(E)-C(isopropyl)= | oxazolidin-5-yl-2,4-dione |
| 305 | 8-fluoro-naphth-2-yl | H | H | -(E)-C(isopropyl)= | thiazolidin-5-yl-2,4-dione |
| 306 | 8-fluoro-naphth-2-yl | H | H | —CH₂-(E)-C(isopropyl)= | oxazolidin-5-yl-2,4-dione |
| 307 | 8-fluoro-naphth-2-yl | H | H | —CH₂—CH(isopropyl)- | imidazol-2-yl |
| 308 | 8-fluoro-naphth-2-yl | H | H | —CH₂—CH(isopropyl)- | oxazolidin-5-yl-2,4-dione |
| 309 | 8-fluoro-naphth-2-yl | H | H | —CH₂—CH(isopropyl)- | 1,3,4-triazol-2-yl |
| 310 | 8-cyano-naphth-2-yl | H | H | —CH(isopropyl)-(E)-CH= | oxazolidin-5-yl-2,4-dione |

TABLE 2

Representative Compounds of Formula (II)

| ID No. | C | R³ | R⁴ | R⁵ | D |
|---|---|---|---|---|---|
| 152 | naphth-2-yl | H | H | methyl | imidazo[2,1-c][1,2,4]triazol-5-yl-6-one |
| 153 | naphth-2-yl | H | H | methyl | imidazo[1,2-a]imidazol-3-yl-2-one |
| 155 | 8-fluoro-naphth-2-yl | H | H | isopropyl | imidazo[1,2-a]imidazol-3-yl-2-one |
| 156 | 8-fluoro-naphth-2-yl | H | H | isopropyl | imidazo[2,1-c][1,2,4]triazol-5-yl-6-one |
| 167 | naphth-2-yl | H | H | methyl | 6,7-dihydro-5H-imidazo[2,1-c][1,2,4]triazol-6-yl |
| 185 | naphth-2-yl | H | H | H | 3-cyano-3-(aminocarbonyloxy)-cyclohex-1-yl |

TABLE 2-continued

Representative Compounds of Formula (II)

| ID No. | C | R³ | R⁴ | R⁵ | D |
|---|---|---|---|---|---|
| 186 | naphth-2-yl | H | H | H | 1-(methyl-sulfonyl)-piperidin-4-yl |
| 187 | naphth-2-yl | H | H | H | 4,5,6,7-tetrahydro-benzo[d]isoxazol-5-yl |
| 188 | naphth-2-yl | H | H | H | (anti)-1-oxa-3-azaspiro[4.5]decan-7-yl-2,4-dione |
| 189 | naphth-2-yl | H | H | H | (syn)-1-oxa-3-azaspiro[4.5]decan-7-yl-2,4-dione |
| 190 | naphth-2-yl | H | H | H | 1-(ethyl-sulfonyl)-piperidin-4-yl |
| 191 | naphth-2-yl | H | H | H | 1λ²,3-diazaspiro[4.5]decan-7-yl-2,4-dione |
| 192 | naphth-2-yl | H | H | H | tetrahydro-pyran-4-yl |
| 194 | naphth-2-yl | H | H | H | piperidin-4-yl |
| 195 | naphth-2-yl | H | H | H | 4,5,6,7-tetrahydro-2H-indazol-5-yl |
| 196 | 1-ethyl-4-fluoro-indazol-6-yl | H | H | H | 2-azaspiro[5.5]undecan-9-yl-1-one |
| 197 | naphth-2-yl | H | H | H | 1-(hydroxymethyl-carbonyl)-piperidin-4-yl |
| 198 | 1-ethyl-4-fluoro-indazol-6-yl | H | H | H | 1-(isopropyl-sulfonyl)-piperidin-4-yl |
| 199 | 6-fluoro-naphth-2-yl | H | H | H | 1-(isopropyl-sulfonyl)-piperidin-4-yl |
| 200 | naphth-2-yl | H | H | H | 1-(isopropyl-sulfonyl)-piperidin-4-yl |
| 201 | naphth-2-yl | H | H | H | 3-(aminocarbonyl)-3-hydroxy-cyclohex-1-yl |
| 203 | naphth-2-yl | H | H | H | 1,3-diazaspiro[4.5]decan-8-yl-2,4-dione |
| 204 | 1-ethyl-4-fluoro-indazol-6-yl | H | H | H | 3-(isopropyl-sulfonyl)-3-azaspiro[5.5]undecan-9-yl |
| 205 | 1-ethyl-4-fluoro-indazol-6-yl | H | H | H | 2-(isopropyl-sulfonyl)-octahydro-cyclopenta[c]pyrrol-5-yl |
| 206 | 1-ethyl-4-fluoro-indazol-6-yl | H | H | H | 8-(isopropyl-sulfonyl)-8-azabicyclo[3.2.1]octan-3-yl |
| 207 | 1-ethyl-4-fluoro-indazol-6-yl | H | H | H | 2-azaspiro[4.5]decan-8-yl-1-one |
| 208 | 1-ethyl-4-fluoro-indazol-6-yl | H | H | H | 8-(isopropyl-amino-carbonyl)-8-azabicyclo[3.2.1]octan-3-yl |
| 209 | 1-ethyl-4-fluoro-indazol-6-yl | H | H | H | 1-(isopropyl-amino-carbonyl)-octahydro-cyclopenta[c]pyrrol-5-yl |
| 210 | 1-ethyl-4-fluoro-indazol-6-yl | H | H | H | 1-(1-(cyanoimino)-1-(isopropylamino)methyl)-octahydro-cyclopenta[c]pyrrol-5-yl |
| 211 | 1-ethyl-4-fluoro-indazol-6-yl | H | H | H | 1-(isopropyl-sulfonyl)-piperidin-3-yl |
| 213 | 1-ethyl-4-fluoro-indazol-6-yl | H | H | H | 1-(isopropyl-sulfonyl)-pyrrolidin-3-yl |
| 214 | 1-ethyl-4-fluoro-indazol-6-yl | H | H | H | 1-(isopropyl-sulfonyl)-azetidin-3-yl |
| 215 | 1-ethyl-4-fluoro-indazol-6-yl | H | H | H | tetrahydro-1H,3H-pyrrolo[1,2-c]oxazol-6-yl-3-one |
| 219 | naphth-2-yl | H | H | amino-carbonyl | cyclopentyl |

TABLE 2-continued

Representative Compounds of Formula (II)

| ID No. | C | R³ | R⁴ | R⁵ | D |
|---|---|---|---|---|---|
| 222 | naphth-2-yl | H | H | methyl | 3,5-dihydro-imidazol-5-yl-4-one |
| 223 | naphth-2-yl | H | H | methyl | 2-methyl-3,5-dihydro-imidazol-5-yl-4-one |
| 236 | 8-fluoro-naphth-2-yl | H | H | isopropyl | 1,5-dihydro-2-(cyanoamino)-imidazol-5-yl-4-one |
| 237 | 8-fluoro-naphth-2-yl | H | H | isopropyl | (Z)-2-(methoxyimino)-imidazolidin-5-yl-4-one |
| 247 | naphth-2-yl | H | H | amino-carbonyl- | 4,5-dihydro-pyrazol-5-yl |
| 248 | 1-ethyl-4-fluoro-indazol-6-yl | H | H | isopropyl | morpholin-2-yl-3-one |
| 282 | naphth-2-yl | H | H | methyl | 1,2,5-thiadiazolidin-3-yl-1,1-dioxide |
| 283 | naphth-2-yl | H | H | methyl | 2-(cyanoimino)-imidazolidin-4-yl |
| 285 | naphth-2-yl | H | H | methyl | 2-(methoxyimino)-imidazolidin-4-yl |
| 286 | naphth-2-yl | H | H | methyl | imidazolidin-5-yl-2-thione |
| 287 | naphth-2-yl | H | H | methyl | 2-imino-imidazolidin-4-yl |
| 288 | naphth-2-yl | H | H | methyl | 2-(hydroxyimino)-imidazolidin-4-yl |
| 289 | naphth-2-yl | H | H | methyl | 2-(dimethylamino)-4,5-dihydro-imidazol-4-yl |
| 290 | naphth-2-yl | H | H | methyl | 2-(methyl-sulfonyl-amino)-4,5-dihydro-imidazol-5-yl |
| 291 | 8-fluoro-naphth-2-yl | H | H | isopropyl | 2-(cyanoimino)-4,5-dihydro-imidazol-5-yl |
| 292 | 8-fluoro-naphth-2-yl | H | H | isopropyl | (Z)-2-(methoxyimino)-imidazolidin-4-yl |
| 293 | 8-fluoro-naphth-2-yl | H | H | isopropyl | (E)-2-(methoxyimino)-imidazolidin-4-yl |
| 294 | 8-fluoro-naphth-2-yl | H | H | isopropyl | 5-oxo-2-thioxo-imidazolidin-4-yl |
| 295 | 1-ethyl-4-fluoro-indazol-6-yl | H | H | hydroxy | 1-(isopropyl-sulfonyl)-piperidin-3-yl |
| 296 | 1-ethyl-4-fluoro-indazol-6-yl | H | H | fluoro | 1-(isopropyl-sulfonyl)-piperidin-3-yl |
| 297 | 1-ethyl-4-fluoro-indazol-6-yl | H | H | H | 1-(isopropyl-sulfonyl)-4,5-dihydro-pyrrol-3-yl |
| 298 | 1-ethyl-4-fluoro-indazol-6-yl | H | H | hydroxy | 1-(isopropyl-sulfonyl)-azetidin-3-yl |
| 299 | 1-ethyl-4-fluoro-indazol-6-yl | H | H | H | 7-oxo-6-oxabicyclo[3.2.1]octan-5-yl |
| 300 | 1-ethyl-4-fluoro-indazol-6-yl | H | H | hydroxy | 6-azabicyclo[3.2.1]octan-4-yl-7-one |

TABLE 3

Representative Compounds of Formula (III)

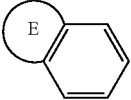

| ID No. | E | R⁶ | R⁷ | Y | Z |
|---|---|---|---|---|---|
| 216 | 8-fluoro-naphth-2-yl | H | H | —C(F)(isopropyl)- | —C(O)—NH₂ |
| 217 | naphth-2-yl | H | H | —C(F)(isopropyl)- | —C(O)—NH₂ |
| 218 | naphth-2-yl | H | H | —C(OH)(isopropyl)- | —C(O)—NH₂ |
| 220 | naphth-2-yl | H | H | —CH(isopropyl)- | —C(O)—NH₂ |
| 221 | naphth-2-yl | H | H | —CH(isopropyl)- | —C(O)—NH—SO₂—CH₃ |
| 224 | naphth-2-yl | H | H | —C(F)(isopropyl)- | —C(O)—NH—SO₂—CH₃ |
| 225 | 4-methyl-3,4-dihydro-2H-benzo[b][1,4]oxazin-7-yl | H | H | —C(OH)(isopropyl)- | —C(O)—NH₂ |
| 226 | naphth-2-yl | H | H | —CH(cyclohexen-1-yl) | —C(O)—NH₂ |
| 227 | 8-fluoro-naphth-2-yl | H | H | —CH(isopropyl)- | —C(O)—NH—CH₂CH₂—N(CH₃)₂ |
| 228 | 8-fluoro-naphth-2-yl | H | H | —CH(isopropyl)- | —C(O)—NH(OCH₃) |
| 229 | 8-fluoro-naphth-2-yl | H | H | —CH(isopropyl)- | —C(O)—NH—CH₂CH₂O—CH₂CH₂O—CH₂CH₂—N(CH₃)₂ |
| 230 | 8-fluoro-naphth-2-yl | H | H | —CH(isopropyl)- | —C(O)—NH(CH(CH₂OH)₂) |
| 231 | 8-fluoro-naphth-2-yl | H | H | —CH(isopropyl)- | —C(O)—NH(C(CH₂OH)₃) |
| 232 | naphth-2-yl | H | H | —C(methyl)(isopropyl)- | —C(O)—NH₂ |
| 233 | 8-fluoro-naphth-2-yl | H | H | —CH(isopropyl)- | —C(O)—NH—CH₂CH₂O—CH₂CH₂—N(CH₃)₂ |
| 234 | 8-fluoro-naphth-2-yl | H | H | —CH(isopropyl)- | —C(O)—NH—CH₂CH₂—OH |
| 238 | 8-fluoro-naphth-2-yl | H | H | —CH(isopropyl)- | —C(O)—NH—CH₂CH₂O—CH₂CH₂O—CH₂CH₂O—CH₃ |
| 239 | 8-fluoro-naphth-2-yl | H | H | —CH(isopropyl)- | —C(O)—NH(isopropyl) |
| 241 | 6-methoxy-naphth-2-yl | H | H | —CH(isopropyl)- | —C(O)—NH—CH₂CH₂—N(CH₃)₂ |
| 242 | 6-fluoro-naphth-2-yl | H | H | —CH(isopropyl)- | —C(O)—NH—CH₂CH₂—N(CH₃)₂ |
| 243 | benzothiazol-5-yl | H | H | —CH(isopropyl)- | —C(O)—NH—CH₂CH₂—N(CH₃)₂ |
| 244 | 4-methyl-3,4-dihydro-2H-benzo[b][1,4]oxazin-7-yl | H | H | —CH(isopropyl)- | —C(O)—NH—CH₂CH₂—N(CH₃)₂ |
| 246 | benzothiazol-6-yl | H | H | —CH(isopropyl)- | —C(O)—NH—CH₂CH₂—N(CH₃)₂ |
| 249 | naphth-2-yl | H | H | —CH(isopropyl)-CH₂— | —C(O)—NH₂ |
| 250 | naphth-2-yl | H | H | —CH(isopropyl)-CH₂— | —C(O)—NH—SO₂—CH₃ |
| 251 | 8-fluoro-naphth-2-yl | H | H | —CH(isopropyl)-CH₂— | —C(O)—NH₂ |
| 253 | 8-fluoro-naphth-2-yl | H | H | —CH₂—CH(isopropyl)- | —C(O)—NH₂ |
| 255 | 8-fluoro-naphth-2-yl | H | H | —C(OH)(isopropyl)- | —C(O)—NH₂ |
| 257 | 8-fluoro-naphth-2-yl | H | H | —CH(isopropyl)-CH₂— | —C(O)—NH(OCH₃) |
| 258 | 8-fluoro-naphth-2-yl | H | H | —CH(isopropyl)-CH₂— | —C(O)—NH—CH₂CH₂—OH |
| 259 | 8-fluoro-naphth-2-yl | H | H | —CH(isopropyl)-CH₂— | —C(O)—NH—CH₂CH₂—N(CH₃)₂ |

TABLE 3-continued

Representative Compounds of Formula (III)

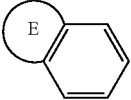

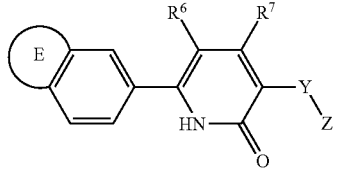

| ID No. | E | R⁶ | R⁷ | Y | Z |
|---|---|---|---|---|---|
| 260 | 8-fluoro-naphth-2-yl | H | H | —CH(isopropyl)-CH₂— | —C(O)—NH(isopropyl)- |
| 265 | 8-fluoro-naphth-2-yl | H | H | —CH(isopropyl)- | —N(CH₃)—C(O)—NH₂ |
| 266 | 8-fluoro-naphth-2-yl | H | H | —CH(isopropyl)- | —NH—C(O)—NH—CH₂CH₂—N(CH₃)₂ |
| 267 | 8-fluoro-naphth-2-yl | H | H | —CH(isopropyl)- | —NH—C(O)—NH₂ |
| 268 | 8-fluoro-naphth-2-yl | H | H | —CH(isopropyl)- | —NH-(E)—C(NH₂)=N—CN |
| 302 | 4-methyl-3,4-dihydro-benzo[b][1,4]oxazin-6-yl | H | H | —CH(isopropyl)- | —C(O)-NH—CH₂CH₂—N(CH₃)₂ |

In an embodiment, the present invention is directed to a compound of formula (I) selected from the group consisting of 6-(1-ethyl-4-fluoro-indazol-6-yl)-3-[1-ethyl-1-(1H-tetrazol-5-yl)propyl]-1H-pyridin-2-one, Compound #3;

6-(1-ethyl-4-fluoro-indazol-6-yl)-3-[1-ethyl-1-(4H-1,2,4-triazol-3-yl)propyl]-1H-pyridin-2-one, Compound #5;

(5E)-5-[2-ethyl-2-[6-(8-fluoro-2-naphthyl)-2-oxo-1H-pyridin-3-yl]butylidene]oxazolidine-2,4-dione, Compound #6;

6-(1-ethyl-4-fluoro-indazol-6-yl)-3-[1-ethyl-1-[(E)-(2-oxopyrrolidin-3-ylidene)methyl]propyl]-1H-pyridin-2-one, Compound #16;

6-(1-ethyl-4-fluoro-indazol-6-yl)-3-[1-ethyl-1-(5-methyl-4H-1,2,4-triazol-3-yl)propyl]-1H-pyridin-2-one, Compound #21;

6-(1-ethyl-4-fluoro-indazol-6-yl)-3-(1-ethyl-1-oxazol-2-yl-propyl)-1H-pyridin-2-one, Compound #30;

6-(1-ethyl-4-fluoro-indazol-6-yl)-3-[1-ethyl-1-(1H-imidazol-2-yl)propyl]-1H-pyridin-2-one, Compound #31;

(5Z)-5-[2-ethyl-2-[6-(1-ethyl-4-fluoro-indazol-6-yl)-2-oxo-1H-pyridin-3-yl]butylidene]oxazolidine-2,4-dione, Compound #55;

(5Z)-5-[2-[6-(8-fluoro-2-naphthyl)-2-oxo-1H-pyridin-3-yl]-3-methyl-butylidene]oxazolidine-2,4-dione, Compound #62;

(5Z)-5-[2-[6-(8-fluoro-2-naphthyl)-5-methyl-2-oxo-1H-pyridin-3-yl]-3-methyl-butylidene]oxazolidine-2,4-dione, Compound #75;

and tautomers and pharmaceutically acceptable salts thereof.

In certain embodiments, the present invention is directed to a compound of formula (I), compounds of formula (II) and/or compounds of formula (III); wherein the compound has a measured $K_i$ (nM) according to the EP3 competition binding assay procedure taught in Biological Example 1, which follows herein, or less than about 500 nM, preferably less than about 250 nM, more preferably less than about 100 nM, more preferably less than about 50 nM, more preferably less than about 25 nM, more preferably less than about 10 nM, more preferably less than about 5 nM, more preferably less than about 2 nM.

Definitions

As used herein, unless otherwise noted, "halogen" shall mean chlorine, bromine, fluorine and iodine. Preferably, the halogen is fluorine, chlorine or bromine, more preferably fluorine.

As used herein when referring to a substituent group, unless otherwise noted, the term "oxo" shall mean a double bonded oxygen group, i.e. a substituent group of the formula =O.

As used herein, unless otherwise noted, the term "thioxo" shall mean a double bonded sulfur group, i.e. a substituent group of the formula =S.

As used herein, unless otherwise noted, the term "imino" shall mean a double bonded nitrogen group, i.e. a substituent group of the formula =NH. One skilled in the art will recognize that wherein said nitrogen atom is substituted, the corresponding group shall be named as a substituted imino. For example, a substituent group of the formula =N—CN shall be referred to herein as cyanoimino, a substituent group of the formula =N—OH shall be referred to herein as hydroxyimino, a substituent group of the formula =N—OCH₃ shall be referred to herein as methoxyimino, etc.

As used herein, unless otherwise noted, the term "$C_{X-Y}$alkyl" wherein X and Y are integers, whether used alone or as part of a substituent group, shall include straight and branched chains of between X and Y carbon atoms. For example, $C_{1-4}$alkyl shall include straight and branched chains of between one and four carbon atoms including methyl, ethyl, propyl, isopropyl, butyl, isobutyl, sec-butyl and t-butyl.

One skilled in the art will recognize that the terms "—(C$_{X-Y}$alkyl)-" and "—C$_{X-Y}$alkyl-" wherein X and Y are integers, shall denote any C$_{X-Y}$alkyl carbon chain as herein defined, wherein said C$_{X-Y}$alkyl chain is divalent and is further bound through two points of attachment, preferably through two terminal carbon atoms.

As used herein, unless otherwise noted, the term "fluorinated C$_{X-Y}$alkyl" wherein X and Y are integers, shall mean any C$_{X-Y}$alkyl group as defined above substituted with at least one fluoro atom, preferably one to three fluoro atoms. Suitable examples include but are not limited to —CF$_3$, —CH$_2$—CF$_3$, —CF$_2$—CF$_2$—CF$_2$—CF$_3$, and the like.

As used herein, unless otherwise noted, "C$_{X-Y}$alkoxy" wherein X and Y are integers, whether used alone or as part of a substituent group, shall denote an oxygen ether radical of the above described C$_{X-Y}$alkyl straight or branched chain alkyl group. For example, C$_{1-4}$alkoxy shall include oxygen ether radicals of straight and branched alkyl chains of between one and four carbon atoms including methoxy, ethoxy, n-propoxy, iso-propoxy, n-butoxy, sec-butoxy and t-butoxy.

As used herein, unless otherwise noted, the term "fluorinated C$_{X-Y}$alkoxy" wherein X and Y are integers, shall denote an oxygen ether radical as defined described, substituted with at least one fluoro atom, preferably one to three fluoro atoms. Suitable examples include but are not limited to —OCF$_3$, —OCH$_2$—CF$_3$, —OCF$_2$—CF$_2$—CF$_2$—CF$_3$, and the like.

As used herein, unless otherwise noted, the term "C$_{X-Y}$cycloalkyl" wherein X and Y are integers, shall mean any stable monocyclic, bicyclic, polycyclic or bridged, saturated ring system consisting of between X and Y carbon atom. For example, the term C$_{3-6}$cycloalkyl shall include cyclopropyl, cyclobutyl, cyclopentyl and cyclohexyl.

As used herein, unless otherwise noted, the term "C$_{X-Y}$cycloalkenyl" wherein X and Y are integers, shall mean any stable monocyclic, bicyclic, polycyclic or bridged, partially unsaturated ring system consisting of between X and Y carbon atom. For example, the term C$_{3-6}$cycloalkenyl shall include cyclopropenyl, cyclobutenyl, cyclopentenyl, cyclohexenyl, and the like.

The term "four to six membered monocyclic heterocyclyl" shall denote any four or six membered monocyclic ring structure, wherein the ring structure may be saturated, partially unsaturated or aromatic, and wherein the ring structure contains at least one heteroatom selected from the group consisting of O, N and S, optionally containing one to three additional heteroatoms independently selected from the group consisting of O, N and S. The four to six membered monocyclic heterocyclyl group may be attached at any heteroatom or carbon atom of the ring such that the result is a stable structure. Suitable examples of four to six membered monocyclic heterocyclylgroups include, but are not limited to azetidinyl, pyrrolidinyl, pyrrolinyl, furanyl, thienyl, pyrrolyl, isopuyrrolyl, pyrazlyl, imidazolyl, isoimidazolyl, triazolyl, tetrazolyl, oxazolyl, isoxazolyl, thiazolyl, isothiazolyl, oxadiazolyl, dioxazolyl, pyranyl, pyridinyl, pyridazinyl, pyrimidinyl, dioxalanyl, imidazolinyl, imidazolidinyl, pyrazolinyl, pyrazolidinyl, pyrazinyl, piperidinyl, piperazinyl, morpholinyl, thiomorpholinyl, tetrahydropyranyl, tetrahydrothiopyranyl, thiazinanyl, triazinyl, oxazinyl, isoxazinyl, and the like.

Preferably, the four to six membered monocyclic heterocyclyl is selected from the group consisting of azetidinyl, pyrrolidinyl, piperidinyl, piperazinyl, morpholinyl, thiomorpholinyl, tetrahydropyranyl, thiopyranyl, tetrahydro-thiopyranyl, thiazinanyl, imidazolyl, imidazolidinyl, benzimidazolyl, 1,5-dihydro-pyrrolyl, thienyl, pyridinyl, oxazolyl, oxazolidinyl, thiazolyl, isoxazolyl, oxadiazolyl, thiazolyl, thiadiazolyl, triazolyl, and tetrazolyl. More preferably, the four to six membered monocyclic heterocyclyl is selected from the group consisting of azetidin-3-yl, pyrrolidin-3-yl, piperidin-1-yl, piperidin-3-yl, piperidin-4-yl, piperazin-1-yl, morpholin-4-yl, thiomorpholin-4-yl, tetrahydropyran-4-yl, thiopyran-4-yl, tetrahydro-thiopyran-4-yl, 1,2-thiazinan-2-yl, imidazol-2-yl, imidazol-2-yl, imidazol-1-yl, imidazolidin-1-yl, imidazolidin-5-yl, benzimidazol-5-yl, 1,5-dihydro-pyrrol-3-yl, thien-2-yl, pyridin-3-yl, oxazol-2-yl, oxazol-5-yl, oxazolidin-5-yl, thiazol-5-yl, isoxazol-3-yl, 1,2,4-oxadiazol-3-yl, 1,3,4-oxadiazol-2-yl, thiazol-2-yl, thiazol-5-yl, thiazol-3-yl, 1,3,4-thiadiazol-2-yl, 1,3,4-triazol-2-yl, 1,3,4-triazol-5-yl, 1,3,4-triazol-1-yl, 1,2,4-triazol-5-yl, 1,2,4-triazol-1-yl and 1,2,3,4-tetrazol-5-yl.

The term "nine to ten membered bicyclic heterocyclyl" shall denote any nine or ten membered bicyclic ring structure, wherein the ring structure may be saturated, partially unsaturated, partially aromatic, benzo-fused or aromatic, and wherein the ring structure contains at least one heteroatom selected from the group consisting of O, N and S, optionally containing one to four additional heteroatoms independently selected from the group consisting of O, N and S. The nine to ten membered bicyclic heterocyclyl group may be attached at any heteroatom or carbon atom of the ring such that the result is a stable structure. Suitable examples of nine to ten membered bicyclic heterocyclyl groups include, but are not limited to indolizinyl, indolyl, isoindolinyl, indazolyl, benzofuryl, benzoxazolyl, anthracil, benzopyranyl, quinolinyl, isoquinolinyl, cinnolinyl, quinazolinyyl, benzothienyl, benzimidazolyl, benzothiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, benzofuryl, isobenzofuryl, indolinyl, chromanyl, chromenyl, 3,4-methylenedioxyphenyl, 2,3-dihydrobenzofuryl, oxetanyl, pyrido[3,4-b]pyridine, purinyl, quinozilinyl, quinoxalinyl, quinazolinyl, benzo[b][1,4]oxazinyl, 3,4-dihydro-benzo[b][1,4]oxazinyl, benzo[b][1,4]dioxinyl, 2,3-dihydro-benzo[b][1,4]dioxinyl, and the like.

When a particular group is "substituted" (e.g., alkyl, cycloalkyl, heterocyclyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

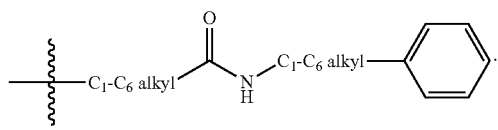

One skilled in the art will recognize that the compounds of formula (I), formula (II) and formula (III) each contain an optionally substituted pyridin-2-one group, which group may tautomerize as shown below

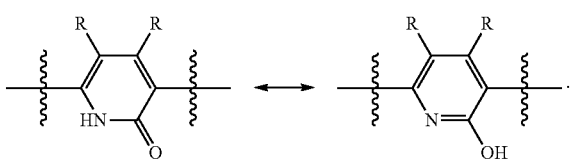

One skilled in the art will further recognize that said group (and as such the corresponding compounds of formula (I), formula (II) and formula (III)) may exist as either of its tautomeric forms, or as any mixture of its tautomeric forms.

Abbreviations used in the specification, particularly the Schemes and Examples, are as listed in Table A, below.

TABLE A

| Abbreviations | | |
|---|---|---|
| AcOH | = | Acetic acid |
| ANOVA | = | Analysis of Variance |
| aq. | = | Aqueous |
| BAST | = | Bis(2-methoxyethyl)aminosulfur trifluoride solution 50% w/w in toluene |
| BINAP | = | 2,2'-Bis(diphenylphosphino)-1,1'-Binaphthyl |
| Boc$_2$O or BOC$_2$O | = | Boc Anhydride (di-tert-Butyl dicarbonate) |
| BSA | = | Bovine Serum Albumin |
| BTEAC | = | Benzyl Triethyl Ammonium Chloride |
| (BuO)$_4$Sn | = | Tetrabutoxystannane |
| cAMP | = | Cyclic Adenosine MonoPhosphate |
| DABCO | = | 1,4-Diazabicyclo[2.2.2]octane |
| DAST | = | Diethylaminosulfur trifluoride |
| DBU | = | 1,8-Diazabicyclo[5.4.0]undec-7-ene |
| DCE | = | 1,2-Dichloroethane |
| DCM | = | Dichloromethane |
| Dess Martin Periodinone or DMP | = | 1,1,1-Triacetoxy-1,1-dihydro-1,2-benziodoxol-3(1H)-one |
| DIAD | = | Diisopropylazodicarboxylate |
| DIBAL | = | Diisobutylammonium hydride |
| DIPEA or DIEA | = | Diisopropylethylamine |
| DMA | = | Dimethyl Acetamide |
| DMAP | = | 4-N,N-Dimethylaminopyridine |
| DME | = | Dimethoxy Ethane |
| DMF | = | N,N-Dimethylformamide |
| DMP | = | Dess Martin Periodinone |
| DMSO | = | Dimethylsulfoxide |
| dppf | = | 1,1'-Bis(diphenylphosphino)ferrocene |
| EDCl | = | 1-Ethyl-3-(3-dimethylaminopropyl)carbodiimide |
| EDTA | = | Ethylene Diamine Tetraacetic Acid |
| eq. or equiv. | = | Equivalents (molar) |
| ESI | = | Electrospray ionization |
| EtBr | = | Ethyl Bromide |
| EtOAc or EA | = | Ethyl acetate |
| EtOH | = | Ethanol |
| EtONa or NaOEt | = | Sodium Ethoxide |
| EtOMs | = | Ethyl mesylate |
| Et$_3$N or TEA | = | Triethylamine |
| Et$_3$SiH | = | Triethylsilane |
| EtSO$_2$Cl | = | Ethanesulfonyl Chloride |
| FSK | = | Forskolin |
| GSIS | = | Glucose Stimulated Insulin Secretion |
| HATU | = | O-(7-Azabenzotriazol-1-yl)-N,N,N'',N''-Tetramethyl Uronium Hexafluorophosphate |
| HBSS | = | Hank's Buffered Salt Solution |
| HEPES | = | 4-(2-Hydroxyethyl)-1-Piperizine Ethane Sulfonic Acid |
| HMDS | = | Hexamethyldisilazane |
| HPBCD | = | Hydroxypropyl-Beta-CycloDextrin |
| HPLC | = | High Pressure Liquid Chromatography |
| IFG | = | Impaired Fasting Glucose |
| IGT | = | Impaired Glucose Tolerance |
| IPA | = | Isopropanol |
| i-PrI | = | Isopropyl Iodide |
| i-Pr—NH$_2$ | = | Isoporpylamine |
| I-PrSO$_2$Cl$_2$ | = | Isopropylsulfonyl Chloride |
| KHMDS | = | Potassium bis(trimethylsilyl)amide |
| KOAc | = | Potassium Acetate |
| LAH | = | Lithium Aluminum Hydride |
| Lawesson's Reagent | = | 2,4-Bis(4-methoxyphenyl)-1,3,2,4-dithiadiphosphetane-2,4-dithione |
| LCMS | = | Liquid Chromatography/Mass Spectroscopy |
| LDA | = | Lithium Diisopropyl Amide |
| LiHMDS | = | Lithium bis(trimethylsilyl)amide |
| mCPBA | = | meta-Chloroperoxybenzoic acid |
| MeCN | = | Acetonitrile |
| MeI | = | Methyl Iodide |
| MeOH | = | Methanol |
| MeOTs | = | Methyl tosylate |
| Me$_2$SO$_4$ | = | Dimethyl Sulfate |
| Mesyl or Ms | = | Methylsulfonyl |
| MS | = | Mass Spectroscopy |
| MsCl | = | Mesyl Chloride (i.e. CH$_3$—SO$_2$—Cl) |
| MsOH | = | Methanesulfonic Acid |
| Mesylate | = | Methane sulfonate (i.e. —O—SO$_2$—CH$_3$) |
| MOM | = | Methoxymethyl acetal (protecting group) |

TABLE A-continued

Abbreviations

| | | |
|---|---|---|
| MTBE | = | Methyl tert-Butyl Ether |
| NAFLD | = | non-alcoholic fatty liver disease |
| NaBH(OAc)$_3$ or STAB | = | Sodium triacetoxyborohydride |
| NaHMDS | = | Sodium bis(trimethylsilyl)amide |
| NaOEt | = | Sodium Ethoxide |
| NaOMe | = | Sodium Methoxide |
| NASH | = | non-alcoholic steatohepatitis (NASH), |
| NBS | = | N-Bromosuccinimide |
| n-BuLi | = | n-Butyl Lithium |
| NCS | = | N-Chlorosuccinimide |
| NH$_4$OAc | = | Ammonium Acetate |
| NMP | = | N-methyl-2-pyrrolidinone |
| NMR | = | Nuclear Magnetic Resonance |
| Oxone | = | Potassium peroxymonosulfate |
| PCC | = | Pyridinium chlorochromate |
| Pd—C | = | Palladium on Carbon Catalyst |
| Pd(OAc)$_2$ | = | Palladium(II)acetate |
| Pd(dppf)Cl$_2$ | = | [1,1'-Bis(diphenylphosphino)ferrocene]dichloropalladium(II) |
| Pd(PPh$_3$)$_4$ | = | Tetrakistriphenylphosphine palladium (0) |
| PE | = | Petroleum Ether |
| Ph | = | Phenyl |
| P(o-tol)$_3$ or (o-tol)$_3$P | = | Tri(ortho-tolyl) Phosphine |
| PPA | = | Phenylpropanolamine |
| PPh$_3$ | = | Triphenyl Phosphine |
| Py | = | Pyridine |
| PyBrop | = | Bromotripyrrolidinophosphonium hexafluorophosphate |
| SELECTFLUOR ® | = | 1-Chloromethyl-4-fluoro-1,4-diazoniabicyclo[2.2.2]octane bis(tetrafluoroborate) |
| SPA | = | Scintillation Proximity Assay |
| RT or rt | = | Room temperature |
| SPA | = | Scintillation Proximity Assay |
| TBAB | = | Tetra-n-butylammonium bromide |
| t-BOC or Boc | = | tert-Butocarbonyl |
| t-BuLi | = | tert-Butyl Lithium |
| t-BuOH | = | tert-Butanol |
| t-BuOK | = | Potassium tert-butoxide |
| t-BuOLi | = | Lithium tert-butoxide |
| t-BuONa | = | Sodium tert-butoxide |
| TEA | = | Triethylamine |
| Tf | = | Trifyl (i.e. —SO$_2$—CF$_3$) |
| TFA | = | Trifluoroacetic Acid |
| TFAA | = | Trifluoroacetic anhydride |
| Tf$_2$O | = | Triflic Anhydride (Trifluoromethanesulfonic anhydride) |
| THF | = | Tetrahydrofuran |
| THP | = | Tetrahydropyran |
| TLC | = | Thin Layer Chromatography |
| TMS | = | Trimethylsilyl |
| TMSCl | = | Trimethylsilyl Chloride |
| TMSCN | = | Trimethylsilyl Cyanide |
| TMSI | = | Trimethylsilyl Iodide |
| TMSN$_3$ | = | Trimethylsilyl Azide |
| TMSOTf | = | Trimethylsilyl Trifluoromethane Sulfonate |
| Tosyl or Ts | = | para-Toluenesulfonyl |
| Tosylate | = | para-Toluene sulfonate (i.e. —O—SO$_2$-(p-toluene) |
| Triflate or OTf | = | Trifluoromethane sulfonate |
| TsCl | = | para-Toluenesulfonic Chloride (i.e. (p-toluene)-SO$_2$—Cl) |
| TsOH or pTSA | = | para-Toluenesulfonic Acid |

As used herein, unless otherwise noted, the term "isolated form" shall mean that the compound of formula (I), compound of formula (II) or compound of formula (III) is present in a form which is separate from any solid mixture with another compound(s), solvent system or biological environment. In an embodiment of the present invention, the compound of formula (I), compound of formula (II) or compound of formula (III) is present in an isolated form.

As used herein, unless otherwise noted, the term "substantially pure form" shall mean that the mole percent of impurities in the isolated compound of formula (I), compound of formula (II) or compound of formula (III) is less than about 5 mole percent, preferably less than about 2 mole percent, more preferably, less than about 0.5 mole percent, most preferably, less than about 0.1 mole percent. In an embodiment of the present invention, the compound of formula (I), compound of formula (II) or compound of formula (III) is present as a substantially pure form.

As used herein, unless otherwise noted, the term "substantially free of a corresponding salt form(s)" when used to described the compound of formula (I), compound of formula (II) or compound of formula (III) shall mean that mole percent of the corresponding salt form(s) in the isolated base of formula (I), compound of formula (II) or compound of formula (III) is less than about 5 mole percent, preferably less than about 2 mole percent, more preferably, less than about 0.5 mole percent, most preferably less than about 0.1 mole percent. In an embodiment of the present invention, the compound of formula (I), compound of formula (II) or compound of formula (III) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

One skilled in the art will further recognize that the reaction or process step(s) as herein described (or claimed) are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, 1,1-dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α-obs]/[α-max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Synthesis Schemes

Compounds of formula (I) wherein X is selected from the group consisting of —CR$^A$R$^B$—, —CR$^A$=, —CR$^A$R$^B$—CH$_2$—, —CH$_2$—CHR$^C$—, and —CR$^A$R$^B$—CR$^C$= may be prepared from intermediate compounds of formula (a-16)

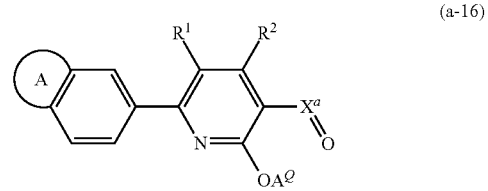

(a-16)

and/or compounds of formula (a-20)

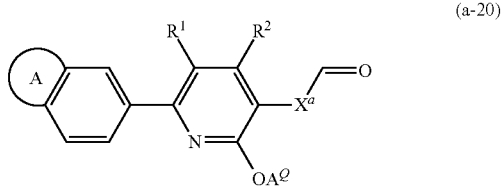

(a-20)

wherein X$^a$=O is —CR$^A$=O, CR$^A$R$^B$—CH=O, —CH$_2$—CR$^C$=O or —CR$^A$R$^B$—CR$^C$=O, and which intermediate compounds may be as described below.

Certain intermediate compounds, useful in the synthesis of compounds of formula (I) of the present invention may be prepared as described in Scheme A-1, below.

Scheme A-1

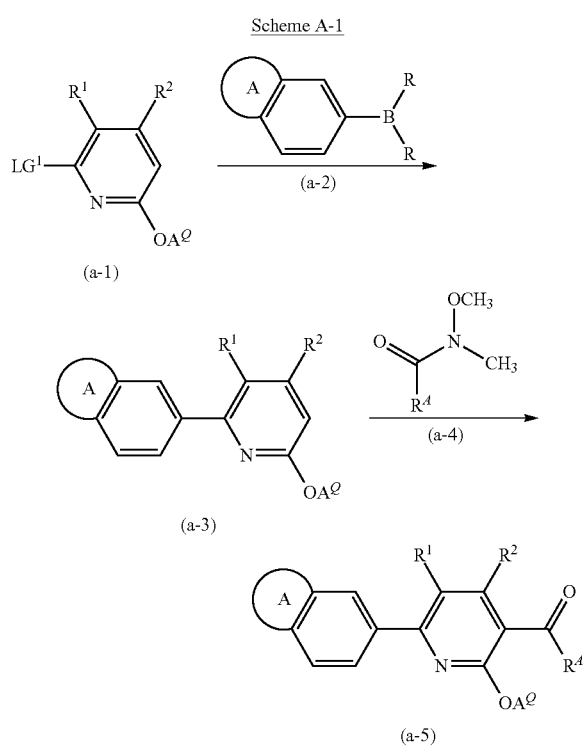

pound of formula (a-2), wherein the two R groups are the same and are selected from the group consisting of OH and OPG⁰, wherein PG⁰ is a suitably selected oxygen protecting group such as methyl, ethyl, isopropyl, and the like, or the two R groups are taken together with the boron atom to which they are bound to form

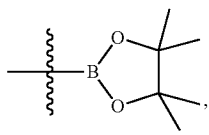 [SMILES: *B1OC(C)(C)C(C)(C)O1]

a known compound or compound prepared by known methods; in the presence of a suitably selected catalyst such as Pd(OAc)$_2$, PdCl$_2$, Pd(PPh$_3$)$_4$, and the like; in the presence of a suitably selected ligand such as PPh$_3$, dppf, BINAP, and the like; in the presence of a suitably selected base such as Na$_2$CO$_3$, K$_3$PO$_4$, t-BuOK, and the like; in a suitably selected organic solvent or mixture of organic solvent and water, such as THF, 1,4-dioxane, a mixture of toluene and water, and the like; at a temperature in the range of form about 60° C. to about 120° C.; to yield the corresponding compound of formula (a-3).

The compound of formula (a-3) is reacted with a suitably selected organometallic reagent such as t-BuLi, LDA, LiH-MDS, and the like; in a suitably selected organic solvent such as diethyl ether, THF, 1,4-dioxane, and the like; at a temperature in the range of from about −78° C. to about 0° C.; and then immediately reacted with a suitably substituted compound of formula (a-4), a known compound or compound prepared by known methods; to yield the corresponding compound of formula (a-5).

Accordingly, a suitably substituted compound of formula (a-1), wherein LG$^1$ is a suitably selected leaving groups such as Br, Cl, OTf, and the like, and wherein A$^Q$ is an alkyl substituent such as methyl, ethyl, and the like, preferably methyl, a known compound or compound prepared by known methods, is reacted with a suitably substituted com- Certain intermediate compounds, useful in the synthesis of compounds of formula (I) of the present invention may be prepared as described in Scheme A-2, below.

Scheme A-2

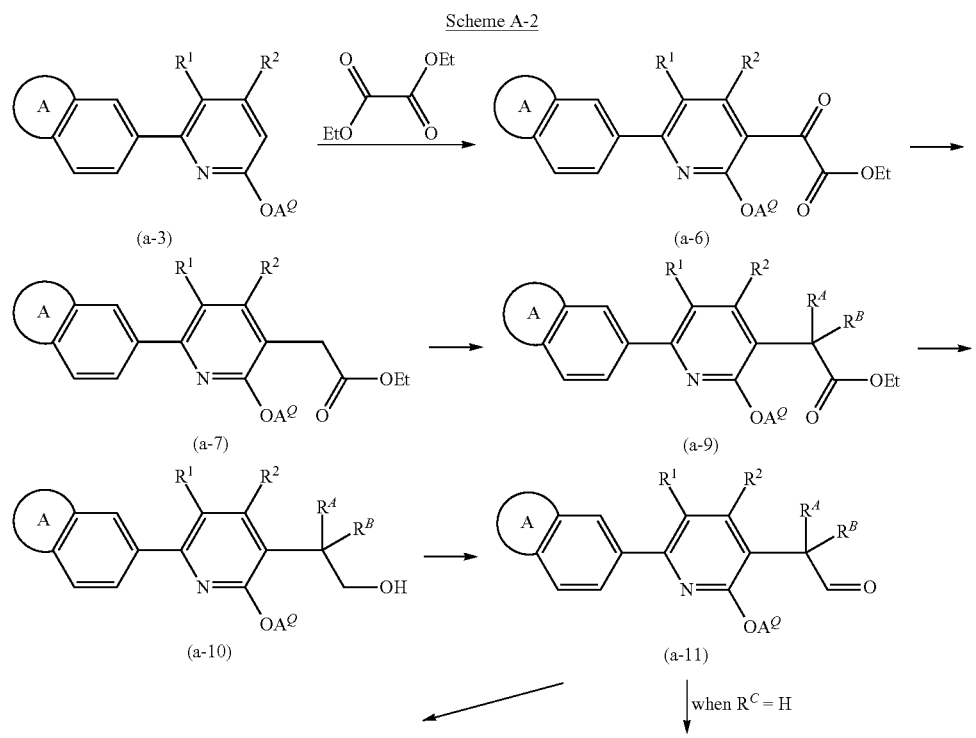

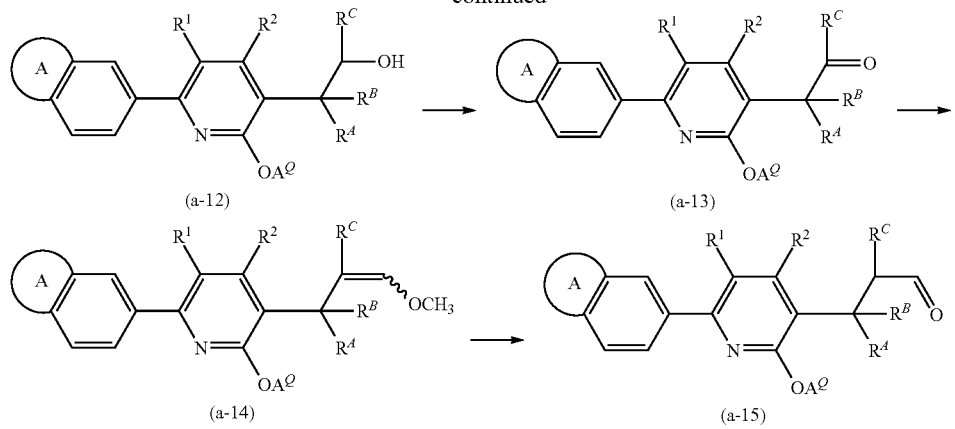

Accordingly, a suitably substituted compound of formula (a-3), prepared for example as described in Scheme A-1 above, is reacted with a suitably selected organometallic reagent such as t-BuLi, LDA, LiHMDS, and the like; in a suitably selected organic solvent such as diethyl ether, THF, 1,4-dioxane, and the like; at a temperature in the range of from about −78° C. to about 0° C.; and them immediately reacted with diethyl oxalate, a known compound; to yield the corresponding compound of formula (a-6).

The compound of formula (a-6) is reacted with a suitably selected reducing agent such as $Et_3SiH$, $NaBH_4$, $NaBH_3(CN)$, and the like; in the presence of a suitably selected acid such as TFA, AcOH, HCl, and the like; in a suitably selected organic solvent such as DCM, diethyl ether, THF, and the like; at a temperature in the range of from about 0° C. to about 25° C.; to yield the corresponding compound of formula (a-7).

The compound of formula (a-7) is optionally reacted with a suitably selected base such as LDA, LiHMDS, KHMDS, and the like; in a suitably selected organic solvent such as diethyl ether, THF, 1,4-dioxane, and the like; at a temperature in the range of from about −78° C. to about 0° C.; and then immediate reacted with a suitably substituted reagent, for example, a suitably substituted alkyl halide, alkyl triflate, alkyl tosylate or alkyl mesylate; to yield the corresponding compound of formula (a-9).

One skilled in the art will recognize that wherein $R^A$ and $R^B$ are the same the compound of formula (a-7) is reacted with a suitably selected base such as LDA, HMDS, LiHMDS, NaHMDS, t-BuONa, t-BuOLi, and the like; wherein the base is preferably present in an amount of about 2.0 eq.; and then reacted with a suitably selected alkylating reagent such as $CH_3I$, EtBr, EtOMs, MeOTs, and the like; wherein the alkyl of the alkylating reagent corresponds to the desired $R^A/R^B$ groups and wherein the alkylating reagent is preferably present in an amount of at least about 2.0 eq.; to yield the corresponding compound of formula (a-9).

Alternatively, wherein $R^A$ and $R^B$ are different the compound of formula (a-7) is reacted with a suitably selected base such as LDA, KHMDS, LiHMDS, NaHMDS, t-BuONa, t-BuOLi, and the like; wherein the base is preferably present in an amount of about 1.0 eq.; and then reacted with a suitably selected alkylating reagent such as $CH_3I$, EtBr, EtOMs, MeOTs, and the like; wherein the alkyl corresponds to the desired $R^A$ group; and wherein the alkylating reagent is preferably present in an amount of about 1.0 eq.; and then reacted with a second suitably selected alkylating reagent wherein the alkyl corresponds to the desired $R^B$ group; and wherein the alkylating reagent is preferably present in an amount of about 1.0 eq.; to yield the corresponding compound of formula (a-9).

Alternatively, wherein $R^A$ and $R^B$ are taken together with the carbon atom to which they are bound to form $C_{3-6}$cycloalkyl of formula (a-7) is reacted with a suitably selected base such as LDA, KHMDS, LiHMDS, NaHMDS, t-BuONa, t-BuOK, and the like; wherein the base is preferably present in an amount of about 2.0 eq.; and then reacted with a suitably selected bis-alkylating reagent such as 1,2-di-Br-ethane, 1-chloro-3-iodo-propane, 1-chloro-4-iodo-butane, and the like; wherein the bis-alkyl of the alkylating reagent corresponds to the desired $R^A/R^B$ groups; and wherein the bis-alkylating reagent is preferably present in an amount of about 1.0 eq.; to yield the corresponding compound of formula (a-9).

The compound of formula (a-9) is reacted with a suitably selected base such as DIBAL, LAH, $LiBH_4$, and the like; in a suitably selected organic solvent such as DCM, diethyl ether, THF, and the like; at a temperature in the range of from about −78° C. to about 0° C.; to yield the corresponding compound of formula (a-10).

The compound of formula (a-10) is reacted with a suitably selected oxidizing agent such as oxyl chloride/DMSO (Swern reagent), PCC, Dess-Martin reagent, and the like; in a suitably selected organic solvent such as DCM, diethyl ether, THF, and the like; at a temperature in the range of rom about 0° C. to about 25° C.; to yield the corresponding compound of formula (a-11).

One skilled in the art will recognize that wherein the desired $R^A$ and $R^B$ are each hydrogen, the compound of formula (a-7) may be substituted for the compound of (a-9) and reacted as described, to yield the corresponding compound of formula (a-11), wherein $R^A$ and $R^B$ are each hydrogen.

The compound of formula (a-11) may be further, optionally reacted with a suitably substituted organometallic reagent such as $R^C$—Li, $R^C$—MgBr, $Zn(R^C)_2$, and the like, a known compound or compound prepared by known methods; in a suitably selected organic solvent such as DCM, diethyl ether, THF, and the like; at a temperature in the range of from about −78° C. to about 0° C.; to yield the corresponding compound of formula (a-12).

The compound of formula (a-11) (when preparing compounds of formula (I) wherein the desired $R^C$ group is hydrogen) or the compound of formula (a-12) (when preparing compounds of formula (I) wherein the desired $R^C$ group is other than hydrogen), is reacted with a suitably selected oxidizing agent such as oxyl chloride/DMSO (Swern reagent), PCC, Dess-Martin reagent, and the like; in a suitably selected organic solvent such as DCM, diethyl ether, THF, and the like; at a temperature in the range of rom about 0° C. to about 25° C.; to yield the corresponding compound of formula (a-13).

The compound of formula (a-13) is reacted with (methoxymethyl)phenyl phosphonium chloride, a known compound; in the presence of a suitably selected base such as LiHMDS, LDA, NaHMDS, and the like; in an organic solvent such as THF, diethyl ether, 1,4-dioxane, and the like; at a temperature in the range of form about −78° C. to about 25° C.; to yield the corresponding compound of formula (a-14).

The compound of formula (a-14) is reacted with a suitably selected acid such as 1N HCl, 1N $H_2SO_4$, 48% HBr, and the like; in a suitably selected organic solvent such as acetonitrile, THF, 1,4-dioxane, and the like; at a temperature in the range of from about 0° C. to about 25° C.; to yield the corresponding compound of formula (a-15).

A suitably substituted compound of formula (a-6) may alternatively, be reacted with a suitably selected fluorinating reagent such as DAST, BAST, SELECTFLUOR®, and the like; in a suitably selected organic solvent such as DCM, 1,2-di-Cl-ethane, chloroform, and the like; at a temperature in the range of from about −78° C. to about 0° C.; to yield the corresponding compound of formula (a-9), wherein $R^A$ and $R^B$ are each fluoro. Said compound is then further reacted as described in Scheme A-2 above, to yield the corresponding compounds of formula (a-11) and formula (a-15) wherein $R^A$ and $R^B$ are each fluoro.

A a suitably substituted compound of formula (a-3) may alternatively be reacted with a suitably selected organometallic reagent such as t-BuLi, LDA, LiHMDS, and the like; in a suitably selected organic solvent such as diethyl ether, THF, 1,4-dioxane, and the like; at a temperature in the range of from about −78° C. to about 0° C.; and them immediately reacted with ethyl glyoxalate, a known compound; to yield the corresponding compound of formula (a-8)

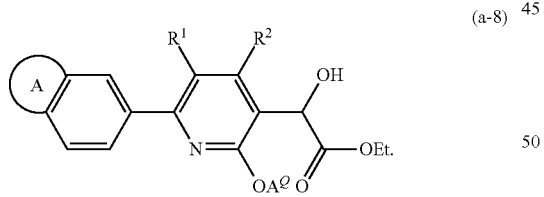

(a-8)

The compound of formula (a-8) is then reacted a suitably selected fluorinating reagent such as DAST, BAST, SELECTFLUOR®, and the like; in a suitably selected organic solvent such as DCM, 1,2-di-Cl-ethane, chloroform, and the like; at a temperature in the range of from about −78° C. to about 0° C.; to yield the corresponding compound of formula (a-9), $R^A$ is hydrogen and $R^B$ is fluoro. Said compound is then further reacted as described in Scheme A-2 above, to yield the corresponding compounds of formula (a-11) and formula (a-15) wherein $R^A$ is hydrogen and $R^B$ is fluoro.

Certain compounds of formula (I) may be prepared from the corresponding compound of formula (a-16) as described in Scheme A-4, below.

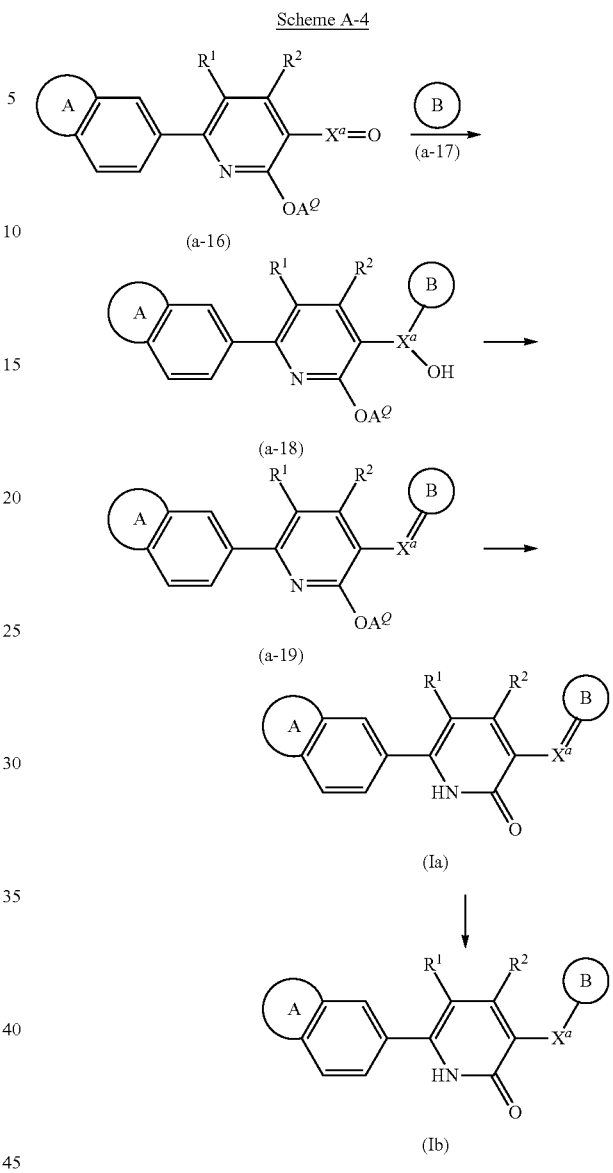

Accordingly, a suitably substituted compound of formula (a-16) wherein $X^a$ is selected from the group consisting of —$CR^A$—, —$CR^AR^B$—CH—, —$CH_2$—$CR^C$— or $CR^AR^B$—$CR^C$—, is reacted with a suitably substituted compound of formula (a-17), a known compound or compound prepared by known methods; in the presence of a suitably selected organometallic agent such as t-BuLi, LDA, LiHMDS, and the like; optionally in the presence of a suitably selected additive such as LiCl, and the like; in a suitably selected organic solvent such as THF, 1,4-dioxane, diethyl ether, and the like; at a temperature in the range of from about −78° C. to about −10° C.; to yield the corresponding compound of formula (a-18).

The compound of formula (a-18) is reacted with a suitably selected acylating agent such as $SOCl_2$, oxyl chloride, MsCl, and the like; in the presence of a suitably selected base such as TEA, pyridine, DIPEA, and the like; in a suitably selected organic solvent such as DCM, THF, toluene, and the like; at a temperature in the range of from about 0° C. to about 25° C.; to yield the corresponding compound of formula (a-19).

The compound of formula (a-19) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ia).

The compound of formula (Ia) is further, optionally reacted with a suitably selected reducing agent such as hydrogen gas, for example hydrogen gas under about 40-55 psi; in the presence of a suitably selected catalyst such as 5-10% Pd on carbon, PtO$_2$, Ni, and the like; in a suitably selected organic solvent such as methanol, THF, ethyl acetate, and the like; at a temperature in the range of from about 25° C. to about 60° C.; to yield the corresponding compound of formula (Ib).

Certain compounds of formula (I) wherein

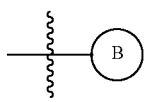

is an optionally substituted imidazol-2-yl, may be prepared as described in Scheme 5, below.

Scheme A-5

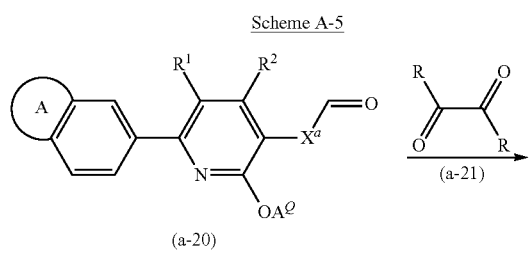

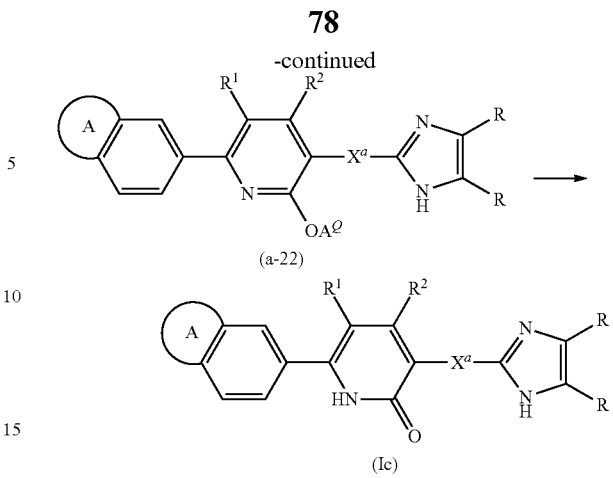

Accordingly, a suitably substituted compound of formula (a-20) wherein Xa is selected from the group consisting of —CR$^A$R$^B$—, —CR$^A$R$^B$—CH$_2$— and —CH$_2$—CR$^C$— is reacted with a suitably substituted compound of formula (a-21), wherein each R represent hydrogen or the desired imidazol-2-yl substituent (if present), an a known compound or compound prepared by known methods; in the presence of a suitably selected source of ammonium such as 7N NH$_3$/methanol, ammonium acetate, ammonium hydroxide, and the like; in a suitably selected organic solvent such as methanol, ethanol, isopropanol, and the like; at a temperature in the range of form about 25° C. to about 70° C.; to yield the corresponding compound of formula (a-22).

The compound of formula (a-22) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ic).

Certain compounds of formula (I) may be prepared as described in Scheme A-6 below.

Scheme A-6

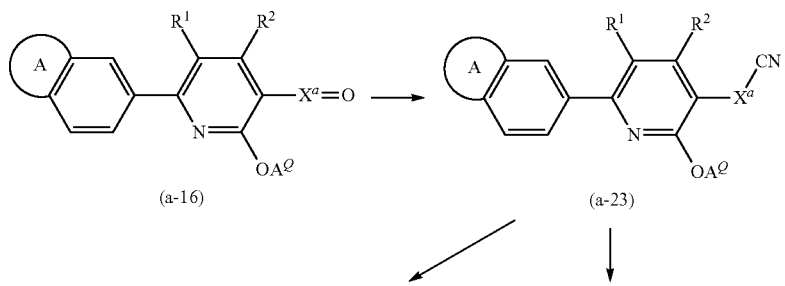

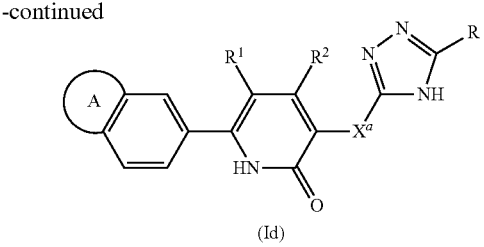

(Id)

Accordingly, a suitably substituted compound of formula (a-20) wherein $X^a$ is selected from the group consisting of —CH—, —CR$^A$—, —CR$^A$R$^B$—CH—, —CH$_2$—CR$^C$— and CR$^A$R$^B$—CR$^C$—, is reacted with toluenesulfonylmethyl isocyanide (also known as tosMIC), a known compound; in the presence of a suitably selected base such as t-BuOK, NaOCH$_2$CH$_3$, NaH, and the like; in a suitably selected organic solvent such as THF, 1,4-dioxane, DME, and the like; at a temperature in the range of form about −78° C. to about 0° C.; to yield the corresponding compound of formula (a-23).

The compound of formula (a-23) is reacted with a suitably selected acid such as PPA, 4N HCl, 1N H$_2$SO$_4$, and the like; in a suitably selected organic solvent such as THF, 1,4-dioxane, DME, and the like; at a temperature in the range of from about 25° C. to about 80° C.; to yield the corresponding compound of formula (a-24).

Alternatively, a suitably substituted compound of formula (a-23) reacted with a suitably selected base such as LDA, LiHMDS, KHMDS, and the like; in wherein $X^a$ is —CH$_2$— is a suitably selected organic solvent such as diethyl ether, THF, 1,4-dioxane, and the like; at a temperature in the range of from about −780° C. to about 0° C.; and then immediate reacted with a suitably substituted alkylating reagent, for example, a suitably substituted C$_{1-6}$alkyl halide, C$_{1-6}$alkyl-OTf, C$_{1-6}$alkyl-OTs, C$_{1-6}$alkyl-OMs, and the like; wherein the reagent is preferably present in an amount of at least about 2 molar equivalents; to yield the corresponding compound of formula (a-23) wherein $X^a$ is —CR$^A$R$^B$— and wherein R$^A$ and R$^B$ are each the same and are the corresponding C$_{1-6}$alkyl.

One skilled in the art will recognize that the compound of formula (a-23) wherein $X^a$ is —CH$_2$— may alternatively be reacted with a suitably substituted R$^A$-substituted reagent or a suitably substituted R$^B$-substituted reagent or reacted sequentially with both a suitably substituted R$^A$-substituted reagent and then with a suitably substituted R$^B$-substituted reagent (wherein the substituted reagent is for example with a suitably substituted halide, triflate, tosylate, mesylate, and the like) or a suitably substituted R$^A$R$^B$ substituted reagent (wherein the suitably substituted reagent is, for example, a suitably substituted di-halide, di-mesylate, di-tosylate, and the like) according to known methods, to yield the corresponding compound of formula (a-23), wherein the desired R$^A$ and/or R$^B$ substituent groups are incorporated into the compound structure.

The compound of formula (a-24) is reacted with hydrazine, a known compound; in the presence of a suitably selected aldehyde equivalent such as DMF-DMA, 1,2-dimethoxy-N,N-dimethylethan-1-amine, (OCH$_3$)$_2$—(R)C=N(CH$_3$)$_2$ (where R represents a desired substituent on the final compound of formula (I)), and the like; in a suitably selected acidic solvent such as acetonitrile, TFA, aqueous formic acid solution, and the like; at a temperature in the range of from about 60° C. to about 100° C.; to yield the corresponding compound of formula (a-25), wherein Z is =C(R)—.

The compound of formula (a-25) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Id).

Alternatively, the compound of formula (a-23) is reacted with a suitably selected source of azide, such as NaN$_3$, TMSN$_3$, and the like; in the presence of an organic or inorganic acid such as NH$_4$Cl, (BuO)$_4$Sn, and the like; in a suitably selected organic solvent such as toluene, THF, 1,4-dioxane, and the like; at a temperature in the range of from about 60° C. to about 110° C.; to yield the corresponding compound of formula (a-25), wherein Z is =N—.

The compound of formula (a-25) is then reacted as described above, to yield the corresponding compound of formula (Id).

One skilled in the art will recognize that the compound of formula (a-24) may alternatively be prepared from the corresponding compound of formula (a-26)

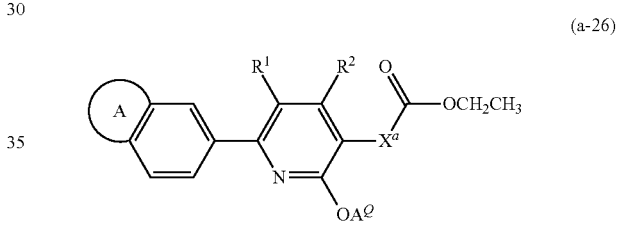

by reacting with a suitably selected source of ammonia such as 7N NH$_3$/methanol, ammonium acetate, ammonium hydroxide, and the like; in a suitably selected polar solvent such as water, methanol, ethanol, and the like; at a temperature in the range of form about 50° C. to about 100° C.

Alternatively, a suitably substituted compound of formula (a-23) or formula (a-27) or formula (a-26) may be reacted with a suitably selected base such as KOH, NaOH, Ba(OH)$_2$, and the like; in a suitably selected organic solvent such as THF, methanol, ethanol, and the like; at a temperature in the range of from about 80° C. to about 120° C.; to yield the corresponding compound of formula (a-28)

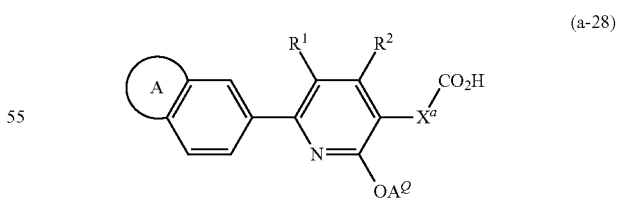

wherein the cyano or ester group is converted to the corresponding acid group; the compound of formula (a-28) is then reacted with a suitably substituted amine; in the presence of a suitably selected coupling agent such as HATU, EDCl, PyBrop, and the like; in the presence of a suitably selected base such as TEA, DIPEA, DBU, and the like; in a suitably selected organic solvent such as DCM, THF, DMF, and the like; at a temperature in the range of from about 25° C. to about 50° C.; to yield the corresponding compound wherein the acid group is converted to the corresponding amide; and said intermediate is then reacted as described above to (by reacting with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (I) wherein X is selected from the group consisting of —CH—, —CR$^A$—, —CR$^A$R$^B$—CH—, —CH$_2$—CR$^C$— and CR$^A$R$^B$—CR$^C$—.

Certain compounds of formula (I) may be prepared as described in Scheme A-7 below.

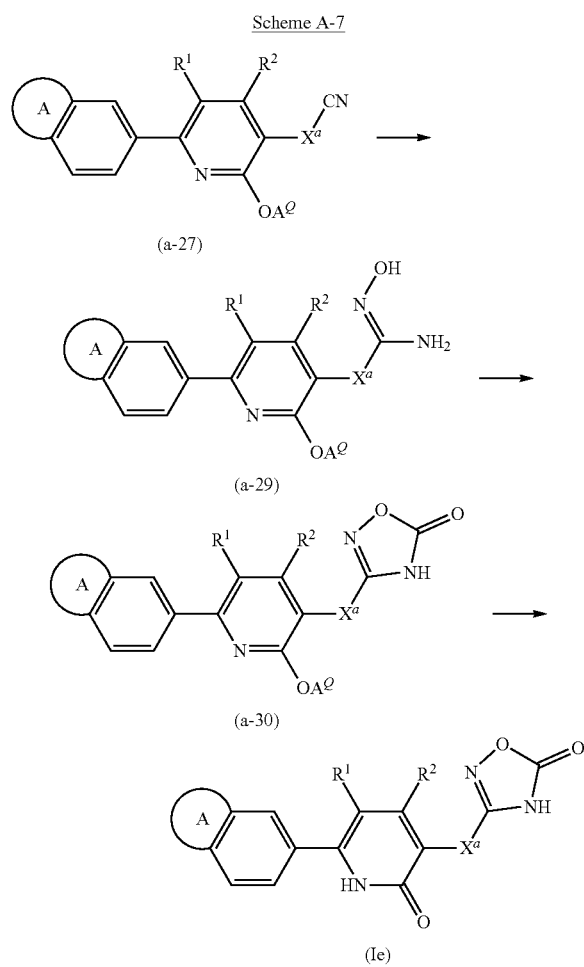

Accordingly, a suitably substituted compound of formula (a-27) wherein Xa is —CR$^A$R$^B$—, —CR$^A$R$^B$—CH$_2$—, CH$_2$—CR$^C$— or —CR$^A$R$^B$—CR$^C$—, is reacted with hydroxylamine, a known compound; in the presence of a suitably selected base such as t-BuOK, NaOEt, NaOMe, and the like; in a suitably selected organic solvent such as ethanol, IPA, t-butanol, and the like; at a temperature in the range of from about 60° C. to about 100° C.; to yield the corresponding compound of formula (a-29).

The compound of formula (a-29) is reacted with CDI, a known compound; in the presence of a suitably selected organic base such as DBU, DABCO, DIPEA, and the like; in a suitably selected organic solvent such as THF, DME, 1,4-dioxane, and the like; at a temperature in the range of from about 60° C. to about 100° C.; to yield the corresponding compound of formula (a-30).

The compound of formula (a-30) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ie).

Certain compounds of formula (I) may be prepared as described in Scheme A-8 below.

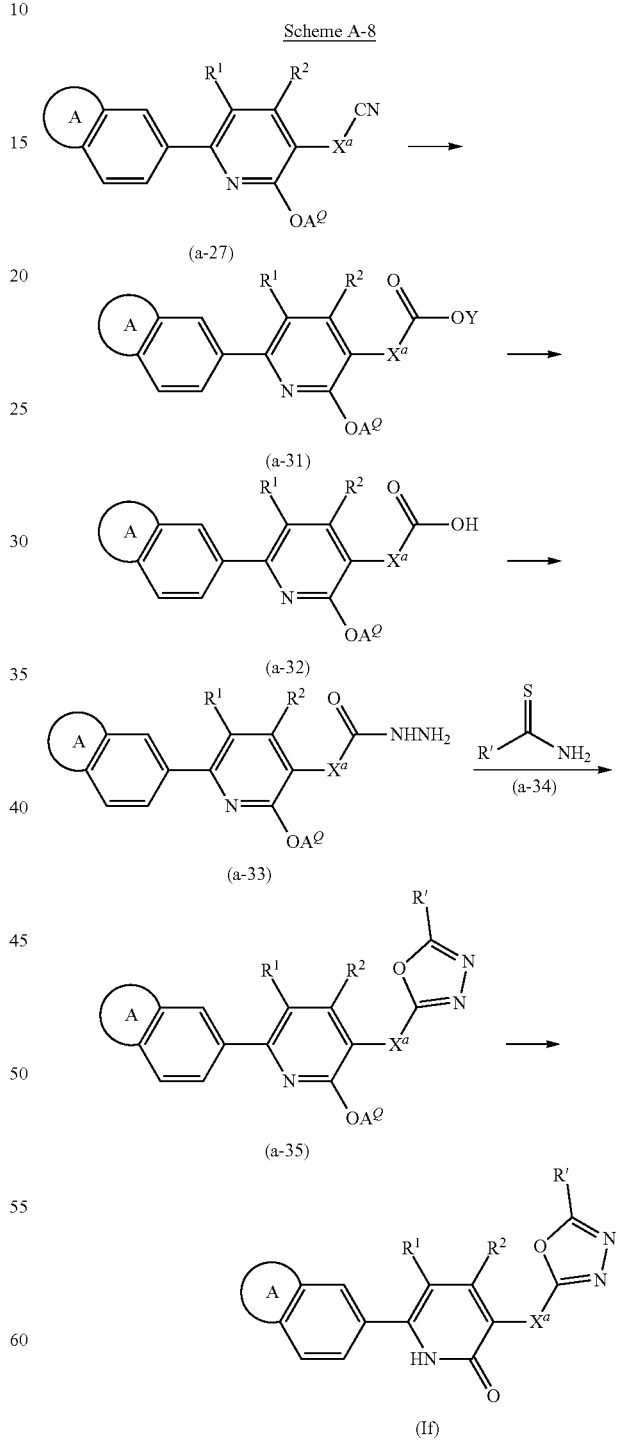

Accordingly, a suitably substituted compound of formula (a-27) wherein Xa is —CR$^A$R$^B$—, —CR$^A$R$^B$—CH$_2$—, CH$_2$—CR$^C$— or —CR$^A$R$^B$—CR$^C$— is reacted with a halogenating agent such as SOCl$_2$, SOBr$_2$, and the like, or with oxalyl chloride, a known compound; in a suitably selected C$_{1-4}$alcohol of the formula Y—OH, such as ethanol, methanol, isopropanol, and the like; at a temperature in the range of from about 0° C. to about 60° C.; to yield the corresponding compound of formula (a-31).

The compound of formula (a-31) is reacted with a suitably selected base such as LiOH, NaOH, KOH, and the like; in a suitably selected solvent or mixture of solvents such as THF, 1,4-dioxane, a mixture of methanol and water, and the like; at a temperature in the range of form about 0° C. to about 60° C.; to yield the corresponding compound of formula (a-32).

The compound of formula (a-32) is reacted with hydrazine, a known compound; in the presence of a suitably selected coupling agent such as HATU, EDCl, PyBrop, and the like; in a suitably selected organic solvent such as THF, 1,4-dioxane, DCM, and the like; at a temperature in the range of form about 0° C. to about 60° C.; to yield the corresponding compound of formula (a-33).

The compound of formula (a-33) is reacted with a suitably substituted orthoformate, a compound of formula (a-34), wherein R' represents a desired substituent on the

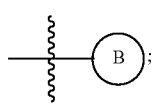

in the presence of a suitably selected catalyst such as NH$_4$Cl, CH$_3$I, NaCl, and the like; in a suitably selected organic solvent such as acetonitrile, ethanol, isopropanol, and the like; at a temperature in the range of from about 60° C. to about 100° C.; to yield the corresponding compound of formula (a-35).

The compound of formula (a-35) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (If).

Certain compounds of formula (I) may be prepared as described in Scheme A-9, below.

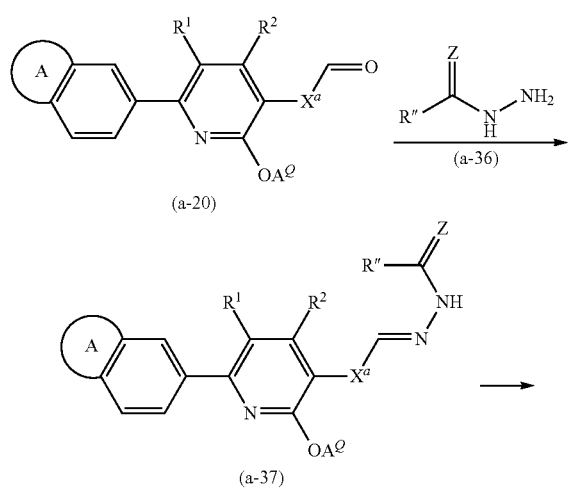

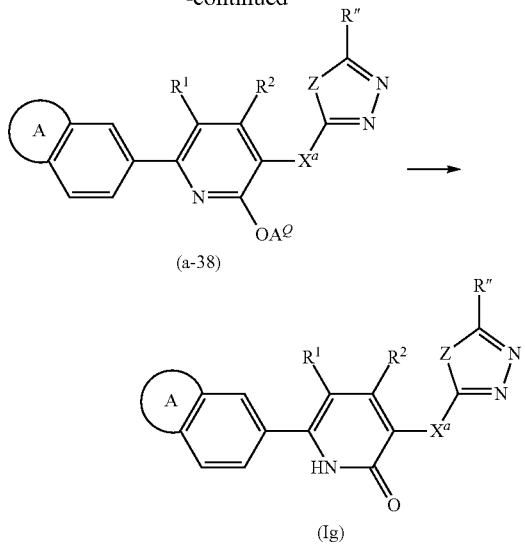

Accordingly, a suitably substituted compound of formula (a-20) wherein X$^a$ is selected from the group consisting of —CHR$^A$—, —CR$^A$R$^B$—, —CR$^A$R$^B$—CH$_2$—, CH$_2$—CR$^C$— or —CR$^A$R$^B$—CR$^C$ is reacted with a suitably substituted hydrazine or thiohydrazine, a compound of formula (a-36), wherein Z is O or S, respectively, and wherein R" represents a desired substituent on the

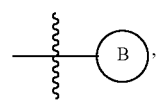

a known compound or compound prepared by known methods; in the presence of a suitably selected acid such as pTSA, MsOH, PPA, and the like; in a suitably selected organic solvent such as methanol, ethanol, isopropanol, and the like; at a temperature in the range of form about 25° C. to about 85° C.; to yield the corresponding compound of formula (a-37).

The compound of formula (a-37) is reacted with I$_2$ or Br$_2$; in the presence of a suitably selected base such as K$_2$CO$_3$, K$_3$PO$_4$, Na$_2$CO$_3$, and the like; in an organic solvent such as THF, 1,4-dioxane, toluene, and the like; at a temperature in the range of form about 60° C. to about 100° C.; to yield the corresponding compound of formula (a-38).

The compound of formula (a-37) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ig).

One skilled in the art will recognize that additional compounds of formula (I) wherein

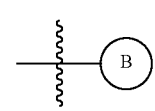

is a nitrogen containing heterocyclyl ring structure may be prepared from a suitably substituted compound of formula (a-20), a known compound or compound prepared by known methods, or compound prepared according as described herein (for example in the Schemes and/or Examples) by reacting said compound according to known ring closure/ring formation chemistry, for example as described in "*Heterocyclic Chemistry*" by J. A. JOULE, K. MILLS, Blackwell publishing; "*Fundamentals of Heterocyclic Chemistry: Importance in Nature and in the Synthesis of Pharmaceuticals*" by L. D. QUIN, J. A. TYRELL, Wiley publishing; and then reacting the resulting compound to convert the —OA$^Q$ group to the =O group; to yield the corresponding compound of formula (I).

Certain compounds of formula (I) may be prepared as described in Scheme A-10, below.

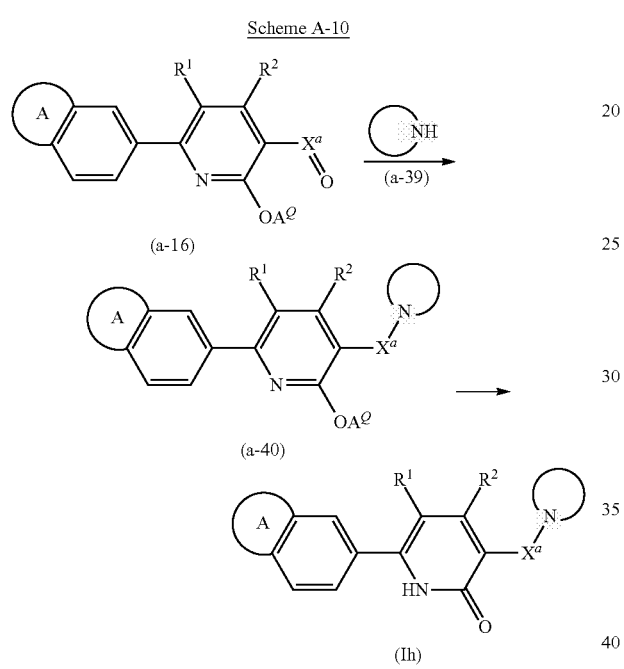

Accordingly, a suitably substituted compound of formula (a-16), wherein $X^a$ is selected from the group consisting of —CR$^A$=, CH$_2$—CR$^C$=, CR$^A$R$^B$—CH=, is reacted with a suitably substituted nitrogen containing, optionally substituted

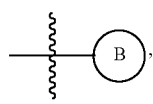

a compound of formula (a-39), a known compound or compound prepared by known methods; in the presence of a suitably selected reducing agent such as NaBH$_4$, NaBH$_3$(CN), NaBH(OAc)$_3$, and the like; in a suitably selected organic solvent such as DCM, THF, methanol, and the like; at a temperature in the range of from about 0° C. to about 25° C.; to yield the corresponding compound of formula (a-40).

The compound of formula (a-40) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ih).

Certain compounds of formula (I) may be prepared as described in Scheme A-11, below.

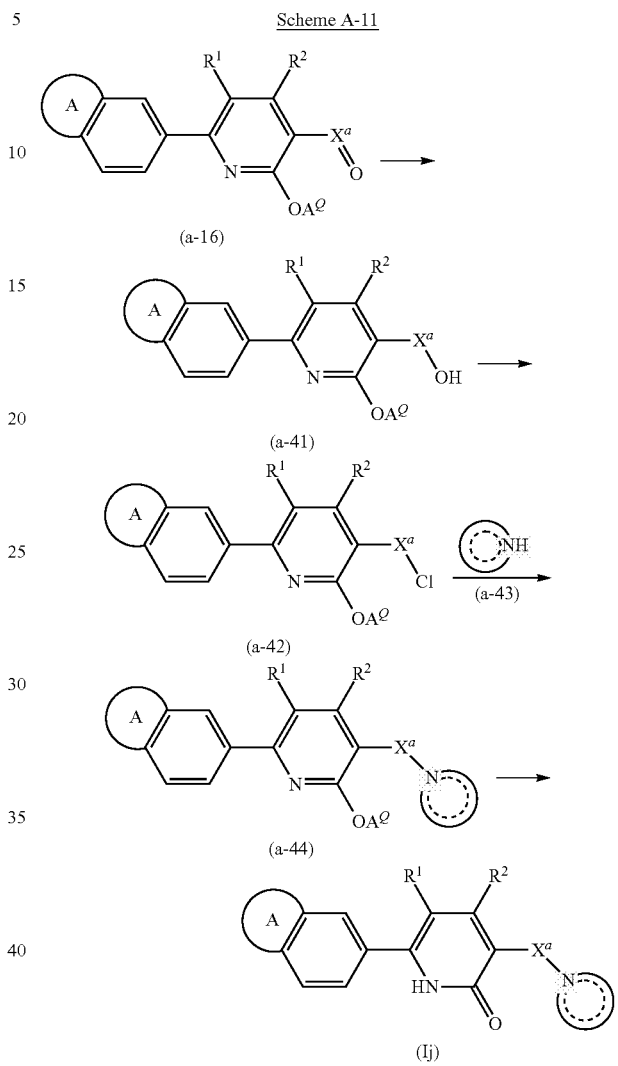

Accordingly, a suitably substituted compound of formula (a-16) wherein $X^a$ is selected from the group consisting of —CR$^A$=, CH$_2$—CR$^C$=, CR$^A$R$^B$—CH=, is reacted with a suitably selected reducing agent such as NaBH$_4$, NaBH$_3$(CN), NaBH(OAc)$_3$, and the like; in a suitably selected organic solvent such as DCM, THF, methanol, and the like; at a temperature in the range of from about 0° C. to about 25° C.; to yield the corresponding compound of formula (a-41).

The compound of formula (a-41) is reacted with a suitably selected chlorinating agent such as mesyl chloride, tosyl chloride, PPh$_3$/CCl$_4$, and the like; in the presence of a suitably selected organic base such as pyridine, TEA, DIPEA, and the like; in a suitably selected organic solvent such as DCM, THF, diethyl ether, and the like; at a temperature in the range of from about 0° C. to about 25° C.; to yield the corresponding compound of formula (a-42).

The compound of formula (a-42) is reacted with a suitably substituted nitrogen containing aryl group, a compound of formula (a-43), a known compound or compound prepared by known methods; in the presence of a suitably selected base such as NaH, Cs$_2$CO$_3$, t-BuOK, and the like; in a suitably selected organic solvent such as THF, diethyl ether, DMF, and the like; at a temperature in the range of from about 0° C. to about 80° C.; to yield the corresponding compound of formula (a-44).

The compound of formula (a-44) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ij).

Certain compound of formula (I) more particularly compounds of formula (I) wherein X is selected from the group consisting of —CR$^A$R$^B$—N(R$^D$)— or —CR$^A$R$^B$—CH$_2$—N(R$^D$)— may be prepared as described in Scheme A-12, below.

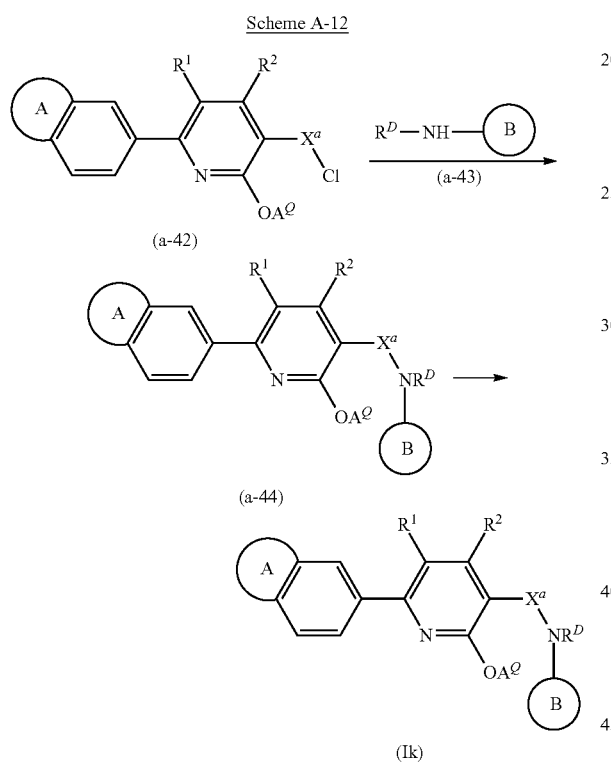

Accordingly, a suitably substituted compound of formula (a-42), wherein X$^a$ is selected from the group consisting of —CR$^A$R$^B$— and —CR$^A$R$^B$—CH$_2$— is reacted with a suitably substituted amine, a compound of formula (a-43), a known compound or compound prepared by known methods; in the presence of a suitably inorganic base reagent such as Cs$_2$CO$_3$, NaH, K$_2$CO$_3$, and the like; in a suitably selected organic solvent such as DMF, THF, NMP, and the like; at a temperature in the range of from about 25° C. to about 100° C.; to yield the corresponding compound of formula (a-44).

The compound of formula (a-44) is then reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Ik).

Certain compounds of formula (I), more particularly compounds of formula (I) wherein X is selected from the group consisting of —CR$^A$R$^B$—N(R$^D$)—SO$_2$— or —CR$^A$R$^B$—CH$_2$—N(R$^D$)—SO$_2$ may be prepared by as described in Scheme A-13 below.

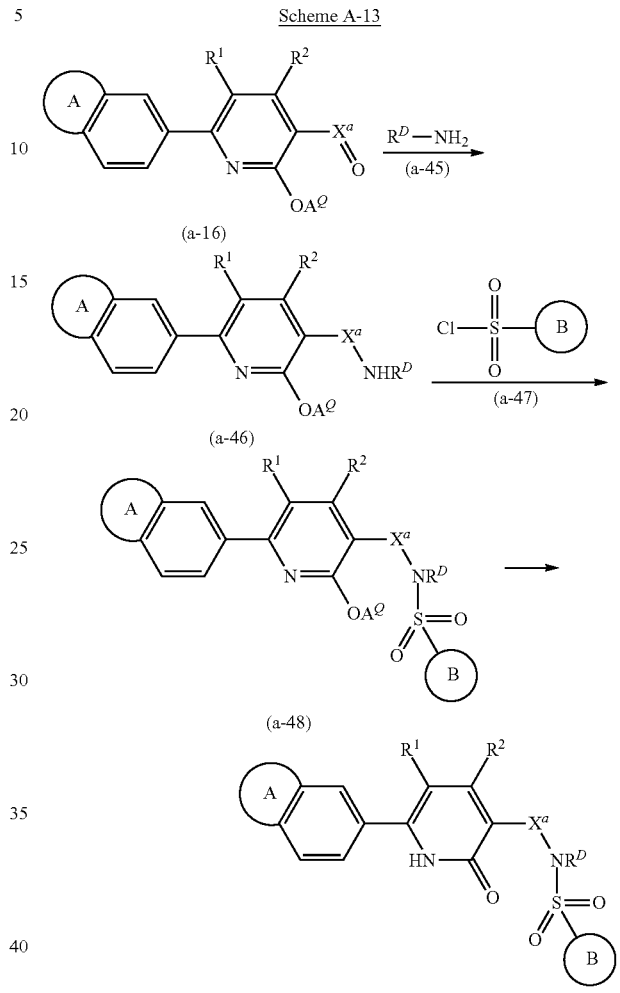

Accordingly, a suitably substituted compound of formula (a-16) wherein X$^a$ is selected from the group consisting of —CR$^A$R$^B$— and —CR$^A$R$^B$—CH$_2$— is reacted with a suitably substituted amine, a compound of formula (a-45), a known compound or compound prepared by known methods; in the presence of a suitably reducing reagent such as NaBH$_4$, NaBH$_3$(CN), NaBH(OAc)$_3$, and the like; in a suitably selected organic solvent such as DCM, THF, methanol, and the like; at a temperature in the range of from about 0° C. to about 25° C.; to yield the corresponding compound of formula (a-46).

The compound of formula (a-46) is reacted with a suitably substituted sulfonyl chloride reagent, a compound of formula (a-47), a known compound or compound prepared by known methods; in the presence of a suitably organic base such as TEA, DIPEA, pyridine, and the like; in a suitably selected organic solvent such as THF, DCM, 1,2-dicholorethane, and the like; at a temperature in the range of from about 0° C. to about 40° C.; to yield the corresponding compound of formula (a-48).

The compound of formula (a-48) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (Im).

Certain compounds of formula (I), more particularly compounds of formula (I) wherein X is —$CR^A R^B$—$CH_2$—$SO_2$— may be prepared as described in Scheme A-14, below.

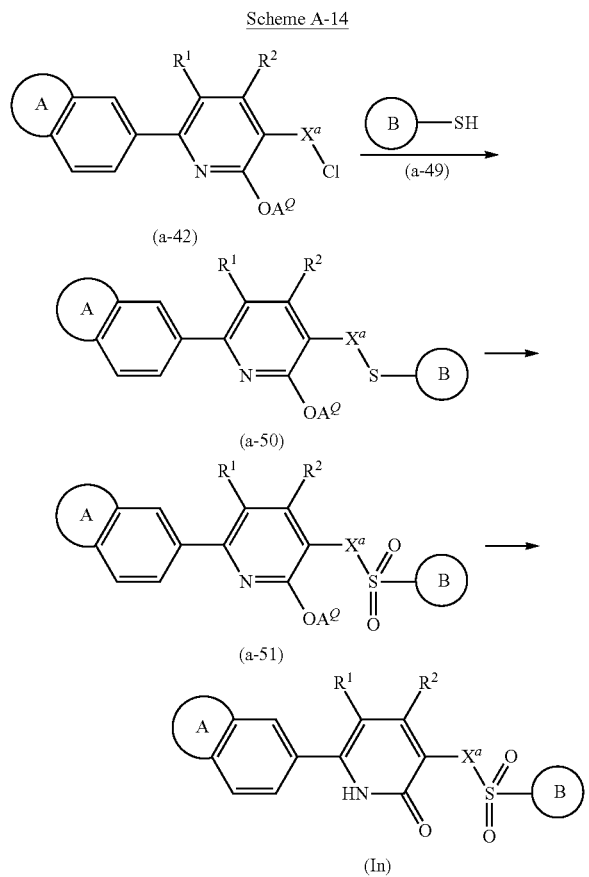

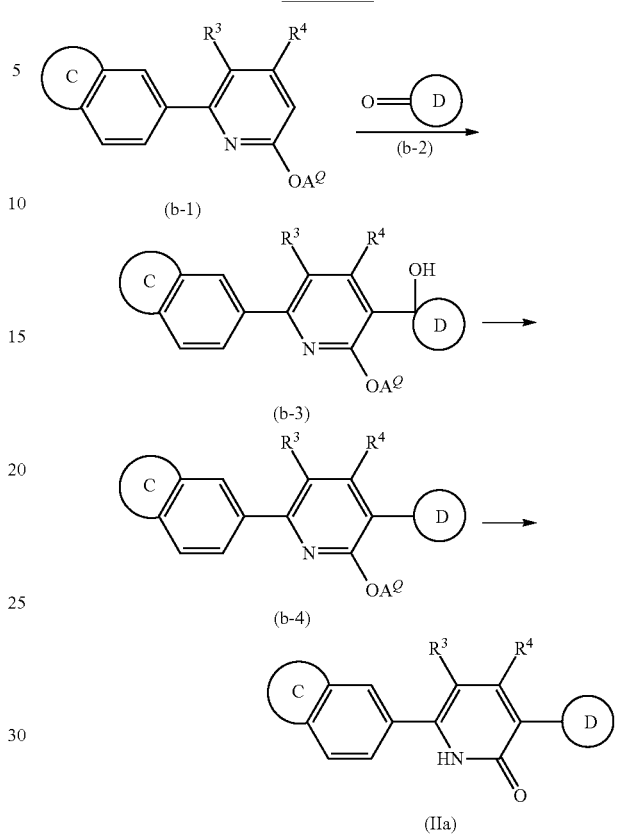

Accordingly, a suitably substituted compound of formula (a-42) wherein $X^a$ is —$CR^A R^B$—$CH_2$— is reacted with a suitably substituted compound of formula (a-49), a known compound or compound prepared by known methods; in the presence of a suitably selected base such as $K_2CO_3$, NaH, $Cs_2CO_3$, and the like; in a suitably selected organic solvent such as DMF, THF, NMP, and the like; at a temperature in the range of from about 25° C. to about 80° C.; to yield the corresponding compound of formula (a-50).

The compound of formula (a-50) is reacted with an oxidative reagent such as mCPBA, OXONE, $H_2O_2$ and the like; in a suitably selected organic solvent such as acetonitrile, DCM, 1,2-dicholorethane, and the like; at a temperature in the range of from about 0° C. to about 40° C.; to yield the corresponding compound of formula (a-51).

The compound of formula (a-51) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (In).

Certain compounds of formula (II), more particularly compounds of formula (II) wherein $R^5$ is hydrogen, may be prepared as described in Scheme B-1.

Accordingly, a suitably substituted compound of formula (b-1), wherein $A^Q$ is a suitably selected alkyl such as methyl, ethyl, and the like, preferably methyl, a known compound or compound prepared by known methods, is reacted with a suitably selected base such as t-BuLi, LDA, LiHMDS, and the like; in a suitably selected organic solvent such as THF, diethyl ether, 1,4-dioxane, and the like; at a temperature in the range of from about −78° C. to about 0° C.; followed by reaction with a suitably substituted compound of formula (b-2), a known compound or compound prepared by known methods; to yield the corresponding compound of formula (b-3).

The compound of formula (b-3) is reacted with a suitably selected reducing agent such as $Et_3SiH$, $NaBH_4$, $NaBH_3(CN)$, and the like; in the presence of a suitably selected acid such as TFA, AcOH, HCl, and the like; in a suitably selected organic solvent such as DCM, diethyl ether, THF, and the like; at a temperature in the range of from about 0° C. to about 25° C.; to yield the corresponding compound of formula (b-4).

The compound of formula (b-4) is reacted with a suitably selected acid such as pyridine hydrochloride, TMSI, TsOH, and the like; in a suitably selected organic solvent such as acetonitrile, THF, 1,4-dioxane, and the like; to yield the corresponding compound of formula (IIa).

One skilled in the art will recognize that the compound of formula (b-3) may alternatively be reacted with a suitably selected fluorinating agent such as DAST, BAST, SELECTFLUOR®, and the like; in a suitably selected organic solvent such as DCM, 1,2-dichloroethane, THF, and the like; at a temperature in the range of from about −78° C. to about 0° C.; to yield the corresponding compound wherein the —OH group is converted to the corresponding —F substituent. Said compound is then reacted with a suitably selected acid, as described above; to yield the corresponding compound of formula (II), wherein $R^5$ is fluoro.

Certain compounds of formula (II), more particularly compounds of formula (II) wherein (D)

is 2-($NR^F R^G$ substituted)-4,5-dihydro-imidazol-5-yl and wherein $R^5$ is selected from the group consisting of hydrogen, $C_{1-4}$alkyl, $C_{3-6}$cycloalkyl and —C(O)$NR^U R^V$ may alternatively be prepared as describe in Scheme B-2.

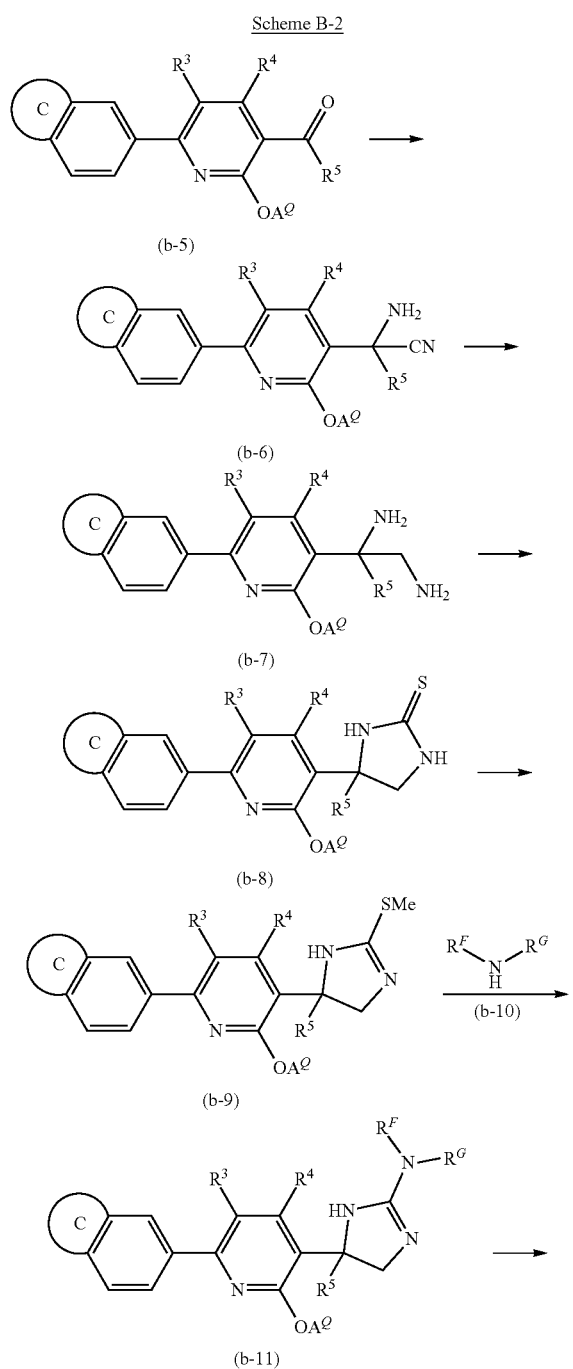

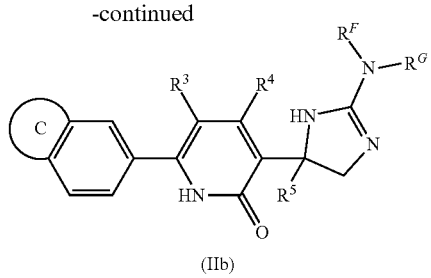

Accordingly, a suitably substituted compound of formula (b-5) wherein $A^Q$ is a suitably selected alkyl such as methyl, ethyl, and the like, preferably methyl, a known compound or compound prepared by known methods is reacted with TMSCN, a known compound; in the presence of a suitably selected source of ammonia such as $NH_4Cl$, 7N $NH_3$/methanol, $(NH_4)_2CO_3$, and the like; in a suitably selected organic solvent such as MeOH, EtOH, IPA, and the like; at a temperature in the range of from about 25° C. to about 80° C.; to yield the corresponding compound of formula (b-6).

The compound of formula (b-6) is reacted with hydrogen gas (for example at 30-60 psi); in the presence of a suitably selected catalyst such as 5-10% Pd/C, $Pt_2O$, Ni, and the like; in a suitably selected organic solvent such as MeOH, THF, ethyl acetate, and the like; at a temperature in the range of from about 25° C. to about 50° C.; to yield the corresponding compound of formula (b-7).

The compound of formula (b-7) is reacted with a suitably selected source of thione such as $CS_2$, thioimidazole, and the like; in the presence of a suitably selected base such as TEA, DIPEA, DBU, and the like; in a suitably selected organic solvent such as DCM, THF, diethyl ether, and the like; at a temperature in the range of from about 0° C. to about 50° C.; to yield the corresponding compound of formula (b-8).

The compound of formula (b-8) is reacted with a suitably selected $C_{1-4}$alkylating agent (for example a methylating agent, an ethylating agent, an isopropylating agent, and the like) such as $CH_3I$, $Me_2SO_4$, $CH_3CH_2I$, i-PrI, and the like; in the presence of a suitably selected base such as TEA, DIPEA, $K_2CO_3$, and the like; in a suitably selected organic solvent such as DCM, THF, DMF, and the like; at a temperature in the range of from about 25° C. to about 80° C.; to yield the corresponding compound of formula (b-9).

The compound of formula (b-9) is reacted with a suitably substituted compound of formula (b-10), a known compound or compound prepared by known methods; in the presence of a suitably selected base such as NaH, $Cs_2CO_3$, t-BuOK, and the like; in a suitably selected organic solvent such as THF, diethyl ether, DMF, and the like; at a temperature in the range of from about 25° C. to about 80° C.; to yield the corresponding compound of formula (b-11).

The compound of formula (b-11) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (IIb).

Certain compounds of formula (II), more particularly compounds of formula (II) wherein (D)

is 1H-imidazo[1,2-a]imidazol-2(3H)-one or 5H-imidazo[2,1-c][1,2,4]triazol-6(7H)-one and wherein $R^5$ is selected from the group consisting of hydrogen, $C_{1-4}$alkyl, $C_{3-6}$cycloalkyl and $-C(O)NR^U R^V$; may alternatively be prepared as described in Scheme B-3.

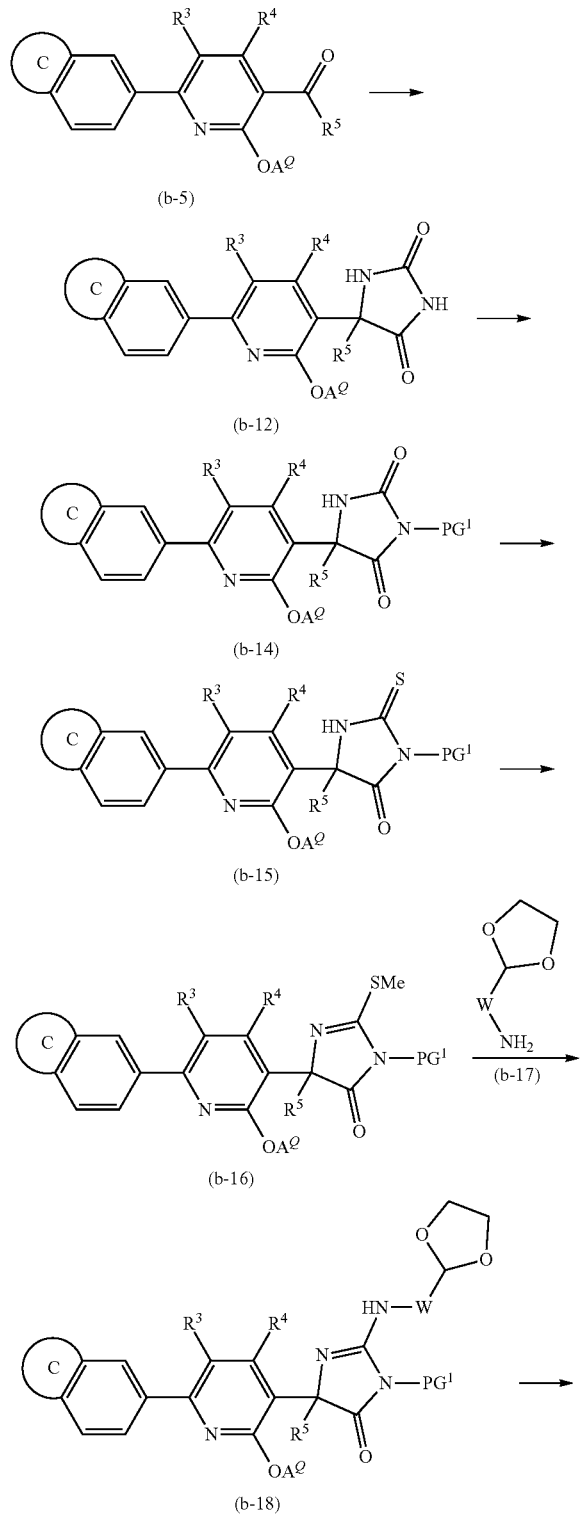

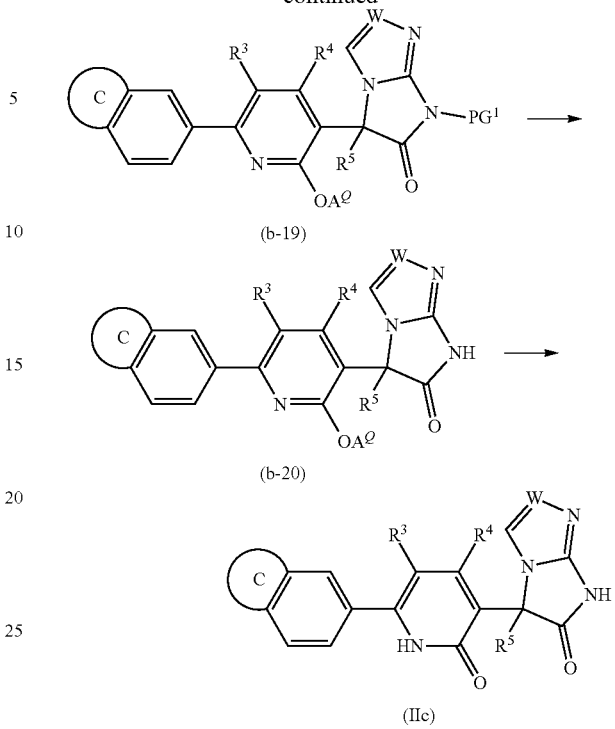

Accordingly, a suitably substituted compound of formula (b-5), wherein $A^Q$ is a suitably selected alkyl such as methyl, ethyl, and the like, preferably methyl, a known compound or compound prepared by known methods, is reacted with TMSCN, a known compound; in the presence of a suitably selected source of ammonia such as $NH_4OH$, $(NH_4)_2CO_3$, and the like; in a suitably selected organic solvent such as MeOH, EtOH, IPA, and the like; at a temperature in the range of from about 60° C. to about 100° C.; to yield the corresponding compound of formula (b-12).

The compound of formula (b-12) is reacted with a suitably selected protecting reagent, a known compound or compound prepared by known methods; in the presence of a suitably selected base such as NaH, $K_2CO_3$, TEA, and the like; in a suitably selected organic solvent such as DCM, THF, DMF, and the like; at a temperature in the range of from about 0° C. to about 50° C.; to yield the corresponding protected compound of formula (b-14), wherein $PG^1$ is the corresponding protecting group, such as benzyl, p-methoxybenzyl (PMB), 3,4-dimethoxy-benzyl, and the like.

The compound of formula (b-14) is reacted with a suitably selected source of sulfur such as S, $P_2S_5$, Lawesson's reagent, and the like; in a suitably selected organic solvent such as toluene, THF, xylene, and the like; at a temperature in the range of from about 60° C. to about 140° C.; to yield the corresponding compound of formula (b-15).

The compound of formula (b-15) is reacted with a suitably selected source of methyl such as MeI, $Me_2SO_4$, and the like; in the presence of a suitably selected base such as TEA, DIPEA, $K_2CO_3$, and the like; in a suitably selected organic solvent such as DCM, THF, DMF, and the like; at a temperature in the range of from about 25° C. to about 80° C.; to yield the corresponding compound of formula (b-16).

The compound of formula (b-16) is reacted with a suitably substituted amine compound of formula (b-17), wherein W is selected from the group consisting of NH and $CH_2$, a known compound or compound prepared by known methods; in the presence of a suitably selected base such as NaH, Cs₂CO₃, t-BuOK, and the like; in a suitably selected organic solvent such as THF, diethyl ether, DMF, and the like; at a temperature in the range of from about 25° C. to about 80° C.; to yield the corresponding compound of formula (b-18).

The compound of formula (b-18) is reacted with a suitably selected acid such as H₂SO₄, PPA, pTSA, and the like; in a suitably selected organic solvent such as toluene, THF, 1,4-dioxane, and the like; at a temperature in the range of from about 60° C. to about 120° C.; to yield the corresponding compound of formula (b-19).

The compound of formula (b-19) is reacted to remove the PG$^Y$ protecting group, for example, reacted with hydrogen gas, at for example 30-60 psi; in the presence of a suitably selected catalyst such as 5-10% Pd/C, PtO₂, Ni, and the like; in a suitably selected organic solvent such as MeOH, THF, ethyl acetate, and the like; at a temperature in the range of from about 25° C. to about 50° C.; to yield the corresponding compound of formula (b-20).

The compound of formula (b-20) is reacted with a suitably selected acid such as pyridine hydrochloride, TMSI, TsOH, and the like; in a suitably selected organic solvent such as acetonitrile, THF, 1,4-dioxane, and the like; at a temperature in the range of form about 25° C. to about 100° C.; to yield the corresponding compound of formula (IIc).

Additional compounds of formula (II) wherein R⁵ is selected from the group consisting of C₁₋₄alkyl, C₃₋₈cycloalkyl and —C(O)NR$^U$R$^V$ may be prepared as described in Scheme B-4, below.

(b-21), wherein R⁵ is selected from the group consisting of C₁₋₄alkyl, C₃₋₈cycloalkyl and —C(O)NR$^U$R$^V$, a known compound or compound prepared by known methods; to yield the corresponding compound of formula (b-22), wherein R⁵ is selected from the group consisting of C₁₋₄alkyl, C₃₋₈cycloalkyl and —C(O)NR$^U$R$^V$.

The compound of formula (b-22) is then substituted for the compound of formula (b-5) in Scheme B-2 or B-3 and reacted as described therein; to yield the corresponding compound of formula (IId).

One skilled in the art will recognize that additional compounds of formula (II) wherein

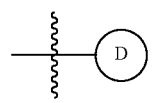

is a nitrogen containing heterocyclyl ring structure and wherein R⁵ is other than OH or fluoro, may be prepared from a suitably substituted compound of formula (b-5), a known compound or compound prepared by known methods, or compound prepared according as described herein (for example in the Schemes and/or Examples) by reacting said compound according to known ring closure/ring formation chemistry, for example as described in, for example, *"Heterocyclic Chemistry"* by J. A. JOULE, K. MILLS, Blackwell publishing; *"Fundamentals of Heterocyclic Chemistry: Importance in Nature and in the Synthesis of Pharmaceuticals"* by L. D. QUIN, J. A. TYRELL, Wiley publishing; *"Advances in Heterocyclic Chemistry"* Volume 1-116, Elsevier publishing; *"Modern Heterocyclic Chemistry"* Volume 1-4, by J. Alvarez-Builla, J. J, Vaquero, J. Barluenga, Wiley publishing; *"Comprehensive Heterocyclic Chemistry"* Volume 1-8, by C. W. Rees, A. R. Katritzky, Pergamon publishing; and then reacting the resulting compound to convert the —OA$^Q$ group to the =O group; to yield the corresponding compound of formula (I).

Compounds of formula (III) wherein Z is selected from the group consisting of —C(O)—NR$^L$R$^M$, —C(O)—NH—OR$^N$, —C(O)—NH—SO₂—R$^N$; —C(O)—NH(CH(CH₂OH)₂), —C(O)NH(C(CH₂OH)₃), —C(O)—NH—(CH₂—CH₂O)$_a$—R$^N$, —C(O)—NH—CH(CH₂O—(CH₂CH₂—O)$_b$—R$^N$)₂, —C(O)—NH—C(CH₂O—(CH₂CH₂—O)$_b$—R$^N$)₃), —C(O)—NH—CH₂CH₂—NR$^P$R$^Q$, and —C(O)—NH—(CH₂CH₂—O)$_a$—CH₂CH₂—NR$^P$R$^Q$, may be prepared as described in Scheme C-1, below.

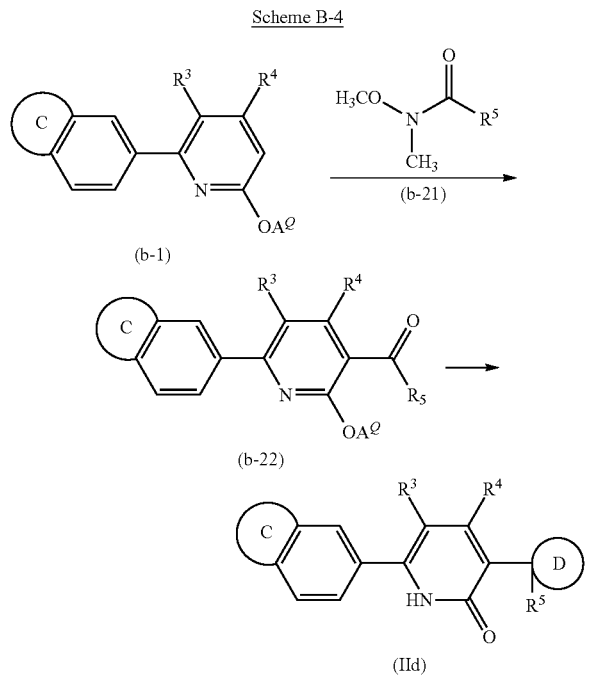

(b-1)

(b-22)

(IId)

Accordingly, a suitably substituted compound of formula (b-1), wherein A$^Q$ is a suitably selected alkyl such as methyl, ethyl, and the like, preferably methyl, a known compound or compound prepared by known methods, is reacted with a suitably selected base such as t-BuLi, LDA, LiHMDS, and the like; in a suitably selected organic solvent such as THF, diethyl ether, 1,4-dioxane, and the like; at a temperature in the range of from about −78° C. to about 0° C.; followed by reaction with a suitably substituted compound of formula

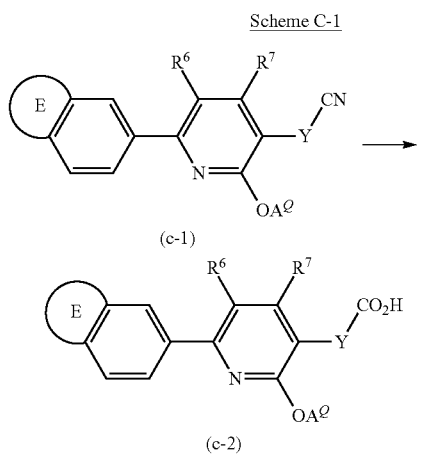

Scheme C-1

(c-1)

(c-2)

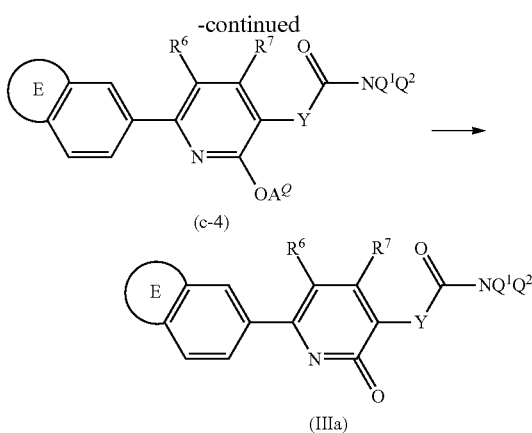

(c-4)

(IIIa)

Accordingly, a suitably substituted compound of formula (c-1), a known compound or compound prepared by known methods, is reacted with a suitably selected base such as KOH, NaOH, Ba(OH)$_2$, and the like; in a suitably selected organic solvent such as THF, methanol, ethanol, and the like; at a temperature in the range of from about 80° C. to about 120° C.; to yield the corresponding compound of formula (c-2).

The compound of formula (c-2) is reacted with a suitably substituted amine compound of formula (c-3), wherein $Q^1$ and $Q^2$ are $R^L$ and $R^M$ or $Q^1$ is hydrogen and $Q^2$ is selected from the group consisting of —$OR^N$, —$SO_2$—$R^N$, —(CH$_2$—CH$_2$O)$_a$—$R^N$, —CH(CH$_2$O—(CH$_2$CH$_2$—O)$_b$—$R^N$)$_2$, —C(CH$_2$O—(CH$_2$CH$_2$—O—)$_b$—$R^N$)$_3$), —CH$_2$CH$_2$—$NR^PR^Q$ and —(CH$_2$CH$_2$—O)$_a$—CH$_2$CH$_2$—$NR^PR^Q$, a known compound or compound prepared by known methods; in the presence of a suitably selected coupling agent such as HATU, EDCl, PyBrop, and the like; in the presence of a suitably selected base such as TEA, DIPEA, DBU, and the like; in a suitably selected organic solvent such as DCM, THF, DMF, and the like; at a temperature in the range of from about 25° C. to about 50° C.; to yield the corresponding compound of formula (c-4).

The compound of formula (c-4) is reacted with a suitably selected acid such as pyridine hydrochloride, TMSI, TsOH, and the like; in a suitably selected organic solvent such as acetonitrile, THF, 1,4-dioxane, and the like; at a temperature in the range of from about 25° C. to about 100° C.; to yield the corresponding compound of formula (IIIa).

One skilled in the art will recognize that the processes described in Schemes C-1 may alternatively be used to make compounds of formula (I), more particularly compounds of formula (I) wherein

is a nitrogen bound, optionally substituted ring group, by substituting a suitably substituted compound of formula (a-27)

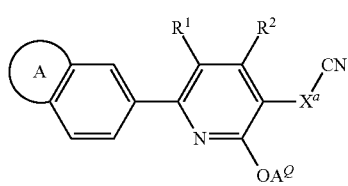

for the compound of formula (c-1) and substituting the desired nitrogen containing

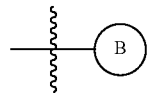

for the compound of formula (c-3), and reacting the compounds as described in Scheme C-1.

Compounds of formula (III) wherein $Y^a$ is selected from the group consisting of —$CR^H$— and —$CR^HR^J$—$CR^K$— and wherein X is selected from the group consisting of —$NR^S$—C(O)—$NR^PR^Q$ and —$NR^S$—C(O)—NH—CH$_2$CH$_2$—$NR^PR^Q$ may be prepared as described in Scheme C-2, below.

Scheme C-2

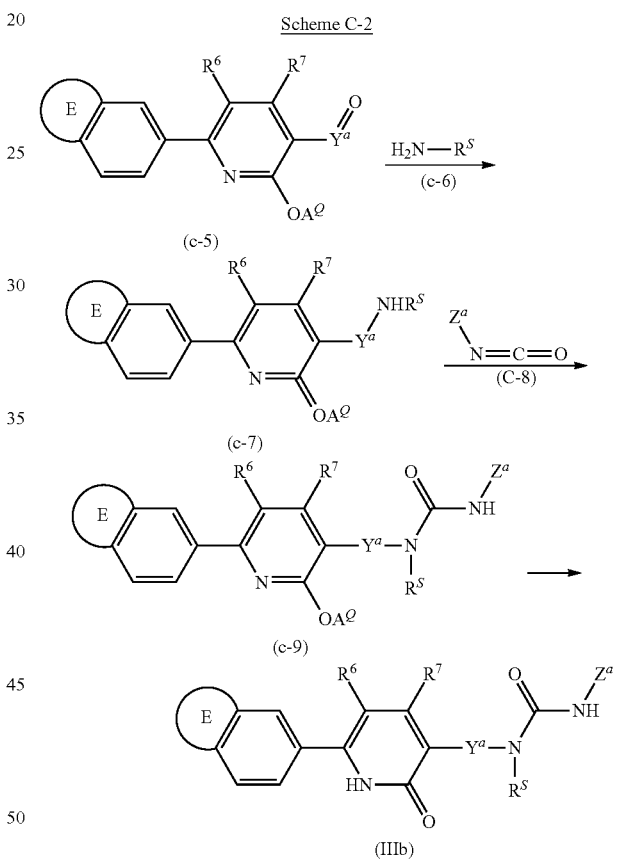

(IIIb)

Accordingly, a suitably substituted compound of formula (c-5), wherein $Y^a$ is selected from the group consisting of —$CR^H$— and —$CR^HR^J$—$CR^K$—, a known compound or compound prepared by known methods, is reacted with a suitably substituted compound of formula (c-6), a known compound or compound prepared by known methods, in the presence of a suitably selected reducing agent such as NaBH(OAc)$_3$, NaBH$_3$CN, NaBH$_4$, and the like; in a suitably selected organic solvent such as DCM, THF, methanol, and the like; at a temperature in the range of from about 0° C. to about 60° C.; to yield the corresponding compound of formula (c-7).

The compound of formula (c-7) is reacted with a suitably substituted isocyanate of formula (c-8), a known compound or compound prepared by known methods; in the presence of a suitably selected base such as TEA, DIPEA, pyridine, and the like; in a suitably selected organic solvent such as DCM, THF, DMF, and the like; at a temperature in the range of from about 25° C. to about 50° C.; to yield the corresponding compound of formula (c-9).

The compound of formula (c-9) is reacted with. a suitably selected acid such as pyridine hydrochloride, TMSI, TsOH, and the like; in a suitably selected solvent such as acetonitrile, THF, 1,4-dioxane, and the like; at a temperature in the range of from about 25° C. to about 100° C.; to yield the corresponding compound of formula (IIIb)

Compounds of formula (III) wherein Y is —CR$^H$R$^J$— and wherein X is selected from the group consisting of —NR$^S$—C(O)—NR$^P$R$^Q$ and —NR$^S$—C(O)—NH—CH$_2$CH$_2$—NR$^P$R$^Q$ may be prepared as described in Scheme C-3, below.

or a compound of the formula NH$_2$—CH$_2$CH$_2$—NR$^P$R$^Q$, a known compound or compound prepared by known methods; in the presence of a suitably selected base such as TEA, DIPEA, pyridine, and the like; in a suitably selected organic solvent such as toluene, THF, 1,4-dioxane, and the like; at a temperature in the range of from about 25° C. to about 80° C.; to yield the corresponding compound of formula (c-12), wherein Z$^a$ is the corresponding —NR$^P$R$^Q$ or —NH—CH$_2$CH$_2$—NR$^P$R$^Q$ group, respectively.

The compound of formula (c-12) is reacted with. a suitably selected acid such as pyridine hydrochloride, TMSI, TsOH, and the like; in a suitably selected solvent such as acetonitrile, THF, 1,4-dioxane, and the like; at a temperature in the range of from about 25° C. to about 100° C.; to yield the corresponding compound of formula (IIIc).

Compounds of formula (III) wherein Z is —NR$^S$—C(NH$_2$)=N—CN (a guanidine derivative) may be prepared as described in Scheme C-4 below.

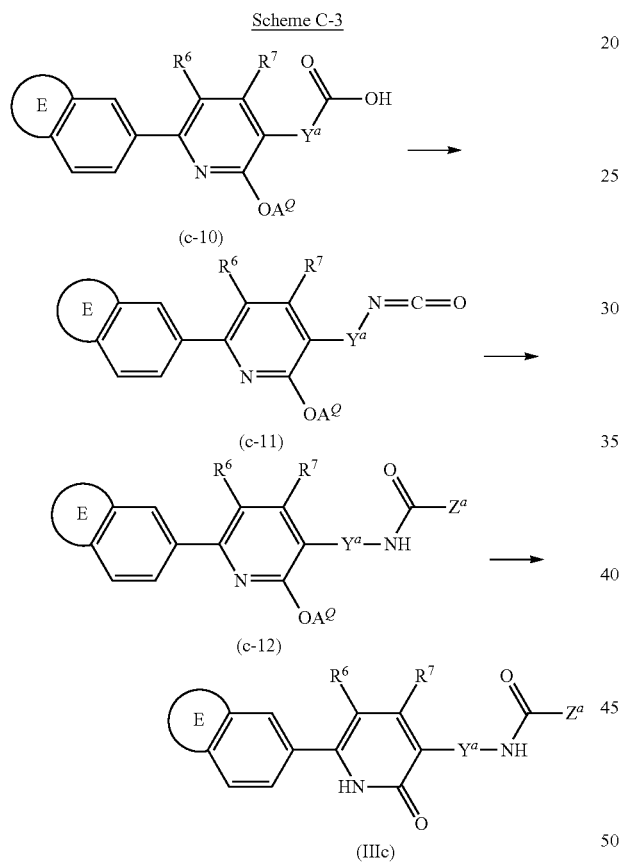

Scheme C-3

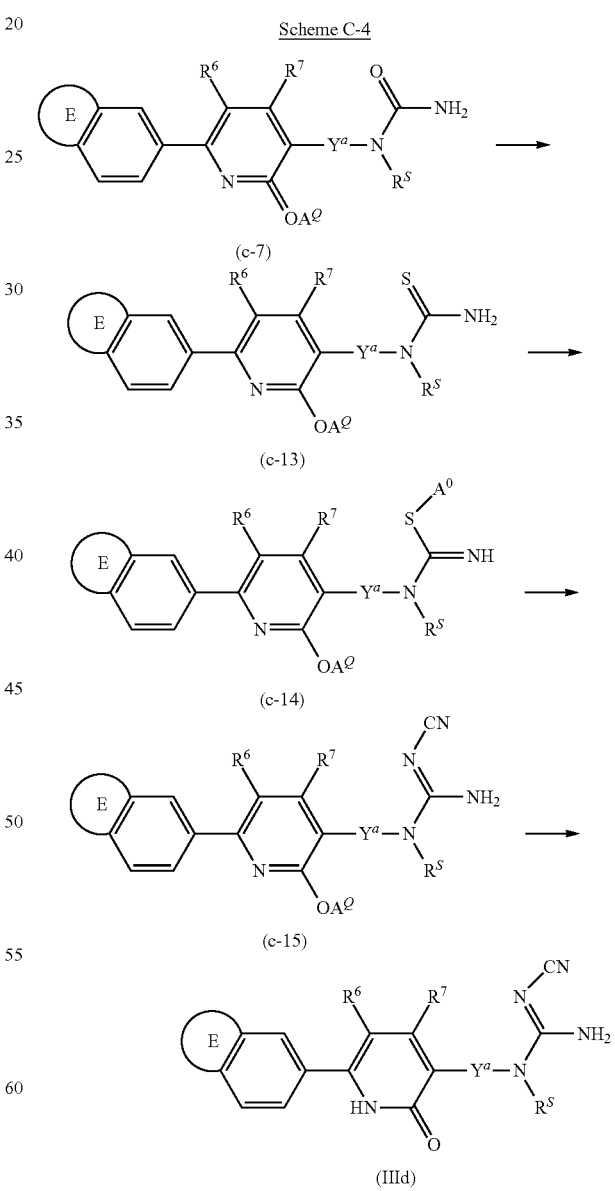

Scheme C-4

Accordingly, a suitably substituted compound of formula (c-10), wherein Y$^a$ is —CR$^H$R$^J$—, a known compound or compound prepared by known methods (for example, according to the methods described for above for the preparation of compounds of formula (a-28), substituting the desired —Y— substituent group for the —X$^a$— substituent group) is reacted with a suitably selected azide source such as DPPA, thionyl chloride/sodium azide, and the like, in the presence of a suitably organic base such as TEA, DIPEA, tributylamine, and the like; in a suitably selected organic solvent such as toluene, THF, 1,4-dioxane, and the like; at a temperature in the range of from about 80° C. to about 110° C.; to yield the corresponding compound of formula (c-11).

The compound of formula (c-11) is reacted with a suitably substituted amine, a compound of the formula NR$^P$R$^Q$—H Accordingly, a suitably substituted compound of formula (c-7) is reacted with a suitably selected source of sulfur such as S, $P_2S_5$, Lawesson's reagent, and the like; in a suitably selected organic solvent such as toluene, THF, xylene, and the like; at a temperature in the range of from about 60° C. to about 140° C.; to yield the corresponding compound of formula (c-13).

The compound of formula (c-13) is reacted with a suitably selected $C_{1-4}$alkylating agent such as $CH_3I$, $(CH_3)_2SO_4$, $CH_3CH_2I$, and the like; in the presence of a suitably selected base such as TEA, DIPEA, $K_2CO_3$, and the like; in a suitably selected organic solvent such as DCM, THF, DMF, and the like; at a temperature in the range of from about 25° C. to about 80° C.; to yield the corresponding compound of formula (c-14), wherein $A^0$ is the corresponding $C_{1-4}$alkyl group.

The compound of formula (c-14) is reacted with cyanoamine, a known compound; in the presence of a suitably selected base such as NaH, $Cs_2CO_3$, t-BuOK, and the like; in a suitably selected organic solvent such as THF, 1,4-dioxane, DMF, and the like; at a temperature in the range of from about 25° C. to about 80° C.; to yield the corresponding compound of formula (c-15).

The compound of formula (c-15) is reacted with. a suitably selected acid such as pyridine hydrochloride, TMSI, TsOH, and the like; in a suitably selected solvent such as acetonitrile, THF, 1,4-dioxane, and the like; at a temperature in the range of from about 25° C. to about 100° C.; to yield the corresponding compound of formula (IIId)

Pharmaceutical Compositions

The present invention further comprises pharmaceutical compositions containing one or more compounds of formula (I), compounds of formula (II) and/or compounds of formula (III) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15 mg/kg/day, or any amount or range therein, preferably from about 0.05 mg/kg/day to about 7.5 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I), compound of formula (II) or compound of formula (III), as the active ingredient(s) is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of disorders mediated by the EP3 receptor is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.05 to about 50.0 mg/kg of body weight per day, or any amount or range therein. More preferably, from about 0.05 to about 15.0 mg/kg of body weight per day, or any amount or range therein.

More preferably, from about 0.05 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLE

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

Compound #303 and #304

(Z) and (E) 5-(1-(6-(8-fluoronaphthalen-2-yl)-2-oxo-1,2-dihydropyridin-3-yl)-2-methylpropylidene)oxazolidine-2,4-dione

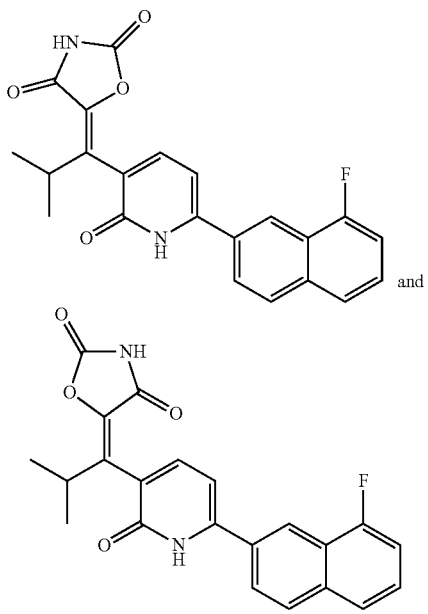

Step 1:
2-(8-fluoronaphthalen-2-yl)-6-methoxypyridine

Into a 250-mL round-bottom flask purged and maintained with an inert atmosphere of nitrogen, were placed a solution of 1-bromo-3-methoxybenzene (4.5 g, 24.06 mmol, 1.00 equiv) in DME/H$_2$O (80/20 mL), 2-(8-fluoronaphthalen-2-yl)-4,4,5,5-tetramethyl-1,3,2-dioxaborolane (7.0 g, 25.72 mmol, 1.07 equiv), Pd(dppf)Cl$_2$.CH$_2$Cl$_2$ (1 g, 1.23 mmol, 0.05 equiv), sodium carbonate (5.1 g, 48.12 mmol, 2.00 equiv). The resulting solution was stirred for 16 h at 90° C. in an oil bath. The resulting solution was then extracted with ethyl acetate (3×100 mL) and the organic layers combined. The resulting mixture was washed with sodium chloride (aq) (3×100 mL). The resulting mixture was concentrated under vacuum. The reaction target product was detected by LCMS. The residue was applied onto a silica gel column with ethyl acetate/petroleum ether (5:95) to yield 2-(8-fluoronaphthalen-2-yl)-6-methoxypyridine as yellow oil.

Mass spectrum (ESI, m/z): Calculated for C$_{16}$H$_{12}$FNO, 254.1 [M+H]$^+$, found 254.0.

Step 2: 1-[6-(8-fluoronaphthalen-2-yl)-2-methoxypyridin-3-yl]-2-methylpropan-1-one Into a 250-mL 3-necked round-bottom flask purged and maintained with an inert atmosphere of nitrogen, were placed a solution of 2-(8-fluoronaphthalen-2-yl)-6-methoxypyridine (2.6 g, 10.27 mmol, 1.00 equiv) in tetrahydrofuran (80 mL). The resulting solution was stirred at −78° C. in a dry ice bath. n-BuLi (2.5M) (10 mL) was added dropwise. The resulting solution was stirred for 2 h at −78° C. in a dry ice bath. N-methoxy-N,2-dimethylpropanamide (2.0 g, 15.25 mmol, 1.49 equiv) was added dropwise. The resulting solution was stirred for 2 h at −78° C. in a dry ice bath. The reaction was then quenched by the addition of NH$_4$Cl (aq). The resulting solution was extracted with ethyl acetate (3×100 mL) and the organic layers combined. The resulting mixture was washed with sodium chloride (aq) (3×100 mL). The resulting mixture was concentrated under vacuum. The residue was applied onto a silica gel column with ethyl acetate/petroleum ether (1:20) to yield 1-[6-(8-fluoronaphthalen-2-yl)-2-methoxypyridin-3-yl]-2-methylpropan-1-one as yellow oil.

Mass spectrum (ESI, m/z): Calculated for C$_{20}$H$_{18}$FNO$_2$, 324.1 [M+H]$^+$, found 324.0.

Step 3: 5-(1-(6-(8-fluoronaphthalen-2-yl)-2-methoxypyridin-3-yl)-1-hydroxy-2-methylpropyl)oxazolidine-2,4-dione Into a 100 mL three neck round-bottom flask, were placed oxazolidine-2,4-dione (515 mg, 5.096 mmol, 1 equiv.), LiCl (648 mg, 15.3 mmol, 3 equiv.) and THF (30 mL). The reaction was purged with an inert atmosphere of nitrogen. The mixture was then added t-BuLi (9.6 mL, 15.3 mmol, 1.6M) dropwise with stirring at −78° C. The resulting solution was stirred for 30 min at −78°. 1-(6-(8-Fluoronaphthalen-2-yl)-2-methoxypyridin-3-yl)-2-methylpropan-1-one (500 mg, 1.546 mmol, 0.3 equiv.)/THF (3 mL) was added to above solution at −78° C. The resulting solution was stirred for 30 min at −78° C. and 1 hrs at room temperature. The reaction progress was monitored by TLC/LCMS (DCM/MeOH=20:1). The reaction was then quenched by the addition of 3 mL of NH$_4$Cl (aqueous). The reaction was extracted with ethyl acetate and concentrated under vacuum. The residue was applied onto a silica gel column with DCM/MeOH (5:95) to yield 5-(1-(6-(8-fluoronaphthalen-2-yl)-2-methoxypyridin-3-yl)-1-hydroxy-2-methylpropyl)oxazolidine-2,4-dione as a white solid.

Mass spectrum (ESI, m/z): Calculated for C$_{23}$H$_{21}$FN$_2$O$_5$, 425.1 (M+H), found 425.1.

Step 4: (Z) and (E)-5-(1-(6-(8-fluoronaphthalen-2-yl)-2-methoxypyridin-3-yl)-2-methylpropylidene)oxazolidine-2,4-dione Into a 8-mL vial, were placed 5-(1-(6-(8-fluoronaphthalen-2-yl)-2-methoxypyridin-3-yl)-1-hydroxy-2-methylpropyl)oxazolidine-2,4-dione (390 mg, 0.919 mmol, 1 equiv.), Py (2.5 mL). SOCl$_2$ (0.2 mL, 3 equiv) was added dropwise at 0° C. The resulting solution was stirred 16 hrs at room temperature. The reaction progress was monitored by TLC/LCMS. The solution was concentrated under vacuum. Sodium carbonate was employed to adjust the pH to 7-8. The resulting solution was extracted with ethyl acetate (2×100 ml) and the organic/aqueous layers were combined. The solution was concentrated under vacuum. The residue product was purified by chromatogram on silica gel with ethyl acetate/petroleum ether (1:3) to yield 5-(1-(6-(8-fluoronaphthalen-2-yl)-2-methoxypyridin-3-yl)-2-methylpropylidene)oxazolidine-2,4-dione as a white solid.

Mass spectrum (ESI, m/z): Calculated for $C_{23}H_{19}FN_2O_4$, 407.1 (M+H), found 407.2.

Step 5: (Z) and (E) 5-(1-(6-(8-fluoronaphthalen-2-yl)-2-oxo-1,2-dihydropyridin-3-yl)-2-methylpropylidene) oxazolidine-2,4-dione Into a 8-mL vial, were placed (Z/E)-5-((6-(8-fluoronaphthalen-2-yl)-2-methoxypyridin-3-yl)methylene)oxazolidine-2,4-dione (50 mg, 0.123 mmol, 1.00 equiv), $CH_3CN$ (3 ml), sodium iodide (92 mg, 0.615 mmol, 5 equiv). To the mixture was then added chlorotrimethylsilane (66 mg, 0.615 mmol, 5.00 equiv) dropwise with stirring at room temperature. The resulting solution was stirred for 2 hrs at 25° C. The reaction progress was monitored by LCMS. The reaction was then quenched by the addition of MeOH (2 mL). The resulting mixture was concentrated under vacuum. The product was purified by by Prep-HPLC with the following conditions (1#-Waters 2767-5): Column, SunFire Prep C18, 5 um, 19*100 mm; mobile phase, Water of 0.05% $NH_4HCO_3$ and $CH_3CN$ (28% $CH_3CN$ up to 38% in 12 min, up to 100% in 2 min, down to 15% in 2 min; Detector, 254 nm to yield (E)-5-(1-(6-(8-fluoronaphthalen-2-yl)-2-oxo-1,2-dihydropyridin-3-yl)-2-methylpropylidene)oxazolidine-2,4-dione a light yellow solid $^1$H NMR (300 MHz, $CD_3OD$) δ: 8.44 (s, 1H), 8.06 (d, J=8.4 Hz, 1H), 7.85-7.89 (m, 1H), 7.76 (d, J=8.4 Hz, 1H), 7.46-7.61 (m, 2H), 7.25-7.31 (m, 1H), 6.83 (d, J=10.8 Hz, 1H), 3.15-3.24 (m, 1H), 1.18 (brm, 6H). $^{19}$F NMR (300 MHz, $CD_3OD$) δ: −124.51. Mass spectrum (ESI, m/z): Calculated for $C_{22}H_{17}FN_2O_4$, 393.1 (M+H), found 393.0 and (Z)-5-(1-(6-(8-fluoronaphthalen-2-yl)-2-oxo-1,2-dihydropyridin-3-yl)-2-methylpropylidene)oxazolidine-2,4-dione as a light yellow solid.

$^1$H NMR (300 MHz, $CD_3OD$) δ: 8.36 (s, 1H), 7.98 (d, J=8.4 Hz, 1H), 7.78 (d, J=8.7 Hz, 1H), 7.67 (d, J=8.4 Hz, 1H), 7.41-7.49 (m, 2H), 7.16-7.23 (m, 1H), 6.74 (d, J=7.2 Hz, 1H), 4.02-4.11 (m, 1H), 1.04 (d, J=6.9 Hz, 6H). $^{19}$F NMR (300 MHz, $CD_3OD$) δ: −124.40. Mass spectrum (ESI, m/z): Calculated for $C_{22}H_{17}FN_2O_4$, 393.1 (M+H), found 393.0.

Example 2

Compound #305

(E)-5-(1-(6-(8-fluoronaphthalen-2-yl)-2-oxo-1,2-dihydropyridin-3-yl)-2-methylpropylidene)thiazolidine-2,4-dione

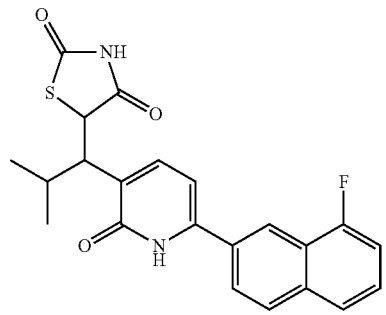

The title compound was prepared according to the procedure as described in Example 1 step 3, reacting 1-(6-(8-fluoronaphthalen-2-yl)-2-methoxypyridin-3-yl)-2-methylpropan-1-one and thiazolidine-2,4-dione followed by dehydration and demethylation to yield the product as an off-while solid.

$^1$H NMR (400 MHz, $CD_3OD$) δ: 8.35 (s, 1H), 7.96-8.00 (m, 1H), 7.78-7.82 (m, 1H), 7.66-7.69 (m, 1H), 7.40-7.49 (m, 1H), 7.17-7.27 (m, 2H), 6.71 (d, J=7.2 Hz, 1H), 2.65-2.68 (m, 1H), 0.99-1.02 (m, 6H). $^{19}$F NMR (400 MHz, $CD_3OD$) δ: −123.43. Mass spectrum (ESI, m/z): Calculated for $C_{22}H_{17}FN_2O_3S$, 409.1 (M+H), found 409.1.

Example 3

Compound #71

5-(1-(6-(8-fluoronaphthalen-2-yl)-2-oxo-1,2-dihydropyridin-3-yl)-2-methylpropyl) thiazolidine-2,4-dione

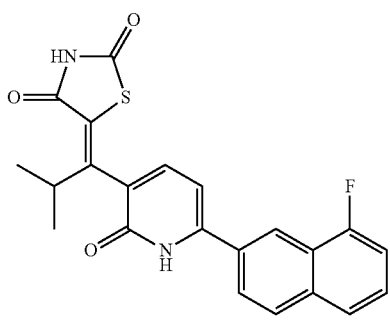 [SMILES: CC(C)/C(=C1/SC(=O)NC1=O)c1ccc(-c2ccc3cccc(F)c3c2)[nH]c1=O]

Step 1: 5-(1-(6-(8-fluoronaphthalen-2-yl)-2-methoxypyridin-3-yl)-2-methylpropyl)thiazolidine-2,4-dione Into a 50-mL round-bottom flask, were placed (E)-5-(1-(6-(8-fluoronaphthalen-2-yl)-2-methoxypyridin-3-yl)-2-methylpropylidene)thiazolidine-2,4-dione (60 mg, 0.142 mmol, 1 equiv), Pd/C (60 mg), AcOH (0.5 mL), 1,4-dioxane (5 mL). To the mixture was then introduced $H_2$ (g). The resulting solution was stirred overnight at 25° C. The reaction was monitored by LCMS. A filtration was performed and the filtrate was concentrated under vacuum to yield 5-(1-(6-(8-fluoronaphthalen-2-yl)-2-methoxypyridin-3-yl)-2-methylpropyl)thiazolidine-2,4-dione as light yellow oil.

Mass spectrum (ESI, m/z): Calculated for $C_{23}H_{21}FN_2O_3S$, 425.1 (M+H), found 425.1.

Step 2: 5-(1-(6-(8-fluoronaphthalen-2-yl)-2-oxo-1,2-dihydropyridin-3-yl)-2-methylpropyl) thiazolidine-2,4-dione Into a 50-mL round-bottom flask, were placed 5-(1-(6-(8-fluoronaphthalen-2-yl)-2-methoxypyridin-3-yl)-2-methylpropyl)thiazolidine-2,4-dione (30 mg, 0.071 mmol, 1 equiv.), $CH_3CN$ (5 mL), NaI (21 mg, 0.140 mmol, 2 equiv.), TMSCl (15 mg, 0.138 mmol, 2 equiv.). The resulting solution was stirred 4 h at 25° C. The reaction was monitored by LCMS. The resulting mixture was concentrated under vacuum. The residue was purified by Prep-HPLC with the following conditions (1#-Waters 2767-5): Column, SunFire Prep C18, 5 um, 19*100 mm; mobile phase, Water of 0.05%

NH$_4$HCO$_3$ and CH$_3$CN (20% CH$_3$CN up to 50% in 10 min, up to 100% in 2 min, down to 20% in 2 min; Detector, 254 nm to yield 5-(1-(6-(8-fluoronaphthalen-2-yl)-2-oxo-1,2-dihydropyridin-3-yl)-2-methylpropyl)thiazolidine-2,4-dione as off white solid.

$^1$H NMR (300 MHz, CD$_3$OD) δ: 8.39-8.41 (m, 1H), 8.05-8.08 (m, 1H), 7.83-7.88 (m, 1H), 7.75-7.78 (m, 1H), 7.51-7.60 (m, 2H), 7.26-7.32 (m, 1H), 6.74-6.79 (m, 1H), 4.95-4.96 (m, 1H), 3.53-3.57 (m, 1H), 2.55-2.58 (m, 1H), 1.12-1.15 (m, 3H), 0.85-0.93 (m, 3H). $^{19}$F NMR (300 MHz, CD$_3$OD) δ: −124.46. Mass spectrum (ESI, m/z): Calculated for C$_{22}$H$_{19}$FN$_2$O$_3$S, 411.1 (M+H), found 411.1.

Example 4

Compound #59 and #60 syn-(6-(8-Fluoronaphthalen-2-yl)-2-oxo-1,2-dihydropyridin-3-yl)-2-methylpropyl) oxazolidine-2,4-dione and anti-(6-(8-fluoronaphthalen-2-yl)-2-oxo-1,2-dihydropyridin-3-yl)-2-methylpropyl) oxazolidine

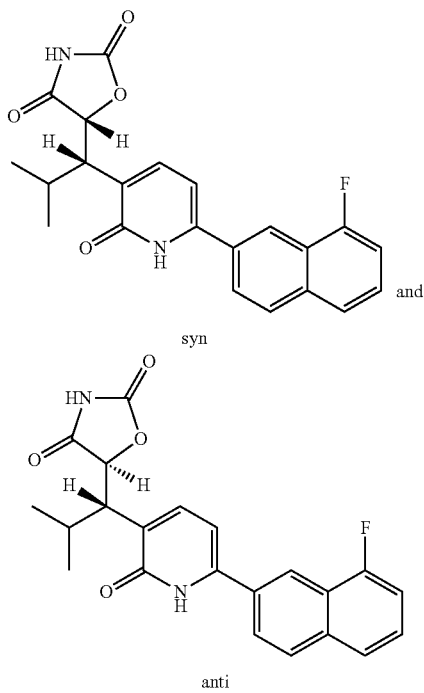

Step 1: ethyl 2-(6-(8-fluoronaphthalen-2-yl)-2-methoxypyridin-3-yl)-2-oxoacetate Into a 250-mL round-bottom flask purged and maintained with an inert atmosphere of nitrogen, were placed 2-(8-fluoronaphthalen-2-yl)-6-methoxypyridine (3.0 g, 11.845 mmol, 1.00 equiv), THF (50 mL). To the mixture was then added t-BuLi (11 mL, 17.6 mmol, 1.5 equiv) dropwise with stirring at −78° C. The resulting solution was stirred 3.0 h at −78° C. Then N-methoxy-N-methylisobutyramide (2.6 g, 17.791 mmol, 1.5 equiv) was added to the mixture and stirred for 3.0 h at −78° C. The reaction progress was monitored by LCMS. The reaction was then quenched by the addition of water. The resulting solution was extracted with ethyl acetate (3×100 mL) and the organic layers combined. The resulting mixture was concentrated under vacuum. The residue was applied onto a silica gel column with ethyl acetate/petroleum ether (5/95) to yield ethyl 2-(6-(8-fluoronaphthalen-2-yl)-2-methoxypyridin-3-yl)-2-oxoacetate as a yellow oil.

Mass spectrum (ESI, m/z): Calculated for C$_{20}$H$_{16}$FNO$_4$, 354.1 (M+H), found 354.0.

Step 2: Ethyl 2-(6-(8-fluoronaphthalen-2-yl)-2-methoxypyridin-3-yl)acetate

Into a 50-mL round-bottom flask, were placed ethyl 2-(6-(8-fluoronaphthalen-2-yl)-2-methoxypyridin-3-yl)-2-oxoacetate (2 g, 5.66 mmol, 1 equiv.), TFA (30 mL), Et$_3$SiH (20 mL) at room temperature. The resulting solution was stirred 6 hrs at 90° C. The reaction progress was monitored by TLC/LCMS. The solution was concentrated under vacuum. The residue was purified by chromatogram on silica gel with ethyl acetate/petroleum ether (20:1) to yield ethyl 2-(6-(8-fluoronaphthalen-2-yl)-2-methoxypyridin-3-yl)acetate as light yellow oil.

Mass spectrum (ESI, m/z): Calculated for C$_{20}$H$_{18}$FNO$_3$, 340.1 (M+H), found 340.1.

Step 3: Ethyl 2-(6-(8-fluoronaphthalen-2-yl)-2-methoxypyridin-3-yl)-3-methylbutanoate Into a 50-mL round-bottom flask, were placed ethyl 2-(6-(8-fluoronaphthalen-2-yl)-2-methoxypyridin-3-yl)acetate (1.030 g, 3.035 mmol, 1 equiv.), DMF (10 mL), potassium 2-methylpropan-2-olate (9.12 mL, 9.12 mmol, 3 equiv.) at room temperature. 2-Iodopropane (1.029 g, 6.053 mmol, 2 equiv.) was added at 0° C. The resulting solution was stirred 3 hrs at room temperature. The reaction progress was monitored by TLC/LCMS. The resulting solution was extracted with ethyl acetate (2×100 mL) and washed with brine (5×). The organic layers were combined. The solution was concentrated under vacuum. The residue was purified by chromatogram on silica gel with ethyl acetate/petroleum ether (15:1) to yield ethyl 2-(6-(8-fluoronaphthalen-2-yl)-2-methoxypyridin-3-yl)-3-methylbutanoate as a yellow solid.

Mass spectrum (ESI, m/z): Calculated for C$_{23}$H$_{24}$FNO$_3$, 382.2 (M+H), found 382.2.

Step 4: 2-(6-(8-Fluoronaphthalen-2-yl)-2-methoxypyridin-3-yl)-3-methylbutan-1-ol Into a 50-mL round-bottom flask, were placed ethyl 2-(6-(8-fluoronaphthalen-2-yl)-2-methoxypyridin-3-yl)-3-methylbutanoate (572 mg, 1.500 mmol, 1 equiv), THF (30 mL). LiAlH$_4$ (3.004 mmol, 2 equiv.) was added in portion at 0° C. The resulting solution was stirred 1 h at room temperature. The reaction progress was monitored by TLC/LCMS (PE:EA=6:1). The reaction was then quenched by Na$_2$SO$_4$.10H$_2$O. A filtration was performed and washed with MeOH. The solution was concentrated under vacuum. The reaction was extracted with ethyl acetate and dried over anhydrous sodium sulfate and concentrated under vacuum. The residue was purified by chromatogram on silica gel with ethyl acetate/petroleum ether (10:1) to yield 2-(6-(8-fluoronaphthalen-2-yl)-2-methoxypyridin-3-yl)-3-methylbutan-1-ol as a colorless oil.

Mass spectrum (ESI, m/z): Calculated for C$_{21}$H$_{22}$FNO$_2$, 340.2 (M+H), found 340.1.

Step 5: 2-(6-(8-Fluoronaphthalen-2-yl)-2-methoxypyridin-3-yl)-3-methylbutanal Into a 25-mL round-bottom flask, were placed 2-(6-(8-fluoronaphthalen-2-yl)-2-methoxypyridin-3-yl)-3-methylbutan-1-ol (380 mg, 1.120 mmol, 1 equiv.), $CH_2Cl_2$ (30 mL). (1,1,1-triacetoxy)-1,1-dihydro-1,2-benziodoxol-3(1H)-one (1.347 g, 3.176 mmol, 3 equiv.) was added in portion at room temperature. The resulting solution was stirred 1 h at room temperature. The reaction progress was monitored by TLC/LCMS (PE:EA=6:1). The reaction was then quenched by $Na_2S_2O_3/NaHCO_3/H_2O$. The reaction was extracted with ethyl acetate and dried over anhydrous sodium sulfate and concentrated under vacuum. The residue was purified by chromatogram on silica gel with ethyl acetate/petroleum ether (10:1) to yield 2-(6-(8-fluoronaphthalen-2-yl)-2-methoxypyridin-3-yl)-3-methylbutanal as a colorless oil.

Mass spectrum (ESI, m/z): Calculated for $C_{21}H_{20}FNO_2$, 338.1 (M+H), found 338.1.

Step 6: 3-(6-(8-fluoronaphthalen-2-yl)-2-methoxypyridin-3-yl)-2-hydroxy-4-methyl pentanenitrile Into a 40-mL vial were placed 2-(6-(8-fluoronaphthalen-2-yl)-2-methoxypyridin-3-yl)-3-methylbutanal (300 mg, 0.899 mmol, 1 equiv.), TMSCN (90 mg, 0.899 mmol, 1 equiv.), $CH_2Cl_2$ (10 mL). The reaction was purged with an inert atmosphere of nitrogen. To the mixture was then added $AlCl_3$ (400 mg, 0.89 mmol, 1 equiv.), at 0° C. The resulting solution was stirred for 60 min at 0° C. The reaction progress was monitored by TLC (PE:EA=3:1). The reaction was then quenched by the addition of water (2 mL). The reaction was extracted with ethyl acetate and concentrated under vacuum. The residue was applied onto a silica gel column with ethyl acetate/petroleum ether (10:90) to yield 3-(6-(8-fluoronaphthalen-2-yl)-2-methoxypyridin-3-yl)-2-hydroxy-4-methylpentanenitrile 324 mg as a colorless oil.

Mass spectrum (ESI, m/z): Calculated for $C_{22}H_{21}FN_2O_2$, 365.2 (M+H), found 365.2.

Step 7: 3-(6-(8-fluoronaphthalen-2-yl)-2-hydroxypyridin-3-yl)-2-hydroxy-4-methyl pentanoate Into a 50-mL round-bottom flask were placed 3-(6-(8-fluoronaphthalen-2-yl)-2-methoxypyridin-3-yl)-2-hydroxy-4-methylpentanenitrile (200 mg, 0.549 mmol, 1 equiv.), MeOH (10 mL). HCl (4 mL) was added dropwise. The resulting solution was stirred for 16 hrs min at 80° C. The reaction progress was monitored by TLC/LCMS (PE:EA=1:1). The solution was concentrated under vacuum. The residue was applied onto a silica gel column with ethyl acetate/petroleum ether (1:1) to yield methyl 3-(6-(8-fluoronaphthalen-2-yl)-2-hydroxypyridin-3-yl)-2-hydroxy-4-methylpentanoate as a colorless oil.

Mass spectrum (ESI, m/z): Calculated for $C_{22}H_{22}FNO_4$, 384.2 (M+H), found 384.0.

Step 8: syn-(6-(8-Fluoronaphthalen-2-yl)-2-oxo-1,2-dihydropyridin-3-yl)-2-methylpropyl) oxazolidine-2,4-dione and anti-(6-(8-fluoronaphthalen-2-yl)-2-oxo-1,2-dihydropyridin-3-yl)-2-methylpropyl) oxazolidine Into a 100-mL round-bottom flask, were placed methyl 3-(6-(8-fluoronaphthalen-2-yl)-2-hydroxypyridin-3-yl)-2-hydroxy-4-methylpentanoate (94 mg, 0.245 mmol, 1.00 equiv.), $CH_2Cl_2$ (4 mL), 2,2,2-trichloroacetyl isocyanate (53.7 mg, 0.270 mmol, 1.00 equiv.). The resulting solution was stirred for 2 hrs at 25° C. The resulting mixture was concentrated under vacuum. To the mixture was then added EtOH (4 mL), $Et_3N$ (0.1 mL). The resulting solution was stirred for 4 hrs at 80° C. The reaction progress was monitored by TLC/LCMS. The resulting mixture was concentrated under vacuum. The residue was dissolved in DMF (2 mL). The residue was purified by Prep-HPLC with the following conditions (1#-Waters 2767-5): Column, SunFire Prep C18, 5 um, 19*100 mm; mobile phase, Water of 0.05% $NH_4HCO_3$ acid and $CH_3CN$ (28% $CH_3CN$ up to 32% in 17 min, up to 100% in 1 min, down to 28% in 1 min; Detector, 254 nm to yield syn-(6-(8-fluoronaphthalen-2-yl)-2-oxo-1,2-dihydropyridin-3-yl)-2-methylpropyl)oxazolidine-2,4-dione as a white solid $^1$H NMR (400 MHz, $CD_3OD$) δ: 8.40 (s, 1H), 8.06 (d, J=8.4 Hz, 1H), 7.83-7.86 (m, 1H), 7.77 (d, J=8.4 Hz, 1H), 7.70 (d, J=7.2 Hz, 1H), 7.52-7.58 (m, 1H), 7.27-7.31 (m, 1H), 6.77 (d, J=7.2 Hz, 1H), 5.23 (d, J=2.8 Hz, 1H), 3.58-3.62 (m, 1H), 2.05-2.25 (m, 1H), 1.26 (d, J=7.2 Hz, 3H), 0.92 (d, J=7.2 Hz, 3H). $^{19}$F NMR (400 MHz, $CD_3OD$) δ: −124.45. Mass spectrum (ESI, m/z): Calculated for $C_{22}H_{19}FN_2O_4$, 395.1 (M+H), found 395.1.

and anti-(6-(8-fluoronaphthalen-2-yl)-2-oxo-1,2-dihydropyridin-3-yl)-2-methylpropyl)oxazolidine-2,4-dione as a white solid.

1H NMR (400 MHz, $CD_3OD$) δ: 8.40 (s, 1H), 8.06-8.08 (m, 1H), 7.85-7.88 (m, 1H), 7.77 (d, J=8.4 Hz, 1H), 7.63 (d, J=7.2 Hz, 1H), 7.53-7.58 (m, 1H), 7.27-7.32 (m, 1H), 6.79 (d, J=7.2 Hz, 1H), 5.28 (d, J=6.0 Hz, 1H), 3.56-3.60 (m, 1H), 2.38-2.47 (m, 1H), 1.16 (d, J=6.4 Hz, 3H), 0.92 (d, J=6.8 Hz, 3H). 19F NMR (400 MHz, $CD_3OD$) δ: −124.40.

Example 5

Compound #62

(Z)-5-(2-(6-(8-fluoronaphthalen-2-yl)-2-oxo-1,2-dihydropyridin-3-yl)-3-methylbutylidene)oxazolidine-2,4-dione

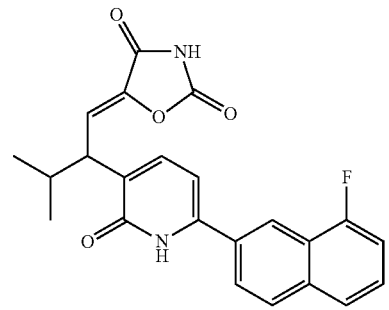 [SMILES: CC(C)C(/C=C1\OC(=O)NC1=O)c1ccc(-c2ccc3cccc(F)c3c2)[nH]c1=O]

Step 1: 5-(2-(6-(8-fluoronaphthalen-2-yl)-2-methoxypyridin-3-yl)-1-hydroxy-3-methylbutyl)oxazolidine-2,4-dione To a rapidly stirred solution of lithium chloride (510 mg, 12.030 mmol, 3.00 equiv.) and oxazolidine-2,4-dione (380 mg, 3.760 mmol, 1.00 equiv.) in THF (8 mL) under $N_2$ atmosphere at −78° C. was added t-BuLi (7.5 mL, 12.00 mmol, 3.00 equiv) dropwise. The reaction mixture was stirred at −78° C. for 20 minutes then warmed up to 0° C. for 5 minutes. The mixture was recooled to −78° C. and a solution of 2-(6-(8-fluoronaphthalen-2-yl)-2-methoxypyridin-3-yl)-3-methylbutanal (400 mg, 1.186 mmol, 0.30 equiv.) in THF (4 mL) was added. The reaction was stirred at −78° C. for 30 minutes. The reaction was monitored by TLC. Saturated aq. NH$_4$Cl was added and the mixture was extracted with EtOAc, and the combined organic layer. The organic layer was dried over Na$_2$SO$_4$ and the solvent was evaporated under reduced pressure. The residue was purified by column chromatography (DCM/MeOH=20:1) to yield 5-(2-(6-(8-fluoronaphthalen-2-yl)-2-methoxypyridin-3-yl)-1-hydroxy-3-methylbutyl)oxazolidine-2,4-dione as a white solid.

Mass spectrum (ESI, m/z): Calculated for $C_{24}H_{23}FN_2O_5$, 439.2 (M+H), found 439.1.

Step 2: (Z)-5-(2-(6-(8-fluoronaphthalen-2-yl)-2-methoxypyridin-3-yl)-3-methylbutylidene) oxazolidine-2,4-dione Into a 25-mL round-bottom flask, were placed 5-(2-(6-(8-fluoronaphthalen-2-yl)-2-methoxypyridin-3-yl)-1-hydroxy-3-methylbutyl)oxazolidine-2,4-dione (30 mg, 0.068 mmol, 1.00 equiv.) in pyridine, then sulfurous dichloride (24 mg, 0.202 mmol, 3.00 equiv) was added to the former solution at 0° C. The resulting solution was stirred for 4.5 h at room temperature. The reaction was monitored by TLC. The solvent was evaporated under reduced pressure. The residue was purified by column chromatography (DCM/MeOH=20:1) to yield (Z)-5-(2-(6-(8-fluoronaphthalen-2-yl)-2-methoxypyridin-3-yl)-3-methylbutylidene)oxazolidine-2,4-dione as a dark brown solid.

Mass spectrum (ESI, m/z): Calculated for $C_{24}H_{21}FN_2O_4$, 421.1 (M+H), found 421.0.

Step 3: (Z)-5-(2-(6-(8-fluoronaphthalen-2-yl)-2-oxo-1,2-dihydropyridin-3-yl)-3-methyl butylidene)oxazolidine-2,4-dione Into a 25-mL round-bottom flask, were placed a solution of (Z)-5-(2-(6-(8-fluoronaphthalen-2-yl)-2-methoxypyridin-3-yl)-3-methylbutylidene)oxazolidine-2,4-dione (60 mg, 0.143 mmol, 1.00 equiv.), NaI (44 mg, 0.294 mmol, 2.00 equiv.) in CH$_3$CN (8 mL), then TMSCl (32 mg, 0.295 mmol, 2.00 equiv.) was added. The resulting solution was stirred for 3.5 h at 30° C., and the reaction was monitored by LCMS. MeOH (0.5 mL) was added to the mixture and the mixture was stirred for 10 minutes at room temperature. The resulting mixture was evaporated under reduced pressure. The residual was purified by Prep-HPLC with the following conditions: (1#waters2767-5): Column, SunFire Prep C18, 19*150 mm 5 umH PrepC-001(T)18600256819513816414 04; mobile phase, Phase A: water with 0.05% NH$_4$HCO$_3$; Phase B: CH$_3$CN (27% CH$_3$CN up to 33% in 10 min, up to 95% CH$_3$CN in 0.1 min, hold 95% in 1.9 min, down to 27% CH$_3$CN in 0.1 min, hold 27% in 1.9 min); Detector, UV220 & 254 nm to yield (Z)-5-(2-(6-(8-fluoronaphthalen-2-yl)-2-oxo-1,2-dihydropyridin-3-yl)-3-methylbutylidene)oxazolidine-2,4-dione obtained as a white solid.

$^1$H NMR (300 MHz, CD$_3$OD) δ: 8.35 (s, 1H), 8.01-8.04 (m, 1H), 7.79-7.83 (m, 1H), 7.71-7.74 (m, 1H), 7.47-7.59 (m, 2H), 7.22-7.28 (m, 1H), 6.74 (d, J=7.2 Hz, 1H), 6.35 (d, J=10.8 Hz, 1H), 3.50-3.72 (m, 1H), 2.31-2.42 (m, 1H), 0.98 (d, J=6.6 Hz, 3H), 0.88 (d, J=7.5 Hz, 3H). $^{19}$F NMR (300 MHz, CD$_3$OD) δ: −77.17,−124.47. Mass spectrum (ESI, m/z): Calculated for $C_{23}H_{19}FN_2O_4$, 407.1 [M−2.14CF$_3$COOH+H], found 407.1.

Example 6

Compound #78 and #79

(R*,Z)-5-(2-(6-(8-fluoronaphthalen-2-yl)-2-oxo-1,2-dihydropyridin-3-yl)-3-methylbutylidene) oxazolidine-2,4-dione and (S*,Z)-5-(2-(6-(8-fluoronaphthalen-2-yl)-2-oxo-1,2-dihydropyridin-3-yl)-3-methylbutylidene) oxazolidine-2,4-dione

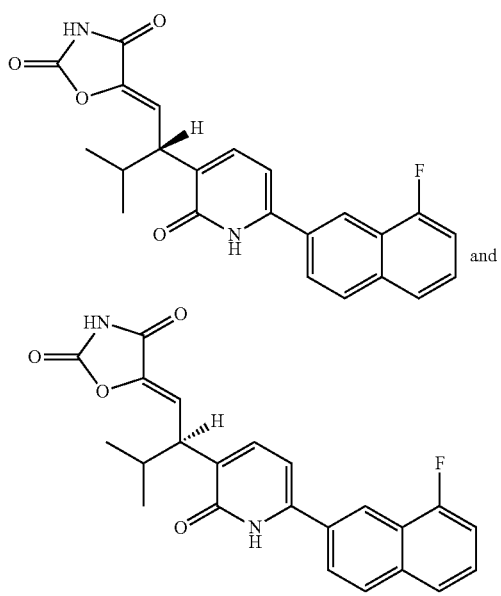

and (Z)-5-(2-(6-(8-fluoronaphthalen-2-yl)-2-oxo-1,2-dihydropyridin-3-yl)-3-methylbutylidene) oxazolidine-2,4-dione as a racemate (200 mg) was purified by chiral SFC (CHIRALPAK AD-H 5 μM 250×20 mm) using mobile phase of Hex (0.1% TFA) and IPA (hold 5.0% IPA in 14 min) method and detector at UV 254/220 nm to yield the corresponding R* enantiomer and S* enantiomer as white solids. Absolute stereochemistry was arbituaIIy assigned. The solids were then individually dissolved in water (10 mL) and ACN (2 mL) and dried by lypholizer to yield (R*, Z)-5-(2-(6-(8-fluoronaphthalen-2-yl)-2-oxo-1,2-dihydropyridin-3-yl)-3-methylbutylidene) oxazolidine-2,4-dione as a light yellow solid.

$^1$H NMR (300 MHz, DMSO-d$_6$) δ 12.43 (s, 1H), 8.62 (s, 1H), 8.25 (d, J=8.6 Hz, 1H), 8.11 (d, J=8.8 Hz, 1H), 7.97 (d, J=8.3 Hz, 1H), 7.66-7.79 (m, 2H), 7.50-7.60 (m, 1H), 6.88-7.03 (m, 1H), 6.48 (d, J=10.9 Hz, 1H), 3.70-3.84 (m, 1H), 2.32-2.47 (m, 1H), 1.07 (d, J=6.6 Hz, 3H), 0.98 (d, J=6.6 Hz, 3H). $^{19}$F NMR (300 MHz, DMSO) δ: −122.23. Mass spectrum (ESI, m/z): Calculated for $C_{23}H_{20}ClFN_2O_4$, 407.1 (M+H), found 407.1.

and (S*, Z)-5-(2-(6-(8-fluoronaphthalen-2-yl)-2-oxo-1,2-dihydropyridin-3-yl)-3-methylbutylidene)oxazolidine-2,4-dione as light yellow solid.

$^1$H NMR (300 MHz, DMSO-d$_6$) δ 12.33 (s, 1H), 8.51 (s, 1H), 8.14 (d, J=8.8 Hz, 1H), 8.06-7.97 (m, 1H), 7.87 (d, J=8.2 Hz, 1H), 7.43-7.59 (m, 2H), 7.31-7.40 (m, 1H), 6.81-6.85 (m, 1H), 6.37 (d, J=11.0 Hz, 1H), 3.67 (t, J=8.9

Hz, 1H), 2.23-2.29 (m, 1H), 0.92 (d, J=6.6 Hz, 3H), 0.83 (d, J=6.6 Hz, 3H). $^{19}$F NMR (300 MHz, DMSO) δ: −122.23. Mass spectrum (ESI, m/z): Calculated for $C_{23}H_{20}ClFN_2O_4$, 407.1 (M+H), found 407.1.

Example 7

Compound #63

(Z)-5-(2-(6-(8-fluoronaphthalen-2-yl)-2-oxo-1,2-dihydropyridin-3-yl)-3-methylbutylidene) thiazolidine-2,4-dione

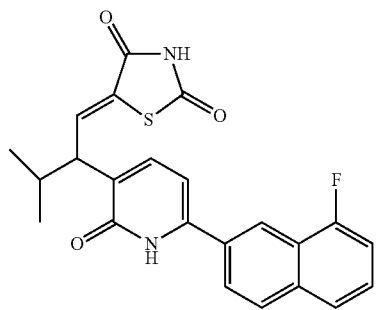 [SMILES: CC(C)C(/C=C1\SC(=O)NC1=O)c1ccc(-c2ccc3cccc(F)c3c2)[nH]c1=O]

The title compound was prepared according to the procedure as described in Example 5 step 1, reacting 2-(6-(8-fluoronaphthalen-2-yl)-2-methoxypyridin-3-yl)-3-methylbutanal and thiazolidine-2,4-dione followed by dehydration and demethylation to yield the product as an off-yellow solid.
$^1$H NMR (400 MHz, CD$_3$OD) δ: 8.43 (s, 1H), 8.07 (d, J=8.8 Hz,1H), 7.87 (d, J=8.8 Hz,1H), 7.77 (d, J=8.4 Hz,1H), 7.53-7.60 (m, 2H), 7.21-7.32 (m, 2H), 6.79 (d, J=7.2 Hz,1H), 3.32-3.38 (m, 1H), 2.35-2.45 (m, 1H), 1.04 (d, J=6.4 Hz,3H), 0.95 (d, J=6.8 Hz,3H). $^{19}$F NMR (400 MHz, CD$_3$OD) δ: −124.42.
Mass spectrum (ESI, m/z): Calculated for $C_{23}H_{19}FN_2O_3S$, 423.1 (M+H), found 423.0.

Example 8

Compound #81 and #74

Syn-3-(1-(1H-imidazol-2-yl)-2-methylpropyl)-6-(8-fluoronaphthalen-2-yl)pyridin-2(1H)-one and anti-3-(1-(1H-imidazol-2-yl)-2-methylpropyl)-6-(8-fluoronaphthalen-2-yl)pyridin-2(1H)-one

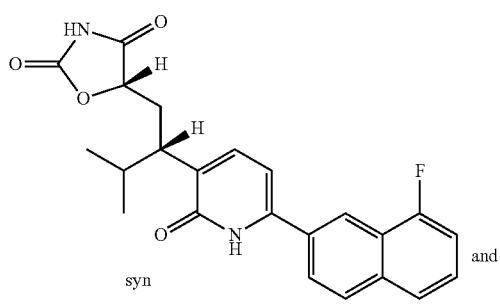
syn

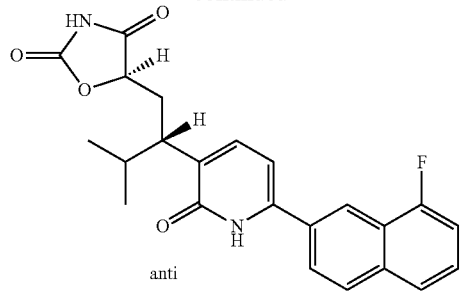
anti

Step 1: Syn-(6-(8-fluoronaphthalen-2-yl)-2-methoxypyridin-3-yl)-3-methyl butyl) oxazolidine-2,4-dione and anti-(6-(8-fluoronaphthalen-2-yl)-2-methoxypyridin-3-yl)-3-methylbutyl) oxazolidine-2,4-dione Into a 50-mL round-bottom flask, were placed a solution of (Z)-5-(2-(6-(8-fluoronaphthalen-2-yl)-2-methoxypyridin-3-yl)-3-methylbutylidene)oxazolidine-2,4-dione (20 mg, 0.048 mmol, 1.00 equiv.) in ethyl acetate (10 mL), Palladium carbon (20 mg). To the mixture was then introduced hydrogen gas. The resulting solution was stirred for 16 h at 25° C. The solids were filtered out. The resulting mixture was concentrated under vacuum. The residue was applied onto a silica gel column with DCM/MeOH (20/1) to yield 5-(2-(6-(8-fluoronaphthalen-2-yl)-2-methoxypyridin-3-yl)-3-methylbutyl)oxazolidine-2,4-dione as yellow oil.
Mass spectrum (ESI, m/z): Calculated for $C_{24}H_{23}FN_2O_4$, 423.2 (M+H), found 423.2.

Step 2: Syn-3-(1-(1H-imidazol-2-yl)-2-methylpropyl)-6-(8-fluoronaphthalen-2-yl)pyridin-2(1H)-one and anti-3-(1-(1H-imidazol-2-yl)-2-methylpropyl)-6-(8-fluoronaphthalen-2-yl)pyridin-2(1H)-one The title compounds were prepared according to the procedure as described in Example 1 step 5 by demethylation of 5-(2-(6-(8-fluoronaphthalen-2-yl)-2-methoxypyridin-3-yl)-3-methylbutyl) oxazolidine-2,4-dione with TMSCl/NaI in CH$_3$CN to yield the compounds as off-yellow solids.
Syn-(6-(8-fluoronaphthalen-2-yl)-2-oxo-1,2-dihydropyridin-3-yl)-3-methylbutyl)oxazolidine-2,4-dione: $^1$H NMR (400 MHz,CD$_3$OD) δ: 8.43 (s, 1H), 8.07 (d, J=8.4 Hz, 1H), 7.86 (d, J=7.2 Hz, 1H), 7.78 (d, J=8.4 Hz, 1H), 7.53-7.58 (m, 2H), 7.28-7.35 (m, 1H), 6.80 (d, J=7.2 Hz, 1H), 4.70-4.73 (m, 1H), 2.90-2.92 (m, 1H), 2.52-2.59 (m, 1H), 2.09-2.14 (m, 2H), 1.02 (d, J=6.6 Hz, 3H), 0.91 (d, J=6.6 Hz, 3H). $^{19}$F NMR (400 MHz,CD$_3$OD) δ: −124.52. Mass spectrum (ESI, m/z): Calculated for $C_{23}H_{21}FN_2O_4$, 409.1 (M+H), found 409.1.
Anti-(6-(8-fluoronaphthalen-2-yl)-2-oxo-1,2-dihydropyridin-3-yl)-3-methylbutyl)oxazolidine-2,4-dione: $^1$H NMR (400 MHz,CD$_3$OD) δ: 8.43 (s, 1H), 8.07 (d, J=8.1 Hz, 1H), 7.87 (d, J=7.2 Hz, 1H), 7.73 (d, J=8.1 Hz, 1H), 7.52-7.69 (m, 2H), 7.28-7.32 (m, 1H), 6.77 (d, J=6.8 Hz, 1H), 4.77-4.80 (m, 1H), 2.98-3.00 (m, 1H), 2.38-2.41 (m, 2H), 2.08-2.18 (m, 1H), 1.04 (d, J=6.4 Hz, 3H), 0.89 (d, J=6.4 Hz, 3H). $^{19}$F NMR (400 MHz,CD$_3$OD) δ: −124.52. Mass spectrum (ESI, m/z): Calculated for $C_{23}H_{21}FN_2O_4$, 409.1 (M+H), found 409.1.

Example 9

Compound #102 and #83

(Z)-5-(2-(6-(8-fluoronaphthalen-2-yl)-5-methyl-2-oxo-1,2-dihydropyridin-3-yl)-3-methylbutylidene)oxazolidine-2,4-dione and (Z)-5-(2-(5-bromo-6-(8-fluoronaphthalen-2-yl)-2-oxo-1,2-dihydropyridin-3-yl)-3-methylbutylidene)oxazolidine-2,4-dione

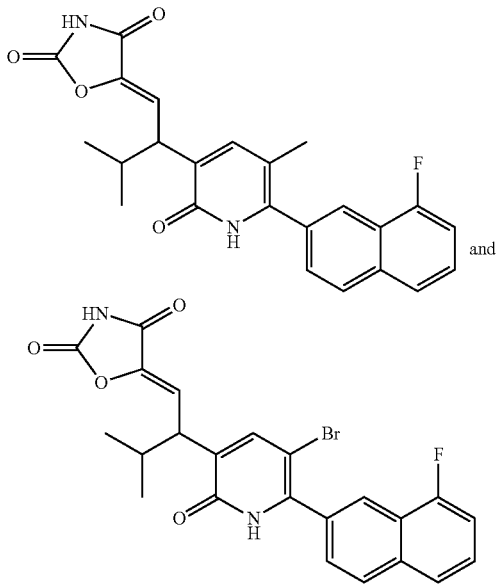

Step 1: (E)-5-(2-(5-bromo-6-(8-fluoronaphthalen-2-yl)-2-methoxypyridin-3-yl)-3-methylbutylidene)oxazolidine-2,4-dione Into a 40-mL vial maintained with an inert atmosphere of nitrogen, were placed (E)-5-(2-(6-(8-fluoronaphthalen-2-yl)-2-methoxypyridin-3-yl)-3-methylbutylidene)oxazolidine-2,4-dione (200 mg, 0.47 mmol, 1 equiv.), NBS (100 mg, 0.57 mmol, 1.2 equiv.), MeOH (5 mL), $CH_3CN$ (5 mL), TFA (1 mL). The resulting solution was stirred for 16 h at 60° C. The mixture was concentrated under vacuum. The residue was purified purified by TLC with ethyl acetate/petroleum ether (1:6) to yield (E)-5-(2-(5-bromo-6-(8-fluoronaphthalen-2-yl)-2-methoxypyridin-3-yl)-3-methylbutylidene)oxazolidine-2,4-dione as yellow oil. Mass spectrum (ESI, m/z): Calculated for $C_{24}H_{20}BrFN_2O_4$, 499.1(M+H), 499.1.

Step 2: (E)-5-(2-(6-(8-fluoronaphthalen-2-yl)-2-methoxy-5-methylpyridin-3-yl)-3-methylbutylidene)oxazolidine-2,4-dione Into a 40-mL vial purged and maintained with an inert atmosphere of nitrogen, were placed (E)-5-(2-(5-bromo-6-(8-fluoronaphthalen-2-yl)-2-methoxypyridin-3-yl)-3-methylbutylidene)oxazolidine-2,4-dione (120 mg, 0.24 mmol, 1 equiv), DMF (5 mL), Pd(OAc)$_2$ (3 mg, 0.013 mmol, 0.05 equiv), (o-tol)$_3$P (7 mg, 0.023 mmol, 0.1 equiv), Sn(CH$_3$)$_4$ (86 mg, 0.48 mmol, 2 equiv). The resulting solution was stirred with 16 h at 100° C. The mixture was quenched by the addition of $H_2O$, extracted with EA. The organic layer was concentrated under vacuum. The residue was purified by TLC with ethyl acetate/petroleum ether (1:6) to yield (E)-5-(2-(6-(8-fluoronaphthalen-2-yl)-2-methoxy-5-methylpyridin-3-yl)-3-methylbutylidene)oxazolidine-2,4-dione as yellow oil. Mass spectrum (ESI, m/z): Calculated for $C_{25}H_{23}FN_2O_4$, 435.5(M+H), 435.1.

Step 3: (Z)-5-(2-(6-(8-fluoronaphthalen-2-yl)-5-methyl-2-oxo-1,2-dihydropyridin-3-yl)-3-methylbutylidene)oxazolidine-2,4-dione and (Z)-5-(2-(5-bromo-6-(8-fluoronaphthalen-2-yl)-2-oxo-1,2-dihydropyridin-3-yl)-3-methylbutylidene)oxazolidine-2,4-dione The title compounds were prepared according to the procedure as described in Example 1 step 5 by demethylation of (E)-5-(2-(6-(8-fluoronaphthalen-2-yl)-2-methoxy-5-methylpyridin-3-yl)-3-methylbutylidene)oxazolidine-2,4-dione and (E)-5-(2-(5-bromo-6-(8-fluoronaphthalen-2-yl)-2-methoxypyridin-3-yl)-3-methylbutylidene)oxazolidine-2,4-dione with TMSCl/NaI in $CH_3CN$ to yield the (Z)-5-(2-(6-(8-fluoronaphthalen-2-yl)-5-methyl-2-oxo-1,2-dihydropyridin-3-yl)-3-methylbutylidene)oxazolidine-2,4-dione as a light yellow solid oil.

$^1$H NMR (300 MHz,CD$_3$OD) δ: 8.12 (s, 1H), 8.02 (d, J=8.4 Hz, 1H), 7.74 (d, J=8.4 Hz, 1H), 7.53 (d, J=8.7 Hz, 1H), 7.48-7.50 (m, 1H), 7.44 (s, 1H), 7.22-7.23 (m, 1H), 6.02 (d, J=10.5 Hz, 1H), 3.69-3.75 (m, 1H), 2.25-2.29 (m, 1H), 2.11 (s, 3H), 0.82-0.97 (m, 6H). $^{19}$F NMR (300 MHz,CD$_3$OD) δ: −124.93. Mass spectrum (ESI, m/z): Calculated for $C_{24}H_{21}FN_2O_4$, 421.1(M+H), 421.0.

and (Z)-5-(2-(5-bromo-6-(8-fluoronaphthalen-2-yl)-2-oxo-1,2-dihydropyridin-3-yl)-3-methylbutylidene)oxazolidine-2,4-dione as a light yellow oil.

$^1$H NMR (300 MHz,CD$_3$OD) δ: 8.20 (s, 1H), 8.01 (d, J=9.0 Hz, 1H), 7.74 (d, J=8.1 Hz, 1H), 7.51-7.63 (m, 2H), 7.41-7.49 (m, 1H), 7.22-7.28 (m, 1H), 5.88 (d, J=9.6 Hz, 1H), 3.67-3.73 (m, 1H), 2.23-2.32 (m, 1H), 0.84-0.97 (m, 6H). $^{19}$F NMR (300 MHz,CD$_3$OD) δ: −76.95, −124.93. Mass spectrum (ESI, m/z): Calculated for $C_{23}H_{18}BrFN_2O_4$, 486.9 (M−0.08CF$_3$COOH+H), 486.9.

Example 10

Compound #112

(Z)-5-(2-(6-(8-fluoronaphthalen-2-yl)-2-methoxypyridin-3-yl)-3-methylbutylidene) oxazolidine-2,4-dione

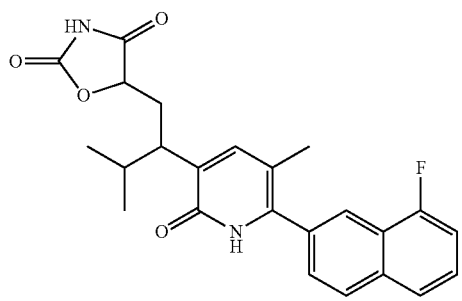 [SMILES: Cc1cc(C(CC2OC(=O)NC2=O)C(C)C)c(=O)[nH]c1-c1ccc2cccc(F)c2c1]

The title compound was prepared according to the procedure as described in Example 8 step 1 by hydrogenation of 5-(2-(6-(8-fluoronaphthalen-2-yl)-2-methoxy-5-methylpyridin-3-yl)-3-methylbutylidene)oxazolidine-2,4-dione followed by demethylation of 5-(2-(6-(8-fluoronaphthalen- 2-yl)-2-methoxy-5-methylpyridin-3-yl)-3-methylbutyl)oxazolidine-2,4-dione with TMSCl/NaI in CH$_3$CN to yield an off-yellow solid.

$^1$H NMR (300 MHz, CD$_3$OD) δ 8.13-8.14 (m, 1H), 8.02-8.05 (m, 1H), 7.74-7.76 (m, 1H), 7.58-7.61 (m, 1H), 7.48-7.51 (m, 1H), 7.36-7.38 (m, 1H), 7.22-7.28 (m, 1H), 4.70-4.87 (m, 1H), 2.75-2.92 (m, 1H), 2.33-2.49 (m, 2H), 2.12-2.17 (m, 1H), 2.07-2.08 (m, 3H), 0.97-1.01 (m, 3H), 0.84-0.87 (m, 3H). $^{19}$F NMR (300 MHz, CD$_3$OD) δ: −124.98. Mass spectrum (ESI, m/z): Calculated for C$_{24}$H$_{23}$FN$_2$O$_4$, 423.2(M+H), 423.2.

Example 11

Compound #64 and #65

Syn-6-(8-fluoronaphthalen-2-yl)-2-oxo-1,2-dihydropyridin-3-yl)-3-methylbutyl)thiazolidine-2,4-dione and Anti-(6-(8-fluoronaphthalen-2-yl)-2-oxo-1,2-dihydropyridin-3-yl)-3-methylbutyl)thiazolidine-2,4-dione

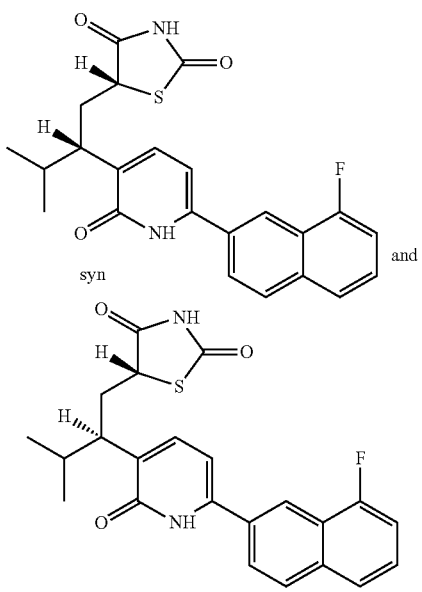

The title compounds were prepared according to the procedure as described in Example 8 step 1 by hydrogenation of (Z)-5-(2-(6-(8-fluoronaphthalen-2-yl)-2-methoxypyridin-3-yl)-3-methylbutylidene)thiazolidine-2,4-dione followed by demethylation of 5-(2-(6-(8-fluoro-naphthalen-2-yl)-2-methoxypyridin-3-yl)-3-methylbutyl)thiazolidine-2,4-dione with TMSCl/NaI in CH$_3$CN to yield Syn-(6-(8-fluoronaphthalen-2-yl)-2-oxo-1,2-dihydropyridin-3-yl)-3-methylbutyl)thiazolidine-2,4-dione as a light pink solid.

$^1$H NMR (300 Hz, CD$_3$OD) δ: 8.39 (s, 1H), 8.04 (d, J=7.8 Hz, 1H), 7.83 (d, J=6.9 Hz, 1H), 7.73 (d, J=8.4 Hz, 1H), 7.48-7.52 (m, 2H), 7.20-7.35 (m, 1H), 6.73 (d, J=7.2 Hz, 1H), 4.25-4.37 (m, 1H), 2.80-2.92 (m, 1H), 2.59-2.72 (m, 1H), 2.30-2.42 (m, 1H), 2.01-2.18 (m, 1H), 1.01 (d, J=6.6 Hz, 3H), 0.82 (d, J=6.6 Hz, 3H). $^{19}$F NMR (300 Hz, CD$_3$OD) δ: −76.90, −124.42. Mass spectrum (ESI, m/z): Calculated for C$_{25.16}$H$_{22.08}$F$_{4.24}$N$_2$O$_{5.16}$S, 425.1 (M−1.08CF$_3$COOH+H), found 425.1.

and Anti-(6-(8-fluoronaphthalen-2-yl)-2-oxo-1,2-dihydropyridin-3-yl)-3-methylbutyl)thiazo-lidine-2,4-dione trifluoroacetic acid as a white solid.

$^1$H NMR (300 MHz, CD$_3$OD) δ: 8.39 (s, 1H), 8.03 (d, J=7.5 Hz, 1H), 7.83 (d, J=8.7 Hz, 1H), 7.73 (d, J=8.4 Hz, 1H), 7.50-7.54 (m, 2H), 7.24-7.28 m, 1H), 6.78 (d, J=7.2 Hz, 1H), 4.02-4.07 (m, 1H), 2.60-2.85 (m, 2H), 1.95-2.21 (m, 2H), 0.99 (d, J=6.6 Hz, 3H), 0.86 (d, J=6.6 Hz, 3H). $^{19}$F NMR (300 MHz, CD$_3$OD) δ: −76.90, −124.46. Mass spectrum (ESI, m/z): Calculated for C$_{24.48}$H$_{21.74}$F$_{3.22}$N$_2$O$_{4.48}$S, 425.1 (M−0.74CF$_3$COOH+H), found 425.0.

Example 12

Compound #262

5-((6-(8-fluoronaphthalen-2-yl)-2-oxo-1,2-dihydropyridin-3-yl)methyl)-5-isopropyloxazolidine-2,4-dione

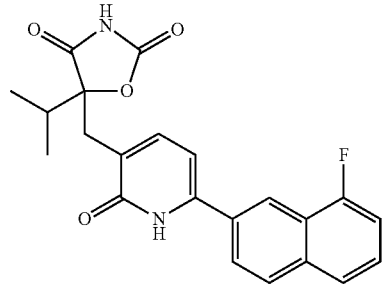 [SMILES: CC(C)C1(Cc2ccc(-c3ccc4cccc(F)c4c3)[nH]c2=O)OC(=O)NC1=O]

Step 1: 6-(8-fluoronaphthalen-2-yl)-2-methoxynicotinaldehyde as a yellow solid

Into a 50-mL round-bottom flask purged and maintained with an inert atmosphere of nitrogen, were placed a solution of 2-(8-fluoronaphthalen-2-yl)-6-methoxypyridine (2 g, 7.897 mmol, 1.00 equiv) in tetrahydrofuran (20 mL) and stirred at −78° C. in a dry ice/EtOH bath. n-BuLi (4.7 mL, 11.75 mmol, 1.50 equiv) was added dropwise at −78° C. The resulting solution was stirred for 3 h at −78° C. in a dry ice/EtOH bath. N,N-dimethylformamide (1.23 mL, 15.902 mmol, 2.00 equiv) was added dropwise. The resulting solution was stirred for 3 h. The reaction was monitored by LCMS. Saturated aq NH$_4$Cl was added and the mixture was extracted with EtOAc, and the combined organic layer. The organic layer was dried over Na$_2$SO$_4$ and the solvent was evaporated under reduced pressure. The residue was purified by column chromatography (ethyl acetate/petroleum ether=5:95) to yield 6-(8-fluoronaphthalen-2-yl)-2-methoxynicotinaldehyde as a yellow solid.

Mass spectrum (ESI, m/z): Calculated for C$_{17}$H$_{12}$FNO$_2$, 282.1 (M+H), found 282.1.

Step 2: (E)-ethyl 3-(6-(8-fluoronaphthalen-2-yl)-2-methoxypyridin-3-yl)acrylate

To a solution of ethyl 2-(trimethylsilyl)acetate (910 mg, 5.677 mmol, 2.00 equiv.) in dry THF (8 mL) was added Lithium bis(trimethylsilyl)amide (5.70 mL, 2.00 equiv) at −78° C., under an argon atmosphere, into a 25-mL round-bottom flask (the flask was evacuated and flushed three times with nitrogen), and the reaction mixture was stirred at this temperature for 30 min. 6-(8-Fluoronaphthalen-2-yl)-2-methoxynicotinaldehyde (800 mg, 2.844 mmol, 1.00 equiv.) in dry THF (8 mL) was added and the reaction was stirred for another 30 min. The reaction progress was monitored by LCMS. A saturated solution of $NH_4Cl$ was added to the reaction mixture. The resulting solution was extracted with ethyl acetate. The organic layers were combined, washed with $Na_2SO_4$ (aq.) and brine, dried and concentrated under vacuum. The residue was applied on a silica gel column and eluted with EA/PE(5:95) to yield (E)-ethyl 3-(6-(8-fluoronaphthalen-2-yl)-2-methoxypyridin-3-yl)acrylate as a yellow oil.

Mass spectrum (ESI, m/z): Calculated for $C_{21}H_{16}FNO_3$, 352.1 (M+H), found 352.0.

Step 3: ethyl 3-(6-(8-fluoronaphthalen-2-yl)-2-methoxypyridin-3-yl)propanoate Into a 50-mL round-bottom flask, were placed (E)-ethyl 3-(6-(8-fluoronaphthalen-2-yl)-2-methoxypyridin-3-yl) acrylate (480 mg, 1.366 mmol, 1.00 equiv.), Pd—C and ethyl acetate. To the mixture was then added $H_2$. The resulting solution was stirred for 4 h at room temperature. The reaction was monitored by LCMS. The solids were filtered out. The resulting solution was concentrated under vacuum. The residue was applied onto a silica gel column with ethyl acetate/petroleum ether (5:95) to yield ethyl 3-(6-(8-fluoronaphthalen-2-yl)-2-methoxypyridin-3-yl)propanoate as yellow oil.

Mass spectrum (ESI, m/z): Calculated for $C_{21}H_{20}FNO_3$, 354.1 (M+H), found 354.0.

Step 4: 2-(6-(8-fluoronaphthalen-2-yl)-2-methoxypyridin-3-yl)ethanol

Into a 100-ml round bottom flask, were placed a solution of ethyl 2-(6-(8-fluoronaphthalen-2-yl)-2-methoxypyridin-3-yl)acetate (1.5 g, 4.42 mmol, 1.00 equiv.) in THF. LAH (340 mg, 8.598 mmol, 2.00 equiv.) in THF was added at 0° C. The resulting solution was stirred for 1.5 h at room temperature. The reaction was monitored by LCMS. The reaction was quenched by the addition of $Na_2SO_4.10H_2O$, and the mixture was filtered and dried by $Na_2SO_4$. The filtrate was combined and concentrated under vacuum to yield 2-(6-(8-fluoronaphthalen-2-yl)-2-methoxypyridin-3-yl)ethanol as a yellow oil.

Mass spectrum (EI, m/z): Calculated for $C_{18}H_{16}FNO_2$, 298.1 (M+H), found 297.9.

Step 5: 2-(6-(8-fluoronaphthalen-2-yl)-2-methoxypyridin-3-yl)acetaldehyde

Into a 100-ml round bottom flask, were placed a solution of 2-(6-(8-fluoronaphthalen-2-yl)-2-methoxypyridin-3-yl) ethanol (1.1 g, 3.70 mmol, 1.00 equiv.) and Dess-Martin periodinane (4.7 mg, 11.08 mmol, 3.00 equiv.) in dichloromethane (60 ml). The resulting solution was stirred for 1.5 h at 25° C. The reaction was monitored by LCMS. The mixture was quenched by the addition of saturated $Na_2S_2O_3.5H_2O$—$NaHCO_3$ solution, stirred for 15 minutes at room temperature until the mixture changed clear. The resulting solution was extracted with DCM. The organic layers were combined, and concentrated under vacuum to yield 2-(6-(8-fluoronaphthalen-2-yl)-2-methoxypyridin-3-yl)acetaldehyde as a yellow oil which was used in the next step without further purification.

Mass spectrum (EI, m/z): Calculated for $C_{18}H_{14}FNO_2$, 296.1 (M+H), found 296.0.

Step 6: 1-(6-(8-fluoronaphthalen-2-yl)-2-methoxypyridin-3-yl)-3-methylbutan-2-ol To a rapidly stirred solution of 2-(6-(8-fluoronaphthalen-2-yl)-2-methoxypyridin-3-yl)acetaldehyde (1.02 g, 3.454 mmol, 1.00 equiv.) in THF (25 mL) under $N_2$ atmosphere at 0° C. was added isopropylmagnesium chloride (5.1 mL, 10.2 mmol, 3.00 equiv.). The reaction mixture was stirred overnight at 25° C. The reaction was monitored by LCMS. Saturated aq. $NH_4Cl$ was added and the mixture was extracted with EtOAc, and the organic layers combined. The organic layer was dried over $Na_2SO_4$ and the solvent was evaporated under reduced pressure. The residue was purified by column chromatography ethyl acetate/petroleum ether (1:6) to yield 1-(6-(8-fluoronaphthalen-2-yl)-2-methoxypyridin-3-yl)-3-methylbutan-2-ol as a yellow solid.

Mass spectrum (EI, m/z): Calculated for $C_{21}H_{22}FNO_2$, 340.2 (M+H), found 340.1.

Step 7: 1-(6-(8-fluoronaphthalen-2-yl)-2-methoxypyridin-3-yl)-3-methyl butan-2-one Into a 50-ml round bottom flask, were placed a solution of 1-(6-(8-fluoronaphthalen-2-yl)-2-methoxypyridin-3-yl)-3-methylbutan-2-ol (320 mg, 0.943 mmol, 1.00 equiv.) and Dess-Martin periodinane (1.2 g, 2.829 mmol, 3.00 equiv.) in dichloromethane (10 mL). The resulting solution was stirred for 2 h at room temperature. The reaction was monitored by LCMS. The mixture was quenched by the addition of saturated $Na_2S_2O_3.5H_2O$—$NaHCO_3$ solution, stirred for 20 minutes at room temperature until the mixture changed clear. The resulting solution was extracted with DCM. The organic layers were combined, and concentrated under vacuum. The residue was applied on a silica gel column (EA: PE=1:3) to yield 1-(6-(8-fluoronaphthalen-2-yl)-2-methoxypyridin-3-yl)-3-methylbutan-2-one as a yellow solid.

Mass spectrum (EI, m/z): Calculated for $C_{21}H_{20}FNO_2$, 338.1 (M+H), found 338.4.

Step 8: 2-((6-(8-fluoronaphthalen-2-yl)-2-methoxypyridin-3-yl)methyl)-2-hydroxy-3-methylbutanenitrile To a rapidly stirred solution of aluminiumtrichloride (43.474 mg, 0.326 mmol, 1.00 equiv.) in DCM (4 ml) under $N_2$ atmosphere at 0° C. was added 1-(6-(8-fluoronaphthalen-2-yl)-2-methoxypyridin-3-yl)-3-methylbutan-2-one (110 mg, 0.326 mmol, 1.00 equiv.) in DCM (2 mL) dropwise. Trimethylsilanecarbonitrile (97.034 mg, 0.978 mmol, 3.00 equiv.) was then added to the solution. The reaction mixture was stirred at 0° C. for 1.5 h. The reaction was monitored by LCMS. The resulting solution was extracted with DCM. The organic layers were combined, and concentrated under vacuum. The residue was applied on a silica gel column (EA: PE=1:6) to yield 2-((6-(8-fluoronaphthalen-2-yl)-2-methoxypyridin-3-yl)methyl)-2-hydroxy-3-methylbutanenitrile as a yellow solid.

Mass spectrum (EI, m/z): Calculated for $C_{22}H_{21}FN_2O_2$, 365.2 (M+H), found 365.1.

Step 9: Methyl 2-((6-(8-fluoronaphthalen-2-yl)-2-oxo-1,2-dihydropyridin-3-yl)methyl)-2-hydroxy-3-methyl butanoate Into a 25-mL round-bottom flask, were placed a solution of 2-((6-(8-fluoronaphthalen-2-yl)-2-methoxypyridin-3-yl)methyl)-2-hydroxy-3-methylbutanenitrile (45 mg, 0.123 mmol, 1.00 equiv.) in methanol (4 mL) and hydrogen chloride (0.75 mL). The resulting solution was stirred overnight at 80° C. The reaction was monitored by TLC. The resulting solution was concentrated and then extracted with EA. The organic layers were combined, and concentrated under vacuum. The residue was applied on a silica gel column (DCM:MeOH=20:1) to yield methyl 2-((6-(8-fluoronaphthalen-2-yl)-2-oxo-1,2-dihydropyridin-3-yl)methyl)-2-hydroxy-3-methylbutanoate as a colorless oil.

Mass spectrum (EI, m/z): Calculated for $C_{22}H_{22}FNO_4$, 384.2 (M+H), found 384.0.

Step 10: 5-((6-(8-fluoronaphthalen-2-yl)-2-oxo-1,2-dihydropyridin-3-yl)methyl)-5-isopropyloxazolidine-2,4-dione Into a 25-mL round-bottom flask, were placed a solution of methyl 2-((6-(8-fluoronaphthalen-2-yl)-2-oxo-1,2-dihydropyridin-3-yl)methyl)-2-hydroxy-3-methylbutanoate (31 mg, 0.081 mmol, 1.00 equiv.) in dichloromethane (5 mL). The reaction was cooled to 0° C. and 2,2,2-trichloroacetyl isocyanate (30 mg, 0.159 mmol, 2.00 equiv.) was added to the solution at this temperature. After warmed to room temperature, the reaction mixture was stirred overnight. The reaction was quenched with methanol (1 mL). The solvents were removed under vacuum and the residue was dissolved in ethanol (5 mL). Triethylamine (16 mg, 0.158 mmol, 2.00 equiv.) was added to the mixture. The resulting mixture was stirred for 3 h at 90° C. The resulting solution was concentrated under vacuum and the residue was purified by Prep-HPLC with the following conditions: (1#waters2767-5): Column, SunFire Prep C18, 19*150 mm 5 umH PrepC-001 (T)18600256819513816414 04; mobile phase, Phase A: water with 0.05% $NH_4HCO_3$; Phase B: $CH_3CN$ (17% $CH_3CN$ up to 40% in 10 min, up to 95% $CH_3CN$ in 0.1 min, hold 95% in 1.9 min, down to 17% $CH_3CN$ in 0.1 min, hold 17% in 1.9 min); Detector, UV220 & 254 nm to yield 5-((6-(8-fluoronaphthalen-2-yl)-2-oxo-1,2-dihydropyridin-3-yl)methyl)-5-isopropyloxazolidine-2,4-dione as a white solid.

$^1$H NMR (400 MHz, $CD_3OD$) δ: 8.41 (s, 1 H), 8.07 (d, J=7.6 Hz, 1 H), 7.88 (d, J=8.0 Hz, 1 H), 7.77 (d, J=8.4 Hz, 1 H), 7.53-7.62 (m, 2 H), 7.30-7.32 (m, 1 H), 6.74 (d, J=6.8 Hz, 1 H), 3.35 (d, J=7.2 Hz, 1 H), 3.17 (d, J=7.2 Hz, 1 H), 2.24-2.33 (m, 1 H), 1.23 (d, J=7.2 Hz, 3 H), 1.17 (d, J=6.4 Hz, 3 H). $^{19}$F NMR (400 MHz, $CD_3OD$) δ: −124.46. Mass spectrum (EI, m/z): Calculated for $C_{22}H_{19}FN_2O_4$, 395.1 (M+H), found 395.0.

Example 13

Compound #306

(E)-5-(1-(6-(8-fluoronaphthalen-2-yl)-2-oxo-1,2-dihydropyridin-3-yl)-3-methylbutan-2-ylidene)oxazolidine-2,4-dione

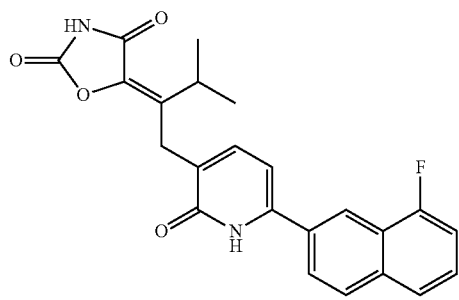 [SMILES: CC(C)/C(Cc1ccc(-c2ccc3cccc(F)c3c2)[nH]c1=O)=C1/OC(=O)NC1=O]

The title compound was prepared according to the procedure as described in Example 1 reacting 1-(6-(8-fluoronaphthalen-2-yl)-2-methoxypyridin-3-yl)-3-methylbutan-2-one and oxazolidine-2,4-dione followed by dehydration and demethylation to yield the product as a white solid.

$^1$H NMR (400 MHz, $CD_3OD$) δ: 8.40 (s, 1 H), 8.05 (d, J=8.8 Hz, 1 H), 7.83-7.85 (m, 1 H), 7.75 (d, J=8.4 Hz, 1 H), 7.47-7.56 (m, 2 H), 7.25-7.30 (m, 1 H), 6.76 (d, J=7.2 Hz, 1 H), 4.05-4.12 (m, 1 H), 3.57 (s, 2 H), 1.17 (d, J=6.8 Hz, 6 H). $^{19}$F NMR (400 MHz, $CD_3OD$) δ: −76.96, −124.50. Mass spectrum (EI, m/z): Calculated for $C_{23.86}H_{19.43}F_{2.29}N_2O_{4.86}$, 407.1 (M−0.43$CF_3COOH$+H), found 407.0.

Example 14

Compound #308

5-(1-(6-(8-fluoronaphthalen-2-yl)-2-oxo-1,2-dihydropyridin-3-yl)-3-methylbutan-2-yl)oxazolidine-2,4-dione

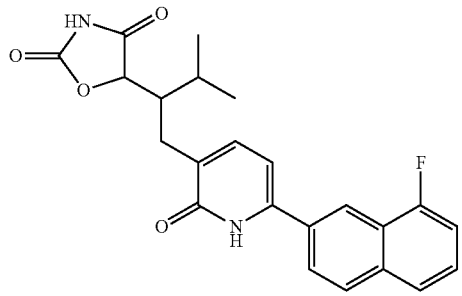 [SMILES: CC(C)C(Cc1ccc(-c2ccc3cccc(F)c3c2)[nH]c1=O)C1OC(=O)NC1=O]

The title compound was prepared according to the procedure as described in Example 8 step 1 by hydrogenation of (E)-5-(1-(6-(8-fluoronaphthalen-2-yl)-2-methoxypyridin-3-yl)-3-methyl butan-2-ylidene)oxazolidine-2,4-dione followed by demethylation of 5-(1-(6-(8-fluoro naphthalen-2-yl)-2-methoxypyridin-3-yl)-3-methylbutan-2-yl) oxazolidine-2,4-dione with TMSCl/NaI in $CH_3CN$ to yield the product as a white solid.

$^1$H NMR (300 MHz, $CD_3OD$) δ: 8.36 (s, 1 H), 8.01 (d, J=9.0 Hz, 1 H), 7.81 (d, J=7.8 Hz, 1 H), 7.73 (d, J=8.1 Hz, 1 H), 7.44-7.56 (m, 2 H), 7.21-7.28 (m, 1 H), 6.63-6.72 (m, 1 H), 4.90-5.00 (m, 1H), 2.46-2.94 (m, 4 H), 1.87-1.90 (m, 1 H), 1.01-1.08 (m, 6 H). $^{19}$F NMR (300 MHz, $CD_3OD$) δ: −76.91, −124.54. Mass spectrum (ESI, m/z): Calculated for $C_{24.42}H_{21.71}F_{3.13}N_2O_{5.42}$, 409.1 (M−0.71$CF_3COOH$+H), found 408.9.

Example 15

Compound #80

5-(2-(6-(8-fluoronaphthalen-2-yl)-2-oxo-1,2-dihydropyridin-3-yl)-3-methylbutylidene)-1-methylimidazolidine-2,4-dione

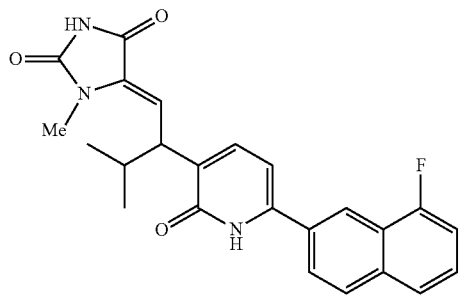 [SMILES: CC(C)C(/C=C1/C(=O)NC(=O)N1C)c1ccc(-c2ccc3cccc(F)c3c2)[nH]c1=O]

The title compound was prepared according to the procedure as described in Example 1 reacting 2-(6-(8-fluoronaphthalen-2-yl)-2-methoxypyridin-3-yl)-3-methylbutanal and 1-methylimidazolidine-2,4-dione followed by dehydration and demethylation to yield the product as a white solid.

Mass spectrum (ESI, m/z): Calculated for $C_{24}H_{24}FN_3O_3$, 420.2 (M+H), found 420.1. $^1$H NMR (400 MHz, $CD_3OD$) δ: 8.38 (s, 1H), 8.04-8.06 (m, 1H), 7.82-7.86 (m, 1H), 7.75 (d, J=8.4 Hz, 1H), 7.61-7.64 (m, 1H), 7.52-7.56 (m, 1H), 7.25-7.30 (m, 1H), 6.81 (d, J=7.2 Hz, 1H), 6.06 (d, J=10.8 Hz, 1H), 4.45-4.51 (m, 1H), 3.42 (s, 3H), 2.43-2.53 (m, 1H), 1.00 (d, J=6.8 Hz, 3H), 0.89 (d, J=4 Hz, 3H). The isomer: $^1$H NMR (400 MHz, $CD_3OD$) δ: 8.38 (s, 1H), 8.04-8.06 (m, 1H), 7.82-7.86 (m, 1H), 7.75 (d, J=8.4 Hz, 1H), 7.61-7.64 (m, 1H), 7.52-7.56 (m, 1H), 7.25-7.30 (m, 1H), 6.72 (d, J=7.2 Hz, 1H), 5.97 (d, J=11.6 Hz, 1H), 4.15-4.21 (m, 1H), 3.06 (s, 3H), 2.13-2.20 (m, 1H), 1.05 (d, J=6.8 Hz, 3H), 0.96 (d, J=6.4 Hz, 3H). $^{19}$F NMR (400 MHz, $CD_3OD$) δ: −124.47.

Example 16

Compound #73

5-(2-(6-(8-fluoronaphthalen-2-yl)-2-oxo-1,2-dihydropyridin-3-yl)-3-methylbutyl)-1-methylimidazolidine-2,4-dione

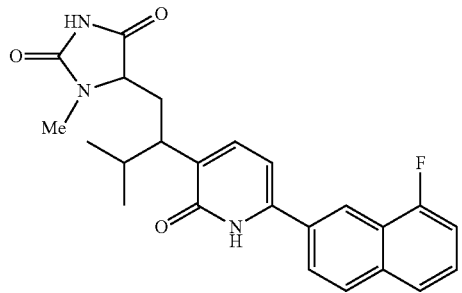 [SMILES: CC(C)C(CC1C(=O)NC(=O)N1C)c1ccc(-c2ccc3cccc(F)c3c2)[nH]c1=O]

The title compound was prepared according to the procedure as described in Example 8 step 1 by hydrogenation of 5-(2-(6-(8-fluoronaphthalen-2-yl)-2-oxo-1,2-dihydropyridin-3-yl)-3-methylbutylidene)-1-methylimidazolidine-2,4-dione to yield the product as a white solid.

Mass spectrum (ESI, m/z): Calculated for $C_{24}H_{24}FN_3O_3$, 422.2 (M+H), found 422.2. $^1$H NMR (400 MHz, $CD_3OD$) δ: 8.42 (s, 1H), 8.06 (d, J=8.8 Hz,1H), 7.85-7.88 (m, 1H), 7.77 (d, J=8 Hz, 1H), 7.47-7.88 (m, 2H), 7.27-7.32 (m, 1H), 6.75 (d, J=7.2 Hz, 1H), 4.01-4.02 (m, 1H), 2.92 (s, 3H), 2.73-2.89 (m, 1H), 2.40-2.55 (m, 1H), 2.18-2.30 (m, 2H), 1.03-1.06 (m, 3H), 0.84-0.88 (m, 3H). The isomer: $^1$H NMR (400 MHz, $CD_3OD$) δ: 8.42 (s, 1H), 8.06 (d, J=8.8 Hz,1H), 7.85-7.88 (m, 1H), 7.77 (d, J=8 Hz, 1H), 7.47-7.88 (m, 2H), 7.27-7.32 (m, 1H), 6.71 (d, J=7.2 Hz, 1H), 3.90-3.92 (m, 1H), 2.73-2.89 (m, 1H), 2.68 (s, 3H), 2.40-2.55 (m, 1H), 1.98-2.15 (m, 2H), 1.03-1.06 (m, 3H), 0.84-0.88 (m, 3H). $^{19}$F NMR (400 MHz, $CD_3OD$) δ: −126.051.

Example 17

Compound #89

5-(2-(6-(8-Fluoronaphthalen-2-yl)-2-oxo-1,2-dihydropyridin-3-yl)-3-methylbutyl) imidazolidine-2,4-dione

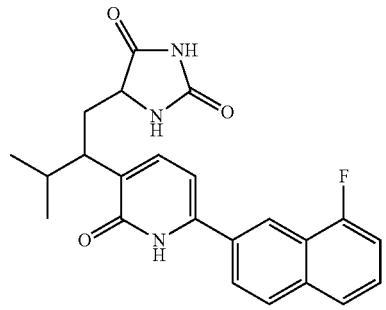 [SMILES: CC(C)C(CC1NC(=O)NC1=O)c1ccc(-c2ccc3cccc(F)c3c2)[nH]c1=O]

Step 1: 5-(2-(6-(8-fluoronaphthalen-2-yl)-2-methoxypyridin-3-yl)-3-methylbutyl) imidazolidine-2,4-dione Into a seal tube were placed 3-(6-(8-fluoronaphthalen-2-yl)-2-methoxypyridin-3-yl)-4-methylpentanal (68 mg, 0.194 mmol, 1 equiv.), ammoniumcarbonate (122 mg, 1.325 mmol, 4 equiv.), ammoniumhydroxide (1 mL), Trimethylsilylcyanide (0.5 mL) in EtOH (2 mL). The reaction mixture was stirred overnight at 100° C. The reaction was monitored by LCMS. The reaction mixture was concentrated under vacuum. The residue was purified by thin layer chromatography developed with DCM/MeOH (20/1) to yield 5-(2-(6-(8-fluoronaphthalen-2-yl)-2-methoxypyridin-3-yl)-3-methylbutyl)imidazolidine-2,4-dione as yellow solid.

Mass spectrum (ESI, m/z): Calculated for $C_{24}H_{24}FN_3O_3$, 422.2 (M+H), found 422.1.

Step 2: 5-(2-(6-(8-fluoronaphthalen-2-yl)-2-oxo-1,2-dihydropyridin-3-yl)-3-methylbutyl) imidazolidine-2,4-dione The title compound was prepared according to the procedure as described in Example 1 step 5 by demethylation of 5-(2-(6-(8-fluoronaphthalen-2-yl)-2-methoxypyridin-3-yl)-3-methylbutyl) imidazolidine-2,4-dione with TMSCl/NaI to yield the product as a white solid.

Mass spectrum (ESI, m/z): Calculated for $C_{23}H_{22}FN_3O_3$, 408.2 (M+H), found 408.2. $^1$H NMR (400 MHz, $CD_3OD$) δ: 8.45 (s, 1H), 8.08 (d, J=8 Hz, 1H), 7.87-7.89 (m, 1H), 7.78 (d, J=8 Hz, 1H), 7.53-7.63 (m, 2H), 7.28-7.33 (m, 1H), 6.86 (d, J=7.2 Hz, 1H), 3.79-3.83 (m, 1H), 2.88-2.93 (m, 1H), 2.24-2.31 (m, 1H), 1.95-2.09 (m, 2H), 1.04 (d, J=6.4 Hz, 3H), 0.91 (d, J=6.8 Hz, 3H). $^{19}$F NMR (400 MHz, $CD_3OD$) δ: −124.49.

Example 18

Compound #132

5-(1-(6-(8-Fluoronaphthalen-2-yl)-2-oxo-1,2-dihydropyridin-3-yl)-2-methylpropyl)imidazolidine-2,4-dione

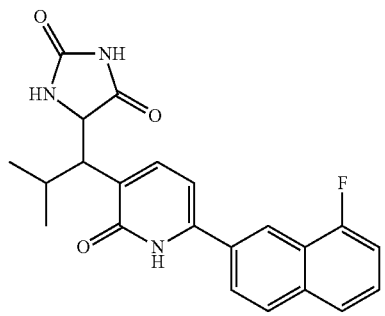 [SMILES: CC(C)C(c1ccc(-c2ccc3cccc(F)c3c2)[nH]c1=O)C1NC(=O)NC1=O]

Step 1: (Z)-6-(8-fluoronaphthalen-2-yl)-2-methoxy-3-(1-methoxy-3-methylbut-1-en-2-yl)pyridine Into a 50-mL round-bottom flask purged and maintained with an inert atmosphere of nitrogen, was added (methoxymethyl)triphenylphosphonium chloride (63 mg, 0.184 mmol, 2 equiv.), THF (5 mL). This was followed by the addition LiHMDS (0.02 mL, 0.02 mmol, 2.5 equiv.) dropwise with stirring at 0° C. The reaction was stirred 1 h at 0° C. 1-(6-(8-Fluoronaphthalen-2-yl)-2-methoxypyridin-3-yl)-2-methylpropan-1-one (30 mg, 0.093 mmol, 1 equiv.) in THF was added to above mixture solution. The reaction was stirred overnight at 0° C. The reaction progress was monitored by TLC (PE:EA=10:1). The reaction was then quenched by the addition of $H_2O$ (5 mL), extracted with ethyl acetate and the organic layers combined. The resulting mixture was concentrated under vacuum. The residue was applied onto a silica gel column with PE:EA=10:1 to yield (Z)-6-(8-fluoronaphthalen-2-yl)-2-methoxy-3-(1-methoxy-3-methylbut-1-en-2-yl)pyridine as a light yellow solid.

Mass spectrum (ESI, m/z): Calculated for $C_{22}H_{22}FNO_2$, 352.2 (M+H), found 352.2.

Step 2: 2-(6-(8-fluoronaphthalen-2-yl)-2-methoxypyridin-3-yl)-3-methylbutanal Into a 50-mL round-bottom flask, were placed (Z)-6-(8-fluoronaphthalen-2-yl)-2-methoxy-3-(1-methoxy-3-methylbut-1-en-2-yl)pyridine (30 mg, 0.085 mmol, 1 equiv), HCl (1 mL), THF (4 mL). The resulting solution was stirred 2 h at 25° C. The reaction was monitored by LCMS. The resulting mixture was concentrated under vacuum. The residue was applied onto a silica gel column with PE:EA=10:1 to yield 2-(6-(8-fluoronaphthalen-2-yl)-2-methoxypyridin-3-yl)-3-methylbutanal as a light yellow oil.

Mass spectrum (ESI, m/z): Calculated for $C_{21}H_{20}FNO_2$, 338.1 (M+H), found 338.1.

Step 3: 5-(1-(6-(8-fluoronaphthalen-2-yl)-2-oxo-1,2-dihydropyridin-3-yl)-2-methylpropyl) imidazolidine-2,4-dione The title compound was prepared according to the procedure as described in Example 17 step 1 by cyclization of 2-(6-(8-fluoronaphthalen-2-yl)-2-methoxypyridin-3-yl)-3-methylbutanal and TMSCN/$(NH_4)_2CO_3$ followed by demethylation of 1-(6-(8-fluoronaphthalen-2-yl)-2-methoxypyridin-3-yl)-2-methylpropyl)imidazolidine-2,4-dione with TMSCl/NaI to yield the product as a white solid.

Mass spectrum (ESI, m/z): Calculated for $C_{22}H_{20}FN_3O_3$, 394.1 (M+H), found 394.1.

Example 19

Compound #69

5-(1-(6-(8-fluoronaphthalen-2-yl)-2-oxo-1,2-dihydropyridin-3-yl)-2-methylpropyl)-1-methylimidazolidine-2,4-dione

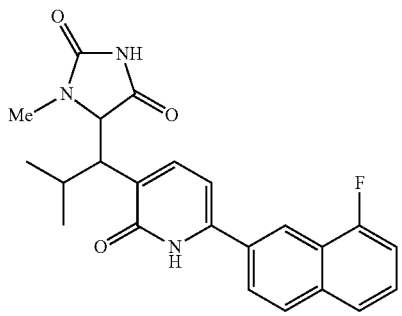 [SMILES: CC(C)C(c1ccc(-c2ccc3cccc(F)c3c2)[nH]c1=O)C1C(=O)NC(=O)N1C]

The title compound was prepared according to the procedure as described in Example 5 step 1 by reacting methylimidazolidine-2,4-dione with (1-(6-(8-fluoronaphthalen-2-yl)-2-methoxypyridin-3-yl)-2-methylpropan-1-one with LDA, dehydrating 5-(1-(6-(8-fluoronaphthalen-2-yl)-2-methoxypyridin-3-yl)-1-hydroxy-2-methylpropyl)-1-methyl imidazolidine-2,4-dione and hydrogenating (E)-5-(1-(6-(8-fluoronaphthalen-2-yl)-2-methoxypyridin-3-yl)-2-methylpropylidene)-1-methylimidazolidine-2,4-dione, followed by demethylation of 5-(1-(6-(8-fluoronaphthalen-2-yl)-2-methoxypyridin-3-yl)-2-methylpropyl)-1-methylimidazolidine-2,4-dione with TMSCl/NaI to yield the product as light yellow solid.

$^1$H NMR (300 MHz, $CD_3OD$) δ: 8.40 (s, 1H), 8.06 (d, J=8.4 Hz, 1H), 7.82-7.86 (m, 1H), 7.76 (d, J=8.4 Hz, 1H), 7.53-7.58 (m, 2H), 7.26-7.32 (m, 1H), 6.74 (d, J=7.2 Hz, 1H), 4.42-4.45 (m, 1H), 3.50-3.60 (m, 1H), 2.99 (s, 3H), 2.55-2.60 (m, 1H), 1.29 (d, J=6.6 Hz, 3H), 0.87 (d, J=6.6 Hz, 3H). Mass spectrum (ESI, m/z): Calculated for $C_{23}H_{22}FN_3O_3$, 408.1 (M+H), found 408.1.

Example 20

Compound #2

(Z)-5-(2-(6-(8-fluoronaphthalen-2-y)-2-yl)-2-oxo-1,2-dihydropyridin-3-yl)-2-methyl propylidene) oxazolidine-2,4-dione

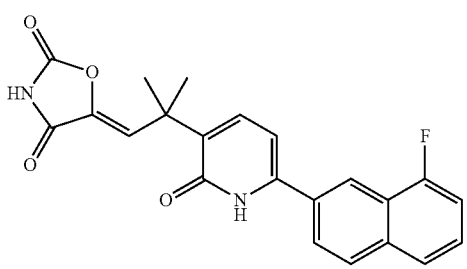 [SMILES: CC(C)(/C=C1\OC(=O)NC1=O)c1ccc(-c2ccc3cccc(F)c3c2)[nH]c1=O]

Step 1: 2-(6-(8-fluoronaphthalen-2-yl)-2-methoxy-pyridin-3-yl)-2-methylpropanoate Into a 100-mL round-bottom flask purged and maintained with an inert atmosphere of nitrogen, were placed ethyl 2-(6-(8-fluoronaphthalen-2-yl)-2-methoxypyridin-3-yl)acetate (200 mg, 0.589 mmol, 1 equiv.), THF (10 ml). This was followed by the addition t-BuOK (1.76 ml, 1.76 mmol, 3 equiv.), dropwise with stirring at 0° C. Then, CH$_3$I (420 mg, 2.959 mmol, 5 equiv.) was added to above solution. The resulting solution was stirred overnight at 25° C. The reaction progress was monitored by LCMS. The reaction was then quenched by the addition of H$_2$O (10 mL), extracted with ethyl acetate and the organic layers combined. The resulting mixture was concentrated under vacuum. The residue was applied onto a silica gel column with PE:EA=6:1 to yield ethyl 2-(6-(8-fluoronaphthalen-2-yl)-2-methoxypyridin-3-yl)-2-methylpropanoate as a light yellow oil.

Mass spectrum (ESI, m/z): Calculated for C$_{22}$H$_{22}$FNO$_3$, 368.2 (M+H), found 368.1.

Step 2: 2-(6-(8-fluoronaphthalen-2-yl)-2-methoxy-pyridin-3-yl)-2-methylpropan-1-ol Into a 100-mL round-bottom flask purged was ethyl 2-(6-(8-fluoronaphthalen-2-yl)-2-methoxypyridin-3-yl)-2-methylpropanoate (200 mg, 0.544 mmol, 1 equiv.), THF (8 ml), LAH (41 mg, 1.080 mmol, 2 equiv.). The resulting solution was stirred 1 h at 25° C. The reaction was monitored by TLC (PE:EA=4:1). The reaction was then quenched by the addition of Na$_2$SO$_4$/10H$_2$O (30 mg). The resulting mixture was concentrated under vacuum. The residue was applied onto a silica gel column with PE:EA=6:1 to yield 2-(6-(8-fluoronaphthalen-2-yl)-2-methoxypyridin-3-yl)-2-methylpropan-1-ol as a light yellow oil.

Mass spectrum (ESI, m/z): Calculated for C$_{20}$H$_{20}$FNO$_2$, 326.1 (M+H), found 326.1.

Step 3: 2-(6-(8-fluoronaphthalen-2-yl)-2-methoxy-pyridin-3-yl)-2-methylpropanal Into a 100-mL round-bottom flask purged was 2-(6-(8-fluoronaphthalen-2-yl)-2-methoxypyridin-3-yl)-2-methyl-propan-1-ol (170 mg, 0.522 mmol, 1 equiv.), DCM (10 mL), DMP (444 mg, 1.047 mmol, 2 equiv.). The resulting solution was stirred overnight at 25° C. The reaction was monitored by TLC (PE:EA=4:1). The resulting mixture was concentrated under vacuum. The residue was applied onto a silica gel column with PE:EA=6:1 to yield 2-(6-(8-fluoronaphthalen-2-yl)-2-methoxypyridin-3-yl)-2-methylpropanal as light yellow oil.

Mass spectrum (ESI, m/z): Calculated for C$_{20}$H$_{18}$FNO$_2$, 324.1 (M+H), found 324.1.

Step 4: (Z)-5-(2-(6-(8-fluoronaphthalen-2-yl)-2-oxo-1,2-dihydropyridin-3-yl)-2-methyl propylidene)oxazolidine-2,4-dione The title compound was prepared according to the procedure as described in Example 5 step 1 by reacting oxazolidine-2,4-dione with 2-(6-(8-fluoronaphthalen-2-yl)-2-methoxypyridin-3-yl)-2-methylpropanal by t-BuLi, dehydrating 5-(2-(6-(8-fluoronaphthalen-2-yl)-2-methoxypyridin-3-yl)-1-hydroxy-2-methylpropyl)oxazolidine-2,4-dione, followed by demethylation of (E)-5-(2-(6-(8-fluoronaphthalen-2-yl)-2-methoxypyridin-3-yl)-2-methyl propylidene)oxazolidine-2,4-dione with TMSCl/NaI to yield the product as a white solid.

$^1$H NMR (400 MHz, CD$_3$OD) δ: 8.42 (s, 1H), 8.07 (d, J=8.4 Hz, 1H), 7.87 (d, J=8.8 Hz, 1H), 7.77 (d, J=8.4 Hz, 1H), 7.70 (d, J=7.6 Hz, 1H), 7.52-7.58 (m, 1H), 7.27-7.31 (m, 1H), 6.77 (d, J=7.6 Hz, 1H), 5.97 (s, 1H), 1.66 (s, 6H). $^{19}$F NMR (400 MHz, CD$_3$OD) δ: −124.52. Mass spectrum (ESI, m/z): Calculated for C$_{22}$H$_{17}$FN$_2$O$_4$, 393.1 (M+H), found 393.1.

Example 21

Compound #1

5-(2-(6-(8-fluoronaphthalen-2-yl)-2-oxo-1,2-dihydropyridin-3-yl)-2-methylpropyl) oxazolidine-2,4-dione

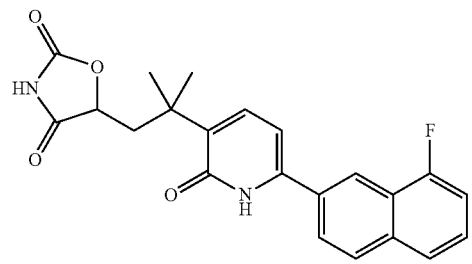 [SMILES: CC(C)(CC1OC(=O)NC1=O)c1ccc(-c2ccc3cccc(F)c3c2)[nH]c1=O]

The title compound was prepared according to the procedure as described in Example 8 step 1 by hydrogenation on (E)-5-(2-(6-(8-fluoronaphthalen-2-yl)-2-methoxypyridin-3-yl)-2-methylpropylidene)oxazolidine-2,4-dione followed by demethylation of 5-(2-(6-(8-fluoronaphthalen-2-yl)-2-methoxypyridin-3-yl)-2-methylpropyl)oxazolidine-2,4-dione with TMSCl/NaI to yield the product as a white solid.

$^1$H NMR (400 MHz, CD$_3$OD) δ: 8.43 (s, 1H), 8.07 (d, J=8.8 Hz, 1H), 7.88 (d, J=8.8 Hz, 1H), 7.77 (d, J=8.4 Hz, 1H), 7.64 (d, J=7.6 Hz, 1H), 7.52-7.58 (m, 1H), 7.28-7.32 (m, 1H), 6.75 (d, J=7.2 Hz, 1H), 4.57 (d, J=8.8 Hz, 1H), 2.66-2.70 (m, 1H), 2.32-2.36 (m, 1H), 1.50 (s, 6H). $^{19}$F NMR (400 MHz, CD$_3$OD) δ: −124.54. Mass spectrum (ESI, m/z): Calculated for C$_{22}$H$_{19}$FN$_2$O$_4$, 395.1 (M+H), found 395.0.

Example 22

Compound #113 and #114

(Z)-5-(3-(6-(8-fluoronaphthalen-2-yl)-2-oxo-1,2-dihydropyridin-3-yl)-4-methylpentan-2-ylidene)oxazolidine-2,4-dione and (E)-5-(3-(6-(8-fluoronaphthalen-2-yl)-2-oxo-1,2-dihydropyridin-3-yl)-4-methylpentan-2-ylidene)oxazolidine-2,4-dione

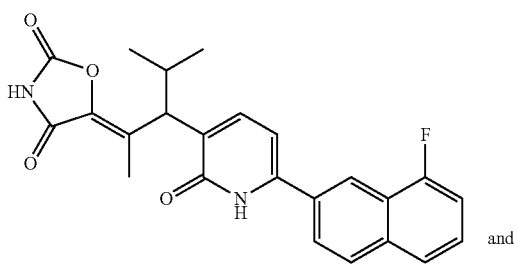

and

131
-continued

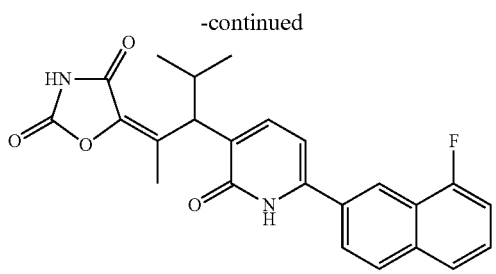

Step 1: 3-(6-(8-fluoronaphthalen-2-yl)-2-methoxy-pyridin-3-yl)-4-methylpentan-2-ol Into a 100-mL round-bottom flask purged and maintained with an inert atmosphere of nitrogen, was 2-(6-(8-fluoronaphthalen-2-yl)-2-methoxypyridin-3-yl)-3-methylbutanal (200 mg, 0.593 mmol, 1 equiv.), THF (8 mL). This was followed by addition of methylmagnesium bromide (1.18 mL, 1.18 mmol, 2 equiv.) dropwise with stirring at 0° C. The reaction was stirred 2 h at 0° C. The reaction progress was monitored by TLC (PE:EA=4:1). The reaction was then quenched by the addition of H$_2$O (20 mL), extracted with ethyl acetate and the organic layers combined. The resulting mixture was concentrated under vacuum. The residue was applied onto a silica gel column with PE:EA=2:1 to yield 3-(6-(8-fluoronaphthalen-2-yl)-2-methoxypyridin-3-yl)-4-methylpentan-2-ol as a light yellow oil.

Mass spectrum (ESI, m/z): Calculated for C$_{22}$H$_{24}$FNO$_2$, 354.2 (M+H), found 354.1.

Step 2: 3-(6-(8-fluoronaphthalen-2-yl)-2-methoxy-pyridin-3-yl)-4-methylpentan-2-one Into a 100-mL round-bottom flask purged was 3-(6-(8-fluoronaphthalen-2-yl)-2-methoxypyridin-3-yl)-4-methyl-pentan-2-ol (200 mg, 0.566 mmol, 1 equiv), DMP (480 mg, 1.132 mmol, 2 equiv.), DCM (10 mL). The resulting solution was stirred overnight at 25° C. The reaction was monitored by TLC (PE:EA=6:1). The resulting mixture was concentrated under vacuum. The residue was applied onto a silica gel column with PE:EA=6:1 to yield 3-(6-(8-fluoronaphthalen-2-yl)-2-methoxypyridin-3-yl)-4-methylpentan-2-one as light yellow oil.

Mass spectrum (ESI, m/z): Calculated for C$_{22}$H$_{22}$FNO$_2$, 352.2 (M+H), found 352.1.

Step 3: (Z)-5-(3-(6-(8-fluoronaphthalen-2-yl)-2-oxo-1,2-dihydropyridin-3-yl)-4-methylpentan-2-ylidene)oxazolidine-2,4-dione and (E)-5-(3-(6-(8-fluoronaphthalen-2-yl)-2-oxo-1,2-dihydropyridin-3-yl)-4-methyl pentan-2-ylidene)oxazolidine-2,4-dione The title compounds were prepared according to the procedure as described in Example 5 step 1 by reacting oxazolidine-2,4-dione with 3-(6-(8-fluoronaphthalen-2-yl)-2-methoxypyridin-3-yl)-4-methylpentan-2-one by t-BuLi, dehydrating of 5-(3-(6-(8-fluoronaphthalen-2-yl)-2-methoxypyridin-3-yl)-2-hydroxy-4-methylpentan-2-yl)oxazolidine-2,4-dione, followed by demethylation of (Z) and (E)-5-(3-(6-(8-fluoronaphthalen-2-yl)-2-methoxypyridin-3-yl)-4-methylpentan-2-ylidene)oxazolidine-2,4-dione with TMSCl/NaI to yield the product as off white solids.

(Z)-5-(3-(6-(8-fluoronaphthalen-2-yl)-2-oxo-1,2-dihydropyridin-3-yl)-4-methylpentan-2-ylidene)oxazolidine-2,4-dione. $^1$H NMR (400 MHz, CD$_3$OD) δ: 8.43 (s, 1H), 8.08 (d, J=8.8 Hz, 1H), 7.87 (d, J=8.8 Hz, 1H), 7.77 (t, J=7.6 Hz, 2H), 7.53-7.59 (m, 1H), 7.28-7.33 (m, 1H), 6.86 (d, J=7.6 Hz, 1H), 4.04 (d, J=11.6 Hz, 1H), 2.47-2.54 (m, 1H), 2.13 (s,3H), 1.04 (d, J=6.4 Hz, 3H), 1.00 (d, J=7.6 Hz, 3H). $^{19}$FH NMR (400 MHz, CD$_3$OD) δ: −124.46. Mass spectrum (ESI, m/z): Calculated for C$_{24}$H$_{21}$FN$_2$O$_4$, 421.1 (M+H), found 421.1.

(E)-5-(3-(6-(8-fluoronaphthalen-2-yl)-2-oxo-1,2-dihydropyridin-3-yl)-4-methylpentan-2-ylidene)oxazolidine-2,4-dione. 1H NMR (400 MHz, CD$_3$OD) δ: 8.43 (s, 1H), 8.07 (d, J=8.4 Hz, 1H), 7.87 (d, J=8.8 Hz, 1H), 7.76-7.79 (m, 2H), 7.53-7.58 (m, 1H), 7.28-7.32 (m, 1H), 6.83 (d, J=7.2 Hz, 1H), 5.02 (d, J=11.6 Hz, 1H), 2.54-2.60 (m, 1H), 1.85 (s, 3H), 1.01 (d, J=6.4 Hz, 3H), 0.99 (d, J=6.4 Hz, 3H). $^{19}$F NMR (400 MHz, CD$_3$OD) δ: −124.49. Mass spectrum (ESI, m/z): Calculated for C$_{24}$H$_{21}$FN$_2$O$_4$, 421.1 (M+H), found 421.1.

Example 23

Compound #94

5-(2-(6-(1-ethyl-4-fluoro-1H-indazol-6-yl)-2-oxo-1,2-dihydropyridin-3-yl)-3-methyl butylidene)-oxazolidine-2,4-dione

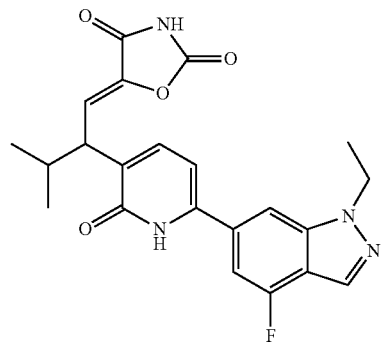 [SMILES: CCn1ncc2c(F)cc(-c3ccc(C(/C=C4\OC(=O)NC4=O)C(C)C)c(=O)[nH]3)cc21]

Step 1: 1-(6-chloro-2-methoxypyridin-3-yl)-2-methylpropan-1-one

A 250 mL flask was charged with a solution of 2-chloro-6-methoxypyridine (20 g, 0.139 mol, 1 equiv.) in THF (300 mL) under nitrogen atmosphere. To the mixture was then added tert-butyllithium (131 mL, 0.210 mol, 1.5 equiv.), which was added dropwise with stirring at −70° C. The reaction mixture was stirred at −78° C. for 2 h. N-methoxy-N-methylisobutyramide (24 g, 0.182 mol, 1.3 equiv.) was then added dropwise. The mixture was stirred for 3.0 h at −78° C. The reaction progress was monitored by LCMS. The reaction was quenched by the addition of ammonium chloride aqueous solution and then extracted with ethyl acetate, the organic layers combined and concentrated under vacuum. The residue was applied onto a silica gel column with PE/EA=100/1 to yield 1-(6-chloro-2-methoxypyridin-3-yl)-2-methylpropan-1-one as yellow oil.

Mass spectrum (ESI, m/z): Calculated for C$_{10}$H$_{12}$ClNO$_2$, 214.1 (M+H), found 214.1.

Step 2: (Z)-6-chloro-2-methoxy-3-(1-methoxy-3-methylbut-1-en-2-yl)pyridine

Into a 500 ml round-bottom flask were placed (Methoxymethyl) triphenylphosphonium chloride (20.5 g, 59.802 mmol, 1.3 eq.) and THF (200 ml) under an atmosphere of nitrogen. The mixture was stirred at 0° C. LiHMDS (61 mL) was added dropwise in 30 min. The reaction mixture was stirred for 1 h at 0° C. A solution of 1-(6-(8-fluoronaphthalen-2-yl)-2-methoxypyridin-3-yl)-2-methyl-propan-1-one (10 g, 46.803 mmol, 1.0 eq.) in THF was added dropwise in 30 min. The mixture was stirred overnight at 0° C. The mixture was quenched by water and concentrated under vacuum. The residue was applied onto a silica gel column with ethyl acetate/petroleum ether (1:15) to yield (Z)-6-chloro-2-methoxy-3-(1-methoxy-3-methyl-but-1-en-2-yl)pyridine as yellow oil.

Mass spectrum (ESI, m/z): Calculated for $C_{12}H_{16}ClNO_2$, 242.1 (M+H), found 242.1.

Step 3: 2-(6-chloro-2-methoxypyridin-3-yl)-3-methylbutanal

To a solution of 4-chloro-2-methoxy-1-(1-methoxy-3-methylbut-1-en-2-yl)benzene (11.7 g, 38.882 mmol, 1.0 eq.) in THF (150 mL). Hydrochloric acid (4 mL) was added. The mixture was stirred overnight at room temperature. The mixture was monitored by LCMS. The mixture was concentrated under vacuum. The residue was applied onto a silica gel column with ethyl acetate/petroleum ether (15/1) to yield 2-(6-chloro-2-methoxypyridin-3-yl)-3-methylbutanal as yellow oil.

Mass spectrum (ESI, m/z): Calculated for $C_{20}H_{16}FNO_2$, 228.1 (M+H), found 227.8.

Step 4: 6-bromo-1-ethyl-4-fluoro-1H-indazole

Into a 25 ml round-bottom flask were placed a solution of 6-bromo-4-fluoro-1H-indazole (500 mg, 2.325 mmol, 1 equiv.) in DMF. Potassium carbonate (355 mg, 2.569 mmol, 1.1 equiv.), and iodoethane (474 mg, 3.039 mmol, 1.5 equiv.) were added. The reaction mixture was stirred for 15 min, and then the mixture was stirred for 1 h at 70° C. The reaction was monitored by LCMS. The mixture was concentrated under vacuum. The residue was purified by chromatogram on silica gel with ethyl acetate/petroleum ether (1:6) to yield 6-bromo-1-ethyl-4-fluoro-1H-indazole as brown oil and 210 mg 6-bromo-2-ethyl-4-fluoro-2H-indazole as brown solid.

Mass spectrum (ESI, m/z): Calculated for $C_9H_8BrFN_2$, 243.0 (M+H), found 242.9.

Step 5: 1-ethyl-4-fluoro-6-(4,4,5,5-tetramethyl-1,3,2-dioxaborolan-2-yl)-1H-indazole Into a 100 ml round-bottom flask were placed a solution of 6-bromo-1-ethyl-4-fluoro-1H-indazole (1.1 g, 4.525 mmol, 1 equiv.) in DMF (15 mL), and 4,4,4',4',5,5,5',5'-octamethyl-2,2'-bi(1,3,2-dioxaborolane) (1.78 g, 7.010 mmol, 1.5 equiv.), potassium acetate (1.6 g, 16.303 mmol, 3.5 equiv.), Pd(dppf)Cl₂ (114 mg, 0.140 mmol, 0.03 equiv.) were added. The mixture was stirred overnight at 90° C. under nitrogen atmosphere. The reaction was monitored by LCMS. The mixture was extracted with ethyl acetate (3×30 mL). The organic layers were combined, washed with sodium carbonate (aq.) and brine, dried and concentrated under vacuum. The residue was purified by thin layer chromatography developed with PE/EA (6/1) to yield a light yellow oil.

Mass spectrum (ESI, m/z): Calculated for $C_{15}H_{20}BFN_2O_2$, 291.2 (M+H), found 291.1.

Step 6. 2-(6-(1-ethyl-4-fluoro-1H-indazol-6-yl)-2-methoxypyridin-3-yl)-3-methylbutanal Into a 50 mL round-bottom flask were placed 2-(6-chloro-2-methoxypyridin-3-yl)-3-methylbutanal (300 mg, 1.318 mmol, 1 equiv.) in ethylene glycol dimethyl ether (20 ml), and then 1-ethyl-4-fluoro-6-(4,4,5,5-tetramethyl-1,3,2-dioxaborolan-2-yl)-1H-indazole (422 mg, 1.454 mmol, 1.3 equiv.), sodiumcarbonate (280 mg, 2.642 mmol, 2 equiv.), and water (1 mL) were added. Pd(dppf)Cl₂.CH₂Cl₂ (33 mg, 0.040 mmol, 0.03 equiv.) was then added. The flask was evacuated and flushed three times with nitrogen. The mixture was stirred overnight at 90° C. under an atmosphere of nitrogen (balloon). The reaction was monitored by LCMS. The resulting solution was distilled in H₂O, extracted with ethyl acetate (3×30 mL). The organic layers were combined and washed with sodium chloride (aq.) dried and concentrated under vacuum. The residue was applied on a silica gel column and eluted with PE/EA (6/1) to yield a yellow solid.

Mass spectrum (ESI, m/z): Calculated for $C_{20}H_{22}FN_3O_2$, 356.2 (M+H), found 356.1.

Step 7: 5-(2-(6-(1-ethyl-4-fluoro-1H-indazol-6-yl)-2-oxo-1,2-dihydropyridin-3-yl)-3-methylbutylidene)-oxazolidine-2,4-dione The title compound was prepared according to the procedure as described in Example 5 by reacting oxazolidine-2,4-dione with 2-(6-(1-ethyl-4-fluoro-1H-indazol-6-yl)-2-methoxypyridin-3-yl)-3-methylbutanal by t-BuLi, dehydrating 5-(2-(6-(1-ethyl-4-fluoro-1H-indazol-6-yl)-2-methoxypyridin-3-yl)-1-hydroxy-3-methylbutyl)oxazolidine-2,4-dione, followed by demethylation of (Z)-5-(2-(6-(1-ethyl-4-fluoro-1H-indazol-6-yl)-2-methoxypyrid in-3-yl)-3-methylbutylidene)oxazolidine-2,4-dione with TMSCl/NaI to yield the product as an off white solid.

¹H NMR (400 MHz, CD₃OD) δ: 8.15 (s, 1H), 7.81 (s, 1H), 7.60 (d, J=7.2 Hz, 1H), 7.20 (d, J=10Hz, 1H), 6.76 (d, J=7.6Hz, 1H), 6.35 (d, J=10.4 Hz, 1H), 4.51-4.60 (m, 2H), 3.70-3.80 (t, J=9.8 Hz, 1H), 2.31-2.40 (m, 1H), 1.53-1.57 (t, J=7.2Hz, 3H), 1.02 (d, J=6.8 Hz, 3H), 0.94 (d, J=6.8Hz, 3H). ¹⁹F NMR (400 MHz, CD₃OD) δ: −119.17. Mass spectrum (ESI, m/z): Calculated for $C_{22}H_{21}FN_4O_4$, 425.2 (M+H), found 425.2.

Example 24

Compound #116

(Z)-5-(2-(6-(4-chloro-1-ethyl-1H-indazol-6-yl)-2-oxo-1,2-dihydropyridin-3-yl)-3-methylbutylidene) oxazolidine-2,4-dione

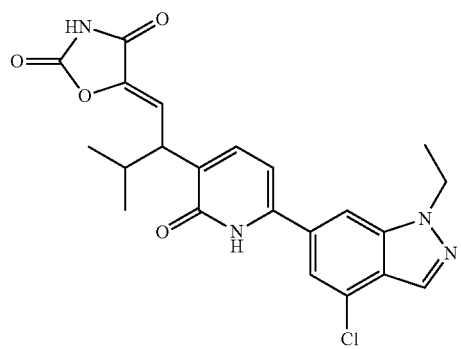 [SMILES: CCn1ncc2c(Cl)cc(-c3ccc(C(/C=C4\OC(=O)NC4=O)C(C)C)c(=O)[nH]3)cc21]

The title compound was prepared according to the procedure as described in Example 5 starting with 6-bromo-4-chloro-1H-indazole, reacting oxazolidine-2,4-dione with 2-(6-(1-ethyl-4-chloro-1H-indazol-6-yl)-2-methoxypyridin-3-yl)-3-methylbutanal by t-BuLi, dehydrating 5-(2-(6-(1-ethyl-4-chloro-1H-indazol-6-yl)-2-methoxypyridin-3-yl)-1-hydroxy-3-methylbutyl) oxazolidine-2,4-dione, followed by demethylation of (Z)-5-(2-(6-(1-ethyl-4-chloro-1H-indazol-6-yl)-2-methoxypyridin-3-yl)-3-methylbutylidene)oxazolidine-2,4-dione with TMSCl/NaI to yield the product as a yellow solid.

$^1$H NMR (400 MHz, CD$_3$OD) δ: 8.14 (s, 1 H), 7.92 (s, 1 H), 7.61 (d, J=7.2 Hz, 1 H), 7.51 (s, 1 H), 6.76 (d, J=7.6 Hz, 1 H), 6.39 (d, J=10.4 Hz, 1 H), 4.53-4.58 (m, 2 H), 3.71-3.76 (m, 1 H), 2.33-2.39 (m, 1 H), 1.53 (t, J=7.2 Hz, 3 H), 1.02 (d, J=6.8 Hz, 3 H), 0.93 (d, J=6.4 Hz, 3 H). Mass spectrum (EI, m/z): Calculated for C$_{22}$H$_{22}$Cl$_2$N$_4$O$_4$, 441.1 (M−HCl+H), found 441.1.

Example 25

Compound #106

(Z)-5-(2-(6-(1-ethyl-4-methyl-1H-indazol-6-yl)-2-oxo-1,2-dihydropyridin-3-yl)-3-methylbutylidene)oxazolidine-2,4-dione

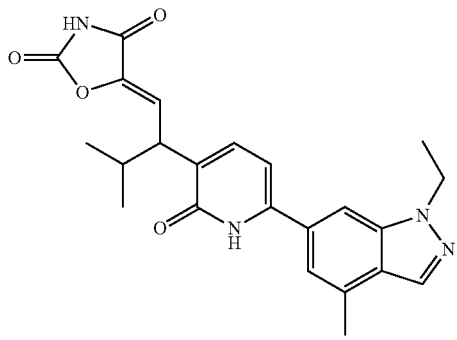 [SMILES: CCn1ncc2c(C)cc(-c3ccc(C(/C=C4\OC(=O)NC4=O)C(C)C)c(=O)[nH]3)cc21]

The title compound was prepared according to the procedure as described in Example 5 starting with 6-bromo-4-methyl-1H-indazole, reacting oxazolidine-2,4-dione with 2-(6-(1-ethyl-4-methyl-1H-indazol-6-yl)-2-methoxypyridin-3-yl)-3-methylbutanal by t-BuLi, dehydrating 5-(2-(6-(1-ethyl-4-methyl-1H-indazol-6-yl)-2-methoxypyridin-3-yl)-1-hydroxy-3-methylbutyl) oxazolidine-2,4-dione, followed by demethylation of (Z)-5-(2-(6-(1-ethyl-4-methyl-1H-indazol-6-yl)-2-methoxypyridin-3-yl)-3-methylbutylidene)oxazolidine-2,4-dione with TMSCl/NaI to yield the product as a white solid.

$^1$H NMR (400 MHz, CD$_3$OD) δ: 8.38 (s, 1 H), 7.74 (d, J=7.4 Hz, 1 H), 7.56 (d, J=7.2 Hz, 1 H), 7.12 (d, J=7.6 Hz, 1 H), 6.66 (d, J=7.2 Hz, 1 H), 6.37 (d, J=10.8 Hz, 1 H), 4.49-4.54 (m, 2 H), 3.70-3.73 (m, 1 H), 2.60 (s, 3 H), 2.29-2.40 (m, 1 H), 1.59-1.63 (m, 3 H), 1.16 (d, J=6.6 Hz, 3 H), 0.92 (d, J=6.4 Hz, 3 H). Mass spectrum (EI, m/z): Calculated for C$_{23}$H$_{24}$N$_4$O$_4$, 421.2 (M+H), found 421.0.

Example 26

Compound #98

(Z)-5-(2-(6-(2-ethyl-4-methyl-2H-indazol-6-yl)-2-oxo-1,2-dihydropyridin-3-yl)-3-methylbutylidene)oxazolidine-2,4-dione

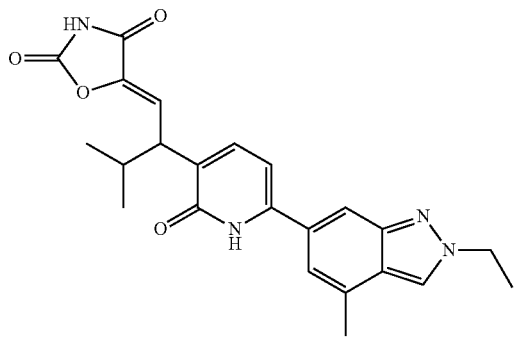 [SMILES: CCn1cc2c(C)cc(-c3ccc(C(/C=C4\OC(=O)NC4=O)C(C)C)c(=O)[nH]3)cc2n1]

The title compound was prepared according to the procedure as described in Example 5 starting with 6-bromo-2-ethyl-4-methyl-2H-indazole, reacting oxazolidine-2,4-dione with 2-(6-(2-ethyl-4-methyl-2H-indazol-6-yl)-2-methoxypyridin-3-yl)-3-methylbutanal by t-BuLi, dehydrating 5-(2-(6-(2-ethyl-4-methyl-2H-indazol-6-yl)-2-methoxypyridin-3-yl)-1-hydroxy-3-methylbutyl)oxazolidine-2,4-dione, followed by demethylation of (Z)-5-(2-(6-(2-ethyl-4-methyl-2H-indazol-6-yl)-2-methoxypyridin-3-yl)-3-methylbutylidene)oxazolidine-2,4-dione with TMSCl/NaI to yield the product as a white solid.

$^1$H NMR (400 MHz, CD$_3$OD) δ: 8.11 (s, 1 H), 7.72 (s, 1 H), 7.57 (d, J=7.2 Hz, 1 H), 7.23 (s, 1 H), 6.70 (d, J=7.2 Hz, 1 H), 6.32 (d, J=10.4 Hz, 1 H), 4.48-4.53 (m, 2 H), 3.71 (t, J=7.2 Hz, 1 H), 2.65 (s, 3 H), 2.28-2.38 (m, 1 H), 1.49 (t, J=7.2 Hz, 3 H), 1.00 (d, J=6.4 Hz, 3 H), 0.92 (d, J=6.8 Hz, 3 H).

Mass spectrum (ESI, m/z): Calculated for C$_{23}$H$_{24}$N$_4$O$_4$, 421.2 (M+H), found 421.2.

Example 27

Compound #97

(Z)-5-(2-(6-(7-chloro-1-methyl-1H-benzo[d]imidazol-5-yl)-2-oxo-1,2-dihydropyridin-3-yl)-3-methylbutylidene)oxazolidine-2,4-dione

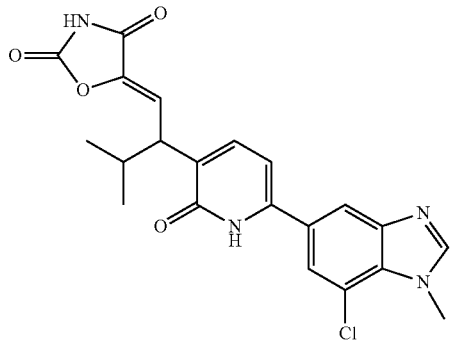 [SMILES: CC(C)C(/C=C1\OC(=O)NC1=O)c1ccc(-c2cc(Cl)c3c(c2)ncn3C)[nH]c1=O]

Step 1: 5-bromo-7-chloro-1H-benzo[d]imidazole 5-bromo-7-chloro-1H-benzimidazole A solution of 5-bromo-3-chlorobenzene-1,2-diamine (2 g, 9.03 mmol) in formic acid (30 ml) was heated at reflux for 16 hours. The reaction progress was monitored by LCMS. Reaction mixture was concentrated under vacuum to yield brown oil. The mixture was extracted by EtOAc from a saturated aqueous solution of NaHCO$_3$, dried over MgSO$_4$ and evaporated under vacuum to yield 5-bromo-7-chloro-1H-benzo[d]imidazole as a pale yellow solid.

Mass spectrum (EI, m/z): Calculated for C$_7$H$_4$BrClN$_2$, 232.5 (M+H), found 233.0.

Step 2: 5-bromo-7-chloro-1-methyl-1H-benzo[d]imidazole

Into a 100-mL round-bottom flask, were placed 5-bromo-7-chloro-1H-1,3-benzodiazole (1 g, 4.320 mmol, 1.00 equiv), THF (40 mL). To the mixture was then added NaH (60%) (0.52 g) in portions at 0° C. The resulting solution was stirred for 1 h at 0° C. To this was then added MeI (1 mL). The resulting solution was stirred for 2 h at 25° C. The reaction progress was monitored by LCMS. The reaction was then quenched by the addition of water (10 mL). The resulting solution was extracted with ethyl acetate (3×30 mL) and the organic layers combined and concentrated under vacuum. The residue was applied onto a silica gel column with ethyl acetate/petroleum ether (1/20) to yield 5-bromo-7-chloro-1-methyl-1H-benzo[d]imidazole as yellow solid.

Mass spectrum (EI, m/z): Calculated for C$_8$H$_6$BrClN$_2$, 246.5 (M+H), found 246.9.

Step 3: (Z)-5-(2-(6-(7-chloro-1-methyl-1H-benzo[d]imidazol-5-yl)-2-oxo-1,2-dihydropyridin-3-yl)-3-methylbutylidene)oxazolidine-2,4-dione The title compound was prepared according to the procedure as described in Example 5 starting with aldol condensation by t-BuLi, dehydration followed by demethylation with TMSCl/NaI to yield the product as a yellow solid.

$^1$H NMR (300 MHz, CD$_3$OD) δ: δ 8.61 (s, 1 H), 8.00 (s, 1 H), 7.78 (s, 1 H), 7.61 (d, J=7.3 Hz, 1 H), 6.76 (d, J=7.4 Hz, 1 H), 6.39 (d, J=10.6 Hz, 1 H), 4.05 (s, 3 H), 3.68-3.78 (m, 1 H), 2.27-2.45 (m, 1 H), 1.03 (d, J=6.7 Hz, 3 H), 0.94 (d, J=6.7 Hz, 3 H). Mass spectrum (EI, m/z): Calculated for C$_{21}$H$_{19}$ClN$_4$O$_4$, 427.1 (M+H), found 426.9.

Example 28

Compound #118

(Z)-5-(3-methyl-2-(6-(1-methyl-1H-indol-5-yl)-2-oxo-1,2-dihydropyridin-3-yl)butylidene)oxazolidine-2,4-dione

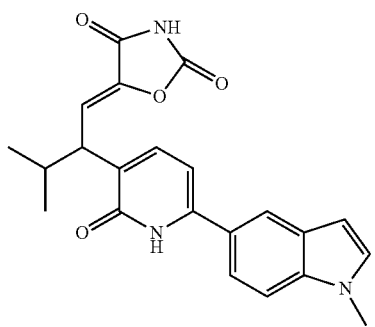 [SMILES: CC(C)C(/C=C1\OC(=O)NC1=O)c1ccc(-c2ccc3c(ccn3C)c2)[nH]c1=O]

The title compound was prepared according to the procedure as described in Example 5 starting with aldol condensation by t-BuLi, dehydration followed by demethylation with TMSCl/NaI to yield the product as white solid.

$^1$H NMR (400 MHz, CD$_3$OD) δ: 7.92 (s, 1H), 7.57 (d, J=7.6 Hz, 1H), 7.47-7.55 (m, 2H), 7.28 (d, J=3.2 Hz, 1H), 6.65 (d, J=7.2 Hz, 1H), 6.57 (d, J=3.2 Hz, 2H), 6.35 (d, J=10.8 Hz, 1H), 3.87 (s, 3H), 2.32-2.40 (m, 3H), 1.02 (d, J=6.4 Hz, 3H), 0.94 (d, J=6.8 Hz, 3H). Mass spectrum (ESI, m/z): Calculated for C$_{22}$H$_{21}$N$_3$O$_4$, 392.2 (M+H), found 392.2.

Example 29

Compound #93

(Z)-5-(2-(6-(benzo[d]isothiazol-6-yl)-2-methoxypyridin-3-yl)-3-methylbutylidene) oxazolidine-2,4-dione

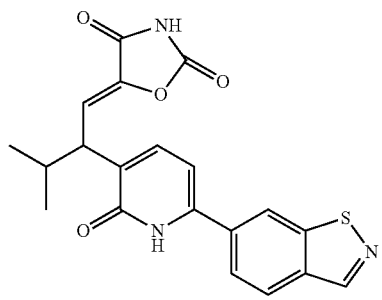 [SMILES: CC(C)C(/C=C1\OC(=O)NC1=O)c1ccc(-c2ccc3cnsc3c2)[nH]c1=O]

The title compound was prepared according to the procedure as described in Example 5 starting with aldol condensation by t-BuLi, dehydration followed by demethylation with TMSCl/NaI to yield the product as yellow solid.

$^1$H NMR (300 MHz, CD$_3$OD) δ: 8.94 (s, 1H), 8.31 (s, 1H), 8.18 (d, J=7.8 Hz, 1H), 7.68 (d, J=9.9 Hz, 1H), 7.50 (d, J=7.5 Hz, 1H), 6.65 (d, J=6.9 Hz, 1H), 6.27 (d, J=10.5 Hz, 1H) 3.59-3.65 (m, 1H),2.24-2.31 (m, 1H), 0.91 (d, J=6.6 Hz, 3H), 0.82 (d, J=6.6 Hz, 3H). Mass spectrum (ESI, m/z): Calculated for C$_{21}$H$_{21}$N$_3$O$_5$S, 396.1 (M+H), found 396.0.

Example 30

Compound #274 and #275

(Z)-5-(2-(6-(8-fluoronaphthalen-2-yl)-2-oxo-2,3-dihydropyridin-3-yl)-3,3-dimethylbutylidene)oxazolidine-2,4-dione and (E)-5-(2-(6-(8-fluoronaphthalen-2-yl)-2-oxo-2,3-dihydropyridin-3-yl)-3,3-dimethylbutylidene)oxazolidine-2,4-dione

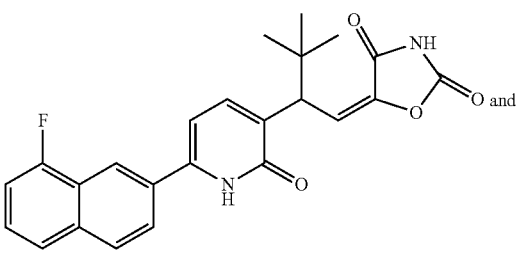

-continued

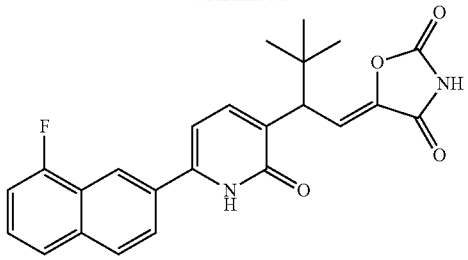

Step 1: Ethyl 2-(6-(8-fluoronaphthalen-2-yl)-2-methoxypyridin-3-yl)-2-hydroxy-3,3-dimethylbutanoate Into a 100-mL round bottle maintained with an inert atmosphere of nitrogen, to a solution of tert-butylmagnesium chloride (5 mL, 5.000 mmol, 2.00 equiv.) in THF (20 mL), add ethyl 2-(6-(8-fluoronaphthalen-2-yl)-2-methoxypyridin-3-yl)-2-oxoacetate (900 mg, 2.500 mmol, 1.00 equiv.) with stirring at 0° C. The resulting solution was stirred 16 h at 20° C. The reaction was concentrated under vacuum. The residue product was purified by chromatogram on silica gel with ethyl acetate/petroleum ether (7:93) to yield ethyl 2-(6-(8-fluoronaphthalen-2-yl)-2-methoxypyridin-3-yl)-2-hydroxy-3,3-dimethylbutanoate as a yellow oil.

Mass spectrum (ESI, m/z): Calculated for $C_{24}H_{26}FNO_4$, 412.2 [M+H], found 412.0.

Step 2: (6-(8-fluoronaphthalen-2-yl)-2-methoxypyridin-3-yl)-3,3-dimethylbutane-1,2-diol Into a 50-mL round bottle, to a solution of ethyl 2-(6-(8-fluoronaphthalen-2-yl)-2-methoxypyridin-3-yl)-2-hydroxy-3,3-dimethylbutanoate (320 mg, 0.780 mmol, 1.00 equiv.) in THF (10 mL), was added LAH (88 mg, 2.300 mmol, 3.00 equiv). The resulting solution was stirred 6 h at 20° C. The mixture was quenched by the addition of $Na_2SO_4 \cdot 10H_2O$, the solid were filtered out, the organic layers was concentrated under vacuum. The residue product was purified by chromatogram on TLC with ethyl acetate/petroleum ether (1:3) to yield (S)-2-(6-(8-fluoronaphthalen-2-yl)-2-methoxypyridin-3-yl)-3,3-dimethylbutane-1,2-diol as yellow oil.

Mass spectrum (ESI, m/z): Calculated for $C_{22}H_{24}FNO_3$, 370.2 [M+H], found 369.9.

Step 3: 3-(2-tert-butyloxiran-2-yl)-6-(8-fluoronaphthalen-2-yl)-2-methoxypyridine Into a 8-mL vial maintained with an inert atmosphere of nitrogen, were placed (S)-2-(6-(8-fluoronaphthalen-2-yl)-2-methoxypyridin-3-yl)-3,3-dimethylbutane-1,2-diol (170 mg, 0.500 mmol, 1.00 equiv.), toluene (10 mL), PPh$_3$ (242 mg, 0.920 mmol, 2.00 equiv.). DEAD (185 mg, 0.920 mmol, 2.00 equiv) was then added with stirring at 0° C. The mixture was stirred at 20° C. for 16 h. The mixture was concentrated under vacuum to yield 3-(2-tert-butyloxiran-2-yl)-6-(8-fluoronaphthalen-2-yl)-2-methoxypyridine as yellow oil.

Mass spectrum (ESI, m/z): Calculated for $C_{22}H_{22}FNO_2$, 352.2 [M+H], found 352.3

Step 4: 2-(6-(8-fluoronaphthalen-2-yl)-2-methoxypyridin-3-yl)-3,3-dimethylbutanal Into a 8-mL vial were placed 3-(2-tert-butyloxiran-2-yl)-6-(8-fluoronaphthalen-2-yl)-2-methoxypyridine (160 mg, 0.400 mmol, 1.00 equiv.), THF (10 mL). BCl$_3$(0.5 mL, 0.500 mmol, 1.10 equiv.) was then added with stirring at 20° C. The mixture was stirred at 20° C. for 5 h. The mixture was quenched by the addition of MeOH. The organic layer was concentrated under vacuum. The residue was purified by TLC with ethyl acetate/petroleum ether (1:6) to yield 2-(6-(8-fluoronaphthalen-2-yl)-2-methoxypyridin-3-yl)-3,3-dimethylbutanal as yellow oil.

Mass spectrum (ESI, m/z): Calculated for $C_{22}H_{22}FNO_2$, 352.2 [M+H], found 351.9.

Step 5: (Z)-5-(2-(6-(8-fluoronaphthalen-2-yl)-2-oxo-2,3-dihydropyridin-3-yl)-3,3-dimethylbutylidene) oxazolidine-2,4-dione and (E)-5-(2-(6-(8-fluoronaphthalen-2-yl)-2-oxo-2,3-dihydropyridin-3-yl)-3,3-dimethylbutylidene)oxazolidine-2,4-dione The title compounds were prepared according to the procedure as described in Example 5 starting with aldol condensation by t-BuLi, dehydration followed by demethylation with TMSCl/NaI to yield the product as yellow solids.

(E)-5-(2-(6-(8-fluoronaphthalen-2-yl)-2-oxo-2,3-dihydropyridin-3-yl)-3,3-dimethyl butylidene)oxazolidine-2,4-dione. $^1$H NMR (300 MHz, CD$_3$OD) δ: 8.33-8.35 (m, 1H), 8.24 (d, J=8.8 Hz, 1H), 7.82 (s, 1H), 7.56-7.69 (m, 2H), 7.23-7.32 (m, 1H), 6.69-6.84 (m, 2H), 6.55 (d, J=9.1 Hz, 1H), 4.78-4.82 (m, 1H), 0.98 (s, 9H). $^{19}$F NMR (300 MHz, CD$_3$OD) δ −77.24, −122.85. Mass spectrum (ESI, m/z): Calculated for $C_{24.9}H_{21.45}F_{2.35}N_2O_{4.9}$, 421.1 [M−0.45CF$_3$COOH+H], found 421.0.

(Z)-5-(2-(6-(8-fluoronaphthalen-2-yl)-2-oxo-2,3-dihydropyridin-3-yl)-3,3-dimethylbutylidene) oxazolidine-2,4-dione. $^1$H NMR (300 MHz,CD$_3$OD) δ 8.26-8.33 (m, 2H), 7.82 (s, 1H), 7.66-7.71 (m, 1H), 7.53-7.58 (m, 1H), 7.23-7.29 (m, 1H), 6.80-6.84 (m, 2H), 6.55 (d, J=9.0 Hz, 1H), 5.74 (d, J=12.1 Hz, 1H), 1.00 (s, 9H). $^{19}$F NMR (300 MHz, CD$_3$OD) δ −77.21, −123.27. Mass spectrum (ESI, m/z): Calculated for $C_{27.6}H_{22}F_{6.4}N_2O_{7.6}$, 421.1 [M−1.80CF$_3$COOH+H], found 421.2.

Example 31

Compound #123

(Z)-5-(2-(6-(8-fluoronaphthalen-2-yl)-2-oxo-2,3-dihydropyridin-3-yl)-2-phenylethylidene) oxazolidine-2,4-dione

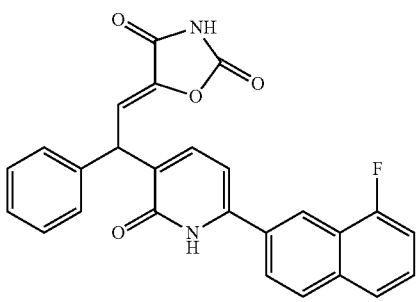 [SMILES: O=C1NC(=O)/C(=C/C(c2ccccc2)c2ccc(-c3ccc4cccc(F)c4c3)[nH]c2=O)O1]

Step 1: (6-chloro-2-methoxypyridin-3-yl)(phenyl)methanone

To 2-chloro-6-methoxypyridine (1 g, 6.965 mmol 1 equiv.) in THF (50 mL) under N$_2$ atmosphere at −78° C. was added t-BuLi (6.5 mL, 1.5 equiv.) dropwise. The reaction mixture was stirred at −78° C. for 3 h, then N-methoxy-N-methylbenzamide (1.28 g, 7.749 mmol 1.1 equiv.) was added. The reaction was stirred at −78° C. for 3 h. The reaction was monitored by TLC (PE/EA=15/1). The reaction was quenched by NH$_4$Cl and the mixture was extracted with EtOAc (3×50 mL). The resulting mixture was evaporated under reduced pressure to yield (6-chloro-2-methoxypyridin-3-yl)(phenyl) methanone as a yellow oil.

$^1$H NMR (400 MHz, CD$_3$OD, ppm) δ: 7.76-7.85 (m, 2 H), 7.72 (d, J=7.7 Hz, 1 H), 7.57-7.67 (m, 1 H), 7.48 (t, J=7.7 Hz, 2 H), 7.06 (d, J=7.7 Hz, 1 H), 3.91 (s, 3H).

Step 2: (E)-6-chloro-2-methoxy-3-(2-methoxy-1-phenylvinyl)pyridine

Into a 250-mL round-bottom flask, were placed (methoxymethyl) triphenylphosphonium chloride (4 g, 11.669 mmol, 2.064 equiv.), in THF (70 mL). To the mixture was then added LIHMDS (15 ml), in portions at 0° C. The resulting solution was stirred for 1 h at 0° C. To the mixture was added (6-chloro-2-methoxypyridin-3-yl) (phenyl) methanone (1.4 g). The resulting solution was stirred for 16 h at 25° C. The reaction progress was monitored by TLC (PE/EA=15/1). The resulting solution was quenched by H$_2$O (20 mL). The mixture was extracted with EtOAc (3×50 mL), the organic layers combined and concentrated under vacuum. The residue was applied onto a silica gel column with PE/EA (95/5) to (E)-6-chloro-2-methoxy-3-(2-methoxy-1-phenylvinyl) pyridine as yellow oil.

Mass spectrum (EI, m/z): Calculated For C$_{15}$H$_{14}$ClNO$_2$, 275.7 [M+H]$^+$, found 275.9.

Step 3: 2-(6-chloro-2-methoxypyridin-3-yl)-2-phenylacetaldehyde

To (Z)-6-chloro-2-methoxy-3-(2-methoxy-1-phenylvinyl) pyridine (800 mg, 2.901 mmol 1 equiv.) in CH$_3$CN (50 mL) was added HBr (1 mL). The reaction mixture was stirred at room temperature for 2 h. The reaction was monitored by TLC (PE/EA=6/1). The reaction was quenched by H$_2$O and the mixture was extracted with EtOAc (3×30 mL). The organic layers combined and concentrated under vacuum. The residue was applied onto a silica gel column with PE/EA=(95/5) to yield 2-(6-chloro-2-methoxypyridin-3-yl)-2-phenylacetaldehyde as yellow oil.

Mass spectrum (EI, m/z): Calculated For C$_{14}$H$_{12}$ClNO$_2$, 261.7 [M+H]$^+$, found 262.1.

Step 4: 2-(6-(8-fluoronaphthalen-2-yl)-2-methoxy-pyridin-3-yl)-2-phenylacetaldehyde Into a 250-mL round-bottom flask purged and maintained with an inert atmosphere of nitrogen, were placed a solution of 2-(6-chloro-2-methoxypyridin-3-yl)-2-phenylacetaldehyde (800 mg, 3.068 mmol, 1.0 equiv.) in DME/H$_2$O (50 mL). 2-(8-Fluoronaphthalen-2-yl)-4,4,5,5-tetramethyl-1,3,2-dioxaborolane (1.25 g, 4.594 mol, 1.5 equiv.), Pd(dppf)Cl$_2$·CH$_2$Cl$_2$ (75 mg, 0.092 mmol, 0.03 equiv.), Na$_2$CO$_3$ (1.14 mg, 10.755 mmol, 3.5 equiv.) were then added. The resulting solution was stirred overnight at 90° C. in an oil bath. The reaction was monitored by TLC (PE/EA=15/1). The resulting solution was quenched by water (25 mL). The mixture was then extracted with EtOAc (3×50 mL), and the organic layers combined and concentrated under vacuum. The residue was applied onto a silica gel column with PE/EA (95/5) to yield 2-(6-(8-fluoronaphthalen-2-yl)-2-methoxypyridin-3-yl)-2-phenylacetaldehyde as a yellow oil.

Mass spectrum (EI, m/z): Calculated For C$_{24}$H$_{18}$FNO$_2$, 371.4 [M+H]$^+$, found 372.1.

Step 5: (Z)-5-(2-(6-(8-fluoronaphthalen-2-yl)-2-oxo-2,3-dihydropyridin-3-yl)-2-phenylethylidene)oxazolidine-2,4-dione The title compound was prepared according to the procedure as described in Example 5 starting with aldol condensation by t-BuLi, dehydration followed by demethylation with TMSCl/NaI to yield the product as a white solid.

$^1$H NMR (400 MHz, Methanol-d$_4$, ppm) 58.43 (s, 1 H), 8.04-8.11 (m, 1 H), 7.87 (d, J=8.7, 1.9 Hz, 1 H), 7.78 (d, J=8.3 Hz, 1 H), 7.65 (d, J=7.3 Hz, 1 H), 7.56 (d, J=8.0 Hz, 1 H), 7.35-7.43 (m, 4 H), 7.24-7.34 (m, 2 H), 6.81 (d, J=7.2 Hz, 1 H), 6.45 (s, 1 H), 5.41 (d, J=10.2 Hz, 1 H), $^{19}$F NMR (400 MHz, Methanol-d$_4$, ppm) δ: −124.442. Mass spectrum (EI, m/z): Calculated For C$_{26}$H$_{17}$FN$_2$O$_4$, 440.4 [M+H]$^+$, found 441.2.

Example 32

Compound #117

(E)-5-(2-(6-(8-fluoronaphthalen-2-yl)-2-oxo-1,2-dihydropyridin-3-yl)-3-phenylpropylidene)oxazolidine-2,4-dione

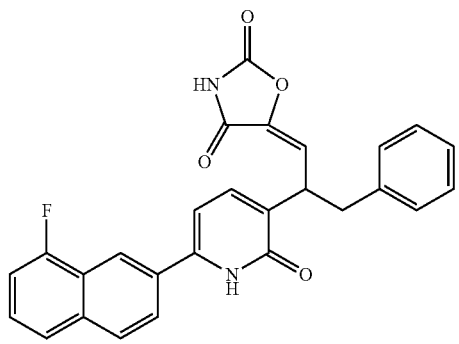 [SMILES: O=C1NC(=O)/C(=C\C(Cc2ccccc2)c2ccc(-c3ccc4cccc(F)c4c3)[nH]c2=O)O1]

The title compound was prepared according to the procedure as described in Example 5 starting with aldol condensation by t-BuLi, dehydration followed by demethylation with TMSCl/NaI to yield the product as an off-white solid.

$^1$H NMR (400 MHz, CD$_3$OD) δ: 8.38 (s, 1 H), 8.04 (d, J=8.8 Hz, 1H), 7.82 (d, J=7.2 Hz, 1H), 7.75 (d, J=8.0 Hz, 1H), 7.49-7.56 (m, 2 H), 7.21-7.30 (m, 5 H), 7.14-7.17 (m, 1 H), 6.69 (d, J=7.2 Hz,1H), 6.36 (d, J=10.0 Hz,1H), 4.25-4.31 (m, 1 H), 3.17-3.30 (m, 1 H), 3.01-3.15 (m, 1 H). $^{19}$F NMR (400 MHz, CD$_3$OD) δ: −124.45. Mass spectrum (EI, m/z): Calculated for C$_{27}$H$_{19}$FN$_2$O$_4$, 455.1 (M+H), found 455.2.

Example 33

Compound #105

5-(3-ethyl-2-(6-(8-fluoronaphthalen-2-yl)-2-oxo-1,2-dihydropyridin-3-yl)pentylidene)oxazolidine-2,4-dione

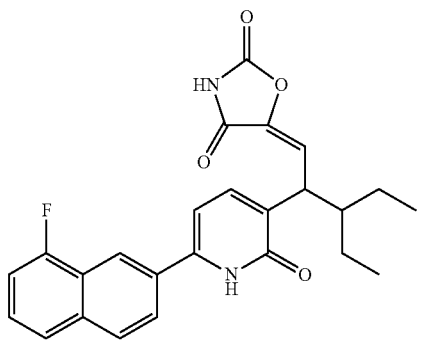 [SMILES: CCC(CC)C(/C=C1/OC(=O)NC1=O)c1ccc(-c2ccc3cccc(F)c3c2)[nH]c1=O]

The title compound was prepared according to the procedure as described in Example 5 starting with aldol condensation by t-BuLi, dehydration followed by demethylation with TMSCl/NaI to yield the product as a white solid.

$^1$H NMR (400 MHz,CD$_3$OD) δ: 8.44 (s, 1H), 8.05 (d, J=8.0 Hz, 1H), 7.84 (d, J=8.8 Hz, 1H), 7.76 (d, J=8.4 Hz, 1H), 7.61 (d, J=7.6 Hz, 1H), 7.51-7.56 (m, 1H), 7.26-7.28 (m, 1H), 6.76-6.80 (m, 1H), 6.33 (d, J=5.2 Hz, 1H), 4.01 (t, J=10 Hz, 1H), 2.11 (s, 1H), 1.54-1.56 (m, 1H), 1.33-1.42 (m, 3H), 0.89-0.93 (m, 6H). $^{19}$F NMR (400 MHz, CD$_3$OD) δ: −124.47. Mass spectrum (ESI, m/z): Calculated For C$_{25}$H$_{23}$FN$_2$O$_4$, 435.2 (M+H), found 435.2.

Example 34

Compound #103

(Z)-5-(2-cyclopropyl-2-(6-(8-fluoronaphthalen-2-yl)-2-oxo-1,2-dihydropyridin-3-yl)ethylidene)oxazolidine-2,4-dione

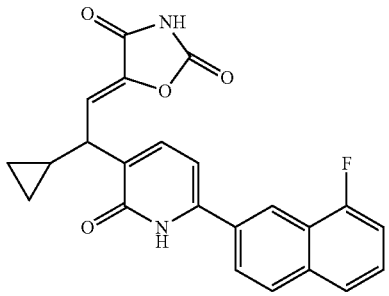 [SMILES: O=C1NC(=O)/C(=C/C(c2ccc(-c3ccc4cccc(F)c4c3)[nH]c2=O)C2CC2)O1]

The title compound was prepared according to the procedure as described in Example 5 starting with aldol condensation by t-BuLi, dehydration followed by demethylation with TMSCl/NaI to yield the product as a white solid.

$^1$H NMR (400 MHz, Methanol-d$_4$) δ 8.43 (s, 1 H), 8.05-8.12 (d, J=11.2 Hz, 1 H), 7.85-7.88 (m, 1 H), 7.76-7.79 (m, 2 H), 7.54-7.59 (m, 1 H), 7.26-7.36 (m, 1 H), 6.82 (d, J=7.2 Hz, 1 H), 6.31 (d, J=9.9 Hz, 1 H), 3.27 (t, J=9.7 Hz, 1 H), 1.48-1.52 (m, 1 H), 0.56-0.71 (m, 2 H), 0.38-0.46 (m, 1 H), 0.27-0.37 (m, 1 H). $^{19}$F NMR (400 MHz, Methanol-d$_4$) δ: −124.477. Mass spectrum (EI, m/z): Calculated for C$_{23}$H$_{17}$FN$_2$O$_4$, 405.1 (M+H), found 405.0.

Example 35

Compound #92

(Z)-5-(2-cyclopentyl-2-(6-(8-fluoronaphthalen-2-yl)-2-oxo-1,2-dihydropyridin-3-yl)ethylidene)oxazolidine-2,4-dione

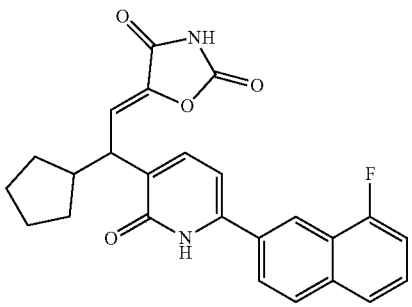 [SMILES: O=C1NC(=O)/C(=C/C(c2ccc(-c3ccc4cccc(F)c4c3)[nH]c2=O)C2CCCC2)O1]

The title compound was prepared according to the procedure as described in Example 5 starting with aldol condensation by t-BuLi, dehydration followed by demethylation with TMSCl/NaI to yield the product as a white solid.

$^1$H NMR (400 MHz, CDCl$_3$) δ: 8.40 (s, 1 H), 8.07 (d, J=8.2 Hz, 1 H), 7.85 (m, 1 H), 7.72 (m, 2 H), 7.50 (m, 1 H), 7.31 (m, 1 H), 6.80 (d, J=7.5 Hz, 1 H), 6.28 (d, J=6.9 Hz, 1 H), 3.70 (m, 1H), 2.55 (m, 1H), 1.69 (m, 6H), 1.28 (m, 2H). Mass spectrum (EI, m/z): Calculated for C$_{25}$H$_{21}$FN$_2$O$_4$, 433.45 [M+H], found 433.6.

Example 36

Compound #134

(Z)-5-(2-cyclohexyl-2-(6-(8-fluoronaphthalen-2-yl)-2-oxo-1,2-dihydropyridin-3-yl)ethylidene)oxazolidine-2,4-dione

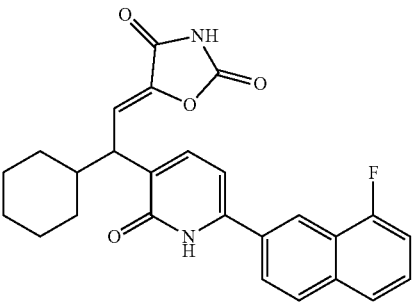 [SMILES: O=C1NC(=O)/C(=C/C(c2ccc(-c3ccc4cccc(F)c4c3)[nH]c2=O)C2CCCCC2)O1]

The title compound was prepared according to the procedure as described in Example 5 starting with aldol condensation by t-BuLi, dehydration followed by demethylation with TMSCl/NaI to yield the product as a white solid.

$^1$H NMR (400 MHz, CDCl$_3$) δ: 8.40 (s, 1 H), 8.07 (d, J=8.2 Hz, 1 H), 7.85 (m, 1 H), 7.72 (m, 2 H), 7.50 (m, 1 H), 7.31 (m, 1 H), 6.80 (d, J=7.5 Hz, 1 H), 6.28 (d, J=6.9 Hz, 1 H), 3.65 (m, 1H), 2.01 (m, 1H), 1.68 (m, 4H), 1.15 (m, 4H),

Example 37

Compound #87

5-(2-(6-(1-ethyl-4-fluoro-1H-indazol-6-yl)-2-oxo-1,2-dihydropyridin-3-yl)-3-methylbutyl)oxazoli-dine-2,4-dione

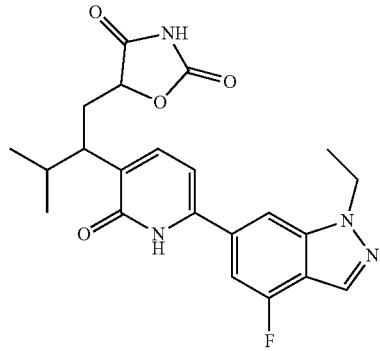 [SMILES: CCn1ncc2c(F)cc(-c3ccc(C(CC4OC(=O)NC4=O)C(C)C)c(=O)[nH]3)cc21]

The title compound was prepared according to the procedure as described in Example 8 step 1 by hydrogenation of 5 (Z)-5-(2-(6-(1-ethyl-4-fluoro-1H-indazol-6-yl)-2-methoxypyridin-3-yl)-3-methylbutylidene)oxazolidine-2,4-dione followed by demethylation of 5-(2-(6-(1-ethyl-4-fluoro-1H-indazol-6-yl)-2-methoxypyridin-3-yl)-3-methylbutyl)oxazolidine-2,4-dione with TMSCl/NaI in CH$_3$CN to yield the product as a light yellow solid.

$^1$H NMR (300 MHz, CD$_3$OD) δ: 8.14 (s, 1H), 7.82 (s, 1H), 7.49-7.54 (t, J=6.75 Hz, 1H), 7.21 (d, J=11.1 Hz, 1H), 6.71-6.78 (m, 1H), 4.68-4.72 (m, 1H), 4.52-4.60 (m, 2H), 2.89-2.98 (m, 1H), 2.08-2.65 (m, 3H), 1.51-1.57 (t, J=3.6 Hz, 3H), 1.01-1.05 (t, J=6.75 Hz, 3H), 0.83-0.90 (m, 1H). $^{19}$F NMR (300 MHz, CD$_3$OD) δ: −119.22. Mass spectrum (ESI, m/z): Calculated for C$_{22}$H$_{23}$FN$_4$O$_4$, 427.2 (M+H), found 427.1.

Example 38

Compound #110 and #120

5-(2-(6-(4-chloro-2-ethyl-2H-indazol-6-yl)-2-oxo-1,2-dihydropyridin-3-yl)-3-methylbutyl)oxazolidine-2,4-dione and 5-(2-(6-(2-ethyl-2H-indazol-6-yl)-2-oxo-1,2-dihydropyridin-3-yl)-3-methylbutyl)oxazolidine-2,4-dione

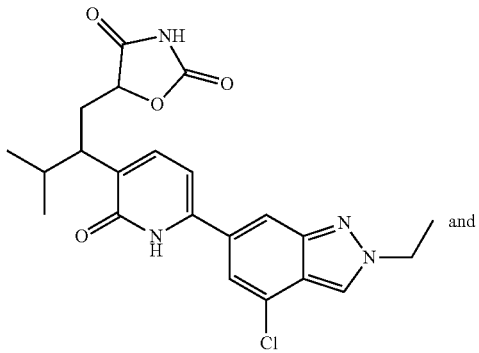

and

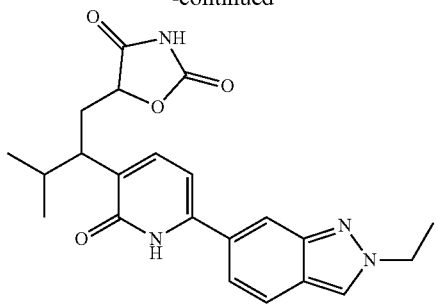

The title compounds were prepared according to the procedure as described in Example 8 step 1 by hydrogenation followed by demethylation to yield the products.

5-(2-(6-(4-chloro-1-ethyl-1H-indazol-6-yl)-2-oxo-1,2-dihydropyridin-3-yl)-3-methylbutyl)oxazolidine-2,4-dione as a white solid. $^1$H NMR(300 MHz, CD$_3$OD) δ: 8.25 (s, 1H), 7.83 (s, 1H), 7.55 (d, J=7.2 Hz, 1H), 7.43 (s, 1H), 6.74 (d, J=7.2 Hz, 1H), 4.84-4.89 (m, 1H), 4.49-4.52 (m, 2H), 2.80-2.92 (m, 1H), 2.40-2.42 (m, 2H), 1.95-2.09 (m, 1H), 1.50 (t, J=7.2 Hz, 3H), 1.06 (d, J=7.2 Hz, 3H), 0.90 (d, J=6.6 Hz, 3H). Mass spectrum (ESI, m/z): Calculated for C$_{22}$H$_{23}$ClN$_4$O$_4$, 443.1 [M+H], found 442.9.

and 5-(2-(6-(1-ethyl-1H-indazol-6-yl)-2-oxo-1,2-dihydropyridin-3-yl)-3-methylbutyl)oxazolidine-2,4-dione as a white solid. $^1$H NMR(300 MHz, CD$_3$OD) δ: 8.24 (s, 1 H), 7.73 (d, J=8.7 Hz, 1H), 7.52-7.58 (m, 2H), 7.41 (d, J=7.2 Hz, 1H), 6.74-6.76 (m, 1H), 4.74-4.78 (m, 1H), 4.50-4.57 (m, 2H), 2.80-2.92 (m, 1H), 2.32-2.68 (m, 1H), 2.15-2.17 (m, 2H), 1.50 (t, J=7.2 Hz, 3H), 1.03 (d, J=6.6 Hz, 3H), 0.90 (d, J=6.6 Hz, 3H). Mass spectrum (EI, m/z): Calculated for C$_{22}$H$_{24}$N$_4$O$_4$, 409.2 [M+H], found 408.9.

Example 39

Compound #126

5-(2-(6-(1-ethyl-4-methyl-1H-indazol-6-yl)-2-oxo-1,2-dihydropyridin-3-yl)-3-methylbutyl)oxazolidine-2,4-dione

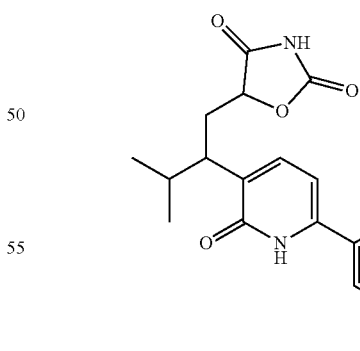

The title compound was prepared according to the procedure as described in Example 8 step 1 by hydrogenation followed by demethylation to yield an off-white solid.

$^1$H NMR(400 MHz, CD$_3$OD) δ: 8.13 (s, 1 H), 7.73 (s, 1 H), 7.50 (t, J=6.8 Hz, 1 H), 7.24 (s, 1 H), 6.67-6.72 (m, 1 H), 4.67-4.70 (m, 1 H), 4.48-4.53 (m, 2 H), 2.88-2.91 (m, 1 H), 2.65 (s, 3 H), 2.39-2.52 (m, 1 H), 2.07-2.38 (m, 2 H), 1.50

(previous column continued:)
0.95 (m, 2H). Mass spectrum (EI, m/z): Calculated for C$_{26}$H$_{23}$FN$_2$O$_4$, 447.48 [M+H], found 447.8.

(t, J=7.2 Hz, 3 H), 1.02 (t, J=6.8 Hz, 3 H), 0.87 (t, J=6.4 Hz, 3 H). Mass spectrum (EI, m/z): Calculated for $C_{23}H_{26}N_4O_4$, 423.2 (M+H), found 423.0.

Example 40

Compound #86

5-(2-(6-(2-ethyl-4-methyl-2H-indazol-6-yl)-2-oxo-1, 2-dihydropyridin-3-yl)-3-methylbutyl)oxazolidine-2, 4-dione

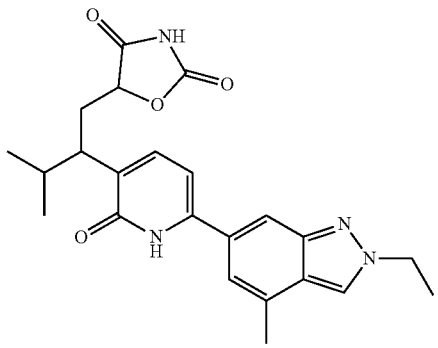 [SMILES: CCn1cc2c(C)cc(-c3ccc(C(CC4OC(=O)NC4=O)C(C)C)c(=O)[nH]3)cc2n1]

The title compound was prepared according to the procedure as described in Example 8 step 1 by hydrogenation followed by demethylation to yield a white solid.

$^1$H NMR (400 MHz, $CD_3OD$) δ: 8.11 (s, 1H), 7.73 (s, 1H), 7.48 (t, J=8.8 Hz, 1H), 7.23 (s, 1H), 6.67-6.72 (m, 1 H), 4.65-4.68 (m, 1 H), 4.48-4.58 (m, 2 H), 2.87-2.95 (m, 1H), 2.65 (s, 3H), 2.39-2.51 (m, 1 H), 2.08-2.13 (m, 2 H), 1.47-1.51 (m, 3 H), 0.98-1.01 (m, 3 H), 0.85-0.92 (m, 3 H). Mass spectrum (ESI, m/z): Calculated for $C_{23}H_{26}N_4O_4$, 423.2 (M+H), found 423.0.

Example 41

Compound #107

5-(2-(6-(7-chloro-1-methyl-1H-benzo[d]imidazol-5-yl)-2-oxo-1,2-dihydropyridin-3-yl)-3-methylbutyl) oxazolidine-2,4-dione

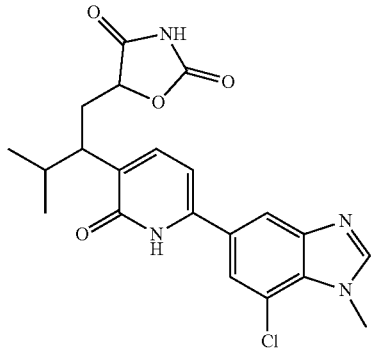 [SMILES: CC(C)C(CC1OC(=O)NC1=O)c1ccc(-c2cc(Cl)c3c(c2)ncn3C)[nH]c1=O]

The title compound was prepared according to the procedure as described in Example 8 step 1 by hydrogenation followed by demethylation to yield a white solid.

$^1$H NMR (400 MHz, $CD_3OD$) δ: 8.32 (s, 1 H), 7.92 (s, 1H), 7.70 (s,1H), 7.49-7.53 (m,1H), 6.69-6.74 (m, 1 H), 4.83-4.89 (m, 1 H), 4.00 (s, 3 H), 2.90-3.14 (m,1H), 2.40-2.44 (m,1H), 2.10-2.19 (m, 2 H), 1.01-1.31 (m, 3 H), 0.87-0.92 (m, 3 H). Mass spectrum (ESI, m/z): Calculated For $C_{21}H_{21}ClN_4O_4$, 429.1 (M+H), found 429.0.

Example 42

Compound #130

5-(2-cyclopentyl-2-(6-(1-ethyl-4-fluoro-1H-indazol-6-yl)-2-oxo-1,2-dihydropyridin-3-yl)ethylidene)-oxazolidine-2,4-dione

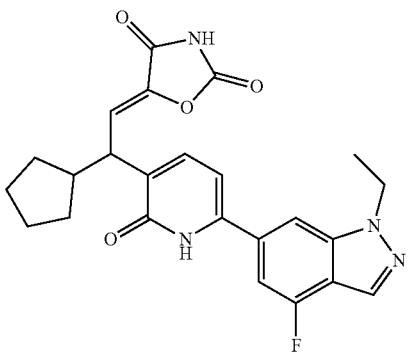 [SMILES: CCn1ncc2c(F)cc(-c3ccc(C(/C=C4\OC(=O)NC4=O)C4CCCC4)c(=O)[nH]3)cc21]

Step 1: Ethyl 2-(6-chloro-2-methoxypyridin-3-yl)-2-cyclopentyl-2-hydroxyacetate

Into a 8 mL tube were placed a solution of 2-chloro-6-methoxypyridine (400 mg, 2.786 mmol, 1.00 equiv.) in THF (10 mL) under an atmosphere of nitrogen. The suspension was stirred at −78° C. and n-BuLi (2 ml, 4.197 mmol, 1.50 equiv.) was added dropwise in 15 min. The mixture was stirred for 1.5 h. The mixture was then cooled to −78° C. A solution of ethyl 2-cyclopentyl-2-oxoacetate (711 mg, 4.197 mmol, 1.50 equiv.) in THF (10 mL) was added dropwise in 15 min. The mixture was stirred for another 1.5 h. The reaction was monitored by LCMS. The mixture was quenched with water and extracted with EtOAc. The organic layer was washed with brine and concentrated under vacuum. The residue was applied onto silica gel column with PE/EA (5/1) to yield ethyl 2-(6-chloro-2-methoxypyridin-3-yl)-2-cyclopentyl-2-hydroxyacetate.

Mass spectrum (ESI, m/z): Calculated for $C_{15}H_{20}ClNO_4$, 314.1[M+H], found 313.8.

Step 2: Ethyl 2-(6-chloro-2-methoxypyridin-3-yl)-2-cyclopentylideneacetate

Into a 100 ml round-bottom flask were placed a solution of ethyl 2-(6-chloro-2-methoxypyridin-3-yl)-2-cyclopentyl-2-hydroxyacetate (200 mg, 0.637 mmol, 1.00 equiv.) and 4-methylbenzenesulfonic acid (1.097 g, 6.37 mmol, 10.00 equiv.) in toluene (50 mL). The mixture was stirred for 2 h at 120° C. The water formed in the reaction was removed via a Dean-Stark tube. The reaction was monitored by LCMS. The mixture was washed with brine. The organic layer was concentrated under vacuum. The residue was applied onto a silica gel column and eluted with PE/EA=10/1 to yield ethyl 2-(6-chloro-2-methoxypyridin-3-yl)-2-cyclopentylideneacetate as yellow oil.

Mass spectrum (ESI, m/z): Calculated for $C_{15}H_{15}ClNO_3$, 296.1 [M+H], found 295.7.

Step 3: Ethyl 2-cyclopentylidene-2-(6-(1-ethyl-4-fluoro-1H-indazol-6-yl)-2-methoxypyridin-3-yl)acetate Into a 50 mL round-bottom flask were placed ethyl 2-(6-chloro-2-methoxypyridin-3-yl)-2-cyclopentylideneacetate (60 mg, 0.204 mmol, 1.00 equiv.) in ethylene glycol dimethyl ether (20 ml), and then 1-ethyl-4-fluoro-6-(4,4,5,5-tetramethyl-1,3,2-dioxaborolan-2-yl)-1H-indazole (77 mg, 0.265 mmol, 1.30 equiv.), sodium carbonate (43 mg, 0.410 mmol, 2.00 equiv.), and water (2 mL) were added. Pd(dppf)Cl$_2$.CH$_2$Cl$_2$ (5 mg, 0.006 mmol, 0.03 equiv.) was then added. The flask was evacuated and flushed three times with nitrogen.

The mixture was stirred overnight at 90° C. under an atmosphere of nitrogen (balloon). The reaction was monitored by LCMS. The resulting solution was poured into H$_2$O, extracted with ethyl acetate (3×30 mL). The organic layers were combined and washed with sodium chloride (aq.), dried and concentrated under vacuum. The residue was applied on a silica gel column and eluted with PE/EA (6/1) to yield ethyl 2-cyclopentylidene-2-(6-(1-ethyl-4-fluoro-1H-indazol-6-yl)-2-methoxypyridin-3-yl)acetate as yellow oil.

Mass spectrum (ESI, m/z): Calculated for $C_{24}H_{26}FN_3O_3$, 424.2 [M+H], found 423.9.

Step 4: Ethyl 2-cyclopentyl-2-(6-(1-ethyl-4-fluoro-1H-indazol-6-yl)-2-methoxypyridin-3-yl)acetate Into a 25 ml round-bottom flask were placed a solution of ethyl 2-cyclopentylidene-2-(6-(1-ethyl-4-fluoro-1H-indazol-6-yl)-2-methoxypyridin-3-yl)acetate (40 mg, 0.094 mmol, 1.00 equiv.) in EA (5 mL), then Palladium on activated carbon (10 mg) was added. The flask was evacuated and flushed three times with H$_2$. The mixture was stirred overnight at room temperature under an atmosphere of hydrogen. Palladium on activated carbon was filtered out. The filtrate was concentrated under vacuum. The residue was applied on a silica gel column and eluted with DCM/MeOH (20/1) to yield ethyl 2-cyclopentyl-2-(6-(1-ethyl-4-fluoro-1H-indazol-6-yl)-2-methoxypyridin-3-yl)acetate as colorless oil.

Mass spectrum (ESI, m/z): Calculated for $C_{24}H_{28}FN_3O_3$, 246.2 [M+H], found 246.0.

Step 5: 5-(2-cyclopentyl-2-(6-(1-ethyl-4-fluoro-1H-indazol-6-yl)-2-oxo-1,2-dihydropyridin-3-yl)ethylidene)-oxazolidine-2,4-dione The title compound was prepared according to the procedure as described in Example 5 starting with aldol condensation by t-BuLi, dehydration followed by demethylation with TMSCl/NaI to yield the product as white solid.

$^1$H NMR (300 MHz, CD$_3$OD) δ: 8.15 (s, 1H), 7.81 (s, 1H), 7.64 (d, J=7.2 Hz, 1H), 7.20 (d, J=11.1 Hz, 1H), 6.76 (d, J=7.2 Hz, 1H), 6.20-6.33 (m, 1H), 4.48-4.60 (m, 2H), 3.72-3.85 (m, 1H), 2.50-2.70 (m, 1H), 1.60-1.89 (m, 6H), 1.51-1.56 (m, 3H), 1.15-1.42 (m, 2H). $^{19}$F NMR (300 MHz, CD$_3$OD) δ: −119.170. Mass spectrum (ESI, m/z): Calculated for $C_{24}H_{23}FN_4O_4$, 451.2 [M+H], found 451.2.

Example 43

Compound #127

5-(2-cyclohexyl-2-(6-(1-ethyl-4-fluoro-1H-indazol-6-yl)-2-oxo-1,2-dihydropyridin-3-yl)ethylidene)oxazolidine-2,4-dione

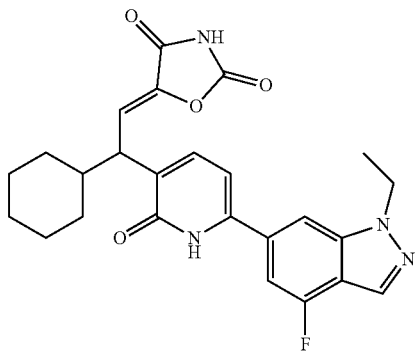 [SMILES: CCn1ncc2c(F)cc(-c3ccc(C(/C=C4\OC(=O)NC4=O)C4CCCCC4)c(=O)[nH]3)cc21]

The title compound was prepared according to the procedure as described in Example 5 starting with aldol condensation by t-BuLi, dehydration followed by demethylation with TMSCl/NaI to yield the product as a light yellow solid.

$^1$H NMR (400 MHz, CD$_3$OD) δ: 8.12 (s, 1H), 7.78 (s, 1H), 7.56 (d, J=7.2 Hz, 1H), 7.18 (m, 1H), 6.72 (d, J=7.2 Hz, 1H), 6.32 (d, J=10.8 Hz, 1H), 4.40-4.55 (m, 2H), 3.69-3.80 (m, 1H), 1.90-2.10 (m, 1H), 1.55-1.9 (m, 4H), 1.42-1.50 (m, 3H), 1.15-1.30 (m, 4H), 0.90-1.01 (m, 2H). $^{19}$F NMR (400 MHz, CD$_3$OD) δ: −119.174. Mass spectrum (EI, m/z): Calculated for $C_{25}H_{25}FN_4O_4$, 465.2 [M+H], found 465.1.

Example 44

Compound #122

(Z)-5-(2-(6-(4-fluoro-1-isopropyl-1H-indazol-6-yl)-2-oxo-1,2-dihydropyridin-3-yl)-3-methylbutylidene)oxazolidine-2,4-dione

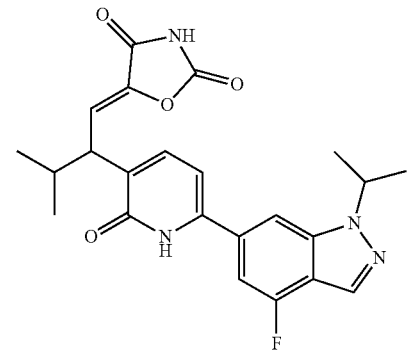 [SMILES: CC(C)C(/C=C1\OC(=O)NC1=O)c1ccc(-c2cc(F)c3cnn(C(C)C)c3c2)[nH]c1=O]

Step 1: 6-bromo-4-fluoro-1-isopropyl-1H-indazole

Into a 25-mL round-bottom flask, were placed a solution of 6-bromo-4-fluoro-1H-indazole (50 mg, 0.233 mmol, 1.00 equiv.) and potassium carbonate (44.993 mg, 0.326 mmol, 1.40 equiv.) in DMF (5 ml), then 2-iodopropane (51.388 mg, 0.302 mmol, 1.30 equiv.) was added. The resulting solution was stirred for 15 minutes at room temperature then stirred overnight at 80° C. The reaction was monitored by LCMS. The mixture was extracted with EtOAc, and the combined organic layer. The organic layer was evaporated under reduced pressure. The residue was purified by column chromatography (PE:EA=3:1) to yield 6-bromo-4-fluoro-1-isopropyl-1H-indazole as a yellow oil.

Mass spectrum (EI, m/z): Calculated For $C_{10}H_{10}BrFN_2$, 257.0 [M+H]$^+$, found 258.9.

Step 2: 4-fluoro-1-isopropyl-6-(4,4,5,5-tetramethyl-1,3,2-dioxaborolan-2-yl)-1H-indazole Into a 50-mL round-bottom flask purged and maintained with an inert atmosphere of nitrogen, were placed a solution of 6-bromo-4-fluoro-1-isopropyl-1H-indazole (250 mg, 0.972 mmol, 1.00 equiv.), bis(pinacolato) diboron (370.387 mg, 1.459 mmol, 1.50 equiv.), Pd(dppf)Cl$_2$·CH$_2$Cl$_2$ (23.822 mg, 0.029 mmol, 0.03 equiv.), potassium acetate (334.010 mg, 3.403 mmol, 3.5 equiv.) in DMF (8 mL). The resulting solution was stirred overnight at 90° C. The reaction was monitored by LCMS. The resulting solution was extracted with EtOAc, and the organic layers combined and concentrated under vacuum. The residue was applied onto a silica gel column with ethyl acetate/petroleum ether (1:3) to yield 4-fluoro-1-isopropyl-6-(4,4,5,5-tetramethyl-1,3,2-dioxaborolan-2-yl)-1H-indazole as a green oil.

Mass spectrum (EI, m/z): Calculated For $C_{16}H_{22}BFN_2O_2$, 305.2 [M+H]$^+$, found 305.1.

Step 3: (Z)-5-(2-(6-(4-fluoro-1-isopropyl-1H-indazol-6-yl)-2-oxo-1,2-dihydropyridin-3-yl)-3-methylbutylidene)oxazolidine-2,4-dione The title compound was prepared according to the procedure as described in Example 5 starting with aldol condensation by t-BuLi, dehydration followed by demethylation with TMSCl/NaI to yield the product as a white solid.

$^1$H NMR (300 MHz, CD$_3$OD, ppm) δ: 8.13 (s, 1 H), 7.80 (s, 1 H), 7.57 (d, J=7.2 Hz, 1 H), 7.16 (d, J=11.1 Hz, 1 H), 6.73 (d, J=7.2 Hz, 1 H), 6.34 (d, J=10.5 Hz, 1 H), 5.03-5.07 (m, 1 H), 3.67-3.74 (m, 1 H), 2.21-2.57 (m, 1 H), 1.58 (d, J=6.6 Hz, 6 H), 1.00 (d, J=8.1 Hz, 3 H), 0.91 (d, J=6.6 Hz, 3 H). $^{19}$F NMR (300 MHz, CD$_3$OD, ppm) δ: −119.24. Mass spectrum (EI, m/z): Calculated For $C_{23}H_{23}FN_4O_4$, 439.2 [M+H]$^+$, found 439.0.

Example 45

Compound #136

(Z)-5-(2-(5-chloro-6-(8-fluoronaphthalen-2-yl)-2-oxo-1,2-dihydropyridin-3-yl)-3-methylbutylidene)oxazolidine-2,4-dione

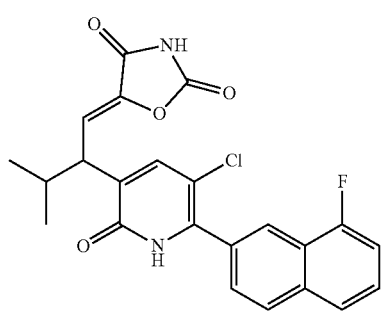 [SMILES: CC(C)C(/C=C1\OC(=O)NC1=O)c1cc(Cl)c(-c2ccc3cccc(F)c3c2)[nH]c1=O]

Into a 10-mL sealed tube, were placed (Z)-5-(2-(6-(8-fluoronaphthalen-2-yl)-2-oxo-1,2-dihydropyridin-3-yl)-3-methylbutylidene)oxazolidine-2,4-dione (30 mg, 0.074 mmol, 1 equiv.), THF (2 mL), CH$_3$CN (2 mL), TFA (0.4 mL), NCS (9.8 mg, 0.074 mmol, 1 equiv.). The solution was stirred at 40° C. for 6 h. The reaction was then quenched by the addition of MeOH. The resulting mixture was concentrated under vacuum, and the residue purified by Prep-HPLC with the following conditions (16#-Waters 2767-5): Column, SunFire Prep C18,19*100 mm, 5 um; mobile phase, Water with 0.05% TFA and CH$_3$CN (40% CH$_3$CN up to 80% in 12 min, up to 100% in 0.1 min); Detector, UV 220 & 254 nm to yield (Z)-5-(2-(5-chloro-6-(8-fluoronaphthalen-2-yl)-2-oxo-1,2-dihydropyridin-3-yl)-3-methylbutylidene)oxazolidine-2,4-dione as a white solid.

$^1$H NMR (300 MHz, CD$_3$OD, ppm) δ: 8.32 (s, 1 H), 8.06 (d, J=7.2 Hz, 1 H), 7.72-7.78 (m, 2H), 7.67 (s, 1H), 7.54-7.59 (m, 1H), 7.27-7.33 (m, 1H), 6.38 (d, J=13.5 Hz, 1H), 3.72-3.75 (m, 1H), 2.32-2.39 (m, 1H), 1.02 (d, J=6.6 Hz, 3H), 0.98 (d, J=6.6 Hz, 3H). $^{19}$F NMR (300 MHz, CD$_3$OD) δ: −77.22, −124.75. Mass spectrum (ESI, m/z): Calculated for $C_{23}H_{18}ClFN_2O_4$, 441.1 [M+H−0.15CF$_3$COOH]$^+$, found 441.1.

Example 46

Compound #111

(Z)-5-(2-(6-(1-ethyl-4-fluoro-1H-indazol-6-yl)-5-methyl-2-oxo-1,2-dihydropyridin-3-yl)-3-methylbutylidene)oxazolidine-2,4-dione

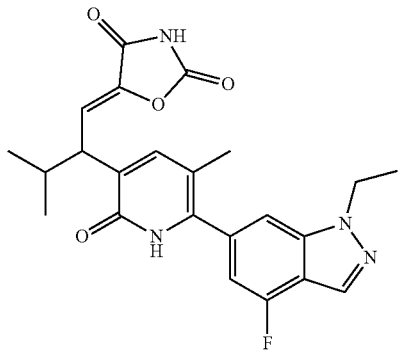 [SMILES: CCn1ncc2c(F)cc(-c3[nH]c(=O)c(C(/C=C4\OC(=O)NC4=O)C(C)C)cc3C)cc21]

Step 1: 3-bromo-2-chloro-6-methoxypyridine

Into a 100-mL vial maintained with an inert atmosphere of nitrogen, to a solution of 3-bromo-2-chloro-6-methoxypyridine (2.00 g, 8.900 mmol, 1.00 equiv.) in 1,4-dioxane (20 mL), added Pd(dppf)Cl$_2$·CH$_2$Cl$_2$ (0.36 g, 0.450 mmol, 0.05 equiv.), Zn(CH$_3$)$_2$(17 mL, 17.000 mmol, 2.00 equiv.). The resulting solution was stirred 16 h at 90° C. The mixture was concentrated under vacuum. The residue product was purified by chromatogram on silica gel with ethyl acetate/petroleum ether (2:98) to yield 2-(6-(1-ethyl-4-fluoro-1H-indazol-6-yl)-2-methoxypyridin-3-yl)-3-methylbutanal as yellow oil.

Mass spectrum (ESI, m/z): Calculated for $C_7H_8ClNO$, 158.0 [M+H], found 157.8.

Step 2: (Z)-5-(2-(6-(1-ethyl-4-fluoro-1H-indazol-6-yl)-5-methyl-2-oxo-1,2-dihydropyridin-3-yl)-3-methylbutylidene)oxazolidine-2,4-dione The title compound was prepared according to the procedure as described in Example 5 going through aldol condensation by t-BuLi, dehydration followed by demethylation with TMSCl/NaI to yield the product as a white solid.

Mass spectrum (ESI, m/z): Calculated for $C_{23}H_{23}FN_4O_4$, 439.2 [M−0.14$CF_3$COOH+H], found 439.2. $^1$H NMR (300 MHz, $CD_3OD$) δ 8.17 (s, 1H), 7.52-7.56 (m, 2H), 6.94 (d, J=10.5 Hz, 1H), 6.39 (d, J=10.5 Hz, 1H), 4.50-4.57 (m, 2H), 3.72 (t, J=9.3 Hz, 1H), 2.33-2.43 (m, 1H), 2.10-2.12 (m, 3H), 1.51 (t, J=9.3 Hz, 3H), 1.02 (d, J=6.6 Hz, 3H), 0.94 (d, J=6.6 Hz, 3H). $^{19}$F NMR (300 MHz, $CD_3OD$) δ −77.45, −119.15.

Example 47

Compound #125

5-(2-(5-chloro-6-(1-ethyl-4-fluoro-1H-indazol-6-yl)-2-oxo-1,2-dihydropyridin-3-yl)-3-methylbutylidene)oxazolidine-2,4-dione

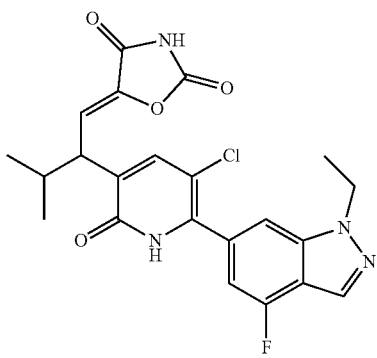 [SMILES: CCn1ncc2c(F)cc(-c3[nH]c(=O)c(C(/C=C4\OC(=O)NC4=O)C(C)C)cc3Cl)cc21]

Step 1: 5-(2-(5-chloro-6-(1-ethyl-4-fluoro-1H-indazol-6-yl)-2-methoxypyridin-3-yl)-3-methylbutylidene) oxazolidine-2,4-dione Into a 40 ml tube were placed a solution of 5-(2-(6-(1-ethyl-4-fluoro-1H-indazol-6-yl)-2-methoxypyridin-3-yl)-3-methylbutylidene)oxazolidine-2,4-dione (200 mg, 0.456 mmol, 1 equiv.) in DMF (1 ml), and NCS (60 mg, 0.50 mmol, 1.1 equv.) was then added. The mixture was stirred for 2 h at 50° C. The reaction was monitored by LCMS. The resulting solution was extracted with ethyl acetate (3×20 mL) of ethyl acetate. The organic layers were combined, washed with sodium carbonate (aq.) and brine, dried and concentrated under vacuum. The residue was applied onto a silica gel column with DCM/MeOH (30/1) to yield the product as a light yellow oil.

Mass spectrum (ESI, m/z): Calculated For $C_{23}H_{22}ClFN_4O_4$, 473.1 [M+H]$^+$, found 473.0.

Step 2: 5-(2-(5-chloro-6-(1-ethyl-4-fluoro-1H-indazol-6-yl)-2-oxo-1,2-dihydropyridin-3-yl)-3-methylbutylidene) oxazolidine-2,4-dione The title compound was prepared according to the procedure as described in Example 5 going through aldol condensation by t-BuLi, dehydration followed by demethylation with TMSCl/NaI to yield the product as a light yellow solid.

$^1$H NMR (400 MHz, $CD_3OD$, ppm) δ: 8.22 (s, 1H), 7.62 (d, J=7.2 Hz, 1H), 7.01 (d, J=4.4 Hz, 1H), 6.48 (d, J=13.6 Hz, 1H), 6.38 (d, J=10.4 Hz, 1H), 4.83-4.92 (m, 2H), 3.69-3.78 (m, 1H), 2.30-2.43 (m, 1H), 1.49-1.53 (t, J=7 Hz, 3H), 1.03 (d, J=6.8 Hz, 3H), 0.95 (d, J=6.8 Hz, 3H). $^{19}$F NMR (400 MHz, $CD_3OD$, ppm) δ: −121.82. Mass spectrum (ESI, m/z): Calculated For $C_{22}H_{20}ClFN_4O_4$, 459.1 [M+H]$^+$, found 459.0.

Example 48

Compound #6

(E)-5-(2-ethyl-2-(6-(8-fluoronaphthalen-2-yl)-2-oxo-1,2-dihydropyridin-3-yl)butylidene)oxazolidine-2,4-dione

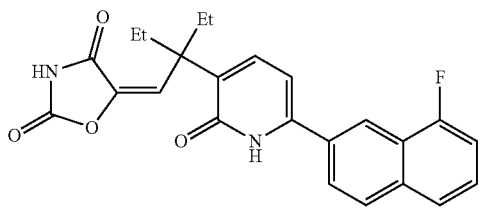 [SMILES: CCC(/C=C1/OC(=O)NC1=O)(CC)c1ccc(-c2ccc3cccc(F)c3c2)[nH]c1=O]

Step 1: Ethyl 2-ethyl-2-(6-(8-fluoronaphthalen-2-yl)-2-methoxypyridin-3-yl)butanoate Into a 100-mL round-bottom flask purged and maintained with an inert atmosphere of nitrogen, to a solution of ethyl 2-(6-(8-fluoronaphthalen-2-yl)-2-oxo-2,3-dihydropyridin-3-yl)acetate (400 mg, 1.4 mmol, 1 equiv.) in DMF (15 mL), followed by addition if t-BuOK (4.4 mL, 4.4 mmol, 3 equiv.) with stirring at 0° C. Iodoethane (690 mg, 4.4 mmol, 3 equiv.) was added and the resulting solution was stirred 16 h at 20° C. The resulted solution was quenched by $H_2O$, extracted with EA, and the organic layer was concentrated under vacuum. The residue was purified by silica gel column with ethyl acetate/petroleum ether (10:90). The collected fractions were combined and concentrated under vacuum to yield ethyl 2-ethyl-2-(6-(8-fluoronaphthalen-2-yl)-2-methoxypyridin-3-yl)butanoate as a yellow solid.

Mass spectrum (ESI, m/z): Calculated For $C_{24}H_{26}FNO_3$, 396.2 [M+H]$^+$, found 396.2.

Step 2: 2-ethyl-2-(6-(8-fluoronaphthalen-2-yl)-2-methoxypyridin-3-yl)butan-1-oll Into a 50-mL round-bottom, to a solution of ethyl 2-cyclopentyl-2-(6-(8-fluoronaphthalen-2-yl)-2-methoxypyridin-3-yl)acetate (400 mg, 1 mmol, 1 equiv.) in THF (15 mL), was added LAH (384 mg, 10 mmol, 10 equiv.) with stirring at 0° C. The resulting solution was stirred 16 h at 20° C. The resulted solution was quenched by $Na_2SO_4 \cdot 10H_2O$. The residue was purified by silica gel column with ethyl acetate/petroleum ether (10:90). The collected fractions were combined and concentrated under vacuum to yield 2-ethyl-2-(6-(8-fluoronaphthalen-2-yl)-2-methoxypyridin-3-yl)butan-1-ol as a yellow oil.

Mass spectrum (ESI, m/z): Calculated For $C_{22}H_{24}FNO_2$, 354.2 $[M+H]^+$, found 354.2.

Step 3: 2-ethyl-2-(6-(8-fluoronaphthalen-2-yl)-2-methoxypyridin-3-yl)butanal

Into a 50-mL round-bottom flask, to a solution of (1-(6-(8-fluoronaphthalen-2-yl)-2-methoxypyridin-3-yl)cyclopentyl)methanol (300 mg, 0.85 mmol, 1 equiv.) in DCM (20 mL), was added DMP (1.1 g, 2.5 mmol, 3 equiv.) with stirring at 0° C. The resulting solution was stirred 3 h at 20° C. The resulted solution was quenched by $Na_2S_2O_3$ (aq), extracted with EA, the organic layers was concentrated under vacuum. The residue was purified by silica gel column with ethyl acetate/petroleum ether (10:90). The collected fractions were combined and concentrated under vacuum to yield 2-ethyl-2-(6-(8-fluoronaphthalen-2-yl)-2-methoxypyridin-3-yl)butanal yellow solid.

Mass spectrum (ESI, m/z): Calculated For $C_{22}H_{22}FNO_2$, 352.2 (M+H), found 352.2.

Step 4: (E)-5-(2-ethyl-2-(6-(8-fluoronaphthalen-2-yl)-2-oxo-1,2-dihydropyridin-3-yl)butylidene)oxazolidine-2,4-dione The title compound was prepared according to the procedure as described in Example 5 going through aldol condensation by t-BuLi, dehydration followed by demethylation with TMSCl/NaI to yield the product as a yellow solid.

$^1$H NMR (400 MHz, $CD_3OD$, ppm) δ: 8.41 (s, 1H), 8.08 (d, J=8.4 Hz, 1H), 7.88 (d, J=8.0 Hz, 1H), 7.78 (d, J=8.4 Hz, 1H), 7.64-7.66 (m, 1H), 7.55-7.58 (m, 1H), 7.28-7.31 (m, 1H), 6.83 (d, J=7.6 Hz, 1H), 6.16 (s, 1H), 2.32-2.34 (m, 2H), 2.04-2.13 (m, 2H), 0.83-0.87 (m, 6H). $^{19}$F NMR (400 MHz,$CD_3OD$, ppm) δ: −124.47. Mass spectrum (ESI, m/z): Calculated For $C_{24}H_{21}FN_2O_4$, 421.1 $[M+H]^+$, found 420.9.

Example 49

Compound #9

5-(2-ethyl-2-(6-(8-fluoronaphthalen-2-yl)-2-oxo-1,2-dihydropyridin-3-yl)butyl)oxazolidine-2,4-dione

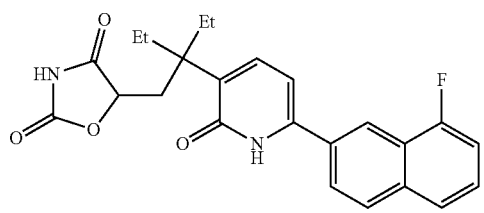 [SMILES: CCC(CC)(CC1OC(=O)NC1=O)c1ccc(-c2ccc3cccc(F)c3c2)[nH]c1=O]

The title compound was prepared according to the procedure as described in Example 8 step 1 by hydrogenation followed by demethylation to yield the product as a white solid.

$^1$H NMR (400 MHz,$CD_3OD$) δ: 8.41 (s, 1H), 8.07 (d, J=8.4 Hz, 1H), 7.88 (d, J=8.7 Hz, 1H), 7.77 (d, J=8.4 Hz, 1H), 7.52-7.54 (m, 2H), 7.27-7.32 (m, 1H), 6.78 (d, J=7.6 Hz, 1H), 4.73-4.75 (m, 1H), 2.67-2.71 (m, 1H), 2.49-2.55 (m, 1H), 2.12-2.20 (m, 2H), 1.82-1.91 (m, 2H), 0.80-0.84 (m, 6H). $^{19}$F NMR (400 MHz, $CD_3OD$) δ: −124.51. Mass spectrum (ESI, m/z): Calculated for $C_{24}H_{23}FN_2O_4$, 422.3 (M+H), found 423.2.

Example 50

Compound #8

(E)-5-((1-(6-(8-fluoronaphthalen-2-yl)-2-oxo-1,2-dihydropyridin-3-yl)cyclopentyl) methylene) oxazolidine-2,4-dione

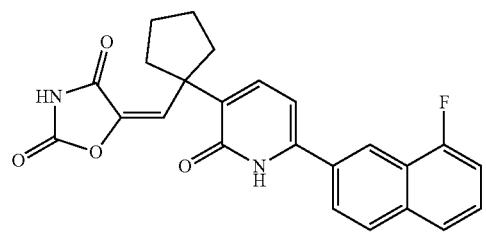 [SMILES: O=C1NC(=O)/C(=C\C2(c3ccc(-c4ccc5cccc(F)c5c4)[nH]c3=O)CCCC2)O1]

Step 1: Ethyl 6-bromo-2-(6-(8-fluoronaphthalen-2-yl)-2-methoxypyridin-3-yl)hexanoate Into a 100-mL round-bottom flask purged and maintained with an inert atmosphere of nitrogen, to a solution of ethyl 2-(6-(8-fluoronaphthalen-2-yl)-2-oxo-2,3-dihydropyridin-3-yl)acetate (500 mg, 1.47 mmol, 1 equiv.) in DMF (20 mL) was added t-BuOK (4.42 mL, 4.42 mmol, 3 equiv.) with stirring at 0° C. 1,4-Dibromobutane (954 mg, 4.42 mmol, 3 equiv.) was added and the resulting solution was stirred 16 h at 20° C. The resulting solution was quenched by $H_2O$, extracted with EA, and the organic layers were concentrated under vacuum.

The residue was purified by silica gel column with ethyl acetate/petroleum ether (10:90). The collected fractions were combined and concentrated under vacuum to yield ethyl 6-bromo-2-(6-(8-fluoronaphthalen-2-yl)-2-methoxypyridin-3-yl)hexanoate as a yellow solid.

Mass spectrum (ESI, m/z): Calculated For $C_{24}H_{25}BrFNO_3$, 476.1 $[M+H]^+$, found 476.1.

Step 2: Ethyl 1-(6-(8-fluoronaphthalen-2-yl)-2-methoxypyridin-3-yl)cyclopentane carboxylate Into a 50-mL round-bottom flask purged and maintained with an inert atmosphere of nitrogen, to a solution of ethyl 6-bromo-2-(6-(8-fluoronaphthalen-2-yl)-2-methoxypyridin-3-yl)hexanoate (500 mg, 1 mmol, 1 equiv.) in DMF (10 mL) was added t-BuOK (3.1 mL, 3 mmol, 3 equiv.) with stirring at 0° C. The resulting solution was stirred 16 h at 20° C. The resulting solution was quenched by $H_2O$, extracted with EA, and the organic layers was concentrated under vacuum. The residue was purified by silica gel column with ethyl acetate/petroleum ether (5:95). The collected fractions were combined and concentrated under vacuum to yield ethyl 1-(6-(8-fluoronaphthalen-2-yl)-2-methoxypyridin-3-yl) cyclopentanecarboxylate as a yellow solid.

Mass spectrum (ESI, m/z): Calculated For $C_{24}H_{24}FNO_3$, 394.2 (M+H), found 394.2.

Step 3: (E)-5-((1-(6-(8-fluoronaphthalen-2-yl)-2-oxo-1,2-dihydropyridin-3-yl)cyclopentyl) methylene) oxazolidine-2,4-dione The title compound was prepared according to the procedure as described in Example 5 going through aldol condensation by t-BuLi, dehydration followed by demethylation with TMSCl/NaI to yield the product as a white solid.

$^1$H NMR (400 MHz, CD$_3$OD, ppm) δ: 8.41 (s, 1H), 8.08 (d, J=8.8 Hz, 1H), 7.87 (d, J=8.0 Hz, 1H), 7.77 (d, J=8.0 Hz, 1H), 7.71-7.74 (m, 1H), 7.52-7.55 (m, 1H), 7.27-7.32 (m, 1H), 6.77 (d, J=7.2 Hz, 1H), 6.10 (s, 1H), 2.38-2.42 (m, 2H), 2.14-2.18 (m, 2H), 1.78-1.91 (m, 4H). $^{19}$F NMR (400 MHz, CD$_3$OD, ppm) δ: −124.50. Mass spectrum (ESI, m/z): Calculated For C$_{24}$H$_{19}$FN$_2$O$_4$, 419.1 [M+H]$^+$, found 419.2.

Example 51

Compound #7

5-((1-(6-(8-fluoronaphthalen-2-yl)-2-oxo-1,2-dihydropyridin-3-yl)cyclopentyl)methyl) oxazolidine-2,4-dione

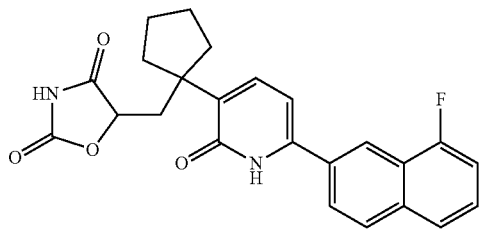 [SMILES: O=C1NC(=O)C(CC2(c3ccc(-c4ccc5cccc(F)c5c4)[nH]c3=O)CCCC2)O1]

The title compound was prepared according to the procedure as described in Example 8 step 1 by hydrogenation followed by demethylation to yield the product as a white solid.

$^1$H NMR (400 MHz, DMSO-d$_6$, ppm) δ: 11.72-11.91 (m, 2H), 8.47 (s, 1H), 8.10 (d, J=8.4 Hz, 1H), 7.96-7.97 (d, J=8.0 Hz, 1H), 7.82 (d, J=8.0 Hz, 1H), 7.54-7.57 (m, 1H), 7.38-7.45 (m, 2H), 6.57 (brs, 1H), 4.56 (d, 8.4 Hz, 1H), 2.67-2.71 (m, 1H), 2.01-2.14 (m, 3H), 1.84-1.99 (m, 2H), 1.68-1.71 (m, 4H). $^{19}$F NMR (400 MHz, DMSO-d$_6$, ppm) δ: −122.21. Mass spectrum (ESI, m/z): Calculated For C$_{24}$H$_{21}$FN$_2$O$_4$, 421.1 [M+H]$^+$, found 421.2.

Example 52

Compound #108

(Z)-5-(3-methyl-2-(6-(4-methyl-3,4-dihydro-2H-benzo[b][1,4]oxazin-6-yl)-2-oxo-1,2-dihydropyridin-3-yl)butylidene)oxazolidine-2,4-dione

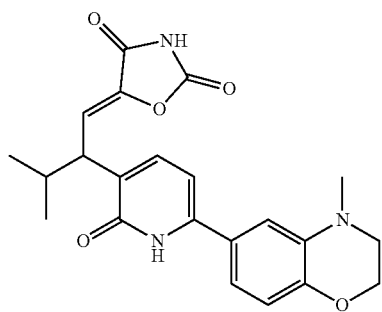 [SMILES: CC(C)C(/C=C1\OC(=O)NC1=O)c1ccc(-c2ccc3c(c2)N(C)CCO3)[nH]c1=O]

Step 1: 6-bromo-4-methyl-3,4-dihydro-2H-benzo[b][1,4]oxazine

Into a 20-mL microwave tube, were placed a solution of 6-bromo-3,4-dihydro-2H-benzo[b][1,4]oxazine (400 mg, 1.869 mmol, 1.0 equiv.) in THF (5 mL). Then, CH$_2$O (5 mL), CH$_3$COOH (1 mL), NaBH$_3$CN (450 mg, 7.258 mmol, 4.0 equiv.) was added. The resulting solution was stirred overnight at 70° C. in an oil bath. The reaction was monitored by TLC (PE/EA=4/1). Water (5 ml) was added to the mixture and the mixture was stirred for 10 minutes at room temperature. The resulting mixture was evaporated under reduced pressure. The residue was applied onto a silica gel column with PE/EA (95/5) to 6-bromo-4-methyl-3,4-dihydro-2H-benzo[b][1,4]oxazine obtained as a yellow oil.

Mass spectrum (EI, m/z): Calcd for C$_9$H$_{10}$BrNO, 228.0 (M+H), found, 229.7.

Step 2: 4-methyl-6-(4,4,5,5-tetramethyl-1,3,2-dioxaborolan-2-yl)-3,4-dihydro-2H-benzo[b][1,4]oxazine Into a 50-mL round-bottom flask purged and maintained with an inert atmosphere of nitrogen, were placed a solution of 6-bromo-4-methyl-3,4-dihydro-2H-benzo[b][1,4]oxazine (100 mg, 0.438 mmol, 1.0 equiv.) in DMF (5 mL). Then 4,4,4',4',5,5,5',5'-octamethyl-2,2'-bi(1,3,2-dioxaborolane) (167 mg, 0.658 mmol, 1.5 equiv.), Pd(dppf)Cl$_2$·CH$_2$Cl$_2$ (10 mg, 0.012 mmol, 0.03 equiv.), KOAc (128 mg, 1.306 mmol 3.0 equiv.) were added. The resulting solution was stirred overnight at 90° C. in an oil bath. The reaction was monitored by TLC (PE/EA=5/1). The resulting solution was quenched by water (10 mL). And the mixture was extracted with EtOAc (3×10 mL), then the organic layers combined and concentrated under vacuum. The residue was applied onto a silica gel column with PE/EA (95/5) to yield 4-methyl-6-(4,4,5,5-tetramethyl-1,3,2-dioxaborolan-2-yl)-3,4-dihydro-2H-benzo[b][1,4]oxazine as yellow oil.

Mass spectrum (EI, m/z): Calculated for C$_{15}$H$_{22}$BNO$_3$, 276.2 (M+H), found 276.0.

Step 3: (Z)-5-(3-methyl-2-(6-(4-methyl-3,4-dihydro-2H-benzo[b][1,4]oxazin-6-yl)-2-oxo-1,2-dihydropyridin-3-yl)butylidene)oxazolidine-2,4-dione The title compound was prepared according to the procedure as described in Example 5 going through aldol condensation by t-BuLi, dehydration followed by demethylation with TMSCl/NaI to yield the product as a yellow solid.

$^1$H NMR (300 MHz, Methanol-d$_4$) δ: 7.48-7.56 (m, 1 H), 6.90-6.95 (m, 2 H), 6.78 (d, J=8.2 Hz, 1 H), 6.46-6.56 (m, 1 H), 6.36 (d, J=10.7 Hz, 1 H), 4.23-4.36 (m, 2 H), 3.62-3.75 (m, 1 H), 3.29-3.31 (m, 2 H), 2.96 (s, 3 H), 2.30-2.37 (m, 1 H), 1.00-1.06 (m, 3 H), 0.84-098 (m, 3 H). Mass spectrum (EI, m/z): Calculated for C$_{23}$H$_{25}$N$_3$O$_5$, 410.2 (M+H), found 409.9.

Example 53

Compound #137

5-(2-cyclopropyl-2-(6-(8-fluoronaphthalen-2-yl)-2-methoxypyridin-3-yl)-1-hydroxyethyl)oxazolidine-2,4-dione

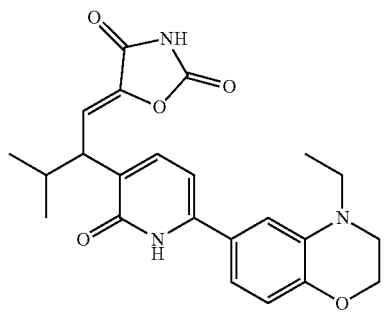 [SMILES: CCN1CCOc2ccc(-c3ccc(C(/C=C4\OC(=O)NC4=O)C(C)C)c(=O)[nH]3)cc21]

The title compound was prepared according to the procedure as described in Example 5 going through aldol condensation by t-BuLi, dehydration followed by demethylation with TMSCl/NaI to yield the product as a green solid.

$^1$H NMR (300 MHz, Methanol-d$_4$) δ 7.53 (d, J=7.3 Hz, 1 H), 6.97 (s, 1 H), 6.82-6.86 (m, 1 H), 6.76-6.81 (m, 1 H), 6.46-6.58 (m, 1 H), 6.36-6.52 (m, 1 H), 4.15-4.27 (m, 2 H), 3.62-3.73 (m, 1 H), 3.42-3.54 (m, 2 H), 3.33-3.38 (m, 2 H), 2.25-2.40 (m, 1 H), 1.15-1.25 (m, 3 H), 1.00 (t, J=7.1 Hz, 3 H), 0.92 (t, J=7.1 Hz, 3 H). Mass spectrum (EI, m/z): Calculated for C$_{23}$H$_{25}$N$_3$O$_5$, 423.4 (M+H), found 424.2.

Example 54

Compound #276

(Z)-5-(2-(6-(2,2-difluorobenzo[d][1,3]dioxol-5-yl)-2-oxo-2,3-dihydropyridin-3-yl)-3-methylbutylidene)oxazolidine-2,4-dione

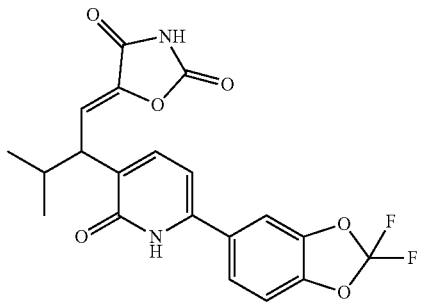 [SMILES: CC(C)C(/C=C1\OC(=O)NC1=O)c1ccc(-c2ccc3c(c2)OC(F)(F)O3)[nH]c1=O]

The title compound was prepared according to the procedure as described in Example 5 going through aldol condensation by t-BuLi, dehydration followed by demethylation with TMSCl/NaI to yield the product as a white solid.

$^1$H NMR (400 MHz, CD$_3$OD) δ: 7.50-7.57 (m, 3H), 7.31-7.33 (m, 1H), 6.57-6.60 (m, 1H), 6.33-6.46 (m, 1H), 3.65-4.27 (m, 1H), 2.31-2.43 (m, 1H), 0.82-0.98 (m, 6H).

$^{19}$F NMR (400 MHz, CD$_3$OD) δ: −56.23, −76.94. Mass spectrum (ESI, m/z): Calculated for C$_{20.66}$H$_{16.33}$F$_{2.99}$N$_2$O$_{6.66}$, 418.3 [M−0.33CF$_3$COOH+H]+, found 418.8.

Example 55

Compound #85

(Z)-5-(2-(6-(2,3-dihydrobenzo[b][1,4]dioxin-6-yl)-2-oxo-2,3-dihydropyridin-3-yl)-3-methylbutylidene)oxazolidine-2,4-dione

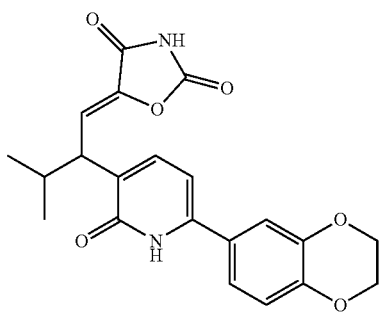 [SMILES: CC(C)C(/C=C1\OC(=O)NC1=O)c1ccc(-c2ccc3c(c2)OCCO3)[nH]c1=O]

The title compound was prepared according to the procedure as described in Example 5 going through aldol condensation by t-BuLi, dehydration followed by demethylation with TMSCl/NaI to yield the product as a white solid.

$^1$H NMR (400 MHz, CD$_3$OD) δ: 7.48 (d, J=8.8 Hz, 1H), 7.12-7.18 (m, 2H), 6.93 (d, J=8.4 Hz, 1H), 6.45-6.53 (m, 1H), 6.34 (d, J=10.8 Hz, 1H), 4.27 (s, 4H), 3.64-3.69 (m, 1H), 2.30-2.35 (m, 1H), 0.98 (d, J=6.8 Hz, 3H), 0.87 (d, J=6.8 Hz, 3H). Mass spectrum (ESI, m/z): Calculated for C$_{21}$H$_{20}$N$_2$O$_6$, 397.1 (M+H), found 396.8.

Example 56

Compound #12

(E)-5-(2-ethyl-2-(6-(1-ethyl-4-fluoro-1H-indazol-5-yl)-2-oxo-1,2-dihydropyridin-3-yl)butylidene)oxazolidine-2,4-dione

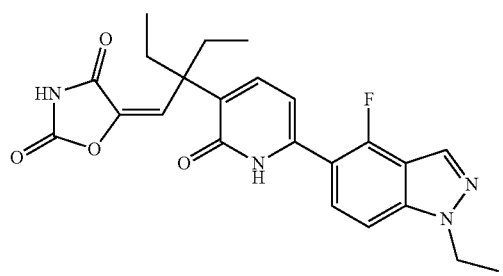 [SMILES: CCn1ncc2c(F)c(-c3ccc(C(/C=C4/OC(=O)NC4=O)(CC)CC)c(=O)[nH]3)ccc21]

Step 1: 4-bromo-3-fluoro-2-methylbenzenamine

Into a 250-mL a round bottle were placed 3-fluoro-2-methylbenzenamine (2.00 g, 15.982 mmol, 1.00 equiv.), NBS (2.99 g, 16.798 mmol, 1.051 equiv.), MeCN (100 mL). The resulting solution was stirred 2 h at 25° C. The reaction was then quenched by $H_2O$. The resulting solution was extracted with EA and the organic layers combined and concentrated under vacuum. The residue was purified by silica gel column with PE:EA=70:30 to yield 4-bromo-3-fluoro-2-methylbenzenamine as yellow solid.

Mass spectrum (EI, m/z): Calculated for $C_7H_7BrFN$, 203.0 [M], found 202.9.

Step 2: 5-bromo-4-fluoro-1H-indazole

Into a 100-mL round bottle were placed 4-bromo-3-fluoro-2-methylbenzenamine (2.70 g, 13.233 mmol, 1.00 equiv.), AcOH (50 mL). $NaNO_2$ (1.10 g, 15.942 mmol, 1.21 equiv.) was then added at 10° C. in portions. The resulting solution was stirred 4 h at 25° C. The reaction was then quenched by $H_2O$. pH was adjusted to 8 by 50% NaOH solution. The resulting solution was extracted with EA and the organic layers combined and concentrated under vacuum. The residue was purified by silica gel column with PE:EA=70:30 to yield 5-bromo-4-fluoro-1H-indazole as yellow solid.

Mass spectrum (ESI, m/z): Calculated for $C_7H_4BrFN_2$, 215.0 [M+H], found 214.7.

Step 3. 5-bromo-1-ethyl-4-fluoro-1H-indazole and 5-bromo-2-ethyl-4-fluoro-2H-indazole Into a 250-mL round bottle were placed 5-bromo-4-fluoro-1H-indazole (2.10 g, 9.766 mmol, 1.00 equiv), iodoethane (2.30 g, 14.747 mmol, 1.51 equiv.), potassium carbonate (2.71 g, 19.608 mmol, 2.01 equiv.), DMF (100 mL). The resulting solution was stirred at 70° C. overnight. The reaction was then quenched by $H_2O$. The resulting solution was extracted with EA and the organic layers combined and concentrated under vacuum. The residue was purified by silica gel column with PE:EA=90:10 to yield 5-bromo-1-ethyl-4-fluoro-1H-indazole as yellow solid.

Mass spectrum (ESI, m/z): Calculated for $C_9H_8BrFN_2$, 243.0 [M+H], found 244.8. and 5-bromo-2-ethyl-4-fluoro-2H-indazole as yellow solid.

Mass spectrum (ESI, m/z): Calculated for $C_9H_8BrFN_2$, 243.0 (M+H), found 244.7.

Step 4: (E)-5-(2-ethyl-2-(6-(1-ethyl-4-fluoro-1H-indazol-5-yl)-2-oxo-1,2-dihydropyridin-3-yl)butylidene)oxazolidine-2,4-dione The title compound was prepared according to the procedure as described in Example 5 going through aldol condensation by t-BuLi, dehydration followed by demethylation with TMSCl/NaI to yield the product as a white solid.

$^1$H NMR (400 MHz, $CD_3OD$) δ:8.18 (s, 1H), 7.60 (d, J=7.6 Hz, 1H), 7.51-7.57 (m, 2H), 6.59 (d, J=7.6 Hz, 1H), 6.13 (s, 1H), 4.48-4.59 (m, 2H), 2.22-2.31 (m, 2H), 2.00-2.09 (m, 2H), 1.49 (t, J=7.2 Hz, 3H), 1.32 (t, J=7.2 Hz, 6H). $^{19}$F NMR (400 MHz, $CD_3OD$) δ: −121.69. Mass spectrum (ESI, m/z): Calculated for $C_{23}H_{23}FN_4O_4$, 439.2[M+H], found 439.1.

Example 57

Compound #14

(E)-5-(2-ethyl-2-(6-(1-ethyl-4-fluoro-2H-indazol-5-yl)-2-oxo-1,2-dihydropyridin-3-yl)butylidene)oxazolidine-2,4-dione

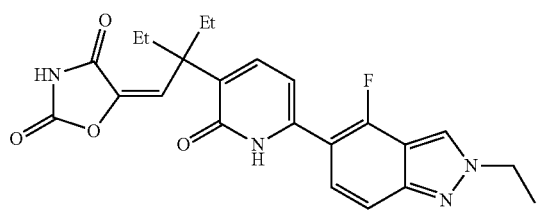 [SMILES: CCn1cc2c(F)c(-c3ccc(C(/C=C4/OC(=O)NC4=O)(CC)CC)c(=O)[nH]3)ccc2n1]

The title compound was prepared according to the procedure as described in Example 5 going through aldol condensation by t-BuLi, dehydration followed by demethylation with TMSCl/NaI to yield the product as a white solid.

$^1$H NMR (300 MHz, $CD_3OD$) δ: 8.35 (s, 1H), 7.62 (d, J=7.5 Hz, 1H), 7.56 (d, J=8.7 Hz, 1H), 7.44-7.47 (m, 1H), 6.63 (d, J=7.5 Hz, 1H), 6.15 (s, 1H), 4.53-4.60 (m, 2H), 2.25-2.30 (m, 2H), 2.05-2.12 (m, 2H), 1.65 (t, J=7.2 Hz, 3H), 0.85 (t, J=7.2 Hz, 6H). $^{19}$F NMR (300 MHz, $CD_3OD$) δ: −120.27.

Mass spectrum (ESI, m/z): Calculated for $C_{23}H_{23}FN_4O_4$, 439.2[M+H], found, 439.1.

Example 58

Compound #11

((E)-5-((1-(6-(8-fluoronaphthalen-2-yl)-2-oxo-1,2-dihydropyridin-3-yl)cyclopropyl) methylene)oxazolidine-2,4-dione

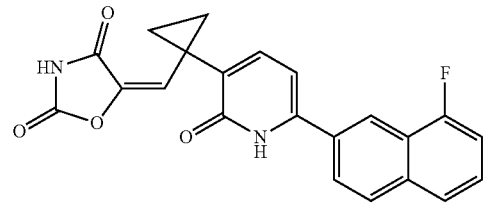 [SMILES: O=C1NC(=O)/C(=C\C2(c3ccc(-c4ccc5cccc(F)c5c4)[nH]c3=O)CC2)O1]

Step 1: Ethyl 1-(6-(8-fluoronaphthalen-2-yl)-2-methoxypyridin-3-yl)cyclopropane carboxylate Into a 40-mL vial maintained with an inert atmosphere of nitrogen, were placed THF (5 mL). To the mixture were then added LDA (0.33 mL, 0.64 mmol, 2.2 equiv.), and ethyl 2-(6-(8-fluoronaphthalen-2-yl)-2-methoxypyridin-3-yl)acetate (100 mg, 0.29 mmol, 1 equiv.), with stirring at 0° C. The mixture was stirred at 0° C. for 20 min. Ethylene sulfate (40 mg, 0.32 mmol, 1.1 equiv.) was added and the resulting solution was stirred 16 h at 30° C. The mixture was quenched by the addition of $H_2O$, extracted with EA, the organic layers was concentrated under vacuum. The residue was purified by silica cal column with ethyl acetate/petroleum ether (30:70) to ethyl 1-(6-(8-fluoronaphthalen-2-yl)-2-methoxypyridin-3-yl)cyclopropanecarboxylate as yellow oil.

Mass spectrum (ESI, m/z): Calculated for $C_{22}H_{20}FNO_3$, 366.1 (M+H), found 365.8.

Step 2: ((E)-5-((1-(6-(8-fluoronaphthalen-2-yl)-2-oxo-1,2-dihydropyridin-3-yl)cyclopropyl) methylene)oxazolidine-2,4-dione The title compound was prepared according to the procedure as described in Example 5 going through aldol condensation by t-BuLi, dehydration followed by demethylation with TMSCl/NaI to yield the product as a yellow solid.

$^1$H NMR (400 MHz, CD$_3$OD) δ: 8.41 (s, 1H), 8.06 (d, J=8.6 Hz, 1H), 7.85 (d, J=8.7 Hz, 1H), 7.76 (d, J=8.3 Hz, 1H), 7.66 (d, J=7.3 Hz, 1H), 7.52-7.57 (m, 1H), 7.26-7.29 (m, 1H), 6.76 (d, J=7.3 Hz, 1H), 5.81 (s, 1H), 1.43-1.45 (m, 2H), 1.29-1.31 (m, 2H). Mass spectrum (ESI, m/z): Calculated for $C_{22.94}H_{15.47}F_{2.41}N_2O_{4.94}$, 391.1 (M−0.47CF$_3$COOH+H), found 390.8.

Example 59

Compound #90 and #91

5-(2-(6-(1-ethyl-4-fluoro-1H-benzo[d]imidazol-5-yl)-2-oxo-1,2-dihydropyridin-3-yl)-3-methylbutylidene)oxazolidine-2,4-dione and 5-(2-(6-(3-ethyl-4-fluoro-3H-benzo[d]imidazol-5-yl)-2-oxo-1,2-dihydropyridin-3-yl)-3-methylbutylidene) oxazolidine-2,4-dione

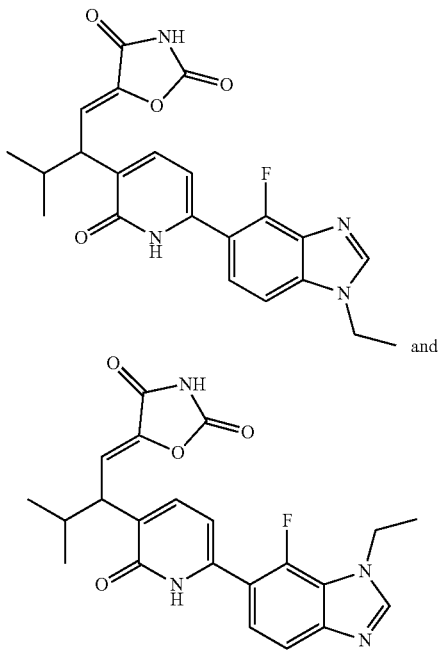

and

Step 1: 4-bromo-3-fluoro-2-nitrobenzenamine

Into a 25 ml round bottom flask were placed a solution of 3-fluoro-2-nitrobenzenamine (100 mg, 0.641 mmol, 1.00 equiv.) in DMF (2 mL). NBS (114 mg, 0.641 mmol, 1.00 equiv.) was added. The mixture was stirred for 1 h at 25° C. The mixture was distilled with EA. The mixture was washed with brine.

The organic layer was concentrated under vacuum. The residue was applied onto a silica gel column and eluted with ethyl acetate/PE (1/1) to yield 4-bromo-3-fluoro-2-nitrobenzenamine as a yellow solid.

Mass spectrum (EI, m/z): Calculated for $C_6H_4BrFN_2O_2$, 235.9[M], found 235.9.

Step 2: 4-bromo-3-fluorobenzene-1,2-diamine

Into a 50 ml flask were placed a solution of 4-bromo-3-fluoro-2-nitrobenzenamine (200 mg, 0.851 mmol, 1.00 equiv.) in MeOH (30 mL), and Fe (144 mg, 2.578 mmol, 3.00 equiv.). NH$_4$Cl (139 mg, 2.599 mmol, 3.00 equiv.) was added. The mixture was stirred overnight at 70° C. The mixture was concentrated under vacuum. The residue was purified by thin layer chromatography developed with PE/EA (1/1) to yield 4-bromo-3-fluorobenzene-1,2-diamine as yellow oil.

Mass spectrum (ESI, m/z): Calculated for $C_6H_6BrFN_2$, 205.0 [M+H], found 204.6.

Step 3: 5-bromo-4-fluoro-1H-benzo[d]imidazole

Into a 25 ml flask were placed a solution of 4-bromo-3-fluorobenzene-1,2-diamine (70 mg, 0.341 mmol, 1.00 equiv.) in formic acid (5 ml). The mixture was stirred for 2 h at 100° C. The mixture was distilled with EA. The mixture was washed with brine. The organic layer was concentrated under vacuum. The residue was applied onto a silica gel column and eluted with ethyl acetate/PE (1/1) to yield 5-bromo-4-fluoro-1H-benzo[d]imidazole as yellow oil.

Mass spectrum (ESI, m/z): Calculated for $C_7H_4BrFN_2$, 216.0 [M+H], found 216.5.

Step 4: 5-bromo-1-ethyl-4-fluoro-1H-benzo[d]imidazole compound with 6-bromo-1-ethyl-7-fluoro-1H-benzo[d]imidazole Into a 50 ml round-bottom flask were placed a solution of 5-bromo-4-fluoro-1H-benzo[d]imidazole (1.30 g, 6.046 mmol, 1.00 equiv.) in DMF (10 mL). Potassium carbonate (1.19 g, 8.610 mmol, 1.40 equiv.) and iodoethane (1.60 g, 10.259 mmol, 1.70 equiv.) were added. The reaction mixture was stirred for 15 min, and then the mixture was stirred for 1 h at 40° C. The reaction was monitored by LCMS. The mixture was concentrated under vacuum. The residue was purified by chromatogram on silica gel with ethyl acetate/petroleum ether (1:6) to yield 5-bromo-1-ethyl-4-fluoro-1H-benzo[d]imidazole compound with 6-bromo-1-ethyl-7-fluoro-1H-benzo[d]imidazole as brown solid.

Mass spectrum (ESI, m/z): Calculated for $C_9H_8BrFN_2$, 243.0 [M+H], found 242.6.

Step 5: 5-(2-(6-(1-ethyl-4-fluoro-1H-benzo[d]imidazol-5-yl)-2-oxo-1,2-dihydropyridin-3-yl)-3-methyl-butyli-dene)oxazolidine-2,4-dione and 5-(2-(6-(3-ethyl-4-fluoro-3H-benzo[d]imidazol-5-yl)-2-oxo-1,2-dihydropyridin-3-yl)-3-methylbutylidene) oxazolidine-2,4-dione The title compounds were prepared according to the procedure as described in Example 5 going through aldol condensation by t-BuLi, dehydration followed by demethylation with TMSCl/NaI to yield the products as white solids.

(Z)-5-(2-(6-(1-ethyl-4-fluoro-1H-benzo[d]imidazol-5-yl)-2-methoxypyridin-3-yl)-3-methyl butylidene)ox-azolidine-2,4-dione as a white solid. ¹H NMR (300 MHz, CD₃OD) δ: 8.81 (s, 1H), 7.68-7.75 (m, 1H), 7.55-7.68 (m, 2H), 6.61 (d, J=7.2 Hz, 1H), 6.39 (d, J=10.8 Hz, 1H), 4.39-4.52 (m, 2H), 3.68-3.80 (m, 1H), 2.30-2.45 (m, 1H), 1.50-1.62 (m, 3H), 1.03 (d, J=6.9 Hz, 3H), 0.95 (d, J=6.6 Hz, 3H). ¹⁹F NMR (300 MHz, CD₃OD) δ: −132.187, −77.527. Mass spectrum (ESI, m/z): Calculated for $C_{22}H_{21}BrN_4O_4$, 425.2 [M−0.99 CF₃COOH+H], found 425.0.

(Z)-5-(2-(6-(3-ethyl-4-fluoro-3H-benzo[d]imidazol-5-yl)-2-methoxypyridin-3-yl)-3-methyl-butylidene)oxazolidine-2,4-dione as a white solid. ¹H NMR (300 MHz, CD₃OD) δ: 8.82-8.95 (m, 1H), 7.55-7.65 (m, 1H), 7.45-7.55 (m, 2H), 6.62 (d, J=7.2 Hz, 1H), 6.39 (d, J=10.8 Hz, 1H), 4.40-4.55 (m, 2H), 3.58-3.70 (m, 1H), 2.15-2.30 (m, 1H), 1.45-1.55 (m, 3H), 1.03 (d, J=6.9 Hz, 3H), 0.95 (d, J=6.6 Hz, 3H). ¹⁹F NMR (300 MHz, CD₃OD) δ: −135.224, −77.475. Mass spectrum (ESI, m/z): Calculated for $C_{22}H_{21}BrN_4O_4$, 425.2 [M−1.34 CF₃COOH+H], found 425.0.

Example 60

Compound #263

5-((6-(8-fluoronaphthalen-2-yl)-2-oxo-1,2-dihydropyridin-3-yl)methyl)-5-isopropylimidazolidine-2,4-dione

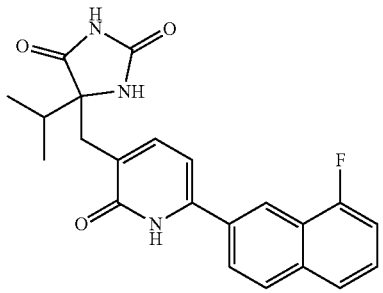 [SMILES: CC(C)C1(Cc2ccc(-c3ccc4cccc(F)c4c3)[nH]c2=O)NC(=O)NC1=O]

Step 1: 5-((6-(8-fluoronaphthalen-2-yl)-2-methoxypyridin-3-yl)methyl)-5-isopropylimidazolidine-2,4-dione Into a sealed tube, were placed a solution of 1-(6-(8-fluoronaphthalen-2-yl)-2-methoxypyridin-3-yl)-3-methylbutan-2-one (50 mg, 0.148 mmol, 1.00 equiv.) in ethanol (3 mL), then ammonium carbonate (50 mg, 0.318 mmol, 2.00 equiv.), ammoniumhydroxide (0.5 mL), trimethylsilanecarbonitrile (0.5 mL) were added in turn. The resulting solution was stirred 24 h at 100° C. in an oil bath. The reaction was monitored by LCMS. The mixture was extracted with EtOAc, then the organic layers combined and concentrated under vacuum. The residue was applied onto a silica gel column with ethyl acetate/petroleum ether (1:2) to yield 5-((6-(8-fluoronaphthalen-2-yl)-2-methoxypyridin-3-yl)methyl)-5-isopropylimidazolidine-2,4-dione as yellow solid.

Mass spectrum (ESI, m/z): Calculated for $C_{23}H_{22}FN_3O_3$, 408.2 (M+H), found 408.1.

Step 2: 5-((6-(8-fluoronaphthalen-2-yl)-2-oxo-1,2-dihydropyridin-3-yl)methyl)-5-isopropylimidazolidine-2,4-dione The title compound was prepared according to the procedure as described in Example 1 step 5 by demethylation with TMSCl/NaI to yield the product as a white solid.

¹H NMR (300 MHz, CD₃OD) δ: 8.39 (s, 1 H), 8.06 (d, J=8.7 Hz, 1 H), 7.75-7.85 (m, 2 H), 7.51-7.59 (m, 2 H), 7.26-7.32 (m, 1 H), 6.73 (d, J=7.2 Hz, 1 H), 3.31-3.36 (m, 1 H), 2.85 (d, J=5.1 Hz, 1H), 2.04-2.19 (m, 1 H), 1.13 (d, J=6.6 Hz, 3 H), 1.00 (d, J=6.9 Hz, 3 H). ¹⁹F NMR (300 MHz, CD₃OD) δ: −76.96, −124.51. Mass spectrum (ESI, m/z): Calculated for $C_{24.9}H_{21.45}F_{5.35}N_3O_{5.9}$, 394.1 (M−1.45CF₃COOH+H), found 394.0.

Example 61

Compound #121

(Z)-5-(3-methyl-2-(6-(1-methyl-1H-pyrrolo[2,3-b]pyridin-5-yl)-2-oxo-1,2-dihydropyridin-3-yl)butylidene)oxazolidine-2,4-dione

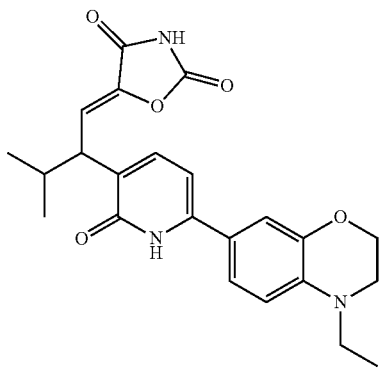 [SMILES: CCN1CCOc2cc(-c3ccc(C(/C=C4\OC(=O)NC4=O)C(C)C)c(=O)[nH]3)ccc21]

The title compound was prepared according to the procedure as described in Example 5 going through aldol condensation by t-BuLi, dehydration followed by demethylation with TMSCl/NaI to yield the product as a white solid.

¹H NMR (400 MHz, CD₃OD) δ7.37 (d, J=7.4 Hz, 1H), 7.05 (d, J=8.5, Hz, 1H), 6.95 (s, 1H), 6.69 (d, J=8.6 Hz, 1H), 6.40 (d, J=7.4 Hz, 1H), 6.14 (d, J=10.7 Hz, 1H), 4.12 (t, J=4.4 Hz, 2H), 3.45 (t, J=6.8 Hz, 1H), 3.28-3.36 (m, 4H), 2.16-2.23 (m, 1H), 1.07 (t, J=7.0 Hz, 3H), 0.88 (d, J=6.7 Hz, 3H), 0.80 (d, J=6.6 Hz, 3H). Mass spectrum (ESI, m/z): Calculated for $C_{23}H_{25}N_3O_5$, 424.2 [M+H], found 423.9.

Example 62

Compound #55

(Z)-5-(2-ethyl-2-(6-(1-ethyl-4-fluoro-1H-indazol-6-yl)-2-oxo-1,2-dihydropyridin-3-yl)butylidene)oxazolidine-2,4-dione

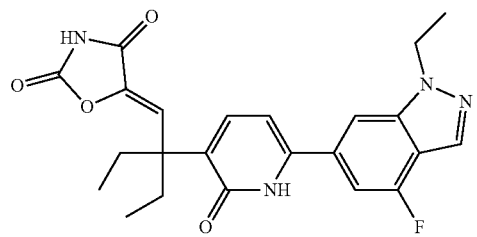 [SMILES: CCn1ncc2c(F)cc(-c3ccc(C(/C=C4\OC(=O)NC4=O)(CC)CC)c(=O)[nH]3)cc21]

Step 1: Ethyl 2-(6-chloro-2-methoxypyridin-3-yl)-2-ethylbutanoate

Into a 50-mL round-bottom flask purged and maintained with an inert atmosphere of nitrogen, to a solution of ethyl 2-(6-chloro-2-methoxypyridin-3-yl)acetate (380 mg, 1.65 mmol, 1.00 equiv.) in DMF (10 mL). t-BuOK (4.9 M, 4.960 mmol, 3.00 equiv.) was then added with stirring at 0° C. Iodoethane (774 mg, 4.960 mmol, 3.00 equiv.) was added and the resulting solution was stirred 16 h at 20° C. The resulting solution was quenched by H₂O, extracted with EA, and the organic layer was concentrated under vacuum. The residue was purified by silica gel column with ethyl acetate/petroleum ether (10:90). The collected fractions were combined and concentrated under vacuum to yield ethyl 2-(6-chloro-2-methoxypyridin-3-yl)-2-ethylbutanoate as yellow oil.

Mass spectrum (ESI, m/z): Calculated for $C_{14}H_{20}ClNO_3$, 286.1 [M+H], found 285.9.

Step 2: Ethyl 2-ethyl-2-(6-(1-ethyl-4-fluoro-1H-indazol-6-yl)-2-methoxypyridin-3-yl)butanoate Into a 20-mL vial maintained with an inert atmosphere of nitrogen, to a solution of ethyl 2-(6-chloro-2-methoxypyridin-3-yl)-2-ethylbutanoate (300 mg, 1.050 mmol, 1.00 equiv.) in DME (10 mL), were added 1-ethyl-4-fluoro-6-(4,4,5,5-tetramethyl-1,3,2-dioxaborolan-2-yl)-1H-indazole (456 mg, 1.500 mmol, 1.50 equiv.), Pd(PPh₃)₄ (121 mg, 0.100 mmol, 0.10 equiv.), Na₂CO₃ (333 mg, 3.10 mmol, 3.00 equiv.), TBAB (338 mg, 1.050 mmol, 1.00 equiv.), H₂O (2 mL). The reaction mixture was irradiated with microwave radiation for 15 min at 140° C. The mixture was concentrated under vacuum. The residue purified by silica gel with ethyl acetate/petroleum ether (5:95). The collected fractions were combined and concentrated under vacuum to yield ethyl 2-ethyl-2-(6-(1-ethyl-4-fluoro-1H-indazol-6-yl)-2-methoxypyridin-3-yl)butanoate as yellow oil.

Mass spectrum (ESI, m/z): Calculated for $C_{23}H_{28}FN_3O_3$, 414.2 [M+H], found 414.3.

Step 3: Ethyl 2-ethyl-2-(6-(1-ethyl-4-fluoro-1H-indazol-6-yl)-2-methoxypyridin-3-yl)butan-1-ol Into a 100-mL round bottle maintained with an inert atmosphere of nitrogen, to a solution of ethyl 2-ethyl-2-(6-(1-ethyl-4-fluoro-1H-indazol-6-yl)-2-methoxypyridin-3-yl)butanoate (300 mg, 0.700 mmol, 1.00 equiv.) in DCM (15 mL). DIBAL (3 mL, 3.000 mmol, 4.00 equiv.) was added with stirring at −78° C., the mixture was stirred for 16 h at 20° C. The mixture was quenched by the addition of NH₄Cl (aq), extracted with DCM, the organic layers was concentrated under vacuum. The residue purified by silica gel with ethyl acetate/petroleum ether (15:85). The collected fractions were combined and concentrated under vacuum to yield ethyl 2-ethyl-2-(6-(1-ethyl-4-fluoro-1H-indazol-6-yl)-2-methoxypyridin-3-yl)butan-1-ol as yellow oil.

Mass spectrum (ESI, m/z): Calculated for $C_{21}H_{26}FN_3O_2$, 372.2 [M+H], found 372.3.

Step 4: 2-ethyl-2-(6-(1-ethyl-4-fluoro-1H-indazol-6-yl)-2-methoxypyridin-3-yl)butanal Into a 50-mL round-bottle were placed 2-ethyl-2-(6-(1-ethyl-4-fluoro-1H-indazol-6-yl)-2-methoxypyridin-3-yl)butan-1-ol (100 mg, 0.270 mmol, 1.00 equiv.), DCM (10 mL), Add DMP (228 mg, 0.540 mmol, 2.00 equiv.). The mixture was stirred at 30° C. for 5 h. The mixture was quenched by the addition of Na₂S₂O₃, extracted with EA, the organic layers was concentrated under vacuum. The residue was purified by TLC with ethyl acetate/petroleum ether (1:6) to 2-ethyl-2-(6-(1-ethyl-4-fluoro-1H-indazol-6-yl)-2-methoxypyridin-3-yl)butanal as yellow oil.

Mass spectrum (ESI, m/z): Calculated for $C_{21}H_{24}FN_3O_2$, 370.2 [M+H], found 370.3.

Step 5: (Z)-5-(2-ethyl-2-(6-(1-ethyl-4-fluoro-1H-indazol-6-yl)-2-oxo-1,2-dihydropyridin-3-yl)butylidene)oxazolidine-2,4-dione Into a 50-mL round-bottom flask, were placed (Z)-5-(2-ethyl-2-(6-(1-ethyl-4-fluoro-1H-indazol-6-yl)-2-methoxypyridin-3-yl)butylidene)oxazolidine-2,4-dione (50 mg, 0.110 mmol, 1.00 equiv.), NaI (49 mg, 0.330 mmol, 3.00 equiv.), TMSCl (35 mg, 0.330 mmol, 3.00 equiv.), CH₃CN (5 mL). The resulting solution was stirred overnight at 30° C. The reaction was then quenched by the addition of MeOH. The resulting mixture was concentrated under vacuum. Add Na₂S₂O₃ (aq), and purified by Prep-HPLC with the following conditions (16#-Waters 2767-5): Column, SunFire Prep C18,19*100 mm, 5 um; mobile phase, Water with 0.05% TFA and CH₃CN (15% CH₃CN up to 60% in 10 min, up to 100% in 0.1 min); Detector, UV 220 & 254 nm to (Z)-5-(2-ethyl-2-(6-(1-ethyl-4-fluoro-1H-indazol-6-yl)-2-oxo-1,2-dihydropyridin-3-yl)butylidene)oxazolidine-2,4-dione as white solid.

$^1$H NMR (300 MHz, CD₃OD) δ 8.09 (s, 1H), 7.77 (s, 1H), 7.57 (d, J=7.5 Hz, 1H), 7.16 (d, J=10.8 Hz, 1H), 6.74 (d, J=7.5 Hz, 1H), 6.09 (s, 1H), 4.47-4.56 (m, 2H), 2.23-2.29 (m, 2H), 1.99-2.17 (m, 2H), 1.48 (t, J=7.2 Hz, 3H), 0.73-0.83 (m, 6H). $^{19}$F NMR (300 MHz, CD₃OD) δ −119.21. Mass spectrum (ESI, m/z): Calculated for $C_{23}H_{23}FN_4O_4$, 439.2 [M+H], found 439.1.

Example 63

Compound #56

5-(2-ethyl-2-(6-(1-ethyl-4-fluoro-1H-indazol-6-yl)-2-oxo-1,2-dihydropyridin-3-yl)butyl)oxazolidine-2,4-dione

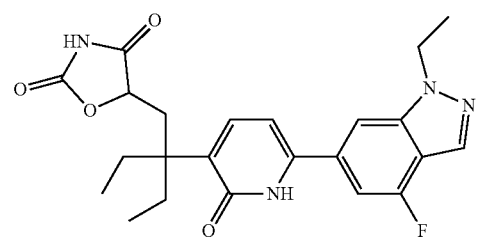 [SMILES: CCn1ncc2c(F)cc(-c3ccc(C(CC)(CC)CC4OC(=O)NC4=O)c(=O)[nH]3)cc21]

The title compound was prepared according to the procedure as described in Example 8 step 1 by hydrogenation followed by demethylation to yield the product as a white solid.

$^1$H NMR (300 MHz, CD₃OD) δ 8.09 (s, 1H), 7.77 (s, 1H), 7.54 (d, J=7.5 Hz, 1H), 7.16 (d, J=10.8 Hz, 1H), 6.69 (d, J=7.5 Hz, 1H), 4.64-4.68 (m, 1H), 4.47-4.54 (m, 2H), 2.54-2.64 (m, 1H), 2.42-2.50 (m, 1H), 2.04-2.18 (m, 2H), 1.74-1.98 (m, 2H), 1.49 (t, J=7.2 Hz, 3H), 0.74-0.79 (m,

6H). $^{19}$F NMR (300 MHz, CD$_3$OD) δ −119.27. Mass spectrum (ESI, m/z): Calculated for C$_{23}$H$_{25}$FN$_4$O$_4$, 441.2 [M+H], found 441.4.

Example 64

Compound #35

(E)-5-(2-ethyl-2-(6-(4-ethyl-3,4-dihydro-2H-benzo[b][1,4]oxazin-6-yl)-2-oxo-1,2-dihydropyridin-3-yl)butylidene)oxazolidine-2,4-dione

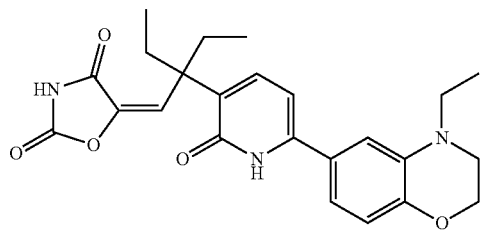 [SMILES: CCN1CCOc2ccc(-c3ccc(C(/C=C4/OC(=O)NC4=O)(CC)CC)c(=O)[nH]3)cc21]

The title compound was prepared according to the procedure as described in Example 62 going through aldol condensation by t-BuLi, dehydration followed by demethylation with TMSCl/NaI to yield the product as a yellow solid.

$^1$H NMR (400 MHz, CD$_3$OD) δ 7.52 (d, J=7.6 Hz, 1H), 6.96 (s, 1H), 6.90 (d, J=8.2 Hz, 1H), 6.82 (d, J=8.2 Hz, 1H), 6.59 (d, J=7.5 Hz, 1H), 6.18 (s, 1H), 4.22-4.34 (m, 2H), 3.42-3.48 (m, 2H), 3.35-3.42 (m, 2H), 2.21-2.28 (m, 2H), 1.97-2.05 (m, 2H), 1.13-1.19 (t, J=7.1 Hz, 3H), 0.75-0.84 (m, 6H). Mass spectrum (ESI, m/z): Calculated for C$_{24}$H$_{27}$N$_3$O$_5$, 438.2 [M+H], found 438.1.

Example 65

Compound #44

5-(2-ethyl-2-(6-(4-ethyl-3,4-dihydro-2H-benzo[b][1,4]oxazin-6-yl)-2-oxo-1,2-dihydropyridin-3-yl)butyl)oxazolidine-2,4-dione

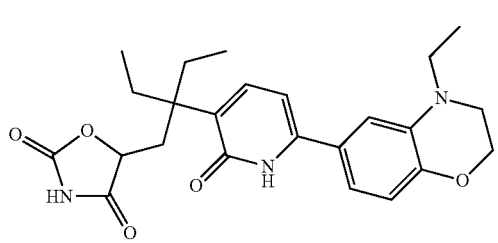 [SMILES: CCN1CCOc2ccc(-c3ccc(C(CC)(CC)CC4OC(=O)NC4=O)c(=O)[nH]3)cc21]

The title compound was prepared according to the procedure as described in Example 8 step 1 by hydrogenation followed by demethylation to yield the product as a yellow solid.

$^1$H NMR (400 MHz, CD$_3$OD) δ 7.51 (d, J=7.5 Hz, 1H), 6.97 (d, J=2.1 Hz, 1H), 6.84-6.90 (m, 1H), 6.78 (d, J=8.2 Hz, 1H), 6.51 (d, J=7.5 Hz, 1H), 4.63-4.73 (m, 1H), 4.20-4.31 (m, 2H), 3.41-3.51 (m, 2H), 3.32-3.38 (m, 2H), 2.61-2.73 (m, 1H), 2.36-2.50 (m, 1H), 1.98-2.23 (m, 2H), 1.71-1.91 (m, 2H), 1.18 (t, J=7.1 Hz, 3H), 0.68-0.86 (m, 6H). Mass spectrum (ESI, m/z): Calculated for C$_{24}$H$_{29}$N$_3$O$_5$, 440.2 [M+H], found 440.4.

Example 66

Compound #28

5-(2-(6-(2,2-dimethyl-2H-chromen-7-yl)-2-oxo-1,2-dihydropyridin-3-yl)-2-ethylbutylidene)oxazolidine-2,4-dione

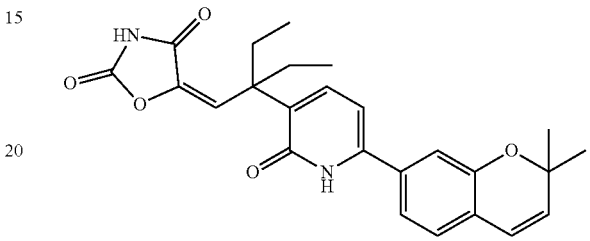

The title compound was prepared according to the procedure as described in Example 62 going through aldol condensation by t-BuLi, dehydration followed by demethylation with TMSCl/NaI to yield the product as a light yellow solid.

$^1$H NMR (300 MHz, CD$_3$OD) δ: 7.54 (d, J=7.5 Hz, 1H), 7.10-7.23 (m, 2H), 7.08 (s, 1H), 6.62 (d, J=7.5 Hz, 1H), 6.44 (d, J=9.9 Hz, 1H), 5.85 (s, 1H), 5.80 (d, J=9.9 Hz, 1H), 2.05-2.30 (m, 4H), 1.46 (s, 6H), 0.75-0.90 (m, 6H). Mass spectrum (ESI, m/z): Calculated for C$_{25}$H$_{26}$N$_2$O$_5$, 435.2 [M+H], found 435.2.

Example 67

Compound #18

5-(2-(6-(2,2-dimethylchromen-7-yl)-2-methoxypyridin-3-yl)-2-ethylbutylidene) oxazolidine-2,4-dione

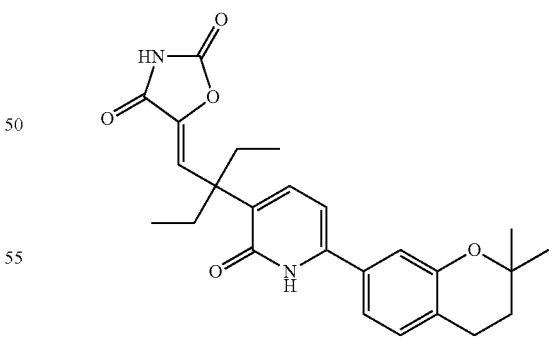

Step 1: 7-bromo-2,2-dimethylchroman-4-one

A solution of 1-(4-bromo-2-hydroxyphenyl)ethanone (1.00 g, 4.649 mmol, 1.00 equiv.), acetone (2.70 g, 46.488 mmol, 10.00 equiv.), and pyrrolidine (330 mg, 4.640 mmol, 1.00 equiv.) in toluene (20 mL) was stirred overnight at 80° C. The reaction was monitored by LCMS. The resulting mixture was purified with flash column chromatography on silica gel (ethyl acetate in petroleum ether, from 0 percent to 8 percent v/v) to yield 7-bromo-2,2-dimethylchroman-4-one.

Mass spectrum (ESI, m/z): Calculated for $C_{11}H_{11}BrO_2$, 255.0[M+H], found 256.9.

Step 2: 7-bromo-2,2-dimethyl-2H-chromene

Into a 50 ml flask were placed a solution of 7-bromo-2,2-dimethylchroman-4-one (815 mg, 3.195 mmol, 1.00 equiv.) in MeOH (20 ml). $NaBH_4$ (488 mg, 12.899 mmol, 4.00 equiv.) was added. The mixture was stirred for 2 h. The reaction was monitored by LCMS. The mixture was concentrated under vacuum. The residue was applied on a silica gel column and eluted with PE/EA (6/1) to yield 7-bromo-2,2-dimethyl-2H-chromene as white solid.

Mass spectrum (ESI, m/z): Calculated for $C_{11}H_{11}O_2$, 239.0 [M+H], found 238.8.

Step 3: 5-(2-(6-(2,2-dimethylchromen-7-yl)-2-methoxypyridin-3-yl)-2-ethylbutylidene) oxazolidine-2,4-dione The title compound was prepared according to the procedure as described in Example 62 going through aldol condensation by t-BuLi, dehydration followed by demethylation with TMSCl/NaI to yield the product as a white solid.

$^1$H NMR (300 MHz, $CD_3OD$) δ: 7.57 (d, J=7.5 Hz, 1H), 7.21-7.23 (m, 1H), 7.14-7.15 (m, 1H), 7.12 (s, 1H), 7.06 (s, 1H), 6.63 (d, J=7.2 Hz, 1H), 6.17 (s, 1H), 2.84-2.89 (m, 2H), 2.18-2.32 (m, 2H), 2.05-2.10 (m, 1H), 1.93-2.02 (m, 1H), 1.85-1.89 (m, 2H), 1.36 (s, 6H), 0.81-0.85 (m, 6H). Mass spectrum (ESI, m/z): Calculated for $C_{25}H_{28}N_2O_5$, 437.2 [M+H], found 437.2.

Example 68

Compound #34

5-(2-ethyl-2-(6-(1-ethyl-3-methyl-1H-indazol-6-yl)-2-oxo-1,2-dihydropyridin-3-yl)butylidene)oxazolidine-2,4-dione

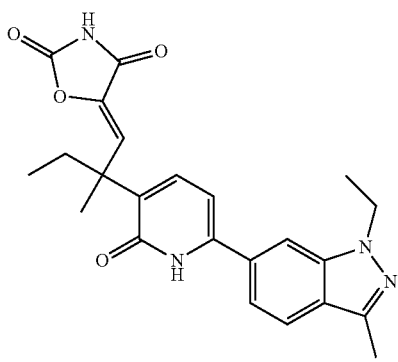 [SMILES: CCn1nc(C)c2ccc(-c3ccc(C(C)(/C=C4\OC(=O)NC4=O)CC)c(=O)[nH]3)cc21]

The title compound was prepared according to the procedure as described in Example 62 going through aldol condensation by t-BuLi, dehydration followed by demethylation with TMSCl/NaI to yield the product as a white solid.

$^1$H NMR (400 MHz, $CD_3OD$) δ: 7.85 (s, 1H), 7.81 (d, J=8.4 Hz, 1H), 7.61 (d, J=7.6 Hz, 1H), 7.40-7.48 (m, 1H), 6.75 (d, J=7.2 Hz, 1H), 6.12 (s, 1H), 4.40-4.48 (m, 2H), 2.57 (s, 3H), 2.22-2.30 (m, 2H), 2.03-2.10 (m, 2H), 1.41-1.50 (m, 3H), 0.78-0.83 (m, 6H). Mass spectrum (ESI, m/z): Calculated for $C_{24}H_{26}N_4O_4$, 435.2 [M+H], found 435.1.

Example 69

Compound #54

(E)-5-(2-ethyl-2-(6-(1-ethyl-5-fluoro-1H-indazol-6-yl)-2-oxo-1,2-dihydropyridin-3-yl)butylidene)oxazolidine-2,4-dione

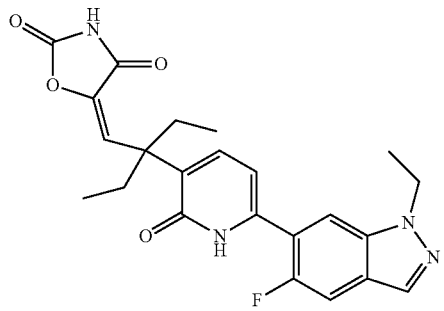 [SMILES: CCn1ncc2cc(F)c(-c3ccc(C(/C=C4/OC(=O)NC4=O)(CC)CC)c(=O)[nH]3)cc21]

The title compound was prepared according to the procedure as described in Example 62 going through aldol condensation by t-BuLi, dehydration followed by demethylation with TMSCl/NaI to yield the product as a white solid.

$^1$H NMR (300 MHz, $CD_3OD$) δ: 8.05 (s, 1H), 7.85 (s, 1H), 7.57-7.60 (m, 2H), 6.63-6.65 (m, 1H), 6.11 (s, 1H), 4.49-4.51 (m, 2H), 2.23-2.27 (m, 2H), 2.05-2.09 (m, 2H), 1.40-1.50 (m, 3H), 0.82-0.95 (m, 6H). $^{19}$F NMR (300 MHz, $CD_3OD$) δ: −128.22. Mass spectrum (ESI, m/z): Calculated for $C_{23}H_{23}FN_4O_4$, 439.2 [M+H], found 439.3.

Example 70

Compound #43

5-(2-ethyl-2-(6-(1-ethyl-5-methyl-1H-indazol-6-yl)-2-oxo-1,2-dihydropyridin-3-yl)butylidene)oxazolidine-2,4-dione

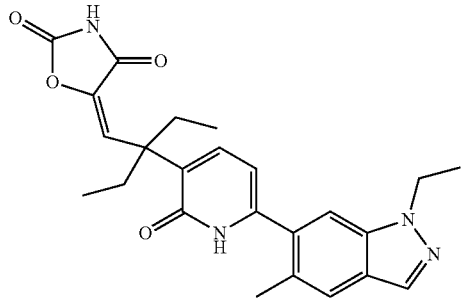 [SMILES: CCn1ncc2cc(C)c(-c3ccc(C(/C=C4/OC(=O)NC4=O)(CC)CC)c(=O)[nH]3)cc21]

The title compound was prepared according to the procedure as described in Example 62 going through aldol condensation by t-BuLi, dehydration followed by demethylation with TMSCl/NaI to yield the product as a light yellow solid.

$^1$H NMR (300 MHz, Methanol-d$_4$) δ: 8.01 (s, 1H), 7.70 (s, 1H), 7.62-7.64 (m, 2 H), 6.43-6.45 (m, 1 H), 6.17 (s, 1 H), 4.45-4.52 (m, 2 H), 2.39 (s, 3 H), 2.67-2.31 (m, 2 H), 2.03-2.10 (m, 2 H), 1.48 (t, J=7.2 Hz, 3H), 0.84-0.89 (m, 6 H). Mass spectrum (ESI, m/z): Calculated for C$_{24}$H$_{26}$N$_4$O$_4$, 435.2 [M+H], found 435.2.

Example 71

Compound #141

5-(2-(6-(8-ethylnaphthalen-2-yl)-2-oxo-1,2-dihydropyridin-3-yl)-3-methylbutylidene)oxazolidine-2,4-dione

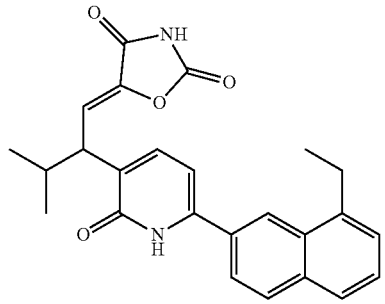 [SMILES: CCc1cccc2ccc(-c3ccc(C(/C=C4\OC(=O)NC4=O)C(C)C)c(=O)[nH]3)cc12]

Step 1: 1-(7-bromonaphthalen-1-yl)ethanone

A solution of 2-bromonaphthalene (2.00 g, 9.659 mmol, 1 equiv.) in DCM (40 ml) was treated with AlCl$_3$ (3.93 g, 29.849 mmol, 3.00 equiv.) at −10° C. and stirred until a dark green mixture was observed. The mixture was cooled to −78° C. and acetyl chloride (1.60 g, 20.383 mmol, 2.00 equiv.) was added dropwise. The reaction was stirred for 3 h at −78° C. and monitored by TLC. The reaction was warmed to 0° C. and treated slowly with aqueous HCl (1N). After cessation of bubbling, the layers were separated. The aqueous layer was extracted with DCM. The organic layers were combined, washed with sodium carbonate (aq.) and brine, dried and concentrated under vacuum. The residue was applied on a silica gel column and eluted with PE/EA (6/1) to yield 2.28 g 1-(7-bromonaphthalen-1-yl)ethanone as yellow oil.

Mass spectrum (ESI, m/z): Calculated for C$_{12}$H$_9$BrO, 249.0[M+H], found 248.8.

Step 2: 7-bromo-1-ethylnaphthalene

Into a 100 ml flask were placed a solution of 1-(7-bromonaphthalen-1-yl)ethanone (2.28 g, 9.153 mmol, 1.00 equiv.) in CHCl$_3$(50 ml), and InBr$_3$ (163 mg, 0.458 mmol, 0.05 equiv.) was added in several portions. Et$_3$SiH (4.26 g, 36.636 mmol, 4.00 equiv.) was then added dropwise. The mixture was stirred for 6 h at room temperature. The mixture was monitored by TLC and H NMR.

The mixture was extracted with ethyl acetate (3×20 mL). The organic layers were combined, washed with sodium carbonate (aq.) and brine, dried and concentrated under vacuum. The residue was purified by silica gel column developed with PE/EA (6/1) to yield a light yellow oil.

$^1$H NMR (300 MHz, CD$_3$OD) δ: 8.13 (s, 1H), 7.77 (d, J=9.0 Hz, 1H), 7.70 (d, J=7.8 Hz, 1H), 7.55 (d, J=6.9 Hz, 1H), 7.32-7.45 (m, 2H), 2.98-3.11 (m, 2H), 1.31-1.38 (m, 3H).

Step 3: 5-(2-(6-(8-ethylnaphthalen-2-yl)-2-oxo-1,2-dihydropyridin-3-yl)-3-methyl butylidene)oxazolidine-2,4-dione The title compound was prepared according to the procedure as described in Example 5 going through aldol condensation by t-BuLi, dehydration followed by demethylation with TMSCl/NaI to yield the product as a light pink solid.

$^1$H NMR (300 MHz, CD$_3$OD) δ: 8.38 (s, 1H), 8.01 (d, J=8.4 Hz, 1H), 7.75-7.80 (m, 2H), 7.59-7.65 (m, 1H), 7.42-7.50 (m, 2H), 6.76 (d, J=7.2 Hz, 1H), 6.41 (d, J=10.8 Hz, 1H), 3.70-3.80 (m, 1H), 3.18-3.30 (m, 2H), 2.25-2.45 (m, 1H), 1.35-1.45 (m, 3H), 0.90-1.02 (m, 3H), 0.83-0.89 (m, 3H). Mass spectrum (ESI, m/z): Calculated for C$_{25}$H$_{24}$N$_2$O$_4$, 417.2 [M+H], found 417.2.

Example 72

Compound #49

5-(2-ethyl-2-(6-(8-ethylnaphthalen-2-yl)-2-oxo-1,2-dihydropyridin-3-yl)butylidene)oxazolidine-2,4-dione

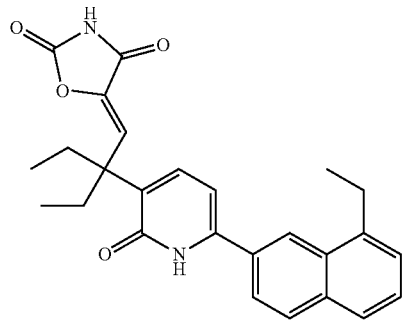 [SMILES: CCc1cccc2ccc(-c3ccc(C(/C=C4\OC(=O)NC4=O)(CC)CC)c(=O)[nH]3)cc12]

The title compound was prepared according to the procedure as described in Example 62 going through aldol condensation by t-BuLi, dehydration followed by demethylation with TMSCl/NaI to yield the product as a white solid.

$^1$H NMR (300 MHz, CD$_3$OD) δ: 8.39 (s, 1H), 8.01 (d, J=8.7 Hz, 1H), 7.74-7.80 (m, 2H), 7.66 (d, J=7.5 Hz, 1H), 7.43-7.52 (m, 2H), 6.80 (d, J=7.5 Hz, 1H), 6.20 (s, 1H), 3.18-3.25 (m, 2H), 2.22-2.35 (m, 2H), 2.05-2.15 (m, 2H), 1.38-1.42 (m, 3H), 0.78-0.85 (m, 6H). Mass spectrum (ESI, m/z): Calculated for C$_{26}$H$_{26}$N$_2$O$_4$, 431.2 [M+H], found 431.2.

Example 73

Compound #135

(Z)-5-(2-(6-(8-isopropylnaphthalen-2-yl)-2-oxo-1,2-dihydropyridin-3-yl)-3-methyl butylidene)oxazolidine-2,4-dione

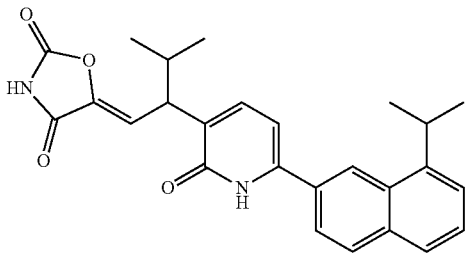 [SMILES: CC(C)c1cccc2ccc(-c3ccc(C(/C=C4\OC(=O)NC4=O)C(C)C)c(=O)[nH]3)cc12]

Step 1: 1-(7-bromonaphthalen-1-yl)ethanone

A solution of 2-bromonaphthalene (5.00 g, 24.147 mmol, 1.00 equiv.) in DCM (20 mL) was treated with AlCl₃ (9.66 g, 72.440 mmol, 3.00 equiv.) at −10° C. and stirred until a dark green mixture was observed. The reaction was cooled to −78° C. and treated slowly with acetyl chloride (3.79 g, 48.294 mmol, 2.00 equiv.). After 5 h, the reaction was warmed to 0° C. and treated slowly with aqueous HCl (1 N, 50 mL). The reaction was monitored by LCMS. After cessation of bubbling, the layers were separated. The aqueous layer was then extracted with CH₂Cl₂. The combined organic layers were dried over Na₂SO₄, filtered and concentrated to clear oil. Chromatography (PE/EA=5:1) yielded 1-(7-bromonaphthalen-1-yl)ethanone (5.20 g, 79% yield) as a yellow solid.

Mass spectrum (ESI, m/z): Calculated for $C_{12}H_9BrO$, 249.0 [M+H], found 250.8.

Step 2: 7-bromo-1-(prop-1-en-2-yl)naphthalene

Potassium tert-butoxide (4.69 g, 41.75 mmol, 2.00 equiv.) was added to the suspension of methyltriphenylphosphonium bromide (14.91 g, 41.75 mmol) in THF (30 mL) at ice-cooled condition. After 1 h stirring at ice-cooled condition, a solution of 1-(7-bromonaphthalen-1-yl)ethanone (5.20 g, 20.875 mmol) in THF (10 mL) was added dropwise. Then the reaction mixture was stirred at room temperature for 1 h. The reaction was monitored by NMR. The reaction mixture was diluted with pet ether and filtered, filtrate was concentrated to yield 7-bromo-1-(prop-1-en-2-yl)naphthalene as a pale yellow oil following column chromatographic purification of the residue using PE:EA=15:1.

¹H NMR (300 MHz, CD₃OD) δ: 8.21 (s, 1H), 7.71 (d, J=6.3 Hz, 2H), 7.56 (d, J=6.6 Hz, 1H), 7.42-7.47 (m, 1H), 7.31 (d, J=6.0 Hz, 1H), 5.43 (s, 1H), 5.04 (s, 1H), 2.20 (s, 3H).

Step 3: Ethyl 2-(2-methoxy-6-(8-(prop-1-en-2-yl)naphthalen-2-yl)pyridin-3-yl)-3-methylbutanoate The title compound was prepared according to the procedure as described in Example 4 going through metalation with t-BuLi followed by treatment with diethyl oxalate, acid-catalyzed dihydroxylation with TFA and triethyl silane, followed by alkylation with i-Pr—I and LDA to yield the product as a yellow oil.

Mass spectrum (ESI, m/z): Calculated for $C_{26}H_{29}NO_3$, 404.2 [M+H], found 404.3.

Step 4: ethyl 2-(6-(8-isopropylnaphthalen-2-yl)-2-methoxypyridin-3-yl)-3-methylbutanoate Into a 25-mL round-bottom flask, were placed ethyl 2-(2-methoxy-6-(8-(prop-1-en-2-yl)naphthalen-2-yl)pyridin-3-yl)-3-methylbutanoate (500 mg, 1.239 mmol, 1.00 equiv.), Pd/C in MeOH (8 mL). To the mixture was then introduced H₂. The resulting solution was stirred overnight at 25° C. The reaction was monitored by LCMS. The solids were filtered out. The resulting solution was concentrated under vacuum. The residue was applied onto a silica gel column with ethyl acetate/petroleum ether (1:15) to yield ethyl 2-(6-(8-isopropylnaphthalen-2-yl)-2-methoxypyridin-3-yl)-3-methylbutanoate as yellow oil.

Mass spectrum (ESI, m/z): Calculated for $C_{26}H_{31}NO_3$, 406.2 [M+H], found 406.1.

Step 5: (Z)-5-(2-(6-(8-isopropylnaphthalen-2-yl)-2-oxo-1,2-dihydropyridin-3-yl)-3-methyl butylidene)oxazolidine-2,4-dione The title compound was prepared according to the procedure as described in Example 5 going through aldol condensation by t-BuLi, dehydration followed by demethylation with TMSCl/NaI to yield the product as a white solid.

¹H NMR (400 MHz, CD₃OD) δ: 8.43 (s, 1H), 7.98 (d, J=8.4 Hz, 1H), 7.73-7.76 (m, 2H), 7.72 (d, J=7.2 Hz, 1H), 7.60 (d, J=7.2 Hz, 2H), 6.73 (d, J=7.2 Hz, 1H), 6.35 (d, J=10.4 Hz, 1H), 3.87-3.94 (m, 1H), 3.70-3.75 (m, 1H), 2.34-2.41 (m, 1H), 1.42 (d, J=6.8 Hz, 6H), 1.00 (d, J=6.8 Hz, 3H), 0.93 (d, J=6.8 Hz, 3H). Mass spectrum (ESI, m/z): Calculated for $C_{26}H_{26}N_2O_4$, 431.2 [M+H], found 431.2.

Example 74

Compound #19

(E)-5-(2-ethyl-2-(6-(8-isopropylnaphthalen-2-yl)-2-oxo-1,2-dihydropyridin-3-yl)butylidene)oxazolidine-2,4-dione

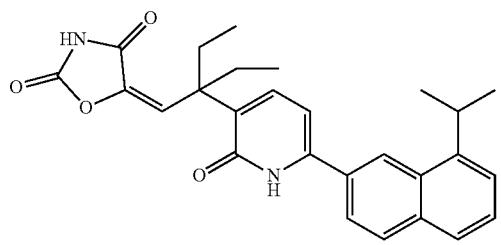 [SMILES: CCC(/C=C1/OC(=O)NC1=O)(CC)c1ccc(-c2ccc3cccc(C(C)C)c3c2)[nH]c1=O]

The title compound was prepared according to the procedure as described in Example 62 going through aldol condensation by t-BuLi, dehydration followed by demethylation with TMSCl/NaI to yield the product as a white solid.

¹H NMR (300 MHz, CD₃OD) δ: 8.45 (s, 1H), 7.99 (d, J=8.7 Hz, 1H), 7.74-7.77 (m, 2H), 7.65 (d, J=7.5 Hz, 1H), 7.53 (d, J=5.1 Hz, 2H), 6.79 (d, J=7.2 Hz, 1H), 6.19 (s, 1H), 3.90-3.95 (m, 1H), 2.25-2.32 (m, 2H), 2.02-2.10 (m, 2H), 1.43 (d, J=6.6 Hz, 6H), 0.85 (t, J=7.5 Hz, 6H). Mass spectrum (ESI, m/z): Calculated for $C_{27}H_{28}N_2O_4$, 445.2 [M+H], found 445.2.

Example 75

Compound #143

5-(3-methyl-2-(2-oxo-6-(8-(trifluoromethyl)naphthalen-2-yl)-1,2-dihydropyridin-3-yl)butylidene)oxazolidine-2,4-dione

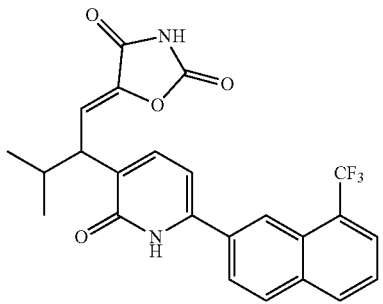 [SMILES: CC(C)C(/C=C1\OC(=O)NC1=O)c1ccc(-c2ccc3cccc(C(F)(F)F)c3c2)[nH]c1=O]

Step 1: 8-iodonaphthalen-2-ol

Into a 25-mL round-bottom flask purged and maintained with an inert atmosphere of nitrogen, were placed a 8-aminonaphthalen-2-ol (5.00 g, 31.410 mmol, 1.00 equiv) in $H_2O$ (50 ml). HCl (15 mL, 3 N) and $NaNO_2$ (3.90 g in 10 mL $H_2O$) were added at 0° C. The resulting solution was stirred 30 min at 0° C. KI (4.40 g in 10 mL $H_2O$) was then added. The resulting solution was stirred 2 h at 0° C. The reaction was monitored by LCMS. The resulting solution was extracted with EtOAc, and then the organic layers combined and concentrated under vacuum. The residue was applied onto a silica gel column with EA/PE (1:10) to yield 8-iodonaphthalen-2-ol as light red solid.

Mass spectrum (ESI, m/z): Calculated for $C_{10}H_7IO$, 271.0 [M+H], found 270.9.

Step 2: 8-iodonaphthalen-2-yl trifluoromethanesulfonate

Into a 25-mL round-bottom flask purged and maintained with an inert atmosphere of nitrogen, were placed a 8-iodonaphthalen-2-ol (1600 mg, 5.924 mmol, 1.00 equiv.) in ethylether (30 ml). NaH (710 mg, 29.622 mmol, 5.00 equiv.) was added at 0° C. The resulting solution was stirred 1 h at 25° C. $Tf_2O$ (2512 mg, 8.903 mmol, 1.50 equiv.) was then added. The reaction was monitored by TLC. The resulting solution was extracted with EtOAc, and then the organic layers combined and concentrated under vacuum. The residue was applied onto a silica gel column with EA/PE (1:10) to yield 8-iodonaphthalen-2-yl trifluoromethanesulfonate as yellow oil.

$^1$H NMR (300 MHz, CDCl$_3$) δ: 8.18-8.16 (m, 1 H), 8.08 (s, 1 H), 7.91-7.88 (m, 2 H), 7.44-7.41 (m, 1 H), 7.31-7.26 (m, 1 H).

Step 3: 8-(trifluoromethyl)naphthalen-2-yl trifluoromethanesulfonate

Into a 100-mL round-bottom flask purged and maintained with an inert atmosphere of nitrogen, were placed a 8-iodonaphthalen-2-yl trifluoromethanesulfonate (2300 mg, 5.720 mmol, 1.00 equiv.) in DMF (50 mL). CuI (5.45 g, 28.598 mmol, 4.00 equiv.), methyl 2,2-difluoro-2-(fluorosulfonyl)acetate (1651 mg, 8.595 mmol, 4.00 equiv.) were then added.

The resulting solution was stirred 2 h at 100° C. The reaction was monitored by LCMS. The resulting solution was extracted with EtOAc, and then the organic layers combined and concentrated under vacuum. The residue was applied onto a silica gel column with EA/PE (1:15) to yield 8-(trifluoromethyl)naphthalen-2-yl trifluoromethanesulfonate as yellow oil.

$^1$H NMR (400 MHz, CDCl$_3$) δ: 8.13-7.97 (m, 4 H), 7.74-7.72 (m, 1 H), 7.55-7.50 (m, 1 H).

Step 4: 5-(3-methyl-2-(2-oxo-6-(8-(trifluoromethyl)naphthalen-2-yl)-1,2-dihydropyridin-3-yl)butylidene)oxazolidine-2,4-dione The title compound was prepared according to the procedure as described in Example 5 going through aldol condensation by t-BuLi, dehydration followed by demethylation with TMSCl/NaI to yield the product as an off-white solid.

$^1$H NMR (400 MHz, Methanol-d$_4$), δ: 8.35 (s, 1 H), 8.21 (d, J=8.0 Hz, 1 H), 8.16 (d, J=8.8 Hz, 1 H), 8.01 (d, J=7.2 Hz, 1 H), 7.87-7.89 (m, 1 H), 7.66-7.70 (m, 1 H), 7.59-7.63 (m, 1 H), 6.66-6.71 (m, 1 H), 6.38 (d, J=10.8 Hz, 1 H), 3.73 (t, J=10.4 Hz, 1 H), 2.35-2.41 (m, 1 H), 1.00-1.02 (m, 3 H), 0.90-0.94 (m, 3 H). $^{19}$F NMR (400 MHz, Methanol-d$_4$) δ: −60.852. Mass spectrum (ESI, m/z): Calculated for $C_{24}H_{19}F_3N_2O_4$, 457.1 [M+H], found 457.1.

Example 76

Compound #23

5-(2-ethyl-2-(2-oxo-6-(8-(trifluoromethyl)naphthalen-2-yl)-1,2-dihydropyridin-3-yl)butylidene)oxazolidine-2,4-dione

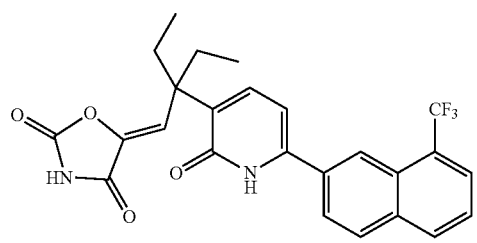 [SMILES: CCC(/C=C1\OC(=O)NC1=O)(CC)c1ccc(-c2ccc3cccc(C(F)(F)F)c3c2)[nH]c1=O]

The title compound was prepared according to the procedure as described in Example 62 going through aldol condensation by t-BuLi, dehydration followed by demethylation with TMSCl/NaI to yield the product as a light-pink solid.

$^1$H NMR (300 MHz, Methanol-d$_4$), δ: 8.34 (s, 1 H), 8.20-8.12 (m, 2 H), 7.99-7.97 (m, 1 H), 7.89-7.83 (m, 1 H), 7.67-7.61 (m, 2 H), 6.72-6.68 (m, 1 H), 6.14 (s, 1 H), 2.29-1.98 (m, 4 H), 0.84-0.77 (m, 6 H). $^{19}$F NMR (300 MHz, Methanol-d$_4$) δ: −60.70, 77.66. Mass spectrum (ESI, m/z): Calculated for C$_{25}$H$_{21}$F$_3$N$_2$O$_4$.471.1 [M+H], found 471.1.

Example 77

Compound #142 and #310

(Z)-7-(5-(1-(2,4-dioxooxazolidin-5-ylidene)-3-methylbutan-2-yl)-6-oxo-1,6-dihydropyridin-2-yl)-1-naphthonitrile and (E)-7-(5-(1-(2,4-dioxooxazolidin-5-ylidene)-3-methylbutan-2-yl)-6-oxo-1,6-dihydropyridin-2-yl)-1-naphthonitrile

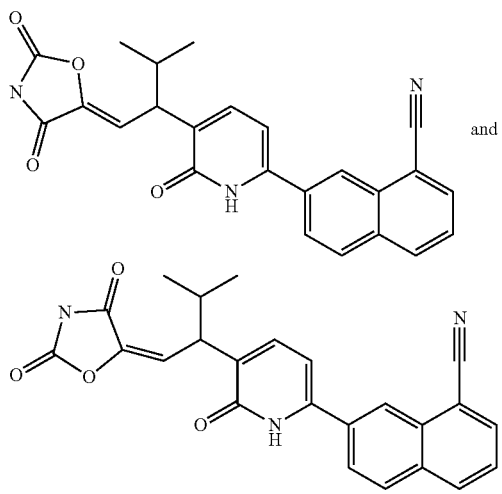

and

Step 1: 8-cyanonaphthalen-2-yl trifluoromethanesulfonate

Into a 50 mL round-bottom flask were placed a solution of 8-iodonaphthalen-2-yl trifluoromethanesulfonate (2.70 g, 6.714 mmol, 1.00 equiv.) in DMF (20 mL). Zn(CN)$_2$ (394 mg, 3.357 mmol, 0.50 equiv.), Pd(PPh$_3$)$_4$ (155 mg, 0.134 mmol, 0.02 equiv.) were then added. The mixture was stirred for 2 h at 120° C. under nitrogen. The reaction was monitored by TLC. The mixture was extracted with ethyl acetate (3×40 mL). The organic layers were combined, washed with sodium carbonate (aq.) and brine, dried and concentrated under vacuum. The residue was purified by chromatogram on silica gel with ethyl acetate/petroleum ether (1:1) to yield 8-cyanonaphthalen-2-yl trifluoromethanesulfonate as yellow oil.

$^1$H NMR (400 MHz, CDCl$_3$) δ: 8.13-8.23 (m, 2H), 8.03-8.12 (m, 2H), 7.63-7.73 (m, 1H), 7.55-7.63 (m, 1H).

Step 2: (Z)-7-(5-(1-(2,4-dioxooxazolidin-5-ylidene)-3-methylbutan-2-yl)-6-oxo-1,6-dihydropyridin-2-yl)-1-naphthonitrile and (E)-7-(5-(1-(2,4-dioxooxazolidin-5-ylidene)-3-methylbutan-2-yl)-6-oxo-1,6-dihydropyridin-2-yl)-1-naphthonitrile The title compounds were prepared according to the procedure as described in Example 5 going through aldol condensation by t-BuLi, dehydration followed by demethylation with TMSCl/NaI to yield (Z)-7-(5-(1-(2,4-dioxooxazolidin-5-ylidene)-3-methylbutan-2-yl)-6-oxo-1,6-dihydropyridin-2-yl)-1-naphthonitrile as a light yellow solid. $^1$H NMR (400 MHz, CD$_3$OD) δ: 8.44 (s, 1H), 8.27 (d, J=8.4 Hz, 1H), 8.17 (d, J=8.8 Hz, 1H), 8.05-8.10 (m, 1 H), 7.92-7.95 (m, 1H), 7.65-7.73 (m, 1H), 7.63 (d, J=7.6 Hz, 1H), 6.80 (d, J=7.2 Hz, 1H), 6.35 (d, J=10.4 Hz, 1H), 3.70-3.80 (m, 1H), 2.25-2.40 (m, 1H), 1.01 (d, J=6.8 Hz, 3H), 0.94 (d, J=6.8 Hz, 3H). Mass spectrum (ESI, m/z): Calculated for C$_{24}$H$_{19}$N$_3$O$_4$: 414.1 [M+H], found: 414.2.

and (E)-7-(5-(1-(2,4-dioxooxazolidin-5-ylidene)-3-methylbutan-2-yl)-6-oxo-1,6-dihydropyridin-2-yl)-1-naphthonitrile as a light yellow solid. $^1$H NMR (400 MHz, CD$_3$OD) δ: 8.42 (s, 1H), 8.27 (d, J=8.4 Hz, 1H), 8.16 (d, J=8.8 Hz, 1H), 8.09 (d, J=7.2 Hz, 1H), 7.90-8.0 (m, 1H), 7.65-7.70 (m, 1H), 7.58-7.63 (m, 1H), 6.72-6.80 (m, 1H), 6.18-6.43 (m, 1H), 3.74-4.37 (m, 1H), 2.30-2.50 (m, 1H), 0.95-1.0 (m, 3H), 0.82-0.90 (m, 3H). Mass spectrum (ESI, m/z): Calculated for C$_{24}$H$_{19}$N$_3$O$_4$: 414.1 [M+H], found: 414.2.

Example 78

Compound #32

(E)-5-(2-(6-(6,8-difluoronaphthalen-2-yl)-2-oxo-1,2-dihydropyridin-3-yl)-2-ethyl butylidene)oxazolidine-2,4-dione

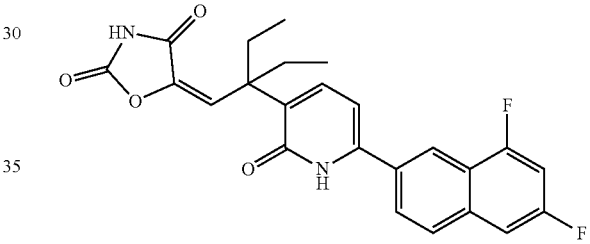

Step 1: 6,8-difluoronaphthalen-2-ol

Into a 100-mL round-bottom flask, were placed a solution of 6,8-difluoro-3,4-dihydronaphthalen-2(1H)-one (2.00 g, 10.979 mmol, 1.00 equiv.) in acetonitrile (20 mL). NBS (2.15 g, 12.077 mmol, 1.10 equiv.) and TMsOTf (122.008 mg, 0.549 mmol, 0.05 equiv.) were then added to the solution in turn. The resulting solution was stirred for 5.0 h at 30° C. The reaction was monitored by NMR. The resulting solution was extracted with EtOAc, and then the organic layers combined and concentrated under vacuum. The residue was applied onto a silica gel column with ethyl acetate/petroleum ether (1:3) to yield 6,8-difluoronaphthalen-2-ol as a white solid.

$^1$H NMR (400 MHz, CD$_3$OD) δ: 7.95 (s, 1H), 7.89 (d, J=9.0 Hz, 1H), 7.45 (d, J=6.9 Hz, 1H), 7.26 (d, J=6.0 Hz, 1H), 7.07-7.13 (m, 1H), 5.10 (brs, 1H).

Step 2: 6,8-difluoronaphthalen-2-yl trifluoromethanesulfonate

Into a 25-mL round-bottom flask, were placed a solution of 6,8-difluoronaphthalen-2-ol (50 mg, 0.278 mmol, 1.00 equiv.) in Et$_2$O (6 mL). NaH (16.651 mg, 0.694 mmol, 2.50 equiv.) was then added to the solution. The resulting solution was stirred for 1.0 h at 0° C. Then Tf$_2$O (117.459 mg, 0.416 mmol, 1.50 equiv.) was added. The reaction was monitored by NMR. The resulting solution was extracted with EtOAc, then the organic layers combined and concentrated under vacuum. The residue was applied onto a silica gel column with ethyl acetate/petroleum ether (1:5) to yield 6,8-difluoronaphthalen-2-yl trifluoromethanesulfonate as a white solid.

$^1$H NMR (300 MHz, CD$_3$OD) δ: 7.95 (s, 1H), 7.89 (d, J=9.0 Hz, 1H), 7.45 (d, J=6.9 Hz, 1H), 7.26 (d, J=6.0 Hz, 1H), 7.07-7.13 (m, 1H).

Step 3: (E)-5-(2-(6-(6,8-difluoronaphthalen-2-yl)-2-oxo-1,2-dihydropyridin-3-yl)-2-ethyl butylidene) oxazolidine-2,4-dione The title compound was prepared according to the procedure as described in Example 62 going through aldol condensation by t-BuLi, dehydration followed by demethylation with TMSCl/NaI to yield the product as a white solid.

$^1$H NMR (300 MHz, CD$_3$OD) δ: 8.38 (s, 1H), 8.03 (d, J=8.7 Hz, 1H), 7.90 (d, J=8.7 Hz, 1H), 7.62 (d, J=7.5 Hz, 1H), 7.49 (d, J=8.7 Hz, 1H), 7.23-7.30 (m, 1H), 6.80 (d, J=7.5 Hz, 1H), 6.16 (s, 1H), 2.23-2.30 (m, 2H), 2.01-2.06 (m, 2H), 0.83 (t, J=7.2 Hz, 6H). $^{19}$F NMR (300 MHz, CD$_3$OD) δ: −119.91, −119.37. Mass spectrum (ESI, m/z): Calculated for C$_{24}$H$_{20}$F$_2$N$_2$O$_4$, 439.1 [M+H], found 439.1.

Example 79

Compound #10

(E)-5-(2-(6-(5,7-difluoronaphthalen-2-yl)-2-oxo-1,2-dihydropyridin-3-yl)-2-ethylbutylidene)oxazolidine-2,4-dione

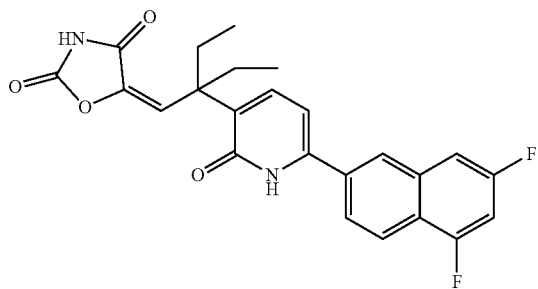 [SMILES: CCC(/C=C1/OC(=O)NC1=O)(CC)c1ccc(-c2ccc3c(F)cc(F)cc3c2)[nH]c1=O]

The title compound was prepared according to the procedure as described in Example 62 going through aldol condensation by t-BuLi, dehydration followed by demethylation with TMSCl/NaI to yield the product as a white solid.

$^1$H NMR (400 MHz, CD$_3$OD) δ: 8.15 (s, 1H), 8.08 (d, J=8.8 Hz, 1H), 7.74 (d, J=7.6 Hz, 1H), 7.53 (d, J=7.6 Hz, 1H), 7.45 (d, J=9.2 Hz, 1H), 7.11-7.16 (m, 1H), 6.71 (d, J=7.6 Hz, 1H), 6.00 (s, 1H), 2.12-2.21 (m, 2H), 1.83-2.01 (m, 2H), 0.90 (t, J=6.4 Hz, 6H). $^{19}$F NMR (400 MHz, CD$_3$OD) δ: −111.77, −120.35. Mass spectrum (ESI, m/z): Calculated for C$_{24}$H$_{20}$F$_2$N$_2$O$_4$, 439.1 [M+H], found 438.9.

Example 80

Compound #13

(E)-6-(1-ethyl-4-fluoro-1H-indazol-6-yl)-3-(3-((2-oxopyrrolidin-3-ylidene) methyl)pentan-3-yl)pyridin-2(1H)-one

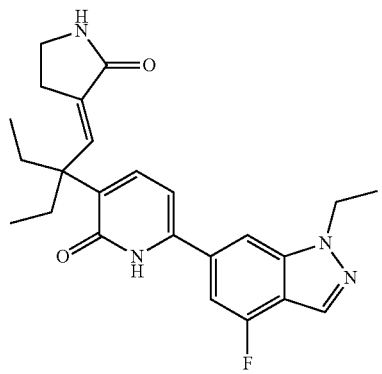 [SMILES: CCn1ncc2c(F)cc(-c3ccc(C(/C=C4\CCNC4=O)(CC)CC)c(=O)[nH]3)cc21]

Step 1: tert-butyl 2-oxopyrrolidine-1-carboxylate

Into a 250-mL round-bottom flask, were placed pyrrolidin-2-one (1.00 g, 11.750 mmol, 1.00 equiv.), DCM (20 mL), Boc$_2$O (3.85 g, 17.625 mmol, 1.50 equiv.), TEA (3.57 g, 35.251 mmol, 3.00 equiv.), DMAP (143 mg, 1.175 mmol, 0.10 equiv.). The resulting solution was stirred overnight at 25° C. The reaction was monitored by TLC (PE:EA=3:1). The resulting solution was concentrated. The residue was applied onto a silica gel column with PE:EA=3:1 to yield tert-butyl 2-oxopyrrolidine-1-carboxylate light yellow oil.

$^1$H NMR (300 MHz, CDCl$_3$) δ: 3.75-3.80 (m, 2H), 2.51-2.56 (m, 2H), 1.97-2.07 (m, 2H), 1.55 (s, 9H).

Step 2: (E)-6-(1-ethyl-4-fluoro-1H-indazol-6-yl)-3-(3-((2-oxopyrrolidin-3-ylidene) methyl)pentan-3-yl) pyridin-2(1H)-one The title compound was prepared according to the procedure as described in Example 62 going through aldol condensation by t-BuLi, dehydration followed by deprotection of Boc group and demethylation with TMSCl/NaI to yield the product as a white solid.

$^1$H NMR (300 MHz, CD$_3$OD) δ: 8.15 (s, 1H), 7.83 (s, 1H), 7.62 (d, J=7.2 Hz, 1H), 7.23 (d, J=11.1 Hz, 1H), 6.79 (d, J=7.5 Hz, 1H), 6.62-6.64 (m, 1H), 4.53-4.58 (m, 2H), 3.29-3.33 (m, 2H), 2.54-2.58 (m, 2H), 2.28-2.35 (m, 2H), 1.93-2.00 (m, 2H), 1.52-1.57 (m, 3H), 0.81-0.86 (m, 6H). $^{19}$F NMR (300 MHz, CD$_3$OD) δ: −119.22. Mass spectrum (ESI, m/z): Calculated for C$_{24}$H$_{27}$FN$_4$O$_2$, 423.2 [M+H], found 423.1.

Example 81

Compound #40

6-(1-ethyl-4-fluoro-1H-indazol-6-yl)-3-(3-((2-oxopyrrolidin-3-yl)methyl)pentan-3-yl)pyridin-2(1H)-one

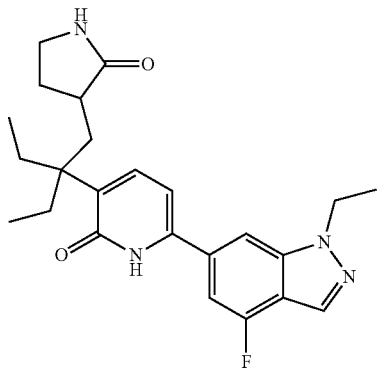 [SMILES: CCn1ncc2c(F)cc(-c3ccc(C(CC)(CC)CC4CCNC4=O)c(=O)[nH]3)cc21]

The title compound was prepared according to the procedure as described in Example 8 step 1 by hydrogenation followed by demethylation to yield the product as a white solid.

$^1$H NMR (400 MHz, CD$_3$OD) δ: 8.10 (s, 1H), 7.80 (s, 1H), 7.67 (d, J=7.2 Hz, 1H), 7.19 (d, J=11.2 Hz, 1H), 6.74 (d, J=7.6 Hz, 1H), 4.50-4.58 (m, 2H), 3.43-3.50 (m, 1H), 3.10-3.20 (m, 2H), 2.85-2.99 (m, 2H), 2.12-2.28 (m, 2H), 1.82-1.95 (m, 1H), 1.55-1.73 (m, 1H), 1.48-1.55 (m, 4H), 1.28-1.40 (m, 1H), 1.05-1.19 (m, 1H), 0.75-0.95 (m, 6H). $^{19}$F NMR (400 MHz, CD$_3$OD) δ: −119.17 Mass spectrum (ESI, m/z): Calculated for C$_{24}$H$_{29}$FN$_4$O$_2$, 425.2 [M+H], found 425.2.

Example 82

Compound #25

(E)-6-(4-ethyl-8-fluoro-3,4-dihydro-2H-benzo[b][1,4]oxazin-6-yl)-3-(3-((2-oxopyrrolidin-3-ylidene)methyl)pentan-3-yl)pyridin-2(1H)-one

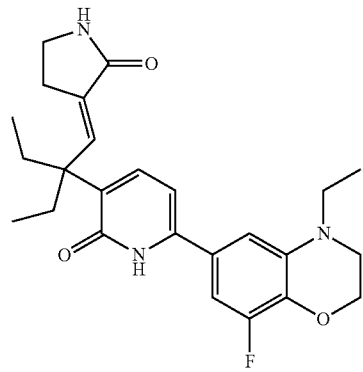 [SMILES: CCN1CCOc2c(F)cc(-c3ccc(C(/C=C4\CCNC4=O)(CC)CC)c(=O)[nH]3)cc21]

The title compound was prepared according to the procedure as described in Example 62 going through aldol condensation by t-BuLi, dehydration followed by deprotection of Boc group and demethylation with TMSCl/NaI to yield the product as a white solid.

$^1$H NMR (300 MHz, DMSO-d$_6$) δ: 7.86 (s, 1H), 7.58 (d, J=7.5 Hz, 1H), 7.42 (d, J=7.5 Hz, 1H), 7.18 (s, 1H), 7.07-7.11 (m, 1H), 4.90 (s, 1H), 4.25-4.28 (m, 2H), 3.37-3.45 (m, 2H), 3.32-3.35 (m, 2H), 3.15-3.18 (m, 2H), 2.71-2.79 (m, 1H), 1.90-2.00 (m, 1H), 1.60-1.80 (m, 4H), 1.08-1.15 (m, 3H), 0.88-0.90 (m, 3H), 0.81-0.85 (m, 3H). $^{19}$F NMR (300 MHz, DMSO-d$_6$) δ: −137.12. Mass spectrum (ESI, m/z): Calculated for C$_{25}$H$_{30}$FN$_3$O$_3$, 440.2 [M+H], found 440.1.

Example 83

Compound #149 and #150

(E)-6-(8-fluoronaphthalen-2-yl)-3-(3-methyl-1-(2-oxopyrrolidin-3-ylidene)butan-2-yl)pyridin-2(1H)-one and (Z)-6-(8-fluoronaphthalen-2-yl)-3-(3-methyl-1-(2-oxopyrrolidin-3-ylidene)butan-2-yl)pyridin-2(1H)-one

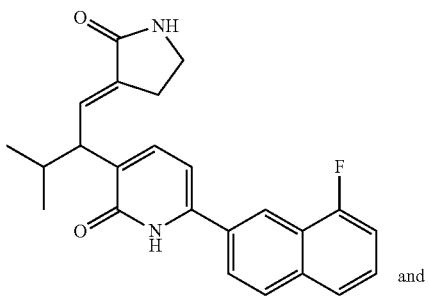

and

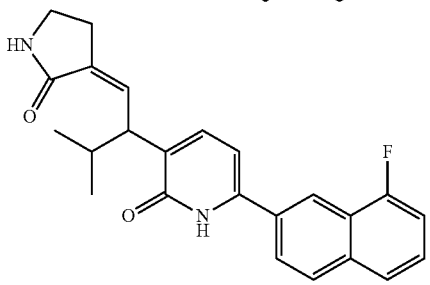

The title compounds were prepared according to the procedure as described in Example 5 going through aldol condensation by t-BuLi, dehydration followed by deprotection of Boc group and demethylation with TMSCl/NaI to yield (E)-6-(8-fluoronaphthalen-2-yl)-3-(3-methyl-1-(2-oxopyrrolidin-3-ylidene)butan-2-yl)pyridin-2(1H)-one as a white solid $^1$H NMR (300 MHz, CD$_3$OD) δ: 8.35 (s, 1H), 8.01 (d, J=8.7 Hz, 1H), 7.80 (d, J=8.7 Hz, 1H), 7.72 (d, J=8.4 Hz, 1H), 7.46-7.53 (m, 2H), 7.22-7.28 (m, 1H), 6.67 (d, J=7.2 Hz, 1H), 6.47 (d, J=10.5 Hz, 1H), 4.57-4.63 (m, 1H), 3.32-3.37 (m, 2H), 2.72-2.87 (m, 2H), 2.37-2.47 (m, 1H), 0.92 (d, J=6.6 Hz, 3H), 0.81 (d, J=6.6 Hz, 3H). $^{19}$F NMR (300 MHz, CD$_3$OD) δ: −124.53. Mass spectrum (ESI, m/z): Calculated for C$_{24}$H$_{23}$FN$_2$O$_2$, 391.0 [M+H], found. 391.0; and (Z)-6-(8-fluoronaphthalen-2-yl)-3-(3-methyl-1-(2-oxopyrrolidin-3-ylidene)butan-2-yl)pyridin-2(1H)-one as a white solid.

¹H NMR (300 MHz, CD₃OD) δ: 8.41 (s, 1H), 8.03 (d, J=8.7 Hz, 1H), 7.81 (d, J=8.7 Hz, 1H), 7.72 (d, J=8.4 Hz, 1H), 7.47-7.56 (m, 2H), 7.22-7.28 (m, 1H), 6.75 (d, J=7.2 Hz, 1H), 6.55 (d, J=10.5 Hz, 1H), 3.51-3.60 (m, 1H), 3.35-3.45 (m, 2H), 2.85-2.95 (m, 2H), 2.13-2.24 (m, 1H), 0.98 (d, J=6.6 Hz, 3H), 0.90 (d, J=6.6 Hz, 3H). ¹⁹F NMR (300 MHz, CD₃OD) δ: −124.49. Mass spectrum (ESI, m/z): Calculated for $C_{24}H_{23}FN_2O_2$, 391.0 [M+H], found, 391.0.

Example 84

Compound #144 and #145

Syn-6-(8-fluoronaphthalen-2-yl)-3-(3-methyl-1-(2-oxopyrrolidin-3-yl)butan-2-yl)pyridin-2(1H)-one and anti-6-(8-fluoronaphthalen-2-yl)-3-(3-methyl-1-(2-oxopyrrolidin-3-yl)butan-2-yl)pyridin-2(1H)-one

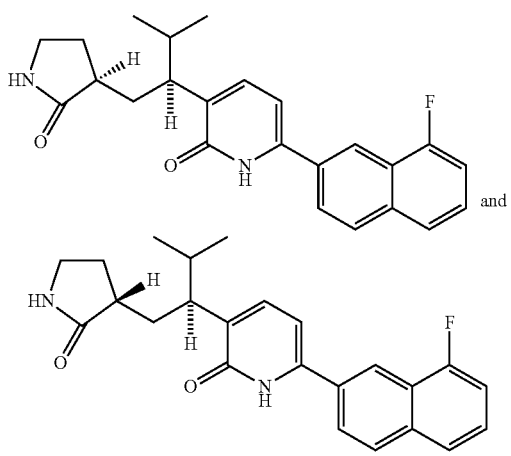

The title compounds were prepared according to the procedure as described in Example 8 step 1 by hydrogenation followed by demethylation to yield the products.

Syn-6-(8-fluoronaphthalen-2-yl)-3-(3-methyl-1-(2-oxopyrrolidin-3-yl)butan-2-yl)pyridin-2(1H)-one as a white solid. ¹H NMR (300 MHz, CD₃OD) δ: 8.38 (s, 1H), 8.03 (d, J=8.7 Hz, 1H), 7.83 (d, J=8.7 Hz, 1H), 7.73 (d, J=8.4 Hz, 1H), 7.47-7.56 (m, 2H), 7.22-7.29 (m, 1H), 6.79 (d, J=7.5 Hz, 1H), 3.31-3.32 (m, 1H), 3.16-3.22 (m, 1H), 2.90-3.00 (m, 1H), 2.06-2.29 (m, 3H), 1.86-1.93 (m, 1H), 1.71-1.78 (m, 1H), 1.56-1.65 (m, 1H), 0.96 (d, J=6.9 Hz, 3H), 0.89 (d, J=6.9 Hz, 3H). ¹⁹F NMR (300 MHz, CD₃OD) δ: −124.52. Mass spectrum (ESI, m/z): Calculated for $C_{24}H_{25}FN_2O_2$, 393.2 [M+H], found, 393.0.

and anti-6-(8-fluoronaphthalen-2-yl)-3-(3-methyl-1-(2-oxopyrrolidin-3-yl)butan-2-yl)pyridin-2(1H)-one as a white solid. ¹H NMR (300 MHz, CD₃OD) δ: 8.38 (s, 1H), 8.03 (d, J=8.7 Hz, 1H), 7.83 (d, J=8.7 Hz, 1H), 7.73 (d, J=8.4 Hz, 1H), 7.47-7.54 (m, 2H), 7.22-7.28 (m, 1H), 6.75 (d, J=7.5 Hz, 1H), 3.11-3.21 (m, 2H), 2.85-2.95 (m, 1H), 2.27-2.37 (m, 2H), 1.98-2.08 (m, 2H), 1.61-1.76 (m, 2H), 0.99 (d, J=6.9 Hz, 3H), 0.84 (d, J=6.9 Hz, 3H). ¹⁹F NMR (300 MHz, CD₃OD) δ: −124.55. Mass spectrum (ESI, m/z): Calculated for $C_{24}H_{25}FN_2O_2$, 393.2 [M+H], found. 393.0.

Example 85

Compound #46 and #47

6-(1-ethyl-4-fluoro-1H-indazol-6-yl)-5-fluoro-3-(3-((2-oxo-2,5-dihydro-1H-pyrrol-3-yl)methyl)pentan-3-yl)pyridin-2(1H)-one and (E)-6-(1-ethyl-4-fluoro-1H-indazol-6-yl)-5-fluoro-3-(3-((2-oxopyrrolidin-3-ylidene)methyl)pentan-3-yl)pyridin-2(1H)-one

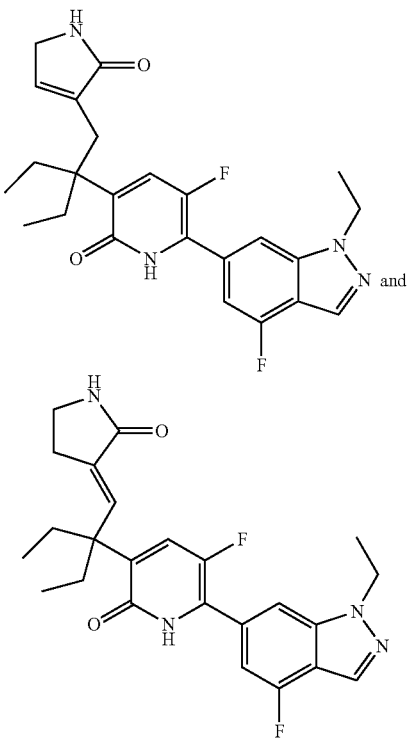

Step 1: Ethyl 2-(6-chloro-5-fluoro-2-methoxypyridin-3-yl)acetate

Into a 100-mL round-bottom flask, were placed 2-(6-chloro-5-fluoro-2-methoxypyridin-3-yl)acetonitrile (800 mg, 3.9 mmol, 1.00 equiv.). EtOH (10 mL), SOCl₂ (2 mL) were added. The reaction was stirred overnight at 90° C. for 16 h. The reaction progress was monitored by TLC. The reaction was concentrated under vacuum. The residue product was purified by chromatogram on silica gel with ethyl acetate/petroleum ether (10:90) to yield ethyl 2-(6-chloro-5-fluoro-2-methoxypyridin-3-yl)acetate as yellow solid.

Mass spectrum (ESI, m/z): Calculated for $C_{10}H_{11}ClFNO_3$, 248.0 [M+H], found 247.8.

Step 2: 6-(1-ethyl-4-fluoro-1H-indazol-6-yl)-5-fluoro-3-(3-((2-oxo-2,5-dihydro-1H-pyrrol-3-yl)methyl)pentan-3-yl)pyridin-2(1H)-one and (E)-6-(1-ethyl-4-fluoro-1H-indazol-6-yl)-5-fluoro-3-(3-((2-oxopyrrolidin-3-ylidene)methyl)pentan-3-yl)pyridin-2(1H)-one Into a 50 mL round bottle, to a solution of (E)-tert-butyl 3-(2-ethyl-2-(6-(1-ethyl-4-fluoro-1H-indazol-6-yl)-5- fluoro-2-methoxypyridin-3-yl)butylidene)-2-oxopyrrolidine-1-carboxylate (30 mg, 0.054 mmol, 1.00 equiv.) in CH$_3$CN (5 mL) were added NaI (24 mg, 0.162 mmol, 3.00 equiv.), TMSCl (18 mg, 0.162 mmol, 3.00 equiv.). The resulting mixture was stirred at 30° C. overnight. The solvent was evaporated and the residue was purified by Prep-HPLC with the following conditions (16#-Waters 2767-5): Column, SunFire Prep C18,19*100 mm, 5 um; mobile phase, Water with 0.05% TFA and CH$_3$CN (50% CH$_3$CN up to 65% in 15 min, up to 100% in 0.1 min); Detector, UV 220 & 254 nm. The resulting solution was concentrated under vacuum to yield 6-(1-ethyl-4-fluoro-1H-indazol-6-yl)-5-fluoro-3-(3-((2-oxo-2,5-dihydro-1H-pyrrol-3-yl)methyl)pentan-3-yl)pyridin-2(1H)-one as white solid. $^1$H NMR (300 MHz, CD$_3$OD) δ 8.08 (s, 1H), 7.89 (s, 1H), 7.28-7.36 (m, 2H), 4.51-4.85 (m, 2H), 3.87-3.88 (m, 1H), 2.91-3.04 (m, 2H), 2.22-2.32 (m, 1H), 1.72-1.94 (m, 4H), 1.51-1.57 (m, 1H), 1.45-1.49 (m, 3H), 1.07-1.12 (m, 3H), 0.93-0.98 (m, 3H). $^{19}$F NMR (300 MHz, CD$_3$OD) δ -77.06, -120.55, -135.05. Mass spectrum (ESI, m/z): Calculated for C$_{26.68}$H$_{30.34}$F$_{2.02}$N$_7$O$_{1.68}$: 441.2 [M-1.11CF$_3$COOH+H], found: 441.2.

and (E)-6-(1-ethyl-4-fluoro-1H-indazol-6-yl)-5-fluoro-3-(3-((2-oxopyrrolidin-3-ylidene)methyl)pentan-3-yl)pyridin-2(1H)-one as a white solid.

$^1$H NMR (300 MHz, CD$_3$OD) δ 8.09 (d, J=1.0 Hz, 1H), 7.81 (s, 1H), 7.54 (d, J=10.9 Hz, 1H), 7.25 (d, J=11.2 Hz, 1H), 5.51 (d, J=6.8 Hz, 1H), 4.40-4.59 (m, 2H), 3.99 (d, J=7.2 Hz, 1H), 3.12-3.23 (m, 2H), 2.99-3.12 (m, 1H), 2.10-2.36 (m, 2H), 1.86-1.96 (m, 2H), 1.64-1.74 (m, 3H), 11.4-1.56 (m, 3H), 0.89-1.01 (m, 3H). $^{19}$F NMR (300 MHz, CD$_3$OD) δ -77.39, -120.30. Mass spectrum (ESI, m/z): Calculated for C$_{38.64}$H$_{33.32}$F$_{23.96}$N$_4$O$_{16.64}$: 441.2 [M-7.32CF$_3$COOH+H], found: 441.2.

Example 86

Compound #146

6-(1-ethyl-4-fluoro-1H-indazol-6-yl)-3-(3-methyl-1-(3-methyl-2-oxopyrrolidin-3-yl)butan-2-yl)pyridin-2(1H)-one

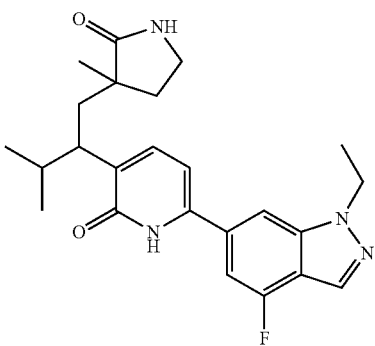 [SMILES: CCn1ncc2c(F)cc(-c3ccc(C(CC4(C)CCNC4=O)C(C)C)c(=O)[nH]3)cc21]

Step 1: (E)-tert-butyl3-(2-(6-(1-ethyl-4-fluoro-1H-indazol-6-yl)-2-methoxypyridin-3-yl)-3-methylbutylidene)-2-oxopyrrolidine-1-carboxylate The title compound was prepared according to the procedure as described in Example 5 going through aldol condensation by t-BuLi, dehydration to yield the product as a light yellow oil.

Mass spectrum (ESI, m/z): Calculated for C$_{29}$H$_{35}$FN$_4$O$_4$, 523.3. [M+H], found. 523.3.

Step 2: Tert-butyl3-(2-(6-(1-ethyl-4-fluoro-1H-indazol-6-yl)-2-methoxypyridin-3-yl)-3-methylbutyl)-2-oxopyrrolidine-1-carboxylate The title compound was prepared according to the procedure as described in Example 8 step 1 by hydrogenation to yield the product as a light yellow oil.

Mass spectrum (ESI, m/z): Calculated for C$_{29}$H$_{37}$FN$_4$O$_4$, 525.3 [M+H], found 525.5.

Step 3: Tert-butyl3-(2-(6-(1-ethyl-4-fluoro-1H-indazol-6-yl)-2-methoxypyridin-3-yl)-3-methylbutyl)-3-methyl-2-oxopyrrolidine-1-carboxylate Into a 100-mL round-bottom flask purged and maintained with an inert atmosphere of nitrogen, were placed tert-butyl 3-(2-(6-(1-ethyl-4-fluoro-1H-indazol-6-yl)-2-methoxypyridin-3-yl)-3-methylbutyl)-2-oxopyrrolidine-1-carboxylate (80 mg, 0.152 mmol, 1.00 equiv), THF (5 ml). This was followed by the addition LiHMDS (0.5 ml, 0.457 mmol, 3.00 equiv) dropwise with stirring at -78° C. The reaction was stirred 1 h at -78° C. CH$_3$I (65 mg, 0.457 mmol, 3.00 equiv) was added to the resulting solution with stirring at -78° C. The reaction was stirred 1 h at -78° C. and maintaining the temperature at 25° C. for 1 h. The reaction progress was monitored by TLC (PE:EA=3:1). The reaction was then quenched by H$_2$O. The resulting mixture was extracted with DCM (3×10 mL).

The organic layers were combined, dried over Na$_2$SO$_4$, filtered and concentrated. The residue obtained was purified by silica gel chromatography (0-30% EtOAc/petroleum ether) to yield a light yellow oil.

Mass spectrum (ESI, m/z): Calculated for C$_{30}$H$_{39}$FN$_4$O$_4$, 539.3 [M+H], found 539.2.

Step 4: 6-(1-ethyl-4-fluoro-1H-indazol-6-yl)-3-(3-methyl-1-(3-methyl-2-oxopyrrolidin-3-yl)butan-2-yl)pyridin-2(1H)-one The title compound was prepared according to the procedure as described in Example 1 step 5 by demethylation with TMSCl/NaI to yield the product as an off-white solid.

$^1$H NMR (300 MHz, DMSO-d$_6$) δ: 8.05-8.20 (m, 2H), 7.36-7.49 (m, 3H), 6.83 (m, 1H), 4.48-4.55 (m, 2H), 2.73-3.11 (m, 3H), 1.61-1.91 (m, 4H), 1.39-1.46 (m, 4H), 0.89-0.99 (m, 3H), 0.76-0.83 (m, 6H). $^{19}$F NMR (300 MHz, DMSO-d$_6$) δ: -74.73, -117.89. Mass spectrum (ESI, m/z): Calculated for C$_{24}$H$_{29}$FN$_4$O$_2$, 425.2 [M+H-1.89CF$_3$COOH], found 425.1.

Example 87

Compound #147 and #148

Syn-6-(1-ethyl-4-fluoro-1H-indazol-6-yl)-3-(3-methyl-1-(2-oxopyrrolidin-3-yl)butan-2-yl)pyridin-2(1H)-one and 6-(1-ethyl-4-fluoro-1H-indazol-6-yl)-3-(3-methyl-1-(2-oxopyrrolidin-3-yl)butan-2-yl)pyridin-2(1H)-one

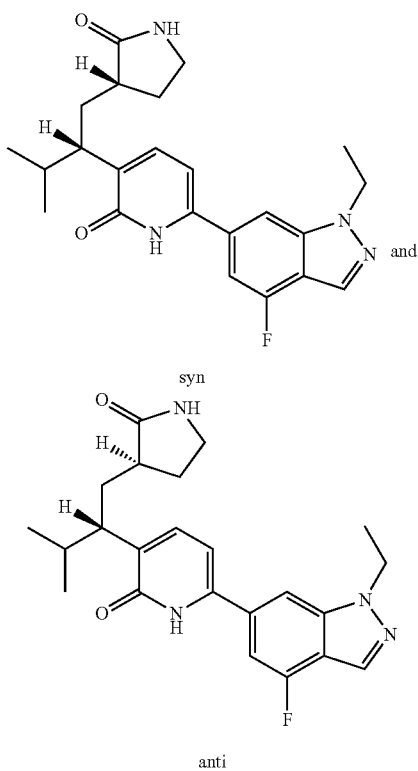

syn anti

The title compounds were prepared according to the procedure as described in Example 8 step 1 by hydrogenation to yield syn-6-(1-ethyl-4-fluoro-1H-indazol-6-yl)-3-(3-methyl-1-(2-oxopyrrolidin-3-yl)butan-2-yl)pyridin-2(1H)-one as a light yellow solid. $^1$H NMR (300 MHz, DMSO-$d_6$) δ: 7.37 (s, 1H), 7.26-7.34 (m, 1H), 6.75-6.97 (m, 3H), 6.55-6.65 (m, 1H), 3.30-3.36 (m, 2H), 3.00-3.15 (m, 2H), 2.60-2.73 (m, 1H), 2.04-2.08 (m, 2H), 1.71-1.88 (m, 2H), 1.39-1.61 (m, 2H), 1.16-1.24 (m, 3H), 0.88 (d, J=6.6 Hz, 3H), 0.77 (d, J=7.5 Hz, 3H). $^{19}$F NMR (300 MHz, DMSO-$d_6$) δ: −74.57, −108.18. Mass spectrum (ESI, m/z): Calculated for $C_{32.9}H_{31.95}F_{15.85}N_4O_{11.9}$, 411.0 [M−4.95CF$_3$COOH+H], found, 411.0.

and anti-6-(1-ethyl-4-fluoro-1H-indazol-6-yl)-3-(3-methyl-1-(2-oxopyrrolidin-3-yl)butan-2-yl)pyridin-2(1H)-one as a light yellow solid. $^1$H NMR (300 MHz, CD$_3$OD) δ: 7.47 (d, J=7.2 Hz, 1H), 6.80 (s, 1H), 6.65-6.72 (m, 2H), 3.32-3.39 (m, 2H), 3.14-3.19 (m, 2H), 2.92-2.94 (m, 1H), 2.21-2.33 (m, 2H), 1.95-2.00 (m, 2H), 1.58-1.71 (m, 2H), 1.24-1.29 (m, 3H), 0.95 (d, J=6.6 Hz, 3H), 0.83 (d, J=7.5 Hz, 3H). $^{19}$F NMR (300 MHz, CD$_3$OD) δ: −77.47, −108.87. Mass spectrum (ESI, m/z): Calculated for $C_{28.28}H_{29.64}F_{8.92}N_4O_{7.28}$, 411.0 (M−2.64CF$_3$COOH+H), found, 411.0.

Example 88

Compound #58

6-(1-ethyl-4-fluoro-1H-indazol-6-yl)-3-(3-((2-oxopiperidin-3-yl)methyl)pentan-3-yl)pyridin-2(1H)-one

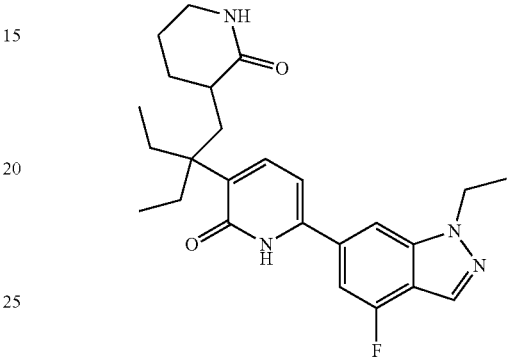

Step 1: ethyl 4-(6-chloro-2-methoxypyridin-3-yl)-4-ethylhex-2-enoate

To a solution of ethyl 2-(trimethylsilyl)acetate (425 mg, 2.652 mmol) in THF (10 mL) was added LiHMDS (2.66 mL) at −78° C. for 1 h. Then 2-(6-chloro-2-methoxypyridin-3-yl)-2-ethylbutanal (300 mg, 1.241 mmol) in THF (5 mL) was added. The resulting mixture was stirred at 25° C. overnight. After cooling down to room temperature, the reaction was quenched with H$_2$O (10 mL). The resulting mixture was extracted with EtOAc (3×10 mL). The organic layers were combined, dried over Na$_2$SO$_4$, filtered and concentrated. The residue obtained was purified by silica gel chromatography (0-10% EtOAc/petroleum ether) to yield ethyl 4-(6-chloro-2-methoxypyridin-3-yl)-4-ethylhex-2-enoate as a yellow oil.

Mass spectrum (ESI, m/z): Calculated for $C_{16}H_{22}ClNO_3$: 312.1[M+H], found: 312.1.

Step 2: methyl 4-(6-chloro-2-methoxypyridin-3-yl)-4-ethylhexanoate

To a solution of ethyl 4-(6-chloro-2-methoxypyridin-3-yl)-4-ethylhex-2-enoate (300 mg, 0.962 mmol) in EtOH (5 mL) charged with H$_2$ was added PtO$_2$ (30 mg). The resulting mixture was stirred at 25° C. overnight. The reaction was filtered and concentrated to yield ethyl 4-(6-chloro-2-methoxypyridin-3-yl)-4-ethylhexanoate as a yellow oil.

Mass spectrum (ESI, m/z): Calculated for $C_{15}H_{22}ClNO_3$: 300.1[M+H], found: 299.5.

Step 3: 5-(2-ethyl-1-hydroxy-2-(2-methoxy-6-(8-(trifluoromethyl)naphthalen-2-yl)pyridin-3-yl)butyl)oxazolidine-2,4-dione To a solution of ethyl 4-(6-chloro-2-methoxypyridin-3-yl)-4-ethylhexanoate (200 mg, 0.667 mmol) in THF (10 mL) was added LDA (1.366 mL) at −78° C. for 1 h. Then 3-bromopropanenitrile (137 mg, 1.023 mmol) in THF (5 mL) was added. The resulting mixture was stirred at 25° C. overnight. After cooling down to room temperature, the reaction was quenched with H₂O (10 mL). The resulting mixture was extracted with EtOAc (3×10 mL). The organic layers were combined, dried over Na₂SO₄, filtered and concentrated. The residue obtained was purified by silica gel chromatography (0-10% EtOAc/petroleum ether) to yield methyl 4-(6-chloro-2-methoxypyridin-3-yl)-2-(2-cyanoethyl)-4-ethylhexanoate as a yellow oil.

Mass spectrum (ESI, m/z): Calculated for $C_{18}H_{25}ClN_2O_3$: 353.2 [M+H], found: 353.1.

Step 4: methyl 2-(3-aminopropyl)-4-(6-chloro-2-methoxypyridin-3-yl)-4-ethylhexanoate To a rapidly stirred solution of methyl 4-(6-chloro-2-methoxypyridin-3-yl)-2-(2-cyanoethyl)-4-ethylhexanoate (90 mg, 0.255 mmol) in MeOH (5 mL), was added HCl (0.1 mL), and then PtO₂ (10 mg) dropwise under H₂ at 10 atm. The resulting mixture was stirred at 25° C. for 4 h. The reaction was filtered and concentrated to yield methyl 2-(3-aminopropyl)-4-(6-chloro-2-methoxypyridin-3-yl)-4-ethylhexanoate as a yellow oil.

Mass spectrum (ESI, m/z): Calculated for $C_{18}H_{29}ClN_2O_3$: 357.2 [M+H], found: 356.7.

Step 5: 3-(2-(6-chloro-2-methoxypyridin-3-yl)-2-ethylbutyl)piperidin-2-one

To a solution of methyl 2-(3-aminopropyl)-4-(6-chloro-2-methoxypyridin-3-yl)-4-ethylhexanoate (45 mg, 0.127 mmol) in MeOH (10 mL) was added K₂CO₃ (104 mg, 0.753 mmol). The resulting mixture was stirred at 90° C. overnight. After cooling down to room temperature, the reaction was quenched with H₂O (10 mL). The resulting mixture was extracted with EtOAc (3×10 mL). The organic layers were combined, dried over Na₂SO₄, filtered and concentrated. The residue was purified by silica gel chromatography (0-30% EtOAc/petroleum ether) to yield 3-(2-(6-chloro-2-methoxypyridin-3-yl)-2-ethylbutyl)piperidin-2-one as a yellow solid.

Mass spectrum (ESI, m/z): Calculated for $C_{17}H_{25}ClN_2O_2$: 325.2[M+H], found: 324.6.

Step 6: 6-(1-ethyl-4-fluoro-1H-indazol-6-yl)-3-(3-((2-oxopiperidin-3-yl)methyl)pentan-3-yl)pyridin-2(1H)-one The title compound was prepared according to the procedure as described in Example 1 step 5 by demethylation with TMSCl/NaI to yield the product as an off-white solid.

¹H NMR (300 MHz, Methanol-d₄), δ: 8.12 (s, 1 H), 7.80 (s, 1 H), 7.52 (s, 1 H), 7.25-7.15 (m, 1 H), 6.73-6.71 (m, 1 H), 4.55-4.53 (m, 2 H), 3.20-3.12 (m, 2 H), 2.50-2.25 (m, 3 H), 2.24-2.02 (m, 1 H), 1.90-1.80 (m, 2 H), 1.79-1.40 (m, 7 H), 1.38-1.25 (m, 1 H), 0.96-0.92 (m, 3 H), 0.66-0.61 (m, 3 H). ¹⁹F NMR (300 MHz, Methanol-d₄) δ: -119.24. Mass spectrum (ESI, m/z): Calculated for $C_{25}H_{31}FN_4O_2$: 439.2, found: 439.2 [M+H].

Example 89

Compound #151

6-(1-ethyl-4-fluoro-1H-indazol-6-yl)-3-(3-methyl-1-(5-oxopyrrolidin-2-yl)butan-2-yl)pyridin-2(1H)-one

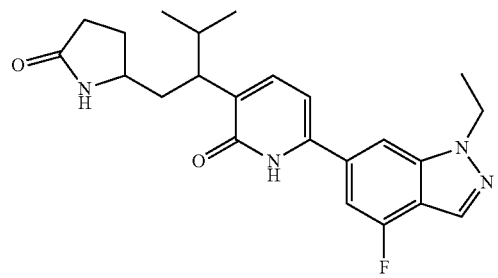 [SMILES: CCn1ncc2c(F)cc(-c3ccc(C(CC4CCC(=O)N4)C(C)C)c(=O)[nH]3)cc21]

Step 1: 1-(4-methoxybenzyl)pyrrolidine-2,5-dione

Into a 250 ml round-bottom flask were placed a solution of pyrrolidine-2,5-dione (3.00 g, 30.276 mmol, 1.00 equiv.) in CH₃CN (100 mL), and 1-(chloromethyl)-4-methoxybenzene (5.70 g, 36.331 mmol, 1.20 equiv.). K₂CO₃ (4.60 g, 33.304 mmol, 1.10 equiv.) was added. The mixture was stirred for 16 h at 25° C. The reaction was monitored by LCMS. The resulting solution was diluted with water (100 mL), then filtered. The solid was dried under infrared light to yield 1-(4-methoxybenzyl)pyrrolidine-2,5-dione as a white solid.

Mass spectrum (ESI, m/z): Calculated for $C_{12}H_{13}NO_3$: 220.1 [M+H], found: 220.2.

Step 2: 5-hydroxy-1-(4-methoxybenzyl)pyrrolidin-2-one

Into a 100 ml round-bottom flask were placed a solution of 1-(4-methoxybenzyl)pyrrolidine-2,5-dione (1.00 g, 4.561 mmol, 1.00 equiv.) in THF (30 mL) at -78° C. DIBAL (5 mL, 5.000 mmol, 1.10 equiv.) was added dropwise under nitrogen atmosphere. The mixture was stirred for 1 hour at -78° C. The reaction was monitored by LCMS. The mixture was quenched with water and extracted with ethyl acetate (3×50 mL). The organic layers were combined, washed with sodium carbonate (aq.) and brine, dried and concentrated under vacuum. The residue was purified by silica gel column developed with PE/EA (1/1) to yield 5-hydroxy-1-(4-methoxybenzyl)pyrrolidin-2-one as a yellow oil.

Mass spectrum (ESI, m/z): Calculated for $C_{12}H_{15}NO_3$: 222.1 [M+H], found: 222.1.

Step 3: 5-methoxy-1-(4-methoxybenzyl)pyrrolidin-2-one

Into a 50 ml flask were placed a solution of 5-hydroxy-1-(4-methoxybenzyl)pyrrolidin-2-one (540 mg, 2.441 mmol, 1.00 equiv.) in MeOH (30 mL). HCl (2 mL) was added in several portions at 0° C. The mixture was stirred for 16 hours at room temperature. The reaction was monitored by LCMS. The mixture was concentrated under vacuum to applied on flash column chromatography silica gel (PE/EA=3/1) to yield 5-methoxy-1-(4-methoxybenzyl)pyrrolidin-2-one (430 mg) as colorless oil.

Mass spectrum (ESI, m/z): Calculated for $C_{13}H_{17}NO_3$: 236.1 [M+H], found: 236.1.

Step 4: 1-(6-chloro-2-methoxypyridin-3-yl)ethanone

A 250 mL flask was charged with a solution of 2-chloro-6-methoxypyridine (5.00 g, 0.035 mol, 1.00 equiv.) in THF (100 mL) under nitrogen atmosphere. To the mixture was then added tert-butyllithium (33 mL, 0.053 mol, 1.30 equiv.) which was added dropwise with stirring at −70° C. The reaction mixture was stirred at −70° C. for 2 h. N-methoxy-N-methylacetamide (4.70 g, 0.046 mol, 1.50 equiv.) was then added dropwise. The mixture was stirred for 3.0 h at −78° C. The reaction progress was monitored by TLC. The reaction was quenched by the addition of Ammonium chloride aqueous solution and then extracted with ethyl acetate, the organic layer was combined and concentrated under vacuum. The residue was applied onto a silica gel column with PE/EA=100/1 to yield 1-(6-chloro-2-methoxypyridin-3-yl)ethanone as a white solid.

Step 5: 6-chloro-2-methoxy-3-(1-(trimethylsilyloxy)vinyl)pyridine

Into a 40 ml tube were placed a solution of 1-(6-chloro-2-methoxypyridin-3-yl)ethanone (700 mg, 3.771 mmol, 1.00 equiv.) in tolene (10 mL). Trimethylsilyl trifluoromethanesulfonate (1.26 g, 5.669 mmol, 1.50 equiv.), TEA (770 mg, 7.609 mmol, 2.00 equiv.) was then added. The mixture was stirred for 2 h at 80° C. The reaction was monitored by LCMS. The mixture was concentrated under vacuum to yield 6-chloro-2-methoxy-3-(1-(trimethylsilyloxy)vinyl)pyridine as a yellow oil.

Mass spectrum (ESI, m/z): Calculated for $C_{11}H_{16}ClNO_2Si$: 258.1[M+H], found: 258.2.

Step 6: 6-chloro-2-methoxy-3-(1-(trimethylsilyloxy)vinyl)pyridine

Into a 50 ml flask were placed a solution of 6-chloro-2-methoxy-3-(1-(trimethylsilyloxy)vinyl)pyridine (700 mg, 2.715 mmol, 1.00 equiv.) in $CH_3CN$ (10 mL), and a solution of 5-methoxy-1-(4-methoxybenzyl)pyrrolidin-2-one (700 mg, 2.975 mmol, 1.10 equiv.) in $CH_3CN$ (10 mL) was added. Triisopropylsilyl trifluoromethanesulfonate (1.66 g, 5.431 mmol, 2.00 equiv.) was then added. The mixture was stirred for 16 h at 25° C. The mixture was concentrated under vacuum. The residue was purified by chromatogram on silica gel with ethyl acetate/petroleum ether (1:6) to yield 5-(2-(6-chloro-2-methoxypyridin-3-yl)-2-oxoethyl)-1-(4-methoxybenzyl)pyrrolidin-2-one as yellow solid.

Mass spectrum (ESI, m/z): Calculated for $C_{20}H_{21}ClN_2O_4$: 411.1 [M+Na], found: 411.3.

Step 7: 5-(2-(6-(1-ethyl-4-fluoro-1H-indazol-6-yl)-2-methoxypyridin-3-yl)-2-oxoethyl)-1-(4-methoxybenzyl)-pyrrolidin-2-one To a solution of 5-(2-(6-chloro-2-methoxypyridin-3-yl)-2-oxoethyl)-1-(4-methoxybenzyl)pyrrolidin-2-one (1.50 g, 3.858 mmol, 1.00 equiv.) in ethylene glycol dimethyl ether (30 ml) was added 1-ethyl-4-fluoro-6-(4,4,5,5-tetramethyl-1,3,2-dioxoborolan-2-yl)-1H-indazole (1.35 g, 4.635 mmol, 1.20 equiv.), sodium carbonate (822 mg, 7.756 mmol, 2.00 equiv.), TBAB (1.25 g, 3.864 mmol, 1.00 equiv.), water (10 mL), $Pd(PPh_3)_4$ (134 mg, 0.116 mmol, 0.03 equiv.). The reaction mixture was stirred overnight at 90° C. under nitrogen atmosphere. The mixture was extracted with ethyl acetate (3×50 mL). The organic layers were combined, washed with sodium carbonate (aq.) and brine, dried and concentrated under vacuum. The residue was purified by chromatogram on silica gel with ethyl acetate/petroleum ether (1:1) to yield 5-(2-(6-(1-ethyl-4-fluoro-1H-indazol-6-yl)-2-methoxypyridin-3-yl)-2-oxoethyl)-1-(4-methoxybenzyl)pyrrolidin-2-one as black solid.

Mass spectrum (ESI, m/z): Calculated for $C_{29}H_{29}FN_4O_4$: 539.2[M+Na], found: 539.4.

Step 8: 5-(2-(6-(1-ethyl-4-fluoro-1H-indazol-6-yl)-2-methoxypyridin-3-yl)-2-hydroxy-3-methylbutyl)-1-(4-methoxybenzyl)pyrrolidin-2-one Into a 100 ml flask were placed a solution of 5-(2-(6-(1-ethyl-4-fluoro-1H-indazol-6-yl)-2-methoxypyridin-3-yl)-2-oxoethyl)-1-(4-methoxybenzyl)pyrrolidin-2-one (1.60 g, 3.097 mmol, 1.00 equiv.) in THF (30 mL). Isopropylmagnesium chloride (2.33 ml, 4.66 mmol, 1.50 equiv.) was added at −78° C. under nitrogen atmosphere. The mixture was stirred for 6 h at 0° C. The reaction was monitored by LCMS. The reaction was quenched with MeOH and concentrated under vacuum and extracted with ethyl acetate (3×50 mL). The organic layers were combined, washed with sodium carbonate (aq.) and brine, dried and concentrated under vacuum. The residue was purified by chromatogram on silica gel with DCM/MeOH (20/1) to yield 5-(2-(6-(1-ethyl-4-fluoro-1H-indazol-6-yl)-2-methoxypyridin-3-yl)-2-hydroxy-3-methylbutyl)-1-(4-methoxybenzyl)pyrrolidin-2-one as brown solid.

Mass spectrum (ESI, m/z): Calculated for $C_{32}H_{37}FN_4O_4$: 583.3 [M+Na], found: 583.4.

Step 9: 5-(2-(6-(1-ethyl-4-fluoro-1H-indazol-6-yl)-2-methoxypyridin-3-yl)-3-methylbut-1-enyl)pyrrolidin-2-one The title compound was prepared according to the procedure as described in Example 1 step 5 by demethylation with TMSCl/NaI to yield the product as a yellow solid.

Mass spectrum (ESI, m/z): Calculated for $C_{24}H_{27}FN_4O_2$: 445.2[M+Na], found: 445.4.

Step 10: 6-(1-ethyl-4-fluoro-1H-indazol-6-yl)-3-(3-methyl-1-(5-oxopyrrolidin-2-yl)butan-2-yl)pyridin-2(1H)-one The title compound was prepared according to the procedure as described in Example 8 step 1 by hydrogenation to yield the product as a white solid.

$^1$H NMR (300 MHz, $CD_3OD$) δ: 8.13 (s, 1H), 7.80 (s, 1H), 7.55 (d, J=7.2 Hz, 1H), 7.16-7.21 (m, 1H), 6.78 (d, J=7.2 Hz, 1H), 4.48-4.60 (m, 2H), 3.35-3.50 (m, 1H), 2.73-2.90 (m, 1H), 2.11-2.35 (m, 3H), 1.60-1.80 (m, 3H), 1.80-2.00 (m, 1H), 1.45-1.53 (m, 3H), 1.02-1.04 (m, 3H), 0.78-0.90 (m, 3H). $^{19}$F NMR (300 MHz, $CD_3OD$) δ: −119.122. Mass spectrum (ESI, m/z): Calculated for $C_{23}H_{27}FN_4O_2$: 411.2 [M+H], found: 411.2.

Example 90

Compound #76

3-(1-(1H-imidazol-2-yl)-2-methylpropyl)-6-(8-fluoronaphthalen-2-yl)pyridin-2(1H)-one

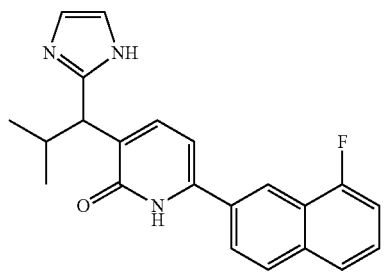 [SMILES: CC(C)C(c1ncc[nH]1)c1ccc(-c2ccc3cccc(F)c3c2)[nH]c1=O]

Step 1: 3-(1-(1H-imidazol-2-yl)-2-methylpropyl)-6-(8-fluoronaphthalen-2-yl)-2-methoxypyridine Into 40 mL vial, 2-(6-(8-fluoronaphthalen-2-yl)-2-methoxypyridin-3-yl)-3-methylbutanal (50 mg, 0.148 mmol, 1 eq.) was dissolved (7M) $NH_3$ in methanol, and then oxalaldehyde (17.2 mg, 0.296 mmol, 2.0 eq.) was added. The reaction mixture was stirred for 16 h at 35° C. The mixture was concentrated under vacuum. The residue was applied onto a silica gel column with ethyl acetate/petroleum ether (1/1) to yield 3-(1-(1H-imidazol-2-yl)-2-methylpropyl)-6-(8-fluoronaphthalen-2-yl)-2-methoxypyridine as an off-white solid.

Mass spectrum (ESI, m/z): Calculated for $C_{23}H_{22}FN_3O$, 376.2 (M+H), found 376.2.

Step 2: 3-(1-(1H-imidazol-2-yl)-2-methylpropyl)-6-(8-fluoronaphthalen-2-yl)pyridin-2(1H)-one Into a 40-mL vial, were placed 3-(1-(1H-imidazol-2-yl)-2-methylpropyl)-6-(8-fluoronaphthalen-2-yl)-2-methoxypyridine (40 mg, 0.107 mmol, 1.00 equiv.), chlorotrimethylsilane (34.6 mg, 0.318 mmol, 3.0 equiv.), sodium iodide (48 mg, 0.320 mmol, 3.0 equiv.), MeCN (10 mL). The resulting solution was stirred overnight at 25° C. The resulting solution was diluted with methanol (1 mL).

The resulting solution was concentrated under vacuum. The residue (40 mg) was purified by Prep-HPLC with the following conditions (1#waters2767-5): Column, SunFire Prep C18,19*150 mm 5 umH PrepC-001 (T)18600256819513816414 04; mobile phase, Phase A:water with 0.05% $NH_4HCO_3$ Phase B:$CH_3CN$ (25% $CH_3CN$ up to 45% in 10 min, up to 100% $CH_3CN$ in 0.1 min, hold 100% in 1.9 min, down to 25% $CH_3CN$ in 0.1 min, hold 25% in 1.9 min); Detector, UV220&254 nm to yield 3-(1-(1H-imidazol-2-yl)-2-methylpropyl)-6-(8-fluoronaphthalen-2-yl)pyridin-2(1H)-one as a white solid.

$^1$H NMR (300 MHz, $CD_3OD$) δ: 8.34 (s, 1H), 7.98-8.01 (m, 1H), 7.69-7.80 (m, 3H), 7.45-7.52 (m, 1H), 7.20-7.26 (m, 1H), 6.90 (s, 2H), 6.74 (d, J=7.5 Hz, 1H), 3.93 (d, J=10.8 Hz, 1H), 2.55-2.67 (m, 1H), 0.90 (d, J=6.6 Hz, 3H), 0.82 (d, J=6.6 Hz, 3H). $^{19}$F NMR (300 MHz, $CD_3OD$) δ: −122.45. Mass spectrum (ESI, m/z): Calculated for $C_{22}H_{20}FN_3O$, 362.2 (M+H), found 362.2.

Example 91

Compound #140

3-(1-(1H-imidazol-2-yl)-3-methyl butan-2-yl)-6-(8-fluoronaphthalen-2-yl)pyridin-2(1H)-one

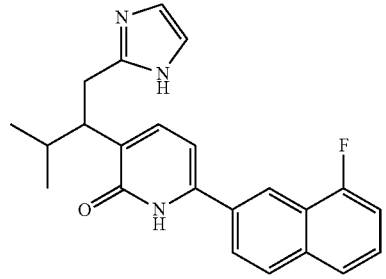 [SMILES: CC(C)C(Cc1ncc[nH]1)c1ccc(-c2ccc3cccc(F)c3c2)[nH]c1=O]

Step 1: (E)-methyl 3-(6-(8-fluoronaphthalen-2-yl)-2-methoxypyridin-3-yl)-4-methylpent-2-enoate Into a 25-mL round-bottom flask were placed a solution of ethyl 2-(trimethylsilyl)acetate (2.53 g, 15.784 mmol, 2.00 equiv.) in THF at −78° C. under nitrogen atmosphere. To the mixture was then added lithium bis(trimethylsilyl)amide (15.8 mL, 15.8 mmol, 2.00 equiv.), which was added dropwise with stirring at −78° C. The reaction mixture was stirred at −78° C. for 30 min. A solution of 1-(6-(8-fluoronaphthalen-2-yl)-2-methoxypyridin-3-yl)-2-methylpropan-1-one (2.4 g, 7.422 mmol, 1.00 equiv.) in THF was then added dropwise. The mixture was stirred for 10 min at −78° C. The reaction progress was monitored by LCMS. The reaction was quenched by the addition of methanol. The reaction mixture was concentrated under vacuum. The residue was purified by thin layer chromatography developed with PE/EA (6:1) to yield (E)-methyl 3-(6-(8-fluoronaphthalen-2-yl)-2-methoxypyridin-3-yl)-4-methylpent-2-enoate as a yellow oil.

Mass spectrum (ESI, m/z): Calculated for $C_{23}H_{22}FNO_3$, 380.2 (M+H), found 380.1.

Step 2: Methyl 3-(6-(8-fluoronaphthalen-2-yl)-2-methoxypyridin-3-yl)-4-methylpentanoate Into a 25 mL round-bottom flask were placed a solution of (E)-methyl 3-(6-(8-fluoronaphthalen-2-yl)-2-methoxypyridin-3-yl)-4-methylpent-2-enoate (2.23 g, 5.877 mmol, 1.00 equiv.) in MeOH and then $PtO_2$ (466 mg, 2.052 mmol, 0.35 equiv.) was added. The mixture was stirred overnight at room temperature under an atmosphere of hydrogen. $PtO_2$ was filtered out. The filtrate was concentrated under vacuum. The residue was applied onto a silica gel column with ethyl acetate/petroleum ether (1:15) to yield methyl 3-(6-(8-fluoronaphthalen-2-yl)-2-methoxypyridin-3-yl)-4-methylpentanoate as a yellow oil.

Mass spectrum (ESI, m/z): Calculated for $C_{23}H_{24}FNO_3$, 382.2 (M+H), found 382.1.

Step 3: 3-(6-(8-fluoronaphthalen-2-yl)-2-methoxypyridin-3-yl)-4-methylpentan-1-ol Into 50 mL round-bottom flask, methyl 3-(6-(8-fluoronaphthalen-2-yl)-2-methoxypyridin-3-yl)-4-methylpentanoate (50 mg, 0.131 mmol, 1 equiv.) was dissolved in THF (20 mL). LAH (10 mg, 0.263 mmol, 2 equiv.) was then added. The mixture was stirred for 1 h at 25° C. The mixture was quenched with $Na_2SO_4 \cdot 10H_2O$ and filtered out. The organic layer was concentrated under vacuum. The residue was applied onto a silica gel column with PE/EA (6:1) to yield 3-(6-(8-fluoronaphthalen-2-yl)-2-methoxypyridin-3-yl)-4-methylpentan-1-ol as a light yellow oil.

Mass spectrum (ESI, m/z): Calculated for $C_{22}H_{24}FNO_2$, 354.2 (M+H), found 354.1.

Step 4: 3-(6-(8-fluoronaphthalen-2-yl)-2-methoxy-pyridin-3-yl)-4-methylpentanal

Into 50-mL round-bottom flask, 3-(6-(8-fluoronaphthalen-2-yl)-2-methoxypyridin-3-yl)-4-methylpentan-1-ol (40 mg, 0.113 mmol, 1 equiv.) was dissolved in THF (20 mL), and then Dess-Martin periodinane (96 mg, 0.226 mmol, 2 equiv.) was added. The mixture was stirred at 3 h at 25° C. and quenched with $Na_2S_2O_3$—$NaHCO_3$ solution. The mixture was extracted with EA. The organic layer was concentrated under vacuum. The residue was applied onto a silica gel column with PE/EA (6:1) to yield 3-(6-(8-fluoronaphthalen-2-yl)-2-methoxypyridin-3-yl)-4-methylpentanal as a light yellow oil.

Mass spectrum (ESI, m/z): Calculated for $C_{22}H_{22}FNO_2$, 352.2 (M+H), found 352.1.

Step 5: 3-(1-(1H-imidazol-2-yl)-3-methylbutan-2-yl)-6-(8-fluoronaphthalen-2-yl)pyridin-2(1H)-one The title compound was prepared according to the procedure as described in Example 90 by condensation of 3-(6-(8-fluoronaphthalen-2-yl)-2-methoxypyridin-3-yl)-4-methylpentanal and oxalaldehyde followed by demethylation of 3-(1-(1H-imidazol-2-yl)-3-methylbutan-2-yl)-6-(8-fluoronaphthalen-2-yl)-2-methoxypyridine with TMSCl/NaI in $CH_3CN$ to yield the products as an off-yellow solid.

$^1$H NMR (400 MHz, $CD_3OD$) δ: 8.37 (s, 1H), 8.05 (d, J=7.2 Hz, 1H), 7.82 (d, J=7.2 Hz, 1H), 7.76 (d, J=8.4 Hz, 1H), 7.52-7.57 (m, 1H), 7.41 (d, J=7.2 Hz, 1H), 7.27-7.31 (m, 1H), 6.83 (s, 2H), 6.69 (d, J=7.2 Hz, 1H), 3.11-3.24 (m, 3H), 2.05-2.21 (m, 1H), 1.08 (d, J=6.8 Hz,3H), 0.94 (d, J=6.8 Hz, 3H). $^{19}$F NMR (400 MHz, $CD_3OD$) δ: −124.56. Mass spectrum (ESI, m/z): Calculated for $C_{23}H_{22}FN_3O$, 376.2 (M+H), found 376.2.

Example 92

Compound #131

6-(8-Fluoronaphthalen-2-yl)-3-(2-methyl-1-(5-methyl-1H-imidazol-2-yl)propyl)pyridin-2(1H)-one

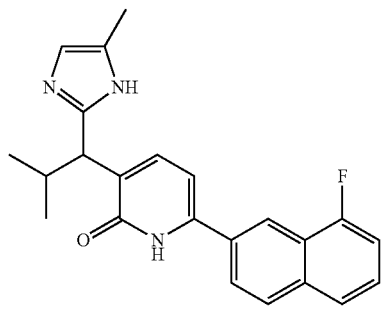 [SMILES: Cc1cnc(C(c2ccc(-c3ccc4cccc(F)c4c3)[nH]c2=O)C(C)C)[nH]1]

The title compound was prepared according to the procedure as described in Example 90 by condensation of 2-(6-(8-fluoronaphthalen-2-yl)-2-methoxypyridin-3-yl)-3-methylbutanal and 2-oxopropanal followed by demethylation of 6-(8-fluoronaphthalen-2-yl)-2-methoxy-3-(2-methyl-1-(5-methyl-1H-imidazol-2-yl)propyl)pyridine with TMSCl/NaI in $CH_3CN$ to yield a white solid.

$^1$H NMR (300 MHz, $CD_3OD$) δ: 8.35 (s, 1H), 8.02 (d, J=9.0 Hz, 1H), 7.80 (d, J=8.7 Hz, 1H), 7.70-7.74 (m, 2H), 7.46-7.53 (m, 1H), 7.21-7.27 (m, 1H), 6.75 (d, J=7.5 Hz, 1H), 6.59 (s, 1H), 3.85 (d, J=11.1 Hz Hz, 1H), 2.54-2.66 (m, 1H), 2.15 (s, 3H), 0.89 (d, J=6.6 Hz, 3H), 0.85 (d, J=6.3 Hz, 3H). $^{19}$F NMR (300 MHz, $CD_3OD$) δ: −124.47. Mass spectrum (ESI, m/z): Calculated for $C_{23}H_{22}FN_3O$, 376.2 (M+H), found 376.1.

Example 93

Compound #67

3-(1-(4,5-Dimethyl-1H-imidazol-2-yl)-2-methylpropyl)-6-(8-fluoronaphthalen-2-yl)pyridin-2(1H)-one

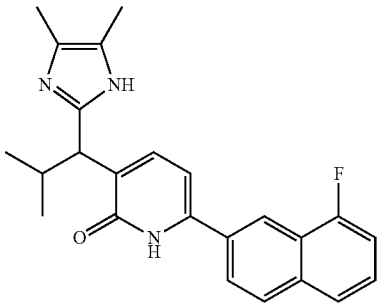 [SMILES: Cc1nc(C(c2ccc(-c3ccc4cccc(F)c4c3)[nH]c2=O)C(C)C)[nH]c1C]

The title compound was prepared according to the procedure as described in Example 90 by condensation of 2-(6-(8-fluoronaphthalen-2-yl)-2-methoxypyridin-3-yl)-3-methylbutanal and 2,3-butanedione followed by demethylation of 3-(1-(4,5-dimethyl-1H-imidazol-2-yl)-2-methylpropyl)-6-(8-fluoronaphthalen-2-yl)-2-methoxypyridine with TMSCl/NaI in $CH_3CN$ to yield an off-white solid.

$^1$H NMR (400 MHz, $CD_3OD$) δ: 8.40 (s, 1 H), 8.06-8.08 (m, 1 H), 7.75-7.85 (m, 3 H), 7.53-7.58 (m, 1 H), 7.27-7.31 (m, 1 H), 6.84 (d, J=7.2 Hz, 1 H), 3.96 (d, J=8.4 Hz, 1 H), 2.73-2.79 (m, 1 H), 2.23 (s, 6 H), 1.02 (d, J=6.4 Hz, 3 H), 0.95 (d, J=6.4 Hz, 3 H). $^{19}$F NMR (400 MHz, $CD_3OD$) δ: −75.00, −124.48.

Mass spectrum (ESI, m/z): Calculated for $C_{27.98}H_{25.99}F_{6.97}N_3O_{4.98}$, 390.2 (M−1.99$CF_3COOH$+H), found 390.2.

Example 94

Compound #82

3-(1-(1H-imidazol-2-yl)-2-methylpropyl)-6-(8-fluoronaphthalen-2-yl)-5-methylpyridin-2(1H)-one

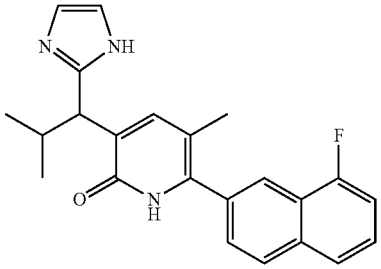 [SMILES: Cc1cc(C(c2ncc[nH]2)C(C)C)c(=O)[nH]c1-c1ccc2cccc(F)c2c1]

Step 1: 2-(5-bromo-6-(8-fluoronaphthalen-2-yl)-2-methoxypyridin-3-yl)-3-methylbutanal Into a 100-mL round bottle maintained with an inert atmosphere of nitrogen, were placed 2-(6-(8-fluoronaphthalen-2-yl)-2-methoxypyridin-3-yl)-3-methylbutanal (200 mg, 0.59 mmol, 1 equiv.), NBS (126 mg, 0.71 mmol, 1.2 equiv.), DMF (5 mL). The resulting solution was stirred for 3 h at 60° C. The mixture was concentrated under vacuum. The residue was purified purified by TLC with ethyl acetate/petroleum ether (1:6) to yield 2-(5-bromo-6-(8-fluoronaphthalen-2-yl)-2-methoxypyridin-3-yl)-3-methylbutanal as a yellow oil.

Mass spectrum (ESI, m/z): Calculated for $C_{21}H_{19}BrFNO_2$, 416.3[M+H], 416.0.

Step 2: 2-(6-(8-fluoronaphthalen-2-yl)-5-methyl-2-oxo-1,2-dihydropyridin-3-yl)-3-methylbutanal Into a 40-mL vial purged and maintained with an inert atmosphere of nitrogen, were placed 2-(5-bromo-6-(8-fluoronaphthalen-2-yl)-2-methoxypyridin-3-yl)-3-methylbutanal (200 mg, 0.48 mmol, 1 equiv.), DMF (5 mL), $PdCl_2$ (5 mg, 0.028 mmol, 0.05 equiv.), $(o-tol)_3P$ (14 mg, 0.046 mmol, 0.1 equiv.), tetramethylstannane (173 mg, 0.96 mmol, 2 equiv.). The resulting solution was stirred with 16 h at 100° C. The mixture was concentrated under vacuum. The residue was purified purified by TLC with ethyl acetate/petroleum ether (1:15) to yield 2-(6-(8-fluoronaphthalen-2-yl)-2-methoxy-5-methylpyridin-3-yl)-3-methylbutanal as a yellow oil.

Mass spectrum (ESI, m/z): Calculated for $C_{22}H_{22}FNO_2$, 352.2 [M+H], 352.1.

Step 3: 3-(1-(1H-imidazol-2-yl)-2-methylpropyl)-6-(8-fluoronaphthalen-2-yl)-5-methylpyridin-2(1H)-one The title compound was prepared according to the procedure as described in Example 90 by condensation of 2-(6-(8-fluoronaphthalen-2-yl)-2-methoxypyridin-3-yl)-3-methylbutanal and oxalaldehyde followed by demethylation of 3-(1-(1H-imidazol-2-yl)-2-methylpropyl)-6-(8-fluoronaphthalen-2-yl)-2-methoxy-5-methyl pyridine with TMSCl/NaI in $CH_3CN$ to yield a white solid.

$^1H$ NMR (300 MHz,$CD_3OD$) δ: 8.11 (s, 1H), 8.03 (d, J=8.4 Hz, 1H), 7.74 (d, J=8.4 Hz, 1H), 7.66 (s, 1H), 7.49-7.51 (m, 2H), 7.23-7.28 (m, 1H), 7.06 (s, 2H), 3.93 (d, J=11.1 Hz, 1H), 3.65-2.72 (m, 1H), 2.09 (s, 3H), 0.94 (d, J=6.6 Hz, 3H), 0.85 (d, J=6.6 Hz, 3H). $^{19}F$ NMR (300 MHz,$CD_3OD$) δ: −76.95, −124.96. Mass spectrum (ESI, m/z): Calculated for $C_{23.64}H_{22.32}F_{1.96}N_3O_{1.64}$, 376.2 [M−0.32$CF_3COOH$+H], found 376.1.

Example 95

Compound #307

3-(2-(1H-Imidazol-2-yl)-3-methylbutyl)-6-(8-fluoronaphthalen-2-yl)pyridin-2(1H)-one

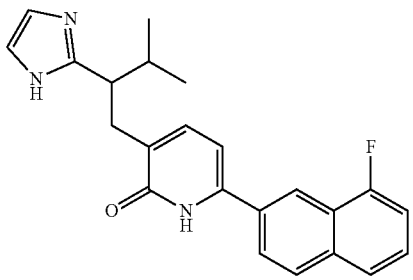 [SMILES: CC(C)C(Cc1ccc(-c2ccc3cccc(F)c3c2)[nH]c1=O)c1ncc[nH]1]

Step 1: 2-((6-(8-fluoronaphthalen-2-yl)-2-methoxypyridin-3-yl)methyl)-3-methylbutan-1-ol Into a 25 mL round-bottom flask were placed a solution of ethyl 2-((6-(8-fluoronaphthalen-2-yl)-2-methoxypyridin-3-yl)methyl)-3-methylbutanoate (50 mg, 0.126 mmol, 1 equiv.) in THF (2 mL) at 0° C., and then lithiumaluminiumtetrahydride (10 mg, 0.263 mmol, 2 equiv.) was added in several portions. The mixture was stirred for 1 h. The mixture was quenched by MeOH and concentrated under vacuum. The residue product was purified by chromatogram on silica gel with ethyl acetate/petroleum ether (10:1) to yield 2-((6-(8-fluoronaphthalen-2-yl)-2-methoxypyridin-3-yl)methyl)-3-methylbutan-1-ol as alight yellow oil.

Mass spectrum (ESI, m/z): Calculated for $C_{22}H_{24}FNO_2$, 354.2 (M+H), found 354.1.

Step 2: 2-((6-(8-fluoronaphthalen-2-yl)-2-methoxypyridin-3-yl)methyl)-3-methylbutanal Into a 25-mL round-bottom flask, were placed 2-((6-(8-fluoronaphthalen-2-yl)-2-methoxypyridin-3-yl)methyl)-3-methylbutan-1-ol (40 mg, 0.113 mmol, 1 equiv.), $CH_2Cl_2$ (2 mL). (1,1,1-Triacetoxy)-1,1-dihydro-1,2-benziodoxol-3(1H)-one (126 mg, 0.297 mmol, 3 equiv.) was then added in portions at room temperature. The resulting solution was stirred 1 h at room temperature. The reaction progress was monitored by TLC/LCMS (PE:EA=6:1). The reaction was then quenched by $Na_2S_2O_3/NaHCO_3/H_2O$. The reaction was extracted with ethyl acetate and dried over anhydrous sodium sulfate and concentrated under vacuum. The residue product was purified by chromatogram on silica gel with ethyl acetate/petroleum ether (10:1) to yield 2-((6-(8-fluoronaphthalen-2-yl)-2-methoxypyridin-3-yl)methyl)-3-methylbutanal as a colorless oil.

Mass spectrum (ESI, m/z): Calculated for $C_{22}H_{22}FNO_2$, 352.2 (M+H), found 352.2.

Step 3: 3-(2-(1H-imidazol-2-yl)-3-methylbutyl)-6-(8-fluoronaphthalen-2-yl)pyridin-2(1H)-one The title compound was prepared according to the procedure as described in Example 90 by condensation of 2-((6-(8-fluoronaphthalen-2-yl)-2-methoxypyridin-3-yl)methyl)-3-methylbutanal and oxalaldehyde followed by demethylation of 3-(2-(1H-imidazol-2-yl)-3-methylbutyl)-6-(8-fluoronaphthalen-2-yl)-2-methoxypyridine with TMSCl/NaI in $CH_3CN$ to yield a light yellow solid.

$^1H$ NMR (400 MHz, $CD_3OD$) δ: 8.34 (s, 1H), 8.04 (d, J=8.8 Hz, 1H), 7.75-7.79 (m, 2H), 7.51-7.57 (m, 1H), 7.26-7.31 (m, 1H), 7.15 (d, J=7.2 Hz, 1H), 6.91 (s, 2H), 6.54 (d, J=7.2 Hz, 1H), 3.21-3.26 (m, 1H), 3.04-3.10 (m, 1H), 2.77-2.84 (m, 1H), 2.03-2.11 (m, 1H), 1.11 (d, J=6.8 Hz, 3H), 0.98 (d, J=6.8 Hz, 3H). $^{19}F$ NMR (400 MHz, $CD_3OD$) δ: −124.60. Mass spectrum (ESI, m/z): Calculated for $C_{23}H_{22}FN_3O$, 376.2 (M+H), found 376.2.

Example 96

Compound #50

3-(3-(1H-imidazol-2-yl)pentan-3-yl)-6-(6,8-difluor-onaphthalen-2-yl)pyridin-2(1H)-one

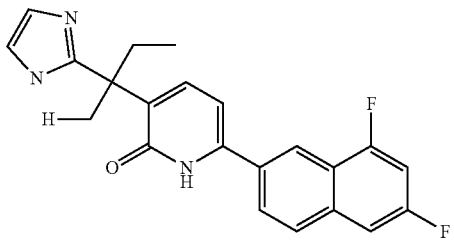 [SMILES: CCC(C)(c1ncc[nH]1)c1ccc(-c2ccc3cc(F)cc(F)c3c2)[nH]c1=O]

The title compound was prepared according to the procedure as described in Example 90 by condensation followed by demethylation to yield the product as a white solid.

$^1$H NMR (300 MHz, CD$_3$OD) δ: 8.39 (s, 1H), 8.03 (d, J=7.8 Hz, 1H), 7.92 (d, J=7.8 Hz, 1H), 7.72 (d, J=7.5 Hz, 1H), 7.54 (d, J=7.2 Hz, 1H), 7.21-7.31 (m, 1H), 6.93 (s, 2H), 6.82 (d, J=7.5 Hz, 1H), 2.44-2.49 (m, 2H), 2.12-2.17 (m, 2H), 0.72 (t, J=7.2 Hz, 6H). $^{19}$F NMR (300 MHz, CD$_3$OD) δ: −111.96, −119.52. Mass spectrum (ESI, m/z): Calculated For C$_{23}$H$_{21}$F$_2$N$_3$O, 394.2 [M+H], found 394.1.

Example 97

Compound #31

3-(3-(1H-imidazol-2-yl)pentan-3-yl)-6-(1-ethyl-4-fluoro-1H-indazol-6-yl)pyridin-2(1H)-one

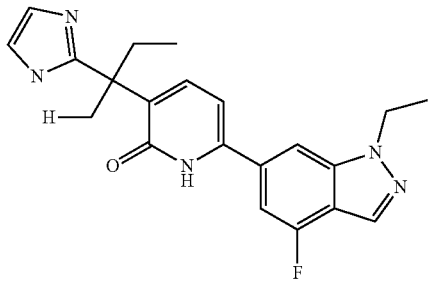 [SMILES: CCn1ncc2c(F)cc(-c3ccc(C(C)(CC)c4ncc[nH]4)c(=O)[nH]3)cc21]

The title compound was prepared according to the procedure as described in Example 90 by condensation followed by demethylation to yield the product as a white solid.

$^1$H NMR (400 MHz, CD$_3$OD) δ 8.12 (s, 1H), 7.77 (s, 1H), 7.67 (d, J=7.6 Hz, 1H), 7.17 (d, J=10.2 Hz, 1H), 6.90 (s, 2H), 6.76 (d, J=7.6 Hz, 1H), 4.49-4.55 (m, 2H), 2.40-2.49 (m, 2H), 2.06-2.15 (m, 2H), 1.49-1.52 (m, 3H), 0.67-0.71 (m, 6H). $^{19}$F NMR (400 MHz, CD$_3$OD) δ: −119.22. Mass spectrum (ESI, m/z): Calculated for C$_{22}$H$_{24}$FN$_5$O, 394.2 [M+H], found 394.3.

Example 98

Compound #20

3-(3-((1H-imidazol-2-yl)methyl)pentan-3-yl)-6-(1-ethyl-4-fluoro-1H-indazol-6-yl)pyridin-2(1H)-one

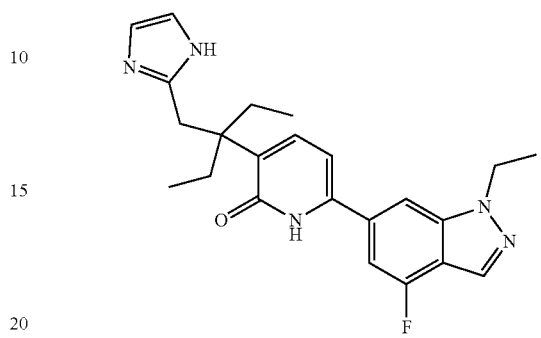

The title compound was prepared according to the procedure as described in Example 90 by condensation followed by demethylation to yield the product as a white solid.

$^1$H NMR (300 MHz, CD$_3$OD) δ: 8.15 (s, 1H), 7.82 (s, 1H), 7.37 (d, J=7.5 Hz, 1H), 7.20 (d, J=11.1 Hz, 1H), 6.85 (s, 2H), 6.67 (d, J=7.5 Hz, 1H), 4.56-4.58 (m, 2H), 3.33-3.36 (m, 2H), 2.00-2.04 (m, 2H), 1.80-1.84 (m, 2H), 1.53-1.57 (m, 3H), 0.83-0.88 (m, 6H). $^{19}$F NMR (300 MHz, CD$_3$OD) δ: −119.23. Mass spectrum (ESI, m/z): Calculated for C$_{23}$H$_{26}$FN$_5$O, 408.2 [M+H], found 408.0.

Example 99

Compound #138

6-(8-Fluoronaphthalen-2-yl)-3-(2-methyl-1-(4H-1,2,4-triazol-3-yl)propyl)pyridin-2(1H)-one

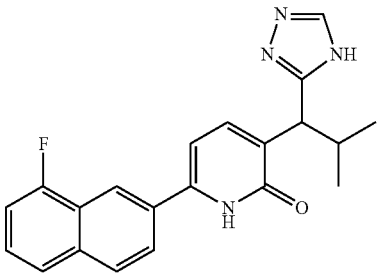 [SMILES: CC(C)C(c1nnc[nH]1)c1ccc(-c2ccc3cccc(F)c3c2)[nH]c1=O]

Step 1: 2-(6-(8-fluoronaphthalen-2-yl)-2-methoxy-pyridin-3-yl)-3-methylbutanamide Into a 50-mL round-bottom flask, were placed 2-(6-(8-fluoronaphthalen-2-yl)-2-methoxypyridin-3-yl)-3-methylbutanoic acid (50 mg, 0.141 mmol, 1.0 equiv.), NH$_4$Cl (15 mg, 0.278 mmol, 2.0 equiv.), HATU (106 mg, 0.279 mmol, 2.0 equiv.), DIPEA (36 mg, 0.279 mmol, 2.0 equiv.), DMF (2.5 mL), DCM (2.5 mL). The resulting solution was stirred overnight at room temperature. The reaction progress was monitored by LCMS. The resulting mixture was concentrated under vacuum. The residue was applied TLC with DCM:MeOH=10:1 to yield 2-(6-(8-fluoronaphthalen-2-yl)-2-methoxypyridin-3-yl)-3-methylbutanamide as a brown oil.

Mass spectrum (ESI, m/z): Calculated For C$_{21}$H$_{21}$FN$_2$O$_2$, 353.2 (M+H), found 353.0.

Step 2: 6-(8-fluoronaphthalen-2-yl)-2-methoxy-3-(2-methyl-1-(4H-1,2,4-triazol-3-yl)propyl) pyridine Into a 50-mL round-bottom flask, were placed 2-(6-(8-fluoronaphthalen-2-yl)-2-methoxypyridin-3-yl)-3-methylbutanamide (60 mg, 0.170 mmol, 1.0 equiv.), DMF-DMA (5 mL). The resulting solution was stirred 2.0 h at 100° C. Then the resulting mixture was concentrated under vacuum. AcOH (5 mL) and $NH_2NH_2$ (0.5 mL) were then added. The resulting solution was stirred 1.0 h at 90° C. The reaction progress was monitored by LCMS. The resulting mixture was concentrated under vacuum. The residue was applied TLC with PE:EA=2:1 to yield 6-(8-fluoronaphthalen-2-yl)-2-methoxy-3-(2-methyl-1-(4H-1,2,4-triazol-3-yl)propyl) pyridine as a brown oil.

Mass spectrum (ESI, m/z): Calculated For $C_{22}H_{21}FN_4O$, 377.2 (M+H), found 377.0.

Step 3: 6-(8-fluoronaphthalen-2-yl)-3-(2-methyl-1-(4H-1,2,4-triazol-3-yl)propyl)pyridin-2(1H)-one Into a 50-mL round-bottom flask were placed 6-(8-fluoronaphthalen-2-yl)-2-methoxy-3-(2-methyl-1-(4H-1,2,4-triazol-3-yl)propyl)pyridine (30 mg, 0.080 mmol, 1.0 equiv.), $CH_3CN$ (5 mL), NaI (36 mg, 0.24 mmol, 3.0 equiv.), TMSCl (26 mg, 0.239 mmol, 3.0 equiv.). The resulting solution was stirred overnight at 30° C. The reaction progress was monitored by LCMS. The reaction was then quenched by the addition of MeOH. The resulting mixture was concentrated under vacuum and purified by Prep-HPLC with the following conditions (16#-Waters 2767-5): Column, SunFire Prep C18,19*100 mm, 5 um; mobile phase, Water with 0.05% $NH_4HCO_3$ and $CH_3CN$ (25% $CH_3CN$ up to 35% in 10 min, up to 100% in 0.1 min, hold 100% in 0.9 min, down to 20% in 0.1 min, hold 20% in 1.4 min); Detector, UV 220 & 254 nm to yield 6-(8-fluoronaphthalen-2-yl)-3-(2-methyl-1-(4H-1,2,4-triazol-3-yl)propyl)pyridin-2(1H)-one as a white solid.

$^1$H NMR (300 MHz,$CD_3OD$) δ: 8.36 (s, 1H), 7.99-8.08 (m, 2H), 7.78-7.84 (m, 2H), 7.72 (d, J=8.4 Hz, 1H), 7.46-7.53 (m, 1H), 7.21-7.27 (m, 1H), 6.76 (d, J=7.5 Hz, 1H), 4.26 (d, J=10.2 Hz, 1H), 2.48-2.61 (m, 1H), 0.95 (d, J=6.9 Hz, 3H), 0.87 (d, J=6.6 Hz, 3H). 19F NMR (300 MHz, $CD_3OD$) δ: −124.42.

Mass spectrum (ESI, m/z): Calculated For $C_{21}H_{19}FN_4O$, 363.2 (M+H), found 363.0.

Example 100

Compound #139

6-(8-Fluoronaphthalen-2-yl)-3-(4-isopropyl-2-(methylthio)-5-oxo-4,5-dihydro-1H-imidazol-4-yl)pyridin-2(1H)-one

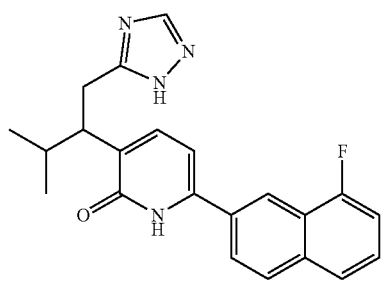 [SMILES: CC(C)C(Cc1ncn[nH]1)c1ccc(-c2ccc3cccc(F)c3c2)[nH]c1=O]

The title compound was prepared according to the procedure as described in Example 99 by condensation of 3-(6-(8-fluoronaphthalen-2-yl)-2-methoxypyridin-3-yl)-4-methyl pentanamide and DMF-DMA followed by demethylation of 6-(8-fluoronaphthalen-2-yl)-2-methoxy-3-(3-methyl-1-(1H-1,2,4-triazol-5-yl)butan-2-yl)pyridine with TMSCl/NaI in $CH_3CN$ to yield a white solid.

$^1$H NMR (400 MHz, $CD_3OD$) δ: 8.37 (s, 1H), 8.00-8.06 (m, 2H), 7.82 (d, J=8.4 Hz, 1H), 7.76 (d, J=8.0 Hz, 1H), 7.51-7.57 (m, 1H), 7.39 (d, J=7.2 Hz, 1H), 7.26-7.38 (m, 1H), 6.68 (d, J=7.2 Hz, 1H), 3.21-3.50 (m, 3H), 2.19-2.28 (m, 1H), 1.10 (d, J=6.4 Hz, 3H), 0.97 (d, J=6.0 Hz, 3H). $^{19}$F NMR (400 MHz, $CD_3OD$) δ: −152.3. Mass spectrum (ESI, m/z): Calculated for $C_{22}H_{21}FN_4O$, 377.2 (M+H), found 377.1.

Example 101

Compound #309

6-(8-Fluoronaphthalen-2-yl)-3-(3-methyl-2-(4H-1,2,4-triazol-3-yl)butyl)pyridin-2(1H)-one

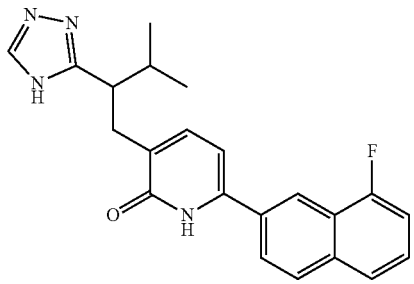 [SMILES: CC(C)C(Cc1ccc(-c2ccc3cccc(F)c3c2)[nH]c1=O)c1nnc[nH]1]

The title compound was prepared according to the procedure as described in Example 99 by condensation of 2-((6-(8-fluoronaphthalen-2-yl)-2-methoxypyridin-3-yl)methyl)-3-methylbutanamide and DMF-DMA followed by demethylation of 6-(8-fluoronaphthalen-2-yl)-2-methoxy-3-(3-methyl-2-(4H-1,2,4-triazol-3-yl)butyl)pyridine with TMSCl/NaI in $CH_3CN$ to yield a light yellow solid.

$^1$H NMR (400 MHz, $CD_3OD$) δ: 8.32 (s, 1H), 8.07 (s, 1H), 8.04 (d, J=7.2 Hz, 1H), 7.73-7.75 (m, 2H), 7.48-7.59 (m, 1H), 7.20-7.30 (m, 1H), 7.17 (d, J=6.8 Hz, 1H), 6.54 (d, J=7.2 Hz, 1H), 3.20-3.30 (m, 2H), 2.79-2.88 (m, 1H), 2.05-2.15 (m, 1H), 1.10 (d, J=6.8 Hz, 3H), 0.87 (d, J=6.8 Hz, 3H). $^{19}$F NMR (400 MHz, $CD_3OD$) δ: −76.95, −124.59. Mass spectrum (ESI, m/z): Calculated for $C_{22.16}H_{21.08}F_{1.24}N_4O_{1.16}$, 377.2 (M−0.08$C_2HF_3O_2$+H), found 377.2.

Example 102

Compound #22

3-(3-(4H-1,2,4-triazol-3-yl)pentan-3-yl)-6-(4-ethyl-8-fluoro-3,4-dihydro-2H-benzo[b][1,4]oxazin-6-yl)pyridin-2(1H)-one

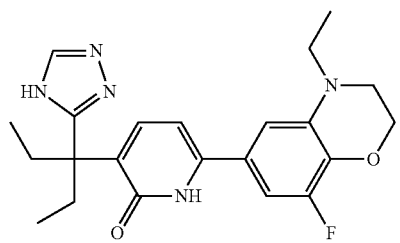 [SMILES: CCN1CCOc2c(F)cc(-c3ccc(C(CC)(CC)c4nnc[nH]4)c(=O)[nH]3)cc21]

The title compound was prepared according to the procedure as described in Example 99 by condensation followed by demethylation to yield the product as an off-white solid.

¹H NMR (300 MHz, CD₃OD) δ 7.81 (s, 1H), 7.62 (d, J=7.2 Hz, 1H), 6.89-6.75 (m, 2H), 6.55 (d, J=7.5 Hz, 1H), 4.24-4.27 (m, 2H), 3.35-3.47 (m, 4H), 2.34-2.46 (m, 2H), 1.89-2.12 (m, 2H), 1.12-1.17 (m, 3H), 0.54-0.71 (m, 6H). ¹⁹F NMR (300 MHz, CD₃OD) δ −138.25. Mass spectrum (ESI, m/z): Calculated for $C_{22}H_{26}FN_5O_2$, 412.2 [M+H], found 412.4.

Example 103

Compound #21

6-(1-ethyl-4-fluoro-1H-indazol-6-yl)-3-(3-(5-methyl-4H-1,2,4-triazol-3-yl)pentan-3-yl)pyridin-2(1H)-one

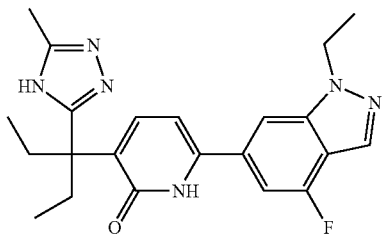 [SMILES: CCn1ncc2c(F)cc(-c3ccc(C(CC)(CC)c4nnc(C)[nH]4)c(=O)[nH]3)cc21]

The title compound was prepared according to the procedure as described in Example 99 by condensation followed by demethylation to yield the product as a white solid.
¹H NMR (300 MHz, CD₃OD) δ 8.09 (s, 1H), 7.75 (s, 1H), 7.67-7.69 (m, 1H), 7.15 (d, J=11.1 Hz, 1H), 6.75 (d, J=7.5 Hz, 1H), 4.47-4.54 (m, 2H), 2.29-2.47 (m, 5H), 1.99-2.18 (m, 2H), 1.46-1.51 (m, 3H), 0.66-0.71 (m, 6H). ¹⁹F NMR (300 MHz, CD₃OD) δ −119.17. Mass spectrum (ESI, m/z): Calculated for $C_{22}H_{25}FN_6O$, 409.2 [M+H], found 409.0.

Example 104

Compound #33

3-(3-(4H-1,2,4-triazol-3-yl)pentan-3-yl)-6-(5,7-difluoronaphthalen-2-yl)pyridin-2(1H)-one

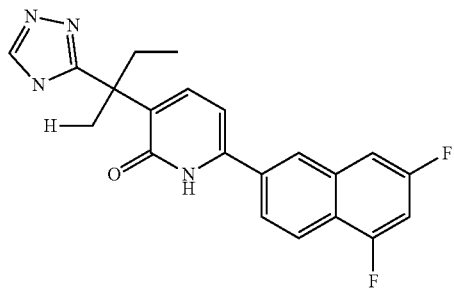 [SMILES: CCC(C)(c1nnc[nH]1)c1ccc(-c2ccc3c(F)cc(F)cc3c2)[nH]c1=O]

The title compound was prepared according to the procedure as described in Example 99 by condensation followed by demethylation to yield the product as a white solid.
¹H NMR (300 MHz, CD₃OD) δ: 8.77 (s, 1H), 8.18-8.76 (m, 2H), 7.56 (t, J=8.7 Hz, 2H), 7.28 (d, J=7.2 Hz, 1H), 7.25 (t, J=9.0 Hz, 1H), 6.90 (d, J=7.5 Hz, 1H), 2.43-2.55 (m, 2H), 2.08-2.20 (m, 2H), 0.78 (t, J=7.5 Hz, 6H). ¹⁹F NMR (300 MHz, CD₃OD) δ: −77.23, −112.45, −120.15. Mass spectrum (ESI, m/z): Calculated for $C_{23.84}H_{20.92}F_{4.76}N_4O_{2.84}$, 395.2 [M−0.92CF₃COOH+H], found 395.1.

Example 105

Compound #5

3-(3-(4H-1,2,4-triazol-3-yl)pentan-3-yl)-6-(1-ethyl-4-fluoro-1H-indazol-6-yl)pyridin-2(1H)-one-one

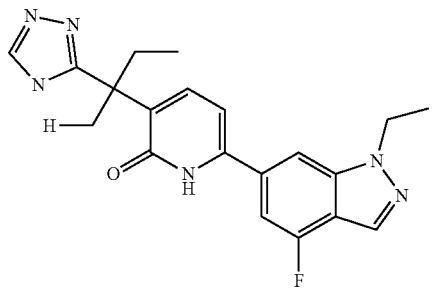 [SMILES: CCn1ncc2c(F)cc(-c3ccc(C(C)(CC)c4nnc[nH]4)c(=O)[nH]3)cc21]

The title compound was prepared according to the procedure as described in Example 99 by condensation followed by demethylation to yield the product as a white solid.
¹H NMR (400 MHz, CD₃OD) δ 8.13 (s, 1H), 7.89-7.94 (m, 1H), 7.78 (s, 1H), 7.72 (d, J=7.6 Hz, 1H), 7.18 (d, J=10.0 Hz, 1H), 6.79 (d, J=7.2 Hz, 1H), 4.50-4.55 (m, 2H), 2.43-2.50 (m, 2H), 2.13-2.16 (m, 2H), 1.51-1.52 (m, 3H), 0.79-0.85 (m, 6H). ¹⁹F NMR (400 MHz, CD₃OD) δ −119.17. Mass spectrum (ESI, m/z): Calculated for $C_{21}H_{23}FN_6O$, 395.2 [M+H], found 395.2.

Example 106

Compound #39

3-(3-(4H-1,2,4-triazol-3-yl)pentan-3-yl)-6-(6,8-difluoronaphthalen-2-yl)pyridin-2(1H)-one

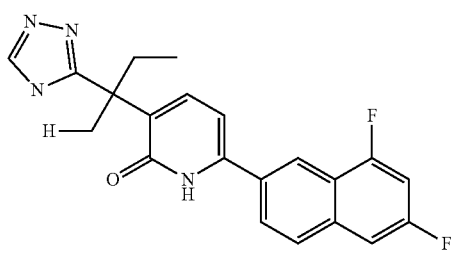 [SMILES: CCC(C)(c1nnc[nH]1)c1ccc(-c2ccc3cc(F)cc(F)c3c2)[nH]c1=O]

The title compound was prepared according to the procedure as described in Example 99 by condensation followed by demethylation to yield the product as a white solid.
¹H NMR (300 MHz, CD₃OD) δ: 8.73 (s, 1H), 8.39 (s, 1H), 8.05 (d, J=8.7 Hz, 1H), 7.82-7.90 (m, 2H), 7.51 (d, J=9.3 Hz, 1H), 7.26-7.49 (m, 1H), 6.88 (d, J=7.5 Hz, 1H), 2.44-2.51 (m, 2H), 2.09-2.17 (m, 2H), 0.77 (t, J=7.2 Hz, 6H). ¹⁹F NMR (300 MHz, CD₃OD) δ: −77.30, −111.45, −119.40. Mass spectrum (ESI, m/z): Calculated for $C_{25.02}H_{21.51}F_{6.53}N_4O_{4.02}$, 428.1 [M−0.84CF₃COOH+H], found 395.1.

Example 107

Compound #279

3-(3-((4H-1,2,4-triazol-3-yl)methyl)pentan-3-yl)-6-(6,8-difluoronaphthalen-2-yl)pyridin-2(3H)-one

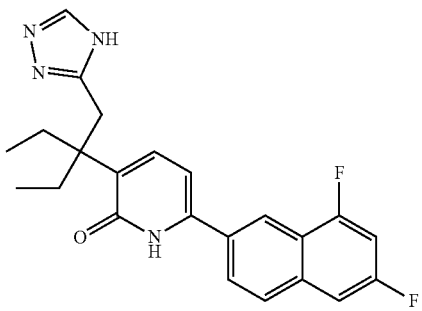 [SMILES: CCC(CC)(Cc1nnc[nH]1)c1ccc(-c2ccc3cc(F)cc(F)c3c2)[nH]c1=O]

The title compound was prepared according to the procedure as described in Example 99 by condensation followed by demethylation to yield the product as a white solid.

$^1$H NMR (400 MHz, CD$_3$OD) δ: 8.39 (s, 1H), 7.87-8.01 (m, 3H), 7.48-7.50 (m, 1H), 7.36 (d, J=7.5 Hz, 1H), 7.22-7.27 (m, 1H), 6.66 (d, J=7.5 Hz, 1H), 3.48 (s, 2H), 2.01-2.08 (m, 2H), 1.77-1.82 (m, 2H), 0.85 (t, J=7.4 Hz, 6H). $^{19}$F NMR (400 MHz, CD$_3$OD) δ: −111.99, −119.49. Mass spectrum (ESI, m/z): Calculated for C$_{23}$H$_{22}$F$_2$N$_4$O, 409.2 [M+H], found 409.1.

Example 108

Compound #15

3-(3-((4H-1,2,4-triazol-3-yl)methyl)pentan-3-yl)-6-(1-ethyl-4-fluoro-1H-indazol-6-yl)pyridin-2(1H)-one

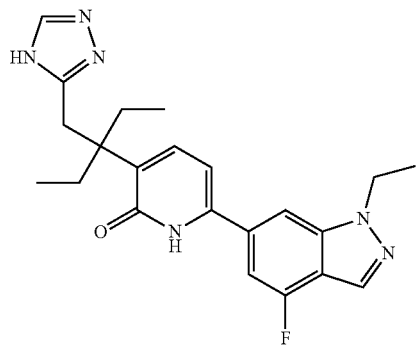 [SMILES: CCn1ncc2c(F)cc(-c3ccc(C(CC)(CC)Cc4nnc[nH]4)c(=O)[nH]3)cc21]

The title compound was prepared according to the procedure as described in Example 99 by condensation followed by demethylation to yield the product as a white solid.

$^1$H NMR (300 MHz, CD$_3$OD) δ: 8.15 (s, 1H), 7.95-8.05 (m, 1H), 7.82 (s, 1H), 7.37 (d, J=7.5 Hz, 1H), 7.17-7.22 (m, 1H), 7.66 (d, J=7.5 Hz, 1H), 4.53-4.60 (m, 2H), 3.48 (s, 2H), 2.04-2.08 (m, 2H), 1.81-1.86 (m, 2H), 1.52-1.57 (m, 3H), 0.85-0.90 (m, 6H). $^{19}$F NMR (300 MHz, CD$_3$OD) δ: −119.24.

Mass spectrum (ESI, m/z): Calculated for C$_{22}$H$_{25}$FN$_6$O, 409.2 [M+H], found 409.1.

Example 109

Compound #26 and #27 and #24

6-(1-ethyl-4-fluoro-1H-indazol-6-yl)-3-(3-(4-methyl-4H-1,2,4-triazol-3-yl)pentan-3-yl)pyridin-2(1H)-one and 6-(1-ethyl-4-fluoro-1H-indazol-6-yl)-3-(3-(1-methyl-1H-1,2,4-triazol-3-yl)pentan-3-yl)pyridin-2(1H)-one and 6-(1-ethyl-4-fluoro-1H-indazol-6-yl)-3-(3-(2-methyl-2H-1,2,4-triazol-3-yl)pentan-3-yl)pyridin-2(1H)-one

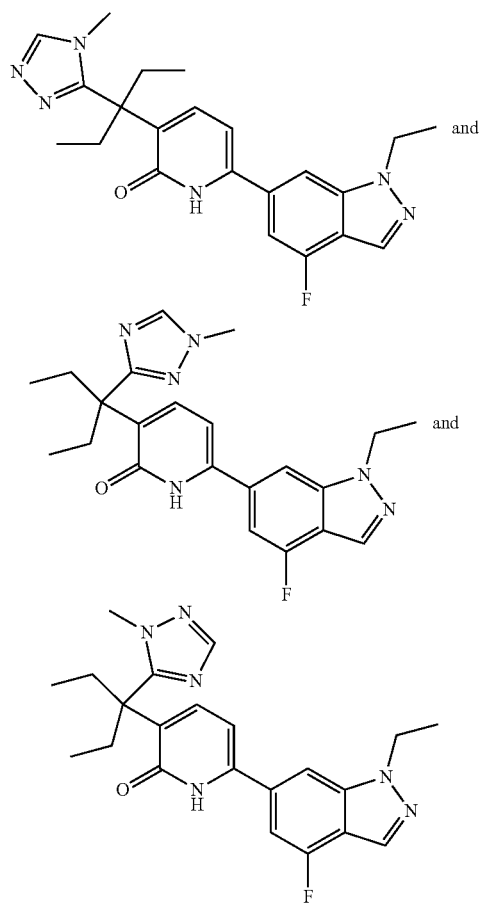

Into a 50-mL round bottle, to a solution of 6-(5-(3-(4H-1,2,4-triazol-3-yl)pentan-3-yl)-6-methoxypyridin-2-yl)-1-ethyl-4-fluoro-1H-indazole (100 mg, 0.245 mmol, 1.00 equiv.) in THF (10 mL), was added NaH (15 mg, 0.367 mmol, 1.50 equiv.) with stirring at 0° C., followed by addition of iodomethane (52 mg, 0.367 mmol, 1.50 equiv.). The reaction mixture was stirred for 2 h at 20° C.

The mixture was quenched by the addition of H$_2$O, extracted with EA, the organic layers was concentrated under vacuum. The residue was purified by TLC with ethyl acetate/petroleum ether (1:2). The collected fractions were combined and concentrated under vacuum to yield 1-ethyl-4-fluoro-6-(6-methoxy-5-(3-(4-methyl-4H-1,2,4-triazol-3-yl)pentan-3-yl)pyridin-2-yl)-1H-indazole as a yellow oil.

Mass spectrum (ESI, m/z): Calculated for C$_{23}$H$_{27}$FN$_6$O, 423.1 [M+H], found 423.3.

The title compounds were then prepared according to the procedure as described in Example 1 step 5 by demethylation to yield 6-(1-ethyl-4-fluoro-1H-indazol-6-yl)-3-(3-(4-methyl-4H-1,2,4-triazol-3-yl)pentan-3-yl)pyridin-2(1H)-one as a white solid. $^1$H NMR (400 MHz, CD$_3$OD) δ 8.28 (s, 1H), 8.13 (s, 1H), 7.82 (s, 1H), 7.76 (d, J=7.6 Hz, 1H), 7.19-7.23 (m, 1H), 6.85 (d, J=7.6 Hz, 1H), 4.51-4.56 (m, 2H), 3.36 (s, 3H), 2.40-2.49 (m, 2H), 2.15-2.25 (m, 2H), 1.51 (t, J=7.2 Hz, 3H), 0.69-0.73 (m, 6H). $^{19}$F NMR (400 MHz, CD$_3$OD) δ −119.08. Mass spectrum (ESI, m/z): Calculated for C$_{22}$H$_{25}$FN$_6$O, 409.2 [M+H], found 409.0.

6-(1-ethyl-4-fluoro-1H-indazol-6-yl)-3-(3-(1-methyl-1H-1,2,4-triazol-3-yl)pentan-3-yl)pyridin-2(1H)-one as a white solid. $^1$H NMR (400 MHz, CD$_3$OD) δ 8.13 (s, 1H), 7.81 (s, 2H), 7.76-7.85 (m, 1H), 7.19-7.23 (m, 1H), 6.85-6.87 (m, 1H), 4.51-4.57 (m, 2H), 3.62 (s, 3H), 2.37-2.46 (m, 2H), 2.14-2.23 (m, 2H), 1.51 (t, J=7.2 Hz, 3H), 0.67-0.74 (m, 6H). $^{19}$F NMR (400 MHz, CD$_3$OD) δ −119.11. Mass spectrum (ESI, m/z): Calculated for C$_{22}$H$_{25}$FN$_6$O, 409.2 [M+H], found 409.0.

and 6-(1-ethyl-4-fluoro-1H-indazol-6-yl)-3-(3-(2-methyl-2H-1,2,4-triazol-3-yl)pentan-3-yl)pyridin-2(1H)-one as a white solid. $^1$H NMR (400 MHz, CD$_3$OD) δ: 8.25 (s, 1H), 8.12-8.13 (m, 1H), 7.76-7.82 (m, 2H), 7.15-7.23 (m, 1H), 6.75-6.84 (m, 1H), 4.51-4.56 (m, 2H), 3.62-3.88 (m, 3H), 2.37-2.46 (m, 2H), 2.06-2.21 (m, 2H), 1.51 (t, J=7.2 Hz, 3H), 0.67-0.77 (m, 6H). $^{19}$F NMR (400 MHz, CD$_3$OD) δ: −119.08. Mass spectrum (ESI, m/z): Calculated for C$_{22}$H$_{25}$FN$_6$O, 409.2 [M+H], found 409.0.

Example 110

Compound #36

3-(3-(4H-1,2,4-triazol-3-yl)pentan-3-yl)-6-(1-ethyl-4-fluoro-1H-indazol-6-yl)-5-fluoropyridin-2(1H)-one

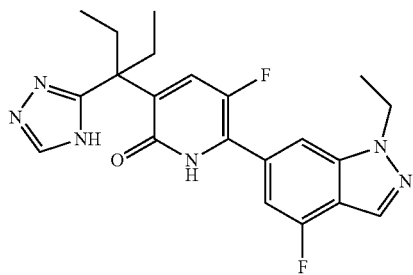 [SMILES: CCn1ncc2c(F)cc(-c3[nH]c(=O)c(C(CC)(CC)c4nnc[nH]4)cc3F)cc21]

Step 1: Methyl 6-chloro-5-fluoro-2-methoxynicotinatel

Into a 250-mL vial maintained with an inert atmosphere of nitrogen, to a solution of methyl 2,6-dichloro-5-fluoronicotinate (2.00 g, 9.100 mmol, 1.00 equiv.) in DCE (50 mL) was added NaOMe (0.74 g, 13.600 mmol, 1.50 equiv.). The reaction mixture was stirred for 16 h at 70° C. The mixture was concentrated under vacuum. The residue was purified by silica gel with ethyl acetate/petroleum ether (8:92). The collected fractions were combined and concentrated under vacuum to methyl 6-chloro-5-fluoro-2-methoxynicotinatel as white solid.

Mass spectrum (ESI, m/z): Calculated for C$_8$H$_7$ClFNO$_3$, 220.0 [M+H], found 220.1.

Step 2: (6-chloro-5-fluoro-2-methoxypyridin-3-yl)methanol

Into a 250-mL round bottle, to a solution of methyl 6-chloro-5-fluoro-2-methoxynicotinatel (2.20 g, 10.000 mmol, 1.00 equiv.) in DCM (100 mL) was added DIBAL (20 mL, 20.000 mmol, 2.00 equiv.) with stirring at −78° C. The mixture was stirred for 2 h at 20° C. The mixture was quenched by the addition of NH$_4$Cl (aq), extracted with DCM, the organic layers was concentrated under vacuum. The residue was purified by silica gel with ethyl acetate/petroleum ether (15:85). The collected fractions were combined and concentrated under vacuum to yield (6-chloro-5-fluoro-2-methoxypyridin-3-yl)methanol as white solid.

Mass spectrum (ESI, m/z): Calculated for C$_7$H$_7$ClFNO$_2$, 192.0 [M+H], found 192.1.

Step 3: 6-chloro-5-fluoro-2-methoxynicotinaldehyde

Into a 250-mL round bottle, to a solution of (6-chloro-5-fluoro-2-methoxypyridin-3-yl)methanol (1.90 g, 9.900 mmol, 1.00 equiv.) in DCM (100 mL), was added DMP (12.60 g, 30.000 mmol, 3.00 equiv.) with stirring at 0° C. The mixture was stirred for 2 h at 20° C. The mixture was quenched by the addition of Na$_2$S$_2$O$_3$ (aq), extracted with DCM, the organic layers was concentrated under vacuum. The residue was purified by silica gel with ethyl acetate/petroleum ether (10:90). The collected fractions were combined and concentrated under vacuum to yield \6-chloro-5-fluoro-2-methoxynicotinaldehyde as yellow oil.

$^1$H NMR (400 MHz, DMSO-d$_6$) δ 10.14 (d, J=2.6 Hz, 1H), 8.18 (d, J=7.7 Hz, 1H), 4.02 (s, 3H).

Step 4: 2-(6-chloro-5-fluoro-2-methoxypyridin-3-yl)acetonitrile

Into a 250-mL round bottle maintained with an inert atmosphere of nitrogen, were placed DME (100 mL), t-BuOK (17 mL, 17.000 mmol, 2.20 equiv.), toluenesulfonylmethyl isocyanide (TosMIC), 1.70 g, 8.700 mmol, 1.10 equiv.) was then added with stirring at −78° C. The mixture was stirred 1 h at −78° C. 6-Chloro-5-fluoro-2-methoxynicotinaldehyde (1.50 g, 7.900 mmol, 1.00 equiv) was added with stirring at −78° C. The resulting solution was stirred 1.5 h at −78° C. Methanol was added and the resulting solution was stirred 16 h at 80° C. The mixture was concentrated under vacuum. The residue was purified by silica gel with ethyl acetate/petroleum ether (8:92). The collected fractions were combined and concentrated under vacuum to yield 2-(6-chloro-5-fluoro-2-methoxypyridin-3-yl)acetonitrile as yellow oil.

Mass spectrum (ESI, m/z): Calculated for C$_8$H$_6$ClFN$_2$O, 201.0 [M+H], found 200.8.

Step 5: 2-ethyl-2-(6-(1-ethyl-5-fluoro-1H-indazol-6-yl)-2-methoxypyridin-3-yl)butanal Into a 100-mL round-bottom flask purged and maintained with an inert atmosphere of nitrogen, to a solution of 2-(6-chloro-5-fluoro-2-methoxypyridin-3-yl)acetonitrile (400 mg, 1.900 mmol, 1.00 equiv.) in DMF (30 mL), was added t-BuOK (10 mL, 9.900 mmol, 5.00 equiv.) with stirring at 0° C. Iodoethane (1.50 g, 9.900 mmol, 5.00 mmol) was then added and the resulting solution was stirred 16 h at 20° C. The resulting solution was quenched by H$_2$O, extracted with EA, and the organic layer was concentrated under vacuum. The residue was purified by silica gel with ethyl acetate/petroleum ether (10:90). The collected fractions were combined and concentrated under vacuum to yield 2-(6-chloro-5-fluoro-2-methoxypyridin-3-yl)-2-ethylbutanenitrile as yellow oil.

$^1$H NMR (400 MHz, CDCl$_3$) δ 7.69 (d, J=8.3 Hz, 1H), 3.95 (s, 3H), 2.24-2.33 (m, 2H), 1.94-2.01 (m, 2H), 0.88 (t, J=7.4 Hz, 6H).

Step 6: 3-(3-(4H-1,2,4-triazol-3-yl)pentan-3-yl)-6-(1-ethyl-4-fluoro-1H-indazol-6-yl)-5-fluoropyridin-2(1H)-one The title compound was prepared according to the procedure as described in Example 99 by condensation followed by demethylation to yield the product as a white solid.

$^1$H NMR (300 MHz, CD$_3$OD) δ: 8.63 (d, J=8.2 Hz, 1H), 8.16 (s, 1H), 7.83 (d, J=11.2 Hz, 2H), 7.27 (d, J=11.2 Hz, 1H), 4.51-4.58 (m, 2H), 2.48-2.55 (m, 2H), 2.14-2.21 (m, 2H), 1.53 (t, J=7.2 Hz, 3H), 0.79 (t, J=7.4 Hz, 6H). $^{19}$F NMR (300 MHz, CD$_3$OD) δ: −77.31, −119.68. Mass spectrum (ESI, m/z): Calculated for C$_{21}$H$_{22}$F$_2$N$_6$O, 413.2 [M+H], found 413.1.

Example 111

Compound #61

3-(2-Methyl-1-(1H-tetrazol-5-yl)propyl)-6-(naphthalen-2-yl)pyridin-2(1H)-one

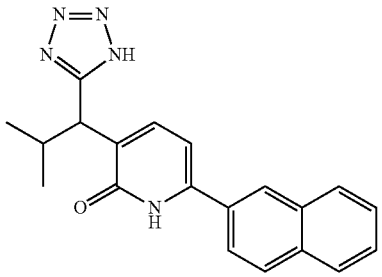 [SMILES: CC(C)C(c1nnn[nH]1)c1ccc(-c2ccc3ccccc3c2)[nH]c1=O]

Step 1: 2-(2-methoxy-6-(naphthalen-2-yl)pyridin-3-yl)-3-methylbutanenitrile

Into a 100-mL round-bottom flask, were placed 2-(2-methoxy-6-(naphthalen-2-yl)pyridin-3-yl)-3-methylbutanamide (40 mg, 0.120 mmol, 1.00 equiv.), DCM (5 mL), 2,2,2-trifluoroacetic anhydride (126 mg, 0.600 mmol, 5 equiv.). The resulting solution was stirred for 5 h at 15° C. The reaction progress was monitored by TLC (PE:EA=6:1). The resulting mixture was concentrated under vacuum. The residue was applied onto a silica gel column with ethyl acetate/petroleum ether (1:6) to yield 2-(2-methoxy-6-(naphthalen-2-yl)pyridin-3-yl)-3-methylbutanenitrile as a light yellow oil.

Mass spectrum (ESI, m/z): Calculated for C$_{21}$H$_{20}$N$_2$O, 317.2 (M+H), found 317.4.

Step 2: 2-methoxy-3-(2-methyl-1-(1H-tetrazol-5-yl)propyl)-6-(naphthalen-2-yl)pyridine Into a 50-mL round-bottom flask, were placed 2-(2-methoxy-6-(naphthalen-2-yl)pyridin-3-yl)-3-methylbutanenitrile (20 mg, 0.063 mmol, 1.00 equiv.), toluene (5 mL), azidotrimethylsilane (36 mg, 0.312 mmol, 5 equiv.), dibutylstannanone (78 mg, 0.313 mmol, 5 equiv). The resulting solution was stirred for overnight at 110° C. The reaction progress was monitored by LCMS. The reaction was then quenched by the addition of water (10 mL). The resulting solution was extracted with ethyl acetate (3×30 mL and the organic layers combined. The resulting mixture was washed with brine (1×30 mL). The mixture was dried over anhydrous sodium sulfate. The solids were filtered out. The resulting mixture was concentrated under vacuum. The residue was applied onto a silica gel column with ethyl acetate/petroleum ether (1:1) to yield 2-methoxy-3-(2-methyl-1-(1H-tetrazol-5-yl)propyl)-6-(naphthalen-2-yl)pyridine as a light yellow oil.

Mass spectrum (ESI, m/z): Calculated for C$_{21}$H$_{21}$N$_5$O, 360.2 (M+H), found 360.2.

Step 3: 3-(2-methyl-1-(1H-tetrazol-5-yl)propyl)-6-(naphthalen-2-yl)pyridin-2(1H)-one Into a 50-mL round-bottom flask, were placed 2-methoxy-3-(2-methyl-1-(1H-tetrazol-5-yl)propyl)-6-(naphthalen-2-yl)pyridine (20 mg, 0.056 mmol, 1.00 equiv.), CH$_3$CN (5 mL), sodium iodide (42 mg, 0.280 mmol, 5 equiv.). To the mixture was then added chlorotrimethylsilane (30 mg, 0.276 mmol, 5.00 equiv.) dropwise with stirring at 0° C. The resulting solution was stirred for 3 h at 25° C. The reaction progress was monitored by LCMS. The reaction was then quenched by the addition of water (10 mL). The resulting solution was extracted with ethyl acetate (3×20 mL) and the organic layers combined. The resulting mixture was washed with brine (1×20 mL). The mixture was dried over anhydrous sodium sulfate. The solids were filtered out. The resulting mixture was concentrated under vacuum. The residue was purified by by Prep-HPLC with the following conditions (1#-Waters 2767-5): Column, SunFire Prep C18, 5 um, 19*100 mm; mobile phase, Water of 0.05% trifluoroacetic acid and CH$_3$CN (20% CH$_3$CN up to 60% in 10 min, up to 100% in 2 min, down to 50% in 2 min; Detector, 254 nm to yield 3-(2-methyl-1-(1H-tetrazol-5-yl)propyl)-6-(naphthalen-2-yl)pyridin-2(1H)-one as a light yellow solid.

$^1$H NMR (300 MHz, CD$_3$OD) δ: 8.22 (s, 1H), 7.90-8.01 (m, 3H), 7.84 (d, J=7.5 Hz, 1H), 7.75-7.78 (m, 1H), 7.56-7.59 (m, 2H), 6.80 (d, J=7.5 Hz, 1H), 4.42 (d, J=10.2 Hz, 1H), 2.64-2.69 (m, 1H), 1.02 (d, J=6.6 Hz, 3H), 0.92 (d, J=6.6 Hz, 3H). Mass spectrum (ESI, m/z): Calculated for C$_{20}$H$_{19}$N$_5$O, 346.2 (M+H), found 346.1.

Example 112

Compound #270

6-(8-Fluoronaphthalen-2-yl)-3-(3-methyl-2-(1H-tetrazol-5-yl)butyl)pyridin-2(1H)-one

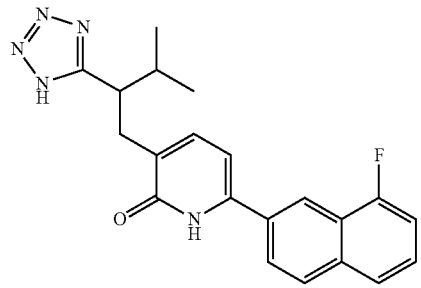 [SMILES: CC(C)C(Cc1ccc(-c2ccc3cccc(F)c3c2)[nH]c1=O)c1nnn[nH]1]

Step 1: 2-((6-(8-fluoronaphthalen-2-yl)-2-methoxy-pyridin-3-yl)methyl)-3-methyl butanenitrile Into a 50 mL round-bottom flask were placed a solution of 2-((6-(8-fluoronaphthalen-2-yl)-2-methoxypyridin-3-yl)methyl)-3-methylbutanamide (150 mg, 0.409 mmol, 1 equiv.) in DCM (5 mL). Trifluoroacetic anhydride (4 mL) was then added. The reaction mixture was stirred for 2 h at room temperature. The reaction was successful and confirmed by LCMS. The mixture was concentrated under vacuum. The residue was applied onto a silica gel column with $CH_2Cl_2$/MeOH (5/1) to yield 2-((6-(8-fluoronaphthalen-2-yl)-2-methoxypyridin-3-yl)methyl)-3-methylbutanenitrile as light solid.

Mass spectrum (ESI, m/z): Calculated for $C_{22}H_{21}FN_2O$, 349.2 (M+H), found 349.2.

Step 2: 6-(8-fluoronaand phthalen-2-yl)-3-(3-methyl-2-(1H-tetrazol-5-yl)butyl)pyridin-2(1H)-one The title compound was prepared according to the procedure as described in Example 111 by condensation of 2-((6-(8-fluoronaphthalen-2-yl)-2-methoxypyridin-3-yl)methyl)-3-methyl butanenitrile by azidotrimethylsilane and dibutylstannanone followed by demethylation of 6-(8-fluoronaphthalen-2-yl)-2-methoxy-3-(3-methyl-2-(1H-tetrazol-5-yl)butyl)pyridine to yield the product as a white solid.

$^1$H NMR (400 MHz, $CD_3OD$) δ: 8.33 (s,1H), 8.02 (d, J=9.2 Hz, 1H), 7.72-7.77 (m, 2H), 7.49-7.55 (m, 1H), 7.24-7.29 (m, 1H), 7.18 (d, J=6.8 Hz, 1H), 6.54 (d, J=7.2 Hz,1H), 3.43-3.49 (m, 1H), 3.25-3.26 (m, 1H), 2.84-2.90 (m, 1H), 2.11-2.17 (m, 1H), 1.08 (d, J=6.8 Hz, 3H), 0.88 (d, J=6.8 Hz, 3H). $^{19}$F NMR (400 MHz, $CD_3OD$) δ: –124.55. Mass spectrum (ESI, m/z): Calculated for $C_{21}H_{20}FN_5O$, 378.2 (M+H), found 378.2.

Example 113

Compound #3

3-(3-(1H-tetrazol-5-yl)pentan-3-yl)-6-(1-ethyl-4-fluoro-1H-indazol-6-yl)pyridin-2(1H)-one

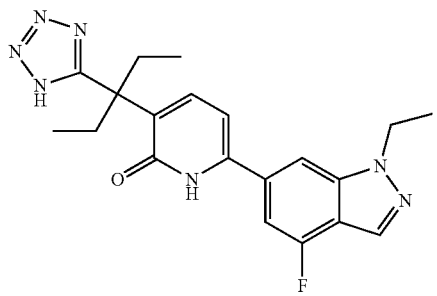 [SMILES: CCn1ncc2c(F)cc(-c3ccc(C(CC)(CC)c4nnn[nH]4)c(=O)[nH]3)cc21]

The title compound was prepared according to the procedure as described in Example 111 by condensation followed by demethylation to yield the product as a white solid.

$^1$H NMR (300 MHz, $CD_3OD$) δ 8.16 (s, 1H), 7.79-7.82 (m, 2H), 7.21 (d, J=10.8 Hz, 1H), 6.84 (d, J=7.2 Hz, 1H), 4.52-4.59 (m, 2H), 2.48-2.55 (m, 2H), 2.15-2.22 (m, 2H), 1.53 (t, J=7.2 Hz, 3H), 0.72-0.77 (m, 6H). $^{19}$F NMR (300 MHz, $CD_3OD$) 5-119.10. Mass spectrum (ESI, m/z): Calculated for $C_{20}H_{22}FN_7O$, 396.2 [M+H], found 396.2.

Example 114

Compound #70

6-(8-fluoronaphthalen-2-yl)-3-(3-methyl-1-(2H-tetrazol-5-yl)butan-2-yl)pyridin-2(1H)-one

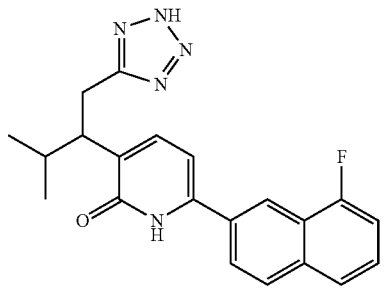 [SMILES: CC(C)C(Cc1nn[nH]n1)c1ccc(-c2ccc3cccc(F)c3c2)[nH]c1=O]

The title compound was prepared according to the procedure as described in Example 111 by condensation followed by demethylation to yield the product as a yellow oil.

$^1$H NMR (400 MHz, $CD_3OD$) δ: 8.40 (s, 1H), 8.05-8.07 (m, 1H), 7.82 (d, J=8.8 Hz, 1H), 7.77 (d, J=8.8 Hz, 1H), 7.53-7.58 (m, 1H), 7.41 (d, J=7.2 Hz, 1H), 7.27-7.32 (m, 1H), 6.70 (d, J=7.2 Hz, 1H), 3.41-3.52 (m, 1H), 3.32-3.38 (m, 1H), 3.13-3.19 (m, 1H), 2.21-2.28 (m, 1H), 1.15 (d, J=6.8 Hz, 3H), 0.96 (d, J=6.8 Hz, 3H). $^{19}$F NMR (400 MHz, $CD_3OD$) δ: –77.04, –124.50. Mass spectrum (ESI, m/z): Calculated For $C_{22.76}H_{20.88}F_{3.64}N_5O_{2.76}$, 378.2 (M–0.88$CF_3COOH$+H), found 378.1.

Example 115

Compound #42

3-(3-(1,3,4-oxadiazol-2-yl)pentan-3-yl)-6-(1-ethyl-4-fluoro-1H-indazol-6-yl)pyridin-2(1H)-one

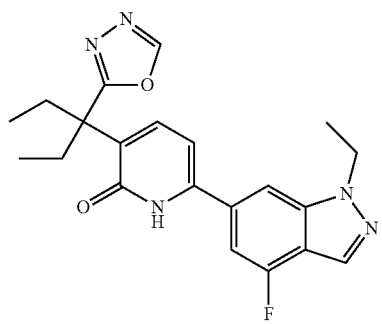 [SMILES: CCn1ncc2c(F)cc(-c3ccc(C(CC)(CC)c4nnco4)c(=O)[nH]3)cc21]

Step 1: 2-ethyl-2-(6-(1-ethyl-4-fluoro-1H-indazol-6-yl)-2-oxo-1,2-dihydropyridin-3-yl) butanoic acid Into a 50 mL round-bottom flask were placed a solution of ethyl 2-ethyl-2-(6-(1-ethyl-4-fluoro-1H-indazol-6-yl)-2-methoxypyridin-3-yl)butanoate (500 mg, 1.209 mmol, 1.00 equiv.) in $CH_3COOH$ (20 mL). HCl (10 mL) was added. The reaction was stirred overnight at 100° C. and monitored by LCMS. The mixture was concentrated under vacuum and extracted with ethyl acetate (3×30 mL). The organic layers were combined, washed with sodium carbonate (aq.) and brine, dried and concentrated under vacuum to yield 2-ethyl-2-(6-(1-ethyl-4-fluoro-1H-indazol-6-yl)-2-oxo-1,2-dihydropyridin-3-yl)butanoic acid as a yellow solid.

Mass spectrum (ESI, m/z): Calculated for C20H22FN3O3, 372.2 [M+H], found 372.3.

Step 2: 2-ethyl-2-(6-(1-ethyl-4-fluoro-1H-indazol-6-yl)-2-oxo-1,2-dihydropyridin-3-yl)butanehydrazide Into a 50 ml flask were placed a solution of 2-ethyl-2-(6-(1-ethyl-4-fluoro-1H-indazol-6-yl)-2-oxo-1,2-dihydropyridin-3-yl)butanoic acid (200 mg, 0.538 mmol, 1.00 equiv.) in DCM/DMF (5 mL/3 mL), and HATU (409 mg, 1.077 mmol, 2.00 equiv.), EDCl (206 mg, 1.077 mmol, 2.00 equiv.), DIPEA (139 mg, 1.077 mmol, 2.00 equiv.) were added. The mixture was stirred for 30 min, and NH2NH2H2O (135 mg, 2.692 mmol, 5.00 equiv.) was added. The mixture was stirred overnight at room temperature. The mixture was extracted with ethyl acetate (3×30 mL). The organic layers were combined, washed with sodium carbonate (aq.) and brine, dried and concentrated under vacuum to yield 2-ethyl-2-(6-(1-ethyl-4-fluoro-1H-indazol-6-yl)-2-oxo-1,2-dihydropyridin-3-yl)butanehydrazide as a yellow solid.

Mass spectrum (ESI, m/z): Calculated for C20H24FN5O2, 386.2 [M+H], found 386.2.

Step 3: 3-(3-(1,3,4-oxadiazol-2-yl)pentan-3-yl)-6-(1-ethyl-4-fluoro-1H-indazol-6-yl)pyridin-2(1H)-one Into a 50 ml round-bottom flask were placed a solution of 2-ethyl-2-(6-(1-ethyl-4-fluoro-1H-indazol-6-yl)-2-oxo-1,2-dihydropyridin-3-yl)butanehydrazide (50 mg, 0.130 mmol, 1.00 equiv.) in EtOH (5 ml).

Triethoxymethane (96 mg, 0.648 mmol, 5.00 equiv.), NH4Cl (35 mg, 0.654 mmol, 5.00 equiv.) was added. The mixture was stirred overnight at 80° C. The reaction was monitored by LCMS. The reaction was concentrated under vacuum. The residue was dissolved in DMF. The solution was purified by Prep-HPLC with the following conditions: Column, SunFire Prep C18, 5 um, 19*100 mm; mobile phase, Water of 0.05% NH4HCO3 and CH3CN (28% CH3CN up to 50% in 10 min, up to 100% in 2 min, down to 28% in 2 min; Detector, 220 nm, 254 nm to yield 3-(3-(1,3,4-oxadiazol-2-yl)pentan-3-yl)-6-(1-ethyl-4-fluoro-1H-indazol-6-yl)pyridin-2(1H)-one as a white solid.

1H NMR (300 MHz, CD3OD) δ: 8.83 (s, 1H), 8.16 (s, 1H), 7.74-7.82 (m, 2H), 7.19-7.23 (m, 1H), 6.83 (d, J=7.5 Hz, 1H), 4.52-4.60 (m, 2H), 2.38-2.55 (m, 2H), 2.10-2.25 (m, 2H), 1.50-1.60 (m, 3H), 0.75-0.85 (m, 6H). 19F NMR (300 MHz, CD3OD) δ: –119.085. Mass spectrum (ESI, m/z): Calculated for C21H22FN5O2, 396.2 [M+H], found 396.2.

Example 116

Compound #38

6-(1-ethyl-4-fluoro-1H-indazol-6-yl)-3-(3-(5-isopropyl-1,3,4-oxadiazol-2-yl)pentan-3-yl)pyridin-2(1H)-one

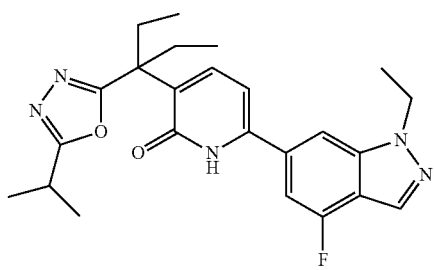 [SMILES: CCn1ncc2c(F)cc(-c3ccc(C(CC)(CC)c4nnc(C(C)C)o4)c(=O)[nH]3)cc21]

Into an 8 ml tube were placed a solution of 2-methylpropanethioamide (12 mg, 0.116 mmol, 1.50 equiv.) in CH3CN (5 mL). Iodomethane (22 mg, 0.155 mmol, 2.00 equiv.) was added. The reaction was stirred for 1.5 h at 50° C.

The mixture was concentrated under vacuum. The residue was dissolved in DMF (5 mL), and 2-ethyl-2-(6-(1-ethyl-4-fluoro-1H-indazol-6-yl)-2-oxo-1,2-dihydropyridin-3-yl)butanehydrazide was added. The reaction was stirred overnight at 140° C. The reaction was monitored by LCMS. The mixture was extracted with ethyl acetate (3×20 mL). The organic layers were combined, washed with sodium carbonate (aq.) and brine, dried and concentrated under vacuum. The residue was dissolved in DMF (2 mL). The solution was purified by Prep-HPLC with the following conditions: Column, SunFire Prep C18, 5 um, 19*100 mm; mobile phase, Water of 0.05% NH4HCO3 and CH3CN (35% CH3CN up to 40% in 10 min, up to 100% in 2 min, down to 30% in 2 min; Detector, 220 nm, 254 nm to yield 6-(1-ethyl-4-fluoro-1H-indazol-6-yl)-3-(3-(5-isopropyl-1,3,4-oxadiazol-2-yl)pentan-3-yl)pyridin-2(1H)-one as a white solid.

1H NMR (400 MHz, CD3OD) δ: 8.13 (s, 1H), 7.80 (s, 1H), 7.71 (d, J=7.6 Hz, 1H), 7.15-7.22 (m, 1 H), 6.80 (d, J=7.2 Hz, 1H), 4.48-4.58 (m, 2H), 3.10-3.20 (m, 1H), 2.30-2.45 (m, 2H), 2.05-2.15 (m, 2H), 1.48-1.53 (m, 3H), 1.35 (s, 6H), 0.72-0.80 (m, 6H). 19F NMR (400 MHz, CD3OD) δ: –119.1.

Mass spectrum (ESI, m/z): Calculated for C24H28FN5O2, 438.2 [M+H], found 438.2.

Example 117

Compound #271

6-(1-ethyl-4-fluoro-1H-indazol-6-yl)-3-(3-(5-methyl-1,3,4-oxadiazol-2-yl)pentan-3-yl)pyridin-2(1H)-one

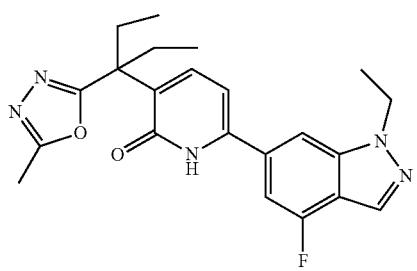 [SMILES: CCn1ncc2c(F)cc(-c3ccc(C(CC)(CC)c4nnc(C)o4)c(=O)[nH]3)cc21]

The title compound was prepared according to the procedure as described in Example 115 by condensation followed by demethylation to yield the product as white solid.

1H NMR (300 MHz, CD3OD) δ: 8.15 (s, 1H), 7.81 (s, 1H), 7.73 (d, J=7.5 Hz, 1H), 7.18-7.22 (m, 1 H), 6.81 (d, J=7.2 Hz, 1H), 4.45-4.60 (m, 2H), 2.49 (s, 3H), 2.30-2.45 (m, 2H), 2.01-2.15 (m, 2H), 1.45-1.55 (m, 2H), 0.71-0.80 (m, 6H). 19F NMR (300 MHz, CD3OD) δ: –119.1. Mass spectrum (ESI, m/z): Calculated for C22H24FN5O2: 410.2 [M–NH2], found: 410.2.

Example 118

Compound #45

6-(1-ethyl-4-fluoro-1H-indazol-6-yl)-3-(3-(5-(trifluoromethyl)-1,3,4-oxadiazol-2-yl)pentan-3-yl)pyridine-2(1H)-one

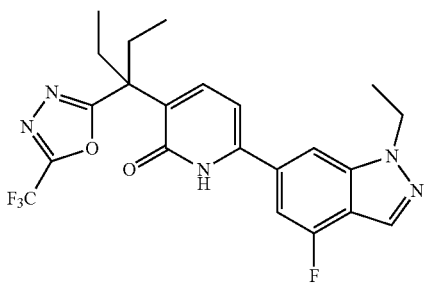 [SMILES: CCn1ncc2c(F)cc(-c3ccc(C(CC)(CC)c4nnc(C(F)(F)F)o4)c(=O)[nH]3)cc21]

Into a 25 ml flask were placed a solution of 2,2,2-trifluoroethanethioamide (50 mg, 0.388 mmol, 1.50 equiv.) in DCM (10 mL). Methyl trifluoromethanesulfonate (85 mg, 0.517 mmol, 2.00 equiv.) was added. The reaction was stirred for 3 h at 25° C. The mixture was concentrated under vacuum. The residue was dissolved in DMF (5 mL), and 2-ethyl-2-(6-(1-ethyl-4-fluoro-1H-indazol-6-yl)-2-oxo-1,2-dihydropyridin-3-yl)butanehydrazide (100 mg, 0.259 mmol, 1.00 equiv.) was added. The reaction was stirred for 2 h at 140° C. The reaction was monitored by LCMS. The mixture was concentrated under vacuum. The residue was dissolved in DMF (2 mL). The solution was purified by Prep-HPLC with the following conditions: Column, SunFire Prep C18, 5 um, 19*100 mm; mobile phase, Water of 0.05% NH$_4$HCO$_3$ and CH$_3$CN (35% CH$_3$CN up to 60% in 10 min, up to 100% in 2 min, down to 35% in 2 min; Detector, 220 nm, 254 nm to yield 6-(1-ethyl-4-fluoro-1H-indazol-6-yl)-3-(3-(5-(trifluoromethyl)-1,3,4-oxadiazol-2-yl)pentan-3-yl)pyridin-2(1H)-one as a white solid.

$^1$H NMR (300 MHz, DMSO-d$_6$) δ: 12.08 (s, 1H), 8.23 (s, 1H), 8.07 (s, 1H), 7.69 (d, J=7.5 Hz, 1H), 7.37 (d, J=11.4 Hz, 1H), 6.80-6.90 (m, 1H), 4.40-4.60 (m, 2H), 2.18-2.35 (m, 2H), 2.00-2.13 (m, 2H), 1.35-1.45 (m, 3H), 0.65-0.80 (m, 6H). $^{19}$F NMR (300 MHz, DMSO-d$_6$) δ: −64.365, −117.608. Mass spectrum (ESI, m/z): Calculated for C$_{22}$H$_{21}$F$_4$N$_5$O$_2$, 464.2 [M+H], found 464.1.

Example 119

Compound #48

3-(3-(5-(dimethylamino)-1,3,4-thiadiazol-2-yl)pentan-3-yl)-6-(1-ethyl-4-fluoro-1H-indazol-6-yl)pyridin-2(1H)-one

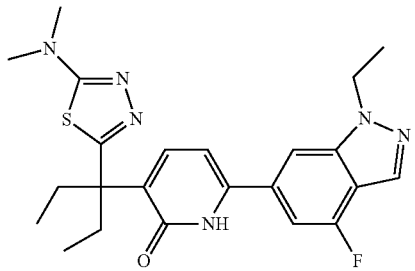 [SMILES: CCn1ncc2c(F)cc(-c3ccc(C(CC)(CC)c4nnc(N(C)C)s4)c(=O)[nH]3)cc21]

Step 1: (E)-2-(2-ethyl-2-(6-(1-ethyl-4-fluoro-1H-indazol-6-yl)-2-methoxypyridin-3-yl)butylidene)-N,N-dimethylhydrazinecarbothioamide Into a 100-mL round-bottom flask, were placed 2-ethyl-2-(6-(1-ethyl-4-fluoro-1H-indazol-6-yl)-2-methoxypyridin-3-yl)butanal (80 mg, 0.217 mmol, 1.00 equiv.), N,N-dimethylhydrazinecarbothioamide (39 mg, 0.325 mmol, 1.00 equiv.), MeOH (5 mL), AcOH (0.5 mL), H$_2$O (0.5 mL). The reaction was stirred overnight at 50° C. The reaction progress was monitored by TLC (PE:EA=1:1). The resulting solution concentrated. The residue was purified by silica gel chromatography (0-50% EtOAc/petroleum ether) to yield (E)-2-(2-ethyl-2-(6-(1-ethyl-4-fluoro-1H-indazol-6-yl)-2-methoxypyridin-3-yl)butylidene)-N,N-dimethylhydrazinecarbothioamide as a light yellow oil.

Mass spectrum (ESI, m/z): Calculated for C$_{24}$H$_{31}$FN$_6$OS, 471.2 [M+H], found. 471.2.

Step 2: 5-(3-(6-(1-ethyl-4-fluoro-1H-indazol-6-yl)-2-methoxypyridin-3-yl)pentan-3-yl)-N,N-dimethyl-1,3,4-thiadiazol-2-amine Into a 100-mL round-bottom flask were placed (E)-2-(2-ethyl-2-(6-(1-ethyl-4-fluoro-1H-indazol-6-yl)-2-methoxypyridin-3-yl)butylidene)-N,N-dimethylhydrazinecarbothioamide (80 mg, 0.170 mmol, 1.00 equiv.), I$_2$ (65 mg, 0.255 mmol, 1.50 equiv.), K$_2$CO$_3$ (70 mg, 0.510 mmol, 3.00 equiv.), 1,4-dioxane (8 mL). The reaction was purged with an inert atmosphere of nitrogen and was stirred 4 h at 90° C. The reaction progress was monitored by TLC (DCM; MeOH=10:1). The resulting solution concentrated. The residue was purified by silica gel chromatography (0-20% DCM/MeOH) to yield 5-(3-(6-(1-ethyl-4-fluoro-1H-indazol-6-yl)-2-methoxypyridin-3-yl)pentan-3-yl)-N,N-dimethyl-1,3,4-thiadiazol-2-amine as a light yellow oil.

Mass spectrum (ESI, m/z): Calculated for C$_{24}$H$_{29}$FN$_6$OS, 469.2 [M+H], found. 469.1.

Step 3: 3-(3-(5-(dimethylamino)-1,3,4-thiadiazol-2-yl)pentan-3-yl)-6-(1-ethyl-4-fluoro-1H-indazol-6-yl)pyridin-2(1H)-one The title compound was prepared according to the procedure as described in Example 1 step 5 by demethylation with TMSCl/NaI to yield the product as an off-white solid.

$^1$H NMR (300 MHz, CD$_3$OD) δ: 8.14 (s, 1H), 7.80 (s, 1H), 7.73 (d, J=7.5 Hz, 1H), 7.20 (d, J=11.1 Hz, 1H), 6.78 (d, J=7.2 Hz, 1H), 4.51-4.58 (m, 2H), 3.10 (s, 6H), 2.50-2.57 (m, 2H), 2.05-2.15 (m, 2H), 1.50-1.55 (m, 3H), 0.78-0.83 (m, 6H). $^{19}$F NMR (300 MHz, CD$_3$OD) δ: −119.14. Mass spectrum (ESI, m/z): Calculated for C$_{23}$H$_{27}$FN$_6$OS, 455.2 [M+H], found 455.3.

Example 120

Compound #52

3-(3-(5-amino-1,3,4-thiadiazol-2-yl)pentan-3-yl)-6-(1-ethyl-4-fluoro-1H-indazol-6-yl)pyridin-2(1H)-one

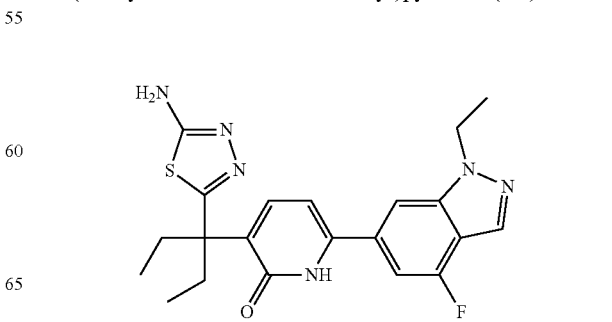

The title compound was prepared according to the procedure as described in Example 119 by condensation followed by demethylation to yield the product as a white solid.

$^1$H NMR (400 MHz, CD$_3$OD) δ: 8.14 (s, 1H), 7.78-7.80 (m, 2H), 7.17-7.20 (m 1H), 6.81 (d, J=6.6 Hz, 1H), 4.51-4.56 (m, 2H), 2.44-2.53 (m, 2H), 2.00-2.09 (m, 2H), 1.50-1.53 (m, 3H), 0.80-0.84 (m, 6H). $^{19}$F NMR (400 MHz, CD$_3$OD) δ: −77.16, −118.93. Mass spectrum (ESI, m/z): Calculated for C$_{22.04}$H$_{23.52}$F$_{2.56}$N$_6$O$_{2.04}$S, 427.2 [M−0.52CF$_3$COOH+H], found 427.3.

Example 121

Compound #57

3-(3-(5-(dimethylamino)-1,3,4-oxadiazol-2-yl)pentan-3-yl)-6-(1-ethyl-4-fluoro-1H-indazol-6-yl)pyridin-2(1H)-one

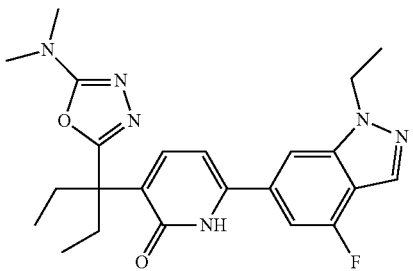 [SMILES: CCn1ncc2c(F)cc(-c3ccc(C(CC)(CC)c4nnc(N(C)C)o4)c(=O)[nH]3)cc21]

Step 1: N,N-dimethylhydrazinecarboxamide

Into a 100-mL round-bottom flask, to a stirred solution of hydrazine hydrate (441 mg, 8.809 mmol, 1.00 equiv.) in EtOH (20 mL) was added a solution of dimethylcarbamyl chloride (947 mg, 8.809 mmol, 1.00 equiv.) in Et$_2$O (10 mL) dropwise over 18 min in an ice-bath. The resulting solution was stirred in the ice-bath for 1 h. The precipitate was removed by vacuum filtration and the filtrated was concentrated to yield a white solid.

Step 2: (E)-2-(2-ethyl-2-(6-(1-ethyl-4-fluoro-1H-indazol-6-yl)-2-methoxypyridin-3-yl)butylidene)-N,N-dimethylhydrazinecarboxamide Into a 100-mL round-bottom flask, were placed 2-ethyl-2-(6-(1-ethyl-4-fluoro-1H-indazol-6-yl)-2-methoxypyridin-3-yl)butanal (80 mg, 0.217 mmol, 1.00 equiv.), N,N-dimethylhydrazinecarboxamide (33 mg, 0.325 mmol, 1.00 equiv.), MeOH (5 mL), AcOH (0.5 mL), H$_2$O (0.5 mL). The reaction was stirred overnight at 50° C. The reaction progress was monitored by TLC (PE:EA=1:1). The resulting solution concentrated. The residue obtained was purified by silica gel chromatography (0-50% EtOAc/petroleum ether) to yield (E)-2-(2-ethyl-2-(6-(1-ethyl-4-fluoro-1H-indazol-6-yl)-2-methoxypyridin-3-yl)butylidene)-N,N-dimethylhydrazine carboxamide as a light yellow oil.

Mass spectrum (ESI, m/z): Calculated for C$_{24}$H$_{31}$FN$_6$O$_2$, 455.2 [M+H], found 0.455.4.

Step 3: 5-(3-(6-(1-ethyl-4-fluoro-1H-indazol-6-yl)-2-methoxypyridin-3-yl)pentan-3-yl)-N,N-dimethyl-1,3,4-oxadiazol-2-amine Into a 100-mL round-bottom flask were placed (E)-2-(2-ethyl-2-(6-(1-ethyl-4-fluoro-1H-indazol-6-yl)-2-methoxypyridin-3-yl)butylidene)-N,N-dimethylhydrazinecarboxamide (50 mg, 0.110 mmol, 1.00 equiv.), I$_2$ (42 mg, 0.165 mmol, 1.50 equiv.), K$_2$CO$_3$ (46 mg, 0.330 mmol, 3.00 equiv.), 1,4-dioxane (8 mL). The reaction was purged with an inert atmosphere of nitrogen and was stirred 4 h at 90° C. The reaction progress was monitored by TLC (DCM; MeOH=10:1). The resulting solution concentrated. The residue obtained was purified by silica gel chromatography (0-20% DCM/MeOH) to yield 5-(3-(6-(1-ethyl-4-fluoro-1H-indazol-6-yl)-2-methoxypyridin-3-yl)pentan-3-yl)-N,N-dimethyl-1,3,4-oxadiazol-2-amine as a light yellow oil.

Mass spectrum (ESI, m/z): Calculated for C$_{24}$H$_{29}$FN$_6$O$_2$, 453.2 [M+H], found 453.1.

Step 4: 3-(3-(5-(dimethylamino)-1,3,4-oxadiazol-2-yl)pentan-3-yl)-6-(1-ethyl-4-fluoro-1H-indazol-6-yl)pyridin-2(1H)-one The title compound was prepared according to the procedure as described in Example 1 step 5 by demethylation with TMSCl/NaI to yield the product as a white solid.

$^1$H NMR (300 MHz, CD$_3$OD) δ: 8.10 (s, 1H), 7.78 (s, 1H), 7.64 (d, J=7.5 Hz, 1H), 7.16 (d, J=10.8 Hz, 1H), 6.75 (d, J=7.5 Hz, 1H), 4.47-4.55 (m, 2H), 2.98 (s, 6H), 2.27-2.37 (m, 2H), 2.00-2.12 (m, 2H), 1.46-1.51 (m, 3H), 0.74-0.79 (m, 6H). $^{19}$F NMR (300 MHz, CD$_3$OD) δ: −119.11. Mass spectrum (ESI, m/z): Calculated for C$_{23}$H$_{27}$FN$_6$O$_2$, 439.2 [M+H], found 439.1.

Example 122

Compound #51

3-(3-(5-amino-1,3,4-oxadiazol-2-yl)pentan-3-yl)-6-(1-ethyl-4-fluoro-1H-indazol-6-yl)pyridin-2(1H)-one

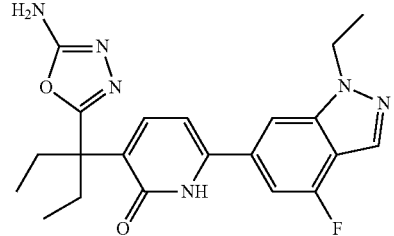 [SMILES: CCn1ncc2c(F)cc(-c3ccc(C(CC)(CC)c4nnc(N)o4)c(=O)[nH]3)cc21]

Into a 50-mL round-bottom flask, were placed 2-ethyl-2-(6-(1-ethyl-4-fluoro-1H-indazol-6-yl)-2-hydroxypyridin-3-yl)butanehydrazide (100 mg, 0.259 mmol, 1.00 equiv.), methyl carbamimidothioate (47 mg, 0.519 mmol, 2.00 equiv.), pyridine (5 mL). The reaction was stirred 2 h at 120° C. The reaction progress was monitored by LCMS. The resulting solution concentrated. The residue obtained was purified by silica gel chromatography (0-20% DCM/MeOH) yield residue. The residue was purified by Prep-HPLC with the following conditions (1#-Waters 2767-5): Column, SunFire Prep C18, 5 um, 19*100 mm; mobile phase, Water of 0.05% NH$_4$HCO$_3$ and CH$_3$CN (20% CH$_3$CN up to 50% in 10 min, up to 100% in 2 min, down to 20% in 2 min; Detector, 254 nm to yield 3-(3-(5-amino-1,3,4-oxadiazol-2-yl)pentan-3-yl)-6-(1-ethyl-4-fluoro-1H-indazol-6-yl)pyridin-2(1H)-one as a white solid.

$^1$H NMR (400 MHz, CD$_3$OD) δ: 8.11 (s, 2H), 7.84-7.90 (m, 2H), 7.55 (d, J=12.0 Hz, 1H), 4.53-4.59 (m, 2H), 1.98-2.07 (m, 4H), 1.51-1.55 (m, 3H), 1.07-1.12 (m, 6H). $^{19}$F NMR (400 MHz, CD$_3$OD) δ: −120.12. Mass spectrum (ESI, m/z): Calculated for C$_{21}$H$_{23}$FN$_6$O$_2$, 411.2 [M+H], found. 411.2.

Example 123

Compound #53

3-(3-(5-ethyl-1,3,4-oxadiazol-2-yl)pentan-3-yl)-6-(1-ethyl-4-fluoro-1H-indazol-6-yl)pyridin-2(1H)-one

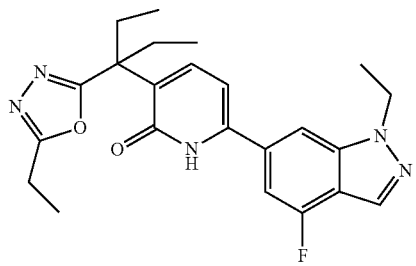 [SMILES: CCc1nnc(C(CC)(CC)c2ccc(-c3cc(F)c4cnn(CC)c4c3)[nH]c2=O)o1]

The title compound was prepared according to the procedure as described in Example 121 by condensation followed by demethylation with TMSCl/NaI to yield the product as a light yellow solid.

$^1$H NMR (300 MHz, CD$_3$OD) δ: 8.10 (s, 1H), 7.77 (s, 1H), 7.69 (d, J=7.5 Hz, 1H), 7.14-7.18 (m, 1 H), 6.77 (d, J=7.5 Hz, 1H), 4.45-4.55 (m, 2H), 2.75-2.85 (m, 2H), 2.28-2.43 (m, 2H), 2.03-2.15 (m, 2H), 1.45-1.52 (m, 3H), 1.25-1.31 (m, 3H), 0.68-0.80 (m, 6H). $^{19}$F NMR (300 MHz, CD$_3$OD) δ: −119.084. Mass spectrum (ESI, m/z): Calculated for C$_{23}$H$_{26}$FN$_5$O$_2$, 424.2[M+H], found 424.2.

Example 124

Compound #30

6-(1-ethyl-4-fluoro-1H-indazol-6-yl)-3-(3-(oxazol-2-yl)pentan-3-yl)pyridin-2(1H)-one

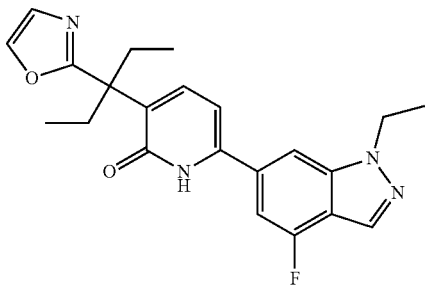 [SMILES: CCn1ncc2c(F)cc(-c3ccc(C(CC)(CC)c4ncco4)c(=O)[nH]3)cc21]

Into a 50-mL round-bottom flask, were placed 2-ethyl-2-(6-(1-ethyl-4-fluoro-1H-indazol-6-yl)-2-methoxypyridin-3-yl)butanamide (15 mg, 0.039 mmol, 1.00 equiv.), vinylene carbonate (4 mg, 0.043 mmol, 1.10 equiv.), PPA (2 mL). The resulting solution was stirred 3.0 h at 165° C. The reaction was then quenched by the addition of H$_2$O, extracted with EA, the organic layers was concentrated under vacuum, then purified by Prep-HPLC with the following conditions (16#-Waters 2767-5): Column, SunFire Prep C18,19*100 mm, 5 um; mobile phase, Water with 0.05% NH$_4$HCO$_3$ and CH$_3$CN (20% CH$_3$CN up to 42% in 10 min, up to 100% in 0.1 min); Detector, UV 220 & 254 nm to yield 6-(1-ethyl-4-fluoro-1H-indazol-6-yl)-3-(3-(oxazol-2-yl)pentan-3-yl)pyridin-2(1H)-one as a white solid.

$^1$H NMR (400 MHz, CD$_3$OD) δ 8.13 (s, 1H), 7.77 (d, J=10.8 Hz, 2H), 7.67 (d, J=7.6 Hz, 1H), 7.18 (d, J=10.8 Hz, 1H), 7.07 (s, 1H), 6.77 (d, J=7.6 Hz, 1H), 4.50-4.55 (m, 2H), 2.36-2.45 (m, 2H), 2.09-2.19 (m, 2H), 1.49-1.52 (m, 3H), 0.70-0.74 (m, 6H). $^{19}$F NMR (400 MHz, CD$_3$OD) δ −119.17.

Mass spectrum (ESI, m/z): Calculated for C$_{22}$H$_{23}$FN$_4$O$_2$, 395.2 [M+H], found 395.3.

Example 125

Compound #41

6-(1-ethyl-4-fluoro-1H-indazol-6-yl)-3-(3-(oxazol-2-ylmethyl)pentan-3-yl)pyridin-2(1H)-one

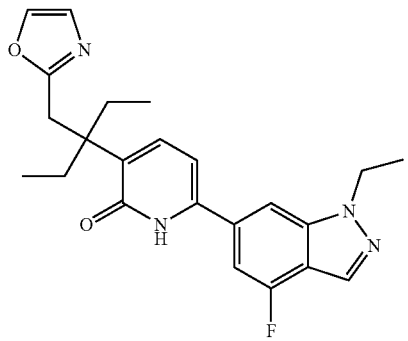 [SMILES: CCn1ncc2c(F)cc(-c3ccc(C(CC)(CC)Cc4ncco4)c(=O)[nH]3)cc21]

The title compound was prepared according to the procedure as described in Example 124 by condensation followed by demethylation to yield the product as as white solid.

$^1$H NMR (300 MHz, CD$_3$OD) δ: 8.15 (s, 1H), 7.83 (s, 1H), 7.71 (s, 1H), 7.39 (d, J=7.5 Hz, 1H), 7.19-7.23 (m, 1H), 7.00 (s, 1H), 6.68 (d, J=7.5 Hz, 1H), 4.56-4.58 (m, 2H), 3.55 (s, 2H), 2.00-2.15 (m, 2H), 1.85-1.95 (m, 2H), 1.53-157 (m, 3H), 0.84-0.89 (m, 6H). $^{19}$F NMR (300 MHz, CD$_3$OD) δ: 119.23.

Mass spectrum (ESI, m/z): Calculated for C$_{23}$H$_{25}$FN$_4$O$_2$, 409.2 [M+H], found. 409.0.

Example 126

Compound #29

6-(1-ethyl-4-fluoro-1H-indazol-6-yl)-3-(3-(isoxazol-3-yl)pentan-3-yl)pyridin-2(1H)-one

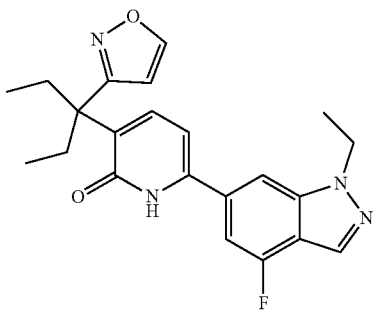 [SMILES: CCn1ncc2c(F)cc(-c3ccc(C(CC)(CC)c4ccon4)c(=O)[nH]3)cc21]

Step 1: 4-ethyl-4-(6-(1-ethyl-4-fluoro-1H-indazol-6-yl)-2-methoxypyridin-3-yl)hex-1-yn-3-ol Into a 50 ml round-bottom flask were placed a solution of 2-ethyl-2-(6-(1-ethyl-4-fluoro-1H-indazol-6-yl)-2-methoxypyridin-3-yl)butanal (500 mg, 1.353 mmol, 1.00 equiv.) in THF (20 mL), the mixture was cooled to −78° C. under nitrogen atmosphere. Ethynylmagnesium bromide (5.42 mL, 2.710 mmol, 2.00 equiv.) was added dropwise. The reaction was stirred overnight and monitored by LCMS. The mixture was quenched with water and extracted with ethyl acetate (3×30 mL). The organic layers were combined, washed with sodium carbonate (aq.) and brine, dried and concentrated under vacuum. The residue was purified by silica gel column developed with PE/EA (6/1) to yield 4-ethyl-4-(6-(1-ethyl-4-fluoro-1H-indazol-6-yl)-2-methoxypyridin-3-yl)hex-1-yn-3-ol as a light yellow solid.

Mass spectrum (ESI, m/z): Calculated for $C_{23}H_{26}FN_3O_2$: 396.2[M+H], found: 396.4.

Step 2: 4-ethyl-4-(6-(1-ethyl-4-fluoro-1H-indazol-6-yl)-2-methoxypyridin-3-yl)hex-1-yn-3-one To a solution of 4-ethyl-4-(6-(1-ethyl-4-fluoro-1H-indazol-6-yl)-2-methoxypyridin-3-yl)hex-1-yn-3-ol in DCM at 0° C. was added Dess-Martin periodinane in several portions. The mixture was stirred for 2 h at 25° C. The reaction was monitored by LCMS. The mixture was quenched by $NaHCO_3/Na_2S_2O_3$ and concentrated under vacuum to applied on flash column chromatography silica gel (PE/EA=3/1) to yield 4-ethyl-4-(6-(1-ethyl-4-fluoro-1H-indazol-6-yl)-2-methoxypyridin-3-yl)hex-1-yn-3-one as a yellow oil.

Mass spectrum (ESI, m/z): Calculated for for $C_{23}H_{24}FN_3O_2$: 394.2[M+H], found: 394.1.

Step 3: 3-(3-(6-(1-ethyl-4-fluoro-1H-indazol-6-yl)-2-methoxypyridin-3-yl)pentan-3-yl) isoxazole To a solution of 4-ethyl-4-(6-(1-ethyl-4-fluoro-1H-indazol-6-yl)-2-methoxypyridin-3-yl)hex-1-yn-3-ol (90 mg, 0.229 mmol, 1.00 equiv.) in EtOH (10 mL) was added $NH_2OH·HCl$ (37 mg, 0.530 mmol, 2.00 equiv.), $Na_2CO_3$ (48 mg, 0.457 mmol, 2.00 equiv.). The mixture was stirred at 80° C. overnight. The reaction was monitored by LCMS. The mixture was concentrated under vacuum. The residue was distilled in toluene (10 mL). TsOH (118 mg, 0.686 mmol, 3.00 equiv.), 4 Å molecular sieves (100 mg) were added. The mixture was stirred overnight at 100° C. The reaction was monitored by LCMS. The mixture was concentrated under vacuum and purified by thin layer chromatography developed with PE/EA (6/1) to yield 3-(3-(6-(1-ethyl-4-fluoro-1H-indazol-6-yl)-2-methoxypyridin-3-yl)pentan-3-yl)isoxazole as a yellow solid.

Mass spectrum (ESI, m/z): Calculated for $C_{23}H_{25}FN_4O_2$: 409.2[M+H], found. 409.4.

Step 4: 6-(1-ethyl-4-fluoro-1H-indazol-6-yl)-3-(3-(isoxazol-3-yl)pentan-3-yl)pyridin-2(1H)-one The title compound was prepared according to the procedure as described in Example 1 step 5 by demethylation with TMSCl/NaI yield the product as white solid.

$^1$H NMR (400 MHz, CD$_3$OD) δ: 8.29 (d, J=2.0 Hz, 1H), 8.15 (s, 1H), 7.81 (s, 1H), 7.67 (d, J=7.6 Hz, 1H), 7.18-7.25 (m, 1H), 6.79 (d, J=7.6 Hz, 1H), 6.25 (d, J=2.0 Hz, 1H), 4.48-4.60 (m, 2H), 2.38-2.50 (m, 2H), 2.00-2.15 (m, 2H), 1.50-1.58 (m, 3H), 0.70-0.80 (m, 6H). $^{19}$F NMR (400 MHz, CD$_3$OD) δ: −119.18. Mass spectrum (ESI, m/z): Calculated for $C_{22}H_{23}FN_4O_2$: 395.2[M+H], found: 395.1.

Example 127 Compound #37

6-(1-ethyl-4-fluoro-1H-indazol-6-yl)-5-fluoro-3-(3-(oxazol-2-yl)pentan-3-yl)pyridin-2(1H)-one

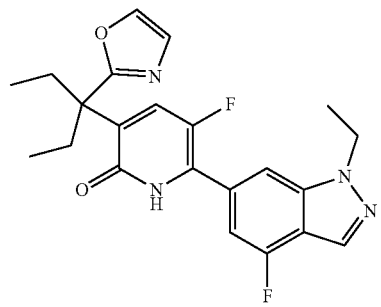 [SMILES: CCn1ncc2c(F)cc(-c3[nH]c(=O)c(C(CC)(CC)c4ncco4)cc3F)cc21]

The title compound was prepared according to the procedure as described in Example 126 by condensation followed by demethylation to yield the product as white solid.

$^1$H NMR (300 MHz, CD$_3$OD) δ 8.15 (s, 1H), 7.81-7.86 (m, 2H), 7.70 (d, J=11.3 Hz, 1H), 7.29 (d, J=11.2 Hz, 1H), 7.13 (s, 1H), 4.51-4.55 (m, 2H), 2.42-2.49 (m, 2H), 2.16-2.23 (m, 2H), 1.52 (t, J=7.2 Hz, 3H), 0.76 (t, J=7.4 Hz, 6H). $^{19}$F NMR (300 MHz, CD$_3$OD) δ −77.38, −119.91. Mass spectrum (ESI, m/z): Calculated for $C_{22}H_{22}F_2N_4O_2$, 413.2 [M+H], found 413.1.

Example 128

Compound #95

3-(1-(6-(8-Fluoronaphthalen-2-yl)-2-oxo-1,2-dihydropyridin-3-yl)-2-methylpropyl)-1,2,4-oxadiazol-5(4H)-one

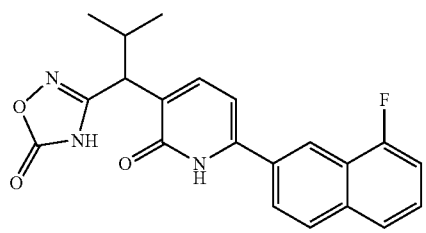 [SMILES: CC(C)C(c1noc(=O)[nH]1)c1ccc(-c2ccc3cccc(F)c3c2)[nH]c1=O]

Step 1: 2-(6-(8-fluoronaphthalen-2-yl)-2-methoxypyridin-3-yl)-3-methylbutanenitrile Into a 100-mL 3-neck-flask purged and maintained with an inert atom of nitrogen, were placed (Z)-5-(2-(6-chloro-2-methoxypyridin-3-yl)-3-methylbutylidene)oxazolidine-2,4-dione (1.1 g, 3.3 mmol, 1 equiv.), 2-hydroxy-2-methylpropanenitrile (575 mg, 6.7 mmol, 2 equiv.), PPh$_3$ (2.6 g, 10 mmol, 3 equiv.), THF (30 mL). DIAD (2.0 g, 10 mmol, 3 equiv.) was then added with stirring at 0° C. The resulting solution was stirred 16 h at 20° C. The mixture was concentrated under vacuum. The residue was purified by silica cal column with ethyl acetate/petroleum ether (6:94) to yield (Z)-5-(2-(6-chloro-2-methoxypyridin-3-yl)-3-methyl-butylidene)oxazolidine-2,4-dione as a yellow oil.

Mass spectrum (ESI, m/z): Calculated for $C_{21}H_{19}FN_2O$, 335.1 (M+H), found 335.1.

Step 2: (Z)-2-(6-(8-fluoronaphthalen-2-yl)-2-methoxypyridin-3-yl)-N'-hydroxy-3-methyl butanimidamide Into a 100-mL sealed tube, were placed 3-(6-(8-fluoronaphthalen-2-yl)-2-methoxypyridin-3-yl)-4-methylpentanenitrile (600 mg, 1.8 mmol, 1 equiv.), EtOH (30 ml), $NH_2OH \cdot HCl$ (1.2 g, 17 mmol, 10 equiv.), EtONa (1.5 g, 22 mmol, 12 equiv.). The solution was stirred at 90° C. overnight. The reaction progress was monitored by TLC/LCMS. The mixture was concentrated under vacuum.

The residue was purified by silica cal column with DCM/MeOH (96:4) to yield 3-(1-(6-(8-fluoronaphthalen-2-yl)-2-methoxypyridin-3-yl)-2-methylpropyl)-1,2,4-oxadiazol-5(4H)-one as a yellow oil.

Mass spectrum (ESI, m/z): Calculated For $C_{21}H_{22}FN_3O_2$, 368.2 (M+H), found 368.1.

Step 3: 3-(1-(6-(8-fluoronaphthalen-2-yl)-2-methoxypyridin-3-yl)-2-methylpropyl)-1,2,4-oxadiazol-5(4H)-one Into a 50-mL sealed tube, were placed (Z)-2-(6-(8-fluoronaphthalen-2-yl)-2-methoxypyridin-3-yl)-N'-hydroxy-3-methylbutanimidamide (500 mg, 1.4 mmol, 1 equiv.), THF (20 mL), DBU (310 mg, 2.0 mmol, 1.5 equiv.), CDI (330 mg, 2.0 mmol, 1.5 equiv.). The solution was stirred at 70° C. overnight. The mixture was concentrated under vacuum. The residue was purified by silica gel column with DCM/MeOH (96:4) to yield 3-(1-(6-(8-fluoronaphthalen-2-yl)-2-methoxypyridin-3-yl)-2-methylpropyl)-1,2,4-oxadiazol-5(4H)-one as a yellow oil.

Mass spectrum (ESI, m/z): Calculated For $C_{22}H_{20}FN_3O_3$, 394.1 (M+H), found 394.1.

Step 4: 3-(1-(6-(8-fluoronaphthalen-2-yl)-2-oxo-1,2-dihydropyridin-3-yl)-2-methylpropyl)-1,2,4-oxadiazol-5(4H)-one The title compound was prepared according to the procedure as described in Example 1 step 5 by demethylation of 3-(1-(6-(8-fluoronaphthalen-2-yl)-2-methoxypyridin-3-yl)-2-methylpropyl)-1,2,4-oxadiazol-5(4H)-one with TMSCl/NaI in $CH_3CN$ to yield the product as a white solid.

$^1$H NMR (300 MHz, $CD_3OD$, ppm) δ: 8.42 (s, 1H), 8.08 (d, J=7.2 Hz, 1H), 7.83-7.88 (m, 1H), 7.72-7.79 (m, 2H), 7.54-7.59 (m, 1H), 7.27-7.33 (m, 1H), 6.83 (d, J=7.5 Hz, 1H), 3.92 (d, J=9.9 Hz, 1H), 2.51-2.57 (m, 1H), 1.09 (d, J=6.6 Hz, 3H), 0.98 (d, J=6.6 Hz, 3H). $^{19}$F NMR (300 MHz, $CD_3OD$, ppm) δ: −124.39. Mass spectrum (ESI, m/z): Calculated For $C_{21}H_{18}FN_3O_3$, 380.1 (M+H), found 380.2.

Example 129

Compound #72

3-(2-(6-(8-Fluoronaphthalen-2-yl)-2-oxo-1,2-dihydropyridin-3-yl)-3-methylbutyl)-1,2,4-oxadiazol-5 (4H)-one

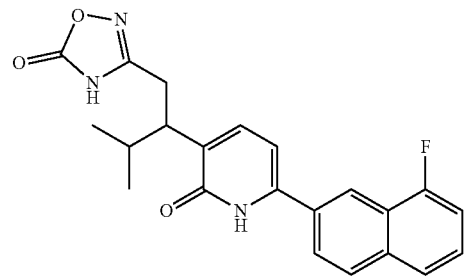 [SMILES: CC(C)C(Cc1noc(=O)[nH]1)c1ccc(-c2ccc3cccc(F)c3c2)[nH]c1=O]

The title compound was prepared according to the procedure as described in Example 128 by reacting 3-(6-(8-fluoronaphthalen-2-yl)-2-methoxypyridin-3-yl)-4-methylpentanenitrile with $NH_2OH \cdot HCl$ and then cyclization of (Z)-3-(6-(8-fluoronaphthalen-2-yl)-2-methoxypyridin-3-yl)-N'-hydroxy-4-methylpentanimidamide by CDI/DBU followed by demethylation of 3-(2-(6-(8-fluoronaphthalen-2-yl)-2-methoxypyridin-3-yl)-3-methylbutyl)-1,2,4-oxadiazol-5(4H)-one with TMSCl/NaI in $CH_3CN$ to yield the product as an off-white solid.

$^1$H NMR (400 MHz, DMSO-$d_6$) δ: 12.22 (s, 1H), 11.99 (brs, 1H), 8.46 (s, 1H), 8.07 (d, J=8.8 Hz, 1H), 7.95 (d, J=8.0 Hz, 1H), 7.80 (d, J=8.4 Hz, 1H), 7.52-7.57 (m, 1H), 7.35-7.40 (m, 2H), 6.79 (brs, 1H), 3.02-3.06 (m, 1H), 2.89-2.91 (m, 2H), 2.05-2.10 (m, 1H). 0.94 (d, J=6.8 Hz, 3H), 0.81 (d, J=6.8 Hz, 3H). $^{19}$F NMR (400 MHz, DMSO-$d_6$) δ: −75.00, −123.71. Mass spectrum (ESI, m/z): Calculated for $C_{22}H_{20}FN_3O_3$–0.98TFA, 394.2 (M+H), found 394.1.

Example 130

Compound #272

3-(1-(5-chloro-6-(8-fluoronaphthalen-2-yl)-2-oxo-1,2-dihydropyridin-3-yl)-3-methylbutan-2-yl)-1,2,4-oxadiazol-5(4H)-one

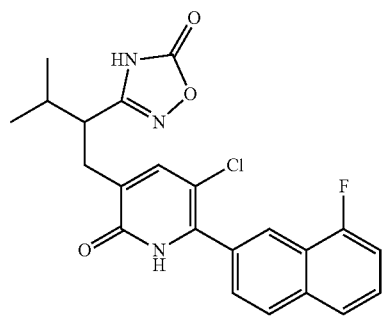 [SMILES: CC(C)C(Cc1cc(Cl)c(-c2ccc3cccc(F)c3c2)[nH]c1=O)c1noc(=O)[nH]1]

The title compound was prepared according to the procedure as described in Example 128 by cyclization followed by demethylation to yield the product as a white solid.

¹H NMR (300 MHz, CD₃OD) δ: 8.23 (s, 1 H), 7.72 (d, J=6.3 Hz, 1 H), 7.68-7.73 (m, 3 H), 7.31-7.45 (m, 1 H), 6.58 (d, J=9.6 Hz, 1 H), 3.29-3.31 (m, 1 H), 3.01-3.18 (m, 1 H), 2.72-2.85 (m, 1 H), 1.94-2.13 (m, 1 H), 1.18 (d, J=6.6 Hz, 3 H), 1.02 (d, J=6.9 Hz, 3 H). ¹⁹F NMR (300 MHz, CD₃OD) δ: −77.14, −129.37. Mass spectrum (ESI, m/z): Calculated for $C_{23.68}H_{19.84}ClF_{3.52}N_3O_{4.68}$, 428.1 (M−0.84CF₃COOH+H), found 428.0.

Example 131

Compound #277

3-(1-(6-(1-ethyl-4-fluoro-1H-indazol-6-yl)-2-oxo-1,2-dihydropyridin-3-yl)-2-methylpropyl)-1,2,4-oxadiazol-5(4H)-one

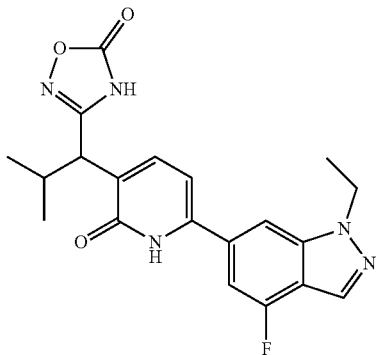 [SMILES: CCn1ncc2c(F)cc(-c3ccc(C(c4noc(=O)[nH]4)C(C)C)c(=O)[nH]3)cc21]

The title compound was prepared according to the procedure as described in Example 128 by cyclization followed by demethylation to yield the product as a white solid.

¹H NMR (300 MHz, CD₃OD) δ: 8.16 (s, 1 H), 7.83 (s, 1 H), 7.73 (d, J=7.5 Hz, 1 H), 7.22 (d, J=11.7 Hz, 1 H), 6.81 (d, J=7.2 Hz, 1 H), 4.52-4.60 (m, 2 H), 3.92 (d, J=9.9 Hz, 1 H), 2.51-2.55 (m, 2 H), 1.51-1.56 (t, J=7.2 Hz, 3 H), 1.10 (d, J=6.6 Hz, 3 H), 0.98 (d, J=6.6 Hz, 3 H). ¹⁹F NMR (300 MHz, CD₃OD) δ: −119.03. Mass spectrum (ESI, m/z): Calculated for $C_{20}H_{20}FN_5O_3$, 398.2 [M+H], found 398.0.

Example 132

Compound #278

3-(1-(6-(4-ethyl-3,4-dihydro-2H-benzo[b][1,4]oxazin-6-yl)-2-oxo-1,2-dihydropyridin-3-yl)-2-methylpropyl)-1,2,4-oxadiazol-5(4H)-one

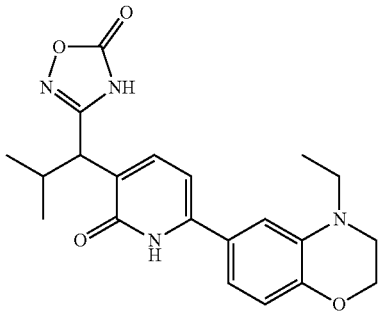 [SMILES: CCN1CCOc2ccc(-c3ccc(C(c4noc(=O)[nH]4)C(C)C)c(=O)[nH]3)cc21]

The title compound was prepared according to the procedure as described in Example 128 by cyclization followed by demethylation to yield the product as a yellow solid.

¹H NMR (300 MHz, CD₃OD) δ: 7.69 (d, J=7.2 Hz, 1H), 6.99 (s, 1H), 6.88 (d, J=6.6 Hz, 1 H), 6.81 (d, J=9.0 Hz, 1H), 6.59 (d, J=7.5 Hz, 1H), 4.25-4.28 (m, 2H), 3.85-3.88 (m, 1H), 3.44-3.51 (m, 2 H), 3.32-3.38 (m, 3H), 2.43-2.51 (m, 1H), 1.20-1.22 (t, J=6.9 Hz, 3H), 1.07 (d, J=6.6 Hz, 3H), 0.95 (d, J=6.6 Hz, 3H). Mass spectrum (ESI, m/z): Calculated for $C_{21}H_{24}N_4O_4$, 397.2 [M+H], found 397.0.

Example 133

Compound #4

3-(3-(4H-1,2,4-triazol-3-yl)pentan-3-yl)-6-(1-ethyl-4-fluoro-1H-indazol-6-yl)pyridin-2(1H)-one-one

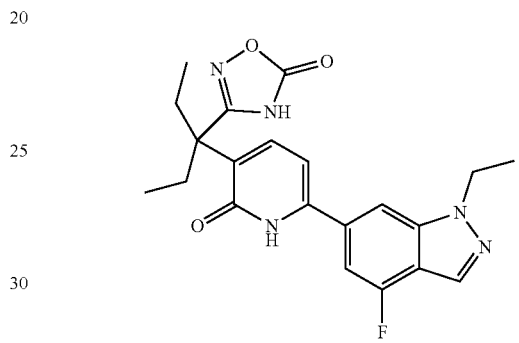

Step 1: 2-(6-chloro-2-methoxypyridin-3-yl)-2-ethylbutanenitrile

Into a 25-mL round-bottom flask purged and maintained with an inert atmosphere of nitrogen, to a solution of 2-(6-chloro-2-methoxypyridin-3-yl)acetonitrile (300 mg, 1.640 mmol, 1.00 equiv.) in DMF (10 mL), was added t-BuOK (4.9 mL, 4.900 mmol, 3.00 equiv.) with stirring at 0° C. Iodoethane (769 mg, 4.900 mmol) was then added and the resulting solution was stirred 16 h at 20° C. The mixture was quenched by the addition of H₂O, extracted with EA, the organic layers was concentrated under vacuum. The residue was purified by chromatogram on silica gel with ethyl acetate/petroleum ether (2:98) to yield 2-(6-chloro-2-methoxypyridin-3-yl)-2-ethylbutanenitrile as a yellow oil.

Mass spectrum (ESI, m/z): Calculated for $C_{12}H_{15}ClN_2O$, 239.1 [M+H], found 238.9.

Step 2: 3-(3-(4H-1,2,4-triazol-3-yl)pentan-3-yl)-6-(1-ethyl-4-fluoro-1H-indazol-6-yl)pyridin-2(1H)-one-one Into a 50-mL round-bottom flask, were placed 3-(3-(6-(1-ethyl-4-fluoro-1H-indazol-6-yl)-2-methoxypyridin-3-yl)pentan-3-yl)-1,2,4-oxadiazol-5(4H)-one (30 mg, 0.070 mmol, 1.00 equiv.), NaI (31 mg, 0.210 mmol, 3.00 equiv.), TMSCl (22 mg, 0.210 mmol, 3.00 equiv.), CH₃CN (5 mL). The resulting solution was stirred overnight at 30° C. The reaction was then quenched by the addition of MeOH. The resulting mixture was concentrated under vacuum.

Na₂S₂O₃ (aq) was added and the resulting residue purified by Prep-HPLC with the following conditions (16#-Waters 2767-5): Column, SunFire Prep C18,19*100 mm, 5 um;

mobile phase, Water with 0.05% TFA and $CH_3CN$ (15% $CH_3CN$ up to 60% in 10 min, up to 100% in 0.1 min); Detector, UV 220 & 254 nm to yield 3-(3-(4H-1,2,4-triazol-3-yl)pentan-3-yl)-6-(1-ethyl-4-fluoro-1H-indazol-6-yl)pyridin-2(1H)-one as a white solid.

$^1$H NMR (400 MHz, $CD_3OD$) δ 8.13 (s, 1H), 7.80 (s, 1H), 7.65 (d, J=9.2 Hz, 1H), 7.18 (d, J=10.8 Hz, 1H), 6.78 (d, J=7.2 Hz, 1H), 4.56 (t, J=8.8 Hz, 2H), 2.21-2.27 (m, 2H), 1.92-1.99 (m, 2H), 1.51 (t, J=6.4 Hz, 3H), 0.79-0.83 (m, 6H). $^{19}$F NMR (400 MHz, $CD_3OD$) δ: −78.00, −132.94. Mass spectrum (ESI, m/z): Calculated for $C_{21}H_{22}FN_5O_3$, 412.2 [M+H], found 412.2.

Example 134

Compound #99

3-(2-(6-(1-ethyl-4-fluoro-1H-indazol-6-yl)-2-oxo-1,2-dihydropyridin-3-yl)-3-methylbutyl)-1,2,4-oxadiazol-5(4H)-one

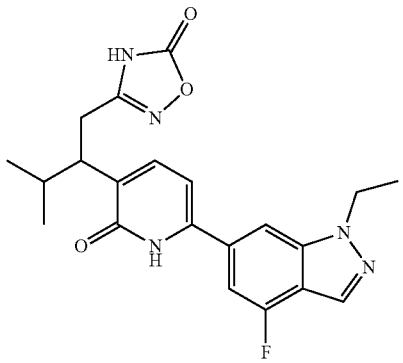 [SMILES: CCn1ncc2c(F)cc(-c3ccc(C(Cc4noc(=O)[nH]4)C(C)C)c(=O)[nH]3)cc21]

Step 1: (Z)-ethyl 3-(6-chloro-2-methoxypyridin-3-yl)-4-methyl pent-2-enoate

To a solution of ethyl 2-(trimethylsilyl)acetate (3.65 g, 22.753 mmol, 2.00 equiv.) in dry THF (70 mL) was added lithium bis(trimethylsilyl)amide (22.75 ml, 22.753 mmol, 2.00 equiv.) at −78° C. under nitrogen atmosphere into a 250-mL round-bottom flask (the flask was evacuated and flushed three times with nitrogen) and the reaction mixture was stirred at this temperature for 45 min. 1-(6-Chloro-2-methoxypyridin-3-yl)-2-methylpropan-1-one (2.43 g, 11.377 mmol, 1.00 equiv.) in dry THF (30 mL) was added into the solution and the reaction was stirred for another 45 min. The reaction progress was monitored by LCMS. A saturated solution of $NH_4Cl$ was added to the reaction mixture. The resulting solution was extracted with ethyl acetate. The organic layers were combined, washed with $Na_2SO_4$ (aq.) and brine, dried and concentrated under vacuum. The residue was applied on a silica gel column and eluted with EA/PE(5/95) to yield (Z)-ethyl 3-(6-chloro-2-methoxypyridin-3-yl)-4-methylpent-2-enoate as a yellow oil.

Mass spectrum (ESI, m/z): Calculated for $C_{14}H_{18}ClNO_3$, 284.1 [M+H], found 284.0.

Step 2: 5-(2-(6-(7-chloro-1-methyl-1H-benzo[d]imidazol-5-yl)-2-methoxypyridin-3-yl)-3-methylbutyl)oxazolidine-2,4-dione Into a 100-mL round-bottom flask, were placed (Z)-ethyl 3-(6-chloro-2-methoxypyridin-3-yl)-4-methylpent-2-enoate (2.10 g, 7.410 mmol, 1.00 equiv.) and platinumoxide hydrate (544.18 mg, 2.220 mmol, 0.30 equiv.) in MeOH (12 mL). To the mixture was then introduced $H_2$. The resulting solution was stirred for 2.0 h at 25° C. The resulting solution was stirred for 3.0 h at 25° C. The reaction was monitored by LCMS. The solids were filtered out. The resulting solution was extracted with ethyl acetate. The organic layers were combined, washed with $Na_2SO_4$ (aq.) and brine, dried and concentrated under vacuum. The residue was applied on a silica gel column and eluted with EA:PE (3:1) to yield 5-(2-(6-(7-chloro-1-methyl-1H-benzo[d]imidazol-5-yl)-2-methoxypyridin-3-yl)-3-methylbutyl)oxazolidine-2,4-dione as a yellow oil.

Mass spectrum (ESI, m/z): Calculated for $C_{14}H_{20}ClNO_3$, 286.1 [M+H], found 286.1.

Step 3: 3-(6-chloro-2-methoxypyridin-3-yl)-4-methylpentanoic acid

Into a 100-mL round-bottom flask, were placed a solution of ethyl 3-(6-chloro-2-methoxypyridin-3-yl)-4-methylpentanoate (1.90 g, 6.649 mmol, 1.00 equiv.) and potassium hydroxide (3.80 g, 67.729 mmol, 10.00 equiv.) in EtOH (4 mL), THF (8 mL), $H_2O$ (8 mL). The resulting solution was stirred overnight at 90° C. The reaction was monitored by LCMS. The resulting solution was extracted with $Et_2O$, and water layers were adjusted to pH 5~6 with 2 N HCl, then extracted with ethyl acetate. The organic layers were combined and concentrated under vacuum. The residue was applied on a silica gel column and eluted with EA/PE (1/1) to yield 3-(6-chloro-2-methoxypyridin-3-yl)-4-methylpentanoic acid as a yellow oil.

Mass spectrum (ESI, m/z): Calculated for $C_{12}H_{16}ClNO_3$, 258.1 [M+H], found 258.1.

Step 4: 3-(6-chloro-2-methoxypyridin-3-yl)-4-methylpentanamide

Into a 50-ml round-bottom flask, were placed a solution of 3-(6-chloro-2-methoxypyridin-3-yl)-4-methylpentanoic acid (20 mg, 0.078 mmol, 1.00 equiv.). Ammoniumchloride (7.30 mg, 0.136 mmol, 2.00 equiv.), N,N,N',N'-tetramethyl-O-(7-azabenzotriazol-1-yl)uronium hexafluorophosphate (53 mg, 0.139 mmol, 2.00 equiv.) in DCM (3 mL) and DMF (3 mL), and then DIPEA (18 mg, 0.139 mmol, 2.00 equiv.) were added. The resulting solution was stirred overnight at 25° C. The reaction was monitored by LCMS. The resulting solution was eluted with $H_2O$, extracted with DCM. The organic layers were combined, washed with brine, dried and concentrated under vacuum. The residue was applied on a silica gel column and eluted with EA/PE (2/1) to yield 3-(6-chloro-2-methoxypyridin-3-yl)-4-methylpentanamide as yellow oil.

Mass spectrum (ESI, m/z): Calculated for $C_{12}H_{17}ClN_2O_2$, 257.1 [M+H], found 257.1.

Step 5: 3-(6-chloro-2-methoxypyridin-3-yl)-4-methylpentanenitrile

Into a 50-ml round-bottom flask, were placed a solution of 3-(6-chloro-2-methoxypyridin-3-yl)-4-methylpentanamide (650 mg, 2.532 mmol, 1.00 equiv.) in DCM (7.5 mL), then TFAA (1.5 mL) was added. The resulting solution was stirred for 2.0 h at 25° C. The reaction was monitored by LCMS. The resulting solution was eluted with $H_2O$, extracted with DCM. The organic layers were combined, washed with brine, dried and concentrated under vacuum.

The residue was applied on a silica gel column and eluted with PE:EA=1:1 to yield 3-(6-chloro-2-methoxypyridin-3-yl)-4-methylpentanenitrile as a yellow oil.

Mass spectrum (ESI, m/z): Calculated for $C_{12}H_{15}ClN_2O$, 239.1 [M+H], found 239.0.

Step 6: 3-(2-(6-(1-ethyl-4-fluoro-1H-indazol-6-yl)-2-oxo-1,2-dihydropyridin-3-yl)-3-methylbutyl)-1,2,4-oxadiazol-5(4H)-one The title compound was prepared according to the procedure as described in Example 128 by cyclization followed by demethylation to yield the product as a yellow solid yellow solid.

$^1$H NMR (400 MHz, CD$_3$OD) δ: 8.13 (s, 1H), 7.79 (s, 1H), 7.42 (d, J=7.2 Hz, 1 H), 7.19 (d, J=10.8 Hz, 1H), 6.68 (d, J=7.2 Hz, 1H), 4.52-4.62 (m, 2H), 3.10-3.15 (m, 1H), 2.82-2.95 (m, 2H), 2.22-2.27 (m, 1 H), 1.52 (t, J=7.2 Hz, 3H), 1.05 (d, J=7.2 Hz, 3H), 0.93 (d, J=6.8 Hz, 3H). $^{19}$F NMR (400 MHz, CD$_3$OD) δ: −76.94, −119.33. Mass spectrum (ESI, m/z): Calculated For $C_{21}H_{22}FN_5O_3$, 412.2 [M+H], found 412.3.

Example 135

Compound #159 and #160 and #161

3-(1-(4H-1,2,4-triazol-3-ylamino)-2-methylpropyl)-6-(8-fluoronaphthalen-2-yl)pyridin-2(1H)-one and 3-(1-(3-amino-4H-1,2,4-triazol-4-yl)-2-methylpropyl)-6-(8-fluoronaphthalen-2-yl)pyridin-2(1H)-one and 3-(1-(3-amino-1H-1,2,4-triazol-1-yl)-2-methylpropyl)-6-(8-fluoronaphthalen-2-yl)pyridin-2(1H)-one

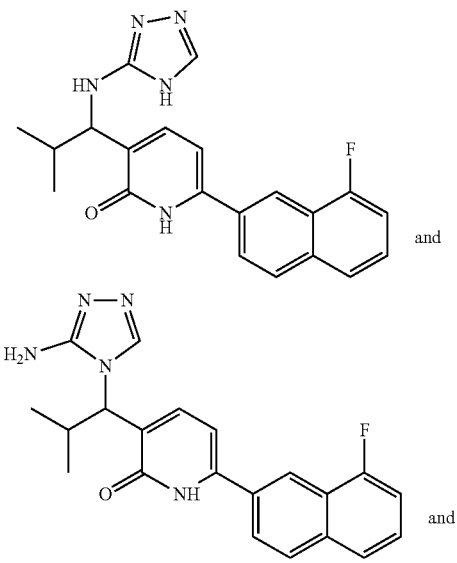

and

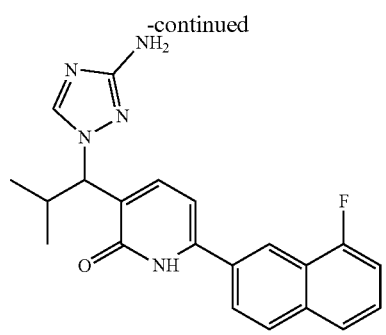

Step 1: 1-(6-(8-fluoronaphthalen-2-yl)-2-methoxypyridin-3-yl)-2-methylpropan-1-ol Into a 50-mL round-bottom flask, were placed 1-(6-(8-fluoronaphthalen-2-yl)-2-methoxypyridin-3-yl)-2-methylpropan-1-one (200 mg, 0.619 mmol, 1 equiv.), MeOH (8 mL), NaBH$_4$ (47 mg, 1.242 mmol, 2 equiv.). The resulting solution was stirred 1 h at 25° C. The reaction was monitored by TLC (PE:EA=4:1). The resulting mixture was concentrated under vacuum. The residue was applied onto a silica gel column with PE:EA=4:1 to yield 1-(6-(8-fluoronaphthalen-2-yl)-2-methoxypyridin-3-yl)-2-methylpropan-1-ol as a light yellow oil.

Step 2: 3-(1-chloro-2-methylpropyl)-6-(8-fluoronaphthalen-2-yl)-2-methoxypyridine Into a 100-mL round-bottom flask, were placed 1-(6-(8-fluoronaphthalen-2-yl)-2-methoxypyridin-3-yl)-2-methylpropan-1-ol (200 mg, 0.615 mmol, 1 equiv.), DCM (8 mL), SOCl$_2$ (122 mg, 1.233 mmol, 2 equiv.). The resulting solution was stirred 1 h at 25° C. The reaction was monitored by TLC (PE:EA=4:1). The resulting mixture was concentrated under vacuum to yield 3-(1-chloro-2-methylpropyl)-6-(8-fluoronaphthalen-2-yl)-2-methoxypyridine as a light yellow oil.

Step 3: N-(1-(6-(8-fluoronaphthalen-2-yl)-2-methoxypyridin-3-yl)-2-methylpropyl)-4H-1,2,4-triazol-3-amine and 4-(1-(6-(8-fluoronaphthalen-2-yl)-2-methoxypyridin-3-yl)-2-methylpropyl)-4H-1,2,4-triazol-3-amine and 1-(1-(6-(8-fluoronaphthalen-2-yl)-2-methoxypyridin-3-yl)-2-methylpropyl)-1H-1,2,4-triazol-3-amine Into a 10-mL sealed tube purged were added 3-(1-chloro-2-methylpropyl)-6-(8-fluoronaphthalen-2-yl)-2-methoxypyridine (100 mg, 0.291 mmol, 1 equiv.), DMF (4 ml), 4H-1,2,4-triazol-3-amine (49 mg, 0.583 mmol, 2 equiv.). The reaction was stirred 2 h at 140° C. The reaction was monitored by LCMS. The reaction was then quenched by the addition of water (10 mL), extracted with ethyl acetate and the organic layers combined. The resulting mixture was concentrated under vacuum. The residue was applied onto a silica gel column with DCM:MeOH=10:1 to yield a mixture of N-(1-(6-(8-fluoronaphthalen-2-yl)-2-methoxypyridin-3-yl)-2-methylpropyl)-4H-1,2,4-triazol-3-amine,4-(1-(6-(8-fluoronaphthalen-2-yl)-2-methoxypyridin-3-yl)-2-methylpropyl)-4H-1,2,4-triazol-3-amine, 1-(1-(6-(8-fluoronaphthalen-2-yl)-2-methoxypyridin-3-yl)-2-methylpropyl)-1H-1,2,4-triazol-3-amine as a light yellow oil.

Mass spectrum (ESI, m/z): Calculated for $C_{22}H_{22}FN_5O$, 392.2 (M+H), found 392.2.

Step 4: 3-(1-(4H-1,2,4-triazol-3-ylamino)-2-methyl-propyl)-6-(8-fluoronaphthalen-2-yl)pyridin-2(1H)-one and 3-(1-(3-amino-4H-1,2,4-triazol-4-yl)-2-methylpropyl)-6-(8-fluoronaphthalen-2-yl)pyridin-2(1H)-one and 3-(1-(3-amino-1H-1,2,4-triazol-1-yl)-2-methylpropyl)-6-(8-fluoronaphthalen-2-yl)pyridin-2(1H)-one The title compounds were prepared according to the procedure as described in Example 1 step 5 by demethylation of N-(1-(6-(8-fluoronaphthalen-2-yl)-2-methoxypyridin-3-yl)-2-methylpropyl)-4H-1,2,4-triazol-3-amine, 4-(1-(6-(8-fluoronaphthalen-2-yl)-2-methoxypyridin-3-yl)-2-methylpropyl)-4H-1,2,4-triazol-3-amine, 1-(1-(6-(8-fluoronaphthalen-2-yl)-2-methoxy pyridin-3-yl)-2-methylpropyl)-1H-1,2,4-triazol-3-amine with TMSCl/NaI to yield 3-(1-(4H-1,2,4-triazol-3-ylamino)-2-methylpropyl)-6-(8-fluoronaphthalen-2-yl)pyridin-2(1H)-one as a white solid. $^1$H NMR (300 MHz, CD$_3$OD) δ: 8.39 (s, 1H), 8.28 (s, 1H), 8.03 (d, J=8.4 Hz, 1H), 7.80-7.88 (m, 2H), 7.73 (d, J=8.4 Hz, 1H), 7.49-7.56 (m, 1H), 7.23-7.29 (m, 1H), 6.79 (d, J=7.5 Hz, 1H), 4.79-4.81 (m, 1H), 2.85-2.97 (m, 1H), 0.99 (d, J=6.4 Hz, 3H), 0.92 (d, J=6.4 Hz, 3H). $^{19}$F NMR (300 MHz, CD$_3$OD) δ: −124.32. Mass spectrum (ESI, m/z): Calculated for C$_{21}$H$_{20}$FN$_5$O, 378.2 (M+H), found 378.1.

3-(1-(3-amino-4H-1,2,4-triazol-4-yl)-2-methylpropyl)-6-(8-fluoronaphthalen-2-yl)pyridin-2(1H)-one as a white solid. $^1$H NMR (300 MHz, CD$_3$OD) δ: 8.36 (s, 1H), 7.96-8.03 (m, 1H), 7.79 (d, J=6.9 Hz, 1H), 7.72 (d, J=8.1 Hz, 1H), 7.47-7.64 (m, 3H), 7.22-7.29 (m, 1H), 6.72 (d, J=7.2 Hz, 1H), 4.33 (d, J=7.5 Hz, 1H), 2.30-2.42 (m, 1H), 1.04 (d, J=6.4 Hz, 3H), 0.94 (d, J=6.4 Hz, 3H). $^{19}$F NMR (300 MHz, CD$_3$OD) δ: −124.46. Mass spectrum (ESI, m/z): Calculated for C$_{21}$H$_{20}$FN$_5$O, 378.2 (M+H), found 378.1.

and 3-(1-(3-amino-1H-1,2,4-triazol-1-yl)-2-methylpropyl)-6-(8-fluoronaphthalen-2-yl)pyridin-2(1H)-one as an off white solid. $^1$H NMR (300 MHz, CD$_3$OD) δ: 8.36 (s, 1H), 8.11 (s, 1H), 7.97-8.05 (m, 2H), 7.80-7.82 (m, 1H), 7.73 (d, J=8.4 Hz, 1H), 7.48-7.58 (m, 1H), 7.23-7.29 (m, 1H), 6.72 (d, J=7.2 Hz, 1H), 5.13 (d, J=11.0 Hz, 1H), 2.70-2.76 (m, 1H), 0.94 (d, J=6.4 Hz, 3H), 0.87 (d, J=6.4 Hz, 3H). $^{19}$F NMR (300 MHz, CD$_3$OD) δ: −124.40.

Calculated for C$_{21}$H$_{20}$FN$_5$O, 378.2 (M+H), found 378.1.

Example 136

Compound #157 and #68 and #158

6-(8-fluoronaphthalen-2-yl)-3-(1-(2-iminothiazol-3(2H)-yl)-2-methylpropyl)pyridin-2(1H)-one and 3-(1-(2-aminothiazol-5-yl)-2-methylpropyl)-6-(8-fluoronaphthalen-2-yl)pyridin-2(1H)-one and 6-(8-fluoronaphthalen-2-yl)-3-(2-methyl-1-(thiazol-2-ylamino)propyl)pyridin-2(1H)-one

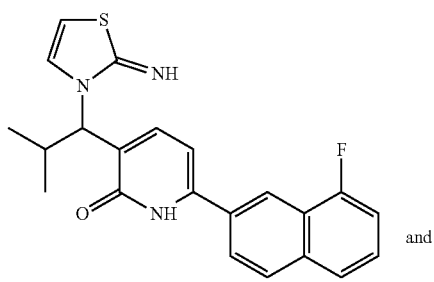

and

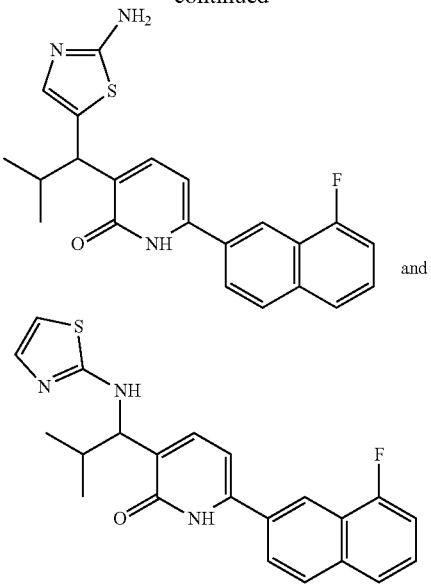

and

The title compounds were prepared according to the procedure as described in Example 135 by coupling 3-(1-chloro-2-methylpropyl)-6-(8-fluoronaphthalen-2-yl)-2-methoxypyridine with thiazol-2-amine and followed by demethylation of the mixture of 3-(1-(6-(8-fluoronaphthalen-2-yl)-2-methoxypyridin-3-yl)-2-methylpropyl)thiazol-2(3H)-imine, 5-(1-(6-(8-fluoronaphthalen-2-yl)-2-methoxypyridin-3-yl)-2-methylpropyl)thiazol-2-amine, N-(1-(6-(8-fluoronaphthalen-2-yl)-2-methoxypyridin-3-yl)-2-methylpropyl)thiazol-2-amine with TMSCl/NaI in CH$_3$CN to yield the products 6-(8-fluoronaphthalen-2-yl)-3-(1-(2-iminothiazol-3(2H)-yl)-2-methylpropyl)pyridin-2(1H)-one as a light yellow semi-solid $^1$H NMR (400 MHz, DMSO-d$_6$) δ: 8.50 (s, 1H), 8.00-7.10 (m, 2H), 7.82-7.84 (m, 1H), 7.54-7.63 (m, 2H), 7.37-7.42 (m, 1H), 7.24 (s, 1H), 6.92-6.94 (m, 1H), 5.97 (brs, 1H), 4.93-4.96 (m, 1H), 2.93-2.95 (m, 1H), 0.90 (d, J=6.4 Hz, 3H), 0.85 (d, J=6.4 Hz, 3H). $^{19}$F NMR (400 MHz, DMSO-d$_6$) δ: −122.35. Mass spectrum (ESI, m/z): Calculated for C$_{22}$H$_{20}$FN$_3$OS, 394.1 (M+H), found 394.1.

3-(1-(2-aminothiazol-5-yl)-2-methylpropyl)-6-(8-fluoronaphthalen-2-yl)pyridin-2(1H)-one as a light yellow solid $^1$H NMR (400 MHz, DMSO-d$_6$) δ: 8.47 (s, 1H), 8.09 (d, J=8.8 Hz, 1H), 7.96 (d, J=9.6 Hz, 1H), 7.82 (d, J=8.4 Hz, 1H), 7.58-7.60 (m, 1H), 7.48 (d, J=7.6 Hz, 1H), 7.39-7.42 (m, 1H), 6.80-6.85 (m, 1H), 6.73 (s, 1H), 6.65 (s, 2H), 3.90 (d, J=10.8 Hz, 1H), 2.32-2.35 (m, 1H), 0.93 (d, J=6.4 Hz, 3H), 0.84 (d, J=6.4 Hz, 3H). $^{19}$F NMR (400 MHz, DMSO-d$_6$) δ: −122.29. Mass spectrum (ESI, m/z): Calculated for C$_{22}$H$_{20}$FN$_3$OS, 394.1 (M+H), found 394.1.

and 6-(8-fluoronaphthalen-2-yl)-3-(2-methyl-1-(thiazol-2-ylamino)propyl)pyridin-2(1H)-one as an off white solid. $^1$H NMR (400 MHz, DMSO-d$_6$) δ: 8.48 (s, 1H), 8.10 (d, J=8.4 Hz, 1H), 7.97 (d, J=8.0 Hz, 1H), 7.82-7.88 (m, 2H), 7.56-7.60 (m, 1H), 7.52 (d, J=8.2 Hz, 1H), 7.38-7.43 (m, 1H), 6.95 (d, J=3.6 Hz, 1H), 6.84-6.86 (m, 1H), 6.56 (d, J=3.6 Hz, 1H), 4.71-4.75 (m, 1H), 2.19-2.24 (m, 1H), 0.93-0.95 (m, 6H). $^{19}$F NMR (400 MHz, DMSO-d$_6$) δ: −122.26. Mass spectrum (ESI, m/z): Calculated for C$_{22}$H$_{20}$FN$_3$OS, 394.1 (M+H), found 394.1.

Example 137

Compound #162

3-(1-(2-amino-1H-imidazol-1-yl)-2-methylpropyl)-6-(8-fluoronaphthalen-2-yl)pyridin-2(1H)-one

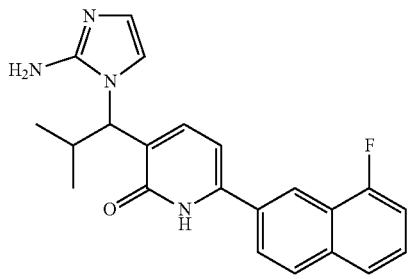 [SMILES: CC(C)C(c1ccc(-c2ccc3cccc(F)c3c2)[nH]c1=O)n1ccnc1N]

The title compound was prepared according to the procedure as described in Example 135 by coupling 3-(1-chloro-2-methylpropyl)-6-(8-fluoronaphthalen-2-yl)-2-methoxypyridine with 2-nitro-1H-imidazole and followed by demethylation of 1-(1-(6-(8-fluoronaphthalen-2-yl)-2-methoxypyridin-3-yl)-2-methylpropyl)-1H-imidazol-2-amine with TMSCl/NaI in CH$_3$CN to yield the product as an off-white solid.

$^1$H NMR (400 MHz, CD$_3$OD) δ: 8.41 (s, 1H), 8.05 (d, J=8.8 Hz, 1H), 7.82-7.88 (m, 2H), 7.75 (d, J=8.4 Hz, 1H), 7.53-7.57 (m, 1H), 7.26-7.29 (m, 1H), 6.82 (s, 2H), 6.52 (s, 1H), 4.94 (d, J=11.6 Hz, 1H), 2.65-2.75 (m, 1H), 1.00 (d, J=6.4 Hz, 3H), 0.92 (d, J=6.4 Hz, 3H). $^{19}$F NMR (400 MHz, CD$_3$OD) δ: −124.37. Mass spectrum (ESI, m/z): Calculated for C$_{22}$H$_{21}$FN$_4$O, 377.2 (M+H), found 377.1.

Example 138

Compound #172

6-(1-ethyl-4-fluoro-1H-indazol-6-yl)-3-(2-methyl-1-(4H-1,2,4-triazol-4-yl)propyl)pyridin-2(1H)-one

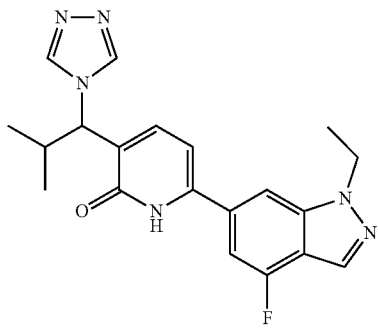 [SMILES: CCn1ncc2c(F)cc(-c3ccc(C(C(C)C)n4cnnc4)c(=O)[nH]3)cc21]

The title compound was prepared according to the procedure as described in Example 135 by coupling followed by demethylation to yield the product as a yellow solid.

$^1$H NMR (300 MHz, CD$_3$OD) δ: 8.65 (s, 1H), 8.15 (s, 1H), 8.06 (d, J=7.5 Hz, 2H), 7.81 (s, 1H), 7.21 (d, J=9.9 Hz, 1H), 6.83 (d, J=7.5 Hz, 1H), 5.47 (d, J=6.9 Hz, 1H), 4.51-4.59 (m, 2H), 2.83-2.91 (m, 1H), 1.53 (t, J=7.2 Hz, 3H), 1.03 (d, J=6.6 Hz, 3H), 0.85 (d, J=6.6 Hz, 3H). $^{19}$F NMR (300 MHz, CD$_3$OD) δ: −119.01. Mass spectrum (ESI, m/z): Calculated for C$_{20}$H$_{21}$FN$_6$O, 381.1 [M+H], found 381.1.

Example 139

Compound #171

6-(1-ethyl-4-fluoro-1H-indazol-6-yl)-3-(2-methyl-1-(1H-tetrazol-1-yl)propyl)pyridin-2(1H)-one

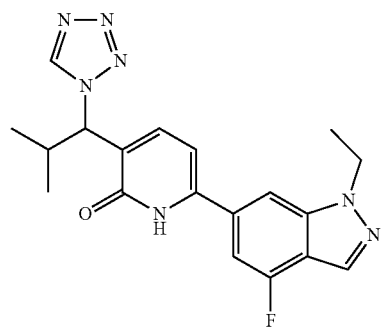 [SMILES: CCn1ncc2c(F)cc(-c3ccc(C(C(C)C)n4cnnn4)c(=O)[nH]3)cc21]

The title compound was prepared according to the procedure as described in Example 135 by coupling followed by demethylation to yield the product as a white solid.

$^1$H NMR (300 MHz, CD$_3$OD) δ:8.71 (s, 1H), 8.10 (s, 1H), 8.05 (d, J=7.5 Hz, 1H), 7.78 (s, 1H), 7.16 (d, J=9.9 Hz, 1H), 6.79 (d, J=7.5 Hz, 1H), 6.17 (d, J=7.5 Hz, 1H), 4.46-4.49 (m, 2H), 2.75-2.88(m, 1H), 1.47 (t, J=7.5 Hz, 3H), 1.01 (d, J=6.6 Hz, 3H), 0.80 (d, J=6.6 Hz, 3H). $^{19}$F NMR (300 MHz, CD$_3$OD) δ: −118.70. Mass spectrum (ESI, m/z): Calculated for C$_{19}$H$_{20}$FN$_7$O, 382.2 [M+H], found 382.0.

Example 140

Compound #154

6-(8-fluoronaphthalen-2-yl)-3-(2-methyl-1-(2-oxoimidazolidin-1-yl)propyl)pyridin-2(1H)-one

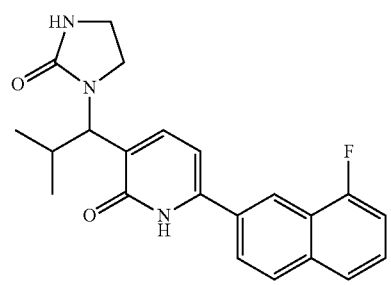 [SMILES: CC(C)C(c1ccc(-c2ccc3cccc(F)c3c2)[nH]c1=O)N1CCNC1=O]

Step 1: N1-(1-(6-(8-fluoronaphthalen-2-yl)-2-methoxypyridin-3-yl)-2-methylpropyl)ethane-1,2-diamine Into a 100-mL round-bottom flask, were placed 1-(6-(8-fluoronaphthalen-2-yl)-2-methoxy pyridin-3-yl)-2-methylpropan-1-one (500 mg, 1.546 mmol, 1 equiv.), ethane-1,2-diamine (278 mg, 4.626 mmol, 3 equiv.), MeOH (8 mL), AcOH (2 mL). The resulting solution was stirred 4 h at 50° C. NaBH$_4$ (294 mg, 7.771 mmol, 1 equiv.) was added and the resulting solution was stirred 1 h at 50° C. The reaction was monitored by TLC (PE:EA=1:1). The resulting mixture was concentrated under vacuum. The residue was applied onto a silica gel column with PE:EA=1:1 to yield N1-(1-(6-(8-fluoronaphthalen-2-yl)-2-methoxypyridin-3-yl)-2-methylpropyl) ethane-1,2-diamine was obtained as light a yellow oil.

Mass spectrum (ESI, m/z): Calculated for $C_{22}H_{26}FN_3O$, 368.2 (M+H), found 368.2.

Step 2: 1-(1-(6-(8-fluoronaphthalen-2-yl)-2-methoxypyridin-3-yl)-2-methylpropyl)imidazolidin-2-one Into a 100-mL round-bottom flask, were placed N1-(1-(6-(8-fluoronaphthalen-2-yl)-2-methoxypyridin-3-yl)-2-methylpropyl)ethane-1,2-diamine (500 mg, 1.361 mmol, 1 equiv.), di(1H-pyrrol-1-yl)methanone (326 mg, 2.035 mmol, 1.5 equiv.), TEA (757 mg, 7.481 mmol, 5.5 equiv.), CHCl$_3$ (10 mL). The resulting solution was stirred overnight at 70° C. The reaction was monitored by TLC (PE:EA=1:1). The resulting mixture was concentrated under vacuum. The residue was applied onto a silica gel column with PE:EA=1:1 to yield a light yellow oil.

Mass spectrum (ESI, m/z): Calculated for $C_{23}H_{24}FN_3O_2$, 394.5 (M+H), found 394.2.

Step 3: 6-(8-fluoronaphthalen-2-yl)-3-(2-methyl-1-(2-oxoimidazolidin-1-yl)propyl)pyridin-2(1H)-one Into a 50-mL round-bottom flask, were placed 1-(1-(6-(8-fluoronaphthalen-2-yl)-2-methoxypyridin-3-yl)-2-methylpropyl)imidazolidin-2-one (100 mg, 0.254 mmol, 1 equiv.), TMSCl (50 mg, 0.460 mmol, 2 equiv.), NaI (80 mg, 0.534 mmol, 2 equiv.), CH$_3$CN (8 mL). The resulting solution was stirred 4 h at 25° C. The reaction was monitored by LCMS. The resulting mixture was concentrated under vacuum. The residue was purified by Prep-HPLC with the following conditions (1#-Waters 2767-5): Column, SunFire Prep C18, 5 um, 19*100 mm; mobile phase, Water of 0.05% NH$_4$CO$_3$ and CH$_3$CN (20% CH$_3$CN up to 50% in 10 min, up to 100% in 2 min, down to 20% in 2 min; Detector, 254 nm to yield 6-(8-fluoronaphthalen-2-yl)-3-(2-methyl-1-(2-oxoimidazolidin-1-yl)propyl)pyridin-2(1H)-one as as an off white solid.

$^1$H NMR (400 MHz, CD$_3$OD) δ: 8.45 (s, 1H), 8.08 (d, J=7.6 Hz, 1H), 7.88 (d, J=8.8 Hz, 1H), 7.78 (d, J=8.4 Hz, 1H), 7.72 (d, J=7.2 Hz, 1H), 7.54-7.59 (m, 1H), 7.29-7.33 (m, 1H), 6.78 (d, J=7.2 Hz, 1H), 4.57 (d, J=11.2 Hz, 1H), 3.52-3.67 (m, 2H), 3.37-3.40 (m, 2H), 2.76-2.82 (m, 1H), 1.07 (d, J=6.8 Hz, 3H), 0.89 (d, J=6.8 Hz, 3H). $^{19}$F NMR (400 MHz, CD$_3$OD) δ: −124.47. Mass spectrum (ESI, m/z): Calculated for $C_{22}H_{22}FN_3O_2$, 380.2 (M+H), found 380.0.

Example 141

Compound #170

(E)-N-(1-(1-(6-(8-fluoronaphthalen-2-yl)-2-oxo-1,2-dihydropyridin-3-yl)-2-methylpropyl)imidazolidin-2-ylidene)cyanamide

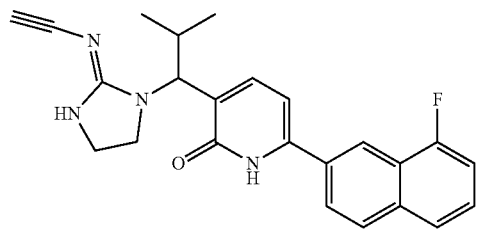 [SMILES: C#C/N=C1\NCCN1C(c1ccc(-c2ccc3cccc(F)c3c2)[nH]c1=O)C(C)C]

Step 1: 1-(1-(6-(8-fluoronaphthalen-2-yl)-2-methoxypyridin-3-yl)-2-methylpropyl) imidazolidine-2-thione Into a 100-mL round-bottom flask, were placed 1-(1-(6-(8-fluoronaphthalen-2-yl)-2-methoxypyridin-3-yl)-2-methylpropyl)imidazolidin-2-one (100 mg, 0.254 mmol, 1 equiv.), Lawesson's Reagent (514 mg, 1.271 mmol, 5 equiv.), toluene (8 mL). The resulting solution was stirred overnight at 100° C. The reaction was monitored by TLC (PE:EA=3:1). The reaction was then quenched by the addition of water (10 mL). extracted with ethyl acetate and the organic layers combined. The resulting mixture was concentrated under vacuum. The residue was applied onto a silica gel column with PE:EA=3:1 to yield 1-(1-(6-(8-fluoronaphthalen-2-yl)-2-methoxypyridin-3-yl)-2-methylpropyl)imidazolidine-2-thione was obtained as a light yellow oil.

Mass spectrum (ESI, m/z): Calculated for $C_{23}H_{24}FN_3OS$, 410.2 (M+H), found 410.2.

Step 2: 6-(8-fluoronaphthalen-2-yl)-2-methoxy-3-(2-methyl-1-(2-(methylthio)-4,5-dihydroimidazol-1-yl)propyl)pyridine Into a 50-mL round-bottom flask, were placed 1-(1-(6-(8-fluoronaphthalen-2-yl)-2-methoxypyridin-3-yl)-2-methylpropyl)imidazolidine-2-thione (60 mg, 0.147 mmol, 1 equiv.), CH$_3$I (42 mg, 0.296 mmol, 2 equiv.), MeOH (6 mL). The resulting solution was stirred overnight at 70° C. The reaction was monitored by TLC (DCM:MeOH=10:1). The resulting mixture was concentrated under vacuum. The residue was applied onto a silica gel column with DCM:MeOH=10:1 to yield 6-(8-fluoronaphthalen-2-yl)-2-methoxy-3-(2-methyl-1-(2-(methylthio)-4,5-dihydroimidazol-1-yl)propyl)pyridine as a light yellow oil.

Mass spectrum (ESI, m/z): Calculated for $C_{24}H_{26}FN_3OS$, 424.2 (M+H), found 424.2.

Step 3: 6-(8-fluoronaphthalen-2-yl)-3-(2-methyl-1-(2-(methylthio)-4,5-dihydroimidazol-1-yl)propyl)pyridin-2(1H)-one Into a 50-mL round-bottom flask, were placed 6-(8-fluoronaphthalen-2-yl)-2-methoxy-3-(2-methyl-1-(2-(methylthio)-4,5-dihydroimidazol-1-yl)propyl)pyridine (40 mg, 0.094 mmol, 1 equiv.), TMSCl (10 mg, 0.092 mmol, 2 equiv.), NaI (14 mg, 0.093 mmol, 2 equiv.), CH$_3$CN (4 ml). The resulting solution was stirred overnight at 25° C. The reaction was monitored by TLC (PE:EA=10:1). The reaction was then quenched by the addition of water (10 mL). The mixture was then extracted with ethyl acetate and the organic layers combined. The resulting mixture was concentrated under vacuum. The residue was applied onto a silica gel column with DCM:MeOH=10:1 to yield 6-(8-fluoronaphthalen-2-yl)-3-(2-methyl-1-(2-(methylthio)-4,5-dihydroimidazol-1-yl)propyl) pyridin-2(1H)-one was obtained as a light yellow oil.

Mass spectrum (ESI, m/z): Calculated for C$_{23}$H$_{24}$FN$_3$OS, 410.2 (M+H), found 410.0.

Step 4: (E)-N-(1-(1-(6-(8-fluoronaphthalen-2-yl)-2-oxo-1,2-dihydropyridin-3-yl)-2-methyl propyl)imidazolidin-2-ylidene)cyanamide Into a 50-mL round-bottom flask, were placed 6-(8-fluoronaphthalen-2-yl)-3-(2-methyl-1-(2-(methylthio)-4,5-dihydroimidazol-1-yl)propyl)pyridin-2(1H)-one (30 mg, 0.073 mmol, 1 equiv.), cyanamide (15 mg, 0.357 mmol, 5 equiv.), K$_2$CO$_3$ (51 mg, 0.369 mmol, 5 equiv.), 1,4-dioxane (5 mL). The resulting solution was stirred overnight at 100° C. The reaction was monitored by LCMS. The resulting mixture was concentrated under vacuum. The residue was purified by Prep-HPLC with the following conditions (1#-Waters 2767-5): Column, SunFire Prep C18, 5 um, 19*100 mm; mobile phase, Water of 0.05% NH$_4$CO$_3$ and CH$_3$CN (20% CH$_3$CN up to 50% in 10 min, up to 100% in 2 min, down to 20% in 2 min; Detector, 254 nm to yield (E)-N-(1-(1-(6-(8-fluoronaphthalen-2-yl)-2-oxo-1,2-dihydropyridin-3-yl)-2-methylpropyl) imidazolidin-2-ylidene)cyanamide as a white solid.

$^1$H NMR (400 MHz, CD$_3$OD) δ: 8.45 (s, 1H), 8.08 (d, J=8.4 Hz, 1H), 7.88 (d, J=8.8 Hz, 1H), 7.74-7.80 (m, 2H), 7.55-7.60 (m, 1H), 7.29-7.34 (m, 1H), 6.81 (d, J=7.2 Hz, 1H), 4.70 (d, J=11.2 Hz, 1H), 3.67-3.80 (m, 2H), 3.50-3.60 (m, 2H), 2.78-2.83 (m, 1H), 1.07 (d, J=6.8 Hz, 3H), 0.90 (d, J=6.8 Hz, 3H). $^{19}$F NMR (400 MHz, CD$_3$OD) δ: −124.42. Mass spectrum (ESI, m/z): Calculated for C$_{23}$H$_{22}$FN$_5$O, 404.2 (M+H), found 404.2.

Example 142

Compound #66

6-(8-fluoronaphthalen-2-yl)-3-(3-methyl-1-morpholinobutan-2-yl)pyridin-2(1H)-one

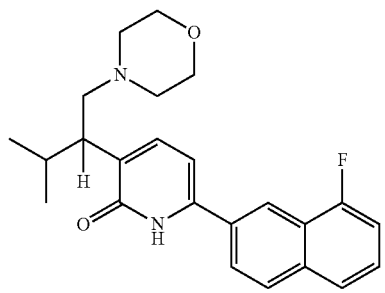 [SMILES: CC(C)C(CN1CCOCC1)c1ccc(-c2ccc3cccc(F)c3c2)[nH]c1=O]

Step 1: 4-(2-(6-(8-fluoronaphthalen-2-yl)-2-methoxypyridin-3-yl)-3-methylbutyl) morpholine Into a 50-mL round-bottom flask, were placed a solution of 2-(6-(8-fluoronaphthalen-2-yl)-2-methoxypyridin-3-yl)-3-methylbutanal (100 mg, 0.297 mmol, 1.00 equiv.), morpholine (51.6 mg, 0.593 mmol, 2.00 equiv.), sodium triacetoxyborohydride (STAB) (119.8 mg, 0.593 mmol, 2.00 equiv.) in THF (15 mL). AcOH (0.1 mL) was then added to the solution. The resulting solution was stirred for 2 h at 20° C. and the reaction was monitored by LCMS. Water (10 ml) was added to the mixture and the mixture was extracted with EA. The resulting mixture was evaporated under reduced pressure. The residue was applied onto a silica gel column with ethyl acetate/petroleum ether (1:5) to yield a residue.

Mass spectrum (EI, m/z): Calculated for C$_{25}$H$_{29}$FN$_2$O$_2$, 409.2 (M+H), found 409.2.

Step 2: 6-(8-fluoronaphthalen-2-yl)-3-(3-methyl-1-morpholinobutan-2-yl)pyridin-2(1H)-one The title compound was prepared according to the procedure as described in Example 1 step 5 by demethylation to yield the product as a white solid.

$^1$H NMR (400 MHz, CD$_3$OD) δ: 8.43 (s, 1 H), 8.08 (d, J=8.8 Hz, 1 H), 7.88 (d, J=6.8 Hz, 1 H), 7.78 (d, J=8.4 Hz, 1 H), 7.53-7.57 (m, 2 H), 7.28-7.32 (m, 1 H), 6.80 (d, J=7.2 Hz, 1 H), 3.50-3.67 (m, 4 H), 3.12-3.15 (m, 1 H), 2.85 (t, J=11.2, 1 H), 2.57-2.66 (m, 3 H), 2.38-2.60 (m, 2 H), 1.99-2.06 (m, 1 H), 1.02 (d, J=6.8 Hz, 3 H), 0.91 (d, J=6.8 Hz, 3 H). Mass spectrum (EI, m/z): Calculated for C$_{24}$H$_{27}$FN$_2$O$_2$, 395.2 (M+H), found 395.1.

Example 143

Compound #115

6-(8-fluoronaphthalen-2-yl)-3-(3-methyl-1-(2-oxopiperidin-1-yl)butan-2-yl)pyridin-2(1H)-one

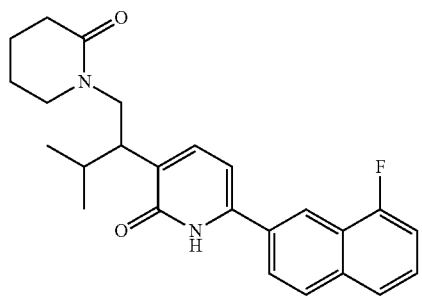 [SMILES: CC(C)C(CN1CCCCC1=O)c1ccc(-c2ccc3cccc(F)c3c2)[nH]c1=O]

Step 1: 2-(6-(8-fluoronaphthalen-2-yl)-2-methoxypyridin-3-yl)-3-methylbutan-1-amine Into a 50 mL round bottle flask, were placed 2-(6-(8-fluoronaphthalen-2-yl)-2-methoxypyridin-3-yl)-3-methylbutan-1-amine (600 mg, 1.778 mmol, 1 equiv.), CH$_3$OH (10 mL), NH$_4$OAc (1.4 g, 18 mmol, 10 equiv.), NaBH$_3$CN (832 mg, 7 mmol, 4 equiv.). The solution was stirred for 16 h at 70° C. The reaction progress was monitored by TLC/LCMS. The reaction was quenched with H$_2$O. The resulting solution was extracted with ethyl acetate (2×100 mL) and the organic layer was combined. The residue product was purified by TLC with D/M (1:10) to yield 2-(6-(8-fluoronaphthalen-2-yl)-2-methoxypyridin-3-yl)-3-methylbutan-1-amine as a colorless oil.

Mass spectrum (ESI, m/z): Calculated for $C_{21}H_{23}FN_2O$, 339.2 (M+H), found 339.2.

Step 2: 5-bromo-N-(2-(6-(8-fluoronaphthalen-2-yl)-2-methoxypyridin-3-yl)-3-methylbutyl) pentanamide Into a 50-mL round bottle flask, were placed 5-bromopentanoyl chloride (884 mg, 4.432 mmol, 3 equiv.), DMAP (746 mg, 3.694 mmol, 2.5 equiv.). $CH_2Cl_2$ (15 mL) was added. The solution was stirred for 30 min at 0° C. 2-(6-(8-Fluoronaphthalen-2-yl)-2-methoxypyridin-3-yl)-3-methylbutan-1-amine (500 mg, 1.477 mmol, 1 equiv.) in $CH_2Cl_2$ (2 mL) was added dropwise. The solution was stirred for 16 h at 50° C. The reaction was monitored with TLC/LCMS. The reaction was then quenched by ice water (5 mL). The resulting solution was extracted with $CH_2Cl_2$ (2×100 mL) and the organic layers were combined. The organic phase was concentrated under vacuum/the solvent was removed (to 5 ml) under vacuum. The residue product was purified by chromatogram on silica gel with ethyl acetate/petroleum ether (1:5) to yield 5-bromo-N-(2-(6-(8-fluoronaphthalen-2-yl)-2-methoxypyridin-3-yl)-3-methylbutyl)pentanamide as a colorless oil.

Mass spectrum (ESI, m/z): Calculated for $C_{26}H_{30}BrFN_2O_2$, 501.2 (M+H), found 501.2.

Step 3: 1-(2-(6-(8-fluoronaphthalen-2-yl)-2-methoxypyridin-3-yl)-3-methylbutyl)piperidin-2-one Into a 50-mL round bottle flask, were placed 5-bromo-N-(2-(6-(8-fluoronaphthalen-2-yl)-2-methoxypyridin-3-yl)-3-methylbutyl)pentanamide (300 mg, 0.120 mmol, 1 equiv.), $CH_3CN$ (15 mL). t-BuOK (0.48 mL, 0.48 mmol, 4 equiv.) was then added dropwise and the reaction mixture was stirred for 16 h at 50° C. The reaction was monitored with TLC/LCMS. The reaction was quenched with $H_2O$. The resulting solution was extracted with ethyl acetate (2×100 ml) and the organic layer was combined. The residue product was purified by TLC with P/E (1:10) to yield 1-(2-(6-(8-fluoronaphthalen-2-yl)-2-methoxypyridin-3-yl)-3-methylbutyl)piperidin-2-one as a colorless oil.

Mass spectrum (ESI, m/z): Calculated for $C_{26}H_{29}FN_2O_2$, 421.2 (M+H), found 421.1.

Step 4: 6-(8-fluoronaphthalen-2-yl)-3-(3-methyl-1-(2-oxopiperidin-1-yl)butan-2-yl)pyridin-2(1H)-one The title compound was prepared according to the procedure as described in Example 1 step 5 by demethylation to yield the product as a yellow solid.

$^1$H NMR (300 MHz, $CD_3OD$) δ: 8.42 (s, 1H), 8.06 (d, J=7.8 Hz, 1H), 7.84-7.87 (m, 2H), 7.51-7.58 (m, 2H), 7.26-7.32 (m, 1H), 6.75 (d, J=6.6 Hz, 1H), 3.99-4.07 (m, 1H), 3.52-3.58 (m, 1H), 3.34-3.38 (m, 1H), 3.11-3.15 (m, 2H), 2.09-2.29 (m, 3H), 1.60-1.66 (m, 4H), 1.07 (d, J=6.6 Hz, 3H), 0.87 (d, J=6.6 Hz, 3H). Mass spectrum (ESI, m/z): Calculated for $C_{28.14}H_{28.57}F_{5.71}N_2O_{5.14}$, 407.2 (M+H-1.571.57$CF_3COOH$), found 407.0.

Example 144

Compound #2

3-(1-(cyclohexylsulfonyl)-3-methylbutan-2-yl)-6-(8-fluoronaphthalen-2-yl)pyridin-2(1H)-one

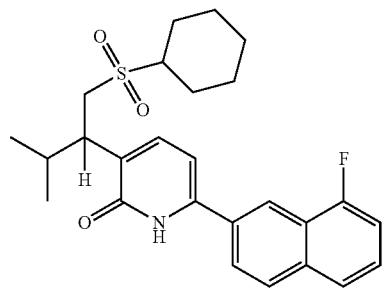 [SMILES: CC(C)C(CS(=O)(=O)C1CCCCC1)c1ccc(-c2ccc3cccc(F)c3c2)[nH]c1=O]

Step 1: 3-(1-chloro-3-methylbutan-2-yl)-6-(8-fluoronaphthalen-2-yl)-2-methoxypyridine Into a 100-mL round-bottom flask, were placed 2-(6-(8-fluoronaphthalen-2-yl)-2-methoxypyridin-3-yl)-3-methylbutan-1-ol (100 mg, 0.295 mmol, 1 equiv.), $SOCl_2$ (145 mg, 1.473 mmol, 5 equiv.), DCM (5 mL). The resulting solution was stirred overnight at 50° C. The reaction was monitored by LCMS. The resulting mixture was concentrated under vacuum to yield 3-(1-chloro-3-methylbutan-2-yl)-6-(8-fluoronaphthalen-2-yl)-2-methoxypyridine as a light yellow oil.

Mass spectrum (ESI, m/z): Calculated for $C_{21}H_{21}ClFNO$, 358.1 (M+H), found 357.9.

Step 2: 3-(1-(cyclohexylthio)-3-methylbutan-2-yl)-6-(8-fluoronaphthalen-2-yl)-2-methoxypyridine Into a 50-mL round-bottom flask, were placed 3-(1-chloro-3-methylbutan-2-yl)-6-(8-fluoronaphthalen-2-yl)-2-methoxypyridine (60 mg, 0.168 mmol, 1 equiv.), DMF (5 mL), NaH (20 mg, 0.838 mmol, 5 equiv.), cyclohexanethiol (58 mg, 0.503 mmol, 5 equiv.). The resulting solution was stirred overnight at 25° C. The reaction was monitored by TLC (PE:EA=6:1). The reaction was then quenched by the addition of water (10 mL), extracted with ethyl acetate and the organic layers combined. The resulting mixture was concentrated under vacuum. The residue was applied onto a silica gel column with PE:EA=6:1 to yield 3-(1-(cyclohexylthio)-3-methylbutan-2-yl)-6-(8-fluoronaphthalen-2-yl)-2-methoxypyridine as a light yellow oil.

Mass spectrum (ESI, m/z): Calculated for $C_{27}H_{32}FNOS$, 438.2 (M+H), found 438.2.

Step 3: 3-(1-(cyclohexylsulfonyl)-3-methylbutan-2-yl)-6-(8-fluoronaphthalen-2-yl)-2-methoxypyridine Into a 50-mL round-bottom flask, were placed 3-(1-(cyclohexylthio)-3-methylbutan-2-yl)-6-(8-fluoronaphthalen-2-yl)-2-methoxypyridine (60 mg, 0.137 mmol, 1 equiv.), $H_2O_2$(0.5 mL), AcOH (2 mL). The resulting solution was stirred overnight at 25° C. The reaction was monitored by LCMS. The reaction was then quenched by the addition of 10 mL of $Na_2S_2O_3$, extracted with ethyl acetate and the organic layers combined. The resulting mixture was concentrated under vacuum. The residue was applied onto a silica gel column with PE:EA=2:1 to yield 3-(1-(cyclohexylsulfonyl)-3-methylbutan-2-yl)-6-(8-fluoronaphthalen-2-yl)-2-methoxypyridine as a light yellow oil.

Mass spectrum (ESI, m/z): Calculated for $C_{27}H_{32}FNO_3S$, 470.2 (M+H), found 470.0.

Step 4: 3-(1-(cyclohexylsulfonyl)-3-methylbutan-2-yl)-6-(8-fluoronaphthalen-2-yl)pyridin-2(1H)-one The title compound was prepared according to the procedure as described in Example 1 step 5 by demethylation of 3-(1-(cyclohexylsulfonyl)-3-methyl butan-2-yl)-6-(8-fluoronaphthalen-2-yl)-2-methoxypyridine with TMSCl/NaI to yield the product as an off-white solid.

$^1$H NMR (300 MHz, CD$_3$OD) δ: 8.40 (s, 1H), 8.07 (d, J=7.2 Hz, 1H), 7.86 (d, J=8.7 Hz, 1H), 7.77 (d, J=8.4 Hz, 1H), 7.52-7.61 (m, 2H), 7.27-7.33 (m, 1H), 6.78 (d, J=7.5 Hz, 1H), 3.86-3.95 (m, 1H), 3.10-3.20 (m, 1H), 2.85-2.90 (m, 1H), 2.20-2.30 (m, 1H), 2.00-2.09 (m, 2H), 1.85-1.95 (m, 2H), 1.65-1.70 (m, 1H), 1.23-1.46 (m, 6H), 1.05 (d, J=6.6 Hz, 3H), 0.90 (d, J=6.6 Hz, 3H). $^{19}$F NMR (300 MHz, CD$_3$OD) δ: −124.52. Mass spectrum (ESI, m/z): Calculated for $C_{26}H_{30}FNO_3S$, 456.2 (M+H), found 456.3.

Example 145

Compound #165

N-(1-(6-(8-fluoronaphthalen-2-yl)-2-oxo-1,2-dihydropyridin-3-yl)-2-methylpropyl)cyclohexanesulfonamide

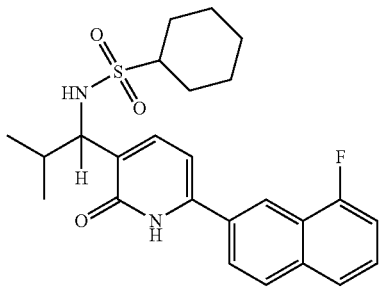 [SMILES: CC(C)C(NS(=O)(=O)C1CCCCC1)c1ccc(-c2ccc3cccc(F)c3c2)[nH]c1=O]

Into a 50-mL round-bottom flask, were placed 3-(1-amino-2-methylpropyl)-6-(8-fluoronaphthalen-2-yl)pyridin-2(1H)-one (30 mg, 0.096 mmol, 1 equiv.), THF (2 mL), DCM (2 mL), cyclohexanesulfonyl chloride (35 mg, 0.192 mmol, 2 equiv.), pyridine (15 mg, 0.192 mmol, 2 equiv.). The resulting solution was stirred overnight at 25° C. The reaction was monitored by LCMS. The resulting mixture was concentrated under vacuum. The residue was purified by Prep-HPLC with the following conditions (1#-Waters 2767-5): Column, SunFire Prep C18, 5 um, 19*100 mm; mobile phase, Water of 0.05% NH$_4$HCO$_3$ and CH$_3$CN (20% CH$_3$CN up to 50% in 10 min, up to 100% in 2 min, down to 20% in 2 min; Detector, 254 nm to yield N-(1-(6-(8-fluoronaphthalen-2-yl)-2-oxo-1,2-dihydropyridin-3-yl)-2-methylpropyl) cyclohexanesulfonamide as an off white semi-solid.

$^1$H NMR (400 MHz, CD$_3$OD) δ: 8.42 (s, 1H), 8.09 (d, J=8.4 Hz, 1H), 7.87 (d, J=8.4 Hz, 1H), 7.79 (d, J=7.6 Hz, 1H), 7.70 (d, J=6.8 Hz, 1H), 7.56-7.60 (m, 1H), 7.29-7.34 (m, 1H), 6.84 (d, J=7.2 Hz, 1H), 4.28 (d, J=8.4 Hz, 1H), 2.68-2.77 (m, 1H), 2.15-2.20 (m, 2H), 1.94-1.97 (m, 1H), 1.83-1.86 (m, 1H), 1.75-1.78 (m, 1H), 1.62-1.65 (m, 1H), 1.19-1.50 (m, 4H), 1.04-1.44 (m, 4H), 0.94 (d, J=6.4 Hz, 3H). $^{19}$F NMR (400 MHz, CD$_3$OD) δ: −124.48. Mass spectrum (ESI, m/z): Calculated for $C_{25}H_{29}FN_2O_3S$, 457.2 (M+H), found 457.2.

Example 146

Compound #166

6-(8-fluoronaphthalen-2-yl)-3-(2-methyl-1-(2-oxopiperidin-1-yl)propyl)pyridin-2(1H)-one

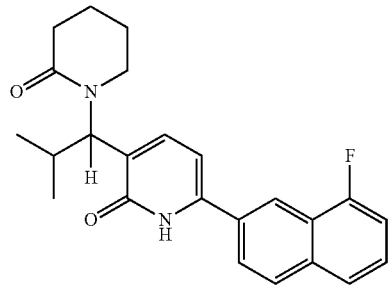 [SMILES: CC(C)C(c1ccc(-c2ccc3cccc(F)c3c2)[nH]c1=O)N1CCCCC1=O]

The title compound was prepared according to the procedure as described in Example 143 by coupling of 1-(6-(8-fluoronaphthalen-2-yl)-2-methoxypyridin-3-yl)-2-methylpropan-1-amine with 5-bromopentanoyl chloride, cyclization and demethylation to yield the product as a yellow solid as an off-white solid.

$^1$H NMR (400 MHz, CD$_3$OD) δ: 8.44 (s, 1H), 8.08 (d, J=8.8 Hz, 1H), 7.78-7.79 (m, 3H), 7.54-7.60 (m, 1H), 7.29-7.34 (m, 1H), 6.81 (d, J=7.2 Hz, 1H), 5.19-5.21 (m, 1H), 3.46-3.49 (m, 1H), 3.24-3.28 (m, 1H), 2.77-2.86 (m, 1H), 2.36-2.40 (m, 2H), 1.71-1.81 (m, 4H), 1.04 (d, J=6.4 Hz, 3H), 0.94 (d, J=6.4 Hz, 3H). $^{19}$F NMR (400 MHz, CD$_3$OD) δ: −124.47. Mass spectrum (ESI, m/z): Calculated for $C_{24}H_{25}FN_2O_2$, 393.2 (M+H), found 393.0.

Examples 147

Compound #163

6-(8-fluoronaphthalen-2-yl)-3-(2-methyl-1-(2-oxopiperidin-1-yl)propyl)pyridin-2(1H)-one

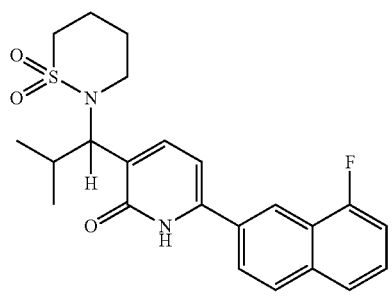 [SMILES: CC(C)C(c1ccc(-c2ccc3cccc(F)c3c2)[nH]c1=O)N1CCCCS1(=O)=O]

The title compound was prepared according to the procedure as described in Example 143 by coupling of 1-(6-(8-fluoronaphthalen-2-yl)-2-methoxypyridin-3-yl)-2-methylpropan-1-amine and 4-chlorobutane-1-sulfonyl chloride, cyclization and demethylation to yield the product as an off-white solid.

$^1$H NMR (300 MHz, CD$_3$OD) δ: 8.42 (s, 1H), 8.08 (d, J=7.5 Hz, 1H), 7.89 (d, J=8.7 Hz, 1H), 7.74-7.80 (m, 2H), 7.53-7.60 (m, 1H), 7.27-7.33 (m, 1H), 6.81 (d, J=7.2 Hz,

1H), 4.74 (d, J=11.4 Hz, 1H), 3.51-3.55 (m, 1H), 3.33-3.40 (m, 1H), 3.10-3.15 (m, 1H), 3.01-3.04 (m, 1H), 2.51-2.55 (m, 1H), 2.00-2.20 (m, 2H), 1.45-1.55 (m, 1H), 1.18-1.22 (m, 1H), 1.13 (d, J=6.6 Hz, 3H), 0.87 (d, J=6.6 Hz, 3H). $^{19}$F NMR (300 MHz, CD$_3$OD) δ: −124.44. Mass spectrum (ESI, m/z): Calculated for C$_{23}$H$_{25}$FN$_2$O$_3$S, 429.2 (M+H), found 429.2.

Example 148

Compound #168

3-(1-(1,1-dioxidothiomorpholino)-2-methylpropyl)-6-(1-ethyl-4-fluoro-1H-indazol-6-yl)pyridin-2(1H)-one

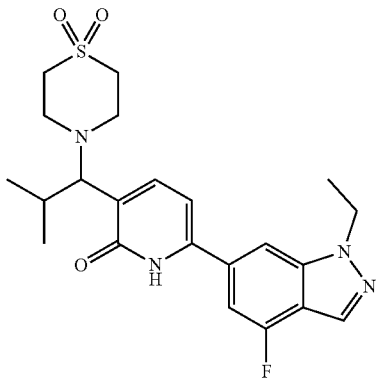 [SMILES: CCn1ncc2c(F)cc(-c3ccc(C(C(C)C)N4CCS(=O)(=O)CC4)c(=O)[nH]3)cc21]

Step 1: 6-(5-(1-chloro-2-methylpropyl)-6-methoxypyridin-2-yl)-1-ethyl-4-fluoro-1H-indazole Into a 100-mL round-bottom flask, were placed 1-(6-(1-ethyl-4-fluoro-1H-indazol-6-yl)-2-methoxypyridin-3-yl)-2-methylpropan-1-ol (150 mg, 2.184 mmol, 1.00 equiv.), DCM (8 mL), SOCl$_2$ (216 mg, 0.728 mmol, 5.00 equiv.). The reaction was stirred 2 h at 25° C. The reaction was monitored by TLC (PE:EA=3:1). The resulting mixture was concentrated under vacuum to yield 6-(5-(1-chloro-2-methylpropyl)-6-methoxypyridin-2-yl)-1-ethyl-4-fluoro-1H-indazole as a light yellow oil.

Step 2: 4-(1-(6-(1-ethyl-4-fluoro-1H-indazol-6-yl)-2-methoxypyridin-3-yl)-2-methylpropyl) thiomorpholine Into a 10-mL sealed tube purged was 6-(5-(1-chloro-2-methylpropyl)-6-methoxypyridin-2-yl)-1-ethyl-4-fluoro-1H-indazole (150 mg, 0.415 mmol, 1.00 equiv.), thiomorpholine (428 mg, 4.145 mmol, 10.00 equiv.), DIEA (536 mg, 4.145 mmol, 10.00 equiv.), CuI (79 mg, 0.415 mmol, 1.00 equiv.), NMP (5 mL). The reaction was stirred 2 h at 180° C. by microwave. The reaction was monitored by TLC (PE:EA=3:1). The reaction was then quenched by saturation NaHCO$_3$ solution. The resulting solution was extracted with EA. The organic layer was washed with water, dried (magnesium sulfate), and concentrated.

The residue was applied onto a silica gel column with PE:EA=3:1 to yield 4-(1-(6-(1-ethyl-4-fluoro-1H-indazol-6-yl)-2-methoxypyridin-3-yl)-2-methylpropyl)thiomorpholine as a light yellow oil.

Mass spectrum (ESI, m/z): Calculated for C$_{23}$H$_{29}$FN$_4$OS, 429.1 [M+H], found 429.4.

Step 3: 4-(1-(6-(1-ethyl-4-fluoro-1H-indazol-6-yl)-2-methoxypyridin-3-yl)-2-methyl propyl)thiomorpholine 1,1-dioxide Into a 50-mL round-bottom flask, were placed 4-(1-(6-(1-ethyl-4-fluoro-1H-indazol-6-yl)-2-methoxypyridin-3-yl)-2-methylpropyl)thiomorpholine (120 mg, 0.280 mmol, 1.00 equiv.), potassium peroxydisulfate (151 mg, 0.560 mmol, 2.00 equiv.), EA (5 mL), H$_2$O (3 mL). The reaction was stirred 4 h at 25° C. The reaction was monitored by LCMS. The reaction was then quenched by saturation NaHCO$_3$ solution. The resulting solution was extracted with EA.

The organic layer was washed with water, dried (magnesium sulfate), and concentrated. The residue was applied onto a silica gel column with PE:EA=3:1 to yield 4-{1-[6-(1-ethyl-4-fluoro-1H-indazol-6-yl)-2-methoxypyridin-3-yl]-2-methylpropyl}-1λ6,4-thiomorpholine-1,1-dione as a light yellow oil.

Mass spectrum (ESI, m/z): Calculated for C$_{23}$H$_{29}$FN$_4$O$_3$S, 461.1 [M+H], found 461.1.

Step 4: 3-(1-(1,1-dioxidothiomorpholino)-2-methylpropyl)-6-(1-ethyl-4-fluoro-1H-indazol-6-yl)pyridin-2(1H)-one The title compound was prepared according to the procedure as described in Example 1 step 5 by demethylation to yield the product as a white solid.

$^{1}$H NMR (400 MHz, CD$_3$OD) δ: 8.16 (s, 1H), 7.84 (s, 1H), 7.56 (d, J=7.2 Hz, 1H), 7.22 (d, J=12.0 Hz, 1H), 6.80 (d, J=7.2 Hz, 1H), 4.54-4.60 (m, 2H), 3.85 (d, J=11.2 Hz, 1H), 3.04-3.09 (m, 6H), 2.93-2.94 (m, 2H), 2.31-2.36 (m, 1H), 1.53-1.56 (m, 3H), 1.17 (d, J=6.4 Hz, 3H), 0.92 (d, J=6.4 Hz, 3H). $^{19}$F NMR (400 MHz, CD$_3$OD) δ: −119.11. Mass spectrum (ESI, m/z): Calculated for C$_{22}$H$_{27}$FN$_4$O$_3$S, 447.1 [M+H], found 447.1.

Example 149

Compound #280 and #281 ethyl 2-(cyclohex-1-en-1-yl)-2-(6-(naphthalen-2-yl)-2-oxo-1,2-dihydropyridin-3-yl)acetate and ethyl 2-cyclohexylidene-2-(6-(naphthalen-2-yl)-2-oxo-1,2-dihydropyridin-3-yl)acetate

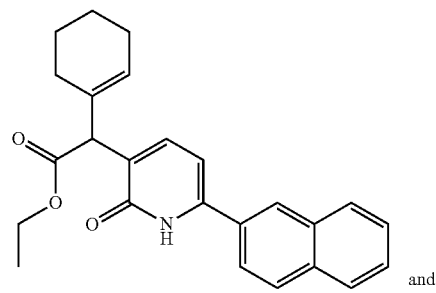

and

-continued

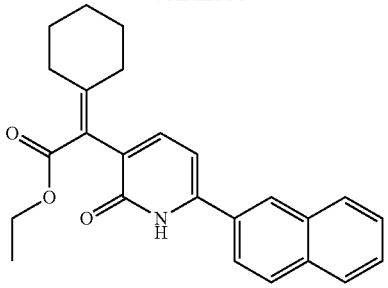

Step 1: ethyl 2-(cyclohex-1-en-1-yl)-2-(2-methoxy-6-(naphthalen-2-yl)pyridin-3-yl)acetate and ethyl 2-cyclohexylidene-2-(2-methoxy-6-(naphthalen-2-yl)pyridin-3-yl)acetate The title compounds were prepared according to the procedure as described in Example 43 step 1 and 2 by coupling with ethyl 2-cyclohexyl-2-oxoacetate followed by de-hydroxylation with pTSA to yield the products as a colorless oil.

Mass spectrum (ESI, m/z): Calculated for $C_{26}H_{27}NO_3$, 402.51 (M+H), found 402.5.

Step 2: ethyl 2-(cyclohex-1-en-1-yl)-2-(6-(naphthalen-2-yl)-2-oxo-1,2-dihydropyridin-3-yl)acetate and ethyl 2-cyclohexylidene-2-(6-(naphthalen-2-yl)-2-oxo-1,2-dihydropyridin-3-yl)acetate The title compounds were prepared according to the procedure as described in Example 1 step 5 by demethylation to yield
Ethyl 2-(cyclohex-1-en-1-yl)-2-(6-(naphthalen-2-yl)-2-oxo-1,2-dihydropyridin-3-yl)acetate as a clear oil. $^1$H NMR (400 MHz, CDCl$_3$) δ: 12.4 (br, s, 1H), 8.32 (s, 1H), 8.05 (d, J=6.5 Hz, 1 H), 7.95 (d, J=7.5 Hz, 1H), 7.88 (d, J=6.5 Hz, 2H), 7.55 (m, 3H), 6.69 (d, J=7.0 Hz, 1H), 5.65 (s, 1H), 4.62 (s, 1H), 4.10 (m, 2H), 2.10 (4H), 1.65 (m, 4H), 1.18 (t, J=7.8 Hz, 3H). Mass spectrum (ESI, m/z): Calculated for $C_{22}H_{19}FN_2O_2$, 388.48 (M+H), found 388.5.
and Ethyl 2-cyclohexylidene-2-(6-(naphthalen-2-yl)-2-oxo-1,2-dihydropyridin-3-yl)acetate as a clear oil. $^1$H NMR (400 MHz, CDCl$_3$) δ: 11.4 (br, s, 1H), 8.30 (s, 1H), 8.05 (d, J=7.5 Hz, 1 H), 7.90 (m, 1H), 7.82 (m, 1H), 7.55 (d, J=7.0 Hz, 2H), 7.38 (d, J=7.8 Hz, 1H), 6.67 (d, J=7.1 Hz, 1H), 4.12 (q, J=6.2 Hz, 2H), 2.62 (m, 2H), 2.20 (m, 2H), 1.72 (m, 2H), 1.55 (m, 4H), 1.15 (t, J=7.0 Hz, 3H). Mass spectrum (ESI, m/z): Calculated for $C_{22}H_{19}FN_2O_2$, 388.48 (M+H), found 388.6.

Example 150

Compound #169

3-(1-(1,1-dioxidothiomorpholino)-2-methylpropyl)-6-(4-ethyl-3,4-dihydro-2H-benzo[b][1,4]oxazin-6-yl)pyridin-2(1H)-one

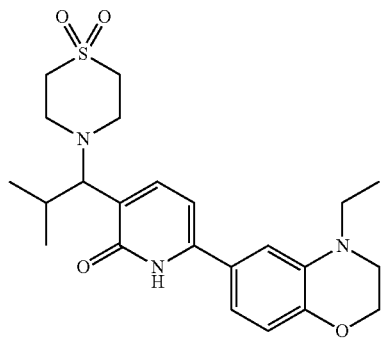 [SMILES: CCN1CCOc2ccc(-c3ccc(C(C(C)C)N4CCS(=O)(=O)CC4)c(=O)[nH]3)cc21]

The title compound was prepared according to the procedure as described in Example 149 by coupling and demethylation to yield the product as an off-white solid.
$^1$H NMR (300 MHz, CD$_3$OD) δ: 7.49 (d, J=7.2 Hz, 1H), 7.00 (s, 1H), 6.89-6.92 (m, 1H), 6.81 (d, J=8.1 Hz, 1H), 6.59 (d, J=7.5 Hz, 1H), 4.27-4.30 (m, 2H), 3.82 (d, J=11.1 Hz, 1H), 3.45-3.50 (m, 2H), 3.37-3.40 (m, 2H), 2.92-3.33 (m, 8H), 2.30 (brs, 1H), 1.15-1.24 (m, 6H), 0.81 (d, J=6.6 Hz, 3H). Mass spectrum (ESI, m/z): Calculated for $C_{23}H_{31}N_3O_4S$, 446.1 [M+H], found 446.0.

Example 151

Compound #164

6-(4-ethyl-3,4-dihydro-2H-benzo[b][1,4]oxazin-6-yl)-3-(2-methyl-1-thiomorpholino propyl)pyridin-2(1H)-one

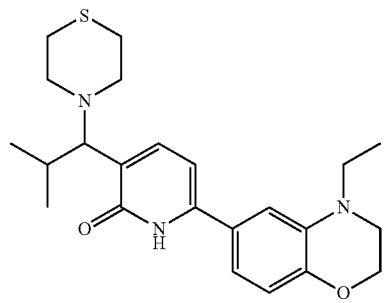 [SMILES: CCN1CCOc2ccc(-c3ccc(C(C(C)C)N4CCSCC4)c(=O)[nH]3)cc21]

The title compound was prepared according to the procedure as described in Example 149 by coupling and demethylation to yield the product as an off-white solid.
$^1$H NMR (300 MHz, CD$_3$OD) δ: 7.45 (d, J=7.2 Hz, 1H), 7.00 (s, 1H), 6.89-6.92 (m, 1H), 6.81 (d, J=8.1 Hz, 1H), 6.59 (d, J=7.5 Hz, 1H), 4.27-4.30 (m, 2H), 3.82 (d, J=11.1 Hz, 1H), 3.45-3.50 (m, 2H), 3.37-3.40 (m, 2H), 2.62-2.70 (m, 8H), 2.20 (brs, 1H), 1.11-1.24 (m, 6H), 0.78 (d, J=6.6 Hz, 3H). Mass spectrum (ESI, m/z): Calculated for $C_{23}H_{31}N_3O_2S$, 414.1 [M+H], found 414.0.

Example 152

Compound #133

4-{2-[6-(1-ethyl-4-fluoroindazol-6-yl)-2-oxo-1H-pyridin-3-yl]-3-methylbutyl},4-thiomorpholine-1,1-dione

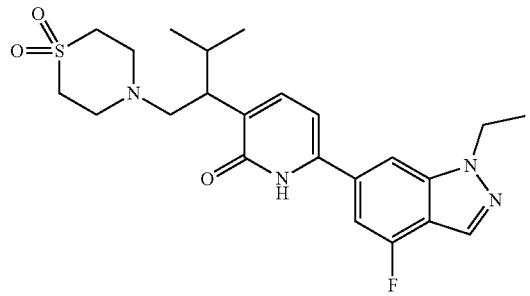 [SMILES: CCn1ncc2c(F)cc(-c3ccc(C(CN4CCS(=O)(=O)CC4)C(C)C)c(=O)[nH]3)cc21]

Step 1: 4-(2-(2-methoxy-6-methylpyridin-3-yl)-3-methylbutyl)thiomorpholine

To a rapidly stirred solution of 2-(2-methoxy-6-methylpyridin-3-yl)-3-methylbutanal (500 mg, 2.410 mmol, 1.00 equiv.) in THF (20 mL) under $N_2$ atmosphere, was added thiomorpholine (430 mg, 4.170 mmol, 1.73 equiv), $CH_3COOH$ (1 mL), and then $NaBH(OAc)_3$ (930 mg, 4.390 mmol, 2.00 equiv.) dropwise. The reaction was stirred 2 h at 25° C. The reaction was monitored by LCMS. The resulting solution was extracted with EtOAc, then the organic layers combined and concentrated under vacuum. The residue was applied onto a silica gel column with ethyl acetate/petroleum ether (1:10) to yield 4-(2-(6-chloro-2-methoxypyridin-3-yl)-3-methylbutyl)thiomorpholine as a colorless oil.

Mass spectrum (ESI, m/z): Calculated for $C_{16}H_{26}N_2OS$, 315.1 [M+H], found 315.2.

Step 2: 4-{2-[6-(1-ethyl-4-fluoroindazol-6-yl)-2-oxo-1H-pyridin-3-yl]-3-methylbutyl},4-thiomorpholine-1,1-dione The title compound was prepared according to the procedure as described in Example 149 by oxidation and demethylation to yield the product as an off-white solid.

$^1$H NMR (400 MHz, Methanol-$d_4$) δ: 8.13 (s, 1H), 7.80 (s, 1H), 7.49 (d, J=7.2 Hz, 1H), 7.18-7.21 (m, 1 H), 6.75 (d, J=7.2 Hz, 1H), 4.51-4.57 (m, 2H), 2.84-3.09 (m, 11H), 2.01-2.03 (m, 1H), 1.52 (t, J=6.4 Hz, 3H), 1.01 (d, J=6.8 Hz, 3H), 0.87 (d, J=6.6 Hz, 3H). $^{19}$F NMR (400 MHz, Methanol-$d_4$) δ: −119.19. Mass spectrum (ESI, m/z): Calculated for $C_{23}H_{29}FN_4O_3S$, 461.2[M+H], found 461.3.

Example 153

Compound #104

3-(1-(1,1-dioxidothiomorpholino)-3-methylbutan-2-yl)-6-(4-ethyl-3,4-dihydro-2H-benzo[b][1,4]oxazin-6-yl)pyridin-2(1H)-one

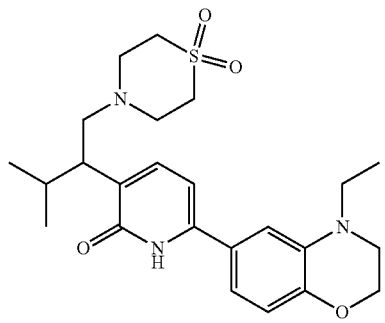 [SMILES: CCN1CCOc2ccc(-c3ccc(C(CN4CCS(=O)(=O)CC4)C(C)C)c(=O)[nH]3)cc21]

The title compound was prepared according to the procedure as described in Example 149 by coupling and demethylation to yield the product as an off-white solid.

$^1$H NMR (400 MHz, Methanol-$d_4$) δ 7.42 (d, J=7.6 Hz, 1 H), 6.96 (s, 1 H), 6.86 (d, J=10.4 Hz, 1 H), 6.78 (d, J=8.4 Hz, 1 H), 6.53 (d, J=7.2 Hz, 1 H), 4.21-4.26 (m, 2 H), 3.45-3.47 (m, 2 H), 3.34-3.36 (m, 2 H), 2.79-3.15 (m, 11 H), 1.96-2.01 (s, 1 H), 1.17-1.20 (m, 3 H), 0.99 (d, J=6.7 Hz, 3 H), 0.85 (d, J=6.7 Hz, 3 H). Mass spectrum (ESI, m/z): Calcd for $C_{24}H_{33}N_3O_4S$, 460.2 (M+H), found 460.1.

Example 154

Compound #109

6-(1-ethyl-4-fluoro-1H-indazol-6-yl)-3-(3-methyl-1-(4-(methylsulfonyl)piperazin-1-yl)butan-2-yl)pyridin-2(1H)-one

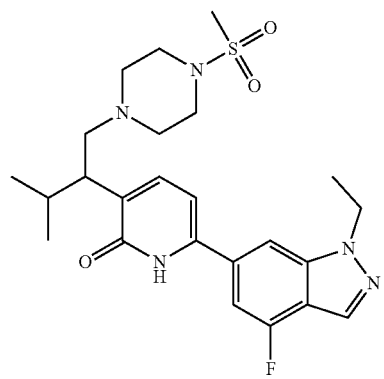 [SMILES: CCn1ncc2c(F)cc(-c3ccc(C(CN4CCN(S(C)(=O)=O)CC4)C(C)C)c(=O)[nH]3)cc21]

Step 1: tert-butyl 4-(2-(6-chloro-2-methoxypyridin-3-yl)-3-methylbutyl)piperazine-1-carboxylate Into a 100-ml round-bottom flask, were placed a solution of 2-(6-chloro-2-methoxypyridin-3-yl)-3-methylbutanal (300 mg, 1.318 mmol, 1.00 equiv.) and tert-butyl piperazine-1-carboxylate (269.94 mg, 1.449 mmol, 1.10 equiv.) in THF (10 mL). Acetic acid (2.37 mg, 0.040 mmol, 0.03 equiv.) was then added. After 15 min sodium triacetoxyborohydride (558.51 mg, 2.635 mmol, 2.00 equiv.) was added. The solution was stirred overnight at room temperature. The reaction was monitored by LCMS. The resulting solution was extracted with EtOAc, then the organic layers combined and concentrated under vacuum. The residue was applied onto a silica gel column with PE:EA=10:1 to yield tert-butyl 4-(2-(6-chloro-2-methoxypyridin-3-yl)-3-methylbutyl)piperazine-1-carboxylate obtained as a yellow oil.

Mass spectrum (ESI, m/z): Calculated for $C_{20}H_{32}ClN_3O_3$, 398.2 [M+H], found 398.1.

Step 2: tert-butyl 4-(2-(6-(1-ethyl-4-fluoro-1H-indazol-6-yl)-2-methoxypyridin-3-yl)-3-methylbutyl)piperazine-1-carboxylate Into a sealed tube purged and maintained with an inert atmosphere of nitrogen, were placed a solution of tert-butyl 4-(2-(6-chloro-2-methoxypyridin-3-yl)-3-methylbutyl)piperazine-1-carboxylate (240 mg, 0.603 mmol, 1.00 equiv.), 1-ethyl-4-fluoro-6-(4,4,5,5-tetramethyl-1,3,2-dioxaborolan-2-yl)-1H-indazole (209.98 mg, 0.724 mmol, 1.20 equiv.), $Pd(PPh_3)_4$ (34.85 mg, 0.030 mmol, 0.05 equiv.), tetrabutylammonium bromide (194.42 mg, 0.603 mmol, 1.00 equiv.), sodium carbonate (127.84 mg, 1.206 mmol, 2.00 equiv.) in DME (10 mL) and water (2 mL). The resulting solution was irradiated with microwave radiation for 20 min at 140° C. The reaction was monitored by LCMS. The resulting solution was extracted with EtOAc, then the organic layers combined and concentrated under vacuum. The residue was applied onto a silica gel column with PE:EA=8:1 to yield tert-butyl 4-(2-(6-(1-ethyl-4-fluoro-1H-indazol-6-yl)-2-methoxypyridin-3-yl)-3-methylbutyl)piperazine-1-carboxylate as a yellow oil.

Mass spectrum (ESI, m/z): Calculated for $C_{29}H_{40}FN_5O_3$, 526.3 [M+H], found 526.3.

Step 3: 1-ethyl-4-fluoro-6-(6-methoxy-5-(3-methyl-1-(piperazin-1-yl)butan-2-yl)pyridin-2-yl)-1H-indazole Into a 25-mL round-bottom flask, were placed a solution of tert-butyl 4-(2-(6-(1-ethyl-4-fluoro-1H-indazol-6-yl)-2-methoxypyridin-3-yl)-3-methylbutyl)piperazine-1-carboxylate (180 mg, 0.342 mmol, 1.00 equiv.) in DCM (6 mL). Trifluoroacetic acid (1 mL) was then added. The solution was stirred overnight at room temperature. The reaction was monitored by LCMS. The resulting solution was adjusted to pH 6~7 with sodium bicarbonate and then extracted with EtOAc. The organic layers combined and concentrated under vacuum. The residue was applied onto a silica gel column with DCM:MeOH=30:1 to yield 1-ethyl-4-fluoro-6-(6-methoxy-5-(3-methyl-1-(piperazin-1-yl)butan-2-yl)pyridin-2-yl)-1H-indazole as a yellow oil.

Mass spectrum (ESI, m/z): Calculated for $C_{24}H_{32}FN_5O$, 426.3 [M+H], found 426.3.

Step 4: 1-ethyl-4-fluoro-6-(6-methoxy-5-(3-methyl-1-(4-(methylsulfonyl)piperazin-1-yl)butan-2-yl)pyridin-2-yl)-1H-indazole Into a 25-ml round-bottom flask, were placed a solution of 1-ethyl-4-fluoro-6-(6-methoxy-5-(3-methyl-1-(piperazin-1-yl)butan-2-yl)pyridin-2-yl)-1H-indazole (110 mg, 0.258 mmol, 1.00 equiv.) in DCM (10 mL). Then methanesulfonyl chloride (59.22 mg, 0.517 mmol, 2.00 equiv.) and triethylamine (52.31 mg, 0.517 mmol, 2.00 equiv.) were added. The solution was stirred for 5.0 h at room temperature. The reaction was monitored by LCMS. The resulting solution was extracted with DCM, then the organic layers combined and concentrated under vacuum. The residue was applied onto a silica gel column with PE:EA=1:1 to yield 1-ethyl-4-fluoro-6-(6-methoxy-5-(3-methyl-1-(4-(methylsulfonyl)piperazin-1-yl)butan-2-yl)pyridin-2-yl)-1H-indazole as a yellow oil.

Mass spectrum (ESI, m/z): Calculated for $C_{25}H_{34}FN_5O_3S$, 504.2 [M+H], found 504.2.

Step 5: 6-(1-ethyl-4-fluoro-1H-indazol-6-yl)-3-(3-methyl-1-(4-(methylsulfonyl)piperazin-1-yl)butan-2-yl)pyridin-2(1H)-one The title compound was prepared according to the procedure as described in Example 149 by demethylation to yield the product as a yellow solid.

$^1$H NMR (300 MHz, CD$_3$OD) δ: 8.15 (s, 1H), 7.81 (s, 1H), 7.52 (d, J=7.2 Hz, 1 H), 7.21 (d, J=9.9 Hz, 1H), 6.77 (d, J=7.2 Hz, 1H), 4.53-4.60 (m, 2H), 3.09-3.16 (m, 4H), 2.80-3.09 (m, 4H), 2.52-2.74 (m, 2 H), 2.41-2.51 (m, 2H), 2.01-2.04 (m, 1H), 1.54 (t, J=7.2 Hz, 3H), 1.03 (d, J=6.9 Hz, 3H), 0.90 (d, J=6.9 Hz, 3H). $^{19}$F NMR (300 MHz, CD$_3$OD) δ: −119.16. Mass spectrum (ESI, m/z): Calculated For $C_{24}H_{32}FN_5O_3S$, 490.2 [M+H], found 490.2.

Example 155

Compound #129

4-{2-[6-(4-ethyl-8-fluoro-2,3-dihydro-1,4-benzoxazin-6-yl)-2-oxo-1H-pyridin-3-yl]-3-methylbutyl}-1,4-thiomorpholine-1,1-dione

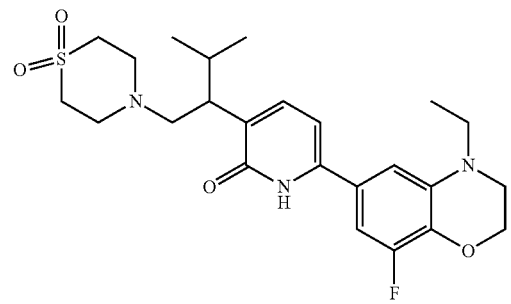 [SMILES: CCN1CCOc2c(F)cc(-c3ccc(C(CN4CCS(=O)(=O)CC4)C(C)C)c(=O)[nH]3)cc21]

Step 1:
5-bromo-2-(2-bromoethoxy)-1-fluoro-3-nitrobenzene

Into a 250-mL round bottle, to a solution of 4-bromo-2-fluoro-6-nitrophenol (5.00 g, 21 mmol, 1.00 equiv.) in DMF (50 mL). 1,2-Dibromoethane (5.90 g, 31 mmol, 1.50 equiv.), K$_2$CO$_3$ (5.80 g, 42 mmol, 2.00 equiv.) were added and the mixture was stirred for 3 h at 80° C. The mixture was quenched by the addition of H$_2$O, extracted with EA, the organic layers was concentrated under vacuum. The residue purified by silica gel with ethyl acetate/petroleum ether (5:95). The collected fractions were combined and concentrated under vacuum to yield 5-bromo-2-(2-bromoethoxy)-1-fluoro-3-nitrobenzene as yellow oil.

$^1$H NMR (400 MHz, CDCl$_3$) δ 7.79 (t, J=2.2 Hz, 1H), 7.56 (d, J=9.9 Hz, 1H), 4.52 (t, J=6.4, Hz, 2H), 3.64-3.88 (m, 2H).

Step 2: 6-bromo-8-fluoro-3,4-dihydro-2H-benzo[b][1,4]oxazine

Into a 100-mL round bottle, to a solution of 5-bromo-2-(2-bromoethoxy)-1-fluoro-3-nitrobenzene (3.90 g, 11.000 mmol, 1.00 equiv.) in EtOH (50 mL), were added Fe (3.00 g, 57 mmol, 5.00 equiv.), NH$_4$Cl (3.00 g, 57 mmol, 5.00 equiv.), and the mixture was stirred for 16 h at 80° C. The solid was filtered out, the organic layer was concentrated under vacuum. The residue purified by silica gel with ethyl acetate/petroleum ether (20:80). The collected fractions were combined and concentrated under vacuum to yield 6-bromo-8-fluoro-3,4-dihydro-2H-benzo[b][1,4]oxazine as yellow solid.

Mass spectrum (ESI, m/z): Calculated for $C_8H_7BrFNO$, 232.0 [M+H], found 231.8.

Step 3: 6-bromo-4-ethyl-8-fluoro-3,4-dihydro-2H-benzo[b][1,4]oxazine

Into a 20-mL vial, to a solution of 6-bromo-8-fluoro-3,4-dihydro-2H-benzo[b][1,4]oxazine (300 mg, 1.300 mmol, 1.00 equiv.) in THF (5 mL), was added NaBH$_4$CN (165 mg, 2.500 mmol, 2.00 equiv.) with stirring at 0° C. Acetaldehyde (1 mL) and CH$_3$COOH (0.5 mL) were then added and the mixture was stirred for 16 h at 70° C. The mixture was concentrated under vacuum. The residue purified by silica gel with ethyl acetate/petroleum ether (20:80). The collected fractions were combined and concentrated under vacuum to yield 6-bromo-4-ethyl-8-fluoro-3,4-dihydro-2H-benzo[b][1,4]oxazine as yellow oil.

Mass spectrum (ESI, m/z): Calculated for $C_{10}H_{11}BrFNO$, 260.0 [M+H], found 259.9.

Step 5: 4-{2-[6-(4-ethyl-8-fluoro-2,3-dihydro-1,4-benzoxazin-6-yl)-2-oxo-1H-pyridin-3-yl]-3-methylbutyl}-1,4-thiomorpholine-1,1-dione The title compound was prepared according to the procedure as described in Example 149 by coupling and demethylation to yield the product as yellow solid.

$^1$H NMR (400 MHz, $CD_3OD$) δ 7.58 (d, J=7.4 Hz, 1H), 6.75-6.80 (m, 2H), 6.38 (d, J=7.4 Hz, 1H), 4.16-4.27 (m, 2H), 3.71 (brs, 2H), 3.44-3.62 (m, 3H), 3.27-3.45 (m, 9H), 3.06-3.13 (m, 1H), 2.11-2.16 (m, 1H), 1.10 (t, J=7.1 Hz, 3H), 0.98 (d, J=6.6 Hz, 3H), 0.82 (d, J=6.6 Hz, 3H). $^{19}$F NMR (400 MHz, $CD_3OD$) δ −77.24, −138.0. Mass spectrum (ESI, m/z): Calculated for $C_{36.44}H_{38.22}F_{19.66}N_3O_{16.44}S$, 478.2 [M−6.22$CF_3COOH$+H], found 478.6.

Example 156

Compound #128

4-{2-[6-(4-ethyl-8-fluoro-3-oxo-2H-1,4-benzoxazin-6-yl)-2-oxo-1H-pyridin-3-yl]-3-methylbutyl},4-thiomorpholine-1,1-dione

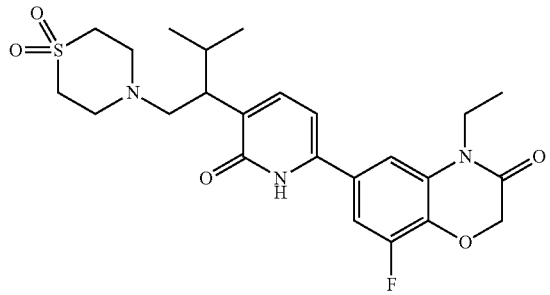 [SMILES: CCN1C(=O)COc2c(F)cc(-c3ccc(C(CN4CCS(=O)(=O)CC4)C(C)C)c(=O)[nH]3)cc21]

Step 1: ethyl 2-(4-bromo-2-fluoro-6-nitrophenoxy)acetate

Into a 25-mL round-bottom flask purged and maintained with an inert atmosphere of nitrogen, were placed a 4-bromo-2-fluoro-6-nitrophenol (500 mg, 2.119 mmol, 1.00 equiv.) in DMF (10 mL), ethyl 2-bromoacetate (424 mg, 2.539 mmol, 1.20 equiv.) and $K_2CO_3$ (588 mg, 4.255 mmol, 2.00 equiv.). The resulting solution was stirred 12 h at 60° C. The reaction was monitored by TLC. The resulting solution was extracted with EtOAc, then the organic layers combined and concentrated under vacuum. The residue was applied onto a silica gel column with EA/PE (1:10) to yield ethyl 2-(4-bromo-2-fluoro-6-nitrophenoxy)acetate as a yellow solid.

$^1$H NMR (400 MHz, $CDCl_3$) δ: 7.79-7.77 (m, 1H), 7.52-7.49 (m, 1H), 4.80 (s, 2 H), 4.27-4.22 (m, 2H), 1.32-1.26 (m, 3H

Step 2: 6-bromo-8-fluoro-2H-benzo[b][1,4]oxazin-3(4H)-one

Into a 25-mL round-bottom flask purged and maintained with an inert atmosphere of nitrogen, were placed ethyl 2-(4-bromo-2-fluoro-6-nitrophenoxy)acetate (408 mg, 1.267 mmol, 1.00 equiv.) and Fe (415 mg, 7.431 mmol, 6.00 equiv.) in EtOH (10 mL). $NH_4Cl$ (393 mg, 7.347 mmol, 6.00 equiv.) was added. The resulting solution was stirred 12 h at 60° C. The reaction was monitored by LCMS. The resulting solution was extracted with EtOAc, and the organic layers combined and concentrated under vacuum. The residue was applied onto a silica gel column with EA/PE (1:10) to yield ethyl 2-(4-bromo-2-fluoro-6-nitrophenoxy)acetate as a yellow solid.

$^1$H NMR (400 MHz, $CDCl_3$) δ: 7.00-9.67 (m, 1H), 6.76-6.75 (m, 1H), 4.68 (s, 2 H).

Step 3: 6-bromo-4-ethyl-8-fluoro-2H-benzo[b][1,4]oxazin-3(4H)-one

Into a 25-mL round-bottom flask purged and maintained with an inert atmosphere of nitrogen, were placed a 6-bromo-8-fluoro-2H-benzo[b][1,4]oxazin-3(4H)-one (50 mg, 0.203 mmol, 1.00 equiv.) and iodoethane (57 mg, 0.365 mmol, 1.80 equiv.) in $CH_3CN$ (5 mL), $K_2CO_3$ (57 mg, 0.412 mmol, 2.00 equiv.) and benzyltriethylammonium chloride (BTEAC) (46 mg, 0.203 mmol, 1.00 equiv.). The resulting solution was stirred 12 h at 60° C. The reaction was monitored by TCL the resulting solution was extracted with EtOAc, then the organic layers combined and concentrated under vacuum. The residue was applied onto a silica gel column with EA/PE (1:10) to yield 6-bromo-4-ethyl-8-fluoro-2H-benzo[b][1,4]oxazin-3(4H)-one as a yellow solid.

$^1$H NMR (400 MHz, $CDCl_3$), δ: 7.06-7.02 (m, 1H), 6.95-6.94 (m, 1H), 4.68 (s, 2 H), 4.02-0.95 (m, 2H), 1.33-1.28 (m, 3H).

Step 4: 4-{2-[6-(4-ethyl-8-fluoro-3-oxo-2H-1,4-benzoxazin-6-yl)-2-oxo-1H-pyridin-3-yl]-3-methylbutyl},4-thiomorpholine-1,1-dione The title compound was prepared according to the procedure as described in Example 149 by coupling and demethylation to yield the product as an off-white solid.

$^1$H NMR (400 MHz, Methanol-$d_4$) δ: 7.60 (s, 1H), 7.31-7.26 (m, 2H), 6.72 (d, J=7.2 Hz, 1H), 4.74 (s, 2 H), 4.12-4.11 (m, 2H), 3.77 (s, 2H), 3.61-3.58 (m, 4 H), 3.48-3.31 (m, 4 H), 3.13-3.09 (m, 1H), 2.17-2.12 (m, 1H), 1.31-1.27 (m, 3H), 0.90 (d, J=6.8 Hz, 3H), 0.79 (s, 3H). $^{19}$F NMR (400 MHz, Methanol-$d_4$) δ: −135.63, −77.36. Mass spectrum (ESI, m/z): Calculated for $C_{24}H_{30}FN_3O_5S$, 492.2 [M+H−1.32 $CF_3COOH$], found 492.2.

Example 157

Compound #119

3-(1-(1,1-dioxidothiomorpholino)-3-methylbutan-2-yl)-6-(8-fluoronaphthalen-2-yl)pyridin-2(1H)-one

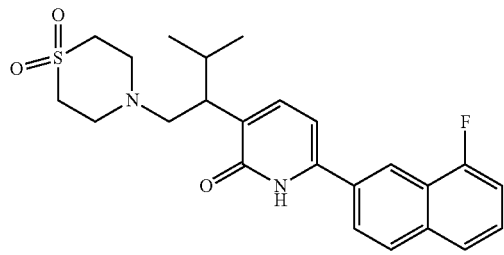 [SMILES: CC(C)C(CN1CCS(=O)(=O)CC1)c1ccc(-c2ccc3cccc(F)c3c2)[nH]c1=O]

The title compound was prepared according to the procedure as described in Example 149 by coupling and demethylation to yield the product as an off-white solid.

$^1$H NMR (400 MHz, CDCl$_3$) δ: 8.40 (s, 1H), 8.05 (d, J=7.5 Hz, 1H), 7.85 (d, J=8.7 Hz, 1H), 7.74-7.80 (m, 2H), 7.52-7.58 (m, 1H), 7.25-7.35 (m, 1H), 6.75 (d, J=7.2 Hz, 1H), 3.10 (m, 1H), 3.05 (m, 4H), 2.95 (m, 4H), 2.84 (m, 2H), 1.01 (d, J=6.8 Hz, 3H), 0.87 (d, J=6.6 Hz, 3H). Mass spectrum (ESI, m/z): Calculated for C$_{24}$H$_{27}$FN$_2$O$_3$S, 443.55 [M+H], found 443.7.

Example 158

Compound #101

6-(8-fluoronaphthalen-2-yl)-3-(3-methyl-1-(4-(methylsulfonyl)piperazin-1-yl)butan-2-yl)pyridin-2(1H)-one

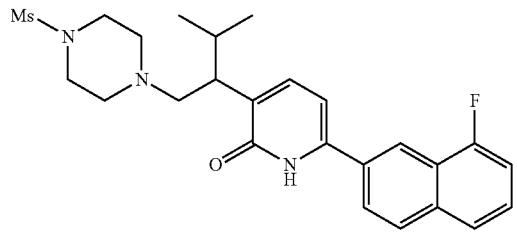 [SMILES: CC(C)C(CN1CCN(S(C)(=O)=O)CC1)c1ccc(-c2ccc3cccc(F)c3c2)[nH]c1=O]

The title compound was prepared according to the procedure as described in Example 149 by coupling and demethylation to yield the product as an off-white solid.

$^1$H NMR (400 MHz, CDCl$_3$) δ: 8.35 (s, 1H), 7.98 (d, J=7.0 Hz, 1H), 7.75 (d, J=8.5 Hz, 1H), 7.76 (m, 2H), 7.55 (m, 1H), 7.31 (m, 1H), 6.70 (d, J=7.0 Hz, 1H), 3.16 (m, 3H), 3.10 (m, 1H), 2.95 (m, 4H), 2.62 (m, 2H), 2.45 (m, 2H), 2.01-2.04 (m, 2H), 1.02 (d, J=6.5 Hz, 3H), 0.92 (d, J=6.5 Hz, 3H).

Mass spectrum (ESI, m/z): Calculated for C$_{25}$H$_{30}$FN$_3$O$_3$S, 472.59 [M+H], found 472.7.

Example 159

Compound #248

2-(6-(1-ethyl-4-fluoro-1H-indazol-6-yl)-2-oxo-1,2-dihydropyridin-3-yl)-2-isopropylmorpholin-3-one

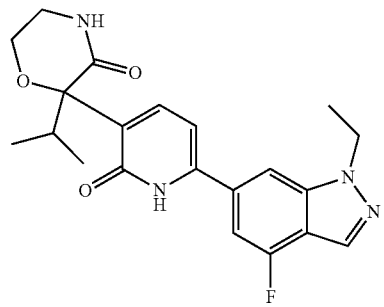 [SMILES: CCn1ncc2c(F)cc(-c3ccc(C4(C(C)C)OCCNC4=O)c(=O)[nH]3)cc21]

Step 1: ethyl 2-(6-chloro-2-methoxypyridin-3-yl)-2-(cyanomethoxy)-3-methylbutanoate Ethyl 2-(6-chloro-2-methoxypyridin-3-yl)-2-(cyanomethoxy)-3-methylbutanoate (600 mg, 2.08 mmol, 1 equiv.) in DMF (5 mL) was treated with NaH (60%, 125 mg, 3.13 mmol, 1.5 equiv.) for 10 min at 0° C. Bromoacetonitrile (139 μL, 2.08 mmol, 1 equiv.) was added dropwise and the reaction was warmed to room temperature for 2 hour. The solution was partitioned between water and ethyl acetate. The organic layer was washed with brine, dried and concentrated and purified by silica gel column to yield the product as a yellow oil.

Mass spectrum (ESI, m/z): Calculated for C$_{15}$H$_{19}$ClN$_2$O$_4$: 327.78 [M+H], found: 327.5.

Step 2: 2-(6-chloro-2-methoxypyridin-3-yl)-2-isopropylmorpholin-3-one

Ethyl 2-(6-chloro-2-methoxypyridin-3-yl)-2-(cyanomethoxy)-3-methylbutanoate (150 mg, 0.46 mmol, 1 equiv.) and K$_2$CO$_3$ (317 mg, 2.295 mmol, 5 equiv.) in EtOH (10 mL) were refluxed overnight. The solvent was removed and the residue was dissolved in EtOH (10 mL) and treated with PtO$_2$ (10 mg, 0.046 mmol, 0.1 equiv.) under 50 psi hydrogenation overnight. The catalyst was filtrated and the residue was worked up to yield the residue which was then purified by silica gel column to yield the product as a white solid.

Mass spectrum (ESI, m/z): Calculated for C$_{13}$H$_{17}$ClN$_2$O$_3$: 285.74 [M+H], found: 285.5.

Step 3: 2-(6-(1-ethyl-4-fluoro-1H-indazol-6-yl)-2-oxo-1,2-dihydropyridin-3-yl)-2-isopropylmorpholin-3-one The title compound was prepared according to the procedure as described in Example 1 step 1 by Suzuki coupling with 1-ethyl-4-fluoro-6-(4,4,5,5-tetramethyl-1,3,2-dioxaborolan-2-yl)-1H-indazole followed by demethylation to yield the product as a white solid.

¹H NMR (400 MHz, CDCl₃) δ: 10.05 (br, s, 1H), 8.11 (s, 1H), 7.98 (d, J=4.5 Hz, 1H), 7.92 (s, 1H0, 7.17 (s, 1H), 7.10 (d, J=7.2 Hz, 1H), 4.52 (q, J=5.0 Hz, 2H), 4.08 (m, 2H), 3.78 (m, 2H), 3.70 (m, 1H), 3.38 (m, 2H), 2.85 (m, 2H), 1.55 (t, J=7.0 Hz, 3H), 1.10 (d, J=6.0 Hz, 3H), 0.88 (d, J=6.0 Hz, 3H). Mass spectrum (ESI, m/z): Calculated for $C_{21}H_{23}FN_4O_3$: 399.44 [M+H], found: 399.5.

Example 160

Compound #247

5-(6-(naphthalen-2-yl)-2-oxo-1,2-dihydropyridin-3-yl)-4,5-di hydro-1H-pyrazole-5-carboxamide

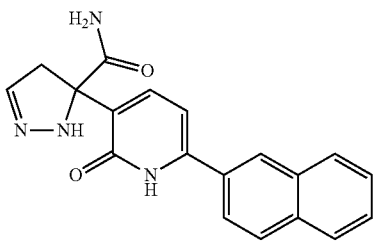 [SMILES: NC(=O)C1(c2ccc(-c3ccc4ccccc4c3)[nH]c2=O)CC=NN1]

Step 1: methyl 2-(6-chloro-2-methoxypyridin-3-yl)acrylate

Methyl 2-(6-chloro-2-methoxypyridin-3-yl)-2-hydroxypropanoate (1 g, 4.08 mmol, 1 equiv.) in toluene (15 mL) was treated with pTSA (70 mg, 0.41 mmol, 0.1 equiv.) and reflux overnight. The solution was partitioned with ethyl acetate and saturated NaHCO₃ and then washed with brine, dried, concentrated to yield the residue which was used in the next step without further purification.

Step 2: methyl 5-(6-chloro-2-methoxypyridin-3-yl)-4,5-dihydro-1H-pyrazole-5-carboxylate Methyl 2-(6-chloro-2-methoxypyridin-3-yl)acrylate (405 mg, 1.8 mmol, 1 equiv.) and TMSCHN₂ (1.8 mL, 2.0 N, 3.6 mmol, 2 equiv.) in THF (10 mL) were heated to reflux overnight. The solvent was removed and the residue was purified by silica gel column to yield the product as a yellow oil.

Mass spectrum (ESI, m/z): Calculated for $C_{11}H_{12}ClN_3O_3$: 270.69 [M+H], found: 270.5.

Step 3: 5-(6-(naphthalen-2-yl)-2-oxo-1,2-dihydropyridin-3-yl)-4,5-dihydro-1H-pyrazole-5-carboxamide The title compound was prepared according to the procedure as described in Example 1 step 1 by Suzuki coupling with naphthalen-2-ylboronic acid followed by hydrolysis, aminolysis and demethylation to yield the product as a white solid.

¹H NMR (400 MHz, CD₃OD) δ: 8.21 (s, 1H), 8.02 (m, 3H), 7.95 (d, J=5.2 Hz, 1H), 7.72 (m, 2H), 7.58 (d, J=7.2 Hz, 2H), 6.80 (m, 1H), 3.35 (m, 2H).

Mass spectrum (ESI, m/z): Calculated for $C_{19}H_{16}N_4O_2$: 333.36 [M+H], found: 333.5.

Example 161

Compound #252

5-((6-(8-fluoronaphthalen-2-yl)-2-oxo-1,2-dihydropyridin-3-yl)methyl)oxazolidine-2,4-dione

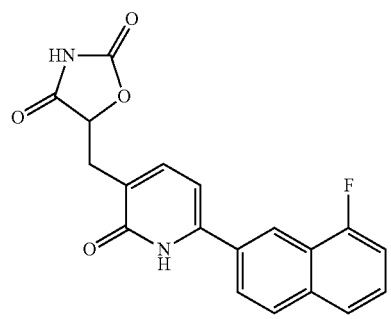 [SMILES: O=C1NC(=O)C(Cc2ccc(-c3ccc4cccc(F)c4c3)[nH]c2=O)O1]

The title compound was prepared according to the procedure as described in Example 5 by coupling, dehydration, hydrogenation and demethylation to yield the product as a white solid.

Mass spectrum (ESI, m/z): Calculated for $C_{19}H_{13}FN_2O_4$, 353.1 (M+H), found 353.0.

Example 162 Compound #17

6-(4-ethyl-8-fluoro-3,4-dihydro-2H-benzo[b][1,4]oxazin-6-yl)-3-(3-((2-oxopyrrolidin-3-yl)methyl)pentan-3-yl)pyridin-2(1H)-one

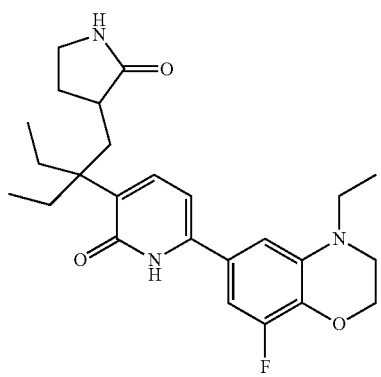 [SMILES: CCN1CCOc2c(F)cc(-c3ccc(C(CC)(CC)CC4CCNC4=O)c(=O)[nH]3)cc21]

The title compound was prepared according to the procedure as described in Example 8 step 1 by hydrogenation and demethylation to yield the product as a white solid.

Mass spectrum (ESI, m/z): Calculated for $C_{25}H_{32}FN_3O_3$, 442.5 (M+H), found 442.2.

Example 163

Compound #124

(Z)-5-(2-(6-(1-cyclopentyl-4-fluoro-1H-indazol-6-yl)-2-oxo-1,2-dihydropyridin-3-yl)-3-methylbutyl-idene)oxazolidine-2,4-dione

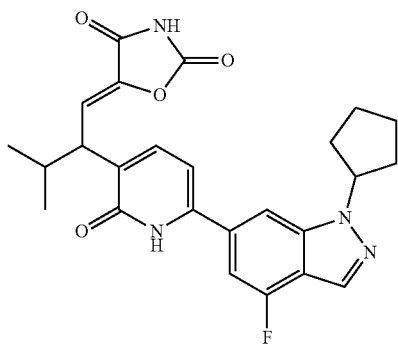 [SMILES: CC(C)C(/C=C1\OC(=O)NC1=O)c1ccc(-c2cc(F)c3cnn(C4CCCC4)c3c2)[nH]c1=O]

The title compound was prepared according to the procedure as described in Example 5 starting with aldol condensation by t-BuLi, dehydration followed by demethylation with TMSCl/NaI to yield the product as a white solid.

$^1$H NMR (300 MHz, CD$_3$OD, ppm) δ: 8.10 (s, 1 H), 7.80 (s, 1 H), 7.57 (d, J=7.2 Hz, 1 H), 7.16 (d, J=11.4 Hz, 1 H), 6.72 (d, J=7.2 Hz, 1 H), 6.30 (d, J=10.8 Hz, 1 H), 5.17-5.25 (m, 1 H), 3.70-3.82 (m, 1 H), 2.09-2.42 (m, 5 H), 1.89-2.07 (m, 2 H), 1.71-1.85 (m, 2 H), 0.99 (d, J=6.6 Hz, 3 H), 0.91 (d, J=6.6 Hz, 3 H). $^{19}$F NMR (300 MHz, CD$_3$OD, ppm) δ: −119.36. Mass spectrum (EI, m/z): Calculated For C$_{25}$H$_{25}$FN$_4$O$_4$, 465.2 [M+H]$^+$, found 465.0.

Example 164

Compound #295

6-(1-ethyl-4-fluoro-1H-indazol-6-yl)-3-(3-hydroxy-1-(isopropylsulfonyl)piperidin-3-yl)pyridin-2(1H)-one

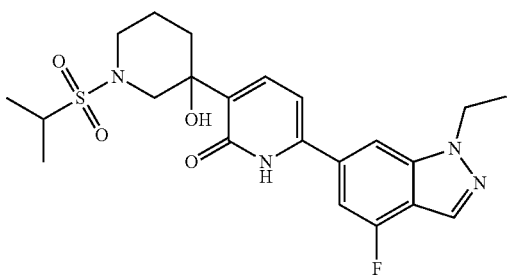 [SMILES: CCn1ncc2c(F)cc(-c3ccc(C4(O)CCCN(S(=O)(=O)C(C)C)C4)c(=O)[nH]3)cc21]

Step 1: tert-butyl 3-(6-(1-ethyl-4-fluoro-1H-indazol-6-yl)-2-methoxypyridin-3-yl)-3-hydroxypiperidine-1-carboxylate Into a 50-mL round bottle maintained with an inert atmosphere of nitrogen, to a solution of 1-ethyl-4-fluoro-6-(6-methoxypyridin-2-yl)-1H-indazole (150 mg, 0.552 mmol, 1.00 equiv.) in THF (5 mL) was added t-BuLi (1.7 N, 0.49 mL, 0.829 mmol, 1.50 equiv.) with stirring at −78° C. The resulting mixture was stirred at −78° C. for 3 h. tert-Butyl 3-oxopiperidine-1-carboxylate (165 mg, 0.829 mmol, 1.50 equiv.) was then added with stirring at −78° C. The resulting mixture was stirred at −78° C. for 2 h. The reaction was quenched with NH$_4$Cl (10 mL). The resulting mixture was extracted with EtOAc (3×10 mL). The organic layers were combined, dried over Na$_2$SO$_4$, filtered and concentrated. The residue obtained was purified by silica gel chromatography (0-10% EtOAc/petroleum ether) to yield tert-butyl 3-(6-(1-ethyl-4-fluoro-1H-indazol-6-yl)-2-methoxypyridin-3-yl)-3-hydroxypiperidine-1-carboxylate as a white solid.

Mass spectrum (EI, m/z): Calculated For C$_{25}$H$_{31}$FN$_4$O$_4$, 471.55 [M+H], found 471.8.

Step 2: 3-(6-(1-ethyl-4-fluoro-1H-indazol-6-yl)-2-methoxypyridin-3-yl)piperidin-3-ol Into a 25 mL flask was added tert-butyl 3-(6-(1-ethyl-4-fluoro-1H-indazol-6-yl)-2-methoxypyridin-3-yl)-3-hydroxypiperidine-1-carboxylate (168 mg, 0.357 mmol, 1.00 equiv.) in dichloromethane (1 mL) and then trifluoroacetic acid (1 mL) at 0° C. The resulting mixture was then warmed to room temperature for 2 hours. The solvent was removed in vacuum and the residue was carried over to next step without further purification.

Mass spectrum (EI, m/z): Calculated For C$_{20}$H$_{23}$FN$_4$O$_2$, 371.43 [M+H], found 371.5.

Step 3: 3-(6-(1-ethyl-4-fluoro-1H-indazol-6-yl)-2-methoxypyridin-3-yl)-1-(isopropylsulfonyl) piperidin-3-ol Into a 25 mL flask was added a solution of 3-(6-(1-ethyl-4-fluoro-1H-indazol-6-yl)-2-methoxypyridin-3-yl)piperidin-3-ol TFA salt (100 mg, 0.206 mmol, 1.00 equiv) in DCM (5 mL). Propane-2-sulfonyl chloride (30 mg, 0.618 mmol, 3.00 equiv.) and Et$_3$N (87 μL, 0.618 mmol, 3.00 equiv.) were then added. The resulting mixture was stirred at 20° C. for 2 h. The reaction was quenched with H$_2$O (10 mL). The resulting mixture was extracted with DCM (3×10 mL). The organic layers were combined, dried over Na$_2$SO$_4$, filtered and concentrated.

The residue was purified by silica gel column to yield 53-(6-(1-ethyl-4-fluoro-1H-indazol-6-yl)-2-methoxypyridin-3-yl)-1-(isopropylsulfonyl) piperidin-3-ol as a yellow oil.

Mass spectrum (EI, m/z): Calculated For C$_{23}$H$_{29}$FN$_4$O$_4$, 477.57 [M+H], found 477.8.

Step 4: 6-(1-ethyl-4-fluoro-1H-indazol-6-yl)-3-(3-hydroxy-1-(isopropylsulfonyl)piperidin-3-yl)pyridin-2(1H)-one The title compound was prepared according to the procedure as described in Example 1 step 5 by demethylation to yield the product as a white solid.

$^1$H NMR (400 MHz, CDCl$_3$) δ: 8.31 (s, 1H), 8.15 (s, 1H), 7.75 (s, 1H), 7.09 (d, J=7.5 Hz, 1H), 7.02 (m, 1H), 4.52 (q, 2H), 4.05 (m, 1H), 3.81 (m, 1H), 3.55 (m, 1H), 3.22 (m, 2H), 2.55 (m, 1H), 2.10 (m, 1H), 1.75 (m, 1H), 1.62 (m, 1H), 1.55 (t, J=6.0 Hz, 3H), 1.40 (d, J=7.0 Hz, 6H). Mass spectrum (ESI, m/z): Calculated for C$_{225}$H$_{27}$FN$_4$O$_4$S, 463.54 [M+H], found: 463.7.

Example 165

Compound #296

6-(1-ethyl-4-fluoro-1H-indazol-6-yl)-3-(3-fluoro-1-(isopropylsulfonyl)piperidin-3-yl)pyridin-2(1H)-one

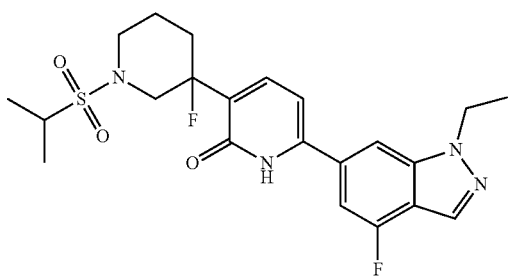 [SMILES: CCn1ncc2c(F)cc(-c3ccc(C4(F)CCCN(S(=O)(=O)C(C)C)C4)c(=O)[nH]3)cc21]

Into a 10 mL flask were added a solution of 6-(1-ethyl-4-fluoro-1H-indazol-6-yl)-3-(3-hydroxy-1-(isopropylsulfonyl)piperidin-3-yl)pyridin-2(1H)-one (25 mg, 0.054 mmol, 1.00 equiv.) in DCM (2 mL) and then DAST (27 mg, 0.162 mmol, 3.00 equiv.). The resulting mixture was stirred at −78° C. for 1 h. The reaction was quenched with MeOH (0.5 mL). The resulting mixture was extracted with DCM (3×10 mL). The organic layers were combined, dried over Na$_2$SO$_4$, filtered and concentrated. The residue was purified by silica gel column to yield a white solid.

$^1$H NMR (400 MHz, CDCl$_3$) δ: 8.15 (s, 1H), 8.01 (s, 1H), 7.68 (s, 1H), 7.15 (d, J=7.5 Hz, 1H), 6.88 (d, J=5.6 Hz, 1H), 4.55 (q, 2H), 3.95 (m, 1H), 3.75 (m, 1H), 3.18 (m, 1H), 2.92 (t, J=5.6 Hz, 1H), 2.70 (m, 1H), 2.05 (m, 1H), 1.90 (m, 1H), 1.72 (m, 1H), 1.58 (t, J=6.0 Hz, 3H), 1.40 (d, J=7.0 Hz, 6H). Mass spectrum (ESI, m/z): Calculated for C$_{22}$H$_{26}$F$_2$N$_4$O$_3$S, 465.53 [M+H], found: 465.7.

Example 166

Compound #297

6-(1-ethyl-4-fluoro-1H-indazol-6-yl)-3-(1-(isopropylsulfonyl)-2,5-dihydro-1H-pyrrol-3-yl)pyridin-2(1H)-one

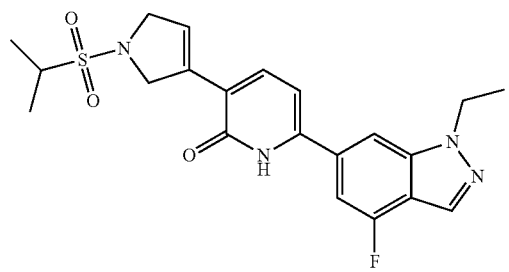 [SMILES: CCn1ncc2c(F)cc(-c3ccc(C4=CCN(S(=O)(=O)C(C)C)C4)c(=O)[nH]3)cc21]

The title compound was prepared according to the procedure as described in Example 164 step 1 to 3 by coupling with tert-butyl-3-oxopyrrolidine-1-carboxylate, de-protection of Boc group followed by demethylation to yield the product as a white solid.

$^1$H NMR (400 MHz, CDCl$_3$) δ: 8.10 (s, 1H), 7.99 (s, 1H), 7.78 (s, 1H), 7.15 (d, J=7.5 Hz, 1H), 6.85 (d, J=7.5 Hz, 1H), 5.75 (m, 1H), 4.55 (m, 2H), 3.55 (m, 1H), 3.52 (m, 1H), 3.22 (m, 1H), 3.20 (m, 1 H), 3.15 (m, 1H), 1.45 (t, J=7.5 Hz, 3H), 1.42 (d, J=6.5 Hz, 6H). Mass spectrum (ESI, m/z): Calculated for C$_{21}$H$_{23}$FN$_4$O$_3$S, 431.50 (M+H), found 431.7.

Example 167

Compound #298

6-(1-ethyl-4-fluoro-1H-indazol-6-yl)-3-(3-hydroxy-1-(isopropylsulfonyl)azetidin-3-yl)pyridin-2(1H)-one

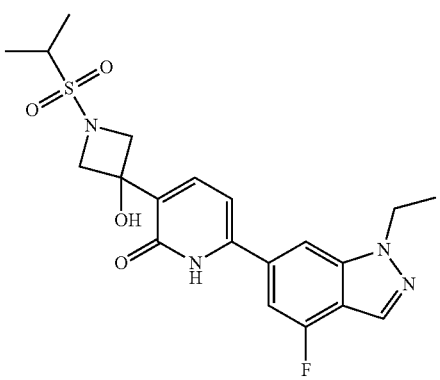 [SMILES: CCn1ncc2c(F)cc(-c3ccc(C4(O)CN(S(=O)(=O)C(C)C)C4)c(=O)[nH]3)cc21]

The title compound was prepared according to the procedure as described in Example 164 step 1 to 3 by coupling with tert-butyl 3-oxoazetidine-1-carboxylate, de-protection of Boc group followed by demethylation to yield the product as a white solid.

$^1$H NMR (400 MHz, CDCl$_3$) δ: 8.11 (s, 1H), 7.98 (s, 1H), 7.88 (d, J=6.0 Hz, 1H), 7.46 (d, J=5.8 Hz, 1H), 7.32 (d, J=8.5 Hz, 1H), 4.89 (m, 1H), 4.65 (d, J=5.6 Hz, 1H), 4.50 (m, 2H), 3.62 (m, 2H), 3.25 (m, 1H), 1.55 (t, J=6.8 Hz, 3H), 1.46 (d, J=6.0 Hz, 6H). Mass spectrum (ESI, m/z): Calculated for C$_{20}$H$_{23}$FN$_4$O$_4$S, 435.49 (M+H), found 435.6.

Example 168

Compound #299

6-(1-ethyl-4-fluoro-1H-indazol-6-yl)-3-syn-7-oxo-6-oxabicyclo[3.2.1]octan-5-yl)pyridin-2(1H)-one

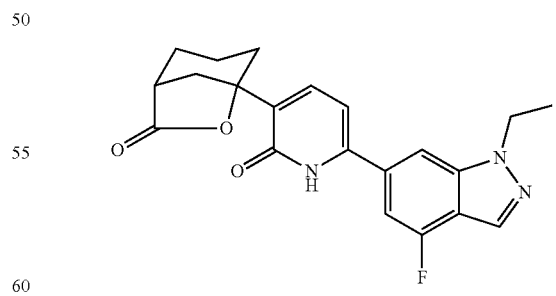

Step 1: ethyl 3-(6-chloro-2-methoxypyridin-3-yl)-3-hydroxycyclohexane-1-carboxylate t-BuLi (1.7 N, 9.9 mL, 16.8 mmol, 1 equiv.) was dropwise added into 2-chloro-6-methoxypyridine (2 mL, 16.8 mmol, 1 equiv.) in THF (15 mL) at −78° C. for 10 min. Ethyl 3-oxocyclohexane-1-carboxylate (2.86 g, 16.8 mmol, 1 equiv.) was added dropwise. The reaction was kept at −78° C. for another 2 hour and quenched with saturated NH$_4$Cl, extracted with ethyl acetate and purified by silica gel column using ethyl acetate/heptanes for 10 to 50% to yield the product as a yellow oil.

Mass spectrum (ESI, m/z): Calculated for C$_{15}$H$_{20}$ClNO$_4$: 314.78 [M+H], found: 314.5.

Step 2: 5-(6-chloro-2-methoxypyridin-3-yl)-6-oxabicyclo[3.2.1]octan-7-one

Ethyl 3-(6-chloro-2-methoxypyridin-3-yl)-3-hydroxycyclohexane-1-carboxylate (500 mg, 1.6 mmol, 1 equiv.) and pTSA (55 mg, 0.32 mmol, 0.2 equiv.) in toluene (10 mL) was heated at 80° C. overnight. The solvent was removed and the residue was purified by silica gel column to yield the product as a residue.

Mass spectrum (ESI, m/z): Calculated for C$_{13}$H$_{14}$ClNO$_3$: 268.71 [M+H], found: 268.5.

Step 3: 6-(1-ethyl-4-fluoro-1H-indazol-6-yl)-3-syn-7-oxo-6-oxabicyclo[3.2.1]octan-5-yl)pyridin-2(1H)-one The title compound was prepared according to the procedure as described in Example 1 step 1 by Suzuki coupling with 1-ethyl-4-fluoro-6-(4,4,5,5-tetramethyl-1,3,2-dioxaborolan-2-yl)-1H-indazole and demethylation to yield the product as an off-white solid.

$^1$H NMR (400 MHz, CDCl$_3$) δ: 12.7 (br, s, 1H), 8.10 (s, 1H), 7.78 (s, 1H), 7.52 (d, J=6.5 Hz, 1H), 7.08 (d, J=7.0 Hz, 1H), 6.67 (d, J=6.0 Hz, 1H), 4.55 (m, 2H), 2.85 (m, 2H), 2.72 (m, 2H), 2.32 (m, 2H), 2.10 (m, 2H), 1.82 (m, 2H), 1.58 (t, J=6.8 Hz, 3H). Mass spectrum (ESI, m/z): Calculated for C$_{21}$H$_{20}$FN$_3$O$_3$: 382.41 [M+H], found: 382.5.

Example 169

Compound #300

4-(6-(1-ethyl-4-fluoro-1H-indazol-6-yl)-2-oxo-1,2-dihydropyridin-3-yl)-4-hydroxy-6-azabicyclo[3.2.1]octan-7-one

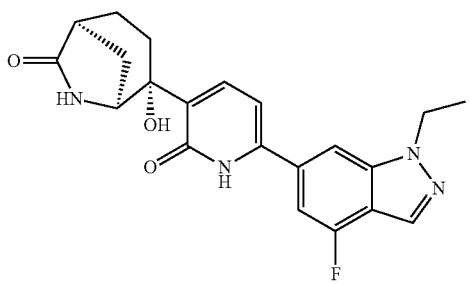 [SMILES: CCn1ncc2c(F)cc(-c3ccc([C@]4(O)CC[C@H]5C[C@@H]4NC5=O)c(=O)[nH]3)cc21]

Step 1: ethyl 4-(6-chloro-2-methoxypyridin-3-yl)cyclohex-3-ene-1-carboxylate

Ethyl 3-(6-chloro-2-methoxypyridin-3-yl)-3-hydroxycyclohexane-1-carboxylate (1.05 g, 3.34 mmol) in DCM (10 mL) and TFA (5 mL) mixed solvent was stirred at room temperature for 2 hour. The solvent was removed and residue was dried over vacuum and used in the next step without further purification.

Mass spectrum (ESI, m/z): Calculated for C$_{15}$H$_{15}$ClNO$_3$: 296.76 [M+H], found: 296.5.

Step 2: ethyl-6-(6-chloro-2-methoxypyridin-3-yl)-7-oxabicyclo[4.1.0]heptane-3-carboxylate Ethyl 4-(6-chloro-2-methoxypyridin-3-yl)cyclohex-3-ene-1-carboxylate (400 mg, 1.35 mmol, 1 equiv.) was treated with mCPBA (70%, 570 mg, 1.62 mmol, 1.2 equiv.) in DCM (10 mL) at 0° C. for 30 min and then warmed to room temperature. The reaction solution was partitioned between DCM and saturated sodium bicarbonate. The organic layer was washed with brine, dried and concentrated and purified by silica gel column to yield the product as a residue.

Mass spectrum (ESI, m/z): Calculated for C$_{15}$H$_{18}$ClNO$_4$: 312.76 [M+H], found: 312.8.

Step 3: ethyl-3-azido-4-(6-chloro-2-methoxypyridin-3-yl)-4-hydroxycyclohexane-1-carboxylate Ethyl-6-(6-chloro-2-methoxypyridin-3-yl)-7-oxabicyclo[4.1.0]heptane-3-carboxylate (200 mg, 0.642 mmol, 1 equiv.) in DMSO (2 mL) was treated with NaN$_3$ (208 mg, 3.21 mmol, 5 equiv.) at 70° C. overnight. The reaction was cooled down to room temperature and stirred for another 6 hour. The solution was partitioned between ethyl acetate and water. The organic layer was dried, filtered and concentrated and purified by silica gel column to yield the product as an off-white solid.

Step 4: ethyl-3-amino-4-(6-chloro-2-methoxypyridin-3-yl)-4-hydroxycyclohexane-1-carboxylate Ethyl-3-azido-4-(6-chloro-2-methoxypyridin-3-yl)-4-hydroxycyclohexane-1-carboxylate (50 mg, 0.141 mmol, 1 equiv.) was dissolved in MeOH (2 mL) and HCl aqueous solution (60 μL) and treated with PtO$_2$ (3.2 mg, 0.014 mmol, 0.1 equiv.) under 50 psi hydrogenation overnight. The catalyst was filtrated to yield the residue which was then purified by silica gel column to yield the product.

Mass spectrum (ESI, m/z): Calculated for C$_{15}$H$_{21}$ClN$_2$O$_4$: 329.79 [M+H], found: 329.5.

Step 5: 4-(6-chloro-2-methoxypyridin-3-yl)-4-hydroxy-6-azabicyclo[3.2.1]octan-7-one Ethyl-3-amino-4-(6-chloro-2-methoxypyridin-3-yl)-4-hydroxycyclohexane-1-carboxylate (30 mg, 0.09 mmol, 1 equiv.) and K$_2$CO$_3$ (12 mg, 0.09 mmol, 1 equiv.) in MeOH (2 mL) was reflux for 2 hour. The solvent was removed and the residue was partitioned between ethyl acetate and water. The organic layer was washed with brine, dried, filtered, concentrated and purified by silica gel column to yield the product as an off-white solid.

Mass spectrum (ESI, m/z): Calculated for C$_{13}$H$_{15}$ClN$_2$O$_3$: 283.72 [M+H], found: 283.7.

Step 6: 4-(6-(1-ethyl-4-fluoro-1H-indazol-6-yl)-2-oxo-1,2-dihydropyridin-3-yl)-4-hydroxy-6-azabicyclo[3.2.1]octan-7-one The title compound was prepared according to the procedure as described in Example 1 step 1 by Suzuki coupling with 1-ethyl-4-fluoro-6-(4,4,5,5-tetramethyl-1,3,2-dioxaborolan-2-yl)-1H-indazole and demethylation to yield the product as an off-white solid.

$^1$H NMR (400 MHz, CD$_3$OD) δ: 8.18 (s, 1H), 7.96 (s, 1H), 7.52 (s, 1H), 7.15 (d, J=6.6 Hz, 1H), 6.74 (d, J=6.5 Hz, 1H), 4.65 (m, 2H), 3.42 (m, 1H), 3.10 (m, 1H), 2.52 (m, 1H), 2.43 (m, 1H), 1.98 (m, 2H), 1.75 (m, 2H), 1.45 (t, J=7.5 Hz, 3H). Mass spectrum (ESI, m/z): Calculated for C$_{21}$H$_{21}$FN$_4$O$_3$: 397.42 [M+H], found: 397.5.

Example 170

Compound #215

6-(6-(1-ethyl-4-fluoro-1H-indazol-6-yl)-2-oxo-1,2-dihydropyridin-3-yl)tetrahydro-1H,3H-pyrrolo[1,2-c]oxazol-3-one

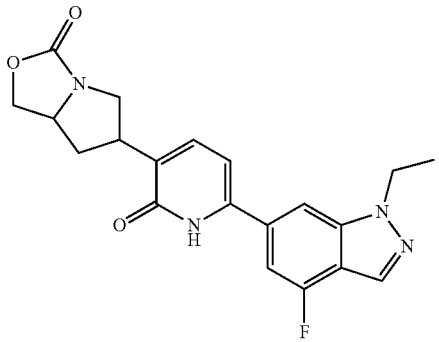 [SMILES: CCn1ncc2c(F)cc(-c3ccc(C4CC5COC(=O)N5C4)c(=O)[nH]3)cc21]

Step 1: 1-(tert-butyl) 2-methyl 4-(6-(1-ethyl-4-fluoro-1H-indazol-6-yl)-2-methoxypyridin-3-yl)pyrrolidine-1,2-dicarboxylate The title compound was prepared according to the procedure as described in Example 164 by reacting 2-chloro-6-methoxypyridine with 1-(tert-butyl) 2-methyl 4-oxopyrrolidine-1,2-dicarboxylate by t-BuLi, de-hydroxylation, reduction and then Suzuki coupling with 1-ethyl-4-fluoro-6-(4,4,5,5-tetramethyl-1,3,2-dioxaborolan-2-yl)-1H-indazole to yield the product as an off-white solid.

Mass spectrum (ESI, m/z): Calculated for C$_{26}$H$_{31}$FN$_4$O$_5$: 499.56 [M+H], found: 499.7.

Step 2: tert-butyl 4-(6-(1-ethyl-4-fluoro-1H-indazol-6-yl)-2-methoxypyridin-3-yl)-2-(hydroxymethyl)pyrrolidine-1-carboxylate 1-(tert-Butyl) 2-methyl 4-(6-(1-ethyl-4-fluoro-1H-indazol-6-yl)-2-methoxypyridin-3-yl)pyrrolidine-1,2-dicarboxylate (80 mg, 0.16 mmol, 1 equiv.) in THF (3 mL) at 0° C. was treated with LAH (1 M, 0.16 mL, 0.16 mmol, 1 equiv.) for 10 min. The reaction was quenched with ice water slowly and partitioned between Rochelle salt water and ethyl acetate. The organic layer was washed with brine, dried and purified by silica gel column to yield the product as a yellow oil.

Mass spectrum (ESI, m/z): Calculated for C$_{25}$H$_{31}$FN$_4$O$_4$: 471.55 [M+H], found: 477.6.

Step 3: 6-(6-(1-ethyl-4-fluoro-1H-indazol-6-yl)-2-methoxypyridin-3-yl)tetrahydro-1H,3H-pyrrolo[1,2-c]oxazol-3-one tert-Butyl 4-(6-(1-ethyl-4-fluoro-1H-indazol-6-yl)-2-methoxypyridin-3-yl)-2-(hydroxymethyl) pyrrolidine-1-carboxylate (23 mg, 0.05 mmol, 1 equiv.) and SOCl$_2$ (18 µL, 0.244 mmol, 5 equiv.) in THF (4 mL) were refluxed overnight. The reaction was cooled down to room temperature and quenched with saturated sodium bicarbonate and extracted with ethyl acetate. The organic layer was washed with brine, dried, filtered and concentrated and purified by silica gel column to yield the product as an off-white solid.

Mass spectrum (ESI, m/z): Calculated for C$_{21}$H$_{21}$FN$_4$O$_3$: 397.42 [M+H], found: 397.5.

Step 4: 6-(6-(1-ethyl-4-fluoro-1H-indazol-6-yl)-2-oxo-1,2-dihydropyridin-3-yl)tetrahydro-1H,3H-pyrrolo[1,2-c]oxazol-3-one The title compound was prepared according to the procedure as described in Example 1 step 5 by demethylation to yield the product as an off-white solid.

$^1$H NMR (400 MHz, CDCl$_3$) δ: 8.18 (s, 1H), 7.75 (s, 2H), 7.10 (d, J=5.6 Hz, 1H), 6.82 (d, J=6.5 Hz, 1H), 4.72 (m, 2H), 4.31 (m, 1H), 4.20 (m, 1H), 3.78 (m, 2H), 2.48 (m, 2H), 1.90 (m, 2H), 1.55 (t, J=6.5 Hz, 3H). Mass spectrum (ESI, m/z): Calculated for C$_{20}$H$_{19}$FN$_4$O$_3$: 383.40 [M+H], found: 383.5.

Example 171

Compound #205

6-(1-ethyl-4-fluoro-1H-indazol-6-yl)-3-(2-(isopropylsulfonyl)-octahydrocyclopenta[c]pyrrol-5-yl)pyridin-2(1H)-one

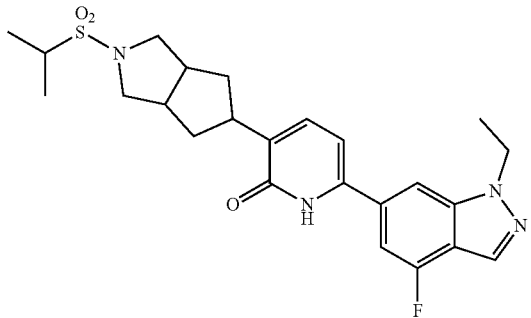 [SMILES: CCn1ncc2c(F)cc(-c3ccc(C4CC5CN(S(=O)(=O)C(C)C)CC5C4)c(=O)[nH]3)cc21]

Step 1: Tert-butyl 5-(6-chloro-2-methoxypyridin-3-yl)-5-hydroxy-hexahydrocyclopenta[c]pyrrole-2(1H)-carboxylate Into a 50-mL round bottle maintained with an inert atmosphere of nitrogen, to a solution of 2-chloro-6-methoxypyridine (200 mg, 1.390 mmol, 1.00 equiv.) in THF (20 mL) was added t-BuLi (1.3 mL, 2.100 mmol, 1.50 equiv) with stirring at −78° C. The resulting mixture was stirred at −78° C. for 3 h. tert-Butyl 5-oxo-hexahydrocyclopenta[c]pyrrole-2(1H)-carboxylate (470 mg, 2.100 mmol, 1.50 equiv.) was then added with stirring at −78° C. The resulting mixture was stirred at −78° C. for 2 h. The reaction was quenched with NH$_4$Cl (10 mL). The resulting mixture was extracted with EtOAc (3×10 mL). The organic layers were combined, dried over Na$_2$SO$_4$, filtered and concentrated. The residue was purified by silica gel chromatography (0-10% EtOAc/petroleum ether) to yield tert-butyl 5-(6-chloro-2-methoxypyridin-3-yl)-5-hydroxy-hexahydrocyclopenta[c]pyrrole-2(1H)-carboxylate as a white solid.

Mass spectrum (ESI, m/z): Calculated for C$_{18}$H$_{25}$ClN$_2$O$_4$: 369.2[M+H], found: 368.9.

Step 2: 5-(6-chloro-2-methoxypyridin-3-yl)-octahydrocyclopenta[c]pyrrole

Into a 50-mL round bottle, to a solution of tert-butyl 5-(6-chloro-2-methoxypyridin-3-yl)-5-hydroxy-hexahydrocyclopenta[c]pyrrole-2(1H)-carboxylate (260 mg, 0.705 mmol, 1.00 equiv.) in TFA (6 mL) was added Et$_3$SiH (3 mL). The resulting mixture was stirred at 90° C. overnight. After cooling down to room temperature, the reaction was concentrated. The residue was purified by TLC (1/10 MeOH/DCM) to yield 5-(6-chloro-2-methoxypyridin-3-yl)-octahydrocyclopenta[c]pyrrole as a yellow oil.

Mass spectrum (ESI, m/z): Calculated for C$_{13}$H$_{17}$ClN$_2$O: 253.1 [M+H], found: 253.1.

Step 3: 5-(6-chloro-2-methoxypyridin-3-yl)-2-(isopropylsulfonyl)-octahydrocyclopenta[c]pyrrole Into a 50-mL round bottle, to a solution of 5-(6-chloro-2-methoxypyridin-3-yl)-octahydrocyclopenta[c]pyrrole (100 mg, 0.390 mmol, 1.00 equiv.) in DCM (10 mL) was added propane-2-sulfonyl chloride (169 mg, 1.200 mmol, 3.00 equiv.), Et$_3$N (120 mg, 1.200 mmol, 3.00 equiv.). The resulting mixture was stirred at 20° C. for 2 h. The reaction was quenched with H$_2$O (100 mL). The resulting mixture was extracted with DCM (3×10 mL). The organic layers were combined, dried over Na$_2$SO$_4$, filtered and concentrated. The residue was purified by TLC (EtOAc/petroleum ether=1/3) to yield 5-(6-chloro-2-methoxypyridin-3-yl)-2-(isopropylsulfonyl)-octahydrocyclopenta[c]pyrrole as a yellow oil.

Mass spectrum (ESI, m/z): Calculated for C$_{16}$H$_{23}$ClN$_2$O$_3$S: 359.1[M+H], found: 359.1.

Step 4: 6-(1-ethyl-4-fluoro-1H-indazol-6-yl)-3-(2-(isopropylsulfonyl)-octahydrocyclopenta[c]pyrrol-5-yl)pyridin-2(1H)-one The title compound was prepared according to the procedure as described in Example 1 step 5 by demethylation to yield the product as a yellow solid.

$^1$H NMR (400 MHz, CD$_3$OD) δ: 8.14 (s, 1H), 7.79 (s, 1H), 7.60 (d, J=7.2 Hz, 1H), 7.19 (d, J=10.6 Hz, 1H), 6.75 (d, J=7.2 Hz, 1H), 4.53-4.58 (m, 2H), 3.33-3.39 (m, 5H), 3.174-3.22 (m, 1H), 2.85 (brs, 2H), 2.38-2.43 (m, 2H), 1.50-1.59 (m, 5H), 1.38-1.48 (m, 6H). $^{19}$F NMR (400 MHz, CD$_3$OD) δ: −77.68, −119.22. Mass spectrum (ESI, m/z): Calculated for C$_{24.5}$H$_{29.25}$F$_{1.75}$N$_4$O$_{3.5}$S, 473.2[M−0.25CF$_3$COOH+H], found: 473.2.

Example 172

Compound #204

6-(1-ethyl-4-fluoroindazol-6-yl)-3-[3-(propane-2-sulfonyl)-3-azaspiro[5.5]undecan-9-yl]-1H-pyridin-2-one

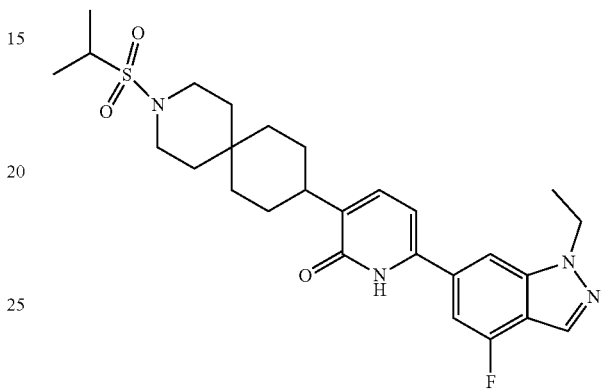

The title compound was prepared according to the procedure as described in Example 171 by coupling and demethylation to yield the product as an off-white solid.

$^1$H NMR (400 MHz, CD$_3$OD) δ 8.17 (s, 1H), 7.78 (s, 1H), 7.55 (d, J=7.2 Hz, 1H), 7.17 (d, J=11.2 Hz, 1H), 6.75 (d, J=7.2 Hz, 1H), 4.53-4.57 (m, 2H), 3.33-3.38 (m, 4H), 2.80-2.84 (m, 1H), 1.81-1.92 (m, 2H), 1.68-1.75 (m, 4H), 1.40-1.65 (m, 8H), 1.22-1.37 (m, 8H). $^{19}$F NMR (400 MHz, CD$_3$OD) δ −77.58, −119.22. Mass spectrum (ESI, m/z): Calculated for C$_{28.46}$H$_{35.73}$F$_{3.19}$N$_4$O$_{4.46}$S, 515.2[M−0.73CF$_3$COOH+H], found: 515.2.

Example 173

Compound #209

5-(6-(1-ethyl-4-fluoro-1H-indazol-6-yl)-2-oxo-1,2-dihydropyridin-3-yl)-N-isopropyl-hexahydrocyclopenta[c]pyrrole-2(1H)-carboxamide

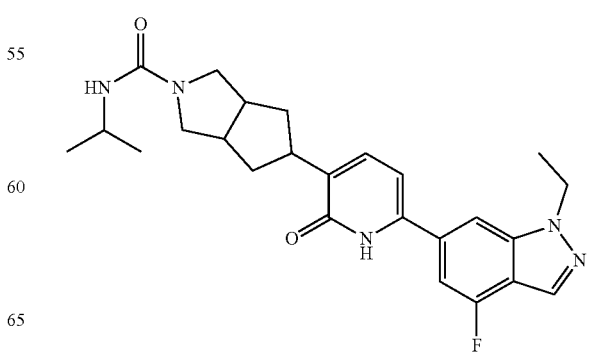

Step 1: 1-ethyl-4-fluoro-6-(6-methoxy-5-(octahydro-cyclopenta[c]pyrrol-5-yl)pyridin-2-yl)-1H-indazole The title compound was prepared according to the procedure as described in Example 157 by coupling and deprotection to yield the product as an brown oil.
Mass spectrum (ESI, m/z): Calculated for $C_{22}H_{25}FN_4O$: 381.2 [M+H], found: 381.2.

Step 2: 5-(6-(1-ethyl-4-fluoro-1H-indazol-6-yl)-2-methoxyypyridin-3-yl)-N-isopropyl-hexahydrocyclopenta[c]pyrrole-2(1H)-carboxamide Into a 50-mL round bottle, to a solution of 1-ethyl-4-fluoro-6-(6-methoxy-5-(octahydrocyclopenta[c]pyrrol-5-yl)pyridin-2-yl)-1H-indazole (150 mg, 0.390 mmol, 1.00 equiv.) in DCM (10 mL) was added 2-isocyanatopropane (100 mg, 1.180 mmol, 3.00 equiv.), TEA (119 mg, 1.180 mmol, 3.00 equiv.). The resulting mixture was stirred at 20° C. overnight. The mixture was concentrated under vacuum. The residue was purified by silica gel with ethyl acetate/ petroleum ether (50:50). The collected fractions were combined and concentrated under vacuum to yield 5-(6-(1-ethyl-4-fluoro-1H-indazol-6-yl)-2-methoxypyridin-3-yl)-N-isopropyl-hexahydrocyclopenta[c]pyrrole-2(1H)-carboxamide as a white solid.
Mass spectrum (ESI, m/z): Calculated for $C_{26}H_{32}FN_5O_2$: 466.3[M+H], found: 466.3.

Step 3: 5-(6-(1-ethyl-4-fluoro-1H-indazol-6-yl)-2-oxo-1,2-dihydropyridin-3-yl)-N-isopropyl-hexahydrocyclopenta[c]pyrrole-2(1H)-carboxamide The title compound was prepared according to the procedure as described in Example 1 step 5 by demethylation to yield the product as a white solid.
$^1$H NMR (300 MHz, CD$_3$OD) δ 8.15 (s, 1H), 7.79 (s, 1H), 7.60 (d, J=7.5 Hz, 1H), 7.17-7.21 (m, 1H), 6.74 (d, J=7.5 Hz, 1H), 4.52-4.57 (m, 2H), 3.85-3.92(m, 1H), 3.33-3.49 (m, 5H), 2.84-2.87 (m, 2H), 2.36-2.38(m, 2H), 1.52-1.57(m, 5H), 1.17-1.19 (m, 6H). $^{19}$F NMR (300 MHz, CD$_3$OD) δ −77.49, −119.22. Mass spectrum (ESI, m/z): Calculated for $C_{25.8}H_{30.4}F_{2.2}N_5O_{2.8}$: 452.2[M−0.4CF$_3$COOH+H], found: 452.2.

Example 174

Compound #201

5-(6-(1-ethyl-4-fluoro-1H-indazol-6-yl)-2-methoxy-pyridin-3-yl)-N-isopropyl-hexahydrocyclopenta[c]pyrrole-2(1H)-carboxamide Step 1: 6-(1-ethyl-4-fluoro-1H-indazol-6-yl)-3-(octahydrocyclopenta[c]pyrrol-5-yl)pyridin-2(1H)-one The title compound was prepared according to the procedure as described in Example 1 step 5 by demethylation to yield the product as a white solid.
Mass spectrum (ESI, m/z): Calculated for $C_{21}H_{23}FN_4O$: 367.2 [M+H], found: 367.1.

Step 2: 5-(6-(1-ethyl-4-fluoro-1H-indazol-6-yl)-2-methoxyypyridin-3-yl)-N-isopropyl-hexahydrocyclopenta[c]pyrrole-2(1H)-carboxamide Into a 50-mL round-bottom, a mixture of dimethyl cyanocarbonimidodithioate (11 mg, 0.082 mmol, 1.00 equiv.) and isopropylamine (5 mg, 0.082 mmol, 1.00 equiv.) in acetonitrile (5 mL) was heated under reflux for 5 hours. After cooling the solution, 6-(1-ethyl-4-fluoro-1H-indazol-6-yl)-3-(octahydrocyclopenta[c]pyrrol-5-yl)pyridin-2(1H)-one (30 mg, 0.082 mmol, 1.00 equiv.) and 3 N sodium hydroxide solution (0.027 mL, 0.820 mmol, 1.00 equiv.) were added. The mixture was stirred for 5 minutes and a solution of silver nitrate (14 mg, 0.082 mmol, 1.00 equiv.) in acetonitrile (0.5 mL) was added dropwise. The reaction mixture was stirred at 0° C. for 2 hours and at room temperature for 2 hours. The reaction mixture was filtered and the residue washed with acetonitrile. The solvent was evaporated and the residue was purified by Prep-HPLC with the following conditions (16#-Waters 2767-5): Column, SunFire Prep C18,19*100 mm, 5 um; mobile phase, Water with 0.05% TFA and CH$_3$CN (50% CH$_3$CN up to 65% in 15 min, up to 100% in 0.1 min); Detector, UV 220 & 254 nm. The resulting solution was concentrated under vacuum to yield (Z)—N'-cyano-5-(6-(1-ethyl-4-fluoro-1H-indazol-6-yl)-2-oxo-1,2-dihydropyridin-3-yl)-N-isopropyl-hexahydrocyclopenta[c]pyrrole-2(1H)-carboximidamide as off-white solid.
$^1$H NMR (300 MHz, CD$_3$OD) δ 8.09 (s, 1H), 7.73 (s, 1H), 7.56 (d, J=7.2 Hz, 1H), 7.13 (d, J=12.0 Hz, 1H), 6.69 (d, J=7.2 Hz, 1H), 4.47-4.49 (m, 2H), 4.15-4.24 (m, 1H), 3.51-3.68 (m, 4H), 3.33-3.34 (m, 1H), 2.83-2.84 (m, 2H), 2.27-2.36 (m, 2H), 1.51-1.57 (m, 2H), 1.46-1.48 (m, 3H), 1.17-1.29 (m, 6H). $^{19}$F NMR (300 MHz, CD$_3$OD) δ: −77.15, −119.19. Mass spectrum (ESI, m/z): Calculated for $C_{26.68}H_{30.34}F_{2.02}N_7O_{1.68}$: 476.2[M−0.34CF$_3$COOH+H], found: 476.2.

Example 175

Compound #203

8-(6-(naphthalen-2-yl)-2-oxo-1,2-dihydropyridin-3-yl)-1,3-diazaspiro[4.5]decane-2,4-dione

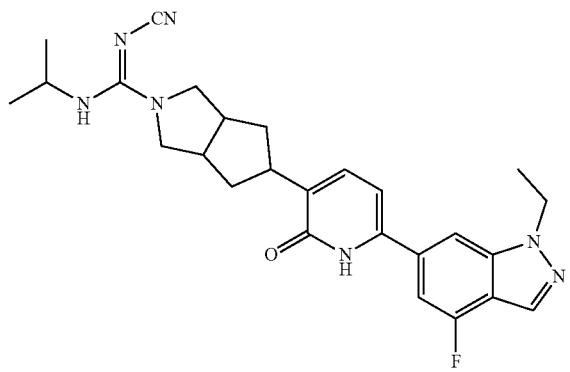 [SMILES: CCn1ncc2c(F)cc(-c3ccc(C4CC5CN(/C(=N\C#N)NC(C)C)CC5C4)c(=O)[nH]3)cc21]

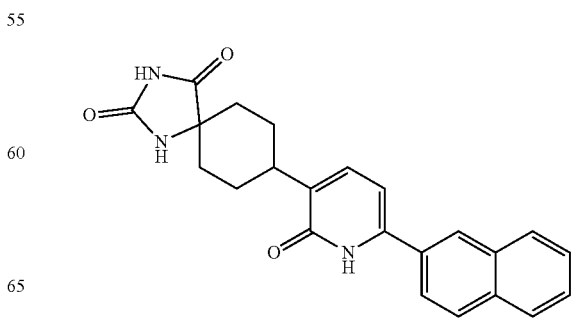

Step 1: 8-(2-methoxy-6-(naphthalen-2-yl)pyridin-3-yl)-1,4-dioxaspiro[4.5]decan-8-ol 2-Methoxy-6-(naphthalen-2-yl)pyridine (500 mg, 2.13 mmol, 1 equiv) in THF (10 mL) was treated dropwise with t-BuLi (1.7 N, 1.32 mL, 2.23 mmol, 1.05 equiv.) at −78° C. for 30 min. Then 1,4-dioxaspiro[4.5]decan-8-one (332 mg, 2.13 mmol, 1 equiv.) in THF (5 mL) was dropwise added into the reaction. The reaction was stirred for another 2 hour at −78° C. and then warmed to room temperature. The reaction was quenched with saturated ammonium chloride and extracted with ethyl acetate. The organic layer was washed with brine, dried and concentrated and purified by silica gel column using 20-80% ethyl acetate in heptanes to yield the title compound as a colorless oil.

Mass spectrum (ESI, m/z): Calculated for $C_{24}H_{25}NO_4$: 391.47 [M+H], found: 391.2.

Step 2: 4-(2-methoxy-6-(naphthalen-2-yl)pyridin-3-yl)cyclohexan-1-one 8-(2-methoxy-6-(naphthalen-2-yl)pyridin-3-yl)-1,4-dioxaspiro[4.5]decan-8-ol (150 mg, 0.4 mmol, 1 equiv.) in mixed solvent of acetone and concentrated HCl (0.2 mL) in THF (7 mL) was stirred at room temperature overnight. The solvent was removed and the residue was partitioned between ethyl acetate and saturated sodium bicarbonate. The organic layer was washed with brine and dried and concentrated to yield a residue which was then filled into a PARR shaker with 5% Pd/C (100 mg) under 50 psi hydrogenation at room temperature for 4 hours. The catalyst was filtered and the residue was concentrated and purified by silica gel column using 5-20% ethyl acetate in heptanes to yield the title product as a colorless oil.

Mass spectrum (ESI, m/z): Calculated for $C_{22}H_{21}NO_2$: 332.42 [M+H], found: 332.6.

Step 3: 8-(6-(naphthalen-2-yl)-2-oxo-1,2-dihydropyridin-3-yl)-1,3-diazaspiro[4.5]decane-2,4-dione The title compound was prepared according to the procedure as described in Example 60 by reacting 4-(2-methoxy-6-(naphthalen-2-yl)pyridin-3-yl)cyclohexan-1-one with $(NH_4)_2CO_3$ and $NH_4OH$ and KCN followed by demethylation to yield the product as a white solid.

$^1$H NMR (400 MHz, $CD_3OD$) δ: 8.15 (s, 1H), 7.95 (m, 2H), 7.75 (m, 1H), 7.58 (m, 2H), 7.43 (m, 1H), 7.30 (m, 1H), 6.92 (m, 1H), 2.65 (m, 1H), 2.10 (m, 2H), 1.82 (m, 2H), 1.52 (m, 2H), 1.32 (m, 2H). Mass spectrum (ESI, m/z): Calculated for $C_{23}H_{21}N_3O_3$, 388.44 (M+H), found 388.7.

Example 176

Compound #191

7-(6-(naphthalen-2-yl)-2-oxo-1,2-dihydropyridin-3-yl)-1,3-diazaspiro[4.5]decane-2,4-dione

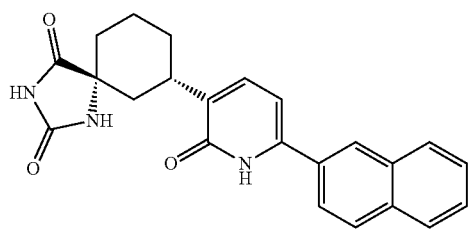 [SMILES: O=C1NC(=O)[C@]2(CCC[C@H](c3ccc(-c4ccc5ccccc5c4)[nH]c3=O)C2)N1]

The title compound was prepared according to the procedure as described in Example 175 by coupling, de-hydroxylation and reacting 6-(naphthalen-2-yl)-3-(3-oxocyclohexyl)pyridin-2(1H)-one with $(NH_4)_2CO_3$ and $NH_4OH$ and KCN followed by demethylation to yield the product as a white solid.

$^1$H NMR (400 MHz, $CD_3OD$) δ: 8.11 (s, 1H), 7.85 (m, 2H), 7.65 (m, 1H), 7.50 (m, 2H), 7.38 (m, 1H), 7.26 (m, 1H), 6.75 (m, 1H), 2.98 (m, 1H), 2.16 (m, 2H), 2.01 (m, 2H), 1.81 (m, 2H), 1.62 (m, 2H). Mass spectrum (ESI, m/z): Calculated for $C_{23}H_{21}N_3O_3$, 388.44 (M+H), found 388.6.

Example 177

Compound #185 and #201

1-cyano-3-(6-(naphthalen-2-yl)-2-oxo-1,2-dihydropyridin-3-yl)cyclohexyl carbamate and 1-hydroxy-3-(6-(naphthalen-2-yl)-2-oxo-1,2-dihydropyridin-3-yl)cyclohexane-1-carboxamide

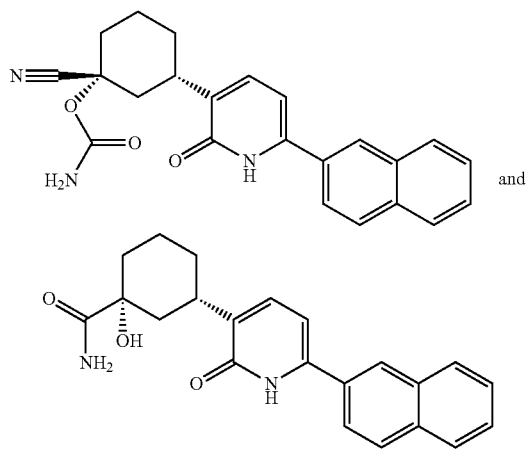

TMSCN (26 μL, 0.198 mmol, 1.3 equiv) was added dropwise to a stirring solution of 6-(naphthalen-2-yl)-3-(3-oxocyclohexyl)pyridin-2(1H)-one (50 mg, 0.151 mmol, 1 equiv.) and $ZnI_2$ (2 mg, 0.004 mmol, 0.023 equiv.) in DCM (4.8 mL) at 23° C. The resulting dark amber solution was stirred at 23° C. for 1 hour. The resulting mixture was then diluted with DCM (20 mL) shake with saturated aq $NaHCO_3$ (10 mL). The organic layer was collected and dried with $MgSO_4$, filter, concentrated to yield a clear orange oil, which was then purified by silica gel column using 20-80% ethyl acetate in heptanes to yield 1-cyano-3-(6-(naphthalen-2-yl)-2-oxo-1,2-dihydropyridin-3-yl)cyclohexyl carbamate as a white solid (15 mg, 26%). Mass spectrum (ESI, m/z): Calculated for $C_{23}H_{21}N_3O_3$: 388.44 [M+H], found: 388.6.

and 1-hydroxy-3-(6-(naphthalen-2-yl)-2-oxo-1,2-dihydropyridin-3-yl)cyclohexane-1-carboxamide as a white solid (28 mg, 50%). $^1$H NMR (400 MHz, $CD_3OD$) δ: 8.10 (s, 1H), 7.95 (m, 2H), 7.69 (m, 1H), 7.58 (m, 2H), 7.45 (m, 1H), 7.32 (m, 1H), 6.68 (m, 1H), 3.25 (m, 1H), 2.32 (m, 2H), 1.82 (m, 3H), 1.53 (m, 3H). Mass spectrum (ESI, m/z): Calculated for $C_{22}H_{22}N_2O_3$: 363.43 [M+H], found: 363.6.

Example 178

Compound #189 and #188

Syn-7-(6-(naphthalen-2-yl)-2-oxo-1,2-dihydropyridin-3-yl)-1-oxa-3-azaspiro[4.5]decane-2,4-dione and anti-7-(6-(naphthalen-2-yl)-2-oxo-1,2-dihydropyridin-3-yl)-1-oxa-3-azaspiro[4.5]decane-2,4-dione

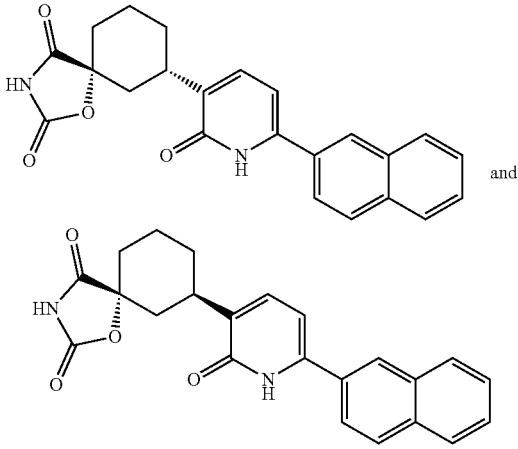
and

The title compounds were prepared according to the procedure as described in Example 4 step 6-9 by reacting 6-(naphthalen-2-yl)-3-(3-oxocyclohexyl)pyridin-2(1H)-one with TMSCN/AlCl₃, hydrolysis and esterification, coupling with 2,2,2-trichloroacetyl isocyanate and base catalyzed cyclization followed by demethylation to yield Syn-7-(6-(naphthalen-2-yl)-2-oxo-1,2-dihydropyridin-3-yl)-1-oxa-3-azaspiro[4.5]decane-2,4-dione as an off white solid. $^1$H NMR (400 MHz, d$_6$-DMSO) δ: 11.5 (br, s, 1H), 8.35 (s, 1H), 7.99 (m, 3H), 7.85 (d, J=6.0 Hz, 1H), 7.55 (m, 2H), 7.44 (d, J=6.0 Hz, 1H), 6.70 (d, J=4.5 Hz, 1H), 4.10 (m, 1H), 2.05 (m, 2H), 1.95 (m, 2H), 1.84 (m, 2H), 1.50 (m, 2H). Mass spectrum (ESI, m/z): Calculated for C$_{23}$H$_{20}$N$_2$O$_4$: 389.42 [M+H], found: 389.5.

and Anti-7-(6-(naphthalen-2-yl)-2-oxo-1,2-dihydropyridin-3-yl)-1-oxa-3-azaspiro[4.5]decane-2,4-dione as an off-white solid. $^1$H NMR (400 MHz, d$_6$-DMSO) δ: 11.8 (br, s, 1H), 8.45 (s, 1H), 8.02 (m, 2H), 7.98 (m, 1H), 7.88 (d, J=6.5 Hz, 1H), 7.62 (m, 2H), 7.45 (d, J=6.0 Hz, 1H), 6.72 (d, J=4.5 Hz, 1H), 4.05 (m, 1H), 2.18 (m, 2H), 1.98~1.82 (m, 4H), 1.35 (m, 2H). Mass spectrum (ESI, m/z): Calculated for C$_{23}$H$_{20}$N$_2$O$_4$: 389.42 [M+H], found: 389.6.

Example 179

Compound #192

6-(naphthalen-2-yl)-3-(tetrahydro-2H-pyran-4-yl)pyridin-2(1H)-one

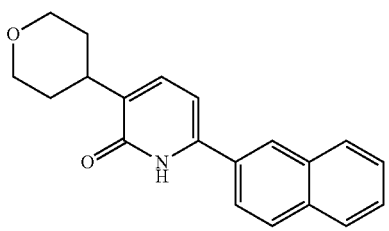 [SMILES: O=c1[nH]c(-c2ccc3ccccc3c2)ccc1C1CCOCC1]

The title compound was prepared according to the procedure as described in Example 164 by coupling with tetrahydro-4H-pyran-4-one, Et₃SiH reduction and demethylation to yield the product as a white solid.
$^1$H NMR (400 MHz, CDCl₃) δ: 8.15 (s, 1H), 8.01 (d, J=6.5 Hz, 1H), 7.95 (m, 3H), 7.70 (d, J=6.0 Hz, 1H), 7.58 (d, J=6.0 Hz, 1H), 7.52 (d, J=6.0 Hz, 1H), 6.81 (d, J=7.6 Hz, 1H), 4.10 (m, 2H), 3.62 (m, 2H), 3.15 (m, 1H), 1.82 (m, 4H). Mass spectrum (ESI, m/z): Calculated for C$_{20}$H$_{19}$NO$_2$, 306.38 (M+H), found 306.5.

Example 180

Compound #194

6-(naphthalen-2-yl)-3-(piperidin-4-yl)pyridin-2(1H)-one

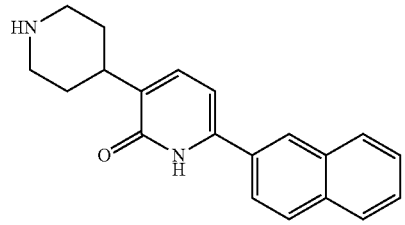 [SMILES: O=c1[nH]c(-c2ccc3ccccc3c2)ccc1C1CCNCC1]

The title compound was prepared according to the procedure as described in Example 164 by coupling with tert-butyl 4-oxopiperidine-1-carboxylate, Et₃SiH reduction and demethylation to yield the product as a white solid.
Mass spectrum (ESI, m/z): Calculated for C$_{20}$H$_{20}$N$_2$O, 305.39 (M+H), found 305.2.

Example 181

Compound #186

3-(1-(methylsulfonyl)piperidin-4-yl)-6-(naphthalen-2-yl)pyridin-2(1H)-one

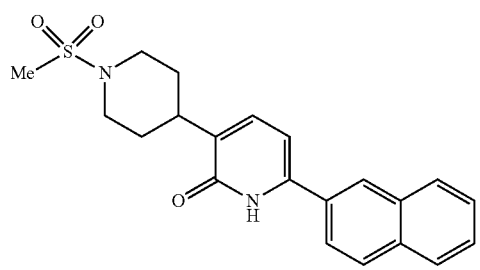 [SMILES: CS(=O)(=O)N1CCC(c2ccc(-c3ccc4ccccc4c3)[nH]c2=O)CC1]

The title compound was prepared according to the procedure as described in Example 164 step 3 by coupling 6-(naphthalen-2-yl)-3-(piperidin-4-yl)pyridin-2(1H)-one with MsCl followed by demethylation to yield the product as a white solid.
$^1$H NMR (400 MHz, CDCl₃) δ: 8.20 (s, 1H), 8.02 (s, 1H), 7.90 (d, J=7.2 Hz, 1H), 7.75 (d, J=7.0 Hz, 1H), 7.58 (m, 2H), 7.45 (m, 1H), 7.12 (m, 1H), 6.75 (d, J=6.0 Hz, 1H), 3.35 (m, 2H), 3.10 (m, 1H), 3.02 (s, 3H), 2.98 (m, 2H), 2.10 (m, 2H), 1.82 (m, 2H). Mass spectrum (ESI, m/z): Calculated for C$_{21}$H$_{22}$N$_2$O$_3$S, 383.48 (M+H), found 383.7.

Example 182

Compound #190

3-(1-(ethylsulfonyl)piperidin-4-yl)-6-(naphthalen-2-yl)pyridin-2(1H)-one

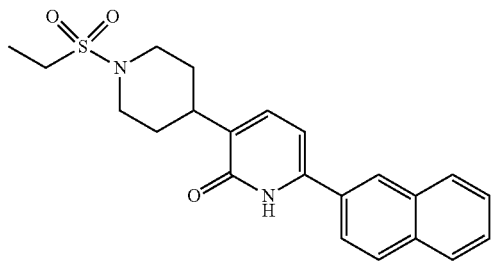 [SMILES: CCS(=O)(=O)N1CCC(c2ccc(-c3ccc4ccccc4c3)[nH]c2=O)CC1]

The title compound was prepared according to the procedure as described in Example 164 step 3 by coupling 6-(naphthalen-2-yl)-3-(piperidin-4-yl)pyridin-2(1H)-one with EtSO$_2$Cl followed by demethylation to yield the product as a white solid.

$^1$H NMR (400 MHz, CDCl$_3$) δ: 8.24 (s, 1H), 7.98 (s, 1H), 7.92 (d, J=5.2 Hz, 1H), 7.70 (d, J=7.0 Hz, 1H), 7.60 (m, 2H), 7.48 (m, 1H), 6.72 (d, J=6.5 Hz, 1H), 3.95 (m, 2H), 3.35 (m, 2H), 3.10 (m, 1H), 2.98 (m, 2H), 2.10 (m, 2H), 1.82 (m, 2H), 1.25 (t, J=7.5 Hz, 3H). Mass spectrum (ESI, m/z): Calculated for C$_{23}$H$_{26}$N$_2$O$_3$S, 397.51 [M+H], found: 397.6.

Example 183

Compound #200

3-(1-(isopropylsulfonyl)piperidin-4-yl)-6-(naphthalen-2-yl)pyridin-2(1H)-one

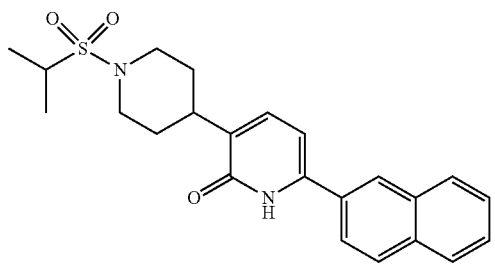 [SMILES: CC(C)S(=O)(=O)N1CCC(c2ccc(-c3ccc4ccccc4c3)[nH]c2=O)CC1]

The title compound was prepared according to the procedure as described in Example 164 step 3 by coupling 6-(naphthalen-2-yl)-3-(piperidin-4-yl)pyridin-2(1H)-one with i-PrSO$_2$Cl followed by demethylation to yield the product as a white solid.

$^1$H NMR (400 MHz, CDCl$_3$) δ: 8.25 (s, 1H), 8.01 (s, 1H), 7.95 (d, J=5.2 Hz, 1H), 7.72 (d, J=6.5 Hz, 1H), 7.62 (m, 2H), 7.50 (m, 1H), 6.75 (d, J=5.5 Hz, 1H), 3.98 (m, 2H), 3.20 (m, 2H), 3.12 (m, 1H), 2.98 (m, 2H), 2.02 (m, 2H), 1.67 (m, 2H), 1.38 (d, J=6.5 Hz, 6H). Mass spectrum (ESI, m/z): Calculated for C$_{23}$H$_{26}$N$_2$O$_3$S, 411.53 [M+H], found: 411.7.

Example 184

Compound #199

6-(6-fluoronaphthalen-2-yl)-3-(1-(isopropylsulfonyl)piperidin-4-yl)pyridin-2(1H)-one

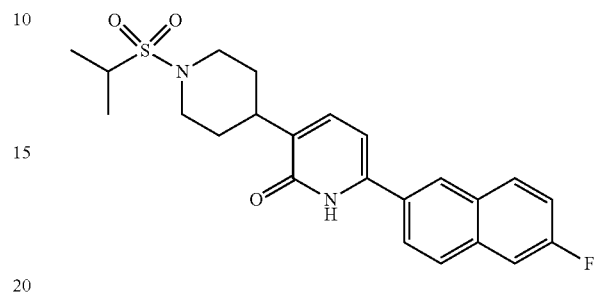

The title compound was prepared according to the procedure as described in Example 164 step 3 by coupling 6-(6-fluoronaphthalen-2-yl)-3-(piperidin-4-yl)pyridin-2(1H)-one with i-PrSO$_2$Cl followed by demethylation to yield the product as a white solid.

$^1$H NMR (400 MHz, CDCl$_3$) δ: 8.21 (s, 1H), 8.02 (s, 1H), 7.95 (d, J=6.2 Hz, 1H), 7.55 (d, J=7.0 Hz, 1H), 7.45 (m, 1H), 7.30 (m, 1H), 6.98 (m, 1H), 6.72 (m, 1H), 3.98 (m, 2H), 3.55 (m, 2H), 3.10 (m, 4H), 2.10 (m, 1H), 1.95 (m, 1H), 1.70 (m, 1H), 1.35 (d, J=7.5 Hz, 6H). Mass spectrum (ESI, m/z): Calculated for C$_{23}$H$_{25}$FN$_2$O$_3$S, 429.52 [M+H], found: 429.7.

Example 185

Compound #198

6-(1-ethyl-4-fluoro-1H-indazol-6-yl)-3-(1-(isopropylsulfonyl)piperidin-4-yl)pyridin-2(1H)-one

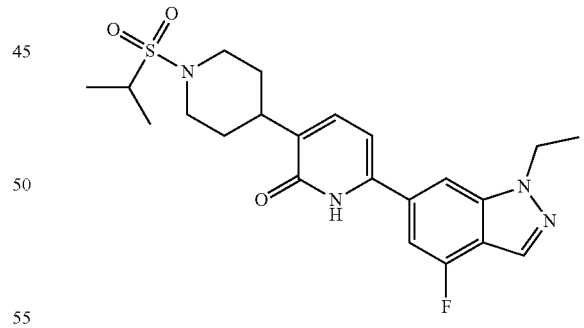

The title compound was prepared according to the procedure as described in Example 164 step 3 by coupling 6-(1-ethyl-4-fluoro-1H-indazol-6-yl)-3-(piperidin-4-yl)pyridin-2(1H)-one with i-PrSO$_2$Cl followed by demethylation to yield the product as a white solid.

$^1$H NMR (400 MHz, CDCl$_3$) δ: 8.15 (s, 1H), 8.01 (s, 1H), 7.68 (s, 1H), 7.15 (d, J=7.5 Hz, 1H), 6.88 (d, J=5.6 Hz, 1H), 4.76 (m, 2H), 4.15 (m, 2H), 3.31 (m, 1H), 3.05 (m, 1H), 2.21 (m, 1H), 1.98 (m, 1H), 1.76 (m, 1H), 1.60 (m, 1H), 1.45 (m, 6H). Mass spectrum (ESI, m/z): Calculated for C$_{22}$H$_{27}$FN$_4$O$_3$S, 447.54 [M+H], found: 447.7.

Example 186

Compound #213

6-(1-ethyl-4-fluoro-1H-indazol-6-yl)-3-(1-(isopropylsulfonyl)pyrrolidin-3-yl)pyridin-2(1H)-one

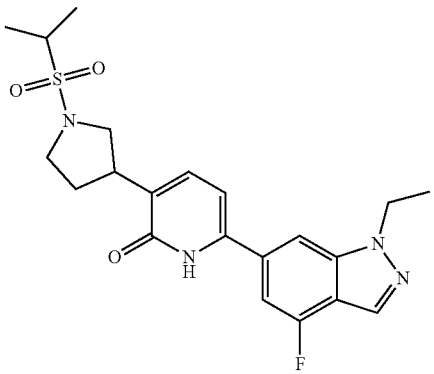 [SMILES: CCn1ncc2c(F)cc(-c3ccc(C4CCN(S(=O)(=O)C(C)C)C4)c(=O)[nH]3)cc21]

The title compound was prepared according to the procedure as described in Example 164 step 3 by coupling 6-(1-ethyl-4-fluoro-1H-indazol-6-yl)-3-(pyrrolidin-3-yl)pyridin-2(1H)-one with i-PrSO$_2$Cl followed by demethylation to yield the product as a white solid.

$^1$H NMR (400 MHz, CDCl$_3$) δ: 12.8 (br, s, 1H), 8.18 (s, 1H), 7.98 (s, 1H), 7.75 (s, 1H), 7.18 (d, J=6.5 Hz, 1H), 6.92 (d, J=7.6 Hz, 1H), 4.52 (m, 2H), 3.65 (m, 1H), 3.52 (m, 1H), 3.42 (m, 1H), 3.23 (m, 1H), 2.28 (m, 1H), 2.12 (m, 1H), 1.55 (t, J=7.0 Hz, 3H), 1.38 (d, J=6.5 Hz, 6H). Mass spectrum (ESI, m/z): Calculated for C$_{21}$H$_{25}$FN$_4$O$_3$S, 433.51 [M+H], found: 433.8.

Example 187

Compound #211

6-(1-ethyl-4-fluoro-1H-indazol-6-yl)-3-(1-(isopropylsulfonyl)piperidin-3-yl)pyridin-2(1H)-one

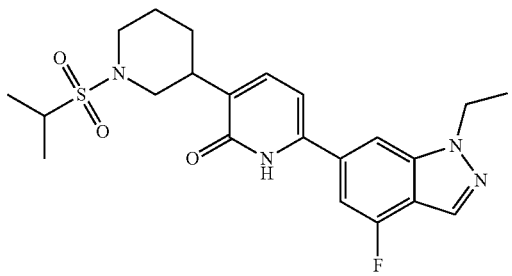 [SMILES: CCn1ncc2c(F)cc(-c3ccc(C4CCCN(S(=O)(=O)C(C)C)C4)c(=O)[nH]3)cc21]

The title compound was prepared according to the procedure as described in Example 164 step 3 by coupling 6-(1-ethyl-4-fluoro-1H-indazol-6-yl)-3-(piperidin-3-yl)pyridin-2(1H)-one with i-PrSO$_2$Cl followed by demethylation to yield the product as a white solid.

$^1$H NMR (400 MHz, CDCl$_3$) δ: 8.12 (s, 1H), 7.99 (s, 1H), 7.72 (s, 1H), 7.18 (d, J=6.5 Hz, 1H), 6.92 (d, J=6.6 Hz, 1H), 4.52 (m, 2H), 3.95 (m, 1H), 3.80 (m, 1H), 3.25 (m, 1H), 3.15 (m, 2H), 3.02 (m, 2H), 2.05 (m, 1H), 1.88 (m, 1H), 1.80 (m, 1H), 1.62 (t, J=6.5 Hz, 3H), 1.40 (d, J=7.5 Hz, 6H). Mass spectrum (ESI, m/z): Calculated for C$_{22}$H$_{27}$FN$_4$O$_3$S, 447.54 [M+H], found: 447.4.

Example 188

Compound #214

6-(1-ethyl-4-fluoro-1H-indazol-6-yl)-3-(1-(isopropylsulfonyl)azetidin-3-yl)pyridin-2(1H)-one

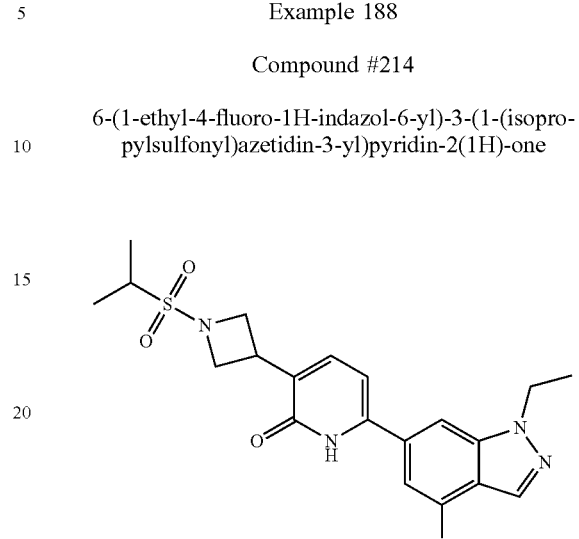

The title compound was prepared according to the procedure as described in Example 164 step 3 by coupling 3-(azetidin-3-yl)-6-(1-ethyl-4-fluoro-1H-indazol-6-yl)pyridin-2(1H)-one with i-PrSO$_2$Cl followed by demethylation to yield the product as a white solid.

$^1$H NMR (400 MHz, CDCl$_3$) δ: 8.05 (s, 1H), 7.96 (s, 1H), 7.69 (d, J=6.0 Hz, 1H), 7.35 (d, J=7.5 Hz, 1H), 7.31 (s, 1H), 4.72 (t, J=9.5 Hz, 1H), 4.48 (m, 1H), 4.45 (m, 2H), 3.78 (m, 1H), 3.45 (m, 2H), 3.15 (m, 1H), 1.56 (t, J=7.8 Hz, 3H), 1.42 (d, J=6.5 Hz, 6H). Mass spectrum (ESI, m/z): Calculated for C$_{20}$H$_{23}$FN$_4$O$_2$S, 419.49 (M+H), found 419.6.

Example 189

Compound #206

6-(1-ethyl-4-fluoro-1H-indazol-6-yl)-3-(8-(isopropylsulfonyl)-8-azabicyclo[3.2.1]octan-3-yl)pyridin-2(1H)-one

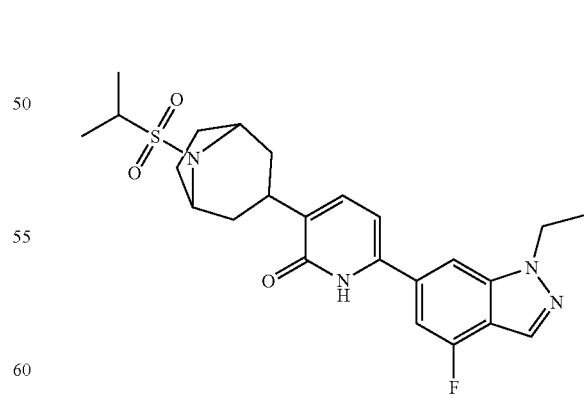

The title compound was prepared according to the procedure as described in Example 164 step 3 by coupling 3-(8-azabicyclo[3.2.1]octan-3-yl)-6-(1-ethyl-4-fluoro-1H-indazol-6-yl)pyridin-2(1H)-one with i-PrSO$_2$Cl followed by demethylation to yield the product as a white solid.

$^1$H NMR (400 MHz, CDCl$_3$) δ: 8.12 (s, 1H), 7.72 (s, 2H), 7.08 (d, J=7.0 Hz, 1H), 6.82 (d, J=4.0 Hz, 1H), 4.56 (q, J=6.1 Hz, 2H), 4.30 (m, 2H), 3.22 (m, 2H), 2.48 (m, 2H), 2.18 (m, 2H), 1.95 (m, 2H), 1.72 (m, 2H), 1.55 (t, J=7.0 Hz, 3H), 1.45 (m, 6H). Mass spectrum (ESI, m/z): Calculated for C$_{24}$H$_{29}$FN$_4$O$_3$S, 473.58 (M+H), found 473.7.

Example 190

Compound #208

3-(6-(1-ethyl-4-fluoro-1H-indazol-6-yl)-2-oxo-1,2-dihydropyridin-3-yl)-N-isopropyl-8-azabicyclo[3.2.1]octane-8-carboxamide

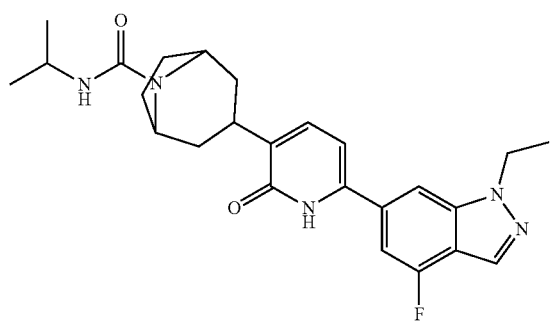 [SMILES: CCn1ncc2c(F)cc(-c3ccc(C4CC5CCC(C4)N5C(=O)NC(C)C)c(=O)[nH]3)cc21]

The title compound was prepared according to the procedure as described in Example 164 step 3 by coupling 3-(8-azabicyclo[3.2.1]octan-3-yl)-6-(1-ethyl-4-fluoro-1H-indazol-6-yl)pyridin-2(1H)-one with 2-isocyanatopropane followed by demethylation to yield the product as a white solid.

$^1$H NMR (400 MHz, CDCl$_3$) δ: 8.10 (s, 1H), 7.72 (s, 1H), 7.65 (s, 1H), 7.08 (d, J=6.0 Hz, 1H), 6.82 (d, J=7.0 Hz, 1H), 4.55 (m, 2H), 4.32 (m, 2H), 4.08 (m, 1H), 2.95 (m, 1H), 2.56 (m, 2H), 2.15 (m, 2H), 1.85 (m, 4H), 1.65 (t, J=7.5 Hz, 3H), 1.38 (m, 6H). Mass spectrum (ESI, m/z): Calculated for C$_{25}$H$_{30}$FN$_5$O$_2$, 452.55 (M+H), found 452.7.

Example 191

Compound #197

6-(1-ethyl-4-fluoro-1H-indazol-6-yl)-3-(1-(2-hydroxyacetyl)piperidin-4-yl)pyridin-2(1H)-one

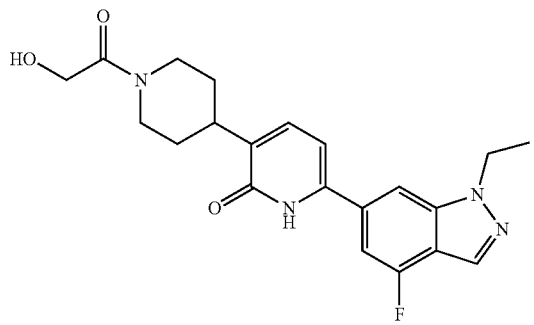 [SMILES: CCn1ncc2c(F)cc(-c3ccc(C4CCN(C(=O)CO)CC4)c(=O)[nH]3)cc21]

The title compound was prepared according to the procedure as described in Example 164 step 3 by coupling 6-(1-ethyl-4-fluoro-1H-indazol-6-yl)-3-(piperidin-4-yl)pyridin-2(1H)-one with 2-hydroxyacetyl chloride followed by demethylation to yield the product as a white solid.

$^1$H NMR (400 MHz, CDCl$_3$) δ: 8.15 (s, 1H), 7.52 (s, 1H), 7.22 (m, 1H), 7.10 (m, 1H), 6.75 (d, J=6.5 Hz, 1H), 4.52 (agq, J=11.5 Hz, 2H), 4.48 (q, J=6.7 Hz, 2H), 3.95 (m, 4H), 3.42 (m, 2H), 3.10 (m, 1H), 3.05 (m, 2H), 1.45 (t, J=8.5 Hz, 3H). Mass spectrum (ESI, m/z): Calculated for C$_{21}$H$_{23}$FN$_4$O$_3$, 399.44 (M+H), found 399.6.

Example 192

Compound #195

6-(naphthalen-2-yl)-3-(4,5,6,7-tetrahydro-2H-indazol-5-yl)pyridin-2(1H)-one

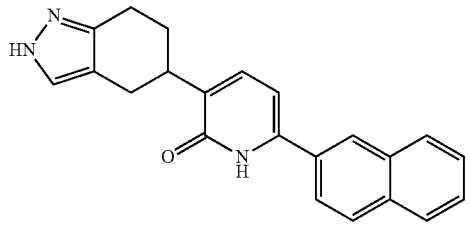 [SMILES: O=c1[nH]c(-c2ccc3ccccc3c2)ccc1C1CCc2n[nH]cc2C1]

Step 1: 2-((dimethylamino)methylene)-4-(2-methoxy-6-(naphthalen-2-yl)pyridin-3-yl)cyclohexan-1-one 6-(Naphthalen-2-yl)-3-(4-oxocyclohexyl)pyridin-2(1H)-one (150 mg, 0.453 mmol, 1 equiv.) in 1,1-dimethoxy-N,N-dimethylmethanamine (4 mL) was heated to 100° C. overnight. The reaction was partitioned between ethyl acetate and water. The organic layer was dried and concentrated and purified by silica gel column using 30% ethyl acetate in heptanes to yield the product as a yellow oil.

Mass spectrum (ESI, m/z): Calculated for C$_{25}$H$_{26}$N$_2$O$_2$, 387.50 [M+H], found: 387.4.

Step 2: 5-(2-methoxy-6-(naphthalen-2-yl)pyridin-3-yl)-4,5,6,7-tetrahydro-2H-indazole 2-((Dimethylamino)methylene)-4-(2-methoxy-6-(naphthalen-2-yl)pyridin-3-yl)cyclohexan-1-one (25 mg, 0.07 mmol, 1 equiv.) and hydrazine (5 mg, 0.14 mmol, 2 equiv.) in EtOH (2 mL) were heated to reflux for 4 hour. The solvent was removed and the residue was purified by silica gel column to yield the product as a colorless oil.

Mass spectrum (ESI, m/z): Calculated for C$_{23}$H$_{21}$N$_3$O, 355.44 [M+H], found: 355.4.

Step 3: 6-(naphthalen-2-yl)-3-(4,5,6,7-tetrahydro-2H-indazol-5-yl)pyridin-2(1H)-one The title compound was prepared according to the procedure as described in Example 1 step 5 by demethylation of 5-(2-methoxy-6-(naphthalen-2-yl)pyridin-3-yl)-4,5,6,7-tetrahydro-2H-indazole with TMSCl/NaI to yield the product as a white solid.

$^1$H NMR (400 MHz, d$_6$-DMSO) δ: 7.35 (s, 1H), 7.20 (s, 1H), 7.15 (d, J=5.0 Hz, 1H), 7.05 (d, J=6.5 Hz, 1H), 6.90 (m, 2H), 6.73 (m, 2H), 6.65 (m, 1H), 5.98 (m, 1H), 2.35 (m, 2H), 2.28 (m, 2H), 2.10 (m, 1H), 1.73 (m, 1 H). Mass spectrum (ESI, m/z): Calculated for $C_{22}H_{19}N_3O$, 342.41 [M+H], found: 342.4.

Example 193

Compound #187

6-(naphthalen-2-yl)-3-(4,5,6,7-tetrahydrobenzo[d]isoxazol-5-yl)pyridin-2(1H)-one

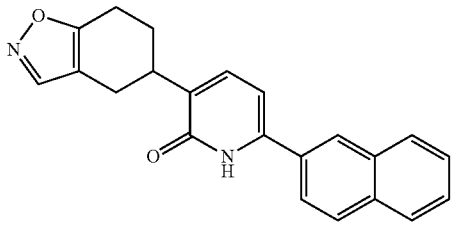 [SMILES: O=c1[nH]c(-c2ccc3ccccc3c2)ccc1C1CCc2oncc2C1]

The title compound was prepared according to the procedure as described in Example 193 by reacting 2-((dimethylamino)methylene)-4-(2-methoxy-6-(naphthalen-2-yl)pyridin-3-yl) cyclohexan-1-one with hydroxylamine followed by demethylation with TMSCl/NaI to yield the product as a white solid.

$^1$H NMR (400 MHz, CDCl$_3$) δ: 8.14 (s, 1H), 8.02 (s, 1H), 7.95 (d, J=5.2 Hz, 1H), 7.86 (s, 1H), 7.70 (d, J=7.5 Hz, 1H), 7.55 (m, 2H), 7.42 (m, 1H), 6.65 (d, J=7.5 Hz, 1H), 3.30 (m, 1H), 3.20 (m, 1H), 2.65 (m, 1H), 2.46 (m, 1H), 2.40 (m, 1H), 1.73 (m, 1H), 1.48 (m, 1H). Mass spectrum (ESI, m/z): Calculated for $C_{22}H_{18}N_2O_2$, 343.14 [M+H], found: 343.3.

Example 194

Compound #196

9-(6-(1-ethyl-4-fluoro-1H-indazol-6-yl)-2-oxo-1,2-dihydropyridin-3-yl)-2-azaspiro[5.5]undecan-1-one

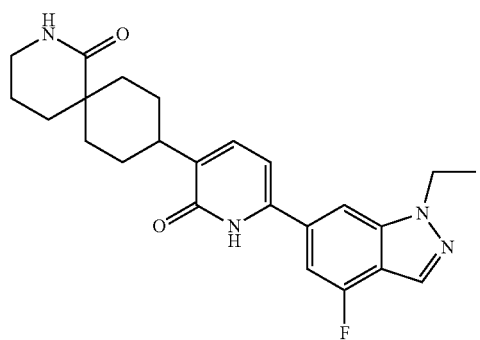 [SMILES: CCn1ncc2c(F)cc(-c3ccc(C4CCC5(CCCNC5=O)CC4)c(=O)[nH]3)cc21]

Step 1: ethyl 4-(6-chloro-2-methoxypyridin-3-yl)cyclohex-3-ene-1-carboxylate

The title compound was prepared according to the procedure described in Example 175 by coupling of 2-chloro-6-methoxypyridine with ethyl 4-oxocyclohexane-1-carboxylate by t-BuLi, de-hydroxylation with HCl to yield the product as a yellow oil.

Mass spectrum (ESI, m/z): Calculated for $C_{15}H_{18}ClNO_3$, 295.76 (M+H), found 295.4.

Step 2: ethyl 4-(6-chloro-2-methoxypyridin-3-yl)-1-(2-cyanoethyl)cyclohex-3-ene-1-carboxylate To a solution of DIPEA (95 μL, 0.672 mmol, 1.4 equiv.) in THF (5 mL) was added dropwise n-BuLi (2.5 N, 270 μL, 0.672 mmol, 1.4 equiv.) at −78° C. for 10 min. Ethyl 4-(6-chloro-2-methoxypyridin-3-yl)cyclohex-3-ene-1-carboxylate (143 mg, 0.48 mmol, 1 equiv.) in THF (1 mL) was added into the reaction at −78° C. The reaction was stirred for another 2 hour at −78° C. 3-Bromopropanenitrile (100 μL, 0.768 mmol, 1.6 equiv.) was added into the reaction dropwise. The reaction was then warmed to room temperature over 2 hour. The solvent was removed and residue was partitioned between ethyl acetate and water. The organic layer was dried and concentrated and purified by silica gel column to yield the product as a yellow oil.

Mass spectrum (ESI, m/z): Calculated for $C_{18}H_{21}ClN_2O_3$, 349.83 (M+H), found 349.4.

Step 3: 9-(6-chloro-2-methoxypyridin-3-yl)-2-azaspiro[5.5]undecan-1-one

Ethyl 4-(6-chloro-2-methoxypyridin-3-yl)-1-(2-cyanoethyl)cyclohex-3-ene-1-carboxylate (150 mg, 0.43 mmol, 1 equiv.) and K$_2$CO$_3$ (297 mg, 2.15 mmol, 5 equiv.) in MeOH (7.5 mL) were refluxed overnight. The solvent was removed and the residue was dissolved in MeOH (10 mL) and HCl concentrated aqueous solution (0.75 mL) and treated with PtO$_2$ (10 mg, 0.043 mmol, 0.1 equiv.) under 50 psi hydrogenation overnight. The catalyst was filtrated and the residue was purified by silica gel column using 1:1 heptanes/ethyl acetate to yield the product as a colorless oil.

Mass spectrum (ESI, m/z): Calculated for $C_{16}H_{21}ClN_2O_2$, 308.81 (M+H), found 308.9.

Step 4: 9-(6-(1-ethyl-4-fluoro-1H-indazol-6-yl)-2-methoxypyridin-3-yl)-2-azaspiro[5.5]undecan-1-one The title compound was prepared according to the procedure described in Example 1 step 1 by Suzuki coupling 9-(6-chloro-2-methoxypyridin-3-yl)-2-azaspiro[5.5]undecan-1-one with 1-ethyl-4-fluoro-6-(4,4,5,5-tetramethyl-1,3,2-dioxaborolan-2-yl)-1H-indazole to yield the product as a white solid.

Mass spectrum (ESI, m/z): Calculated for $C_{24}H_{29}FN_4O_2$, 437.53 (M+H), found 437.7.

Step 5: 9-(6-(1-ethyl-4-fluoro-1H-indazol-6-yl)-2-oxo-1,2-dihydropyridin-3-yl)-2-azaspiro[5.5]undecan-1-one The title compound was prepared according to the procedure described in Example 1 step 5 by demethylation with TMSCl/NaI to yield the product as a white solid.

$^1$H NMR (400 MHz, CDCl$_3$) δ: 8.10 (s, 1H), 7.79 (d, J=6.0 Hz, 1H), 7.75 (s, 1H), 7.05 (d, J=7.5 hz, 1H), 6.95 (d, J=4.2 Hz, 1H), 6.32 (br, s, 1H), 4.52 (q, J=5.5 Hz, 2H), 3.31 (br, s, 2H), 2.98 (m, 1H), 2.10 (m, 4H), 1.85 (m, 2H), 1.80 (m, 2H), 1.72 (m, 2H), 1.55 (m, 3H), 1.40 (m, 2H). Mass spectrum (ESI, m/z): Calculated for $C_{24}H_{27}FN_4O_2$, 423.50 (M+H), found 423.3.

Example 195

Compound #207

8-(6-(1-ethyl-4-fluoro-1H-indazol-6-yl)-2-oxo-1,2-dihydropyridin-3-yl)-2-azaspiro[4.5]decan-1-one

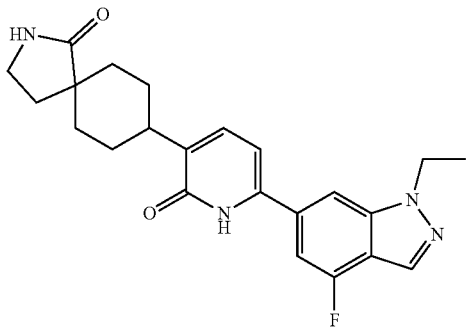 [SMILES: CCn1ncc2c(F)cc(-c3ccc(C4CCC5(CCNC5=O)CC4)c(=O)[nH]3)cc21]

The title compound was prepared according to the procedure as described in Example 194 step 1-5 by reacting ethyl 4-(6-chloro-2-methoxypyridin-3-yl)cyclohex-3-ene-1-carboxylate with 2-bromoacetonitrile followed by cyclization, Suzuki coupling and demethylation to yield the product as a white solid.

$^1$H NMR (400 MHz, CDCl$_3$) δ: 8.10 (s, 1H), 7.78 (m, 1H), 7.72 (s, 1H), 7.06 (d, J=7.5 Hz, 1H), 6.89 (d, J=5.5 Hz, 1H), 5.72 (s, br, 1H), 4.52 (q, J=6.2 Hz, 2H), 3.38 (m, 2H), 3.01 (m, 1H), 2.25 (m, 2H), 2.02 (m, 4H), 1.82 (m, 2H), 1.45 (t, J=6.8 Hz, 3H), 1.40 (m, 2H). Mass spectrum (ESI, m/z): Calculated for C$_{23}$H$_{25}$FN$_4$O$_2$, 408.48 (M+H), found 408.7.

Example 196

Compound #282

3-(3-methyl-1,1-dioxido-1,2,5-thiadiazolidin-3-yl)-6-(naphthalen-2-yl)pyridin-2(1H)-one

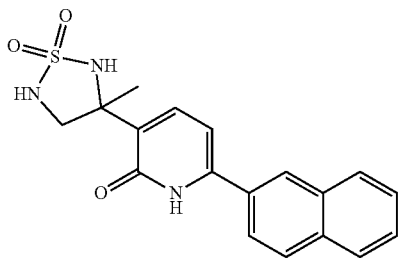 [SMILES: CC1(c2ccc(-c3ccc4ccccc4c3)[nH]c2=O)CNS(=O)(=O)N1]

Step 1: 2-amino-2-[2-methoxy-6-(naphthalen-2-yl)pyridin-3-yl]propanenitrile

Into a 40-mL vial, were placed a solution of 1-[2-methoxy-6-(naphthalen-2-yl)pyridin-3-yl]ethan-1-one (1 g, 3.60 mmol, 1.00 equiv.) in NH$_3$ (in methanol) (30 mL), TMSCN (560 mg, 5.60 mmol, 1.57 equiv.), NH$_4$Cl (380 mg, 7.20 mmol, 1.97 equiv.). The resulting solution was stirred for 2 days at 25° C. The resulting mixture was concentrated under vacuum. The resulting solution was diluted with of EA. The solids were filtered out. The resulting mixture was concentrated under vacuum to yield 2-amino-2-[2-methoxy-6-(naphthalen-2-yl)pyridin-3-yl]propanenitrile as a yellow oil.

Mass spectrum (ESI, m/z): Calculated for C$_{19}$H$_{17}$N$_3$O, 287.1 (M+H–NH$_2$), found 287.1.

Step 2: 2-[2-methoxy-6-(naphthalen-2-yl)pyridin-3-yl]propane-1,2-diamine

Into a 100-mL round-bottom flask, were placed a solution of 2-amino-2-[2-methoxy-6-(naphthalen-2-yl)pyridin-3-yl]propanenitrile (1 g, 3.30 mmol, 1.00 equiv.) in ether (30 mL), LAH (250 mg, 6.59 mmol, 2.00 equiv.). The resulting solution was stirred for 1 h at 25° C. The reaction was then quenched by the addition of sodium sulfate.10H$_2$O. The solids were filtered out. The resulting mixture was concentrated under vacuum. The residue was applied onto a silica gel column with dichloromethane/methanol (1:1) to yield 2-[2-methoxy-6-(naphthalen-2-yl)pyridin-3-yl]propane-1,2-diamine as a yellow oil.

Mass spectrum (ESI, m/z): Calculated for C$_{19}$H$_{21}$N$_3$O, 308.2 (M+H), found 308.1.

Step 3: 3-(2-methoxy-6-(naphthalen-2-yl)pyridin-3-yl)-3-methyl-1,2,5-thiadiazolidine 1,1-dioxide Into a 50-mL round-bottom flask, were placed a solution of 2-[2-methoxy-6-(naphthalen-2-yl)pyridin-3-yl]propane-1,2-diamine (50 mg, 0.16 mmol, 1.00 equiv.) in pyridine (10 mL), sulfamoylamine (31 mg, 0.32 mmol, 1.98 equiv.). The resulting solution was stirred for 16 h at 115° C. in an oil bath. The resulting mixture was concentrated under vacuum. The resulting solution was extracted with ethyl acetate (3×50 mL) and the organic layers combined. The resulting mixture was washed with 3×50 mL of sodium chloride (aq). The resulting mixture was concentrated under vacuum. The residue (40 mg) was purified by Prep-HPLC with the following conditions (1#waters2767-5): Column, SunFire Prep C18,19*150 mm 5 umH PrepC-001(T) 18600256819513816414 04; mobile phase, Phase A:water with 0.05% TFA Phase B:CH$_3$CN (15% CH$_3$CN up to 80% in 10 min, up to 100% CH$_3$CN in 0.1 min, hold 100% in 1.9 min, down to 15% CH$_3$CN in 0.1 min, hold 15% in 1.9 min); Detector, UV220&254 nm, to yield 3-(2-methoxy-6-(naphthalen-2-yl)pyridin-3-yl)-3-methyl-1,2,5-thiadiazolidine 1,1-dioxide as a light yellow solid.

$^1$H NMR (400 MHz, DMSO) δ: 8.66 (s, 1H), 8.28 (d, J=8.8 Hz, 1H), 7.94-8.05 (m, 4H), 7.78 (d, J=7.6 Hz, 1H), 7.53-7.58 (m, 3H), 7.08 (brm, 1H), 4.10 (s, 3H), 3.92 (d, J=12.4 Hz, 1H), 3.76 (d, J=9.6 Hz, 1H), 1.60 (s, 3H).

Mass spectrum (ESI, m/z): Calculated for C$_{19}$H$_{19}$N$_3$O$_3$S, 370.1 (M+H), found 370.0.

Step 4: 3-(3-methyl-1,1-dioxido-1,2,5-thiadiazolidin-3-yl)-6-(naphthalen-2-yl)pyridin-2(1H)-one Into a 50-mL 3-necked round-bottom flask purged and maintained with an inert atmosphere of nitrogen, were placed a solution of 3-[2-methoxy-6-(naphthalen-2-yl)pyridin-3-yl]-3-methyl-1-[6],2,5-thiadiazolidine-1,1-dione (120 mg, 0.32 mmol, 1.00 equiv.) in dichloromethane (15 mL). The resulting solution was stirred at −78° C. in a dry ice bath. BBr$_3$(121 mg, 0.49 mmol, 1.50 equiv.) was then added dropwise. The resulting solution was stirred for 5 h at 25° C. The reaction was then quenched by the addition of methanol. The resulting mixture was concentrated under vacuum. The residue (100 mg) was purified by Prep-HPLC with the following conditions (1#waters2767-5): Column, SunFire Prep C18,19*150 mm 5 umH PrepC-001(T) 18600256819513816414 04; mobile phase, Phase A:water with 0.05% TFA; Phase B:CH$_3$CN (15% CH$_3$CN up to 80% in 10 min, up to 100% CH$_3$CN in 0.1 min, hold 100% in 1.9 min, down to 15% CH$_3$CN in 0.1 min, hold 15% in 1.9 min); Detector, UV220&254 nm to yield 3-(3-methyl-1,1-dioxido-1,2,5-thiadiazolidin-3-yl)-6-(naphthalen-2-yl)pyridin-2(1H)-one as a yellow solid.

$^1$H NMR (400 MHz, DMSO-d$_6$) δ: 12.00 (bs, 1H), 8.36 (s, 1H), 7.95-8.02 (m, 3H), 7.78-7.86 (m, 2H), 7.57-7.61 (m, 2H), 7.41 (s, 1H), 7.06 (t, J=7.6 Hz, 1H), 6.79 (d, J=6.8 Hz, 1H), 3.91-3.96 (m, 1H), 3.23-3.33 (m, 1H), 1.61 (s, 3H).

Mass spectrum (ESI, m/z): Calculated for C$_{18}$H$_{17}$N$_3$O$_3$S, 356.1 (M+H), found 356.0.

Example 197

Compound #283

N-[4-methyl-4-[6-(naphthalen-2-yl)-2-oxo-1,2-dihydropyridin-3-yl]imidazolidin-2-ylidene]amino]carbonitrile

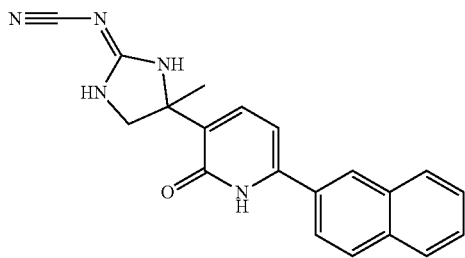 [SMILES: CC1(c2ccc(-c3ccc4ccccc4c3)[nH]c2=O)CN/C(=N\C#N)N1]

Step 1: (E/Z)-4-[2-methoxy-6-(naphthalen-2-yl) pyridin-3-yl]-4-methylimidazolidin-2-ylidene] amino]carbonitrile Into a 50-mL round-bottom flask, were placed a solution of 2-[2-methoxy-6-(naphthalen-2-yl)pyridin-3-yl]propane-1,2-diamine (50 mg, 0.16 mmol, 1.00 equiv.) in ethanol (10 mL), [bis(methylsulfanyl)methylidene](cyano)amine (36 mg, 0.25 mmol, 1.51 equiv.), potassium hydroxide (18 mg, 0.32 mmol, 1.97 equiv.). The resulting solution was stirred for 16 h at 80° C. in an oil bath. The reaction mixture was cooled. The resulting mixture was concentrated under vacuum. The residue (40 mg) was purified by Prep-HPLC with the following conditions (1#waters2767-5): Column, SunFire Prep C18,19*150 mm 5 umH PrepC-001(T) 18600256819513816414 04; mobile phase, Phase A:water with 0.05% TFA Phase B:CH$_3$CN (20% CH$_3$CN up to 80% in 10 min, up to 100% CH$_3$CN in 0.1 min, hold 100% in 1.9 min, down to 20% CH$_3$CN in 0.1 min, hold 20% in 1.9 min); Detector, UV220&254 nm to yield [[(2Z)-4-[2-methoxy-6-(naphthalen-2-yl)pyridin-3-yl]-4-methylimidazolidin-2-ylidene]amino]carbonitrile as a white solid.

$^1$H NMR (400 MHz, DMSO-d$_6$) δ: 8.66 (s, 1H), 8.59 (s, 1H), 8.28 (d, J=8.4 Hz, 1H), 7.94-8.05 (m, 4H), 7.76-7.81 (m, 2H), 7.54-7.57 (m, 2H), 4.08 (s, 3H), 3.73 (d, J=10.0 Hz, 1H), 3.61 (d, J=10.0 Hz, 1H), 1.58 (s, 3H). Mass spectrum (ESI, m/z): Calculated for C$_{21}$H$_{19}$N$_5$O, 358.2 (M+H), found 358.1.

Step 2: (E/Z)—N-[4-methyl-4-[6-(naphthalen-2-yl)-2-oxo-1,2-dihydropyridin-3-yl]imidazolidin-2-ylidene]amino]carbonitrile The title compound was prepared according to the procedure described in Example 1 step 5 by demethylation of (E/Z)-4-[2-methoxy-6-(naphthalen-2-yl)pyridin-3-yl]-4-methylimidazolidin-2-ylidene]amino]carbonitrile with TMSCl/NaI to yield the product as a light yellow solid.

$^1$H NMR (400 MHz, DMSO-d$_6$) δ: 8.44 (s, 1H), 8.36 (s, 1H), 7.96-8.02 (m, 3H), 7.81-7.88 (m, 2H), 7.58-7.60 (m, 2H), 7.52 (d, J=6.8 Hz, 1H), 6.77 (br, m, 1H), 3.64-3.69 (m, 2H), 1.57 (s, 3H). Mass spectrum (ESI, m/z): Calculated for C$_{20}$OH$_{17}$N$_5$O, 344.1 (M+H), found 344.1.

Example 198

Compound #285

[E]-3-[-2-(hydroxyimino)-4-methylimidazolidin-4-yl]-6-(naphthalen-2-yl)-1,2-dihydropyridin-2-one

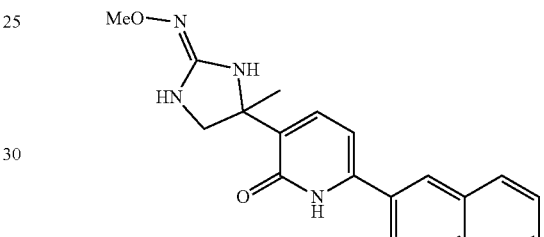

Step 1: 4-[2-methoxy-6-(naphthalen-2-yl)pyridin-3-yl]-4-methylimidazolidine-2-thione Into a 100-mL round-bottom flask, were placed a solution of 2-[2-methoxy-6-(naphthalen-2-yl)pyridin-3-yl]propane-1,2-diamine (700 mg, 2.28 mmol, 1.00 equiv.) in ethanol/H$_2$O (30/5 mL). CS$_2$ (6 mL), triethylamine (2 mL) was added. The resulting solution was stirred for 3 h at 70° C. in an oil bath. The reaction progress was monitored by TLC/LCMS (ethyl acetate/petroleum ether=1:1). The reaction mixture was cooled with a water bath. The resulting mixture was concentrated under vacuum. The resulting solution was extracted with ethyl acetate (3×30 mL) and the organic layers combined and dried over anhydrous sodium sulfate. The residue was applied onto a silica gel column with ethyl acetate/petroleum ether (1:4) to yield 4-[2-methoxy-6-(naphthalen-2-yl)pyridin-3-yl]-4-methylimidazolidine-2-thione as a yellow solid.

Mass spectrum (ESI, m/z): calcd for C$_{20}$H$_{19}$N$_3$OS, found 350.1 [M+H]$^+$ Step 2: 2-methoxy-3-[5-methyl-2-(methylsulfanyl)-4,5-dihydro-1H-imidazol-5-yl]-6-(naphthalen-2-yl) pyridine Into a 25-mL round-bottom flask purged and maintained with an inert atmosphere of nitrogen, were placed a solution of 4-[2-methoxy-6-(naphthalen-2-yl)pyridin-3-yl]-4-methylimidazolidine-2-thione (450 mg, 1.29 mmol, 1.00 equiv.) in methanol (20 mL). iodomethane (264 mg, 1.86 mmol, 1.50 equiv.) was added. The resulting solution was stirred for 1.5 h at 70° C. in an oil bath. The reaction progress was monitored by TLC (ethyl acetate/petroleum ether=1:1). The reaction mixture was cooled with a water bath. The resulting mixture was concentrated under vacuum. The resulting solution was extracted with ethyl acetate (3×30 mL) and the organic layers combined and dried over anhydrous sodium sulfate. The residue was applied onto a silica gel column with ethyl acetate/petroleum ether (1:5), to yield 2-methoxy-3-[5-methyl-2-(methylsulfanyl)-4,5-dihydro-1H-imidazol-5-yl]-6-(naphthalen-2-yl)pyridine as a yellow oil.

Mass spectrum (ESI, m/z): Calculated for $C_{21}H_{21}N_3OS$, found 364.1 [M+H]$^+$.

Step 3: (E)-N-methoxy-4-[2-methoxy-6-(naphthalen-2-yl)pyridin-3-yl]-4-methylimidazolidin-2-imine and (2Z)—N-methoxy-4-[2-methoxy-6-(naphthalen-2-yl)pyridin-3-yl]-4-methylimidazolidin-2-imine Into a 25-mL round-bottom flask purged and maintained with an inert atmosphere of nitrogen, were placed 2-methoxy-3-[5-methyl-2-(methylsulfanyl)-4,5-dihydro-1H-imidazol-5-yl]-6-(naphthalen-2-yl)pyridine (50 mg, 0.14 mmol, 1.00 equiv.), O-methylhydroxylamine hydrochloride (347 mg, 4.15 mmol, 30.00 equiv.), potassium carbonate (193 mg, 1.40 mmol, 10.00 equiv.), 4 Å molecular sieves (2 g), tetrahydrofuran (20 mL). The resulting solution was stirred overnight at 120° C. in an oil bath. The reaction progress was monitored by TLC/LCMS (ethyl acetate/petroleum ether=1:1). The reaction was then quenched by the addition of water (10 mL). The resulting solution was extracted with ethyl acetate (2×30 mL) and the organic layers combined and concentrated under vacuum to yield (2E/Z)—N-methoxy-4-[2-methoxy-6-(naphthalen-2-yl)pyridin-3-yl]-4-methylimidazolidin-2-imine as a yellow oil.

Mass spectrum (ESI, m/z): Calculated for $C_{21}H_{21}N_3OS$, found 364.2. [M+H]$^+$.

Step 4: [E]-3-[2-(hydroxyimino)-4-methylimidazolidin-4-yl]-6-(naphthalen-2-yl)-1,2-dihydropyridin-2-one and 3-[(2Z)-2-(hydroxyimino)-4-methylimidazolidin-4-yl]-6-(naphthalen-2-yl)-1,2-dihydropyridin-2-one Into a 8-mL vial purged and maintained with an inert atmosphere of nitrogen, were placed a solution of NaI (9 mg, 1.00 equiv.) in acetonitrile (1 mL), TMSCl (10.2 mg, 0.09 mmol, 1.50 equiv.) was added. N-[(2E)-4-[2-methoxy-6-(naphthalen-2-yl)pyridin-3-yl]-4-methylimidazolidin-2-ylidene]hydroxylamine (22.9 mg, 0.07 mmol, 1.00 equiv.). The resulting solution was stirred for 1 h at room temperature. The reaction progress was monitored by TLC/LCMS (dichloromethane/methanol=5:1). The reaction was then quenched by the addition of water (0.3 mL). The solids were filtered out. The residue (4 mL) was purified by Prep-HPLC with the following conditions (1#-Waters 2767-5): Column, SunFire Prep C18, 5 um, 19*100 mm; mobile phase, Water of 0.05% NH$_4$HCO$_3$ and CH$_3$CN (20% CH$_3$CN up to 90% in 10 min; Detector, UV 220&254 nm to yield 3-[(2E)-2-(hydroxyimino)-4-methylimidazolidin-4-yl]-6-(naphthalen-2-yl)-1,2-dihydro pyridin-2-one as a yellow solid.

$^1$H NMR (300 MHz, Methanol-d$_4$, ppm): δ 8.22 (s, 1H), 8.00 (m, 3H), 7.77 (d, J=7.4 Hz, 1H), 7.74 (d, J=7.4 Hz, 1H), 7.66 (d, J=7.4 Hz, 1H), 6.79 (d, J=7.4 Hz, 1H), 3.96 (m, 2H), 3.82 (s, 3H), 1.78 (s, 3H). Mass spectrum (ESI, m/z): Calculated for $C_{21}H_{21}N_3OS$, found 349.2 M+H]$^+$ and 2.4 mg (11%) of 3-[(2Z)-2-(hydroxyimino)-4-methylimidazolidin-4-yl]-6-(naphthalen-2-yl)-1,2-dihydropyridin-2-one as a light yellow solid. $^1$H NMR (400 MHz, CD$_3$OD) δ: 8.21 (s, 1H), 7.97-8.21 (m, 2H), 7.90-7.94 (m, 1H), 7.75-7.77 (m, 1H), 7.71 (d, J=7.2 Hz, 1H), 7.55-7.59 (m, 2H), 6.76 (d, J=7.2 Hz, 1H), 3.61-3.68 (m, 5H), 1.66 (s, 3H). Mass spectrum (ESI, m/z): Calculated for $C_{21}H_{21}N_3OS$, 349.2 (M+H), found 349.2.

Example 199

Compound #286

4-[2-hydroxy-6-(naphthalen-2-yl)pyridin-3-yl]-4-methylimidazolidine-2-thione

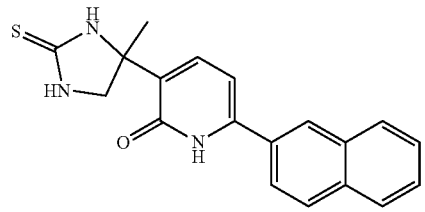 [SMILES: CC1(c2ccc(-c3ccc4ccccc4c3)[nH]c2=O)CNC(=S)N1]

The title compound was prepared according to the procedure described in Example 1 step 5 by demethylation of 4-[2-methoxy-6-(naphthalen-2-yl)pyridin-3-yl]-4-methylimidazolidine-2-thione with TMSCl/NaI to yield the product as a white solid.

$^1$H NMR (300 MHz, DMSO-d$_6$) δ: 8.75 (s, 1H), 8.37 (s, 1H), 8.18 (s, 1H), 7.95-8.03 (m, 3H), 7.85 (d, J=7.4 Hz, 1H), 7.52-7.60 (m, 3H), 7.17 (bs, 1H), 6.79 (bs, 1H), 3.65-3.67 (m, 2H), 1.55 (s, 3H). Mass spectrum (ESI, m/z): Calculated for $C_{21}H_{21}N_3OS$, 336.1 (M+H), found 336.0.

Example 200

Compound #287

3-(2-amino-4-methyl-4,5-dihydro-1H-imidazol-4-yl)-6-(naphthalen-2-yl)pyridin-2(1H)-one

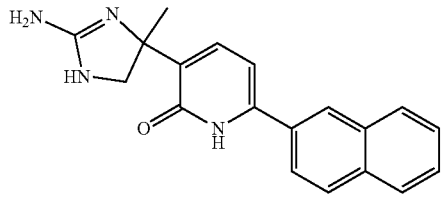 [SMILES: CC1(c2ccc(-c3ccc4ccccc4c3)[nH]c2=O)CNC(N)=N1]

The title compound was prepared according to the procedure described in Example 198 by displacement of 2-methoxy-3-[5-methyl-2-(methylsulfanyl)-4,5-dihydro-1H-imidazol-5-yl]-6-(naphthalen-2-yl)pyridine with ammonium hydroxide followed by demethylation with TMSCl/NaI to yield the product as a light yellow solid.

$^1$H NMR (300 MHz, DMSO-d$_6$) δ: 8.36 (s, 1H), 7.95-8.03 (m, 3H), 7.85 (d, J=8.4 Hz, 1H), 7.50-7.60 (m, 3H), 6.80 (d, J=6.9 Hz, 1H), 3.79 (d, J=10.5 Hz, 1H), 3.70 (d, J=10.2 Hz,

1H), 1.61 (s, 3H). Mass spectrum (ESI, m/z): Calculated for $C_{19}H_{18}N_4O$, 319.2 (M+H), found 319.1.

Example 201

Compound #167

3-[6-methyl-5H,6H,7H-imidazo[2,1-c][1,2,4]triazol-6-yl]-6-(naphthalen-2-yl)-1,2-dihydropyridin-2-one

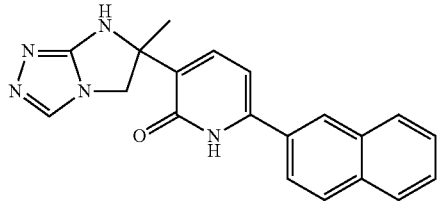 [SMILES: CC1(c2ccc(-c3ccc4ccccc4c3)[nH]c2=O)Cn2cnnc2N1]

Step 1: 3-[(2Z)-2-hydrazinylidene-4-methylimidazolidin-4-yl]-2-methoxy-6-(naphthalen-2-yl)pyridine Into a 50-mL round-bottom flask, were placed a solution of 2-methoxy-3-[4-methyl-2-(methylsulfanyl)-4,5-dihydro-1H-imidazol-4-yl]-6-(naphthalen-2-yl)pyridine (250 mg, 0.69 mmol, 1.00 equiv.) in methanol (10 mL), hydrazine hydrate (31 mg, 0.68 mmol, 0.99 equiv.). The resulting solution was stirred for 16 h at 80° C. in an oil bath. The resulting mixture was concentrated under vacuum. The residue was applied onto a silica gel column with dichloromethane/methanol (10:1) to yield 3-[(2Z)-2-hydrazinylidene-4-methylimidazolidin-4-yl]-2-methoxy-6-(naphthalen-2-yl)pyridine as a yellow solid.

Mass spectrum (ESI, m/z): Calculated for $C_{20}H_{21}N_5O$, 348.2 (M+H), found 348.1.

Step 2: 2-methoxy-3-[6-methyl-5H,6H,7H-imidazo[2,1-c][1,2,4]triazol-6-yl]-6-(naphthalen-2-yl)pyridine Into a 50-mL round-bottom flask, were placed a solution of 3-[(2Z)-2-hydrazinylidene-4-methylimidazolidin-4-yl]-2-methoxy-6-(naphthalen-2-yl)pyridine (240 mg, 0.69 mmol, 1.00 equiv.) in N,N-dimethylformamide (10 mL), (diethoxymethoxy)ethane (153 mg, 1.03 mmol, 1.49 equiv.). The resulting solution was stirred for 16 h at 75° C. in an oil bath. The resulting mixture was concentrated under vacuum. The residue (150 mg) was purified by Flash-Prep-HPLC with the following conditions (CombiFlash-1): Column, C18 silica gel; mobile phase, water (0.05% $NH_4HCO_3$) and $CH_3CN=35\%$ increasing to water (0.05% $NH_4HCO_3$) and $CH_3CN=75\%$ within 30 min; Detector, UV 254 nm to yield 2-methoxy-3-[6-methyl-5H,6H,7H-imidazo[2,1-c][1,2,4]triazol-6-yl]-6-(naphthalen-2-yl)pyridine as a yellow solid.

Mass spectrum (ESI, m/z): Calculated for $C_{21}H_{19}N_5O$, 358.2 (M+H), found 358.2.

Step 3: 3-[6-methyl-5H,6H,7H-imidazo[2,1-c][1,2,4]triazol-6-yl]-6-(naphthalen-2-yl)-1,2-dihydropyridin-2-one The title compound was prepared according to the procedure described in Example step 51 by demethylation with TMSCl/NaI to yield the product as light yellow oil.

$^1$H NMR (400 MHz, DMSO-$d_6$) δ: 9.15 (bs, 1H), 8.56 (s, 1H), 8.37 (s, 1H), 7.97-8.04 (m, 3H), 7.84-7.86 (m, 1H), 7.59-7.67 (m, 3H), 6.82 (bs, 1H), 4.38-4.45 (m, 2H), 1.79 (s, 3H). Mass spectrum (ESI, m/z): Calculated for $C_{20}H_{17}N_5O$, 344.1 (M+H), found 344.1.

Example 202

Compound #222

3-(4-methyl-5-oxo-4,5-dihydro-1H-imidazol-4-yl)-6-(naphthalen-2-yl)-1,2-dihydropyridin-2-one

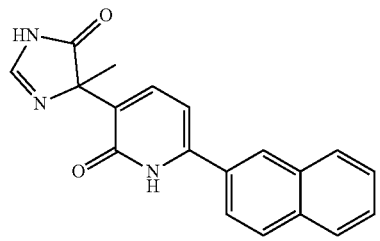 [SMILES: CC1(c2ccc(-c3ccc4ccccc4c3)[nH]c2=O)N=CNC1=O]

Step 1: 2-amino-2-[2-methoxy-6-(naphthalen-2-yl)pyridin-3-yl]propanamide

Into a 50-mL round-bottom flask, were placed a solution of 2-amino-2-[2-methoxy-6-(naphthalen-2-yl)pyridin-3-yl]propanenitrile (500 mg, 1.65 mmol, 1.00 equiv.) in methanol (20 mL), sodium hydroxide (99 mg, 2.48 mmol, 1.50 equiv.), $H_2O_2$ (30%) (374 mg, 11.00 mmol, 6.67 equiv.). The resulting solution was stirred for 1 h at 25° C. The resulting solution was extracted with ethyl acetate (3×100 mL) and the organic layers combined. The resulting mixture was washed with sodium chloride (aq) (3×50 mL). The resulting mixture was concentrated under vacuum. The residue was applied onto a silica gel column with dichloromethane/methanol (20:1) to yield 2-amino-2-[2-methoxy-6-(naphthalen-2-yl)pyridin-3-yl]propanamide as a light yellow solid.

Mass spectrum (ESI, m/z): Calculated for $C_{19}H_{19}N_3O_2$, 322.1 (M+H), found 322.1.

Step 2: 4-[2-methoxy-6-(naphthalen-2-yl)pyridin-3-yl]-4-methyl-4,5-dihydro-1H-imidazol-5-one Into a 50-mL round-bottom flask, were placed a solution of 2-amino-2-[2-methoxy-6-(naphthalen-2-yl)pyridin-3-yl]propanamide (100 mg, 0.31 mmol, 1.00 equiv.) in toluene (10 mL), (diethoxymethoxy)ethane (69 mg, 0.47 mmol, 1.50 equiv.), AcOH (2 mg, 0.03 mmol, 0.11 equiv.). The resulting solution was stirred for 16 h at 60° C. in an oil bath. The resulting mixture was concentrated under vacuum. Water was added. The resulting solution was extracted with ethyl acetate (3×50 mL) and the organic layers combined. The resulting mixture was washed with sodium chloride (aq) (3×50 mL). The mixture was dried over anhydrous sodium sulfate. The solids were filtered out. The resulting mixture was concentrated under vacuum to yield 4-[2-methoxy-6-(naphthalen-2-yl)pyridin-3-yl]-4-methyl-4,5-dihydro-1H-imidazol-5-one as a yellow solid.

Mass spectrum (ESI, m/z): Calculated for $C_{20}H_{17}N_3O_2$, 332.1 (M+H), found 332.1.

Step 3: 3-(4-methyl-5-oxo-4,5-dihydro-1H-imidazol-4-yl)-6-(naphthalen-2-yl)-1,2-dihydropyridin-2-one The title compound was prepared according to the procedure described in Example 1 step 5 by demethylation with TMSCl/NaI to yield the product as a light yellow solid.

$^1$H NMR (400 MHz, CD$_3$OD) δ: 9.46 (s, 1H), 8.27 (s, 1H), 7.95-8.07 (m, 4H), 7.77-7.80 (m, 1H), 7.59-7.64 (m, 2H), 6.91 (d, J=7.6 Hz, 1H), 1.96 (s, 3H).

Mass spectrum (ESI, m/z): Calculated for C$_{19}$H$_{15}$N$_3$O$_2$, 318.1 (M+H), found 318.1.

Example 203

Compound #223

3-(2,4-dimethyl-5-oxo-4,5-dihydro-1H-imidazol-4-yl)-6-(naphthalen-2-yl)-1,2-dihydropyridin-2-one

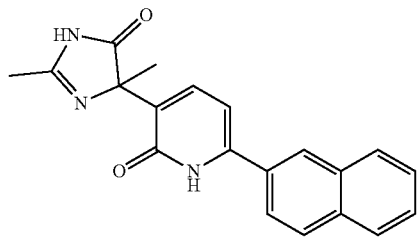 [SMILES: CC1=NC(C)(c2ccc(-c3ccc4ccccc4c3)[nH]c2=O)C(=O)N1]

The title compound was prepared according to the procedure described in Example 202 by condensation followed by demethylation with TMSCl/NaI to yield the product as a white solid.

$^1$H NMR (400 MHz, CD$_3$OD) δ: 8.26 (s, 1H), 8.01-8.05 (m, 3H), 7.95-7.97 (m, 1H), 7.78 (d, J=8.8 Hz, 1H), 7.59-7.64 (m, 2H), 6.90 (d, J=7.6 Hz, 1H), 2.54 (s, 3H), 1.86 (s, 3H). Mass spectrum (ESI, m/z): Calculated for C$_{20}$H$_{17}$N$_3$O$_2$, 332.1 (M+H), found 332.0.

Example 204

Compound #288

3-[(2E)-2-(hydroxyimino)-4-methylimidazolidin-4-yl]-6-(naphthalen-2-yl)-1,2-dihydropyridin-2-one

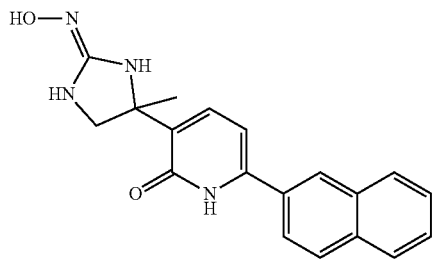 [SMILES: CC1(c2ccc(-c3ccc4ccccc4c3)[nH]c2=O)CN/C(=N\O)N1]

The title compound was prepared according to the procedure described in Example 198 by displacement of 2-methoxy-3-[5-methyl-2-(methylsulfanyl)-4,5-dihydro-1H-imidazol-5-yl]-6-(naphthalen-2-yl)pyridine with hydroxylamine followed by demethylation with TMSCl/NaI to yield the product as an off-white solid.

$^1$H NMR (400 MHz, Methanol-d$_4$) δ: 8.25 (s, 1H), 8.02-8.04 (m, 2H), 7.94-8.00 (m, 1H), 7.77-7.79 (m, 1H), 7.70 (d, J=7.2 Hz, 1H), 7.59-7.62 (m, 2H), 6.81 (d, J=7.6 Hz, 1H), 3.91-4.01 (m, 2H), 1.79 (s, 3H). Mass spectrum (ESI, m/z): Calculated for C$_{20}$H$_{19}$N$_3$OS, 335.1, found 335.2, [M+H]$^+$ Example 205

Compound #289

3-[2-(dimethylamino)-4-methyl-4,5-dihydro-1H-imidazol-4-yl]-6-(naphthalen-2-yl)-1,2-dihydropyridin-2-one

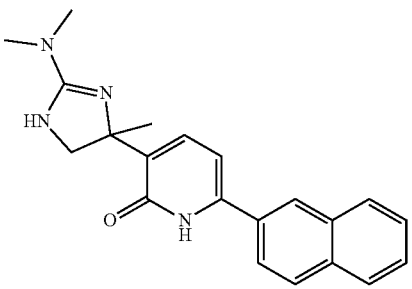 [SMILES: CN(C)C1=NC(C)(c2ccc(-c3ccc4ccccc4c3)[nH]c2=O)CN1]

The title compound was prepared according to the procedure described in Example 198 by displacement of 2-methoxy-3-[5-methyl-2-(methylsulfanyl)-4,5-dihydro-1H-imidazol-5-yl]-6-(naphthalen-2-yl)pyridine with dimethylamine HCl salt followed by demethylation with TMSCl/NaI to yield the product as a light yellow solid.

$^1$H NMR (300 MHz, Methanol-d$_4$, ppm) δ: 8.12 (s, 1H), 7.82-7.92 (m, 3H), 7.61-7.68 (m, 2H), 7.47-7.50 (m, 2H), 6.70 (d, J=7.5 Hz, 1H), 3.78-3.87(m, 2H), 3.03(s, 6H), 1.68 (s, 3H). Mass spectrum (ESI, m/z): Calculated for C$_{20}$H$_{19}$N$_3$OS, 347.2 (M+H), found 347.2.

Example 206

Compound #290

N-[4-methyl-4-[6-(naphthalen-2-yl)-2-oxo-1,2-dihydropyridin-3-yl]-4,5-dihydro-1H-imidazol-2-yl]methanesulfonamide

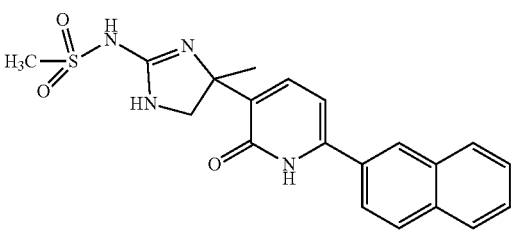 [SMILES: CC1(c2ccc(-c3ccc4ccccc4c3)[nH]c2=O)CNC(NS(C)(=O)=O)=N1]

The title compound was prepared according to the procedure described in Example 198 by displacement of 2-methoxy-3-[5-methyl-2-(methylsulfanyl)-4,5-dihydro-1H-imidazol-5-yl]-6-(naphthalen-2-yl)pyridine with ammonium hydroxide followed by demethylation with TMSCl/NaI to yield the product as a white solid.

$^1$H NMR (300 MHz, Methanol-$d_4$, ppm) δ: 8.19 (s, 1H), 7.94-7.98 (m, 2H), 7.88-7.91 (m, 1H), 7.72-7.75 (m, 1H), 7.64 (d, J=7.5 Hz, 1H), 7.52-7.57 (m, 2H), 6.75 (d, J=7.2 Hz, 1H), 3.75-3.84 (m, 2H), 2.92 (s, 3H), 1.69 (s, 3H). Mass spectrum (ESI, m/z): Calculated for $C_{20}H_{19}N_3OS$, 397.1 (M+H), found 397.0.

Example 207

Compound #152

3-[5-methyl-6-oxo-5H, 6H, 7H-imidazo[2,1-c][1,2,4]triazol-5-yl]-6-(naphthalen-2-yl)-1,2-dihydropyridin-2-one

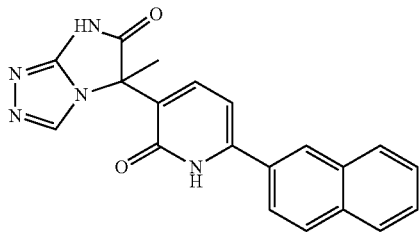 [SMILES: CC1(c2ccc(-c3ccc4ccccc4c3)[nH]c2=O)C(=O)Nc2nncn21]

Step 1: 3-benzyl-5-[2-methoxy-6-(naphthalen-2-yl) pyridin-3-yl]-5-methyl-2-sulfanylidene imidazolidin-4-one Into a 50-mL round-bottom flask purged and maintained with an inert atmosphere of nitrogen, were placed 2-amino-2-[2-methoxy-6-(naphthalen-2-yl)pyridin-3-yl]propanenitrile (2 g, 6.59 mmol, 1.00 equiv.), N,N-dimethylformamide (30 m L), (isothiocyanatomethyl)benzene (1.475 g, 9.89 mmol, 1.50 equiv.). The resulting solution was stirred overnight at room temperature. The reaction was then quenched by the addition of water (3 mL). The reaction progress was monitored by TLC/LCMS (ethyl acetate/petroleum ether=1:1). The resulting solution was extracted with ethyl acetate and the organic layers combined and concentrated under vacuum. The residue was applied onto a silica gel column with ethyl acetate/petroleum ether (1:3). The product was dissolved in DMF, hydrogen chloride (2M) (3 mL) was added. The resulting solution was stirred for 6 h at 100° C. in an oil bath. The reaction progress was monitored by TLC/LCMS (ethyl acetate/petroleum ether=1:1). The resulting solution was extracted with ethyl acetate and the organic layers combined and concentrated under vacuum. The mixture was dried over anhydrous sodium sulfate. The residue was applied onto a silica gel column with ethyl acetate/petroleum ether (1:5) to yield 3-benzyl-5-[2-methoxy-6-(naphthalen-2-yl)pyridin-3-yl]-5-methyl-2-sulfanylideneimidazolidin-4-one as a yellow solid.

Mass spectrum (ESI, m/z): Calculated for $C_{27}H_{23}N_3O_2S$, 454.2 (M+H), found 454.1.

Step 2: 1-benzyl-4-[2-methoxy-6-(naphthalen-2-yl) pyridin-3-yl]-4-methyl-2-(methyl sulfanyl)-4,5-dihydro-1H-imidazol-5-one Into a 50-mL round-bottom flask purged and maintained with an inert atmosphere of nitrogen, were placed 3-benzyl-5-[2-methoxy-6-(naphthalen-2-yl)pyridin-3-yl]-5-methyl-2-sulfanylideneimidazolidin-4-one (485 mg, 1.02 mmol, 1.00 equiv., 95%), methanol (20 mL), iodomethane (0.4 mL, 2.00 equiv.), sodium hydroxide (44 mg, 1.10 mmol, 1.00 equiv.). The resulting solution was stirred for 2 h at 40° C. in an oil bath. The reaction progress was monitored by TLC (ethyl acetate/petroleum ether=1:1). The resulting mixture was concentrated under vacuum. The residue was dissolved in of ethyl acetate. The solids were filtered out. The resulting mixture was concentrated under vacuum. The residue was applied onto a silica gel column with ethyl acetate/petroleum ether (5:1) to yield 1-benzyl-4-[2-methoxy-6-(naphthalen-2-yl) pyridin-3-yl]-4-methyl-2-(methylsulfanyl)-4, 5-dihydro-1H-imidazol-5-one as a yellow solid.

Mass spectrum (ESI, m/z): Calculated for $C_{28}H_{25}N_3O_4S$, 468.2 [M+H]$^+$, found 468.1.

Step 3: N-1-benzyl-4-[2-methoxy-6-(naphthalen-2-yl) pyridin-3-yl]-4-methyl-5-oxo-4,5-dihydro-1H-imidazol-2-yl]carbohydrazide Into a 25-mL round-bottom flask purged and maintained with an inert atmosphere of nitrogen, were placed 1-benzyl-4-[2-methoxy-6-(naphthalen-2-yl)pyridin-3-yl]-4-methyl-2-(methylsulfanyl)-4,5-dihydro-1H-imidazol-5-one (424 mg, 0.9 mmol, 1.00 equiv.), methanol (10 mL), formohydrazide (540 mg, 9 mmol, 10.00 equiv.). The resulting solution was stirred overnight at 70° C. in an oil bath. The reaction progress was monitored by TLC/LCMS (ethyl acetate/petroleum ether=1:1). The resulting mixture was concentrated under vacuum. The residue was applied onto a silica gel column with ethyl acetate/petroleum ether (1:5) to yield N-1-benzyl-4-[2-methoxy-6-(naphthalen-2-yl) pyridin-3-yl]-4-methyl-5-oxo-4,5-dihydro-1H-imidazol-2-yl]carbohydrazide as a white solid.

Mass spectrum (ESI, m/z): Calculated for $C_{28}H_{25}N_5O_3$, 480.2, [M+H]$^+$, found 480.1.

Step 4: 7-benzyl-5-[2-methoxy-6-(naphthalen-2-yl) pyridin-3-yl]-5-methyl-5H,6H,7H-imidazo[2,1-c][1,2,4]triazol-6-one Into a 25-mL round-bottom flask purged and maintained with an inert atmosphere of nitrogen, were placed N-[1-benzyl-4-[2-methoxy-6-(naphthalen-2-yl) pyridin-3-yl]-4-methyl-5-oxo-4,5-dihydro-1H-imidazol-2-yl]carbohydrazide (272 mg, 0.57 mmol, 1.00 equiv.), acetaldehyde (10 mL). The resulting solution was stirred overnight at 120° C. in an oil bath. The reaction progress was monitored by TLC/LCMS (dichloromethane/methanol=20:1). The resulting mixture was concentrated under vacuum. The reaction was then quenched by the addition of water (10 mL). The resulting solution was extracted with of ethyl acetate and the organic layers combined. The residue was applied onto a silica gel column with ethyl acetate/petroleum ether (1:2) to yield 7-benzyl-5-[2-methoxy-6-(naphthalen-2-yl)pyridin-3-yl]-5-methyl-5H,6H,7H-imidazo[2,1-c][1,2,4]triazol-6-one as a yellow solid.

Mass spectrum (ESI, m/z): Calculated for $C_{28}H_{23}N_5O_2$, 462.2, [M+H]$^+$, found 462.3.

Step 5: 3-[7-benzyl-5-methyl-6-oxo-5H,6H,7H-imidazo[2,1-c][1,2,4]triazol-5-yl]-6-(naphthalen-2-yl)-1,2-dihydropyridin-2-one The title compound was prepared according to the procedure described in Example 1 step 5 by demethylation with TMSCl/NaI to yield the product as a yellow solid.

Mass spectrum (ESI, m/z): Calculated for $C_{27}H_{21}N_5O_2$, 448.2, $[M+H]^+$, found 448.1.

Step 6: 3-[5-methyl-6-oxo-5H, 6H, 7H-imidazo[2,1-c][1,2,4]triazol-5-yl]-6-(naphthalen-2-yl)-1,2-dihydropyridin-2-one Into a 25-mL round-bottom flask purged and maintained with an inert atmosphere of nitrogen, were placed 3-[7-benzyl-5-methyl-6-oxo-5H,6H,7H-imidazo[2,1-c][1,2,4]triazol-5-yl]-6-(naphthalen-2-yl)-1,2-dihydropyridin-2-one (40 mg, 0.09 mmol, 1.00 equiv.), toluene (5 mL), trichloroaluminum (70 mg, 0.52 mmol, 6.00 equiv.), amine hydrochloride (28.6 mg, 0.53 mmol, 6.00 equiv.). The resulting solution was stirred for 4 h at 60° C. in an oil bath. The reaction progress was monitored by TLC/LCMS (dichloromethane/methanol=10:1). The reaction was then quenched by the addition of water (1 mL). The resulting solution was extracted with of ethyl acetate and the organic layers combined and concentrated under vacuum. The residue (60 mg) dissolved in DMF was purified by Prep-HPLC with the following conditions (1#-Waters 2767-5): Column, SunFire Prep C18, 5 um, 19*100 mm; mobile phase, Water of 0.05% TFA and $CH_3CN$ (20% $CH_3CN$ up to 90% in 10 min, up to 100% in 2 min, down to 20% in 2 min; Detector, UV 220&254 nm to yield 3-[5-methyl-6-oxo-5H,6H,7H-imidazo[2,1-c][1,2,4]triazol-5-yl]-6-(naphthalen-2-yl)-1,2-dihydropyridin-2-one as a white solid.

$^1$H NMR (400 MHz, $CD_3OD$, ppm) δ: 8.44 (s, 1H), 8.25 (s, 1H), 8.10 (d, J=7.6 Hz, 1H), 8.00-8.04 (m, 2H), 7.94-7.96 (m, 1H), 7.78 (d, J=8.4 Hz, 1H), 7.59-7.61 (m, 2H), 6.88 (d, J=7.2 Hz, 1H), 2.01 (s, 3H). Mass spectrum (ESI, m/z): Calculated for $C_{20}H_{15}N_5O_2$, 358.1, $[M-H]^+$, found 358.0.

Example 208

Compound #153

3-methyl-3-(6-(naphthalen-2-yl)-2-oxo-1,2-dihydropyridin-3-yl)-1H-imidazo[1,2-a]imidazol-2(3H)-one

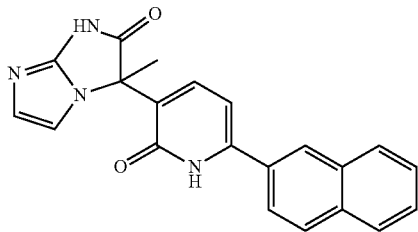 [SMILES: CC1(c2ccc(-c3ccc4ccccc4c3)[nH]c2=O)C(=O)Nc2nccn21]

Step 1: 2-((1,3-dioxolan-2-yl)methylamino)-1-benzyl-4-(2-methoxy-6-(naphthalen-2-yl)pyridin-3-yl)-4-methyl-1H-imidazol-5(4H)-one Into 50 ml round-bottom flask, 3-benzyl-5-(2-methoxy-6-(naphthalen-2-yl)pyridin-3-yl)-5-methyl-2-thioxoimidazolidin-4-one (500 mg, 1.102 mmol, 1.00 equiv.) was dissolved in methanol, and then (1,3-dioxolan-2-yl)methanamine (227 mg, 2.201 mmol, 2.00 equiv.) and $Et_3N$ (557 mg, 5.504 mmol, 5.00 equiv.) was added. The mixture was stirred at ambient temperature and t-BuOOH (497 mg, 5.515 mmol, 5.00 equiv.) was added dropwise. The reaction mixture was stirred for 16 h at 25° C. The mixture was quenched by ice-water and extracted with ethyl acetate. The organic layers combined and concentrated under vacuum. The residue was applied onto a silica gel column with ethyl acetate/petroleum ether (1/1) to yield 2-((1,3-dioxolan-2-yl)methylamino)-1-benzyl-4-(2-methoxy-6-(naphthalen-2-yl)pyridin-3-yl)-4-methyl-1H-imidazol-5(4H)-one as yellow oil.

Mass spectrum (ESI, m/z): Calculated for $C_{31}H_{30}N_4O_4$, 523.2 $[M+H]^+$, found 523.3.

Step 2: 1-benzyl-3-(2-hydroxy-6-(naphthalen-2-yl)pyridin-3-yl)-3-methyl-1H-imidazo[1,2-a]imidazol-2(3H)-one Into 50 ml round-bottom flask, 2-((1,3-dioxolan-2-yl)methylamino)-1-benzyl-4-(2-methoxy-6-(naphthalen-2-yl)pyridin-3-yl)-4-methyl-1H-imidazol-5(4H)-one (200 mg, 1.191 mmol, 1.00 equiv.) was dissolved in 1,2-dichloroethane, and then TFA was added. The reaction mixture was stirred for 16 h at 100° C. The pH value of the solution was adjusted to 6 with $NaHCO_3$ (aq) and extracted with ethyl acetate. The organic layers combined and concentrated under vacuum. The residue was applied onto a silica gel column with DCM/MeOH (20/1) to yield 1-benzyl-3-(2-hydroxy-6-(naphthalen-2-yl)pyridin-3-yl)-3-methyl-1H-imidazo[1,2-a]imidazol-2(3H)-one as light yellow solid.

Mass spectrum (ESI, m/z): Calculated for $C_{28}H_{22}N_4O_2$, 447.2 (M+H), found 447.1.

Step 3: 3-methyl-3-(6-(naphthalen-2-yl)-2-oxo-1,2-dihydropyridin-3-yl)-1H-imidazo[1,2-a]imidazol-2(3H)-one The title compound was prepared according to the procedure described in Example 207 step 6 by de-benzylation to yield the product as an off-white solid.

$^1$H NMR (400 MHz, $CD_3OD$, ppm) δ: 8.25 (s, 1H), 8.16 (d, J=7.6 Hz, 1H), 8.00-8.05 (m, 2H), 7.95-7.97 (m, 1H), 7.77-7.79 (m, 1H), 7.59-7.64 (m, 2H), 7.27 (d, J=2.0 Hz, 1H), 7.23 (d, J=2.4 Hz, 1H), 6.92 (d, J=7.6 Hz, 1H), 1.86 (s, 3H). Mass spectrum (ESI, m/z): Calculated for $C_{21}H_{16}N_4O_2$, 357.1 $[M+H]^+$, found 357.1.

Example 209

Compound #291

N-(4-(6-(8-fluoronaphthalen-2-yl)-2-oxo-1,2-dihydropyridin-3-yl)-4-isopropyl-4,5-dihydro-1H-imidazol-2-yl)cyanamide

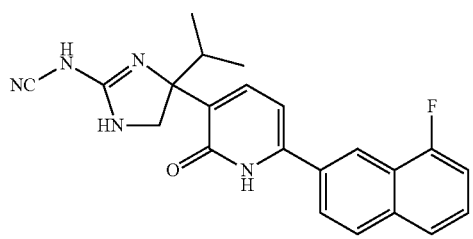 [SMILES: CC(C)C1(c2ccc(-c3ccc4cccc(F)c4c3)[nH]c2=O)CNC(NC#N)=N1]

Step 1: 5-(6-(8-fluoronaphthalen-2-yl)-2-methoxypyridin-3-yl)-5-isopropylimidazolidine-2,4-dione Into 100 ml seal tube, 1-(6-(8-fluoronaphthalen-2-yl)-2-methoxypyridin-3-yl)-2-methylpropan-1-one (2.0 g, 6.185 mmol, 1.0 eq.) was dissolved in ethanol (15 mL), trimethylsilanecarbonitrile (0.92 g, 9.274 mmol, 1.5 eq.), ammonium hydroxide (2 mL) and (NH₄)₂CO₃ (1.12 g, 11.656 mmol, 2 eq.) was added. The mixture was stirred for 24 h at 100° C. The mixture was concentrated under vacuum. The residue was applied onto a silica gel column with PE/EA (2/1) to yield 5-(6-(8-fluoronaphthalen-2-yl)-2-methoxypyridin-3-yl)-5-isopropylimidazolidine-2,4-dione as a yellow solid.

Mass spectrum (ESI, m/z): Calculated for $C_{22}H_{20}FN_3O_3$, 394.1 $[M+H]^+$, found 394.1.

Step 2: 4-(6-(8-fluoronaphthalen-2-yl)-2-methoxypyridin-3-yl)-4-isopropylimidazolidin-2-one Into 100 ml round-bottom flask, 5-(6-(8-fluoronaphthalen-2-yl)-2-methoxypyridin-3-yl)-5-isopropylimidazolidine-2,4-dione (1.2 g, 3.050 mmol, 1.0 eq.) was dissolved in THF, LAH (0.58 g, 15.282 mmol, 5.0 eq.) was added. The mixture was stirred for 16 h at 80° C. The mixture was quenched by Na₂SO₄.10H₂O and filtered out. The organic layer was concentrated under vacuum. The residue was applied onto a silica gel column with DCM/MeOH (10/1) to yield 4-(6-(8-fluoronaphthalen-2-yl)-2-methoxypyridin-3-yl)-4-isopropylimidazolidin-2-one as yellow solid.

Mass spectrum (ESI, m/z): Calculated for $C_{22}H_{22}FN_3O_2$, 380.2 $[M+H]^+$, found 380.2.

Step 3: 4-(6-(8-fluoronaphthalen-2-yl)-2-methoxypyridin-3-yl)-4-isopropylimidazolidine-2-thione Into 100 ml round-bottom flask, 4-(6-(8-fluoronaphthalen-2-yl)-2-methoxypyridin-3-yl)-4-isopropylimidazolidin-2-one (500 mg, 1.318 mmol, 1.0 eq.) was dissolved in toluene (30 mL), Lawesson's Reagent (2.66 g, 6.577 mmol, 5.0 eq.) was added. The mixture was stirred for 16 h at 100° C. The mixture was concentrated under vacuum. The residue was applied onto a silica gel column with PE/EA (1/1) to yield 4-(6-(8-fluoronaphthalen-2-yl)-2-methoxypyridin-3-yl)-4-isopropylimidazolidine-2-thione as yellow oil.

Mass spectrum (ESI, m/z): Calculated for $C_{22}H_{22}FN_3OS$, 396.1 $[M+H]^+$, found 396.3.

Step 4: 6-(8-fluoronaphthalen-2-yl)-3-(5-isopropyl-2-(methylthio)-4,5-dihydro-1H-imidazol-5-yl)-2-methoxypyridine Into 40 ml vial, 4-(6-(8-fluoronaphthalen-2-yl)-2-methoxypyridin-3-yl)-4-isopropylimidazolidine-2-thione (250 mg, 0.632 mmol, 1.0 eq.) was dissolved in methanol (5 mL) and iodomethane (48 mg, 0.338 mmol, 2.0 eq.) was added. The mixture was stirred for 2 h at 70° C. The mixture was concentrated under vacuum. The residue was applied onto a silica gel column with DCM/MeOH (10/1) to yield 6-(8-fluoronaphthalen-2-yl)-3-(5-isopropyl-2-(methylthio)-4,5-dihydro-1H-imidazol-5-yl)-2-methoxypyridine as light yellow solid.

Mass spectrum (ESI, m/z): Calculated for $C_{23}H_{24}FN_3OS$, 410.2 $[M+H]^+$, found 410.3.

Step 5: N-(4-(6-(8-fluoronaphthalen-2-yl)-2-methoxypyridin-3-yl)-4-isopropyl-4,5-dihydro-1H-imidazol-2-yl)cyanamide Into a 40-mL vial, were placed 6-(8-fluoronaphthalen-2-yl)-3-(4-isopropyl-2-(methylthio)-4,5-dihydro-1H-imidazol-4-yl)-2-methoxypyridine (300 mg, 0.733 mmol, 1.00 equiv.), cyanamide (154 mg, 3.663 mmol, 5.0 equiv.), N-ethyl-N-isopropylpropan-2-amine (189 mg, 1.462 mmol, 2.0 equiv.). The resulting solution was stirred overnight at 90° C. The mixture was concentrated under vacuum. The residue was applied onto a silica gel column with DCM/MeOH (10/1) to yield N-(4-(6-(8-fluoronaphthalen-2-yl)-2-methoxypyridin-3-yl)-4-isopropyl-4,5-dihydro-1H-imidazol-2-yl)cyanamide as a yellow solid.

Mass spectrum (ESI, m/z): Calculated for $C_{23}H_{22}FN_5O$, 404.2 $[M+H]^+$, found 404.4.

Step 6: N-(4-(6-(8-fluoronaphthalen-2-yl)-2-oxo-1,2-dihydropyridin-3-yl)-4-isopropyl-4,5-dihydro-1H-imidazol-2-yl)cyanamide The title compound was prepared according to the procedure described in Example 1 step 5 by demethylation with TMSCl/NaI to yield the product as a light yellow solid.

¹H NMR (400 MHz, CD₃OD, ppm) δ: 8.55 (s, 1H), 8.45 (s, 1H), 8.10 (d, J=8.0 Hz, 1H), 7.87 (d, J=8.0 Hz, 1H), 7.80 (d, J=8.0 Hz, 1H), 7.65 (d, J=7.2 Hz, 1H), 7.56-7.61 (m, 1H), 7.30-7.34 (m, 2H), 6.86 (d, J=7.2 Hz, 1H), 4.21 (d, J=11.6 Hz, 1H), 4.14 (d, J=12.0 Hz, 1H), 2.71-2.76 (m, 1H), 1.03 (d, J=7.2 Hz, 3H), 0.97 (d, J=6.8 Hz, 3H). ¹⁹F NMR (400 MHz, CD₃OD, ppm) δ: −77.04, −124.44. Mass spectrum (ESI, m/z): Calculated For $C_{22}H_{20}FN_5O$, 389/43 $[M+H]^+$, found 390.2.

Example 210

Compound #156

5-(6-(8-fluoronaphthalen-2-yl)-2-methoxypyridin-3-yl)-5-isopropyl-5H-imidazo[2,1-c][1,2,4]triazol-6(7H)-one

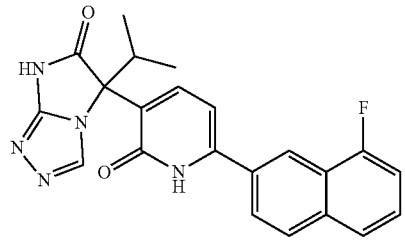 [SMILES: CC(C)C1(c2ccc(-c3ccc4cccc(F)c4c3)[nH]c2=O)C(=O)Nc2nncn21]

Step 1: 3-benzyl-5-(6-(8-fluoronaphthalen-2-yl)-2-methoxypyridin-3-yl)-5-isopropylimidazolidine-2,4-dione Into a 100-mL round-bottom flask, were placed 5-(6-(8-fluoronaphthalen-2-yl)-2-methoxypyridin-3-yl)-5-isopropylimidazolidine-2,4-dione (1 g, 2.542 mmol, 1.00 equiv.), (bromomethyl)benzene (522 mg, 3.052 mmol, 1.20 equiv.), K₂CO₃ (527 mg, 3.813 mmol, 1.50 equiv.), DMF (10 mL). The resulting solution was stirred for 4 h at 25° C. The reaction progress was monitored by PE:EA=3:1. The reaction was then quenched by the addition of water (30 mL). The resulting solution was extracted with ethyl acetate (3×50 mL) and the organic layers combined. The resulting mixture was washed with brine (1×50 mL). The mixture was dried over anhydrous sodium sulfate. The solids were filtered out. The resulting mixture was concentrated under vacuum. The residue was applied onto a silica gel column with ethyl acetate/petroleum ether (1:3) to yield 3-benzyl-5-(6-(8-fluoronaphthalen-2-yl)-2-methoxypyridin-3-yl)-5-isopropylimidazolidine-2,4-dione as a light yellow oil.

Mass spectrum (ESI, m/z): Calculated for $C_{21}H_{21}NO_3$, 484.2 (M+H), found 484.4.

Step 2: 1-benzyl-4-(6-(8-fluoronaphthalen-2-yl)-2-methoxypyridin-3-yl)-4-isopropyl-2-(methylthio)-1H-imidazol-5(4H)-one The title compound was prepared according to the procedure described in Example 209 step 3-4 by treatment with Lawesson's agent followed by reacting with MeI to yield the title compounds as a light yellow oil.

Mass spectrum (ESI, m/z): Calculated for $C_{30}H_{28}FN_3O_2S$, 514.2 (M+H), found 514.4.

Step 3: N'-(1-benzyl-4-(6-(8-fluoronaphthalen-2-yl)-2-methoxypyridin-3-yl)-4-isopropyl-5-oxo-4,5-dihydro-1H-imidazol-2-yl)formohydrazide Into a 50-mL round-bottom flask, were placed 1-benzyl-4-(6-(8-fluoronaphthalen-2-yl)-2-methoxypyridin-3-yl)-4-isopropyl-2-(methylthio)-1H-imidazol-5(4H)-one (80 mg, 0.156 mmol, 1.00 equiv.), MeOH (5 mL), formohydrazide (47 mg, 0.783 mmol, 5.00 equiv.). The resulting solution was stirred for overnight at 80° C. The reaction progress was monitored by LCMS. The resulting mixture was concentrated under vacuum. The residue was applied onto TLC with ethyl acetate/petroleum ether (1:1) to yield N'-(1-benzyl-4-(6-(8-fluoronaphthalen-2-yl)-2-methoxypyridin-3-yl)-4-isopropyl-5-oxo-4,5-dihydro-1H-imidazol-2-yl)formohydrazide as a light yellow oil.

Mass spectrum (ESI, m/z): Calculated for $C_{30}H_{28}FN_5O_3$, 526.2 (M+H), found 526.4.

Step 4: 7-benzyl-5-(6-(8-fluoronaphthalen-2-yl)-2-methoxypyridin-3-yl)-5-isopropyl-5H-imidazo[2,1-c][1,2,4]triazol-6(7H)-one Into a 50-mL round-bottom flask, were placed N'-(1-benzyl-4-(6-(8-fluoronaphthalen-2-yl)-2-methoxypyridin-3-yl)-4-isopropyl-5-oxo-4,5-dihydro-1H-imidazol-2-yl)formohydrazide (100 mg, 0.190 mmol, 1.00 equiv.), AcOH (5 mL). The resulting solution was stirred for overnight at 100° C. The reaction progress was monitored by LCMS. The resulting mixture was concentrated under vacuum. The residue was applied onto TLC with ethyl acetate/petroleum ether (1:1) to yield 7-benzyl-5-(6-(8-fluoronaphthalen-2-yl)-2-methoxypyridin-3-yl)-5-isopropyl-5H-imidazo[2,1-c][1,2,4]triazol-6(7H)-one as a light yellow oil.

Mass spectrum (ESI, m/z): Calculated for $C_{30}H_{26}FN_5O_2$, 508.2 (M+H), found 508.1.

Step 5: 5-(6-(8-fluoronaphthalen-2-yl)-2-methoxypyridin-3-yl)-5-isopropyl-5H-imidazo[2,1-c][1,2,4]triazol-6(7H)-one The title compound was prepared according to the procedure described in Example 207 by de-benzylation followed by demethylation with TMSCl/NaI to yield the product as a colorless oil.

$^1$H NMR (300 MHz, CD$_3$OD) δ: 8.57 (s, 1H), 8.40 (s, 1H), 7.98-8.06 (m, 2H), 7.81-7.84 (m, 1H), 7.74 (d, J=8.4 Hz, 1H), 7.50-7.57 (m, 1H), 7.24-7.30 (m, 1H), 6.81 (d, J=7.8 Hz, 1H), 1.22-1.33 (m, 1H), 1.02 (d, J=6.9 Hz, 3H), 0.92 (d, J=6.9 Hz, 3H). $^{19}$F NMR (300 MHz, CD$_3$OD) δ: −77.18, −124.30. Mass spectrum (ESI, m/z): Calculated for $C_{29.78}H_{21.89}F_{12.67}N_5O_{9.78}$, 404.1 (M−3.89CF$_3$COOH+H), found 404.2.

Example 211

Compound #292

(Z)-6-(8-fluoronaphthalen-2-yl)-3-(4-isopropyl-2-(methoxyimino)imidazolidin-4-yl)pyridin-2(1H)-one

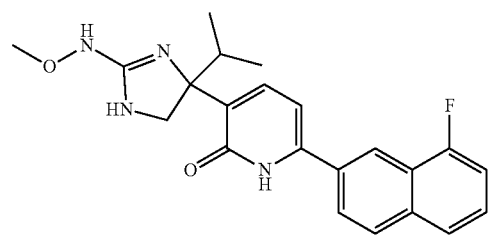 [SMILES: CONC1=NC(c2ccc(-c3ccc4cccc(F)c4c3)[nH]c2=O)(C(C)C)CN1]

The title compound was prepared according to the procedure described in Example 198 by displacement with methoxyamine followed by demethylation with TMSCl/NaI to yield the product as a white solid.

$^1$H NMR (400 MHz, CD$_3$OD, ppm) δ: 8.43 (s, 1H), 8.08 (d, J=8.4 Hz, 1H), 7.88 (d, J=8.8 Hz, 1H), 7.78 (d, J=8.0 Hz, 1H), 7.70 (d, J=7.2 Hz, 1H), 7.54-7.59 (m, 1H), 7.28-7.33 (m, 1H), 6.82 (d, J=7.2 Hz, 1H), 3.92 (d, J=10.4 Hz, 1H), 3.73 (d, J=10.0 Hz, 1H), 3.65 (s, 3H), 2.70-2.79 (m, 1H), 1.04 (d, J=6.8 Hz, 3H), 0.92 (d, J=6.8 Hz, 3H). $^{19}$F NMR (300 MHz, CD$_3$OD, ppm) δ: −124.47. Mass spectrum (ESI, m/z): Calculated for $C_{22}H_{23}FN_4O_2$, 395.2 [M+H]$^+$, found 395.2.

Example 212

Compound #293

(E)-6-(8-fluoronaphthalen-2-yl)-3-(4-isopropyl-2-(methoxyimino)imidazolidin-4-yl)-5-methylpyridin-2(1H)-one

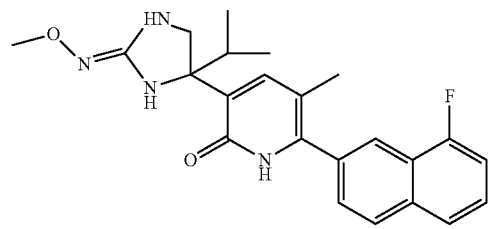 [SMILES: CO/N=C1\NCC(c2cc(C)c(-c3ccc4cccc(F)c4c3)[nH]c2=O)(C(C)C)N1]

Step 1: 5-(5-bromo-6-(8-fluoronaphthalen-2-yl)-2-methoxypyridin-3-yl)-5-isopropylimidazolidine-2,4-dione Into 50 ml round-bottom flask, 5-(6-(8-fluoronaphthalen-2-yl)-2-methoxypyridin-3-yl)-5-isopropylimidazolidine-2,4-dione (200 mg, 0.508 mmol, 1 eq.) was dissolved in acetonitrile (10 mL), methanol (10 mL), 1-bromopyrrolidine-2,5-dione (135 mg, 0.758 mmol, 1.5 eq.), 2,2,2-trifluoroacetic acid (0.3 mL). The mixture was stirred for 16 h at 60° C. The mixture was concentrated under vacuum. The residue was applied onto a silica gel column with PE/EA (1/2) to yield 5-(5-bromo-6-(8-fluoronaphthalen-2-yl)-2-methoxypyridin-3-yl)-5-isopropylimidazolidine-2,4-dione as a yellow solid.

Mass spectrum (ESI, m/z): Calculated For $C_{22}H_{19}BrFN_3O_3$, 472.1 (M+H), found 472.1.

Step 2: 5-(6-(8-fluoronaphthalen-2-yl)-2-methoxy-5-methylpyridin-3-yl)-5-isopropylimidazolidine-2,4-dione Into 50 ml 3-rounds-bottom flask purged and maintained with an inert atmosphere of nitrogen, 5-(5-bromo-6-(8-fluoronaphthalen-2-yl)-2-methoxypyridin-3-yl)-5-isopropylimidazolidine-2,4-dione (200 mg, 0.423 mmol, 1 eq.) was dissolved in DMF (15 mL). Pd(OAc)$_2$ (9.5 mg, 0.042 mmol, 0.1 eq.), (O-Tol)$_3$P (12.8 mg, 0.042 mmol, 0.1 eq.) and tetramethylstannane (113.7 mg, 0.636 mmol, 1.5 eq.) were then added. The mixture was stirred for 16 h at 100° C. The mixture was concentrated under vacuum. The residue was applied onto a silica gel column with PE/EA (1/3) to yield 5-(6-(8-fluoronaphthalen-2-yl)-2-methoxypyridin-3-yl)-5-isopropyl-1-methylimidazolidine-2,4-dione as yellow solid.

Mass spectrum (ESI, m/z): Calculated for $C_{23}H_{22}FN_3O_3$, 408.2 (M+H), found 408.2.

Step 3: (E)-6-(8-fluoronaphthalen-2-yl)-3-(4-isopropyl-2-(methoxyimino)imidazolidin-4-yl)-5-methylpyridin-2(1H)-one The title compound was prepared according to the procedure described in Example 209 by reduction, sulfonation and displacement with methoxyamide followed by demethylation with TMSCl/NaI to yield the product as a white solid.

$^1$H NMR (300 MHz, CD$_3$OD) δ: 8.39 (s, 1H), 8.05 (d, J=8.7 Hz, 1H), 7.81-7.84 (m, 1H), 7.74 (d, J=8.1 Hz, 1H), 7.62 (d, J=7.5 Hz, 1H), 7.49-7.56 (m, 1H), 7.24-7.30 (m, 1H), 6.81 (d, J=7.5 Hz, 1H), 4.15 (d, J=11.4Hz, 1H), 3.97 (d, J=11.1Hz, 1H), 3.82 (s, 3H), 3.38 (s, 3H), 2.69-2.86 (m, 1H), 1.04 (d, J=6.6 Hz, 3H), 0.84 (d, J=6.9 Hz, 3H). $^{19}$F NMR (300 MHz, CD$_3$OD) δ: −77.03, −124.46. Mass spectrum (ESI, m/z): Calculated for $C_{29.2}H_{28.1}F_{10.3}N_4O_{8.2}$, 409.2 (M+H−3.10CF$_3$COOH), found 409.2.

Example 213

Compound #294

6-(8-fluoronaphthalen-2-yl)-3-(4-isopropyl-5-oxo-2-thioxoimidazolidin-4-yl)pyridin-2(1H)-one

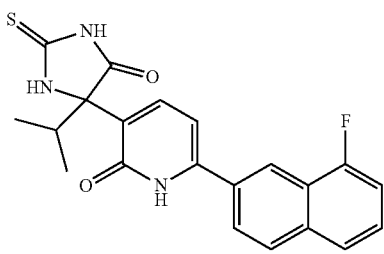 [SMILES: CC(C)C1(c2ccc(-c3ccc4cccc(F)c4c3)[nH]c2=O)NC(=S)NC1=O]

Step 1: 5-(6-(8-fluoronaphthalen-2-yl)-2-methoxypyridin-3-yl)-5-isopropyl-2-thioxoimidazolidin-4-one Into 100 ml round-bottom flask, 5-(6-(8-fluoronaphthalen-2-yl)-2-methoxypyridin-3-yl)-5-isopropylimidazolidine-2,4-dione (500 mg, 1.271 mmol, 1.0 eq.) was dissolved in toluene (30 mL), and Lawesson's Reagent (1.54 g, 3.807 mmol, 3.0 eq.) was added. The mixture was stirred for 16 h at 100° C. The mixture was concentrated under vacuum. The residue was applied onto a silica gel column with PE/EA (3/1) to yield 5-(6-(8-fluoronaphthalen-2-yl)-2-methoxypyridin-3-yl)-5-isopropyl-2-thioxoimidazolidin-4-one as yellow oil.

Mass spectrum (ESI, m/z): Calculated for $C_{22}H_{20}FN_3O_2S$, 410.1 (M+H), found 410.1.

Step 2: 6-(8-fluoronaphthalen-2-yl)-3-(4-isopropyl-5-oxo-2-thioxoimidazolidin-4-yl)pyridin-2(1H)-one The title compound was prepared according to the procedure described in Example 1 step 5 by demethylation with TMSCl/NaI to yield the product as a white solid.

$^1$H NMR (300 MHz, DMSO-d$_6$) δ: 9.81 (s, 1H), 8.46 (s, 1H), 8.12 (d, J=8.1 Hz, 1H), 7.93-7.94 (m, 1H), 7.84 (d, J=8.4 Hz, 1H), 7.56-7.71 (m, 2H), 7.39-7.45 (m, 1H), 6.79 (brm, 1H), 2.71-2.85 (m, 1H), 0.92-0.97 (m, 6H). $^{19}$F NMR (300 MHz, DMSO-d$_6$) δ: −72.61,−121.23. Mass spectrum (ESI, m/z): Calculated for $C_{21}H_{18}FN_3O_2S$, 396.1 (M−6.357CF3COOH+H), found 396.1.

Example 214

Compound #236

N-(4-(6-(8-fluoronaphthalen-2-yl)-2-oxo-1, 2-dihydropyridin-3-yl)-4-isopropyl-5-oxo-4,5-dihydro-1H-imidazol-2-yl)cyanamide

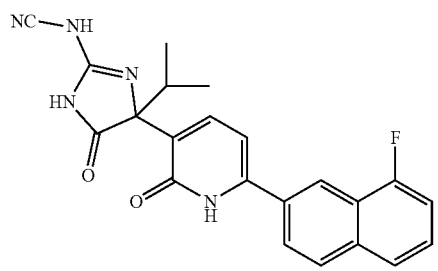 [SMILES: CC(C)C1(c2ccc(-c3ccc4cccc(F)c4c3)[nH]c2=O)N=C(NC#N)NC1=O]

The title compound was prepared according to the procedure described in Example 198 by displacement with cyanoamide followed by demethylation with TMSCl/NaI to yield the product as a white solid.

$^1$H NMR (300 MHz, DMSO) δ: 12.36 (s, 1H), 11.84 (s, 1H), 9.50 (s, 1H), 8.53 (s, 1H), 8.20 (d, J=10.8 Hz, 1H), 7.86-8.08 (m, 1H), 7.83 (d, J=8.1 Hz, 1H), 7.75 (d, J=8.4 Hz, 1H), 7.56-7.63 (m, 1H), 7.39-7.45 (m, 1H), 6.74-6.89 (m, 1H), 2.65-2.72 (m, 1H), 0.90-1.04 (t, J=8.1 Hz, 6H). $^{19}$F NMR (300 MHz, DMSO) δ: −73.88, −122.03. Mass spectrum (ESI, m/z): Calculated for $C_{22.17}H_{18.085}F_{1.255}N_5O_{2.17}$, 404.1 (M−0.085 CF$_3$COOH+H), found 404.0.

Example 215

Compound #237

(Z)-6-(8-fluoronaphthalen-2-yl)-3-(4-isopropyl-2-(methoxyimino)-5-oxoimidazolidin-4-yl)pyridin-2(1H)-one

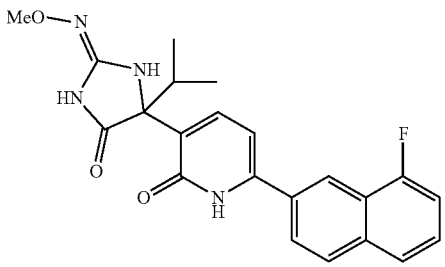 [SMILES: CO/N=C1\NC(=O)C(c2ccc(-c3ccc4cccc(F)c4c3)[nH]c2=O)(C(C)C)N1]

The title compound was prepared according to the procedure described in Example 198 by displacement with methoxyamine followed by demethylation with TMSCl/NaI to yield the product as a white solid.

$^1$H NMR (300 MHz, DMSO) δ: 12.40 (brs, 1H), 10.97 (brs, 1H), 8.44 (s, 1H), 8.11-8.13 (m, 1H), 7.82-7.94 (m, 3H), 7.75 (brs, 1H), 7.55-7.61 (m, 1H), 7.38-7.44 (m, 1H), 6.87 (brm, 1H), 3.62 (s, 3H), 2.27-2.50 (m, 1H), 0.89-0.93 (m, 6H). $^{19}$F NMR (300 MHz, DMSO) δ: −73.97, −122.05. Mass spectrum (ESI, m/z): Calculated for $C_{22.838}H_{21.419}F_{2.257}N_4O_{3.838}$, 409.2 (M−0.419CF$_3$COOH+H), found 409.1.

Example 216

Compound #155

3-(6-(8-fluoronaphthalen-2-yl)-2-oxo-1,2-dihydropyridin-3-yl)-3-isopropyl-1H-imidazo[1,2-a]imidazol-2(3H)-one

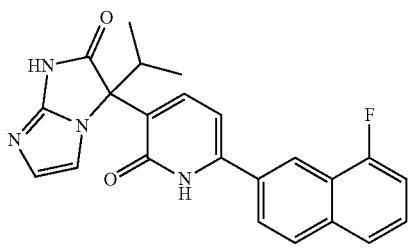 [SMILES: CC(C)C1(c2ccc(-c3ccc4cccc(F)c4c3)[nH]c2=O)C(=O)Nc2nccn21]

The title compound was prepared according to the procedure described in Example 208 to yield the product as an off-white solid.

$^1$H NMR (400 MHz, CD$_3$OD) δ: 8.45 (s, 1H), 8.09 (d, J=8.4 Hz, 1H), 7.86-7.93 (m, 2H), 7.78 (d, J=8.0 Hz, 1H), 7.53-7.59 (m, 1H), 7.05-7.32 (m, 2H), 6.77-6.84 (m, 2H), 3.32-3.33 (m, 1H), 0.70-1.03 (m, 6H). $^{19}$F NMR (400 MHz, CD$_3$OD) δ: −124.34. Mass spectrum (ESI, m/z): Calculated for $C_{23}H_{19}FN_4O_3$, 403.1 (M+H), found 403.1.

Example 217

Compound #249

4-methyl-3-(6-(naphthalen-2-yl)-2-oxo-1,2-dihydropyridin-3-yl)pentanamide

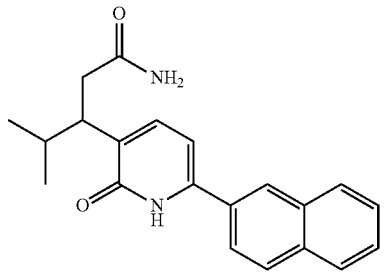 [SMILES: CC(C)C(CC(N)=O)c1ccc(-c2ccc3ccccc3c2)[nH]c1=O]

Step 1: 3-(2-methoxy-6-(naphthalen-2-yl)pyridin-3-yl)-4-methylpentanamide

Into a 50-mL round-bottom flask, were placed 3-(2-methoxy-6-(naphthalen-2-yl)pyridin-3-yl)-4-methylpentanoic acid (90 mg, 0.258 mmol, 1.00 equiv.), DMF (3 mL), DCM (3 mL), ammonium chloride (68 mg, 1.271 mmol, 5 equiv.), 2-(3H-[1,2,3]triazolo[4,5-b]pyridin-3-yl)-1,1,3,3-tetramethylisouronium hexafluorophosphate(V) (490 mg, 1.289 mmol, 5 equiv.), N-ethyl-N-isopropylpropan-2-amine (166 mg, 1.284 mmol, 5 equiv.). The resulting solution was stirred for 5 h at 25° C. The reaction progress was monitored by LCMS. The reaction was then quenched by the addition of water (10 mL). The resulting solution was extracted with ethyl acetate (3×30 mL) and the organic layers combined. The resulting mixture was washed with brine (1×30 mL). The mixture was dried over anhydrous sodium sulfate. The solids were filtered out. The resulting mixture was concentrated under vacuum. The residue was applied onto a silica gel column with ethyl acetate/petroleum ether (1:2) to yield 3-(2-methoxy-6-(naphthalen-2-yl)pyridin-3-yl)-4-methylpentanamide as a light yellow oil.

Mass spectrum (ESI, m/z): Calculated for $C_{22}H_{24}N_2O_2$, 349.2 (M+H), found 349.1.

Step 2: 4-methyl-3-(6-(naphthalen-2-yl)-2-oxo-1,2-dihydropyridin-3-yl)pentanamide The title compound was prepared according to the procedure described in Example 1 step 5 by demethylation with TMSCl/NaI to yield the product as a light yellow oil.

$^1$H NMR (300 MHz, CD$_3$OD) δ: 8.21 (s, 1H), 7.98-8.01 (m, 2H), 7.91-7.94 (m, 1H), 7.74-7.78 (m, 1H), 7.56-7.60 (m, 2H), 7.50 (d, J=7.2 Hz, 1H), 6.74 (d, J=7.2 Hz, 1H), 3.08-3.17 (m, 1H), 2.66-2.70 (m, 2H), 2.11-2.18 (m, 1H), 1.01 (d, J=6.9 Hz, 3H), 0.91 (d, J=6.9 Hz, 3H). Mass spectrum (ESI, m/z): Calculated for $C_{21}H_{22}N_2O_2$, 335.2 (M+H), found 335.1.

Example 218

Compound #250

4-methyl-N-(methylsulfonyl)-3-(6-(naphthalen-2-yl)-2-oxo-1,2-dihydropyridin-3-yl)pentanamide

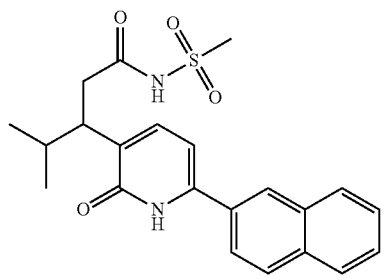 [SMILES: CC(C)C(CC(=O)NS(C)(=O)=O)c1ccc(-c2ccc3ccccc3c2)[nH]c1=O]

Step 1: 3-(2-methoxy-6-(naphthalen-2-yl)pyridin-3-yl)-4-methyl-N-(methylsulfonyl) pentanamide Into a 50-mL round-bottom flask, were placed 3-(2-methoxy-6-(naphthalen-2-yl)pyridin-3-yl)-4-methylpentanoic acid (90 mg, 0.258 mmol, 1.00 equiv.), DCM (5 mL), methanesulfonamide (49 mg, 0.515 mmol, 2 equiv.), N,N-dimethylpyridin-4-amine (63 mg, 0.516 mmol, 2 equiv.), N1-((ethylimino)methylene)-N3,N3-dimethylpropane-1,3-diamine hydrochloride (99 mg, 0.516 mmol, 2 equiv.). The resulting solution was stirred for 5 h at 25° C. The reaction progress was monitored by LCMS. The reaction was then quenched by the addition of water (10 mL). The resulting solution was extracted with ethyl acetate (3×30 mL) and the organic layers combined. The resulting mixture was washed with brine (1×20 mL). The mixture was dried over anhydrous sodium sulfate. The solids were filtered out. The resulting mixture was concentrated under vacuum. The residue was applied onto a silica gel column with ethyl acetate/petroleum ether (1:2) to yield 3-(2-methoxy-6-(naphthalen-2-yl)pyridin-3-yl)-4-methyl-N-(methylsulfonyl)pentanamide as a light yellow oil.

Mass spectrum (ESI, m/z): Calculated for $C_{23}H_{26}N_2O_4S$, 427.2 (M+H), found 427.2.

Step 2: 4-methyl-N-(methylsulfonyl)-3-(6-(naphthalen-2-yl)-2-oxo-1,2-dihydropyridin-3-yl)pentanamide The title compound was prepared according to the procedure described in Example 1 step 5 by demethylation with TMSCl/NaI to yield the product as a light yellow oil.

$^1$H NMR (300 MHz, CD$_3$OD) δ: 8.21 (s, 1H), 7.97-8.01 (m, 2H), 7.91-7.94 (m, 1H), 7.59-7.60 (m, 1H), 7.54-7.58 (m, 2H), 7.50 (d, J=7.2 Hz, 1H), 6.75 (d, J=7.2 Hz, 1H), 3.11-3.20 (m, 1H), 3.08 (s, 3H), 2.78 (d, J=7.5 Hz, 2H), 2.11-2.21 (m, 1H), 1.01 (d, J=6.6 Hz, 3H), 0.91 (d, J=6.6 Hz, 3H).

Mass spectrum (ESI, m/z): Calculated for $C_{22}H_{24}N_2O_4S$, 413.1 (M+H), found 413.2.

Example 219

Compound #220

3-methyl-2-(6-(naphthalen-2-yl)-2-oxo-1,2-dihydropyridin-3-yl)butanamide

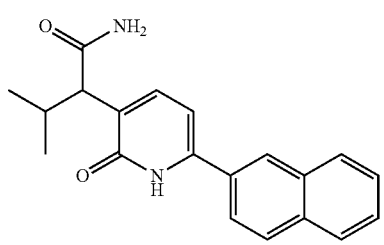 [SMILES: CC(C)C(C(N)=O)c1ccc(-c2ccc3ccccc3c2)[nH]c1=O]

Step 1: 2-(2-methoxy-6-(naphthalen-2-yl)pyridin-3-yl)-3-methylbutanoic acid

The title compound was prepared by hydrolysis of ethyl 2-(2-methoxy-6-(naphthalen-2-yl)pyridin-3-yl)-3-methylbutanoate with NaOH to yield the product as a light yellow oil.

Mass spectrum (ESI, m/z): Calculated for $C_{21}H_{21}NO_3$, 336.2 (M+H), found 336.4.

Step 2: 2-(2-methoxy-6-(naphthalen-2-yl)pyridin-3-yl)-3-methylbutanamide

The title compound was prepared by aminolysis with SOCl$_2$ and NH$_3$/MeOH solution to yield the product as light yellow oil.

Mass spectrum (ESI, m/z): Calculated for $C_{21}H_{22}N_2O_2$, 335.2 (M+H), found 335.2.

Step 3: 3-methyl-2-(6-(naphthalen-2-yl)-2-oxo-1,2-dihydropyridin-3-yl)butanamide The title compound was prepared according to the procedure described in Example 1 step 5 by demethylation with TMSCl/NaI to yield the product as a light yellow solid.

$^1$H NMR (400 MHz, CD$_3$OD) δ: 8.24 (s, 1H), 8.02 (d, J=8.0 Hz, 2H), 7.93-7.95 (m, 1H), 7.78-7.84 (m, 2H), 7.58-7.60 (m, 2H), 6.83 (d, J=7.2 Hz, 1H), 3.55 (d, J=10.4 Hz, 1H), 2.35-2.46 (m, 1H), 1.10 (d, J=6.4 Hz, 3H), 0.88 (d, J=6.4 Hz, 3H). Mass spectrum (ESI, m/z): Calculated for $C_{20}H_{20}N_2O_2$, 321.2 (M+H), found 321.3.

Example 220

Compound #221

3-methyl-N-(methylsulfonyl)-2-(6-(naphthalen-2-yl)-2-oxo-1,2-dihydropyridin-3-yl)butanamide

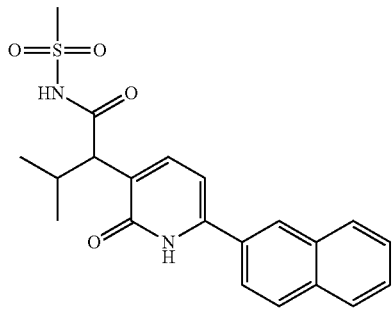 [SMILES: CC(C)C(C(=O)NS(C)(=O)=O)c1ccc(-c2ccc3ccccc3c2)[nH]c1=O]

The title compound was prepared according to the procedure described in Example 218 by coulping with methanesulfonamide followed by demethylation with TMSCl/NaI to yield the product as a light yellow oil.

$^1$H NMR (400 MHz, CD$_3$OD) δ: 8.22 (s, 1H), 7.98-8.01 (m, 2H), 7.93-7.94 (m, 1H), 7.85 (d, J=7.5 Hz, 1H), 7.77 (d, J=8.7 Hz, 1H), 7.55-7.59 (m, 2H), 6.82 (d, J=7.5 Hz, 1H), 3.62 (d, J=10.2 Hz, 1H), 3.10 (s, 3H), 2.35-2.46 (m, 1H), 1.12 (d, J=6.6 Hz, 3H), 0.86 (d, J=6.6 Hz, 3H). Mass spectrum (ESI, m/z): Calculated for C$_{21}$H$_{22}$N$_2$O$_4$S, 399.1 (M+H), found 399.2.

Example 221

Compound #219

1-(6-(naphthalen-2-yl)-2-oxo-2,3-dihydropyridin-3-yl)cyclopentanecarboxamide

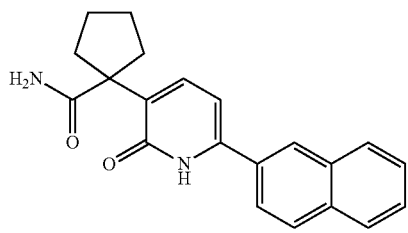 [SMILES: NC(=O)C1(c2ccc(-c3ccc4ccccc4c3)[nH]c2=O)CCCC1]

Step 1: Ethyl 1-(2-methoxy-6-(naphthalen-2-yl)pyridin-3-yl)cyclopentanecarboxylate Into a 8-mL vial purged and maintained with nitrogen, were placed ethyl 2-(2-methoxy-6-(naphthalen-2-yl)pyridin-3-yl)acetate (100 mg, 0.3 mmol, 1 equiv.), DMF (4 mL), t-BuOK (1 mL, 1 mmol, 3 equiv.), 1,4-dibromobutane (215 mg, 1 mmol, 3 equiv.). The resulting solution was stirred for 3 h at 25° C. The resulting solution was diluted with H$_2$O. The resulting solution was extracted with EtOAc and the organic layers combined and concentrated under vacuum. The residue was purified by TLC with PE:EA=12/1 to yield ethyl 1-(2-methoxy-6-(naphthalen-2-yl)pyridin-3-yl)cyclopentanecarboxylate as yellow oil.

Mass spectrum (ESI, m/z): Calculated for C$_{24}$H$_{25}$NO$_3$, 376.2 (M+H), found 376.2.

Step 2: 1-(2-methoxy-6-(naphthalen-2-yl)pyridin-3-yl)cyclopentanecarboxylic acid Into a 100-mL round bottle were placed ethyl 1-(2-methoxy-6-(naphthalen-2-yl)pyridin-3-yl)cyclopentanecarboxylate (150 mg, 0.4 mmol, 1 equiv.), KOH (500 mg, 8.9 mmol, 20 equiv.), THF (5 mL), H$_2$O (5 mL), EtOH (5 mL). The resulting solution was stirred for 2 d at 100° C. The pH value of the solution was adjust to 6 with HCl (con.). The resulting solution was extracted with EtOAc and the organic layers combined and concentrated under vacuum to yield 1-(2-methoxy-6-(naphthalen-2-yl)pyridin-3-yl)cyclopentanecarboxylic acid as yellow solid.

Mass spectrum (ESI, m/z): Calculated for C$_{22}$H$_{21}$NO$_3$, 348.2 [M+H]$^+$, found 348.1.

Step 3: Ethyl 1-(2-methoxy-6-(naphthalen-2-yl)pyridin-3-yl)cyclopentanecarboxylate Into a 100-mL round bottle were placed 1-(2-methoxy-6-(naphthalen-2-yl)pyridin-3-yl)cyclopentanecarboxylic acid (190 mg, 0.54 mmol, 1 equiv.), NH$_4$Cl (60 mg, 1.1 mmol, 2 equiv.), HATU (420 mg, 1.1 mmol, 2 equiv.), DIEA (150 mg, 1.1 mmol, 2 equiv.), DMF (5 mL), DCM (5 mL). The resulting solution was diluted with H$_2$O. The resulting solution was extracted with DCM and the organic layers combined and concentrated under vacuum. The residue was purified by TLC with PE:EA=1/1 to yield ethyl 1-(2-methoxy-6-(naphthalen-2-yl)pyridin-3-yl)cyclopentanecarboxylate as yellow oil.

Mass spectrum (ESI, m/z): Calculated for C$_{22}$H$_{22}$N$_2$O$_2$, 347.2 [M+H]$^+$, found 347.1.

Step 4: 1-(6-(naphthalen-2-yl)-2-oxo-2,3-dihydropyridin-3-yl)cyclopentanecarboxamide The title compound was prepared according to the procedure described in Example 1 step 5 by demethylation with TMSCl/NaI to yield the product as a yellow solid.

$^1$H NMR (300 MHz, DMSO-d$_6$, ppm) δ: 8.37 (s, 1H), 7.96-8.02 (m, 3H), 7.84-7.86 (m, 1H), 7.58-7.60 (m, 2H), 7.46-7.48 (m, 1H), 6.89-6.96 (m, 1H), 6.63-6.71 (m, 2H) 2.33-2.35 (m, 2H), 1.85-1.88 (m, 2H), 1.57-1.65 (m, 4H).

Mass spectrum (ESI, m/z): Calculated for C$_{21}$H$_{20}$N$_2$O$_2$, 355.2 [M+Na]$^+$, found 355.1.

Example 222

Compound #232

2,3-dimethyl-2-(6-(naphthalen-2-yl)-2-oxo-1,2-dihydropyridin-3-yl)butanamide

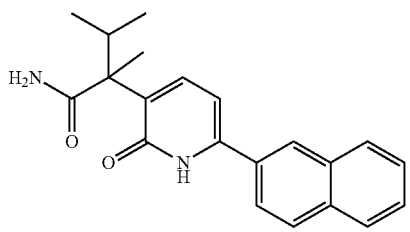 [SMILES: CC(C)C(C)(C(N)=O)c1ccc(-c2ccc3ccccc3c2)[nH]c1=O]

Step 1: Ethyl 1-(2-methoxy-6-(naphthalen-2-yl)pyridin-3-yl)cyclopentanecarboxylate Into a 100-mL round bottle purged and maintained with nitrogen, were placed ethyl 2-(2-methoxy-6-(naphthalen-2-yl)pyridin-3-yl)acetate (300 mg, 0.825 mmol, 1 equiv.), DMF (5 mL), t-BuOK (1.6 mL, 1.6 mmol, 2 equiv.), iodomethane (340 mg, 2.4 mmol, 3 equiv.). The resulting solution was stirred for 16 h at 25° C. The resulting solution was diluted with H$_2$O. The resulting solution was extracted with EtOAc and the organic layers combined and concentrated under vacuum. The residue was purified by silica gel column with PE:EA=90/10 to yield ethyl 1-(2-methoxy-6-(naphthalen-2-yl) pyridin-3-yl)cyclopentanecarboxylate as yellow oil.

Mass spectrum (ESI, m/z): Calculated for C$_{24}$H$_{27}$NO$_3$, 378.2 (M+H), found 378.2.

Step 2: 2,3-dimethyl-2-(6-(naphthalen-2-yl)-2-oxo-1,2-dihydropyridin-3-yl)butanamide The title compound was prepared according to the procedure described in Example 221 by hydrolysis, aminolysis followed by demethylation with TMSCl/NaI to yield the product as a white solid.

$^1$H NMR (300 MHz, Methanol-d$_4$, ppm) δ: 8.31 (s, 1 H), 7.91-8.02 (m, 3H), 7.78 (d, J=7.5 Hz, 1H), 7.70 (d, J=7.2 Hz, 1H), 7.55-7.59 (m, 2H), 6.79 (d, J=7.5 Hz, 1H), 3.08-3.17 (m, 1H), 1.59 (s, 3H), 1.06 (d, J=6.6 Hz, 3H), 0.86 (d, J=6.6 Hz, 3H). Mass spectrum (ESI, m/z): Calculated for C$_{21}$H$_{22}$N$_2$O$_2$, 357.2 [M+Na]$^+$, found 357.1.

Example 223

Compound #175

N-(4,5-dichlorothiophen-2-ylsulfonyl)-2-(6-(8-fluoronaphthalen-2-yl)-2-oxo-1,2-dihydropyridin-3-yl)-3-methylbutanamide

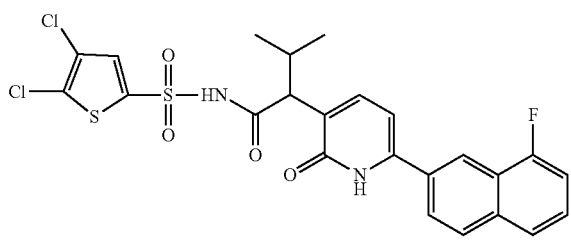 [SMILES: CC(C)C(C(=O)NS(=O)(=O)c1cc(Cl)c(Cl)s1)c1ccc(-c2ccc3cccc(F)c3c2)[nH]c1=O]

Step 1: 2-(6-(8-fluoronaphthalen-2-yl)-2-methoxypyridin-3-yl)-3-methylbutanoic acid Into a 50-mL round-bottom flask, were placed ethyl 2-(6-(8-fluoronaphthalen-2-yl)-2-methoxypyridin-3-yl)-3-methylbutanoate (40 mg, 0.105 mmol, 1.0 equiv.), KOH (73 mg, 1.304 mmol, 10 equiv.), THF (1 mL), EtOH (1 mL), H$_2$O (1 mL). The resulting solution was stirred for 1 h at 100° C. in an oil bath. The reaction progress was monitored by LCMS. The resulting mixture was concentrated under vacuum. The reaction was dilute by the addition of water. The resulting solution was extracted with diethyl ether (3×20 mL) and the water layers combined and adjust pH=3 by HCl (2N). Then the resulting solution was extracted with ethyl acetate (3×20 mL) and the organic layers combined. The mixture was dried over anhydrous sodium sulfate. The solids were filtered out. The resulting mixture was concentrated under vacuum to yield 2-(6-(8-fluoronaphthalen-2-yl)-2-methoxypyridin-3-yl)-3-methylbutanoic acid as a yellow oil.

Mass spectrum (ESI, m/z): Calculated For C$_{21}$H$_{20}$FNO$_3$, 354.1 (M+H), found 354.2.

Step 2: N-(4,5-dichlorothiophen-2-ylsulfonyl)-2-(6-(8-fluoronaphthalen-2-yl)-2-oxo-1,2-dihydropyridin-3-yl)-3-methylbutanamide The title compound was prepared according to the procedure described in Example 218 by coulping with m 4,5-dichlorothiophene-2-sulfonamide followed by demethylation with TMSCl/NaI to yield the product as off-white solid.

$^1$H NMR (300 MHz, DMSO-d$_6$) δ: 8.38-8.49 (m, 1H), 8.10-8.17 (m, 1H), 7.81-7.98 (m, 1H), 7.70-7.85 (m, 2H), 7.50-7.65 (m, 2H), 7.32-7.49 (m, 1H), 7.79-7.95 (m, 1H), 3.61-3.75 (m, 1H), 2.15-2.30 (m, 1H), 0.63-0.94 (m, 6H). $^{19}$F NMR (300 MHz, DMSO-d$_6$) δ: −122.19. Mass spectrum (ESI, m/z): Calculated For C$_{24}$H$_{19}$C$_{12}$FN$_2$O$_4$S$_2$, 553.0 (M+H), found 553.0.

Example 224

Compound #239

2-(6-(8-fluoronaphthalen-2-yl)-2-oxo-1,2-dihydropyridin-3-yl)-N-isopropyl-3-methylbutanamide

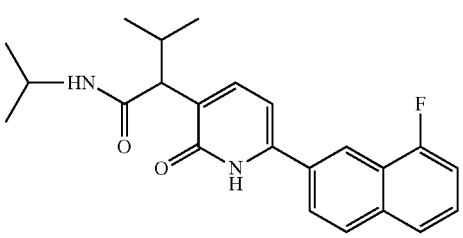 [SMILES: CC(C)NC(=O)C(c1ccc(-c2ccc3cccc(F)c3c2)[nH]c1=O)C(C)C]

The title compound was prepared according to the procedure described in Example 221 by coulping with i-Pr—NH$_2$ followed by demethylation with TMSCl/NaI to yield the product as a yellow solid.

$^1$H NMR (300 MHz, DMSO-d$_6$) δ: 8.48 (s, 1H), 8.10 (d, J=8.1 Hz, 1H), 7.97-7.99 (m, 2H), 7.83 (d, J=8.4 Hz, 1H), 7.75 (d, J=7.5 Hz, 1H), 7.53-7.60 (m, 1H), 7.37-7.43 (m, 1H), 6.86-6.91 (m, 1H), 3.76-3.88 (m, 1H), 3.51 (d, J=10.2 Hz, 1H), 2.08-2.19 (m, 1H), 1.02-1.28 (m, 9H), 0.99 (d, J=5.4 Hz, 3H). $^{19}$F NMR (300 MHz, DMSO-d$_6$) δ: −74.54,

−122.27. Mass spectrum (ESI, m/z): Calculated For $C_{23.216}H_{25.108}F_{1.324}N_2O_{2.216}$, 381.2 (M−0.108CF$_3$COOH+H), found 381.1.

Example 225

Compound #176

2-(6-(8-fluoronaphthalen-2-yl)-2-oxo-1,2-dihydro-pyridin-3-yl)-3-methyl-N-(thiazol-2-yl)butanamide

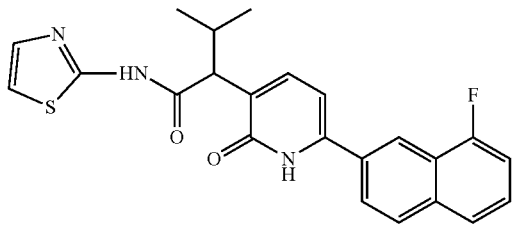 [SMILES: CC(C)C(C(=O)Nc1nccs1)c1ccc(-c2ccc3cccc(F)c3c2)[nH]c1=O]

The title compound was prepared according to the procedure described in Example 221 by coulping with 2-aminothiazole followed by demethylation with TMSCl/NaI to yield the product as a yellow solid.

$^1$H NMR (300 MHz,DMSO-d$_6$) δ: 12.35 (s, 1H), 8.48 (s, 1H), 8.11 (d, J=7.8Hz, 1H), 7.95-7.98 (m, 1H), 7.75-7.84 (m, 2H), 7.52-7.61 (m, 1H), 7.41-7.47 (m, 2H), 7.21-7.27 (m, 1H), 6.84-6.93 (m, 1H), 3.97 (d, J=9.9Hz, 1H), 2.33-2.43 (m, 1H), 0.90-1.03 (m, 3H), 0.79-0.88 (m, 3H). $^{19}$F NMR (300 MHz, DMSO-d$_6$) δ: −122.21, −74.36. Mass spectrum (ESI, m/z): Calculated For $C_{24.17}H_{20.585}F_{2.755}N_3O_{3.17}S$, 422.1 (M−0.585CF$_3$COOH+H), found 422.1.

Example 226

Compound #256

N-(4,5-dichlorothiophen-2-ylsulfonyl)-3-(6-(8-fluoronaphthalen-2-yl)-2-oxo-1,2-dihydropyridin-3-yl)-4-methylpentanamide

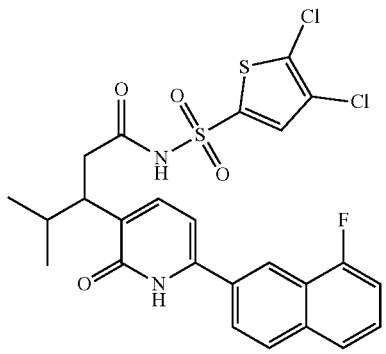 [SMILES: CC(C)C(CC(=O)NS(=O)(=O)c1cc(Cl)c(Cl)s1)c1ccc(-c2ccc3cccc(F)c3c2)[nH]c1=O]

The title compound was prepared according to the procedure described in Example 221 by coulping with 4,5-dichlorothiophene-2-sulfonamide followed by demethylation with TMSCl/NaI to yield the product as a white solid.

$^1$H NMR (400 MHz,CD$_3$OD) δ: 8.39 (s, 1H), 8.06 (d, J=8.0 Hz, 1H), 7.81-7.86 (m, 1H), 7.77 (d, J=7.6 Hz, 1H), 7.52-7.58 (m, 1H), 7.42-7.44 (m, 1H), 7.27-7.32 (m, 2H), 6.62-6.64 (m, 1H), 3.24-3.32 (m, 1H), 2.59-2.65 (m, 2H), 2.06-2.11 (m, 1H), 0.90-0.95 (m, 6H). $^{19}$F NMR (400 MHz, CD$_3$OD) δ: −76.99, −124.37. Mass spectrum (ESI, m/z): Calculated For $C_{26.68}H_{21.84}C_{12}F_{3.52}N_2O_{5.68}S_2$, 567.0 (M−0.84CF$_3$COOH+H), found 567.0.

Example 227

Compound #251

3-(6-(8-fluoronaphthalen-2-yl)-2-oxo-1,2-dihydro-pyridin-3-yl)-4-methylpentanamide

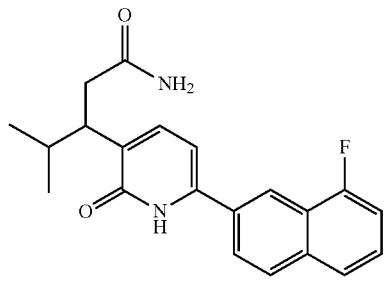 [SMILES: CC(C)C(CC(N)=O)c1ccc(-c2ccc3cccc(F)c3c2)[nH]c1=O]

The title compound was prepared according to the procedure described in Example 221 by coulping with ammonia followed by demethylation with TMSCl/NaI to yield the product as a white solid.

$^1$H NMR (300 MHz, CD$_3$OD) δ: 8.42 (s, 1H), 8.08 (d, J=8.4 Hz, 1H), 7.85-7.88 (m, 1H), 7.79 (d, J=8.4 Hz, 1H), 7.52-7.60 (m, 2H), 7.28-7.34 (m, 1H), 6.78 (d, J=7.2 Hz, 1H), 3.11-3.21 (m, 1H), 2.66-2.76 (m, 2H), 2.13-2.20 (m, 1H), 1.03 (d, J=6.6 Hz, 3H), 0.94 (d, J=6.6 Hz, 3H). $^{19}$F NMR (300 MHz, CD$_3$OD) δ: −77.49, −124.57. Mass spectrum (ESI, m/z): Calculated for $C_{23.66}H_{22.33}F_{4.99}N_2O_{4.66}$, 353.2 (M−1.33CF$_3$COOH+H), found 353.2.

Example 228

Compound #228

2-(6-(8-fluoronaphthalen-2-yl)-2-oxo-1,2-dihydro-pyridin-3-yl)-N-methoxy-3-methylbutanamide

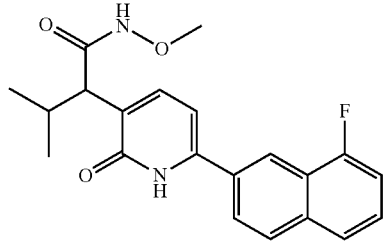 [SMILES: CONC(=O)C(c1ccc(-c2ccc3cccc(F)c3c2)[nH]c1=O)C(C)C]

The title compound was prepared according to the procedure described in Example 221 by coulping with hydroxylamine HCl followed by demethylation with TMSCl/NaI to yield the product as a white solid.

$^1$H NMR (400 Hz, CD$_3$OD) δ: 8.43 (s, 1H), 8.08 (d, J=8.8 Hz,1H), 7.88-7.93 (m, 2H), 7.78 (d, J=8.4 Hz,1H), 7.53-7.58 (m, 1H), 7.28-7.33 (m, 1H), 6.84 (d, J=7.2 Hz,1H), 3.69 (s,

3H), 3.43-3.69 (m, 1H), 2.31-2.39 (m, 1H), 1.10 (d, J=6.8 Hz,3H), 0.89 (d, J=6.8 Hz,3H). $^{19}$F NMR (400 Hz, CD$_3$OD) δ: −124.41.

Mass spectrum (ESI, m/z): Calculated for C$_{21}$H$_{21}$FN$_2$O$_3$, 369.2 (M+H), found 369.1.

Example 229

Compound #257

3-(6-(8-fluoronaphthalen-2-yl)-2-oxo-1,2-dihydro-pyridin-3-yl)-N-methoxy-4-methylpentanamide

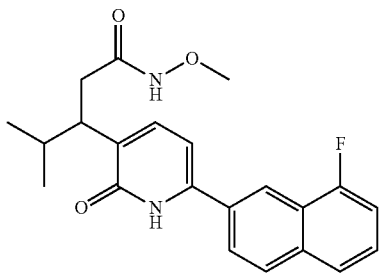 [SMILES: CONC(=O)CC(c1ccc(-c2ccc3cccc(F)c3c2)[nH]c1=O)C(C)C]

The title compound was prepared according to the procedure described in Example 221 by coulping with hydroxylamine HCl followed by demethylation with TMSCl/NaI to yield the product as a yellow semi solid.

$^1$H NMR (400 MHz,CD$_3$OD) δ: 8.40 (s, 1H), 8.07 (d, J=8.4 Hz, 1H), 7.84-7.87 (m, 1H), 7.78 (d, J=8.4 Hz, 1H), 7.53-7.58 (m, 1H), 7.31-7.33 (m, 1H), 7.28-7.30 (m, 1H), 6.76 (d, J=7.2 Hz, 1H), 3.53 (s, 3H), 3.06-3.10 (m, 1H), 2.56 (d, J=7.6 Hz, 2H), 2.17-2.25 (m, 1H), 1.03 (d, J=6.8 Hz, 3H), 0.97 (d, J=6.8 Hz, 3H). $^{19}$F NMR (400 MHz, CD$_3$OD) δ: −77.47, −124.56. Mass spectrum (ESI, m/z): Calculated For C$_{23.58}$H$_{23.79}$F$_{3.37}$N$_2$O$_{4.58}$, 383.2 (M−0.79CF$_3$COOH+H), found 383.1.

Example 230

Compound #234

2-(6-(8-fluoronaphthalen-2-yl)-2-oxo-1,2-dihydro-pyridin-3-yl)-N-(2-hydroxyethyl)-3-methylbutanamide

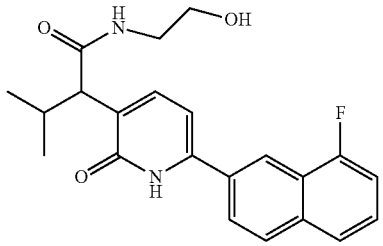 [SMILES: CC(C)C(C(=O)NCCO)c1ccc(-c2ccc3cccc(F)c3c2)[nH]c1=O]

The title compound was prepared according to the procedure described in Example 221 by coulping with 2-hydroxy-ethylamine followed by demethylation with TMSCl/NaI to yield the product as an off white solid.

Mass spectrum (ESI, m/z): Calculated For C$_{24}$H$_{24}$F$_4$N$_2$O$_5$, 383.2 (M−0.41CF$_3$COOH+H), found 383.1.

Example 231

Compound #258

3-(6-(8-fluoronaphthalen-2-yl)-2-oxo-1,2-dihydro-pyridin-3-yl)-N-(2-hydroxyethyl)-4-methyl pentanamide

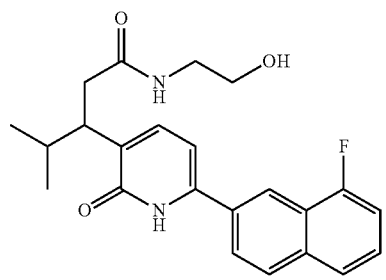 [SMILES: CC(C)C(CC(=O)NCCO)c1ccc(-c2ccc3cccc(F)c3c2)[nH]c1=O]

The title compound was prepared according to the procedure described in Example 221 by coulping with 2-hydroxy-ethylamine followed by demethylation with TMSCl/NaI to yield the product as an off white solid.

$^1$H NMR (400 MHz,CD$_3$OD) δ: 8.41 (s, 1H), 8.06-8.08 (m, 1H), 7.85-7.87 (m, 1H), 7.77 (d, J=8.0 Hz, 1H), 7.51-7.58 (m, 2H), 7.28-7.32 (m, 1H), 6.77 (d, J=7.2 Hz, 1H), 3.44-3.49 (m, 2H), 3.12-3.22 (m, 3H), 2.67-2.69 (m, 2H), 2.13-2.19 (m, 1H), 1.03 (d, J=6.8 Hz, 3H), 0.91 (d, J=6.8 Hz, 3H). $^{19}$F NMR (400 MHz, CD$_3$OD) δ: −77.61, −124.53. Mass spectrum (ESI, m/z): Calculated For C$_{24.96}$H$_{25.98}$F$_{3.94}$N$_2$O$_{4.96}$, 397.2 (M−0.98CF$_3$COOH+H), found 397.1.

Example 232

Compound #267

1-(1-(6-(8-fluoronaphthalen-2-yl)-2-oxo-1,2-dihydropyridin-3-yl)-2-methyl propyl)urea

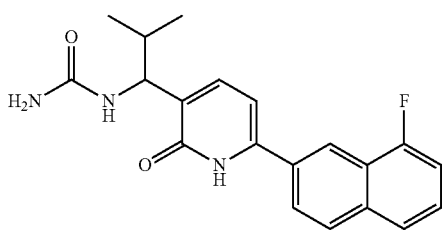 [SMILES: CC(C)C(NC(N)=O)c1ccc(-c2ccc3cccc(F)c3c2)[nH]c1=O]

Step 1: 2-(1-(6-(8-fluoronaphthalen-2-yl)-2-methoxypyridin-3-yl)-2-methylpropyl) isoindoline-1,3-dione Into a 50-mL round-bottom flask, were placed 1-(6-(8-fluoronaphthalen-2-yl)-2-methoxypyridin-3-yl)-2-methylpropan-1-ol (325 mg, 0.999 mmol, 1.0 equiv.), isoindoline-1,3-dione (441 mg, 2.997 mmol, 3.0 equiv.), DIAD (606 mg, 3 mmol, 3.0 equiv.), PPh$_3$ (786 mg, 3 mmol, 3.0 equiv.), THF (20 mL). The resulting solution was stirred 1.0 h at room temperature. The reaction progress was monitored by LCMS. The resulting mixture was concentrated under vacuum. The residue was applied onto a silica gel column with ethyl acetate/petroleum ether (40/60) to yield 2-(1-(6-(8-fluoronaphthalen-2-yl)-2-methoxypyridin-3-yl)-2-methylpropyl)isoindoline-1,3-dione as a white solid.

Mass spectrum (ESI, m/z): Calculated For C$_{28}$H$_{23}$FN$_2$O$_3$, 455.2 (M+H), found 455.2.

Step 2: 1-(6-(8-fluoronaphthalen-2-yl)-2-methoxypyridin-3-yl)-2-methylpropan-1-amine Into a 50-mL round-bottom flask, were placed 2-(1-(6-(8-fluoronaphthalen-2-yl)-2-methoxypyridin-3-yl)-2-methylpropyl)isoindoline-1,3-dione (190 mg, 0.418 mmol, 1.0 equiv.), MeOH (20 mL), NH$_2$NH$_2$ (0.5 mL). The resulting solution was stirred 3.0 h at room temperature. The reaction progress was monitored by LCMS. The resulting solution was concentrated under vacuum. The residue was applied TLC with DCM:MeOH=20:1 to yield 1-(6-(8-fluoronaphthalen-2-yl)-2-methoxypyridin-3-yl)-2-methylpropan-1-amine as a brown oil.

Mass spectrum (ESI, m/z): Calculated For C$_{20}$H$_{21}$FN$_2$O, 325.2 (M+H), found 325.0.

Step 3: 1-(1-(6-(8-fluoronaphthalen-2-yl)-2-methoxypyridin-3-yl)-2-methylpropyl)urea Into a 50-mL round-bottom flask, were placed 1-(6-(8-fluoronaphthalen-2-yl)-2-methoxypyridin-3-yl)-2-methylpropan-1-amine (20 mg, 0.062 mmol, 1.0 equiv.), THF (3 mL), AcOH (0.1 mL), KCNO (10 mg, 0.123 mmol, 2.0 equiv.), H$_2$O (1 mL). The resulting solution was stirred overnight at room temperature. The reaction progress was monitored by LCMS. The resulting solution was concentrated under vacuum. The residue was applied TLC with PE:EA=3:1 to yield 1-(1-(6-(8-fluoronaphthalen-2-yl)-2-methoxypyridin-3-yl)-2-methylpropyl)urea as a brown oil.

Mass spectrum (ESI, m/z): Calculated For C$_{21}$H$_{22}$FN$_3$O$_2$, 368.2 (M+H), found 368.1.

Step 4: 1-(1-(6-(8-fluoronaphthalen-2-yl)-2-oxo-1,2-dihydropyridin-3-yl)-2-methyl propyl)urea The title compound was prepared according to the procedure described in Example 1 step 5 by demethylation with TMSCl/NaI to yield the product as a white solid.

$^1$H NMR (400 MHz, CD$_3$OD) δ: 8.41 (s, 1H), 8.07 (d, J=8.0 Hz, 1H), 7.85-7.87 (m, 1H), 7.78 (d, J=8.4 Hz, 1H), 7.52-7.58 (m, 2H), 7.28-7.30 (m, 1H), 6.77 (d, J=7.2 Hz, 1H), 4.54-4.55 (m, 1H), 2.29-2.37 (m, 1H), 1.00 (d, J=6.8 Hz, 3H), 0.94 (d, J=6.8 Hz, 3H). $^{19}$F NMR (400 MHz, CD$_3$OD) δ: −124.49.

Mass spectrum (ESI, m/z): Calculated For C$_{20}$H$_{20}$FN$_3$O$_2$, 354.2 (M+H), found 354.0.

Example 233

Compound #253

2-((6-(8-fluoronaphthalen-2-yl)-2-oxo-1,2-dihydropyridin-3-yl)methyl)-3-methylbutanamide

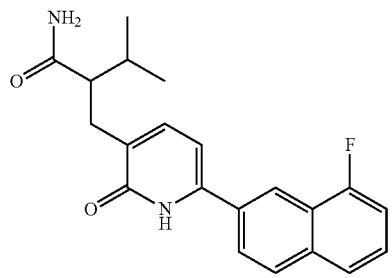 [SMILES: CC(C)C(Cc1ccc(-c2ccc3cccc(F)c3c2)[nH]c1=O)C(N)=O]

Step 1: ethyl 2-((6-(8-fluoronaphthalen-2-yl)-2-methoxypyridin-3-yl)methyl)-3-methyl butanoate Into a 25-ml round-bottom flask purged and maintained with an inert atmosphere of nitrogen were added ethyl 2-((6-(8-fluoronaphthalen-2-yl)-2-methoxypyridin-3-yl)methyl)-3-methylbutanoate (100 mg, 0.283 mmol, 1.00 equiv.) in dry THF (8 mL), then LDA (0.3 ml, 0.6 mmol, 2.0 equiv.) via syringe at −78° C. The resulting solution was stirred at −78° C. for 1.5 hour, and then Isopropyl iodide (0.06 ml, 0.596 mmol, 2.0 equiv.) was added at −78° C. and the mixture was stirred at this temperature for 1.5 h. The reaction mixture was stirred overnight allowing to warm to room temperature. The reaction was monitored by LCMS. The resulting solution was extracted with ethyl acetate. The organic layers were combined and concentrated under vacuum. The residue was applied on a silica gel column and eluted with EA/PE (1:10) to yield ethyl 2-((6-(8-fluoronaphthalen-2-yl)-2-methoxypyridin-3-yl)methyl)-3-methylbutanoate as a yellow oil.

Mass spectrum (ESI, m/z): Calculated for C$_{24}$H$_{26}$FNO$_3$, 396.2 (M+H), found 396.1.

Step 2: 2-((6-(8-fluoronaphthalen-2-yl)-2-oxo-1,2-dihydropyridin-3-yl)methyl)-3-methylbutanamide The title compound was prepared according to the procedure described in Example 219 by hydrolysis, aminolysis followed by demethylation with TMSCl/NaI to yield the product as a white solid.

$^1$H NMR (400 MHz, CD$_3$OD) δ: 8.38 (s, 1H), 8.06 (d, J=8.4 Hz, 1H), 7.84 (d, J=10.0 Hz, 1H), 7.77 (d, J=8.0 Hz, 1H), 7.52-7.59 (m, 2H), 7.28-7.32 (m, 1H), 6.73 (d, J=7.2 Hz, 1H), 2.95-3.03 (m, 1H), 2.48-2.63 (m, 2H), 1.90-1.94 (m, 1H), 1.13 (d, J=6.8 Hz, 3H), 1.07 (d, J=6.8 Hz, 3H). $^{19}$F NMR (400 MHz, CD$_3$OD) δ: −124.62. Mass spectrum (ESI, m/z): Calculated for C$_{21}$H$_{21}$FN$_2$O$_2$, 353.2 (M+H), found 353.0.

Example 234

Compound #227

N-(2-(dimethylamino)ethyl)-2-(6-(8-fluoronaphthalen-2-yl)-2-oxo-1,2-dihydropyridin-3-yl)-3-methylbutanamide

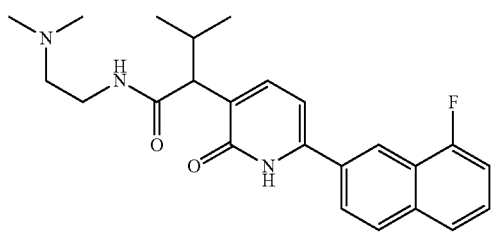 [SMILES: CC(C)C(C(=O)NCCN(C)C)c1ccc(-c2ccc3cccc(F)c3c2)[nH]c1=O]

The title compound was prepared according to the procedure described in Example 221 by coulping with 2-dimethylamino-ethylamine followed by demethylation with TMSCl/NaI to yield the product as a yellow solid.

$^1$H NMR (300 MHz, CD$_3$OD) δ: 8.07 (s, 1H), 8.04 (d, J=7.2 Hz, 1H), 7.74-7.84 (m, 3H), 7.51-7.57 (m, 1H), 7.24-7.28 (m, 1H), 6.86 (d, J=7.5 Hz, 1H), 3.71-3.80 (m, 1H), 3.33-3.45 (m, 2H), 3.19-3.29 (m, 2H), 3.10 (d, J=8.4 Hz, 6H), 2.36-2.44 (m, 1H), 1.06 (d, J=6.6 Hz, 3H), 0.93 (d, J=6.6 Hz, 3H). $^{19}$F NMR (300 MHz, CD$_3$OD) δ: −77.25, −124.53. Mass spectrum (ESI, m/z): Calculated for C$_{28.68}$H$_{37.36}$FN$_3$O$_{6.68}$, 410.2 [M−2.43CF$_3$COOH+H], found 410.3.

Example 235

Compound #238

2-(6-(8-fluoronaphthalen-2-yl)-2-oxo-1,2-dihydropyridin-3-yl)-N-(2-(2-(2-methoxyethoxy)ethoxy)ethyl)-3-methylbutanamide

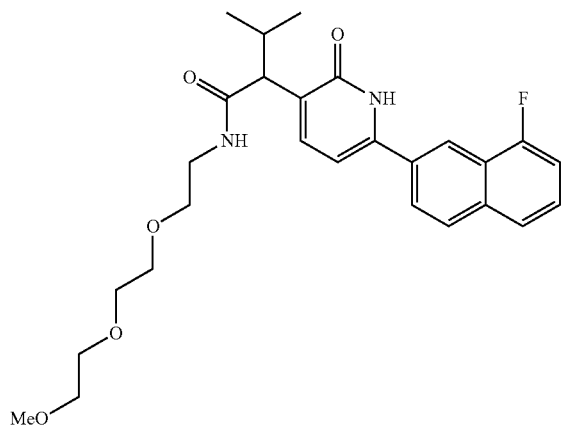 [SMILES: COCCOCCOCCNC(=O)C(c1ccc(-c2ccc3cccc(F)c3c2)[nH]c1=O)C(C)C]

The title compound was prepared according to the procedure described in Example 221 by coulping with 2-(2-(2-methoxyethoxy)ethoxy)ethan-1-amine followed by demethylation with TMSCl/NaI to yield the product as a light yellow oil.

$^1$H NMR (300 MHz, CD$_3$OD) δ: 8.38 (s, 1H), 8.02 (d, J=7.8 Hz, 1H), 7.71-7.83 (m, 3H), 7.47-7.55 (m, 1H), 7.23-7.29 (m, 1H), 6.78 (d, J=7.2 Hz, 1H), 3.45-3.57 (m, 11H), 3.31-3.34 (m, 1H), 3.27-3.28 (m, 4H), 2.33-2.37 (m, 1H), 1.04 (d, J=6.6 Hz, 3H), 0.83 (d, J=6.6 Hz, 3H). $^{19}$F NMR (300 MHz, CD$_3$OD) δ: −124.43. Mass spectrum (ESI, m/z): Calculated for C$_{27}$H$_{33}$FN$_2$O$_5$, 485.2 [M+H]$^+$, found 485.4.

Example 236

Compound #174

2-(6-(8-fluoronaphthalen-2-yl)-2-oxo-1,2-dihydropyridin-3-yl)-3-methyl-N-(tetrahydro-2H-pyran-4-yl)butanamide

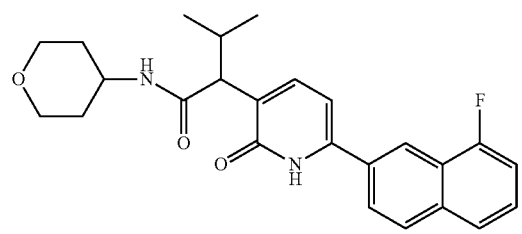 [SMILES: CC(C)C(C(=O)NC1CCOCC1)c1ccc(-c2ccc3cccc(F)c3c2)[nH]c1=O]

The title compound was prepared according to the procedure described in Example 221 by coulping with tetrahydro-2H-pyran-4-amine followed by demethylation with TMSCl/NaI to yield the product as a yellow solid.

$^1$H NMR (300 MHz, CD$_3$OD) δ: 8.38 (s, 1H), 8.03 (d, J=7.2 Hz, 1H), 7.79-7.83 (m, 2H), 7.73 (d, J=8.1 Hz, 1H), 7.47-7.52 (m, 1H), 7.23-7.28 (m, 1H), 6.79 (d, J=7.5 Hz, 1H), 3.83-3.91 (m, 3H), 3.38-3.49 (m, 3H), 2.22-2.31 (m, 1H), 1.81-1.82 (m, 1H), 1.68-1.70 (m, 1H), 1.44-1.52 (m, 2H), 1.04 (d, J=6.6 Hz, 3H), 0.81 (d, J=6.6 Hz, 3H). $^{19}$F NMR (300 MHz, CD$_3$OD) δ: −77.41, −124.43. Mass spectrum (ESI, m/z): Calculated for C$_{25.2}$H$_{27.4}$FN$_2$O$_{3.2}$, 423.2 [M−0.1CF3COOH+H], found 423.2.

Example 237

Compound #177

N-(azetidin-3-yl)-2-(6-(8-fluoronaphthalen-2-yl)-2-oxo-1,2-dihydropyridin-3-yl)-3-methylbutanamide

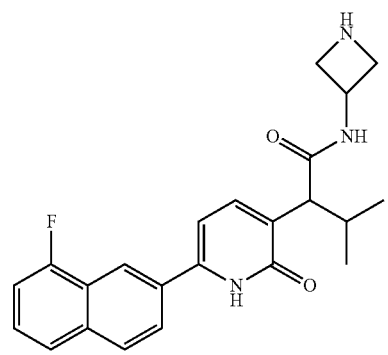 [SMILES: CC(C)C(C(=O)NC1CNC1)c1ccc(-c2ccc3cccc(F)c3c2)[nH]c1=O]

Step 1: N-(azetidin-3-yl)-2-(6-(8-fluoronaphthalen-2-yl)-2-methoxypyridin-3-yl)-3-methylbutanamide Into a 50-mL round-bottom flask, were placed tert-butyl 3-(2-(6-(8-fluoronaphthalen-2-yl)-2-methoxypyridin-3-yl)-3-methylbutanamido)azetidine-1-carboxylate (100 mg, 0.197 mmol, 1.0 equiv.), TFA (1 mL), DCM (4 mL). The resulting solution was stirred overnight at room temperature. The reaction progress was monitored by LCMS. The resulting mixture was concentrated under vacuum. The residue was applied TLC with MeOH:DCM=1:10 to yield N-(azetidin-3-yl)-2-(6-(8-fluoronaphthalen-2-yl)-2-methoxypyridin-3-yl)-3-methylbutanamide as a brown oil.

Mass spectrum (ESI, m/z): Calculated For $C_{24}H_{26}FN_3O_2$, 408.2 (M+H), found 408.1.

Step 2: N-(azetidin-3-yl)-2-(6-(8-fluoronaphthalen-2-yl)-2-oxo-1,2-dihydropyridin-3-yl)-3-methylbutanamide The title compound was prepared according to the procedure described in Example 1 step 5 by demethylation with TMSCl/NaI to yield the product as an orange solid.

$^1$H NMR (300 MHz, CD$_3$OD) δ: 8.36 (s, 1H), 8.02-8.06 (m, 1H), 7.72-7.83 (m, 3H), 7.49-7.56 (m, 1H), 7.23-7.30 (m, 1H), 6.80 (d, J=7.5 Hz, 1H), 4.55-4.63 (m, 1H), 4.23-4.29 (m, 2H), 4.06-4.20 (m, 2H), 3.53 (d, J=10.8 Hz, 1H), 2.33-2.41 (m, 1H), 1.05 (d, J=6.3 Hz, 3H), 0.85 (d, J=6.9 Hz, 3H). $^{19}$F NMR (300 MHz, CD$_3$OD) δ: −77.22, −124.52. Mass spectrum (ESI, m/z): Calculated For $C_{28.3}H_{26.65}F_{8.95}N_3O_{7.3}$, 394.2 (M−2.65CF$_3$COOH+H), found 394.2.

Example 238

Compound #260

3-(6-(8-fluoronaphthalen-2-yl)-2-oxo-1,2-dihydropyridin-3-yl)-N-isopropyl-4-methylpentanamid

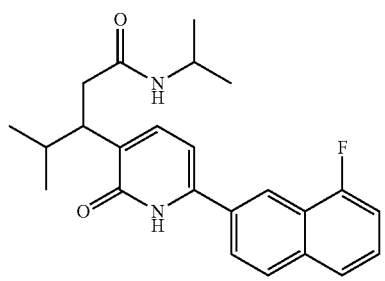 [SMILES: CC(C)NC(=O)CC(c1ccc(-c2ccc3cccc(F)c3c2)[nH]c1=O)C(C)C]

The title compound was prepared according to the procedure described in Example 221 by coulping with i-Pr—NH$_2$ followed by demethylation with TMSCl/NaI to yield the product as white solid.

$^1$H NMR (300 MHz, CD$_3$OD) δ: 8.38 (s, 1H), 8.04-8.07 (m, 1H), 7.75-7.85 (m, 2H), 7.45-7.58 (m, 2H), 7.26-7.32 (m, 1H), 6.73 (d, J=7.2 Hz, 1H), 3.79-3.90 (m, 1H), 3.02-3.10 (m, 1H), 2.57-2.63 (m, 2H), 2.11-2.23 (m, 1H), 1.00-1.06 (m, 6H), 0.88-0.94 (m, 6H). $^{19}$F NMR (400 MHz, CD$_3$OD) δ: −125.00. Mass spectrum (EI, m/z): Calculated for $C_{23}H_{25}NO_4$, 395.2 (M+H), found 395.2.

Example 239

Compound #259

N-(2-(dimethylamino)ethyl)-3-(6-(8-fluoronaphthalen-2-yl)-2-oxo-1,2-dihydropyridin-3-yl)-4-methylpentanamide

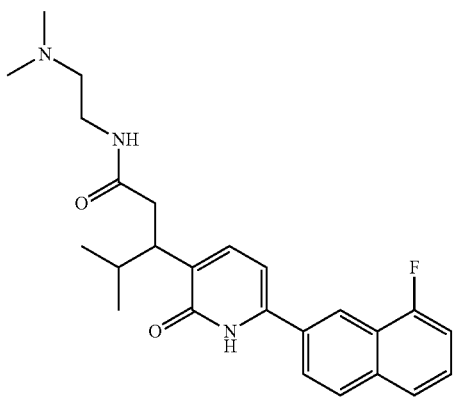 [SMILES: CC(C)C(CC(=O)NCCN(C)C)c1ccc(-c2ccc3cccc(F)c3c2)[nH]c1=O]

The title compound was prepared according to the procedure described in Example 221 by coulping with 2-dimethylamino-ethylamine followed by demethylation with TMSCl/NaI to yield the product as light yellow solid.

$^1$H NMR (400 MHz, CD$_3$OD) δ: 8.41 (s, 1H), 8.07 (d, J=8.8 Hz, 1H), 7.86 (d, J=8.8 Hz, 1H), 7.78 (d, J=8.0 Hz, 1H), 7.53-7.59 (m, 1H), 7.49 (d, J=7.2 Hz, 1H), 7.28-7.33 (m, 1H), 6.77 (d, J=7.2 Hz, 1H), 3.15-3.34 (m, 2H), 3.07-3.13 (m, 1H), 2.66-2.68 (m, 2H), 2.34-2.36 (m, 2H), 2.23 (s, 6H), 2.15-2.23 (m, 1H), 1.04 (d, J=6.8 Hz, 3H), 0.91 (d, J=6.8 Hz, 3H). $^{19}$F NMR (400 MHz, CD$_3$OD) δ: −124.64. Mass spectrum (EI, m/z): Calculated for $C_{25}H_{30}FN_3O_2$, 424.2 (M+H), found 424.3.

Example 240

Compound #254

3-(6-(8-fluoronaphthalen-2-yl)-2-oxo-1,2-dihydropyridin-3-yl)-4-methyl-N-(thiazol-2-yl)pentanamide

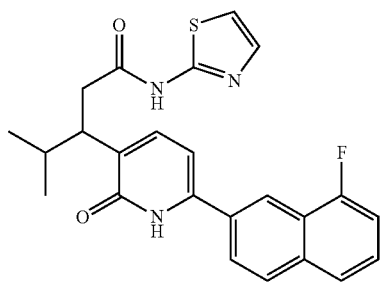 [SMILES: CC(C)C(CC(=O)Nc1nccs1)c1ccc(-c2ccc3cccc(F)c3c2)[nH]c1=O]

The title compound was prepared according to the procedure described in Example 221 by coulping with 2-aminothiazole followed by demethylation with TMSCl/NaI to yield the product as light yellow solid.

$^1$H NMR (400 MHz, CD$_3$OD) δ: 8.37 (s, 1H), 7.99-8.01 (m, 1H), 7.77-7.78 (m, 1H), 7.68-7.74 (m, 2H), 7.51-7.55

(m, 1H), 7.33 (d, J=4.4 Hz, 1H), 6.99 (d, J=3.6 Hz, 1H), 6.80 (d, J=6.4 Hz, 1H), 6.57 (d, J=9.2 Hz, 1H), 3.60-3.65 (m, 1H), 3.10-3.15 (m, 1H), 2.95-3.02 (m, 1H), 2.11-2.12 (m, 1H), 1.13 (d, J=6.8 Hz, 3H), 0.86 (d, J=6.8 Hz, 3H) $^{19}$F NMR (400 MHz, CD$_3$OD) δ: −127.95. Mass spectrum (EI, m/z): Calculated for C$_{24}$H$_{22}$FN$_3$O$_2$S, 436.1 (M+H), found 436.2.

Example 241

Compound #261

3-(6-(8-fluoronaphthalen-2-yl)-2-oxo-1,2-dihydropyridin-3-yl)-N-(1H-imidazol-2-yl)-4-methylpentanamide

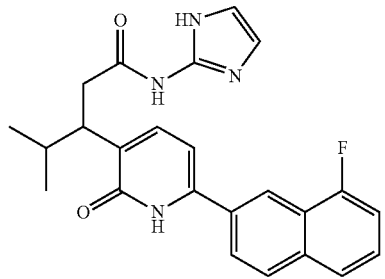 [SMILES: CC(C)C(CC(=O)Nc1ncc[nH]1)c1ccc(-c2ccc3cccc(F)c3c2)[nH]c1=O]

The title compound was prepared according to the procedure described in Example 221 by coulping with 2-aminoimidazole followed by demethylation with TMSCl/NaI to yield the product as light yellow solid.

$^1$H NMR (300 MHz, CD$_3$OD) δ: 8.38 (s, 1H), 8.04 (d, J=8.4 Hz, 1H), 7.75-7.84 (m, 2H), 7.55-7.58 (m, 2H), 7.26-7.32 (m, 1H), 7.10 (s, 2H), 6.76 (d, J=7.5 Hz, 1H), 3.01-3.33 (m, 1H), 2.99-3.01 (m, 2H), 2.13-2.22 (m, 1H), 1.06 (d, J=6.6 Hz, 3H), 0.94 (d, J=6.9 Hz, 3H). $^{19}$F NMR (300 MHz, CD$_3$OD) δ: −76.92, −124.58. Mass spectrum (EI, m/z): Calculated for C$_{28.62}$H$_{25.31}$F$_{7.93}$N$_4$O$_{6.62}$, 419.2 (M−2.31CF$_3$COOH+H), found 419.1.

Example 242

Compound #182

2-(6-(8-fluoronaphthalen-2-yl)-2-oxo-1,2-dihydropyridin-3-yl)-3-methyl-N-(1-methylazetidin-3-yl)butanamide

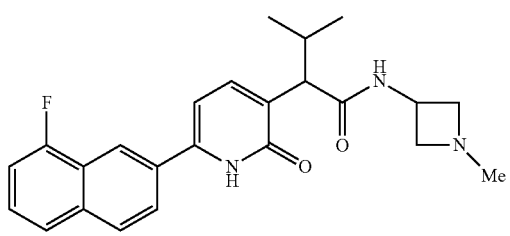 [SMILES: CC(C)C(C(=O)NC1CN(C)C1)c1ccc(-c2ccc3cccc(F)c3c2)[nH]c1=O]

Step 1: 2-(6-(8-fluoronaphthalen-2-yl)-2-methoxypyridin-3-yl)-3-methyl-N-(1-methyl azetidin-3-yl)butanamide Into a 50-mL round-bottom flask, were placed N-(azetidin-3-yl)-2-(6-(8-fluoronaphthalen-2-yl)-2-methoxypyridin-3-yl)-3-methylbutanamide (70 mg, 0.172 mmol, 1.0 equiv.), formaldehyde (6 mg, 0.200 mmol, 1.1 equiv.), MeOH (10 mL), AcOH (0.2 mL). The resulting solution was stirred 2.0 h at 80° C. Then placed NaBH(OAc)$_3$ (72 mg, 0.340 mmol, 2.0 equiv.). The resulting solution was stirred 3.0 h at 50° C. The reaction progress was monitored by LCMS. The resulting mixture was concentrated under vacuum. The residue was applied TLC with PE:EA=1:1 to yield 2-(6-(8-fluoronaphthalen-2-yl)-2-methoxypyridin-3-yl)-3-methyl-N-(1-methylazetidin-3-yl)butanamide as a brown oil.

Mass spectrum (ESI, m/z): Calculated For C$_{25}$H$_{28}$FN$_3$O$_2$, 422.2 (M+H), found 422.3.

Step 2: 2-(6-(8-fluoronaphthalen-2-yl)-2-oxo-1,2-dihydropyridin-3-yl)-3-methyl-N-(1-methylazetidin-3-yl)butanamide The title compound was prepared according to the procedure described in Example 1 step 5 by demethylation with TMSCl/NaI to yield the product as white solid.

$^1$H NMR (300 MHz, CD$_3$OD) δ: 8.39 (s, 1H), 8.03 (d, J=8.7 Hz, 1H), 7.72-7.84 (m, 3H), 7.50-7.55 (m, 1H), 7.23-7.29 (m, 1H), 6.79 (d, J=7.5 Hz, 1H), 4.32-4.82 (m, 1H), 3.62-3.70 (m, 2H), 3.47-3.59 (m, 1H), 2.93-3.04 (m, 2H), 2.28-2.35 (m, 4H), 1.02 (d, J=6.3 Hz, 3H), 0.83 (d, J=6.6 Hz, 3H). 19F NMR (300 MHz, CD$_3$OD) δ: −124.46. Mass spectrum (ESI, m/z): Calculated For C$_{24}$H$_{26}$FN$_3$O$_2$, 406.1 (M−H), found 406.1.

Example 243

Compound #229

N-(2-(2-(2-(dimethylamino)ethoxy)ethoxy)ethyl)-2-(6-(8-fluoronaphthalen-2-yl)-2-oxo-1,2-dihydropyridin-3-yl)-3-methylbutanamide

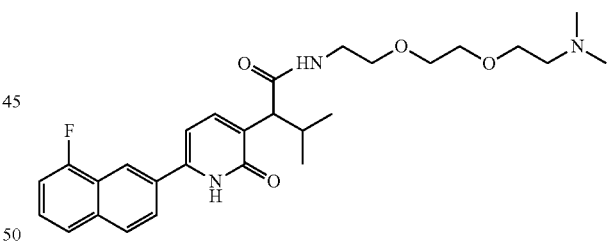

Step 1: N-(2-(2-(2-aminoethoxy)ethoxy)ethyl)-2-(6-(8-fluoronaphthalen-2-yl)-2-methoxypyridin-3-yl)-3-methylbutanamide Into a 50-mL round-bottom flask, were placed tert-butyl 2-(2-(2-(2-(6-(8-fluoronaphthalen-2-yl)-2-methoxypyridin-3-yl)-3-methylbutanamido)ethoxy)ethoxy)ethylcarbamate (80 mg, 0.137 mmol, 1.0 equiv.), DCM (12 mL), TFA (3 mL). The resulting solution was stirred overnight at room temperature. The reaction progress was monitored by LCMS. The resulting mixture was concentrated under vacuum. The residue was applied TLC with MeOH: DCM=1:10 to yield N-(2-(2-(2-aminoethoxy)ethoxy)ethyl)-2-(6-(8-fluoronaphthalen-2-yl)-2-methoxypyridin-3-yl)-3-methylbutanamide as a brown oil.

Mass spectrum (ESI, m/z): Calculated For $C_{27}H_{34}FN_3O_4$, 484.3 (M+H), found 484.2.

Step 2: N-(2-(2-(2-(dimethylamino)ethoxy)ethoxy) ethyl)-2-(6-(8-fluoronaphthalen-2-yl)-2-methoxypyridin-3-yl)-3-methylbutanamide Into a 8-mL closed tube, were placed N-(2-(2-(2-aminoethoxy)ethoxy)ethyl)-2-(6-(8-fluoronaphthalen-2-yl)-2-methoxypyridin-3-yl)-3-methylbutanamide (80 mg, 0.165 mmol, 1.0 equiv.), MeOH (10 mL), formaldehyde (37%) (1 mL), AcOH (0.5 mL), NaBH(OAc)$_3$ (70 mg, 0.330 mmol, 2.0 equiv.). The resulting solution was stirred overnight at 70° C. The reaction progress was monitored by LCMS. The resulting mixture was concentrated under vacuum. The residue was applied TLC with PE:EA=1:1 to yield N-(2-(2-(2-(dimethylamino)ethoxy)ethoxy)ethyl)-2-(6-(8-fluoronaphthalen-2-yl)-2-methoxypyridin-3-yl)-3-methylbutanamide as a brown oil.

Mass spectrum (ESI, m/z): Calculated For $C_{29}H_{38}FN_3O_4$, 512.3 (M+H), found 512.3.

Step 3: N-(2-(2-(2-(dimethylamino)ethoxy)ethoxy) ethyl)-2-(6-(8-fluoronaphthalen-2-yl)-2-oxo-1,2-dihydropyridin-3-yl)-3-methylbutanamide The title compound was prepared according to the procedure described in Example 1 step 5 by demethylation with TMSCl/NaI to yield the product as a white solid.

$^1$H NMR (300 MHz, CD$_3$OD) δ: 8.38 (s, 1H), 8.03 (d, J=9.9 Hz, 1H), 7.72-7.84 (m, 3H), 7.48-7.55 (m, 1H), 7.23-7.29 (m, 1H), 6.79 (d, J=7.5 Hz, 1H), 3.47-3.55 (m, 9H), 3.27-3.34 (m, 2H), 2.47-2.51 (m, 2H), 2.32-2.43 (m, 1H), 2.21 (s, 6H), 1.04 (d, J=6.6 Hz, 3H), 0.81 (d, J=6.9 Hz, 3H). $^{19}$F NMR (300 MHz, CD$_3$OD) δ: −124.45. Mass spectrum (ESI, m/z): Calculated For $C_{28}H_{36}FN_3O_4$, 496.3 (M−H), found 496.2.

Example 244

Compound #233

N-(2-(2-(dimethylamino)ethoxy)ethyl)-2-(6-(8-fluoronaphthalen-2-yl)-2-oxo-1,2-dihydropyridin-3-yl)-3-methylbutanamide

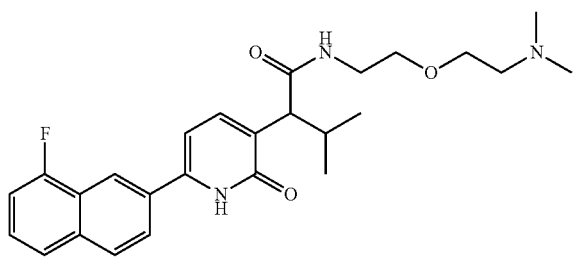 [SMILES: CC(C)C(C(=O)NCCOCCN(C)C)c1ccc(-c2ccc3cccc(F)c3c2)[nH]c1=O]

The title compound was prepared according to the procedure described in Example 221 by coulping with 2-(2-aminoethoxy)-N,N-dimethylethan-1-amine followed by demethylation with TMSCl/NaI to yield the product as brown oil.

$^1$H NMR (300 MHz, CD$_3$OD) δ: 8.37 (s, 1H), 8.02-8.06 (m, 1H), 7.72-7.83 (m, 3H), 7.48-7.55 (m, 1H), 7.23-7.29 (m, 1H), 6.81 (d, J=7.2 Hz, 1H), 3.71-3.74 (m, 2H), 3.41-3.57 (m, 5H), 3.27-3.40 (m, 2H), 2.88 (s, 6H), 2.34-2.42 (m, 1H), 1.05 (d, J=6.6 Hz, 3H), 0.85 (d, J=6.4 Hz, 3H). $^{19}$F NMR (300 MHz, CD$_3$OD) δ: −76.88, −124.49. Mass spectrum (ESI, m/z): Calculated For $C_{32.04}H_{35.02}F_{10.06}N_3O_{9.04}$, 454.2 (M−3.02CF$_3$COOH+H), found 454.2.

Example 245

Compound #241

6-(8-fluoronaphthalen-2-yl)-3-(2-methyl-1-(5-methyl-1H-imidazol-2-yl)propyl)pyridin-2(1H)-one

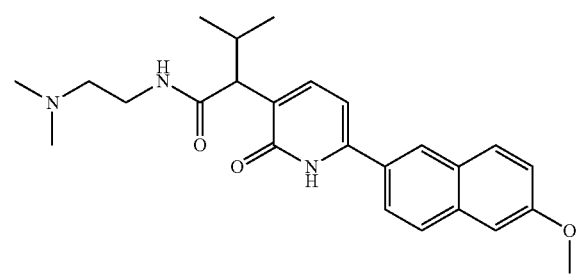

The title compound was prepared according to the procedure described in Example 221 by coulping with 2-dimethylamino-ethylamine followed by demethylation with TMSCl/NaI to yield the product as a yellow solid.

$^1$H NMR (300 MHz, CD$_3$OD) δ: 8.13 (s, 1H), 7.85-7.91 (m, 2H), 7.68-7.72 (m, 2H), 7.30 (s, 1H), 7.18-7.22 (m, 1H), 6.82 (d, J=7.2 Hz, 1H), 3.93 (s, 3H), 3.71-3.80 (m, 1H), 3.18-3.46 (m, 4H), 2.92 (s, 6H), 2.37-2.45 (m, 1H), 1.07 (d, J=6.3 Hz, 3H), 0.93 (d, J=6.6 Hz, 3H). Mass spectrum (ESI, m/z): Calculated for $C_{25}H_{31}N_3O_3$, 422.2 (M+H), found 422.2.

Example 246

Compound #242

N-(2-(dimethylamino)ethyl)-2-(6-(6-fluoronaphthalen-2-yl)-2-oxo-1,2-dihydropyridin-3-yl)-3-methylbutanamide

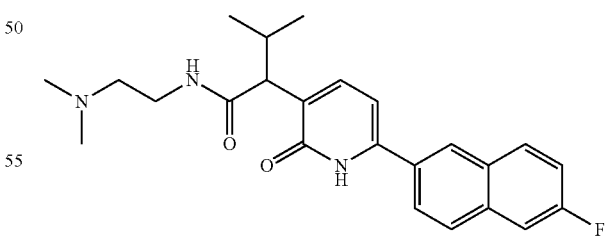

The title compound was prepared according to the procedure described in Example 221 by coulping with 2-dimethylamino-ethylamine followed by demethylation with TMSCl/NaI to yield the product as a light yellow solid.

$^1$H NMR (300 MHz, CD$_3$OD) δ: 8.24 (s, 1H), 7.94-8.05 (m, 2H), 7.76-7.82 (m, 2H), 7.55-7.59 (m, 1H), 7.33-7.40 (m, 1H), 6.88 (d, J=7.2 Hz, 1H), 3.70-3.79 (m, 1H), 3.39-3.48 (m, 2H), 3.19-3.34 (m, 2H), 2.91 (d, J=7.2 Hz, 6H), 2.39-2.43 (m, 1H), 1.05 (d, J=6.3 Hz, 3H), 0.89 (d, J=6.6 Hz, 3H). $^{19}$F NMR (300 MHz, CD$_3$OD) δ: −75.52, −114.05. Mass spectrum (ESI, m/z): Calculated for C$_{24.84}$H$_{28.42}$F$_{2.26}$N$_3$O$_{2.84}$, 410.2 (M+H−0.42CF$_3$COOH), found 410.0.

Example 247

Compound #244

N-(2-(dimethylamino)ethyl)-3-methyl-2-(6-(4-methyl-3,4-dihydro-2H-benzo[b][1,4]oxazin-7-yl)-2-oxo-1,2-dihydropyridin-3-yl)butanamide

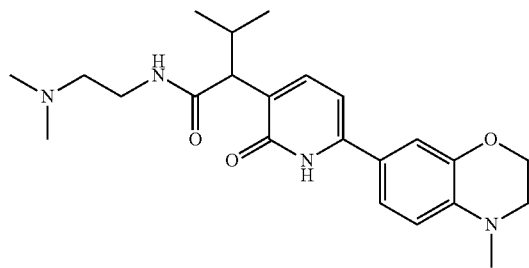 [SMILES: CC(C)C(C(=O)NCCN(C)C)c1ccc(-c2ccc3c(c2)OCCN3C)[nH]c1=O]

The title compound was prepared according to the procedure described in Example 221 by coulping with 2-dimethylamino-ethylamine followed by demethylation with TMSCl/NaI to yield the product as white solid.

$^1$H NMR (300 MHz, CD$_3$OD) δ: 7.68 (s, 1H), 7.18-7.22 (m, 1H), 7.08 (s, 1H), 6.79 (d, J=8.4 Hz, 1H), 6.64 (d, J=7.5 Hz, 1H) 4.28-4.31 (m, 2H), 3.72-3.79 (m, 1H), 3.20-3.46 (m, 6H), 2.90-2.97 (m, 9H), 2.39-2.42 (m, 1H), 1.06 (d, J=6.0 Hz, 3H), 0.92 (d, J=6.9 Hz, 3H). Mass spectrum (ESI, m/z): Calculated for C$_{23}$H$_{32}$N$_4$O$_3$, 413.2 (M+H), found 413.2.

Example 248

Compound #302

N-(2-(dimethylamino)ethyl)-3-methyl-2-(6-(4-methyl-3,4-dihydro-2H-benzo[b][1,4]oxazin-6-yl)-2-oxo-1,2-dihydropyridin-3-yl)butanamide

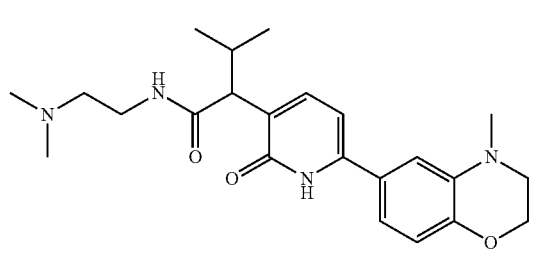 [SMILES: CC(C)C(C(=O)NCCN(C)C)c1ccc(-c2ccc3c(c2)N(C)CCO3)[nH]c1=O]

The title compound was prepared according to the procedure described in Example 221 by coulping with 2-dimethylamino-ethylamine followed by demethylation with TMSCl/NaI to yield the product as a yellow solid.

$^1$H NMR (400 MHz, CD$_3$OD) δ: 7.72 (d, J=7.6 Hz, 1H), 6.92-6.98 (m, 2H), 6.80 (d, J=8.0 Hz, 1H), 6.68 (d, J=7.2 Hz, 1H), 4.30-4.33 (m, 2H), 3.72-3.78 (m, 1H), 3.40-3.47 (m, 2H), 3.20-3.33 (m, 5H), 2.89-2.96 (m, 9H), 2.37-2.44 (m, 1H), 0.82 (d, J=8 Hz, 3H), 0.67 (d, J=8 Hz, 3H). Mass spectrum (ESI, m/z): Calculated for C$_{23}$H$_{32}$N$_4$O$_3$, 413.2 (M+H), found 413.2.

Example 249

Compound #246

2-(6-(benzo[d]thiazol-6-yl)-2-oxo-1,2-dihydropyridin-3-yl)-N-(2-(dimethylamino)ethyl)-3-methylbutanamide

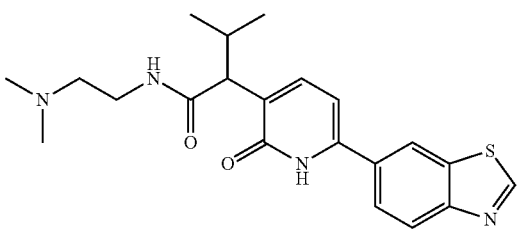 [SMILES: CC(C)C(C(=O)NCCN(C)C)c1ccc(-c2ccc3ncsc3c2)[nH]c1=O]

The title compound was prepared according to the procedure described in Example 221 by coulping with 2-dimethylamino-ethylamine followed by demethylation with TMSCl/NaI to yield the product as white solid.

$^1$H NMR (300 MHz, CD$_3$OD) δ: 9.38 (s, 1H), 8.46 (s, 1H), 8.21 (d, J=8.7 Hz, 1H), 7.87-7.90 (m, 1H), 7.82 (d, J=7.5 Hz, 1H), 6.79 (d, J=7.2 Hz, 1H), 3.53 (d, J=10.8 Hz, 1H), 3.27-3.39 (m, 2H), 2.44-2.49 (t, J=6.9 Hz, 2H), 2.35-2.43 (m, 1H), 2.28 (s, 6H), 1.08 (d, J=6.6 Hz, 3H), 0.94 (d, J=6.6 Hz, 3H). Mass spectrum (ESI, m/z): Calculated for C$_{21}$H$_{26}$N$_4$O$_2$S, 399.2 (M+H), found 399.1.

Example 250

Compound #243

2-(6-(benzo[d]thiazol-5-yl)-2-oxo-1,2-dihydropyridin-3-yl)-N-(2-(dimethylamino)ethyl)-3-methylbutanamide

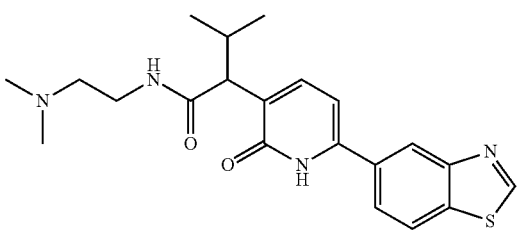 [SMILES: CC(C)C(C(=O)NCCN(C)C)c1ccc(-c2ccc3scnc3c2)[nH]c1=O]

The title compound was prepared according to the procedure described in Example 221 by coulping with 2-dimethylamino-ethylamine followed by demethylation with TMSCl/NaI to yield the product as a white solid.

$^1$H NMR (300 MHz, CD$_3$OD) δ: 9.33 (s, 1H), 8.36 (s, 1H), 8.20 (d, J=8.4 Hz, 1H), 7.74-7.79 (m, 2H), 6.81 (d, J=7.2 Hz, 1H), 3.69-3.78 (m, 1H), 3.32-3.45 (m, 2H), 3.20-3.28 (m, 2H), 2.91 (s, 6H), 2.36-2.45 (m, 1H), 1.06 (d, J=6.6 Hz, 3H), 0.91 (d, J=6.6 Hz, 3H). Mass spectrum (ESI, m/z): Calculated for C$_{21}$H$_{26}$N$_4$O$_2$S, 399.2 (M+H), found 399.0.

Example 251

Compound #265

1-(1-(6-(8-fluoronaphthalen-2-yl)-2-oxo-1,2-dihydropyridin-3-yl)-2-methylpropyl)-1-methylurea

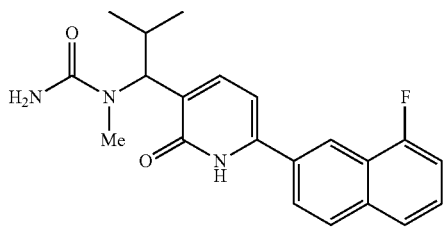 [SMILES: CC(C)C(c1ccc(-c2ccc3cccc(F)c3c2)[nH]c1=O)N(C)C(N)=O]

Step 1: 1-(6-(8-fluoronaphthalen-2-yl)-2-methoxypyridin-3-yl)-N,2-dimethylpropan-1-amine Into a 50-mL round-bottom flask, were placed 1-(6-(8-fluoronaphthalen-2-yl)-2-methoxypyridin-3-yl)-2-methylpropan-1-amine (50 mg, 0.154 mmol, 1 equiv.), formaldehyde (10 mg, 0.333 mmol, 2 equiv.), DCE (5 mL). The resulting solution was stirred 1 h at 25° C. Sodium triacetoxyborohydride (STAB) (65 mg, 0.307 mmol, 2 equiv.) was added to above mixture solution. The resulting solution was stirred 1 h at 25° C. The reaction was monitored by TLC (DCM:MeOH=10:1). The reaction was then quenched by the addition of water (10 mL) and extracted with DCM and the organic layers combined. The resulting mixture was concentrated under vacuum. The residue was applied onto a silica gel column with DCM:MeOH=10:1 to yield 1-(6-(8-fluoronaphthalen-2-yl)-2-methoxypyridin-3-yl)-N,2-dimethylpropan-1-amine was obtained as a light yellow solid.

Mass spectrum (ESI, m/z): Calculated for $C_{21}H_{23}FN_2O$, 339.2 (M+H), found 339.2.

Step 2: 1-(1-(6-(8-fluoronaphthalen-2-yl)-2-methoxypyridin-3-yl)-2-methylpropyl)-1-methylurea Into a 50-mL round-bottom flask, were placed 1-(6-(8-fluoronaphthalen-2-yl)-2-methoxypyridin-3-yl)-N,2-dimethylpropan-1-amine (30 mg, 0.089 mmol, 1 equiv.), potassium cyanate (36 mg, 0.444 mmol, 5 equiv.), AcOH (2 mL), THF (2 mL), $H_2O$ (2 mL). The resulting solution was stirred overnight at 25° C. The reaction was monitored by TLC (DCM:MeOH=10:1). The mixture was then extracted with ethyl acetate and the organic layers combined. The resulting mixture was concentrated under vacuum. The residue was applied onto a silica gel column with DCM:MeOH=10:1 to yield 1-(1-(6-(8-fluoronaphthalen-2-yl)-2-methoxypyridin-3-yl)-2-methylpropyl)-1-methylurea was obtained as a light yellow oil.

Mass spectrum (ESI, m/z): Calculated for $C_{22}H_{24}FN_3O_2$, 382.2 (M+H), found 382.2.

Step 3: 1-(1-(6-(8-fluoronaphthalen-2-yl)-2-oxo-1,2-dihydropyridin-3-yl)-2-methylpropyl)-1-methylurea The title compound was prepared according to the procedure described in Example 1 step 5 by demethylation with TMSCl/NaI to yield the product as off white solid.

$^1$H NMR (400 MHz, $CD_3OD$) δ: 8.49 (s, 1H), 8.10 (d, J=8.8 Hz, 1H), 7.87-7.94 (m, 1H), 7.77-7.80 (m, 2H), 7.54-7.60 (m, 1H), 7.29-7.38 (m, 1H), 6.85 (d, J=6.8 Hz, 1H), 4.74-4.88 (m, 1H), 2.76 (s, 3H), 2.51-2.55 (m, 1H), 1.07 (d, J=6.4 Hz, 3H), 0.92 (d, J=6.4 Hz, 3H). $^{19}$F NMR (400 MHz, $CD_3OD$) δ: −124.40. Mass spectrum (ESI, m/z): Calculated for $C_{21}H_{22}FN_3O_2$, 368.2 (M+H), found 368.2.

Example 252

Compound #266

1-(2-(dimethylamino)ethyl)-3-(1-(6-(8-fluoronaphthalen-2-yl)-2-oxo-1,2-dihydropyridin-3-yl)-2-methylpropyl)urea

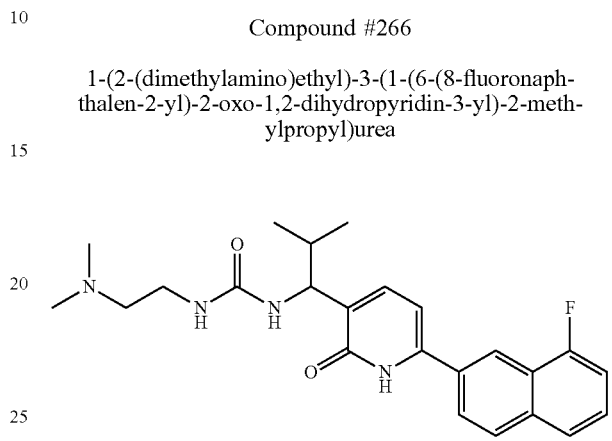

The title compound was prepared according to the procedure described in Example 251 by coulping followed by demethylation with TMSCl/NaI to yield the product as light yellow oil.

$^1$H NMR (400 MHz, $CD_3OD$) δ: 8.42 (s, 1H), 8.08 (d, J=7.6 Hz, 1H), 7.85 (d, J=8.8 Hz, 1H), 7.78 (d, J=8.4 Hz, 1H), 7.54-7.60 (m, 2H), 7.29-7.34 (m, 1H), 6.78 (d, J=7.2 Hz, 1H), 4.56 (d, J=7.6 Hz, 1H), 3.42-3.57 (m, 2H), 3.22-3.25 (m, 2H), 2.92 (d, J=8.4 Hz, 6H), 2.25-2.34 (m, 1H), 1.02 (d, J=6.8 Hz, 3H), 0.94 (d, J=6.8 Hz, 3H). $^{19}$F NMR (400 MHz, $CD_3OD$) δ: −78.55, −124.55. Mass spectrum (ESI, m/z): Calculated for $C_{24}H_{29}FN_4O_2$, 425.2 (M−1.95$CF_3COOH$+H), found 425.2.

Example 253

Compound #268

(E)-2-cyano-1-(1-(6-(8-fluoronaphthalen-2-yl)-2-oxo-1,2-dihydropyridin-3-yl)-2-methylpropyl)guanidine

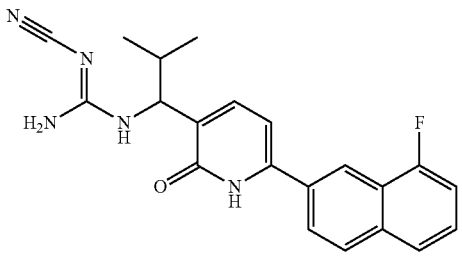 [SMILES: CC(C)C(N/C(N)=N/C#N)c1ccc(-c2ccc3cccc(F)c3c2)[nH]c1=O]

Step 1: (Z)-methyl N'-cyano-N-(1-(6-(8-fluoronaphthalen-2-yl)-2-oxo-1,2-dihydropyridin-3-yl)-2-methylpropyl)carbamimidothioate Into a 50-mL round-bottom flask, were placed 3-(1-amino-2-methylpropyl)-6-(8-fluoronaphthalen-2-yl)pyridin-2(1H)-one (80 mg, 0.258 mmol, 1 equiv.), dimethyl cyanocarbonimidodithioate (75 mg, 0.513 mmol, 2 equiv.), EtOH (5 mL), TEA (52 mg, 0.514 mmol, 2 equiv.). The resulting solution was stirred overnight at 70° C. The reaction was monitored by LCMS. The resulting mixture was concentrated under vacuum. The residue was applied onto a silica gel column with DCM:MeOH=10:1 to yield (Z)-methyl N'-cyano-N-(1-(6-(8-fluoronaphthalen-2-yl)-2-oxo-1,2-dihydropyridin-3-yl)-2-methylpropyl)carbamimidothioate as light yellow oil.

Mass spectrum (ESI, m/z): Calculated for $C_{22}H_{21}FN_4OS$, 409.1 (M+H), found 409.1.

Step 2: (E)-2-cyano-1-(1-(6-(8-fluoronaphthalen-2-yl)-2-oxo-1,2-dihydropyridin-3-yl)-2-methylpropyl) guanidine Into a 10-mL sealed tube, were placed (Z)-methyl N'-cyano-N-(1-(6-(8-fluoronaphthalen-2-yl)-2-oxo-1,2-dihydropyridin-3-yl)-2-methylpropyl)carbamimidothioate (50 mg, 0.122 mmol, 1 equiv.), $NH_3$ in MeOH (3 mL). The resulting solution was stirred overnight at 70° C. The reaction was monitored by LCMS. The resulting mixture was concentrated under vacuum. The residue was purified by Prep-HPLC with the following conditions (1#-Waters 2767-5): Column, SunFire Prep C18, 5 um, 19*100 mm; mobile phase, Water of 0.05% TFA and $CH_3CN$ (20% $CH_3CN$ up to 50% in 10 min, up to 100% in 2 min, down to 20% in 2 min; Detector, 254 nm to yield (E)-2-cyano-1-(1-(6-(8-fluoronaphthalen-2-yl)-2-oxo-1,2-dihydropyridin-3-yl)-2-methylpropyl)guanidine trifluoroacetic acid as off white solid.

$^1$H NMR (400 MHz, DMSO-$d_6$) δ: 8.48 (s, 1H), 8.11 (d, J=8.0 Hz, 1H), 7.96-7.97 (m, 1H), 7.84 (d, J=8.4 Hz, 1H), 7.56-7.61 (m, 1H), 7.39-7.44 (m, 2H), 7.19 (brs, 1H), 6.75 (brm, 2H), 4.45-4.50 (m, 1H), 2.24-2.28 (m, 1H), 0.90 (d, J=6.4 Hz, 3H), 0.82 (d, J=6.4 Hz, 3H). $^{19}$F NMR (400 MHz, DMSO-$d_6$) δ: −73.41, −122.17. Mass spectrum (ESI, m/z): Calculated for $C_{21.48}H_{20.24}F_{1.72}N_5O_{1.48}$, 378.2 (M−0.24$CH_3COOH$+H), found 378.2.

Example 254

Compound #230

N-(1,3-dihydroxypropan-2-yl)-2-(6-(8-fluoronaphthalen-2-yl)-2-oxo-1,2-dihydropyridin-3-yl)-3-methylbutanamide

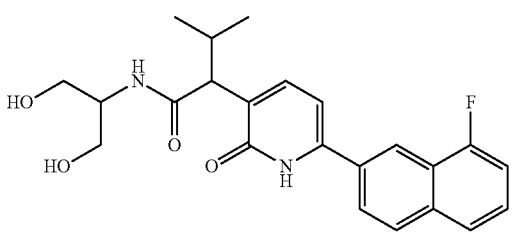 [SMILES: CC(C)C(C(=O)NC(CO)CO)c1ccc(-c2ccc3cccc(F)c3c2)[nH]c1=O]

The title compound was prepared according to the procedure described in Example 221 by coulping with 2-aminopropane-1,3-diol followed by demethylation with TMSCl/NaI to yield the product as a white solid.

$^1$H NMR (300 MHz, $CD_3OD$) δ: 8.37 (s, 1H), 8.01-8.04 (m, 1H), 7.71-7.83 (m, 3H), 7.47-7.54 (m, 1H), 7.22-7.28 (m, 1H), 6.79 (d, J=7.2 Hz, 1H), 3.84-3.91 (m, 1H), 3.48-3.65 (m, 5H), 2.32-2.40 (m, 1H), 1.06 (d, J=6.6 Hz, 3H), 0.83 (d, J=6.6 Hz, 3H). $^{19}$F NMR (300 MHz, $CD_3OD$) δ: −124.43. Mass spectrum (ESI, m/z): Calculated for $C_{23}H_{25}FN_2O_4$, 413.2 (M+H), found 413.1.

Example 255

Compound #231

N-(1,3-dihydroxy-2-(hydroxymethyl)propan-2-yl)-2-(6-(8-fluoronaphthalen-2-yl)-2-oxo-1,2-dihydropyridin-3-yl)-3-methylbutanamide

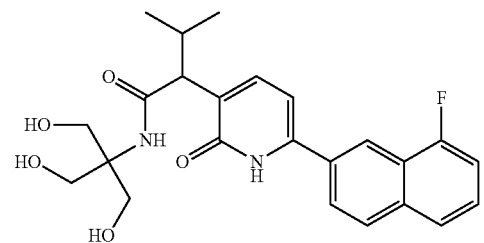 [SMILES: CC(C)C(C(=O)NC(CO)(CO)CO)c1ccc(-c2ccc3cccc(F)c3c2)[nH]c1=O]

The title compound was prepared according to the procedure described in Example 221 by coulping with 2-amino-2-(hydroxymethyl)propane-1,3-diol followed by demethylation with TMSCl/NaI to yield the product as a white solid.

$^1$H NMR (300 MHz, $CD_3OD$) δ: 8.39 (s, 1H), 8.03 (d, J=8.7 Hz, 1H), 7.82 (d, J=8.7 Hz, 1H), 7.71-7.76 (m, 2H), 7.48-7.54 (m, 1H), 7.22-7.28 (m, 1H), 6.80 (d, J=7.2 Hz, 1H), 3.63-3.70 (m, 6H), 3.47 (d, J=7.8 Hz, 1H), 2.34-2.42 (m, 1H), 1.08 (d, J=5.4 Hz, 3H), 0.83 (d, J=6.6 Hz, 3H). $^{19}$F NMR (300 MHz, $CD_3OD$) δ: −124.46. Mass spectrum (ESI, m/z): Calculated for $C_{24}H_{27}FN_2O_5$, 443.2 (M+H), found 443.1.

Example 256

Compound #183

2-(6-(8-fluoronaphthalen-2-yl)-2-oxo-1,2-dihydropyridin-3-yl)-3-methyl-N-(tetrahydro-2H-thiopyran-4-yl)butanamide

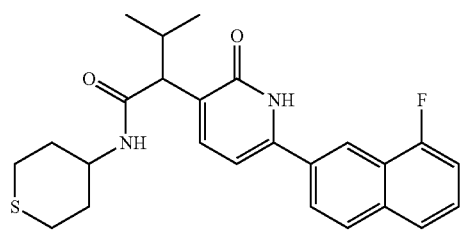 [SMILES: CC(C)C(C(=O)NC1CCSCC1)c1ccc(-c2ccc3cccc(F)c3c2)[nH]c1=O]

The title compound was prepared according to the procedure described in Example 221 by coulping with tetrahydro-2H-thiopyran-4-amine followed by demethylation with TMSCl/NaI to yield the product a white solid.

$^1$H NMR (400 MHz, $CD_3OD$) δ: 8.43 (s, 1H), 8.08 (d, J=8.8 Hz, 1H), 7.77-7.88 (m, 3H), 7.54-7.59 (m, 1H), 7.28-7.33 (m, 1H), 6.84 (d, J=7.6 Hz, 1H), 3.66-3.71 (m, 1H), 3.49 (d, J=10.8 Hz, 1H), 2.63-2.73 (m, 4H), 2.35-2.42

(m, 1H), 2.16-2.19 (m, 1H), 2.02-2.06 (m, 1H), 1.57-1.67 (m, 2H), 1.08 (d, J=6.4 Hz, 3H), 0.87 (d, J=6.8 Hz, 3H). $^{19}$F NMR (400 MHz, CD$_3$OD) δ: −124.41.

Mass spectrum (ESI, m/z): Calculated for C$_{25}$H$_{27}$FN$_2$O$_2$S, 439.2 (M+H), found 439.1.

Example 257

Compound #179

N-(1,1-dioxo-1l6-thian-4-yl)-2-[6-(8-fluoronaphthalen-2-yl)-2-oxo-1,2-dihydropyridin-3-yl]-3-methylbutanamide

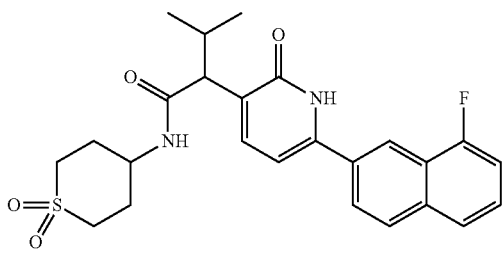 [SMILES: CC(C)C(C(=O)NC1CCS(=O)(=O)CC1)c1ccc(-c2ccc3cccc(F)c3c2)[nH]c1=O]

The title compound was prepared according to the procedure described in Example 221 by coulping with 4-aminotetrahydro-2H-thiopyran 1,1-dioxide followed by demethylation with TMSCl/NaI to yield the product as a white solid.

$^1$H NMR (300 MHz, CD$_3$OD) δ: 8.39 (s, 1H), 8.03 (d, J=9.6 Hz, 1H), 7.71-7.83 (m, 3H), 7.47-7.55 (m, 1H), 7.22-7.28 (m, 1H), 6.80 (d, J=7.5 Hz, 1H), 3.90-4.01 (m, 1H), 3.48 (d, J=10.8 Hz, 1H), 3.04-3.18 (m, 4 H), 2.22-2.37 (m, 2 H), 2.01-2.13 (m, 3 H), 1.04 (d, J=6.6 Hz, 3H), 0.83 (d, J=6.6 Hz, 3H). $^{19}$F NMR (300 MHz, CD$_3$OD) δ: −77.55, −124.45. Mass spectrum (ESI, m/z): Calculated for C$_{26.46}$H$_{27.73}$F$_{3.19}$N$_2$O$_{5.46}$S, 471.2 (M−0.73CF$_3$COOH+H), found 471.1.

Example 258

Compound #178

2-(6-(8-fluoronaphthalen-2-yl)-2-oxo-1,2-dihydropyridin-3-yl)-3-methyl-N-(pyrrolidin-3-yl)butanamide

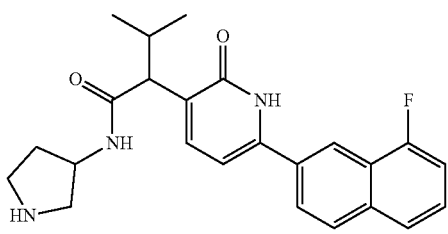 [SMILES: CC(C)C(C(=O)NC1CCNC1)c1ccc(-c2ccc3cccc(F)c3c2)[nH]c1=O]

The title compound was prepared according to the procedure described in Example 221 by coulping with tert-butyl 3-aminopyrrolidine-1-carboxylate followed by de-Boc protection (i.e. removal of the Boc protecting group) and demethylation with TMSCl/NaI to yield the product as a light pink solid.

$^1$H NMR (400 MHz, CD$_3$OD) δ: 8.38 (s, 1 H), 8.05-8.07 (m, 1 H), 7.75-7.84 (m, 3 H), 7.52-7.57 (m, 1 H), 7.26-7.31 (m, 1 H), 6.79-6.85 (m, 1 H), 3.47-4.12 (m, 6 H), 2.35-2.58 (m, 2 H), 1.90-2.18 (m, 1 H), 1.08 (d, J=6.4 Hz, 3 H), 0.88 (d, J=8.4 Hz, 3 H). $^{19}$F NMR (400 MHz, CD$_3$OD) δ: −77.59, −124.62. Mass spectrum (ESI, m/z): Calculated for C$_{29.58}$H$_{28.79}$F$_{9.37}$N$_3$O$_{7.58}$, 408.2 (M−2.79 CF$_3$COOH+H), found 408.2.

Example 259

Compound #184

2-(6-(8-fluoronaphthalen-2-yl)-2-oxo-2,3-dihydropyridin-3-yl)-3-methyl-N-(1-(methylsulfonyl) piperidin-4-yl)butanamide

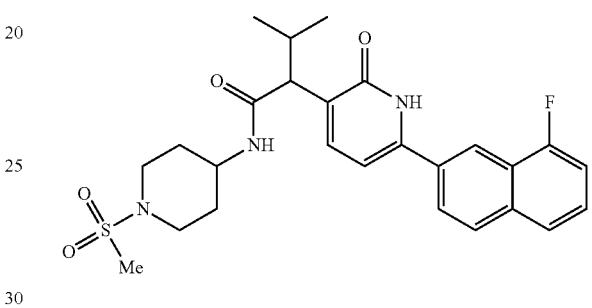

The title compound was prepared according to the procedure described in Example 221 by coulping with 1-(methylsulfonyl)piperidin-4-amine followed by demethylation with TMSCl/NaI to yield the product as a colorless oil.

$^1$H NMR (300 MHz, CD$_3$OD) δ: 8.40 (s, 1H), 8.03 (d, J=8.7 Hz, 1H), 7.79-7.83 (m, 2H), 7.72-7.78 (m, 1H), 7.47-7.55 (m, 1H), 7.22-7.29 (m, 1H), 6.89 (d, J=7.5 Hz, 1H), 3.74-3.77 (m, 1H), 3.56-3.63 (m, 2H), 3.46 (d, J=10.8 Hz, 1H), 2.84-2.88 (m, 2H), 2.79 (s, 3H), 2.56-2.36 (m, 1H), 1.93-1.98 (m, 1H), 1.81-1.86 (m, 1H), 1.47-1.55 (m, 2H), 1.04 (d, J=6.6 Hz, 3H), 0.83 (d, J=6.9 Hz, 3H). $^{19}$F NMR (300 MHz, CD$_3$OD) δ: 0.76.96, −124.42. Mass spectrum (ESI, m/z): Calculated for C$_{26.3}$H$_{30.15}$F$_{1.45}$N$_3$O$_{4.3}$S, 500.2 [M−0.15CF$_3$COOH+H], found 500.3.

Example 260

Compound #181

2-(6-(8-fluoronaphthalen-2-yl)-2-oxo-1,2-dihydropyridin-3-yl)-3-methyl-N-(1-methyl-1H-benzo[d]imidazol-5-yl)butanamide

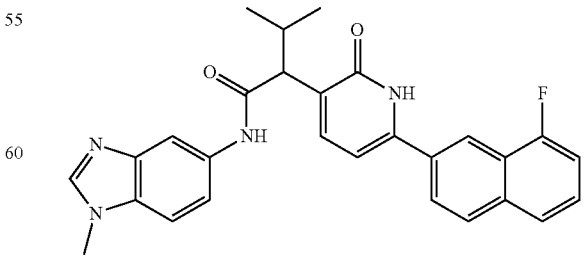

The title compound was prepared according to the procedure described in Example 221 by coulping with 1-methyl-1H-benzo[d]imidazol-5-amine followed by demethylation with TMSCl/NaI to yield the product as a light yellow solid.

¹H NMR (400 MHz, CD₃OD) δ: 9.30 (s, 1 H), 8.49 (s, 1 H), 8.43 (s, 1 H), 8.08 (d, J=8.8 Hz, 1 H), 7.92 (d, J=7.2 Hz, 1 H), 7.86-7.88 (m, 2 H), 7.78 (d, J=8.4 Hz, 1 H), 7.67 (d, J=8.8 Hz, 1 H), 7.54-7.59 (m, 1 H), 7.28-7.33 (m, 1 H), 6.88 (d, J=7.6 Hz, 1 H), 4.13 (s, 3 H), 3.76 (d, J=10.8 Hz, 1 H), 2.50-2.59 (m, 1 H), 1.17 (d, J=6.4 Hz, 3 H), 0.96 (d, J=6.8 Hz, 3 H). ¹⁹F NMR (400 MHz, CD₃OD) δ: −77.16, −124.43. Mass spectrum (ESI, m/z): Calculated for $C_{31.82}H_{26.91}F_{6.73}N_4O_{5.82}$, 469.2 (M−1.91CF₃COOH+H), found 469.2.

Example 261

Compound #180

2-(6-(8-fluoronaphthalen-2-yl)-2-oxo-1,2-dihydropyridin-3-yl)-3-methyl-N-(pyridin-4-yl)butanamide

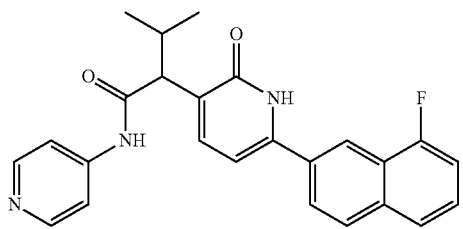

The title compound was prepared according to the procedure described in Example 221 by coulping with 4-aminopyridine followed by demethylation with TMSCl/NaI to yield the product as a white solid.

¹H NMR (300 MHz, CD₃OD) δ: 8.33-8.38 (m, 3 H), 8.02 (d, J=8.4 Hz, 1 H), 7.71-7.84 (m, 3 H), 7.53 (d, J=5.4 Hz, 2 H), 7.46-7.52 (m, 1 H), 7.21-7.28 (m, 1 H), 6.81 (d, J=7.5 Hz, 1 H), 3.69 (d, J=10.5 Hz, 1 H), 2.41-2.53 (m, 1 H), 1.09 (d, J=6.6 Hz, 3 H), 0.88 (d, J=6.6 Hz, 3 H). ¹⁹F NMR (300 MHz, CD₃OD) δ: −124.39. Mass spectrum (ESI, m/z): Calculated for $C_{25}H_{22}FN_3O_2$, 416.2 (M+H), found 416.1.

Example 262

Compound #218

2-hydroxy-3-methyl-2-(6-(naphthalen-2-yl)-2-oxo-1,2-dihydropyridin-3-yl)butanamide

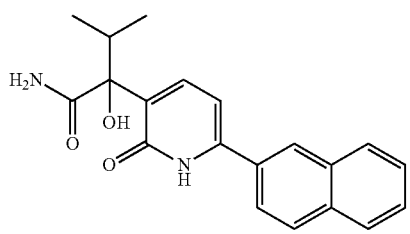 [SMILES: CC(C)C(O)(C(N)=O)c1ccc(-c2ccc3ccccc3c2)[nH]c1=O]

To 5-isopropyl-5-(6-(naphthalen-2-yl)-2-oxo-1,2-dihydropyridin-3-yl)oxazolidine-2,4-dione (prepared according to JIN, J., et al., "Novel 3-*Oxazolidinedione-6-aryl-pyridinones as Potent, Selective, and Orally Active EP₃Receptor Antagonists*", ACS Med. Chem. Lett., 2010, pp 316-320, Vol. 1) (200 mg, 0.551 mmol, 1 equiv.) in mixed solvent of THF (2 mL) and water (2 mL) was added NaOH (66 mg, 1.656 mmol, 3 equiv.) at room temperature. The result solution was heated to reflux for 6 hours. The solvent was neutralized with 1 N HCl. The solvent was removed and the residue was partitioned between ethyl acetate and water. The organic layer was washed with water and brine, dried over anhydrous Na₂SO₄, filtered and concentrated and purified by silica gel column to yield the title product as a white solid.

¹H NMR (400 MHz, CDCl₃) δ: 12.2 (br, s, 1H), 8.31 (d, J=7.5 Hz, 1 H), 8.25 (s, 1H), 8.08 (m, 2H), 7.98 (m, 1H), 7.72 (d, J=7.0 Hz, 1H), 7.61 (m, 2H), 7.02 (d, J=7.5 Hz, 1H), 6.21 (br, s, 1H), 2.95 (m, 1H), 0.95 (d, J=7.0 Hz, 3H), 0.85 (d, J=7.0 Hz, 3H). Mass spectrum (ESI, m/z): Calculated for $C_{20}H_{20}N_2O_3$, 337.39 (M+H), found 337.5.

Example 263

Compound #217

2-fluoro-3-methyl-2-(6-(naphthalen-2-yl)-2-oxo-1,2-dihydropyridin-3-yl)butanamide

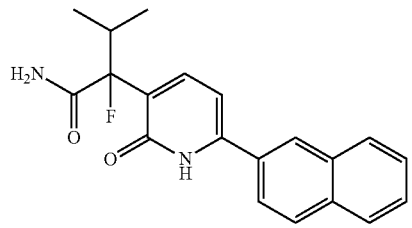 [SMILES: CC(C)C(F)(C(N)=O)c1ccc(-c2ccc3ccccc3c2)[nH]c1=O]

The title compound was prepared according to the procedure described in Example 165 by fluorination of 2-hydroxy-3-methyl-2-(6-(naphthalen-2-yl)-2-oxo-1,2-dihydropyridin-3-yl)butanamide with DAST to yield the product as a white solid.

¹H NMR (400 MHz, CDCl₃) δ: 8.21 (d, J=5.5 Hz, 1 H), 8.02 (m, 2H), 7.95 (m, 2H), 7.72 (d, J=7.0 Hz, 1H), 7.61 (d, J=5.8 Hz, 2H), 6.90 (d, J=5.1 Hz, 1H), 5.55 (br, s, 1H), 3.10 (m, 1H), 1.01 (d, J=7.0 Hz, 3H), 0.85 (d, J=7.0 Hz, 3H). Mass spectrum (ESI, m/z): Calculated for $C_{22}H_{19}FN_2O_2$, 339.38 (M+H), found 339.5.

Example 264

Compound #216

2-fluoro-2-(6-(8-fluoronaphthalen-2-yl)-2-oxo-1,2-dihydropyridin-3-yl)-3-methylbutanamide

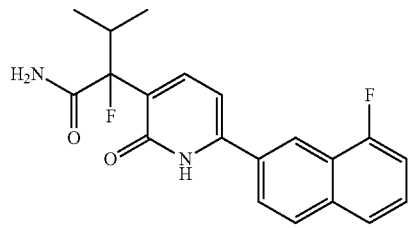 [SMILES: CC(C)C(F)(C(N)=O)c1ccc(-c2ccc3cccc(F)c3c2)[nH]c1=O]

The title compound was prepared according to the procedure described in Example 165 by fluorination of 2-(6-

(8-fluoronaphthalen-2-yl)-2-oxo-1,2-dihydropyridin-3-yl)-2-hydroxy-3-methylbutanamide with DAST to yield the product as a white solid.

$^1$H NMR (400 MHz, CDCl$_3$) δ: 12.7 (s, br, 1H), 8.51 (s, 1H), 8.05 (m, 1H), 7.92 (d, J=7.0 Hz, 1H), 7.78 (d, J=7.2 Hz, 1H), 7.72 (dd, J=7.5, 4.5 Hz, 1H), 7.52 (m, 1H), 7.26 (m, 1H), 6.81 (d, J=7.2 Hz, 1H), 5.42 (br, s, 1H), 3.02 (m, J=10.5, 1H), 0.90 (d, J=5.6 Hz, 3H), 0.75 (d, J=5.5 Hz, 3H). Mass spectrum (ESI, m/z): Calculated for C$_{20}$H$_{18}$F$_2$N$_2$O$_2$, 357.37 (M+H), found 357.4.

Example 265

Compound #224

2-fluoro-3-methyl-N-(methylsulfonyl)-2-(6-(naphthalen-2-yl)-2-oxo-1,2-dihydropyridin-3-yl)butanamide

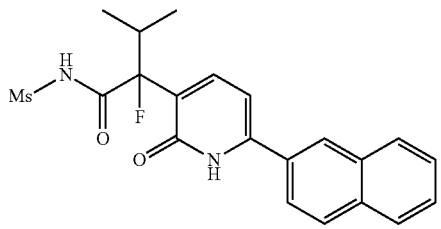 [SMILES: CC(C)C(F)(C(=O)NS(C)(=O)=O)c1ccc(-c2ccc3ccccc3c2)[nH]c1=O]

The title compound was prepared according to the procedure described in Example 171 by reacting 2-fluoro-2-(6-(8-fluoronaphthalen-2-yl)-2-oxo-1,2-dihydropyridin-3-yl)-3-methyl butanamide with MsCl to yield the product as a white solid.

$^1$H NMR (400 MHz, CDCl$_3$) δ: 8.18 (s, 1H), 8.05 (d, J=7.5 Hz, 1 H), 7.95 (d, J=8.5 Hz, 2H), 7.92 (m, 1H), 7.68 (d, J=6.5 Hz, 1H), 7.62 (d, J=7.0 Hz, 2H), 6.91 (d, J=6.1 Hz, 1H), 3.10 (m, 1H), 1.02 (d, J=6.0 Hz, 3H), 0.82 (d, J=6.5 Hz, 3H). Mass spectrum (ESI, m/z): Calculated for C$_{21}$H$_{21}$FN$_2$O$_4$S, 417.47 (M+H), found 417.5.

Example 266

Compound #173

N-((3,5-difluorophenyl)sulfonyl)-2-fluoro-2-(6-(8-fluoronaphthalen-2-yl)-2-oxo-1,2-dihydropyridin-3-yl)-3-methylbutanamide

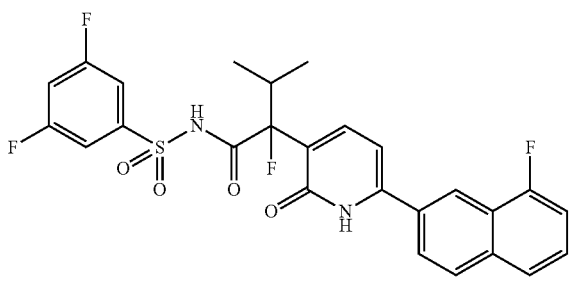 [SMILES: CC(C)C(F)(C(=O)NS(=O)(=O)c1cc(F)cc(F)c1)c1ccc(-c2ccc3cccc(F)c3c2)[nH]c1=O]

The title compound was prepared according to the procedure described in Example 171 by reacting 2-fluoro-2-(6-(8-fluoronaphthalen-2-yl)-2-oxo-1,2-dihydropyridin-3-yl)-3-methyl butanamide with 3,5-di-fluoro-phenyl-sulfonylchloride to yield the product as a white solid.

$^1$H NMR (400 MHz, CDCl$_3$) δ: 12.5 (s, br, 1H), 8.48 (s, 1H), 8.02 (m, 1H), 7.89 (d, J=6.0 Hz, 1H), 7.73 (d, J=7.0 Hz, 1H), 7.65 (d, J=7.5 Hz, 1H), 7.56 (m, 2H), 7.52 (m, 1H), 7.26 (m, 1H), 7.03 (m, 1H), 6.81 (d, J=7.2 Hz, 1H), 3.10 (m, J=9.5, 1H), 0.95 (d, J=5.6 Hz, 3H), 0.81 (d, J=5.5 Hz, 3H). Mass spectrum (ESI, m/z): Calculated for C$_{26}$H$_{20}$F$_4$N$_2$O$_4$S, 533.51 (M+H), found 533.8.

Example 267

Compound #225

2-hydroxy-3-methyl-2-(6-(4-methyl-3,4-dihydro-2H-benzo[b][1,4]oxazin-7-yl)-2-oxo-1,2-dihydropyridin-3-yl)butanamide

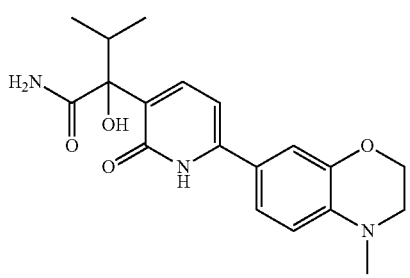 [SMILES: CC(C)C(O)(C(N)=O)c1ccc(-c2ccc3c(c2)OCCN3C)[nH]c1=O]

The title compound was prepared according to the procedure described in Example 262 by ring-opening of 5-isopropyl-5-(6-(4-methyl-3,4-dihydro-2H-benzo[b][1,4]oxazin-7-yl)-2-oxo-1,2-dihydropyridin-3-yl)oxazolidine-2,4-dione with NaOH to yield the product as a white solid.

$^1$H NMR (400 MHz, CDCl$_3$) δ: 8.01 (s, 1H), 7.92 (d, J=5.6 Hz, 1 H), 7.72 (d, J=6.5 Hz, 1H), 7.58 (m, 1H), 6.97 (d, J=7.0 Hz, 1H), 6.10 (s, br, 1H), 3.95 (s, 3H), 3.42 (m, 2H), 3.35 (m, 2H), 3.05 (m, 1H), 1.10 (m, 3H), 0.92 (m, 3H). Mass spectrum (ESI, m/z): Calculated for C$_{19}$H$_{23}$N$_3$O$_4$, 358.41 (M+H), found 358.2.

Example 268

Compound #255

3-(6-(8-fluoronaphthalen-2-yl)-2-oxo-1,2-dihydropyridin-3-yl)-3-hydroxy-4-methylpentanamide

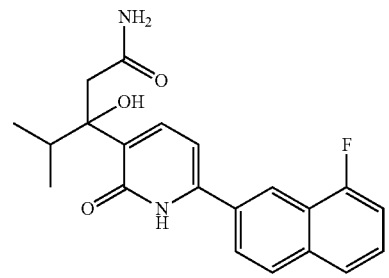 [SMILES: CC(C)C(O)(CC(N)=O)c1ccc(-c2ccc3cccc(F)c3c2)[nH]c1=O]

Step 1: 3-(6-(8-fluoronaphthalen-2-yl)-2-methoxy-pyridin-3-yl)-3-hydroxy-4-methylpentanamide Trimethylsilyl N-(trimethylsilyl)acetimidate (314 mg, 1.546 mmol, 1 equiv.) in THF (5 mL) was treated with n-BuLi (2.5 N, 618 μL, 1.546 mmol, 1 equiv.) dropwise at −78° C. for 5 min and the reaction was stirred for another 30 min at −78° C. Then 2-(8-fluoronaphthalen-2-yl)-6-methoxypyridine (500 mg, 1.546 mmol, 1 equiv.) in THF (1 mL) was dropwise added into the reaction and stirred for another 2 hours. The reaction was warmed to room temperature and quenched with saturated ammonium chloride. The solvent was removed and the residue was partitioned between ethyl acetate and water. The organic layer was washed with brined, dried and concentrated and purified by silica gel column using 10~50% ethyl acetate/heptanes to yield the title product as a colorless oil.

Step 2: 3-(6-(8-fluoronaphthalen-2-yl)-2-oxo-1,2-dihydropyridin-3-yl)-3-hydroxy-4-methyl pentanamide The title compound was prepared according to the procedure described in Example 1 step 5 by demethylation with TMSCl/NaI to yield the product as a white solid.

$^1$H NMR (400 MHz, CDCl$_3$) δ: 11.9 (br, s, 1H), 8.01 (d, J=5.5 Hz, 1 H), 7.81 (d, J=6.5 Hz, 1H), 7.70 (m, 2H), 7.52 (m, 1H), 7.24 (m, 2H), 6.75 (d, J=7.1 Hz, 1H), 6.45 (br, s, 1H), 3.01 (m, 1H), 2.72 (abq, J=9.5 Hz, 1H0, 2.38 (abq, J=9.0 Hz, 1H), 1.21 (d, J=7.0 Hz, 3H), 0.88 (d, J=7.0 Hz, 3H). Mass spectrum (ESI, m/z): Calculated for C$_{21}$H$_{21}$FN$_2$O$_3$, 369.41 (M+H), found 369.7.

Example 269

Compound #226

2-(cyclohex-1-en-1-yl)-2-(6-(naphthalen-2-yl)-2-oxo-1,2-dihydropyridin-3-yl)acetamide

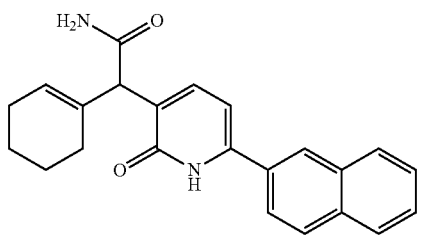 [SMILES: NC(=O)C(C1=CCCCC1)c1ccc(-c2ccc3ccccc3c2)[nH]c1=O]

The title compound was prepared according to the procedure described in Example 219 by hydrolysis, aminolysis of ethyl 2-(cyclohex-1-en-1-yl)-2-(6-(naphthalen-2-yl)-2-oxo-1,2-dihydropyridin-3-yl)acetate to yield the product as a white solid.

$^1$H NMR (400 MHz, CDCl$_3$) δ: 8.25 (s, 1H), 8.05 (d, J=6.5 Hz, 1 H), 7.95 (m, 3 H), 7.72 (d, J=7.0 Hz, 1H), 7.62 (m, 2H), 6.95 (d, J=6.5 Hz, 1H), 6.10 (s, br, 1H), 5.85 (s, 1H), 4.55 (s, 1H), 2.10 (m, 2H), 2.02 (m, 2H), 1.75 (m, 4H). Mass spectrum (ESI, m/z): Calculated for C$_{23}$H$_{22}$N$_2$O$_2$, 359.44 (M+H), found 359.2.

BIOLOGICAL EXAMPLES

Biological Example 1

[3H]-PGE2 Binding Assay

EP3 competition binding was determined using the following materials and experimental conditions:

| | |
|---|---|
| Beads = | Perkin Elmer RPNQ0001 |
| [3H]PGE2 = | Perkin Elmer NET428025UC |
| 384-well plate = | Perkin Elmer 6007290 |
| EP3 membrane = | Millipore HTS092M |
| Membrane concentration = | 2 μg/well |
| Beads concentration = | 0.25 mg/well |
| [3H]-PGE2 = | 2 nM; DMSO - 0.1% |
| Binding buffer = | 50 mM Tris, 10 mM MgCl$_2$, 1 mM EDTA, PH 7.4. |

The reaction system was prepared by mixing 5 μl of unlabeled compound; 5 μl of diluted [3H]-PGE2; 5 μl of diluted membrane; and 15 μl of SPA beads dissolved in binding buffer (adding in the following sequence: Unlabeled compound, [3H]-PGE2, Membrane and Beads).

Procedure:

The binding buffer was removed from refrigeration (@ 4° C.) and allowed to warm to room temperature. Test compound (@ stock concentration of 10 nM in DMSO) was serial dilutes (1:3) with 100% DMSO using Echo plate. Diluted test compound (30 nL) was dispensed to the 384-well assay plate (using Echo 550 Labcyte System). To each well was then added assay buffer (5 μl) and each well was spun. Beads were weighed out, dissolved in assay buffer to a concentration of 0.25 mg/15 μl. Original membrane was diluted with assay buffer to a concentration of 2 μg/5 μl. Original [3H]-PGE2 with diluted with assay buffer to a concentration of 12 nM. To each test well were then added diluted [3H]-PGE2 (5 μl), diluted membrane (5 μl), and dissolved beads (15 μl). The plate was equilibrated at room temperature on a plate shaker for 2 hours and then read with a TOPCOUNT scintillation plate reader. Results were analyzed using a Prism program with non-linear regression, one-site fit for Ki.

Biological Example 2

CHO Cell cAMP Assay

This assay monitored the cAMP generation in CHO cells over-expressing the EP3 receptor in the presence or absence of antagonist stimulated with Forskolin (FSK, CAS No. 66428-89-5) and a known EP3 Agonist (sulprostone, CAS No. 60325-46-4). For detection, a homogeneous competitive immunoassay (Time Resolved Fluorescence Energy Transfer (hTR-FRET)) was used.

Cells (6K cells per well) were plated in Poly-D-Lysine coated plates the day before the assay was to be run and were incubated at 37° C. One hour before the assay the media was removed and replaced with assay buffer (500 mL HBSS (+Ca)+2.5 mL 1M HEPES+6.66 mL 7.5% BSA) (starved at 37° C.). At the start of the assay the buffer was removed from the cells and replaced with buffer containing test compound(s). Sulprostone at an EC$_{80}$ dose (700 nM) and FSK at an EC$_{70}$ dose (2 μM) were added to initiate the reaction (37° C. for 30 minutes).

FSK increases cAMP production and sulprostone decreases cAMP production produced by FSK. In this assay, EP3 antagonists will increase the cAMP to the level of cAMP generated by FSK alone.

The reaction was terminated with the addition of cAMP detection reagents (labeled cAMP and labeled cAMP antibody in lysis buffer (HTRF reagent, which utilizes a cryptate-labeled anti-cAMP and d2-labeled cAMP-d2 is an HTRF acceptor fluorophore)). Approximately one hour later the plates were read on an Envision (Perkin Elmer) in HTRF mode. Well results were calculated based on a ratio of counts at 665 nm and 615 nm (data output was a calculation of the ratio: (read @665 nm/read @ 615 nm)*1000. For test compounds dosed serially, well results were converted to nM cAMP using a cAMP standard run on each plate. nM cAMP from a set of wells dosed with test compound(s) were plotted. nM cAMP was calculated for each well from a standard curve located on each plate (P1-12 and P13-24) by first calculating the slope and deriving the intercept (b):

$$m = \frac{\Delta NS_{cAMP\_standard\_curve}}{\Delta [standard\_curve]}$$

$$NS_{cAMP\_standard\_curve} = m(nM\ cAMP\_standard\_curve) + b$$

$NS_P$, $NS_N$, $NS_{sample}$ were converted to nM cAMP using the following equation:

$$nM\_cAMP = \frac{NS - b}{m}$$

$IC_{50}$ values were determined from a 4-point fit (Hill equation) of a single 11-point compound dosing. A best-fit curve was determined by the minimum sum of squares method plotting cAMP produced vs compound concentration.

Representative compounds of the present invention (including compounds of formula (I), compounds of formula (II) and compounds of formula (III)) were tested according to the procedures as described in Biological Example 1 and Biological Example 2 above, with results as listed in Table BIO-1 below. A notation of "NT" indicates that the compound was Not Tested in the assay listed.

TABLE BIO-1

Biological Assay Results

| ID NO. | [3H]-PGE2 Binding Ki (μM) | CHO_cAMP IC$_{50}$ (μM) |
|---|---|---|
| 1 | 0.039 | 0.088 |
| 2 | 0.038 | 0.057 |
| 3 | 0.017 | 0.349 |
| 4 | 0.088 | 1.800 |
| 5 | 0.017 | 0.293 |
| 6 | 0.013 | 0.061 |
| 7 | 0.039 | 0.149 |
| 8 | 0.050 | 0.066 |
| 9 | 0.023 | 0.108 |
| 10 | 0.028 | NT |
| 11 | 0.028 | 0.055 |
| 12 | 1.346 | >20 |
| 13 | 0.003 | 0.022 |
| 14 | >10 | >20 |
| 15 | 0.007 | NT |
| 16 | 0.006 | 0.017 |
| 17 | 0.014 | NT |
| 18 | 2.639 | >20 |
| 19 | 0.121 | NT |
| 20 | 0.011 | NT |
| 21 | 0.034 | 0.849 |
| 22 | 0.097 | 0.204 |
| 23 | 0.228 | NT |
| 24 | 0.054 | NT |
| 25 | >10 | NT |
| 26 | 0.328 | NT |
| 27 | 0.039 | NT |
| 28 | 5.623 | >20 |
| 29 | 0.003 | 0.009 |
| 30 | 0.002 | 0.012 |
| 31 | 0.037 | 0.482 |
| 32 | 0.292 | NT |
| 33 | 0.735 | NT |
| 34 | 0.267 | 17.595 |
| 35 | 0.024 | 0.215 |
| 36 | 0.195 | NT |
| 37 | 0.024 | NT |
| 38 | 0.013 | NT |
| 39 | 0.089 | NT |
| 40 | 0.011 | 0.044 |
| 41 | 0.002 | NT |
| 42 | 0.009 | 0.020 |
| 43 | 5.668 | >20 |
| 44 | 0.093 | 0.505 |
| 45 | 0.059 | NT |
| 46 | 0.452 | NT |
| 47 | 0.025 | NT |
| 48 | 0.002 | NT |
| 49 | 0.017 | 0.091 |
| 50 | 1.083 | NT |
| 51 | 2.058 | NT |
| 52 | 0.019 | NT |
| 53 | 0.006 | NT |
| 54 | 0.121 | NT |
| 55 | 0.003 | 0.033 |
| 56 | 0.020 | 0.230 |
| 57 | 0.006 | NT |
| 58 | 0.007 | NT |
| 59 | 0.085 | 0.611 |
| 60 | 0.027 | 0.092 |
| 61 | 0.043 | 0.376 |
| 62 | 0.009 | 0.021 |
| 63 | 0.013 | 0.027 |
| 64 | 0.008 | 0.009 |
| 65 | 0.006 | 0.017 |
| 66 | 0.004 | 0.014 |
| 67 | 0.007 | 0.050 |
| 68 | 0.016 | 0.039 |
| 69 | 0.046 | 0.323 |
| 70 | 0.034 | 0.134 |
| 71 | 0.025 | 0.112 |
| 72 | 0.034 | 0.070 |
| 73 | 0.017 | 0.065 |
| 74 | 0.008 | 0.027 |
| 75 | 0.023 | 0.092 |
| 76 | 0.007 | 0.033 |
| 77 | 0.016 | 0.060 |
| 78 | 0.011 | 0.010 |
| 79 | 0.007 | 0.009 |
| 80 | 0.006 | 0.011 |
| 81 | 0.006 | 0.015 |
| 82 | 0.023 | 0.137 |
| 83 | NT | NT |
| 84 | 0.007 | 0.026 |
| 85 | 0.044 | 0.122 |
| 86 | 0.114 | 0.916 |
| 87 | 0.032 | 0.149 |
| 88 | NT | NT |
| 89 | 0.010 | 0.031 |
| 90 | 0.633 | 5.434 |
| 91 | >10 | >20 |
| 92 | 0.009 | 0.007 |

TABLE BIO-1-continued

Biological Assay Results

| ID NO. | [3H]-PGE2 Binding Ki (µM) | CHO_cAMP IC$_{50}$ (µM) |
|---|---|---|
| 93 | 1.067 | 9.940 |
| 94 | 0.020 | 0.181 |
| 95 | 0.015 | 0.041 |
| 96 | 0.017 | 0.039 |
| 97 | 0.179 | 0.666 |
| 98 | >10 | >20 |
| 99 | 0.921 | 4.881 |
| 100 | 0.028 | 0.102 |
| 101 | 0.015 | 0.120 |
| 102 | NT | NT |
| 103 | 0.022 | 0.033 |
| 104 | 0.053 | 0.375 |
| 105 | 0.013 | 0.023 |
| 106 | 0.050 | 0.555 |
| 107 | >10 | >20 |
| 108 | 0.171 | 0.602 |
| 109 | 0.027 | 0.115 |
| 110 | >10 | >20 |
| 111 | 0.162 | 0.585 |
| 112 | 0.057 | 0.212 |
| 113 | NT | NT |
| 114 | NT | NT |
| 115 | 0.002 | 0.011 |
| 116 | 0.008 | 0.076 |
| 117 | 0.033 | 0.205 |
| 118 | 0.044 | 0.131 |
| 119 | 0.009 | 0.068 |
| 120 | >10 | >20 |
| 121 | 0.073 | 0.363 |
| 122 | 0.032 | 0.278 |
| 123 | 0.023 | 0.185 |
| 124 | 0.202 | 19.187 |
| 125 | 0.487 | 0.658 |
| 126 | 0.065 | 0.382 |
| 127 | 0.046 | 0.548 |
| 128 | 0.154 | 18.001 |
| 129 | 0.006 | 0.149 |
| 130 | 0.012 | 0.072 |
| 131 | 0.012 | 0.036 |
| 132 | 0.050 | 0.310 |
| 133 | 0.012 | 0.235 |
| 134 | 0.004 | 0.008 |
| 135 | 0.085 | NT |
| 136 | 0.379 | 0.367 |
| 137 | 0.054 | 0.218 |
| 138 | 0.012 | 0.021 |
| 139 | 0.010 | 0.017 |
| 140 | 0.011 | 0.076 |
| 141 | 0.025 | NT |
| 142 | 0.121 | NT |
| 143 | 0.308 | 0.734 |
| 144 | 0.007 | NT |
| 145 | 0.001 | 0.002 |
| 146 | 0.006 | NT |
| 147 | 0.632 | NT |
| 148 | 0.787 | NT |
| 149 | 0.002 | 0.009 |
| 150 | 0.005 | 0.008 |
| 151 | 0.011 | NT |
| 152 | 0.428 | 2.138 |
| 153 | 0.043 | 0.400 |
| 154 | 0.009 | 0.028 |
| 155 | 0.005 | 0.020 |
| 156 | 0.057 | 0.508 |
| 157 | 0.024 | 0.064 |
| 158 | 0.009 | 0.010 |
| 159 | 0.022 | 0.185 |
| 160 | 0.013 | 0.044 |
| 161 | 0.027 | 0.095 |
| 162 | 0.013 | 0.117 |
| 163 | 0.014 | 0.122 |
| 164 | 0.026 | 0.485 |
| 165 | 0.031 | 0.250 |
| 166 | 0.006 | 0.040 |
| 167 | 0.151 | 0.779 |
| 168 | 0.026 | 0.130 |
| 169 | 0.051 | 0.476 |
| 170 | 0.023 | 0.038 |
| 171 | 0.029 | NT |
| 172 | 0.025 | NT |
| 173 | 0.153 | 1.304 |
| 174 | 0.002 | 0.003 |
| 175 | 0.110 | 0.171 |
| 176 | 0.028 | 0.067 |
| 177 | 0.014 | 0.347 |
| 178 | 0.020 | 0.220 |
| 179 | 0.003 | 0.006 |
| 180 | 0.006 | 0.024 |
| 181 | 0.004 | 0.006 |
| 182 | 0.041 | 0.638 |
| 183 | 0.003 | 0.001 |
| 184 | 0.002 | 0.002 |
| 185 | 0.031 | 0.314 |
| 186 | 0.040 | 2.825 |
| 187 | >10 | >20 |
| 188 | 0.015 | 0.120 |
| 189 | 0.016 | 0.109 |
| 190 | 0.032 | 0.614 |
| 191 | 0.005 | 0.020 |
| 192 | 0.060 | 1.327 |
| 194 | >10 | >20 |
| 195 | 0.042 | 0.286 |
| 196 | 0.008 | 0.087 |
| 197 | 0.169 | 0.967 |
| 198 | 0.019 | 0.530 |
| 199 | >10 | >20 |
| 200 | 0.038 | 1.249 |
| 201 | 0.010 | 0.013 |
| 203 | 0.106 | 1.415 |
| 204 | 0.012 | NT |
| 205 | 0.051 | NT |
| 206 | 0.025 | NT |
| 207 | 0.015 | NT |
| 208 | 0.158 | NT |
| 209 | 0.020 | NT |
| 210 | 0.042 | NT |
| 211 | 0.005 | 0.037 |
| 213 | 0.007 | 0.281 |
| 214 | >10 | >20 |
| 215 | 0.165 | NT |
| 216 | 0.026 | 0.426 |
| 217 | 0.049 | 1.138 |
| 218 | 0.050 | 0.509 |
| 219 | 0.108 | 4.069 |
| 220 | 0.018 | 0.191 |
| 221 | 0.051 | 0.243 |
| 222 | 0.327 | 4.271 |
| 223 | 0.496 | 3.579 |
| 224 | 1.290 | 10.755 |
| 225 | 0.343 | 4.574 |
| 226 | 0.186 | 4.957 |
| 227 | 0.033 | 0.445 |
| 228 | 0.003 | 0.010 |
| 229 | 0.012 | 0.142 |
| 230 | 0.010 | 0.041 |
| 231 | 0.025 | 0.099 |
| 232 | 0.125 | 1.635 |
| 233 | 0.015 | 0.325 |
| 234 | 0.004 | 0.023 |
| 236 | 0.002 | 0.006 |
| 237 | 0.004 | 0.012 |
| 238 | 0.005 | 0.012 |
| 239 | 0.001 | 0.002 |
| 241 | 0.637 | 9.629 |
| 242 | 0.398 | 3.957 |
| 243 | 2.595 | 14.031 |
| 244 | 0.501 | 2.393 |
| 246 | >10 | 17.041 |
| 247 | 0.771 | 2.400 |
| 248 | 0.010 | NT |

TABLE BIO-1-continued

Biological Assay Results

| ID NO. | [3H]-PGE2 Binding Ki (µM) | CHO_cAMP IC$_{50}$ (µM) |
|---|---|---|
| 249 | 0.005 | 0.053 |
| 250 | 0.069 | 0.931 |
| 251 | 0.003 | 0.005 |
| 252 | 0.180 | 0.499 |
| 253 | 0.012 | 0.059 |
| 254 | 0.344 | 2.742 |
| 255 | 0.009 | 0.115 |
| 256 | 0.164 | 0.579 |
| 257 | 0.002 | 0.023 |
| 258 | 0.008 | 0.136 |
| 259 | 0.028 | 0.242 |
| 260 | 0.006 | 0.015 |
| 261 | 0.020 | 0.024 |
| 262 | 0.152 | 0.282 |
| 263 | 0.108 | 0.336 |
| 264 | 0.050 | 0.310 |
| 265 | 0.034 | 0.249 |
| 266 | 0.028 | 0.736 |
| 267 | 0.006 | 0.014 |
| 268 | 0.006 | 0.017 |
| 270 | 0.164 | 0.540 |
| 271 | 0.006 | NT |
| 272 | >10 | >20 |
| 273 | 0.027 | 0.067 |
| 274 | >10 | >20 |
| 275 | 6.14 | >20 |
| 276 | 5.65 | 7.60 |
| 277 | 0.107 | 0.548 |
| 278 | 0.368 | 0.591 |
| 279 | 0.060 | NT |
| 280 | 0.076 | 0.671 |
| 281 | 0.037 | 0.527 |
| 282 | 0.740 | 0.900 |
| 283 | 0.049 | 0.180 |
| 285 | 0.035 | 0.164 |
| 286 | 0.064 | 0.179 |
| 287 | 0.157 | 8.68 |
| 288 | 0.180 | 0.656 |
| 289 | 1.80 | >20 |
| 290 | 0.116 | 1.912 |
| 291 | 0.003 | 0.019 |
| 292 | 0.002 | 0.006 |
| 293 | 0.014 | 0.207 |
| 294 | 0.006 | 0.056 |
| 295 | 0.002 | 0.079 |
| 296 | 0.001 | 0.103 |
| 297 | 0.008 | 0.194 |
| 298 | 0.979 | 8.30 |
| 299 | 0.029 | NT |
| 300 | 0.005 | NT |
| 302 | NT | NT |
| 303 | 0.014 | 1.284 |
| 304 | 0.270 | 0.680 |
| 305 | 0.022 | 0.063 |
| 306 | 0.054 | 0.111 |
| 307 | 0.053 | 0.385 |
| 308 | 0.046 | 0.210 |
| 309 | 0.012 | 0.066 |
| 310 | 0.071 | NT |

Biological Example 3

IV Infused EP3 Antagonists on Circulating Insulin and Glucose in the Sulprostone Infusion IVGTT Model Jugular vein and carotid artery cannulated male Sprague Dawley rats (~250 g, available from Charles River) were housed one rat per suspended cage in a temperature-controlled room with 12-hour light/dark cycle. The rats were allowed ad libitum access to water and maintained on a regular diet. Animals were acclimated for minimum 5 days prior to the start of the experiment. Experimental procedures were carried out in accordance with institutional standards for animal care and were approved by the institute's animal care and use committee.

A blood sample for insulin and blood chemistry was collected at 20 min (t=−20) prior to the start of dosing with sulprostone and/or test compound (EP3 antagonist). Sulprostone solution was prepared in 10 U/ml heparin saline solution at a concentration of 0.09 mg/ml. Test compound solution was prepared in 20% HPBCD (pH=7) at a concentration of 0.048 mg/ml (1×K$_i$), 0.336 mg/ml (7×k$_i$) and 0.480 mg/ml (10×K$_i$). Final test compound solution was mixed 1:1 volume with sulprostone solution immediately prior to starting the experiment. Tested compound solution (at 0.096 mpk, 0.671 mpk or 0.959 mpk (mg/kg)) or saline bolus at 2 ml/kg was injected into the animals and a blood sample was taken for exposure analysis at 2 min after the bolus. After 18 min, another blood sample was taken for exposure analysis and also for measurement of insulin and blood chemistry (t=0). Animals were then injected (through infusion syringe) with a 50% glucose solution (1 g/kg) followed by IV infusion at 2 ml/kg/h with the vehicle (20% HPBCD, pH=7), 3 µg/kg/min sulprostone only or a mixture of 3 µg/kg/min sulprostone and the test compound at 0.0268 mpk/h, 0.188 mpk/h and 0.268 mpk/h. Blood samples were then collected at 2, 5, 10, 15, 20, 30 min post infusion for measurement of insulin and blood chemistry. Another blood sample was collected at 31 min post infusion for exposure analysis.

Blood samples from all animals were collected into Heparin treated tubes. Background was measured via a glucometer at the 0 and 2 min time points to ensure that the animal received the glucose bolus. Plasma insulin was measured via a Meso Scale Discovery metabolic assay (available from Meso Scale). Plasma glucose, free fatty acid (FFA), triglycerides, cholesterol and ketones were measured on an OLYMPUS AU400E chemistry analyzer. Observations on animal health were recorded throughout the procedure. Samples from time points (after the bolus) 2, 20 and 50 min were submitted for measurement of exposure by plasma drug concentration.

Statistical analysis was performed using the program Prism (Graphpad, Monrovia, Calif.) with either a repeated measures 2-way ANOVA (glucose and insulin curves with Bonferroni's multiple comparison test) or a one-way ANOVA and Tukey's multiple comparison test (AUC). AUC=Integrated area under the stimulated glucose excursion and insulin curve from t=0 to t=30 minutes and from t=0 to t=10 min. AIR is calculated as the mean insulin at 2, 5 and 10 min after glucose bolus—baseline.

Testing according to the procedure describe above, Compound #62, prepared for example as described in Example 5 was shown to reverse suppression of glucose stimulate insulin secretion (GSIS) by sulprostone at 7×K$_i$ and 10×K$_i$ (targeted, mEP3 K$_i$=8.6 nM) in SD rats.

Formulation Example 1

Solid, Oral Dosage Form—Prophetic Example

As a specific embodiment of an oral composition, 100 mg of, for example Compound #62 prepared as in Example 5, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:

1. A compound of formula (III)

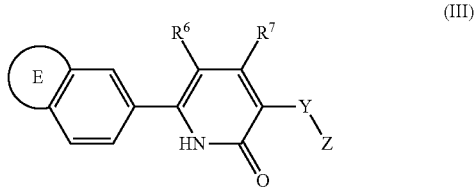

wherein

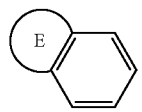

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl;

wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is optionally substituted on the phenyl portion of the

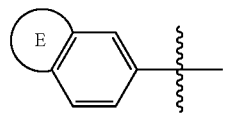 [SMILES: *c1ccccc1]

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, chroman-7-yl, chromen-7-yl, benzo[d][1,3]dioxol-5-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl; is further optionally substituted on the

portion of the

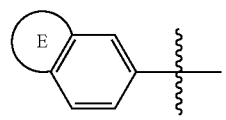 [SMILES: *c1ccccc1]

bicycle with one to two substituents independently selected from the group consisting of halogen, oxo, cyano, $C_{1-3}$alkyl, fluorinated $C_{1-2}$alkyl, $C_{1-3}$alkoxy, fluorinated $C_{1-2}$alkoxy and $C_{3-6}$cycloalkyl;

$R^6$ is selected from the group consisting of hydrogen, halogen and $C_{1-4}$alkyl;

$R^7$ is selected from the group consisting of hydrogen, halogen and $C_{1-4}$alkyl;

Y is selected from the group consisting of —$CR^HR^J$— and —$CR^HR^J$—$CHR^K$—;

wherein $R^H$ and $R^J$ are each independently selected from the group consisting of hydrogen, halogen, hydroxy, $C_{1-4}$alkyl, fluorinated $C_{1-2}$alkyl, $C_{3-6}$cycloalkyl, $C_{5-6}$cycloalkenyl, phenyl, benzyl and phenyl-ethyl-; provided that when one of $R^H$ or $R^J$ is $C_{3-6}$cycloalkyl, $C_{5-6}$cycloalkenyl, phenyl, benzyl or phenylethyl-, then the other of $R^H$ or $R^J$ is hydrogen; and wherein $R^K$ is selected from the group consisting of hydrogen and $C_{1-4}$alkyl;

alternatively, when Y is —$CR^HR^J$—, then $R^H$ and $R^J$ may be taken together with the carbon atom to which they are bound to form $C_{3-6}$cycloalkyl;

Z is selected from the group consisting of —C(O)—$NR^LR^M$, —C(O)—NH—$OR^N$, —C(O)—NH—$SO_2$—$R^N$; —C(O)—NH(CH($CH_2$OH)$_2$), —C(O)—NH(C($CH_2$OH)$_3$), —C(O)—NH—$(CH_2CH_2O)_a$—$R^N$, —C(O)—NH—CH($CH_2$O—$(CH_2CH_2O)_b$—$R^N$)$_2$, —C(O)—NH—C($CH_2$O—$(CH_2CH_2O)_b$—$R^N$)$_3$), —C(O)—NH—$CH_2CH_2$—$NR^PR^Q$, —C(O)—NH—$(CH_2CH_2O)_a$—$CH_2CH_2$—$NR^PR^Q$, —$NR^S$—C(O)—$NR^PR^Q$, —$NR^S$—C(O)—NH—$CH_2CH_2$—$NR^PR^Q$ and —$NR^S$—C($NH_2$)=N—CN;

wherein a is an integer from 1 to 6;

wherein b is an integer from 0 to 3;

wherein $R^L$ and $R^M$ are each independently selected from the group consisting of hydrogen and $C_{1-4}$alkyl;

wherein $R^N$ is selected from the group consisting of hydrogen and $C_{1-2}$alkyl;

wherein $R^P$ and $R^Q$ are each independently selected from the group consisting of hydrogen and $C_{1-2}$alkyl;

and wherein $R^S$ is selected from the group consisting of hydrogen and $C_{1-2}$alkyl;

or a tautomer or a pharmaceutically acceptable salt thereof.

2. A compound as in claim 1, wherein

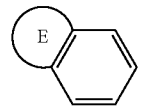

is selected from the group consisting of naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl and 2,3-dihydro-benzo[b][1,4]dioxin-6-yl;

wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is optionally substituted on the phenyl portion of the

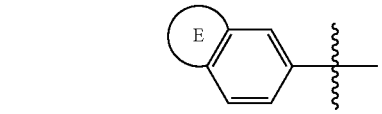 [SMILES: *c1ccccc1]

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy;

and wherein the naphth-2-yl, indol-5-yl, indazol-5-yl, indazol-6-yl, benzimidazol-5-yl, benzimidazol-6-yl, benzothiazol-5-yl, benzothiazol-6-yl, benzoisothiazol-6-yl, 3,4-dihydro-2H-benzo[b][1,4]oxazin-6-yl, 3,4-dihydro-2H-benzo[b][1,4]oxazin-7-yl or 2,3-dihydro-benzo[b][1,4]dioxin-6-yl is further optionally substituted on the

portion of the

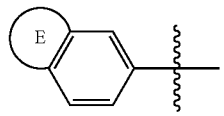

bicycle with one to two substituents independently selected from the group consisting of halogen, oxo, $C_{1-3}$alkyl, fluorinated $C_{1-2}$alkyl, $C_{1-3}$alkoxy and fluorinated $C_{1-2}$alkoxy;

$R^6$ is selected from the group consisting of hydrogen, fluoro and $C_{1-2}$alkyl;

$R^7$ is selected from the group consisting of hydrogen, fluoro and $C_{1-2}$alkyl;

Y is selected from the group consisting of —$CR^HR^J$— and —$CR^HR^J$—$CHR^K$—;

wherein $R^H$ and $R^J$ are each independently selected from the group consisting of hydrogen, halogen, hydroxy, $C_{1-4}$alkyl, fluorinated $C_{1-2}$alkyl, $C_{3-6}$cycloalkyl and $C_{5-6}$cycloalkenyl; provided that when one of $R^H$ or $R^J$ is $C_{3-6}$cycloalkyl or $C_{5-6}$cycloalkenyl, then the other of $R^H$ or $R^J$ is hydrogen; and wherein $R^K$ is selected from the group consisting of hydrogen and $C_{1-4}$alkyl;

alternatively, when Y is —$CR^HR^J$—, then $R^H$ and $R^J$ may be taken together with the carbon atom to which they are bound to form $C_{5-6}$cycloalkyl;

Z is selected from the group consisting of —C(O)—$NR^LR^M$, —C(O)—NH—$OR^N$, —C(O)—NH—$SO_2$—$R^N$; —C(O)—NH(CH(CH$_2$OH)$_2$), —C(O)—NH(C(CH$_2$OH)$_3$), —C(O)—NH—(CH$_2$CH$_2$O)$_a$—$R^N$, —C(O)—NH—CH(CH$_2$O—(CH$_2$CH$_2$O)$_b$—$R^N$)$_2$, —C(O)—NH—C(CH$_2$O—(CH$_2$CH$_2$O)$_b$—$R^N$)$_3$), —C(O)—NH—CH$_2$CH$_2$—$NR^PR^Q$, —C(O)—NH—(CH$_2$CH$_2$O)$_a$—CH$_2$CH$_2$—$NR^PR^Q$, —$NR^S$—C(O)—$NR^PR^Q$, —$NR^S$—C(O)—NH—CH$_2$CH$_2$—$NR^PR^Q$ and —$NR^S$—C(NH$_2$)=N—CN;

wherein a is an integer from 1 to 4;
wherein b is an integer from 0 to 3;
wherein $R^L$ and $R^M$ are each independently selected from the group consisting of hydrogen and $C_{1-4}$alkyl;
wherein $R^N$ is selected from the group consisting of hydrogen and $C_{1-2}$alkyl;
wherein $R^P$ and $R^Q$ are each independently selected from the group consisting of hydrogen and $C_{1-2}$alkyl;
and wherein $R^S$ is selected from the group consisting of hydrogen and $C_{1-2}$alkyl;
or a tautomer or a pharmaceutically acceptable salt thereof.

3. A compound as in claim 2, wherein

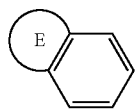

is selected from the group consisting of naphth-2-yl, benzothiazol-5-yl, benzothiazol-6-yl, 3,4-dihydro-benzo[b][1,4]oxazin-6-yl and 3,4-dihydro-benzo[b][1,4]oxazin-7-yl;

wherein the naphth-2-yl, benzothiazol-5-yl, benzothiazol-6-yl, 3,4-dihydro-benzo[b][1,4]oxazin-6-yl or 3,4-dihydro-benzo[b][1,4]oxazin-7-yl is optionally substituted on the phenyl or

portion of the

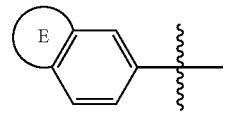

with a substituent selected from the group consisting of halogen, $C_{1-3}$alkyl and $C_{1-2}$alkoxy;

$R^6$ is hydrogen;

$R^7$ is hydrogen;

Y is selected from the group consisting of —$CR^HR^J$— and —$CR^HR^J$—$CHR^K$—;

wherein $R^H$ and $R^J$ are each independently selected from the group consisting of hydrogen, halogen, hydroxy, $C_{1-4}$alkyl and $C_{5-6}$cycloalkenyl; provided that when one of $R^H$ or $R^J$ is $C_{5-6}$cycloalkenyl, then the other of $R^H$ or $R^J$ is hydrogen; and wherein $R^K$ is selected from the group consisting of hydrogen and $C_{1-4}$alkyl;

Z is selected from the group consisting of —C(O)—$NR^LR^M$, —C(O)—NH—$OR^N$, —C(O)—NH—$SO_2$—$R^N$; —C(O)—NH(CH(CH$_2$OH)$_2$), —C(O)—NH(C(CH$_2$OH)$_3$), —C(O)—NH—(CH$_2$CH$_2$O)$_a$—$R^N$, —C(O)—NH—CH$_2$CH$_2$—$NR^PR^Q$, —C(O)—NH—(CH$_2$CH$_2$O)$_a$—CH$_2$CH$_2$—$NR^PR^Q$, —$NR^S$—C(O)—$NR^PR^Q$, —$NR^S$—C(O)—NH—CH$_2$CH$_2$—$NR^PR^Q$ and —$NR^S$—C(NH$_2$)=N—CN;

wherein a is an integer from 1 to 3;
wherein $R^L$ and $R^M$ are each independently selected from the group consisting of hydrogen and $C_{1-4}$alkyl;
wherein $R^N$ is selected from the group consisting of hydrogen and methyl;
wherein $R^P$ and $R^Q$ are each independently selected from the group consisting of hydrogen and methyl;
and wherein $R^S$ is selected from the group consisting of hydrogen and methyl;
or a tautomer or a pharmaceutically acceptable salt thereof.

4. A compound as in claim 3, wherein

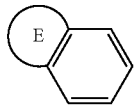

is selected from the group consisting of naphth-2-yl, 6-fluoro-naphth-2-yl, 8-fluoro-naphth-2-yl, 6-methoxy-naphth-2-yl, benzothiazol-5-yl, benzothiazol-6-yl, 4-methyl-3,4-dihydro-benzo[b][1,4]oxazin-6-yl and 4-methyl-3,4-dihydro-benzo[b][1,4]oxazin-7-yl;

$R^6$ is hydrogen;
$R^7$ is hydrogen;
Y is selected from the group consisting of —CH(isopropyl), —C(OH)(isopropyl)-, —C(F)(isopropyl)-, —C(methyl)(isopropyl)-, —CH(cyclohex-1-en-1-yl), —CH(isopropyl)-CH$_2$— and —CH$_2$—CH(isopropyl)-;
Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$—N(CH$_3$)$_2$, —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—O—CH$_3$, —C(O)—NH—SO$_2$—CH$_3$, —NH—C(O)—NH$_2$, —N(CH$_3$)—C(O)—NH$_2$, —NH—C(O)—NH—CH$_2$CH$_2$—N(CH$_3$)$_2$ and —NH-(E)-C(NH$_2$)=N—CN;
or a tautomer or a pharmaceutically acceptable salt thereof.

5. A compound as in claim 4, wherein

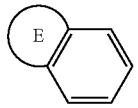

is selected from the group consisting of naphth-2-yl and 8-fluoro-naphth-2-yl;

$R^6$ is hydrogen;
$R^7$ is hydrogen;
Y is selected from the group consisting of —CH(isopropyl), —C(OH)(isopropyl)-, —C(F)(isopropyl)-, —C(methyl)(isopropyl)-, —CH(cyclohex-1-en-1-yl), —CH(isopropyl)-CH$_2$— and —CH$_2$—CH(isopropyl)-;
Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$—N(CH$_3$)$_2$, —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—O—CH$_3$, —C(O)—NH—SO$_2$—CH$_3$, —NH—C(O)—NH$_2$, —N(CH$_3$)—C(O)—NH$_2$, —NH—C(O)—NH—CH$_2$CH$_2$—N(CH$_3$)$_2$ and —NH-(E)-C(NH$_2$)=N—CN;
or a tautomer or a pharmaceutically acceptable salt thereof.

6. A compound as in claim 4, wherein

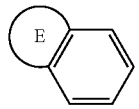

is selected from the group consisting of naphth-2-yl and 8-fluoro-naphth-2-yl;

$R^6$ is hydrogen;
$R^7$ is hydrogen;
Y is selected from the group consisting of —CH(isopropyl), —C(OH)(isopropyl)-, —C(F)(isopropyl)-, —CH(isopropyl)-CH$_2$— and —CH$_2$—CH(isopropyl)-;
Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$—N(CH$_3$)$_2$, —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—O—CH$_3$, —C(O)—NH—SO$_2$—CH$_3$, —NH—C(O)—NH$_2$, —N(CH$_3$)—C(O)—NH$_2$, —NH—C(O)—NH—CH$_2$CH$_2$—N(CH$_3$)$_2$ and —NH-(E)-C(NH$_2$)=N—CN;
or a tautomer or a pharmaceutically acceptable salt thereof.

7. A compound as in claim 4, wherein

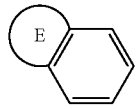

is selected from the group consisting of naphth-2-yl and 8-fluoro-naphth-2-yl;

$R^6$ is hydrogen;
$R^7$ is hydrogen;
Y is selected from the group consisting of —CH(isopropyl), —C(OH)(isopropyl)-, —CH(isopropyl)-CH$_2$— and —CH$_2$—CH(isopropyl)-;
Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH(C(CH$_2$OH)$_3$), —C(O)—NH—CH$_2$CH$_2$OH, —C(O)—NH—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—N(CH$_3$)$_2$, —C(O)—NH—CH$_2$CH$_2$O—CH$_2$CH$_2$O—CH$_2$CH$_2$—CH$_3$, —NH—C(O)—NH$_2$, and —NH-(E)-C(NH$_2$)=N—CN;
or a tautomer or a pharmaceutically acceptable salt thereof.

8. A compound as in claim 4, wherein

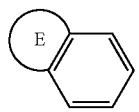

is selected from the group consisting of naphth-2-yl and 8-fluoro-naphth-2-yl;

$R^6$ is hydrogen;
$R^7$ is hydrogen;
Y is selected from the group consisting of —CH(isopropyl), —C(OH)(isopropyl)- and —CH(isopropyl)-CH$_2$—;
Z is selected from the group consisting of —C(O)—NH$_2$, —C(O)—NH(isopropyl), —C(O)—NH(OCH$_3$), —C(O)—NH(CH(CH$_2$OH)$_2$), —C(O)—NH—CH$_2$CH$_2$OH, —C(O)—NH—CH$_2$CH$_2$O—CH$_2$CH$_2$O—CH$_2$CH$_2$O—CH$_3$, —NH—C(O)—NH$_2$, and —NH-(E)-C(NH$_2$)=N—CN;
or a tautomer or a pharmaceutically acceptable salt thereof.

9. A compound as in claim 4, wherein

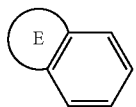

is selected from the group consisting of naphth-2-yl and 8-fluoro-naphth-2-yl;
$R^6$ is hydrogen;
$R^7$ is hydrogen;
Y is selected from the group consisting of —CH(isopropyl), and —CH(isopropyl)-CH$_2$—;
Z is selected from the group consisting of —C(O)—NH$_2$, —C(O)—NH(isopropyl), —C(O)—NH(OCH$_3$), —C(O)—NH—CH$_2$CH$_2$OH and —C(O)—NH—CH$_2$CH$_2$O—CH$_2$CH$_2$O—CH$_2$CH$_2$O—CH$_3$;
or a tautomer or a pharmaceutically acceptable salt thereof.

10. A pharmaceutical composition comprising a pharmaceutically acceptable carrier and a compound of claim 1.

11. A pharmaceutical composition made by mixing a compound of claim 1 and a pharmaceutically acceptable carrier.

12. A process for making a pharmaceutical composition comprising mixing a compound of claim 1 and a pharmaceutically acceptable carrier.

13. A method of antagonism of the EP3 receptor, comprising administering to a subject in need thereof a therapeutically effective amount of the compound of claim 1.

14. The method of claim 13, wherein the subject has a disorder selected from the group consisting of Type I diabetes mellitus, impaired glucose tolerance (IGT), impaired fasting glucose (IFG), gestational diabetes, Type II diabetes mellitus, Syndrome X (also known as Metabolic Syndrome), obesity, nephropathy, neuropathy, retinopathy, restenosis, thrombosis, coronary artery disease, hypertension, angina, atherosclerosis, heart disease, heart attack, ischemia, stroke, nerve damage or poor blood flow in the feet, neurodegenerative disorders, non-alcoholic steatohepatitis (NASH), non-alcoholic fatty liver disease (NAFLD), liver fibrosis, cataracts, polycystic ovarian syndrome, premature labor, irritable bowel syndrome, bladder over-activity, inflammation, pain and cancer.

15. A method of antagonism of the EP3 receptor comprising administering to a subject in need thereof a therapeutically effective amount of the composition of claim 10.

16. A method of treating a condition selected from the group consisting of Type I diabetes mellitus, impaired glucose tolerance (IGT), impaired fasting glucose (IFG), gestational diabetes, Type II diabetes mellitus, Syndrome X (also known as Metabolic Syndrome), and obesity comprising administering to a subject in need thereof, a therapeutically effective amount of the compound of claim 1.

* * * * *